United States Patent
Kim et al.

(10) Patent No.: US 11,091,501 B2
(45) Date of Patent: Aug. 17, 2021

(54) HETEROCYCLIC COMPOUNDS AS RSV INHIBITORS

(71) Applicant: Enanta Pharmaceuticals, Inc., Watertown, MA (US)

(72) Inventors: In Jong Kim, Lexington, MA (US); Jianming Yu, Plainsboro, NJ (US); Joseph Panarese, Malden, MA (US); Kevin McGrath, Brighton, MA (US); Solymar Negretti-Emmanuelli, Watertown, MA (US); Thomas P. Blaisdell, Brighton, MA (US); Brian C. Shook, Holliston, MA (US); Yat Sun Or, Watertown, MA (US)

(73) Assignee: Enanta Pharmaceuticals, Inc., Watertown, MA (US)

(*) Notice: Subject to any disclaimer, the term of this patent is extended or adjusted under 35 U.S.C. 154(b) by 0 days.

(21) Appl. No.: 16/023,422

(22) Filed: Jun. 29, 2018

(65) Prior Publication Data
US 2019/0002479 A1    Jan. 3, 2019

Related U.S. Application Data

(60) Provisional application No. 62/527,384, filed on Jun. 30, 2017.

(51) Int. Cl.
| | | |
|---|---|---|
| A61K 31/55 | (2006.01) | |
| C07D 519/00 | (2006.01) | |
| C07D 495/04 | (2006.01) | |
| A61P 31/16 | (2006.01) | |

(52) U.S. Cl.
CPC .......... C07D 519/00 (2013.01); A61P 31/16 (2018.01)

(58) Field of Classification Search
CPC .... C07D 519/00; C07D 495/04; A61K 31/55; A61P 31/16
USPC .............. 514/217, 443; 540/586; 549/43
See application file for complete search history.

(56) References Cited

U.S. PATENT DOCUMENTS

| | | | |
|---|---|---|---|
| 4,010,153 A | 3/1977 | Kajfez et al. | |
| 4,511,510 A | 4/1985 | Mauri | |
| 4,988,692 A | 1/1991 | Gasc et al. | |
| 5,571,809 A | 11/1996 | Hargrave et al. | |
| 5,637,697 A | 6/1997 | Finch et al. | |
| 5,646,140 A | 7/1997 | Sugg et al. | |
| 5,681,833 A | 10/1997 | Castro et al. | |
| 7,582,624 B2 | 9/2009 | Carter et al. | |
| 8,999,969 B2 | 4/2015 | Mackman et al. | |
| 9,732,098 B2 | 8/2017 | Hunt et al. | |
| 9,957,281 B2 | 5/2018 | Shook et al. | |
| 10,358,441 B2 | 7/2019 | Kim et al. | |
| 10,398,706 B2 | 9/2019 | Shook et al. | |
| 2006/0040923 A1 | 2/2006 | Carter et al. | |
| 2006/0083741 A1 | 4/2006 | Hoffman et al. | |
| 2007/0142403 A1 | 6/2007 | Powell et al. | |
| 2007/0185094 A1 | 8/2007 | Lattmann et al. | |
| 2007/0185096 A1 | 8/2007 | Powell et al. | |

(Continued)

FOREIGN PATENT DOCUMENTS

| | | |
|---|---|---|
| EP | 0167919 A2 | 1/1986 |
| EP | 0703222 A1 | 3/1996 |

(Continued)

OTHER PUBLICATIONS

Chapman et al., "RSV604, a novel inhibitor of Respiratory Syncytial Virus Replication" Antimicrob. Agents and Chemotherap. (2007), 51 (9), pp. 3346-3353. (Year: 2007).*

(Continued)

*Primary Examiner* — Joseph R Kosack
*Assistant Examiner* — Sagar Patel
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, esters, or prodrugs thereof:

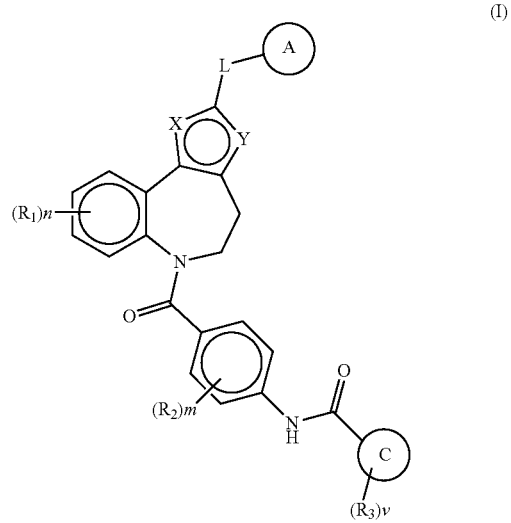

which inhibit Respiratory Syncytial Virus (RSV). The present invention further relates to pharmaceutical compositions comprising the aforementioned compounds for administration to a subject suffering from RSV infection. The invention also relates to methods of treating an RSV infection in a subject by administering a pharmaceutical composition comprising the compounds of the present invention.

19 Claims, No Drawings

(56) References Cited

U.S. PATENT DOCUMENTS

| | | |
|---|---|---|
| 2007/0293482 A1 | 12/2007 | Dowdell et al. |
| 2008/0139536 A1 | 6/2008 | Dowdell et al. |
| 2009/0274655 A1 | 11/2009 | Grimes et al. |
| 2010/0015063 A1 | 1/2010 | Carter et al. |
| 2012/0196846 A1 | 8/2012 | Mackman et al. |
| 2014/0038947 A1 | 2/2014 | Glick et al. |
| 2014/0100365 A1 | 4/2014 | Gavai et al. |
| 2015/0065504 A1 | 3/2015 | Wang et al. |
| 2015/0299210 A1 | 10/2015 | Bailey et al. |
| 2016/0244460 A1 | 8/2016 | Wang et al. |
| 2017/0022221 A1 | 1/2017 | Blaisdell et al. |
| 2017/0226127 A1 | 8/2017 | Estrada et al. |
| 2017/0226129 A1 | 8/2017 | Yu et al. |
| 2017/0305935 A1 | 10/2017 | Hunt et al. |
| 2017/0355717 A1 | 12/2017 | Hunt et al. |
| 2018/0193352 A1 | 7/2018 | Shook et al. |
| 2018/0237425 A1 | 8/2018 | Kim et al. |
| 2018/0258102 A1 | 9/2018 | Shook et al. |
| 2018/0354912 A1 | 12/2018 | Or et al. |
| 2019/0002478 A1 | 1/2019 | Kim et al. |
| 2019/0002479 A1 | 1/2019 | Kim et al. |
| 2019/0040084 A1 | 2/2019 | Yu et al. |
| 2019/0092791 A1 | 3/2019 | Hunt et al. |
| 2019/0152968 A1 | 5/2019 | Blaisdell et al. |
| 2019/0177283 A1 | 6/2019 | Hague |
| 2019/0192535 A1 | 6/2019 | Shook et al. |
| 2019/0315766 A1 | 10/2019 | Yu et al. |

FOREIGN PATENT DOCUMENTS

| | | | | |
|---|---|---|---|---|
| JP | 2004043456 A | * | 2/2004 | |
| WO | 9308175 A1 | | 4/1993 | |
| WO | 9426718 A1 | | 11/1994 | |
| WO | 2004026843 A1 | | 4/2004 | |
| WO | 2004106310 A1 | | 12/2004 | |
| WO | 2005042530 A1 | | 5/2005 | |
| WO | 2005089769 A1 | | 9/2005 | |
| WO | 2005090319 A1 | | 9/2005 | |
| WO | 2006081389 A1 | | 8/2006 | |
| WO | 2010103306 A1 | | 9/2010 | |
| WO | 2011005842 A1 | | 1/2011 | |
| WO | 2011151651 A1 | | 12/2011 | |
| WO | 2012068622 A1 | | 5/2012 | |
| WO | 2012080446 A1 | | 6/2012 | |
| WO | 2012080447 A1 | | 6/2012 | |
| WO | 2012080449 A1 | | 6/2012 | |
| WO | 2012080450 A1 | | 6/2012 | |
| WO | 2012080451 A1 | | 6/2012 | |
| WO | 2013096681 A1 | | 6/2013 | |
| WO | 2013186332 A1 | | 12/2013 | |
| WO | 2013186334 A1 | | 12/2013 | |
| WO | 2014031784 A1 | | 2/2014 | |
| WO | 2014047369 A1 | | 3/2014 | |
| WO | 2014060411 A1 | | 4/2014 | |
| WO | 2014125444 A1 | | 8/2014 | |
| WO | 2014184350 A1 | | 11/2014 | |
| WO | 2015026792 A1 | | 2/2015 | |
| WO | 2015110446 A1 | | 7/2015 | |
| WO | 2016022464 A1 | | 2/2016 | |
| WO | 2016055791 A1 | | 4/2016 | |
| WO | 2016055792 A1 | | 4/2016 | |
| WO | WO-2016055792 A1 | * | 4/2016 | ............... A61P 29/00 |
| WO | 2016097761 A1 | | 6/2016 | |
| WO | 2016138158 A1 | | 9/2016 | |
| WO | 2016166546 A1 | | 10/2016 | |
| WO | 2017015449 A1 | | 1/2017 | |
| WO | 2017123884 A1 | | 7/2017 | |
| WO | 2017175000 A1 | | 10/2017 | |

OTHER PUBLICATIONS

STN Registry database entry: CAS RN 1350148-32-1 (Entered STN: Dec. 7, 2011) (Year: 2011).*

STN Registry database entry: CAS RN 1349533-81-8 (Entered STN: Dec. 6, 2011). (Year: 2011).*

STN Registry database entry: CAS RN 1348849-53-5 (Entered STN: Dec. 5, 2011). (Year: 2011).*

STN Registry database entry: CAS RN 1349749-23-0 (Entered STN: Dec. 6, 2011). (Year: 2011).*

STN Registry database entry: CAS RN 1348594-72-8 (Entered STN: Dec. 4, 2011) (Year: 2011).*

STN Registry database entry: CAS RN 1349463-13-3 (Entered STN: Dec. 6, 2011). (Year: 2011).*

STN Registry database entry: CAS RN 1348924-24-2 (Entered STN: Dec. 5, 2011). (Year: 2011).*

Contreras-Romo et al., "Exploring the ligand recognition properties of the human vasopressin V1a receptor using QSAR and molecular modeling studies", Chem. Biol. Drug. Des. 2014; 83: pp. 207-223. (Year: 2014).*

Translation of Japanese Patent Publication: JP-2004043456-A. (Year: 2004).*

PUBCHEM-CID: 10595203, p. 3, Fig, Oct. 25, 2006, 1-9.

Albright, et al., (Document No. 129:54301) retrieved from STN; entered in STN on Jun. 17, 1998.

Albright, et al., (Document No. 130:153583) retrieved from STN; entered in STN on Feb. 16, 1999.

Andrzej, et al., (Document No. 144:274313) retrieved from STN; entered in STN on Mar. 3, 2006.

Carter, M. C. et al., "1,4-Benzodiazepines as Inhibitors of Respiratory Syncytial Virus", Journal of Medicinal Chemistry, vol. 49, Mar. 9, 2006, 2311-2319.

Fordyce, et al., "Discovery of novel benzothienoazepine derivatives as potent inhibitors of respiratory syncytial virus", Bioorganic & Medicinal Chemistry Letters, 27, 2017, 2201-2206.

Heeney, et al., (Document No. 153:359062) retrieved from STN; entered in STN on Sep. 2, 2010.

Henderson, E. A. et al., "1,4-Benzodiazepines as Inhibitors of Respiratory Syncytial Virus. The Identification of a Clinical Candidate", Journal of Medicinal Chemistry, vol. 50, Mar. 7, 2007, 1685-1692.

Lee, et al., (Document No. 140:69941) retrieved from STN; entered in STN on Jul. 8, 2003.

Mayo Clinic Staff, Respiratory syncytial virus (RSV) [online], retrieved from internet on Jun. 25, 2017.; URL http://www.mayoclinic.org/diseases-condiitons/respiratory-syncytial-virus/basics/prevention.

Offel, M. et al., "Synthesis of Substituted 3-Anilino-5-phenyl-1,3-dihydro-2H-I, 4-benzodiazepine-2-ones and their Evaluation as Cholecystokinin-Ligands", Archiv Der Pharmazie, vol. 339, No. 4, Apr. 1, 2006, 163-173.

Peesapati, et al., (Document No. 120:244848) retrieved from STN; entered in STN on May 14, 1994.

Wang, et al., (Document No. 160:385666) retrieved from STN; entered in STN on Feb. 27, 2014.

Xiong, et al., (Document No. 160:101182) retrieved from STN; entered in STN on Nov. 12, 2013.

Xiong, H., "Discovery of a Potent Respiratory Syncytial Virus RNA Polymerase Inhibitor", Bioorganic & Medicinal Chemistry Letters, 23, 2013, 6789-6793.

Zheng, et al., (Document No. 161:399872) retrieved from STN; entered in STN on Jul. 23, 2014.

Aquino, Christopher J. et al., "Discovery of 1,5-Benzodiazepines with Peripheral Cholecystokinin (CCK-A) Receptor Agonist Activity. 1. Optimization of the Agonist "Trigger—, J. Med. Chem. 1996, 39, 1996, 562-569.

Setoi, Hiroyuki et al., "Preparation of heterocyclylbenzamide derivatives as vasopressin antagonists", Document No. 131:116236, retrieved from STN; entered in STN on Aug. 6, 1999, Aug. 6, 1999.

Armstrong, et al., "An Efficient Asymmetric Synthesis of (R)-3-Amino-2,3,4,5-tetrahydro-1H-Nbenzazepine-2-one", Tetrahedron Letters, 35(20), 1994, 3239-3242.

Karmakar, et al., "Crystallization-Induced Dynamic Resolution toward the Synthesis of (S)-7-Amino-5H,7H-dibenzo[b,d]-azepin-6-one: An Important Scaffold for γ-Secretase Inhibitors", Organic Process Research & Development, 20, 2016, 1717-1720.

(56) References Cited

OTHER PUBLICATIONS

Olszewska, Wieslawa et al., "Emerging drugs for respiratory syncytial virus infection", Expert Opin. Emerg. Drugs (2009), 14(2), 207-217.
Perron, Michel et al., "GS-5806 Inhibits a Broad Range of Respiratory Syncytial Virus Clinical Isolates by Blocking the Virus-Cell Fusion Process", Antimicrobial Agents and Chemotherapy, 2016, 60(3), 1264-1273.
Reider, et al., "Metalated Allylaminosilane: A New, Practical Reagent for Stereoselective a-Hydroxyallylation of Aldehydes to Erythro-1,2-diol Skeletons", J. Org. Chem, 52, 1987, 957.
Sudo, Kenji et al., "YM-53403, a unique anti-respiratory syncytial virus agent with a novel mechanism of action", Antiviral Research, 2005, vol. 65, 2005, 125-131.
Bond, S. et al., "1,2,3,9b-Tetrahydro-5H-imidazo[2,1-a]isoindol-5-ones as a new class of respiratory syncytial virus (RSV) fusion inhibitors. Part 2: Identification of BTA9881 as a preclinical candidate", Bioorg & Med Chem Lett, 25, 2015, 976-981.
Mackman, R. L. et al., "Discovery of an Oral Respiratory Syncytial Virus (RSV) Fusion Inhibitor (GS-5806) and Clinical Proof of Concept in a Human RSV Challenge Study", J. Med. Chem., 58, 2015, 1630-1643.
Wang, G. et al., "Discovery of 4'-Chloromethyl-2'-deoxy-3',5'-di-O-isobutyryl-2'-fluorocytidine (ALS-8176), A First-in-Class RSV Polymerase Inhibitor for Treatment of Human Respiratory Syncytial Virus Infection", J. Med. Chem., 58, 2015, 1862-1878.

\* cited by examiner

HETEROCYCLIC COMPOUNDS AS RSV INHIBITORS

RELATED APPLICATIONS

This application claims the benefit of U.S. Provisional Application No. 62/527,384, filed on Jun. 30, 2017. The entire teachings of the above application are incorporated herein by reference.

TECHNICAL FIELD

The present invention relates generally to compounds and pharmaceutical compositions useful as Respiratory Syncytial Virus (RSV) inhibitors.

BACKGROUND OF THE INVENTION

Human respiratory syncytial virus (HRSV) is a negative-sense, single stranded, RNA paramyxovirus (K M. Empey, et al., Rev. Anti-Infective Agents, 2010, 50 (1 May), 1258-1267). RSV is the leading cause of acute lower respiratory tract infections (ALRI) and affects patients of all ages. The symptoms in adults are usually not severe and are typically analogous to a mild cold. However, in infants and toddlers the virus can cause lower respiratory tract infections including bronchiolitis or pneumonia with many of them requiring hospitalization. Nearly all children have been infected by age 3. There are known high-risk groups that infection with RSV is more likely to progress into the ALRI. Premature infants and/or infants suffering from lung or cardiac disease are at the highest risk to develop ALRI. Additional high-risk groups include the elderly, adults with chronic heart and/or lung disease, stem cell transplant patients and the immuno-suppressed.

Currently, there is no vaccine available to prevent HRSV infection. Palivizumab is a monoclonal antibody that is used prophylactically to prevent HRSV infection in high risk infants, e.g. premature infants, and infants with cardiac and/or lung disease. The high cost of palivizumab treatment limits its use for general purposes. Ribavirin has also been used to treat HRSV infections but its effectiveness is limited. There is a major medical need for new and effective HRSV treatments that can be used generally by all population types and ages.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, WO 2016/055792, WO 2016/097761, and J. Med. Chem. 2015, 58, 1630-1643. Examples of other N-protein inhibitors for treatment of HRSV have been disclosed in the following publications: WO 2004/026843, J. Med. Chem. 2006, 49, 2311-2319, and J. Med. Chem. 2007, 50, 1685-1692. Examples of L-protein inhibitors for HRSV have been disclosed in the following publications: WO 2011/005842, WO 2005/042530, Antiviral Res. 2005, 65, 125-131, and Bioorg. Med. Chem. Lett. 2013, 23, 6789-6793, Bioorg. Med. Chem. Lett. 2017, 27, 2201-2206. Examples of nucleosides/polymerase inhibitors have been disclosed in the following publications: WO 2013/242525 and J. Med. Chem. 2015, 58, 1862-1878.

There is a need for the development of effective treatments for HRSV. The present invention has identified these novel compounds and their inhibitory activity against HRSV. The invention includes methods to prepare the compounds as well as methods of using these compounds to treat disease.

SUMMARY OF THE INVENTION

The present invention provides compounds represented by Formula (I), and pharmaceutically acceptable salts, esters and prodrugs thereof that can be used to treat or prevent viral (particularly HRSV) infection:

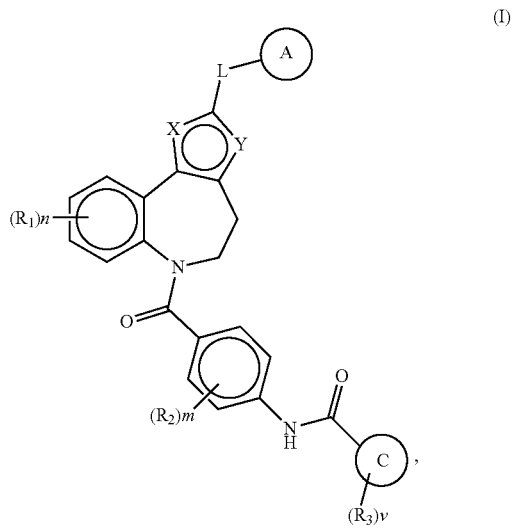

(I)

wherein:
Ⓐ is selected from the group consisting of:
1) optionally substituted aryl;
2) optionally substituted heteroaryl;
3) optionally substituted —$C_3$-$C_{12}$ cycloalkyl;
4) optionally substituted —$C_3$-$C_{12}$ cycloalkenyl;
5) optionally substituted 3- to 12-membered heterocycloalkyl;
6) optionally substituted arylalkyl;
7) optionally substituted heteroarylalkyl;
8) optionally substituted-$C_3$-$C_{12}$ cycloalkyl-$C_1$-$C_6$ alkyl;
9) optionally substituted-$C_3$-$C_{12}$ cycloalkenyl-$C_1$-$C_6$ alkyl;
10) optionally substituted 3- to 12-membered heterocycloalkyl-$C_1$-$C_6$ alkyl; and
11) optionally substituted —$C_1$-$C_8$ alkyl;
Ⓒ is aryl or heteroaryl, which, when possible, is optionally substituted with one or more substituents which are not $R_3$;
L is absent —CONH—, —NHCO—, —NHCO$_2$—, or —NHS(O)$_2$—;
One of X and Y is selected from O, S, and NR$_4$, and the other is N or CR$_5$;
Each $R_1$ and $R_2$ is independently selected from the group consisting of: halogen, cyano, nitro, hydroxyl, protected hydroxyl, amino, protected amino, optionally substituted —$C_1$-$C_8$ alkyl, and optionally substituted —$C_1$-$C_8$ alkoxy;
Each $R_3$ is selected from the group consisting of:
1) halogen;
2) optionally substituted —$C_1$-$C_8$ alkoxy;
3) optionally substituted —$C_1$-$C_8$ alkyl;
4) optionally substituted —$C_2$-$C_8$ alkenyl;

5) optionally substituted —$C_2$-$C_8$ alkynyl;
6) optionally substituted —$C_3$-$C_{12}$ cycloalkyl;
7) optionally substituted —$C_3$-$C_{12}$ cycloalkenyl;
8) optionally substituted 3- to 12-membered heterocycloalkyl;
9) optionally substituted aryl;
10) optionally substituted heteroaryl;
11) optionally substituted arylalkyl;
12) optionally substituted aryloxy;
13) —$C(O)R_{12}$;
14) —$C(O)NR_{13}R_{14}$;
15) —$C(O)NR_{11}S(O)_2R_{12}$;
16) —$S(O)_2NR_{13}R_{14}$;
17) —$NR_{13}R_{14}$;
18) —$NR_{11}S(O)_2R_{12}$;
19) —$NR_{11}C(O)R_{12}$;
20) —$NR_{11}C(O)NR_{13}R_{14}$; and
21) —$NR_{11}C(O)NHS(O)_2R_{12}$;

n is 0, 1, 2, 3 or 4;
m is 0, 1, 2, 3 or 4;
v is 0, 1, 2, or 3;
$R_4$ is hydrogen or optionally substituted —$C_1$-$C_8$ alkyl;
$R_5$ is hydrogen, halogen, optionally substituted —$C_1$-$C_8$ alkyl, or optionally substituted —$C_1$-$C_8$ alkoxy;
$R_{12}$ at each occurrence is independently selected from the group consisting of:
1) Hydrogen;
2) Halogen;
3) Hydroxyl;
4) optionally substituted —$C_1$-$C_8$ alkoxy;
5) optionally substituted —$C_1$-$C_8$ alkyl;
6) optionally substituted —$C_2$-$C_8$ alkenyl;
7) optionally substituted —$C_2$-$C_8$ alkynyl;
8) optionally substituted —$C_3$-$C_8$ cycloalkyl;
9) optionally substituted —$C_3$-$C_8$ cycloalkenyl;
10) optionally substituted 3- to 8-membered heterocycloalkyl;
11) optionally substituted aryl;
12) optionally substituted arylalkyl;
13) optionally substituted heteroaryl; and
14) optionally substituted heteroarylalkyl;

$R_{11}$, $R_{13}$ and $R_{14}$ are each independently selected from hydrogen, optionally substituted —$C_1$-$C_8$-alkyl, optionally substituted —$C_2$-$C_8$-alkenyl, optionally substituted —$C_2$-$C_8$-alkynyl; optionally substituted —$C_3$-$C_8$-cycloalkyl, optionally substituted 3- to 8-membered heterocyclic, optionally substituted aryl, optionally substituted arylalkyl, optionally substituted heteroaryl, and optionally substituted heteroarylalkyl; alternatively, $R_{13}$ and $R_{14}$ are taken together with the nitrogen atom to which they are attached to form an optionally substituted heterocyclic ring.

Each preferred group stated above can be taken in combination with one, any or all other preferred groups.

DETAILED DESCRIPTION OF THE INVENTION

In one embodiment the present invention provides a compound represented by Formula (I) as described above, or a pharmaceutically acceptable salt, ester or prodrug thereof.

In certain embodiments, the present invention relates to compounds of Formula (I), and pharmaceutically acceptable salts, esters and prodrugs thereof, wherein Ⓐ is optionally substituted aryl; preferably Ⓐ is optionally substituted phenyl. The optional substituents are preferably independently selected from, but not limited to, halogen, —CN, —OH, —$NH_2$, —$NO_2$, —$CH_3$, —$CF_3$, —$OCH_3$, —$OCF_3$, —$SO_2CH_3$, —$CH_2N(CH_3)_2$, and —$C(O)CH_3$. In preferred embodiments, there are 0 to 2 substituents and, more preferably, 0 or 1 substituent.

In certain embodiments, the present invention relates to compounds of Formula (I), and pharmaceutically acceptable salts, esters and prodrugs thereof, wherein Ⓐ is optionally substituted heteroaryl; preferably optionally substituted fused bicyclic heteroaryl. When present the substituent or substituents are preferably independently selected from halogen, —CN, —OH, —$NH_2$, —$NO_2$, —$CH_3$, —$CF_3$, —$OCH_3$, —$OCF_3$, —$SO_2CH_3$, —$CH_2N(CH_3)_2$, and —$C(O)CH_3$. In preferred embodiments, there are 0 to 2 substituents and, more preferably, 0 or 1 substituent.

In one embodiment, the present invention relates to compounds of Formula (I), and pharmaceutically acceptable salts, esters and prodrugs thereof, wherein Ⓐ is derived from one of the following by removal of a hydrogen atom:

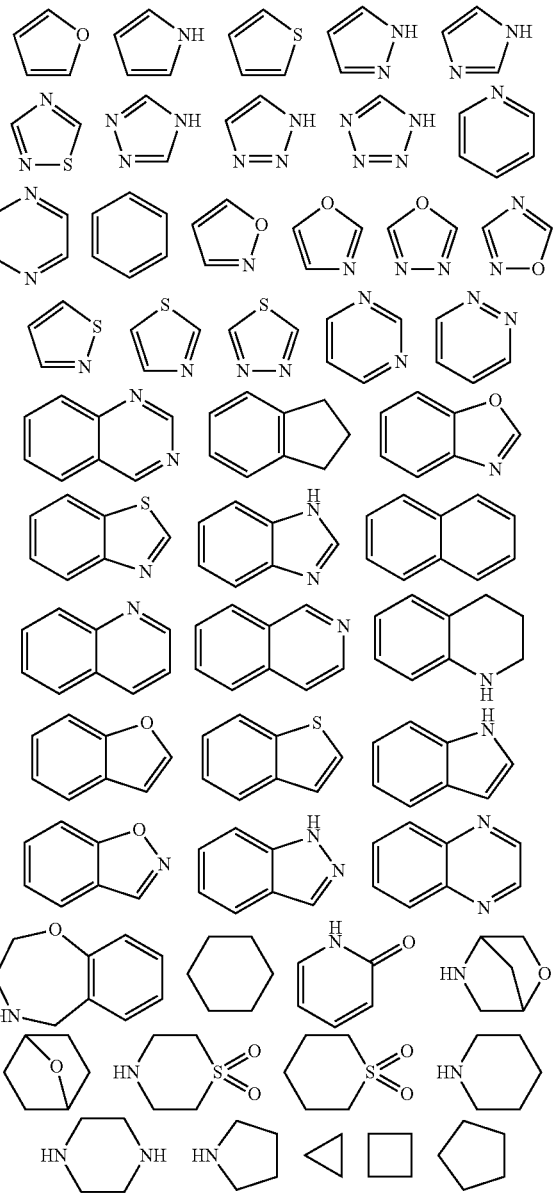

-continued

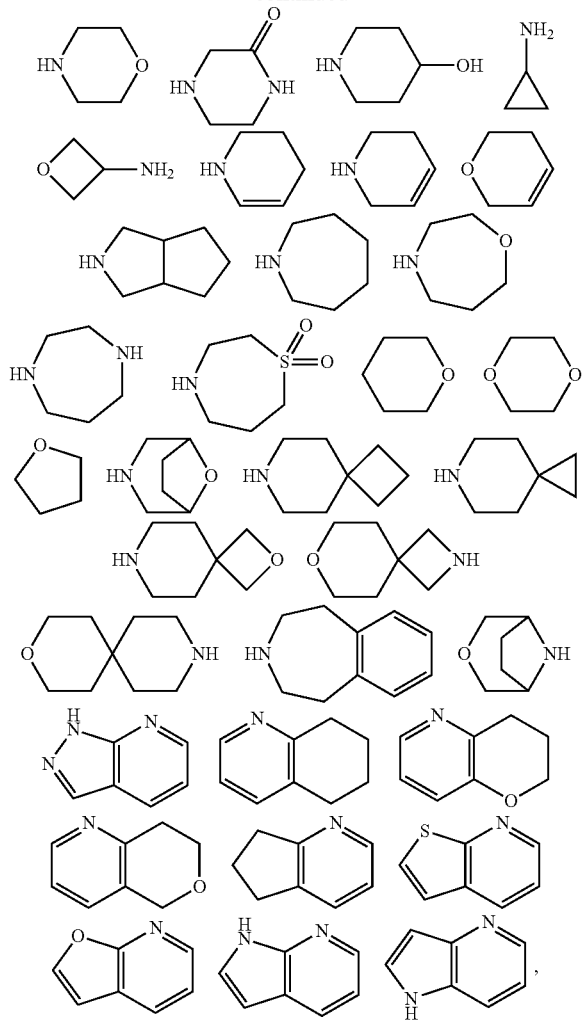

wherein each of the above is optionally substituted when possible. When Ⓐ is a 5/6 fused bicyclic heteroaryl, it is preferably attached to L via an available atom in the 5-membered ring. Preferably, when present, the substituents are independently selected from, but not limited to, —CN, —F, —CH₃, —CF₃, —OCH₃, and —OCF₃.

In one embodiment, the present invention relates to compounds of Formula (I), and pharmaceutically acceptable salts, esters and prodrugs thereof, wherein Ⓐ is one of the following:

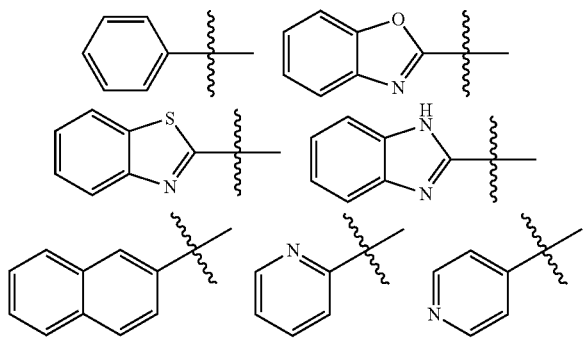

-continued

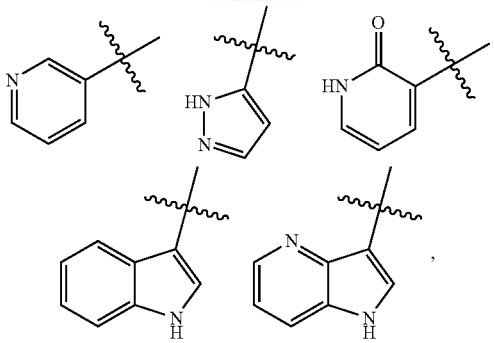

wherein each of the above is optionally substituted. Preferably, when present, the substituents are independently selected from, but not limited to, —F, —Cl, —CH₃, —CF₃, —OCH₃, and —OCF₃.

In certain embodiments, the present invention relates to compounds of Formula (I), and pharmaceutically acceptable salts, esters and prodrugs thereof, wherein Ⓒ is heteroaryl, preferably Ⓒ is pyridinyl or fused bicyclic heteroaryl, each of which is optionally substituted with one or more substituents in addition to any R₃ groups. When present, preferably these substituents, are independently selected from, but not limited to, —CN, —OH, —NH₂, —NO₂, —SO₂CH₃, and —CH₂N(CH₃)₂.

In certain embodiments, the present invention relates to compounds of Formula (I), and pharmaceutically acceptable salts, esters and prodrugs thereof, wherein Ⓒ is optionally substituted bicyclic aryl, or bicyclic heteroaryl.

In one embodiment, the present invention relates to compounds of Formula (I), and pharmaceutically acceptable salts, esters and prodrugs thereof, wherein Ⓒ is derived from one of the following by removal of a hydrogen atom:

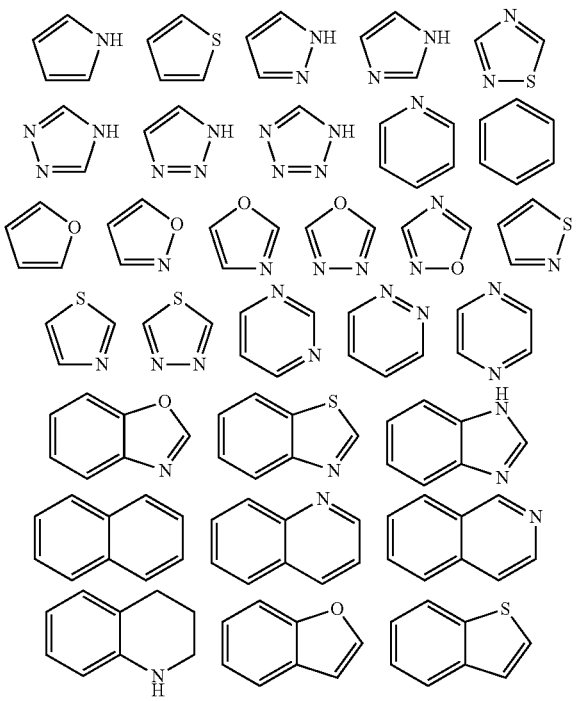

-continued
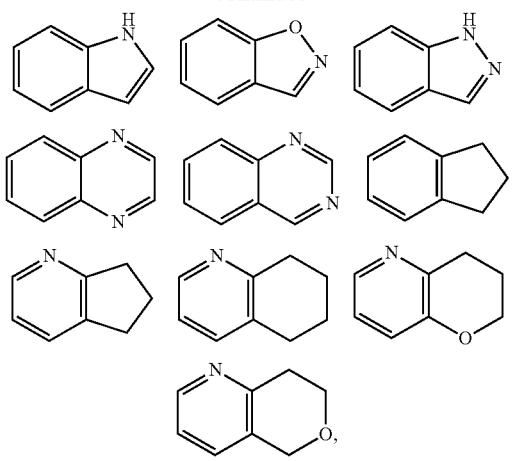
wherein each of the above is, in addition to any R₃ groups present, optionally further substituted with one or more substituents which are not R₃.
In one embodiment, the present invention relates to compounds of Formula (I), and pharmaceutically acceptable salts, esters and prodrugs thereof, wherein Ⓒ is one of the following:
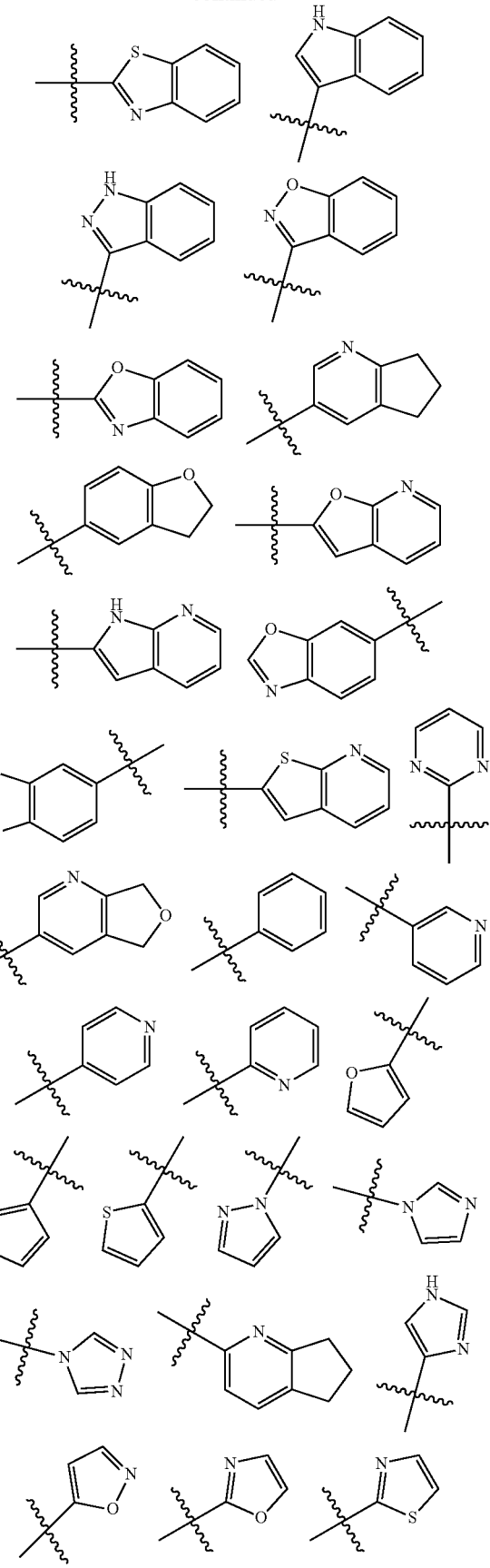

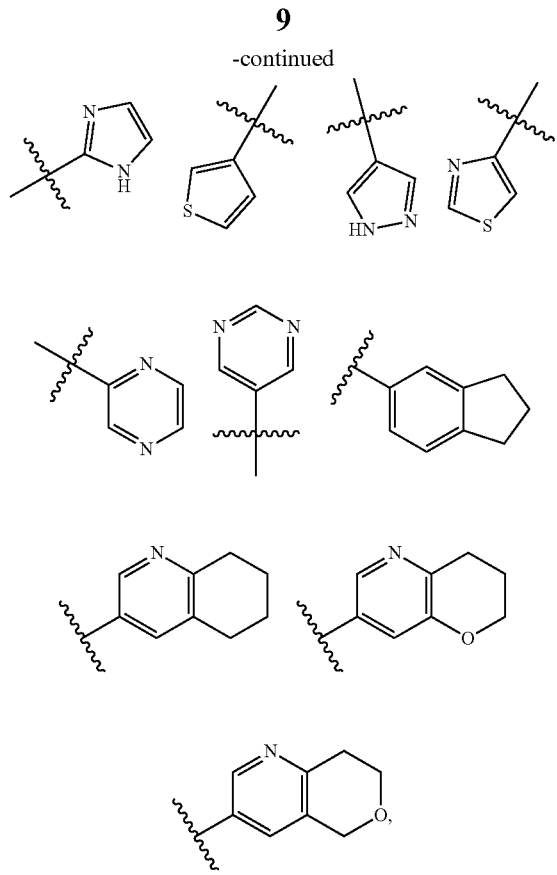

wherein each of the above is, in addition to any $R_3$ groups present, optionally further substituted with one or more substituents which are not $R_3$.

In certain embodiments,

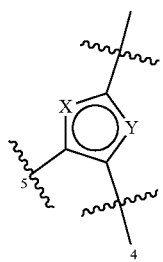

is selected from the groups below, where "4" and "5" indicate respectively the point of attachment to the 4- and 5-positions of the benzoazepine ring system:

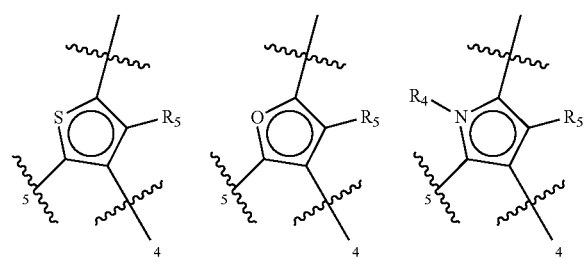

wherein $R_4$ and $R_5$ are previously defined, preferably, $R_4$ is hydrogen; $R_5$ is hydrogen or halogen.

In certain embodiments, the present invention relates to compounds of Formula (I), and pharmaceutically acceptable salts, esters and prodrugs thereof, wherein n is 0, 1, 2 or 3, and, when n is 1, 2, or 3, each $R_1$ is independently halogen or optionally substituted $—C_1-C_8$ alkyl. Preferably each $R_1$ is independently —Cl, —F, —CH$_3$, or —CF$_3$; and n is 1, 2, or 3.

In certain embodiments, the present invention relates to compounds of Formula (I), and pharmaceutically acceptable salts, esters and prodrugs thereof, wherein m is 0, 1 or 2, and, when m is 1 or 2, each $R_2$ is independently halogen or optionally substituted $—C_1-C_8$ alkyl. Preferably m is 1 and $R_2$ is —F, —Cl, —CH$_3$, or —CF$_3$.

In certain embodiments, the present invention relates to compounds of Formula (I), and pharmaceutically acceptable salts, esters and prodrugs thereof, wherein each $R_1$ is —Cl, —F, —CH$_3$, or —CF$_3$; n is 1 or 2; and m is 0.

In certain embodiments, the present invention relates to compounds of Formula (I), and pharmaceutically acceptable salts, esters and prodrugs thereof, wherein one $R_3$ is optionally substituted aryl or optionally substituted heteroaryl.

In certain embodiments, the present invention relates to compounds of Formula (I), and pharmaceutically acceptable salts, esters and prodrugs thereof, wherein one $R_3$ is optionally substituted 3- to 12-membered heterocycloalkyl, preferably optionally substituted 3- to 12-membered spiro bicyclic heterocycloalkyl.

In certain embodiments, the present invention relates to compounds of Formula (I), and pharmaceutically acceptable salts, esters and prodrugs thereof, wherein one $R_3$ is —NR$_{13}$R$_{14}$, wherein R$_{13}$ and R$_{14}$ are previously defined.

In certain embodiments, the present invention relates to compounds of Formula (I), and pharmaceutically acceptable salts, esters and prodrugs thereof, wherein one $R_3$ is —$NR_{13}R_{14}$, wherein $R_{13}$ and $R_{14}$ are taken together with the nitrogen atom to which they are attached to form an optionally substituted 3- to 10- or 3- to 12-membered heterocyclic, preferably the said heterocyclic is spiro heterocyclic.

In one embodiment, the present invention relates to compounds of Formula (I), or a pharmaceutically acceptable salt thereof, v is not 0 and one $R_3$ is derived from one of the groups below by removal of one hydrogen atom, wherein each of these groups is optionally substituted:

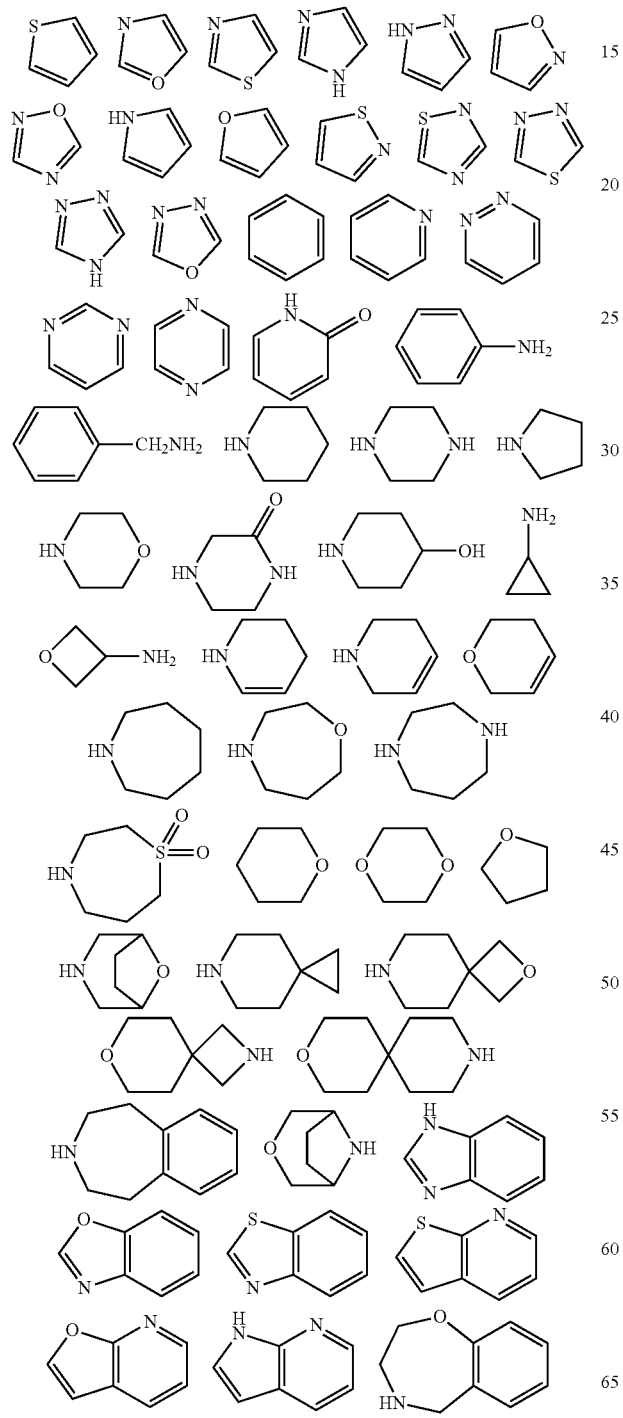

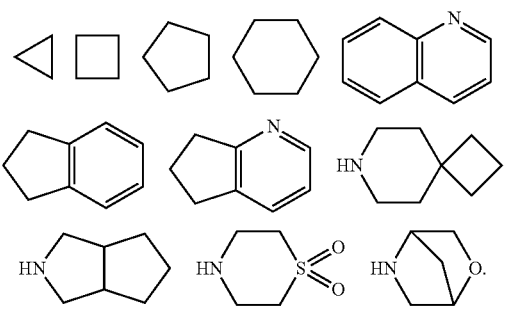

In one embodiment, the present invention relates to compounds of Formula (I), or a pharmaceutically acceptable salt thereof, wherein v is not 0 and one $R_3$ is selected from the groups shown below, each of which can be optionally substituted:

-continued
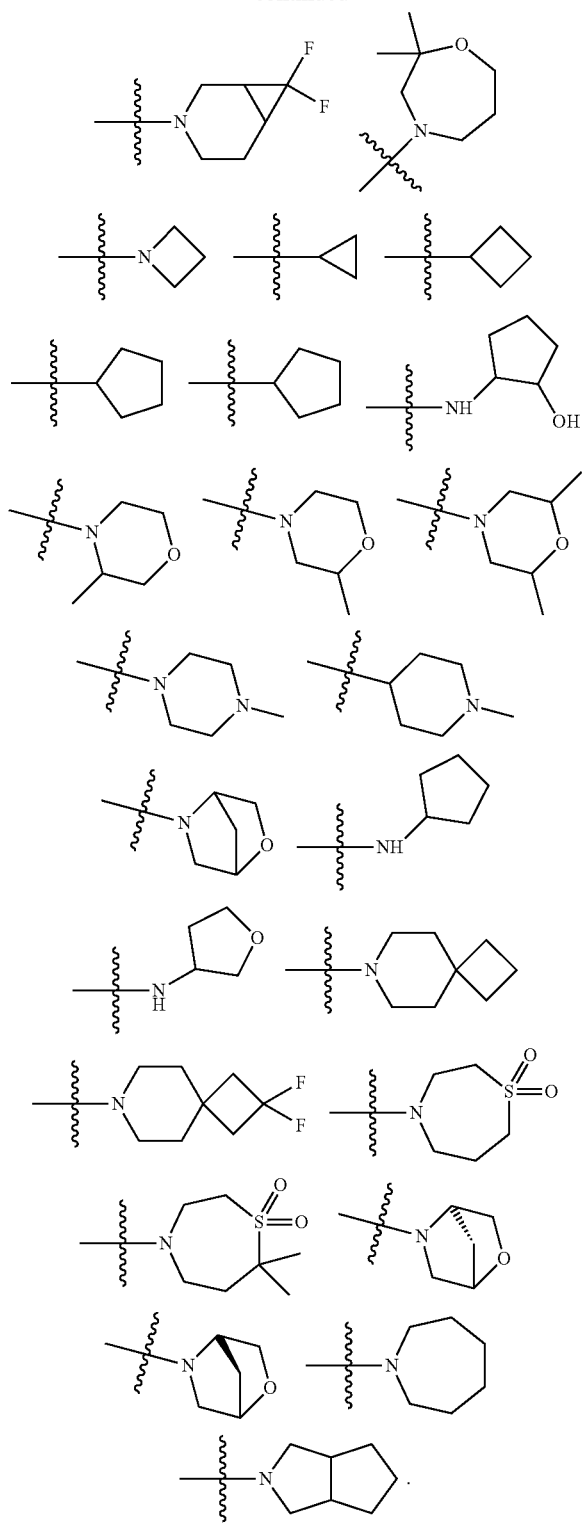
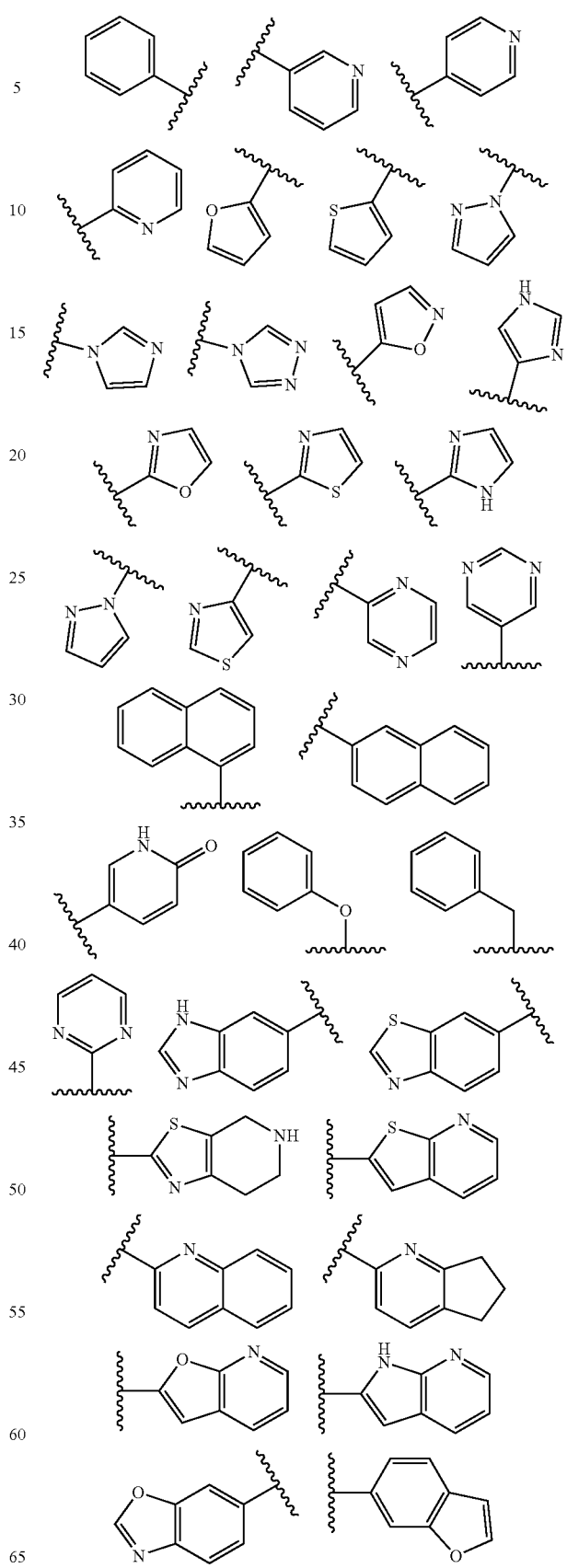
In one embodiment, the present invention relates to compounds of Formula (I), or a pharmaceutically acceptable salt thereof, wherein v is not 0 and one $R_3$ is selected from the groups shown below, each of which can be optionally substituted:

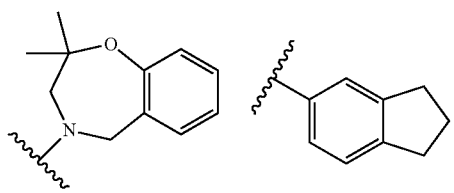
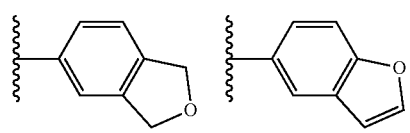
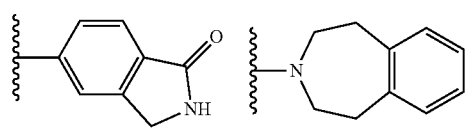
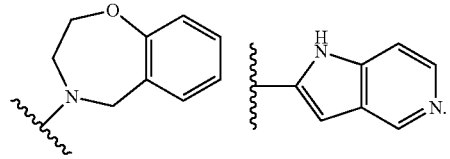
In certain embodiments, v is 0 to 3, 0 to 2, 1 or 0. More preferably, v is 1 or 2.
In another embodiment, the invention provides a compound represented by Formula (IIa)~(IIe) or a pharmaceutically acceptable salt, ester or prodrug thereof:
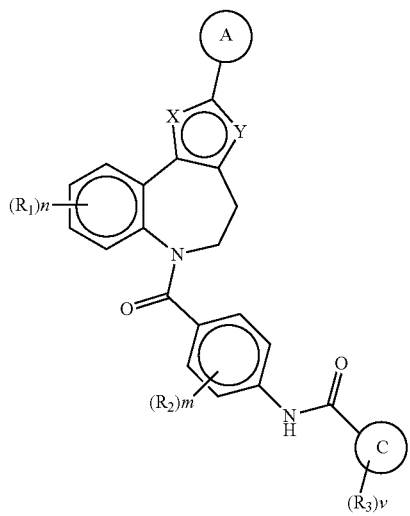
(IIb)
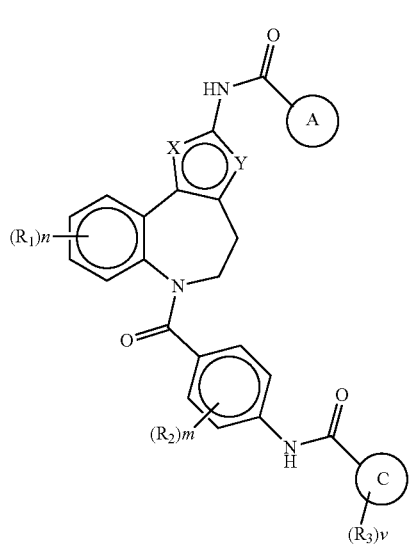
(IIc)
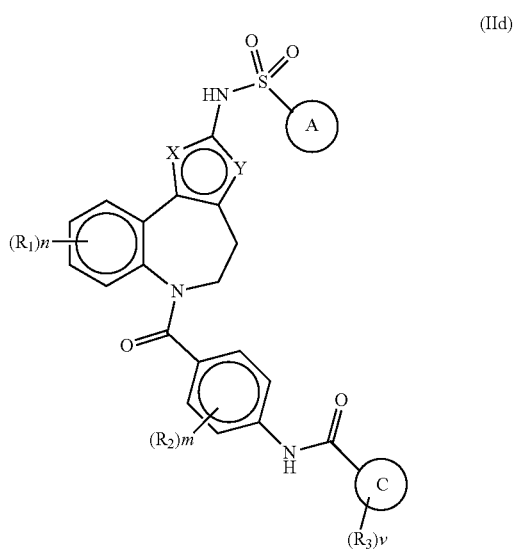
(IIa)
(IId)

(IIe)

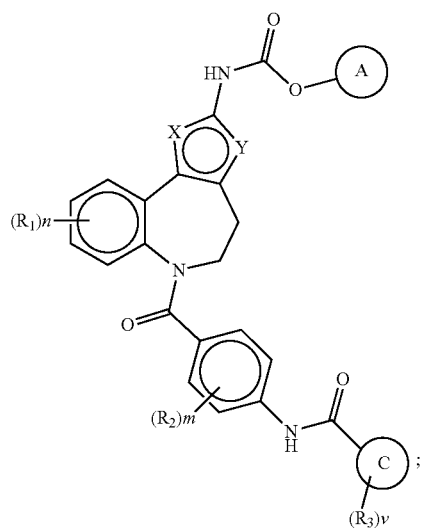

(IIa-2)

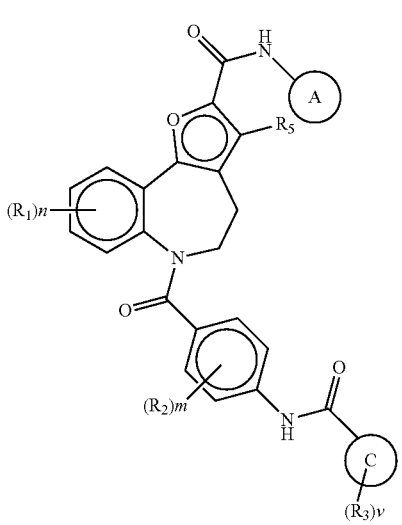

(IIa-3)

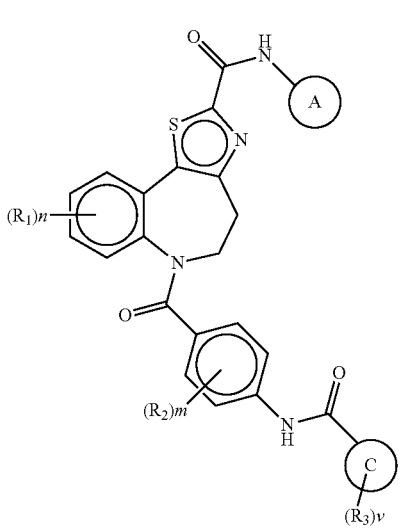

wherein Ⓐ, Ⓒ, X, Y, $R_1$, $R_2$, $R_3$, n, m, and v are as previously defined,

In another embodiment, invention provides a compound represented by Formula (IIa)~(IIe), or a pharmaceutically acceptable salt, ester or prodrug thereof, wherein each $R_1$ is halogen and n is 1, 2 or 3; preferably, each $R_1$ is —F, and n is 1 or 2.

In another embodiment, the invention provides a compound represented by one of Formulas (IIa-1)~(IIa-4), (IIb-1)~(IIb-4), or (IIc-1)~(IIc-4), or a pharmaceutically acceptable salt, ester or prodrug thereof:

(IIa-1)

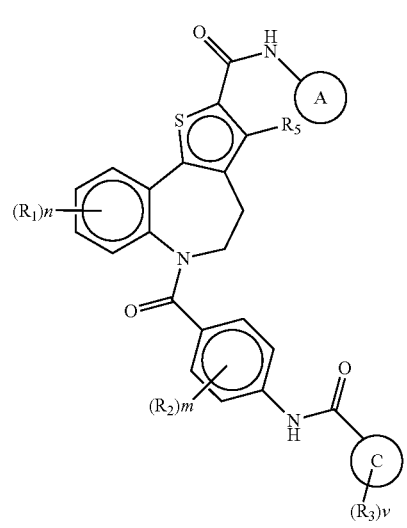

(IIa-4)

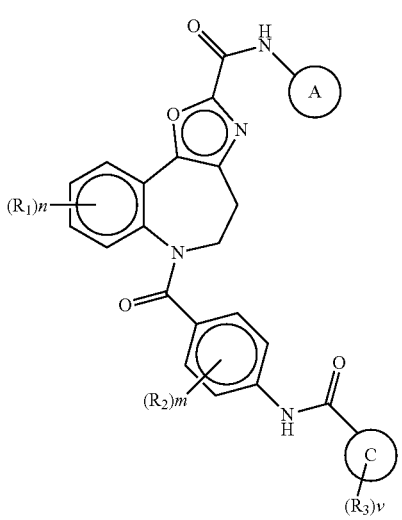

-continued (IIb-1)

(IIb-2)

(IIb-3)

(IIb-4)

(IIc-1)

(IIc-2)

-continued
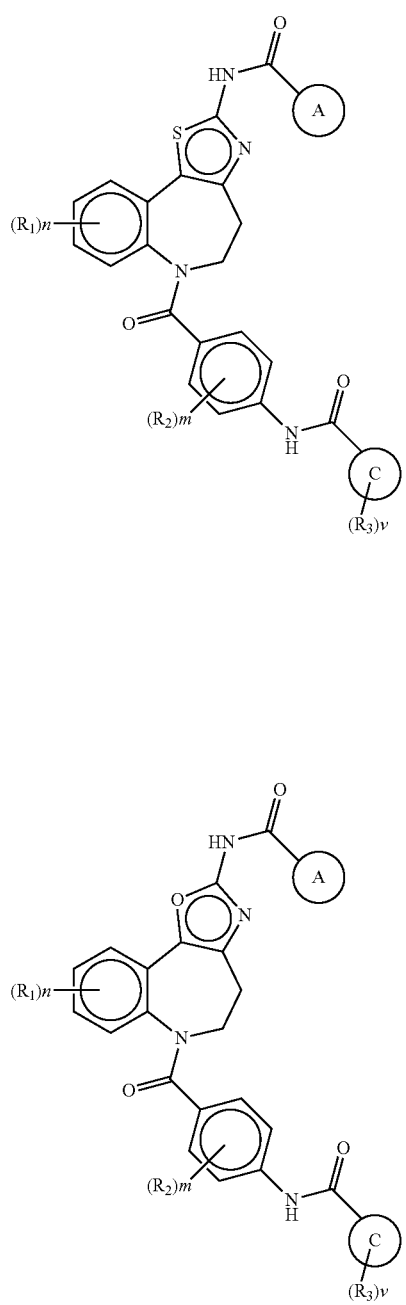
(IIc-3)
(IIc-4)
wherein Ⓐ, Ⓒ, $R_1$, $R_2$, $R_3$, $R_5$, n, m, and v are as previously defined. Preferably $R_5$ is hydrogen or —F.
In another embodiment, the invention provides a compound represented by one of Formulae (IIIa)~(IIId), or a pharmaceutically acceptable salt, ester or prodrug thereof:
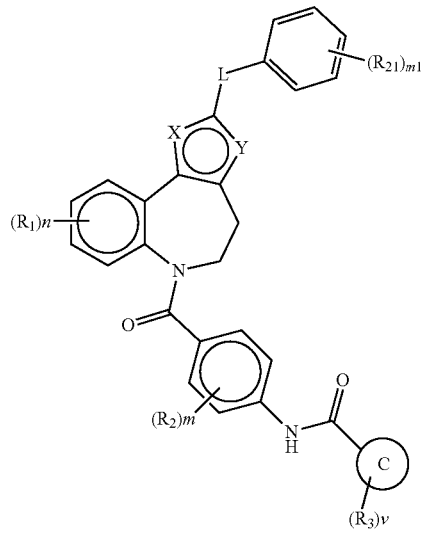
(IIIa)
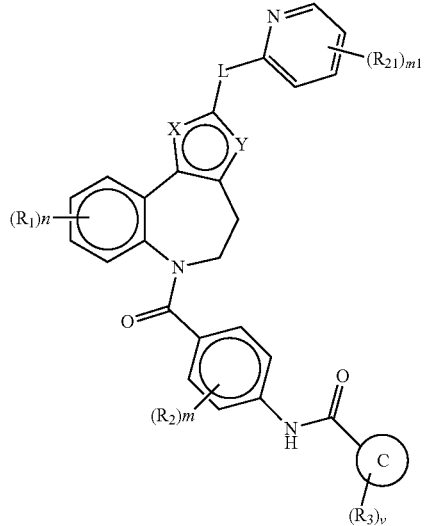
(IIIb)
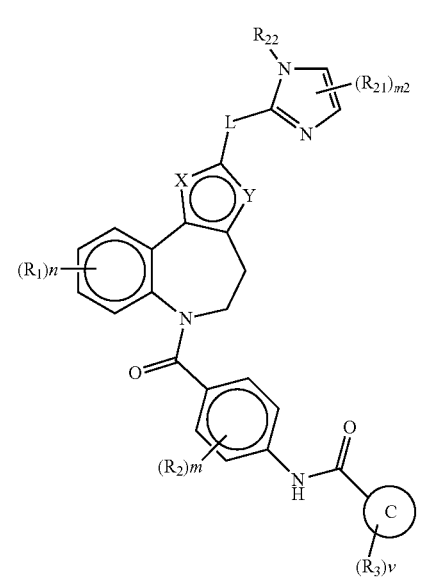
(IIIc)

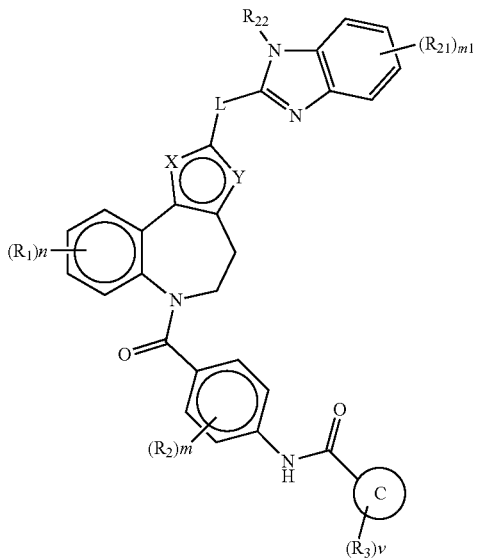

(IIId)

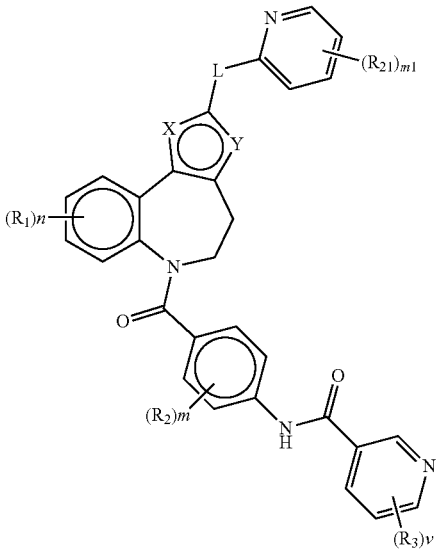

(IIIb-1)

wherein ⓒ, X, Y, L, R$_1$, R$_2$, R$_3$, n, m, and v are as previously defined; m1 is 0, 1, 2, 3 or 4; m2 is 0, 1 or 2; each R$_{22}$ is independently selected from hydrogen and —CH$_3$; and each R$_{21}$ is independently selected from halogen, —NH$_2$, optionally substituted —C$_1$-C$_3$ alkyl, and optionally substituted —C$_1$-C$_3$ alkoxy. Preferably each R$_{21}$ is independently selected from —F, —Cl, —NH$_2$, and optionally substituted —CH$_3$.

In another embodiment of the invention is a compound represented by one of Formulae (IIIa)~(IIId), or a pharmaceutically acceptable salt, ester or prodrug thereof, wherein R$_1$ is halogen, n is 1, 2 or 3; preferably R$_1$ is —F and n is 1 or 2.

In another embodiment, the invention provides a compound represented by one of Formulae (IIIa-1)~(IIId-1), or (IIIa-2)~(IIId-2), or a pharmaceutically acceptable salt, ester or prodrug thereof:

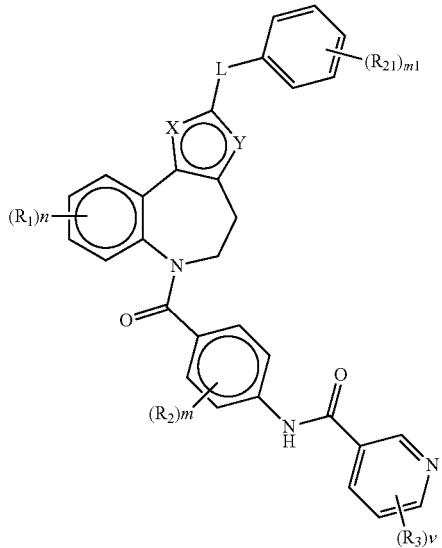

(IIIa-1)

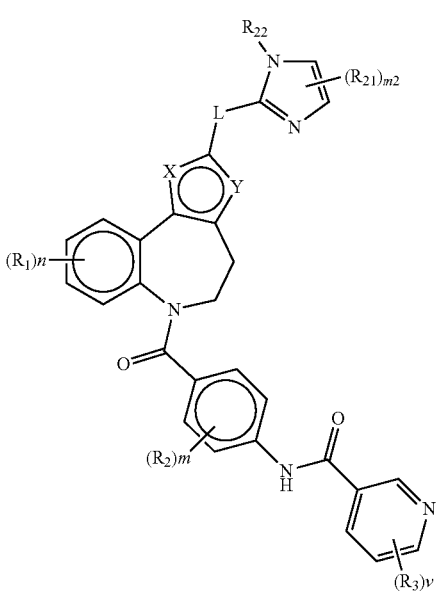

(IIIc-1)

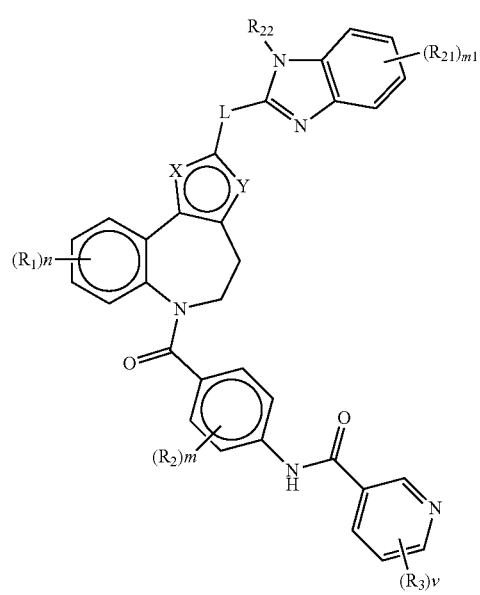
(IIId-1)
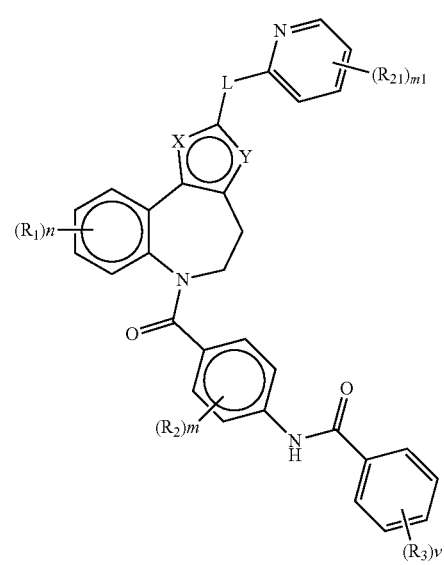
(IIIb-2)
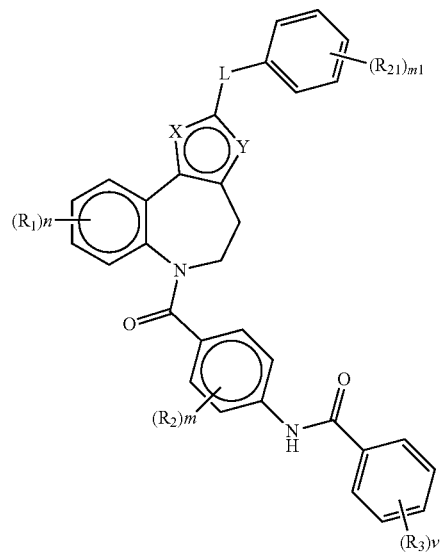
(IIIa-2)
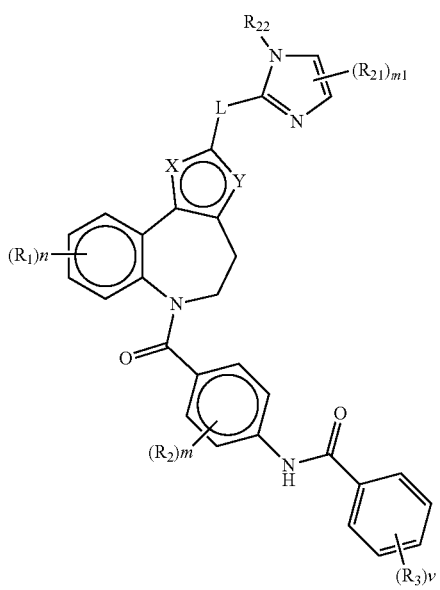
(IIIc-2)

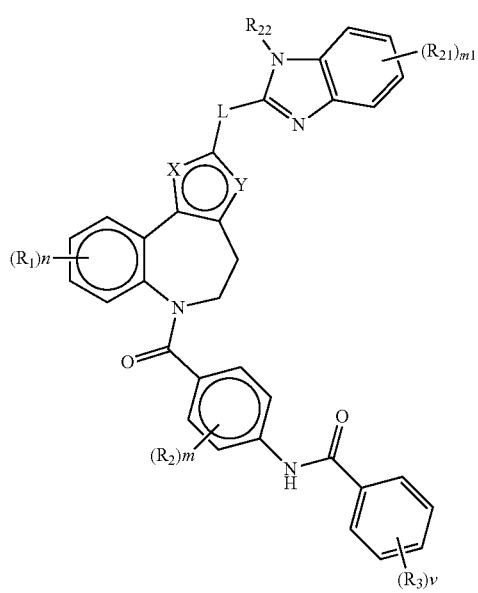

(IIId-2)

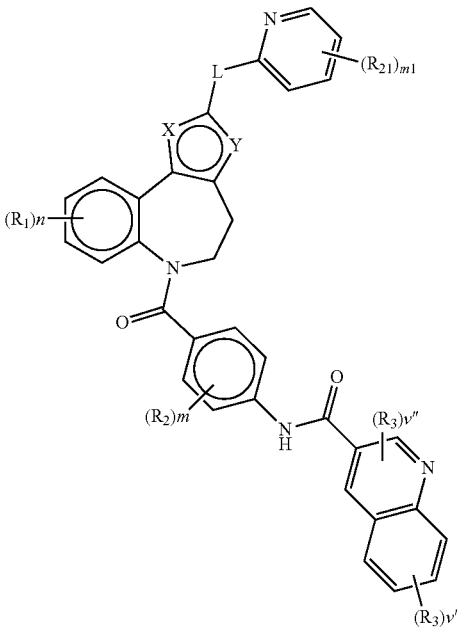

(IIIb-3)

wherein X, Y, L, $R_1$, $R_2$, $R_3$, $R_{21}$, $R_{22}$, m1, m2, n, m, and v are as previously defined. Preferably each $R_{21}$ is independently selected from —F, —Cl, —NH$_2$, and optionally substituted —CH$_3$; more preferably each $R_1$ is halogen; n is 1, 2 or 3; and each $R_{21}$ is independently selected from —F, —Cl, —NH$_2$, and optionally substituted —CH$_3$.

In another embodiment, the invention provides a compound represented by one of Formulae (IIIa-3)~(IIId-3), and (IIIa-4)~(IIId-4), or a pharmaceutically acceptable salt, ester or prodrug thereof:

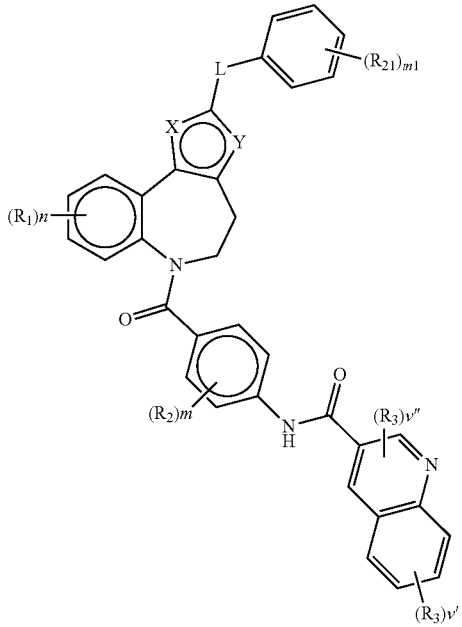

(IIIa-3)

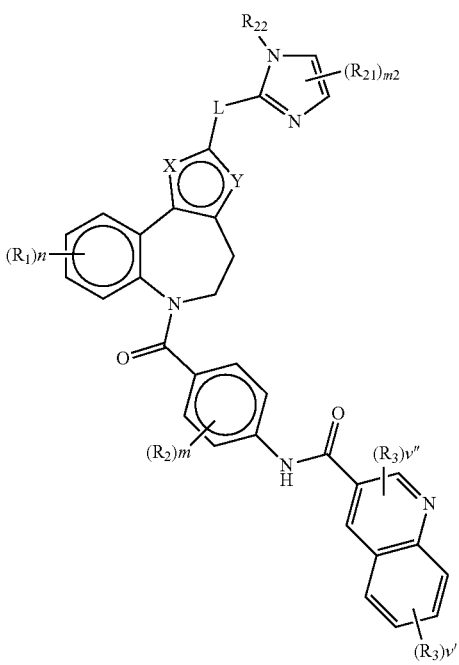

(IIIc-3)

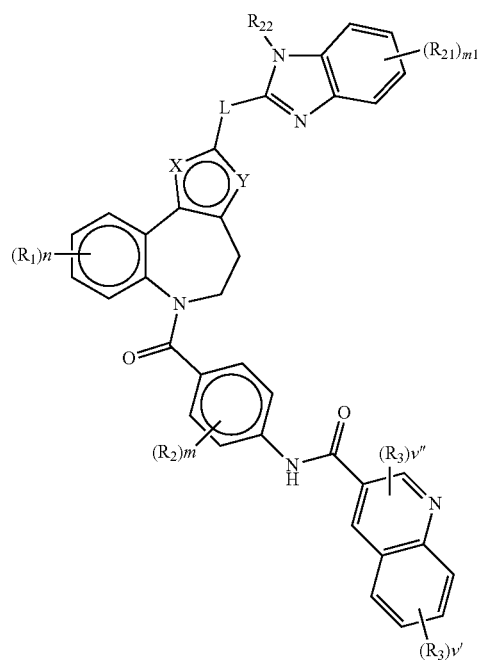
(IIId-3)
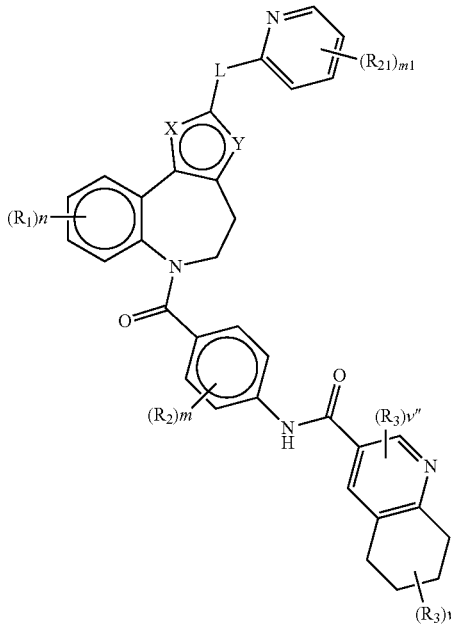
(IIIb-4)
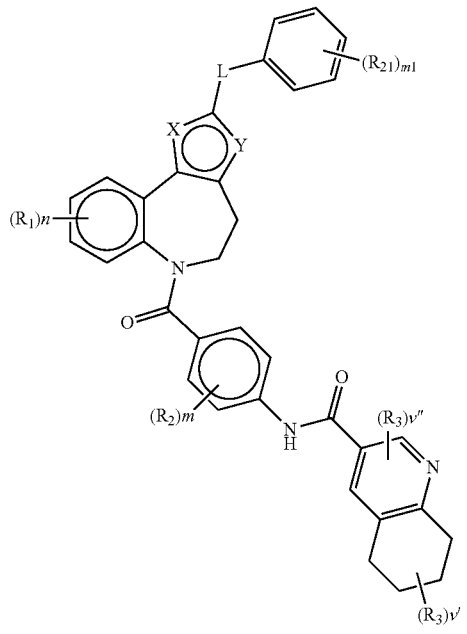
(IIIa-4)
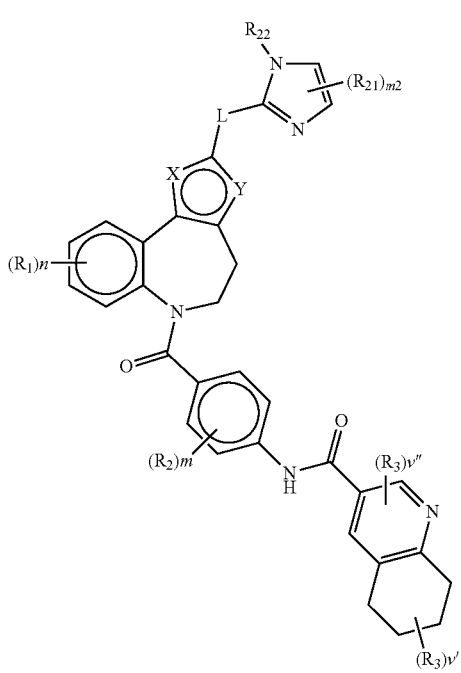
(IIIc-4)

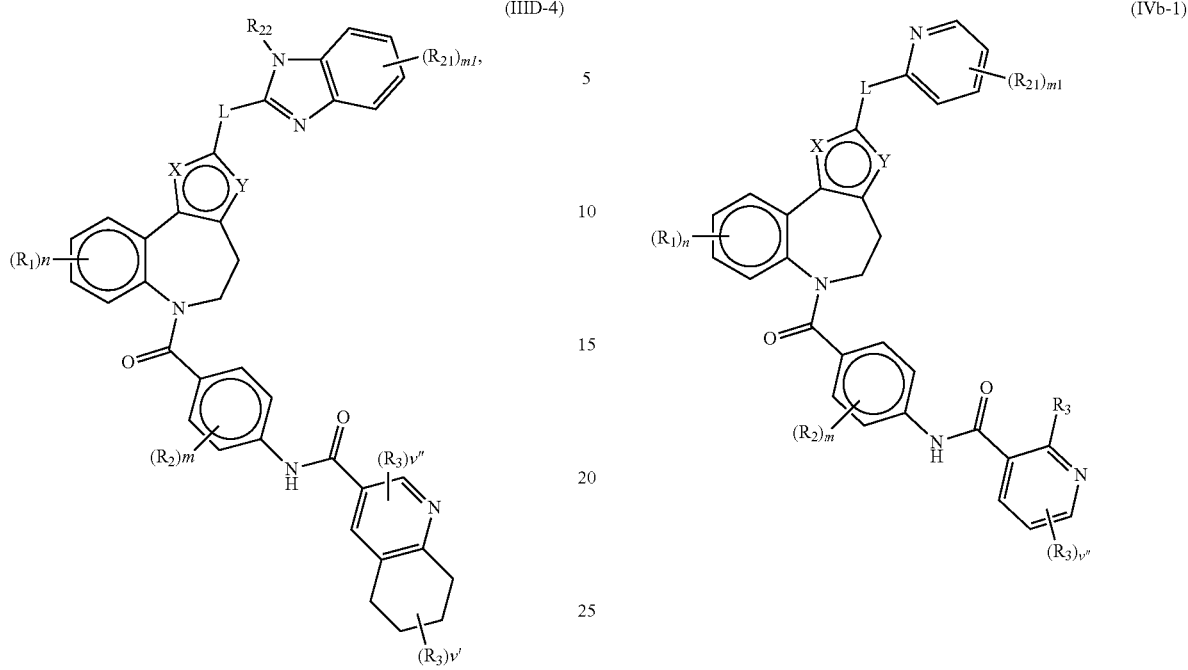

(IIID-4)

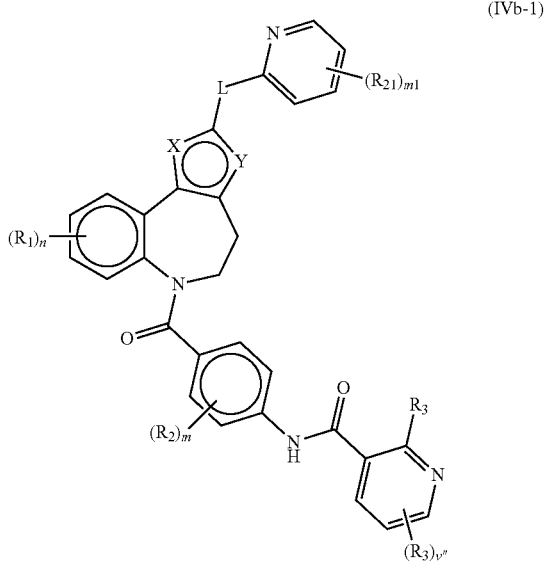

(IVb-1)

wherein X, Y, L, $R_1$, $R_2$, $R_3$, $R_{21}$, $R_{22}$, m1, m2, n, and m are as previously defined; v' is 0, 1, 2, or 3; and v" is 0, 1, or 2; provided that the sum of v' and v" is not more than 3. Preferably each $R_{21}$ is independently selected from —F, —Cl, —NH$_2$, and optionally substituted —CH$_3$; more preferably each $R_1$ is halogen; n is 1, 2 or 3; and each $R_{21}$ is independently selected from —F, —Cl, —NH$_2$, and optionally substituted —CH$_3$.

In another embodiment, the invention provides a compound represented by one of Formulae (IVa-1)~(IVd-1), (IVa-2)~(IVd-2), (IVa-3)~(IVd-3), and (IVa-4)~(IVd-4), or a pharmaceutically acceptable salt, ester or prodrug thereof:

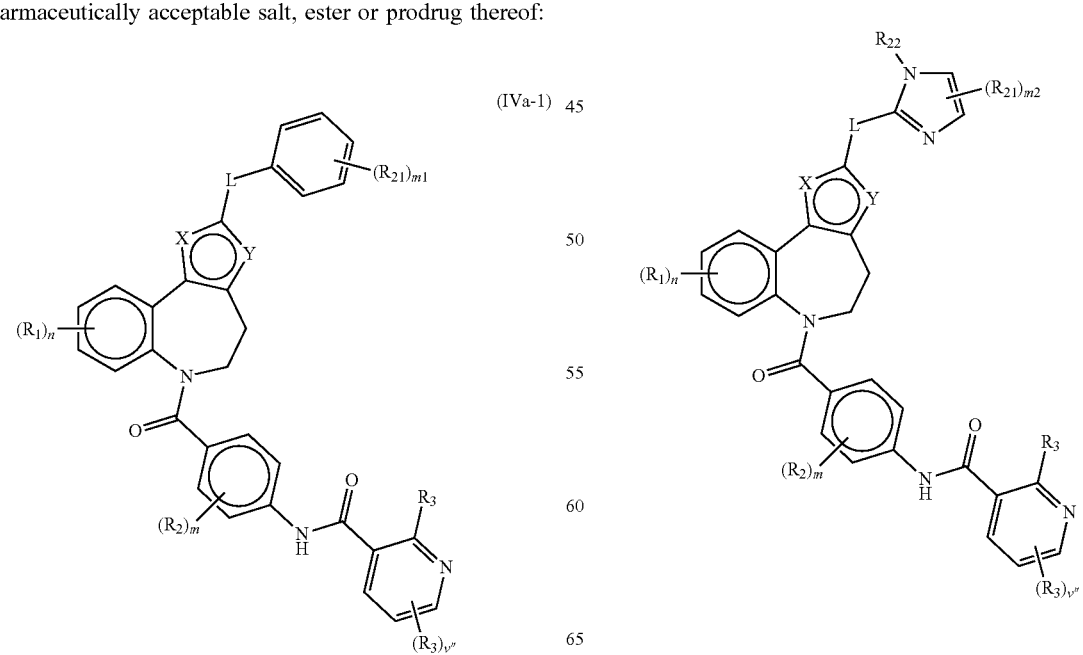

(IVa-1)

(IVc-1)

-continued
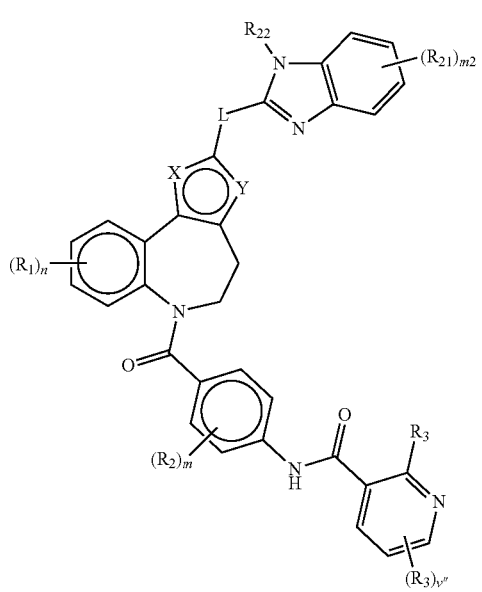
(IVd-1)
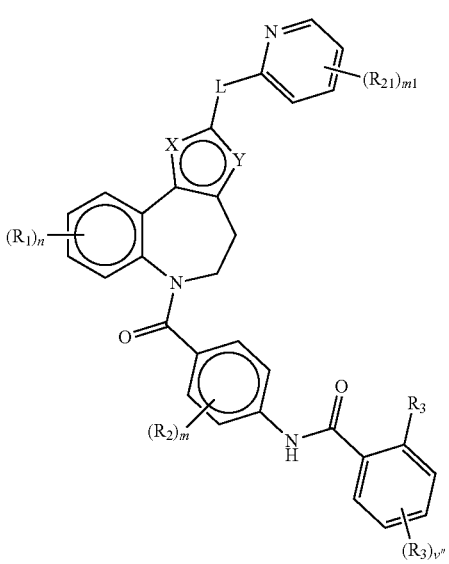
(IVb-2)
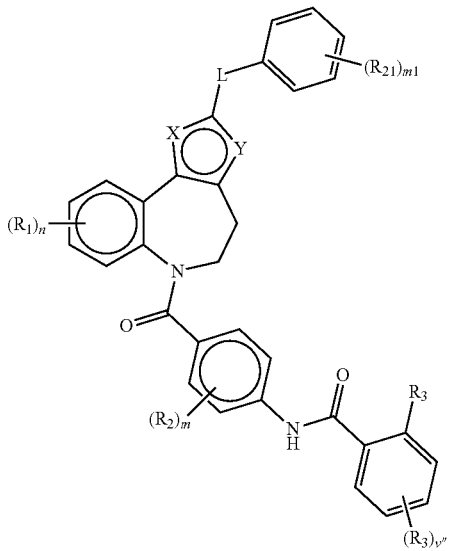
(IVa-2)
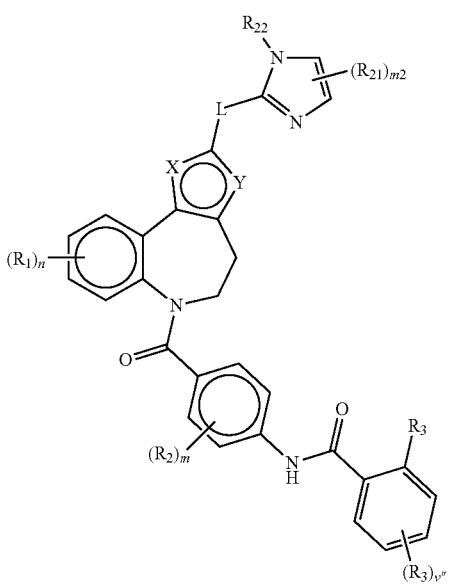
(IVc-2)

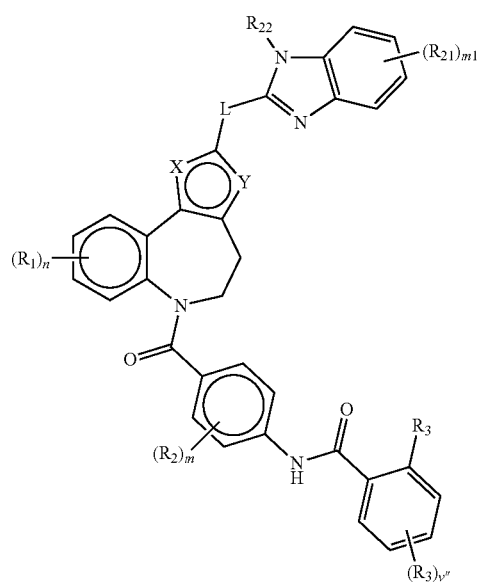
(IVd-2)
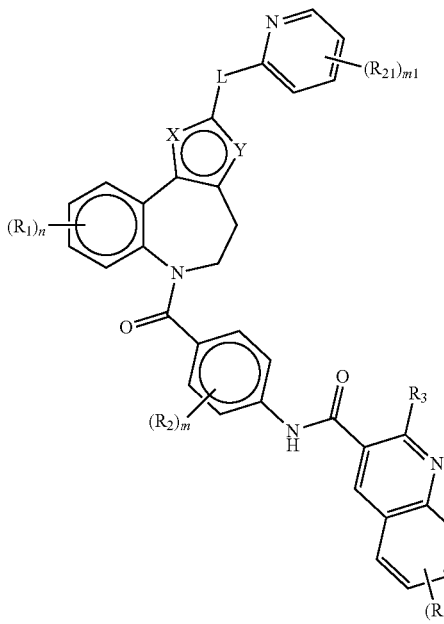
(IVb-3)
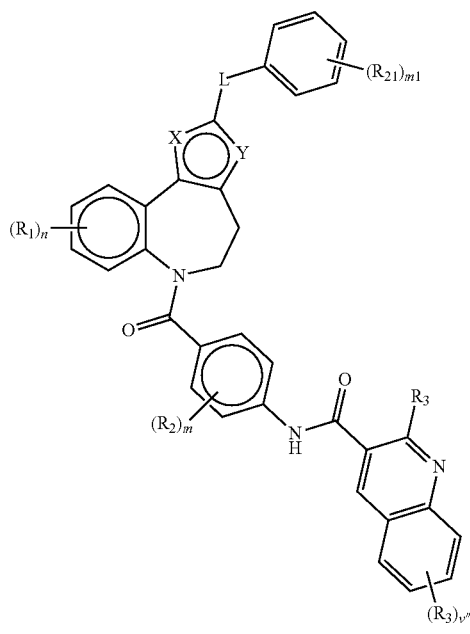
(IVa-3)
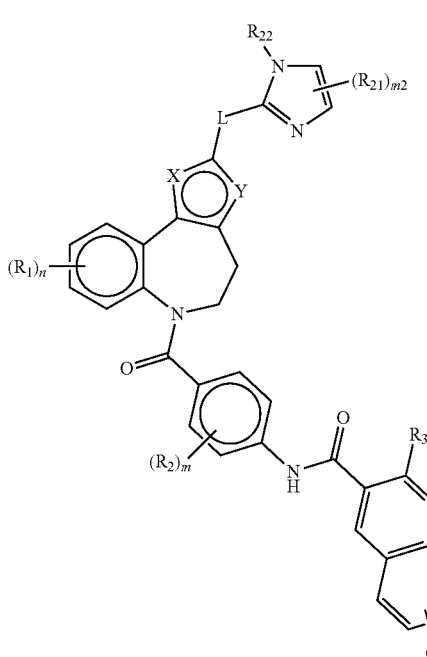
(IVc-3)

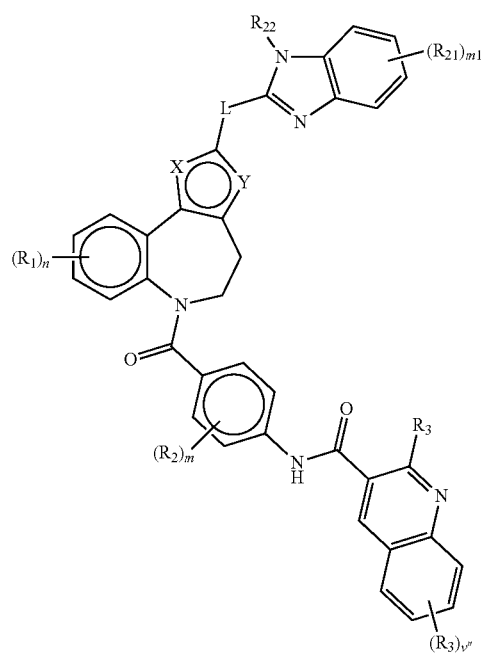
(IVd-3)
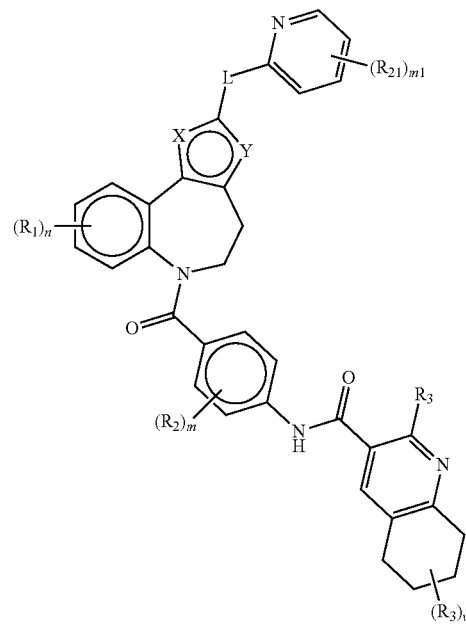
(IVb-4)
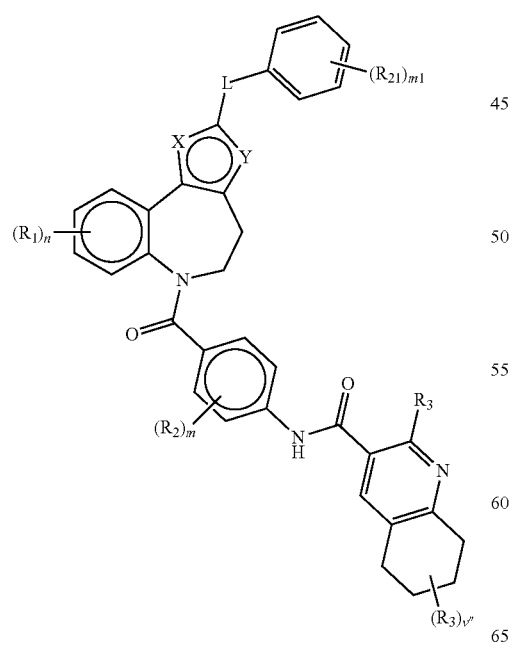
(IVa-4)
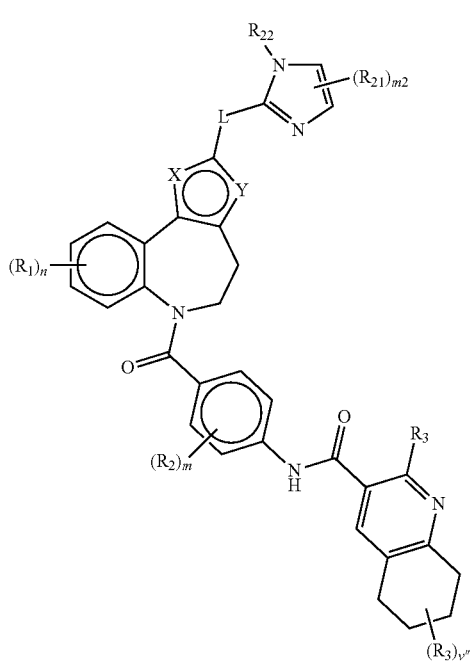
(IVc-4)

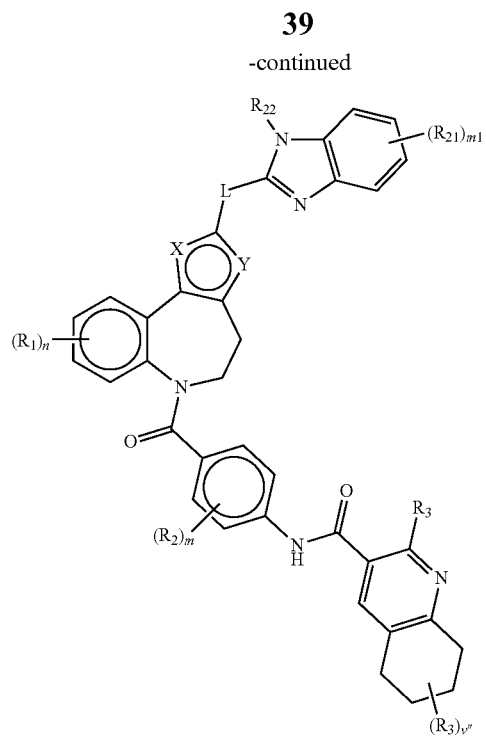

(IVd-4)

wherein X, Y, L, $R_1$, $R_2$, $R_3$, $R_{21}$, $R_{22}$, m1, m2, n, m and v" are as previously defined. Preferably each $R_{21}$ is independently selected from —F, —Cl, —NH$_2$, and optionally substituted —CH$_3$; more preferably each $R_1$ is halogen; n is 1, 2 or 3; and each $R_{21}$ is independently selected from —F, —Cl, —NH$_2$, and optionally substituted —CH$_3$.

In certain embodiments of the compounds of Formulae (IVa-1)~(IVd-1), (IVa-2)~(IVd-2), (IVa-3)~(IVd-3), (IVa-4)~(IVd-4), v" is 0 or 1. When v" is 1, the $R_3$ group which is not fixed is preferably methyl.

In another embodiment of the invention is a compound represented by one of Formulae (IVa-1)~(IVd-1), (IVa-2)~(IVd-2), (IVa-3)~(IVd-3), and (IVa-4)~(IVd-4), or a pharmaceutically acceptable salt, ester or prodrug thereof, wherein the $R_3$ which is fixed is selected from the groups shown below, each of which can be optionally substituted:

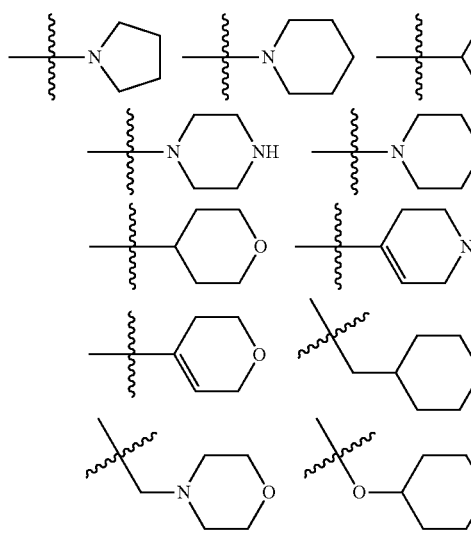

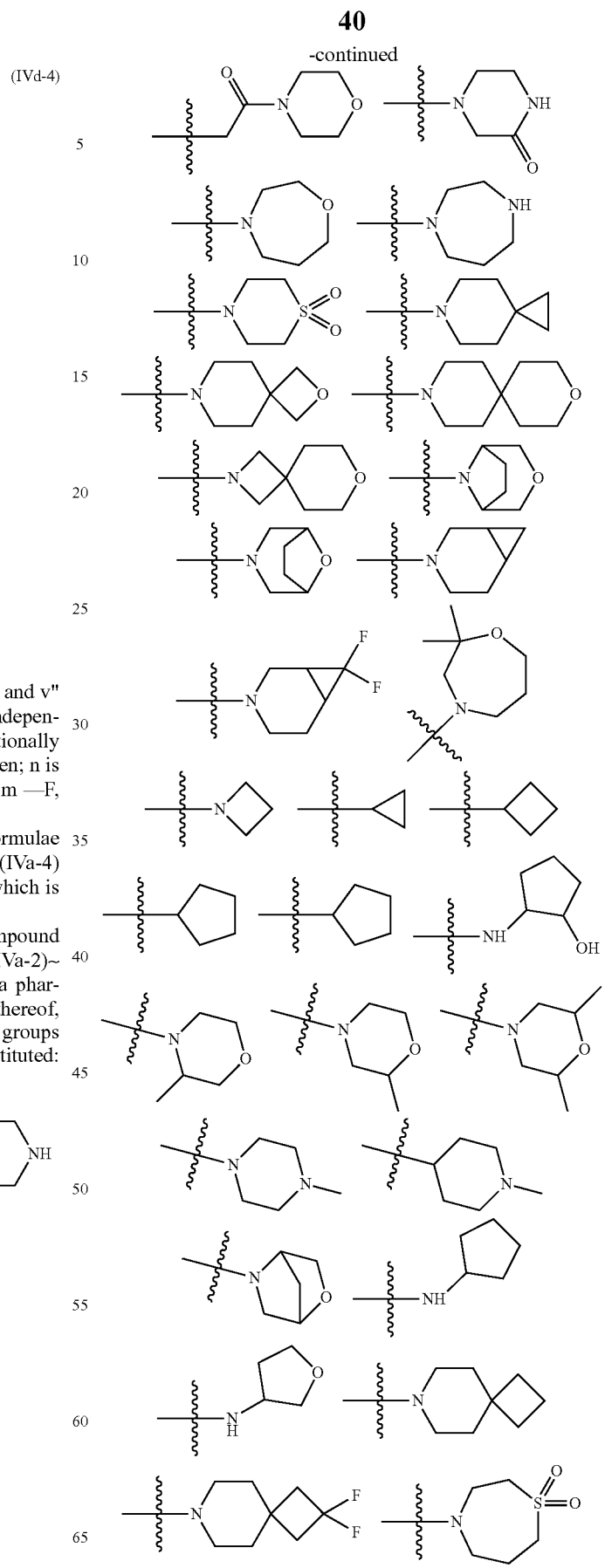

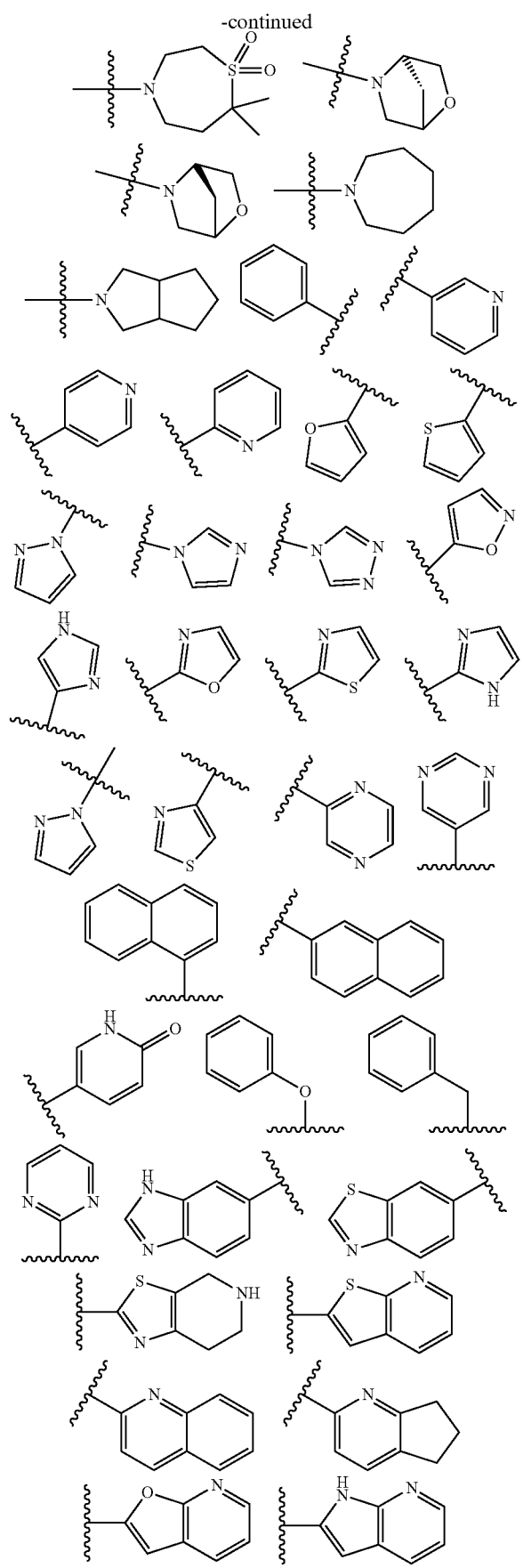
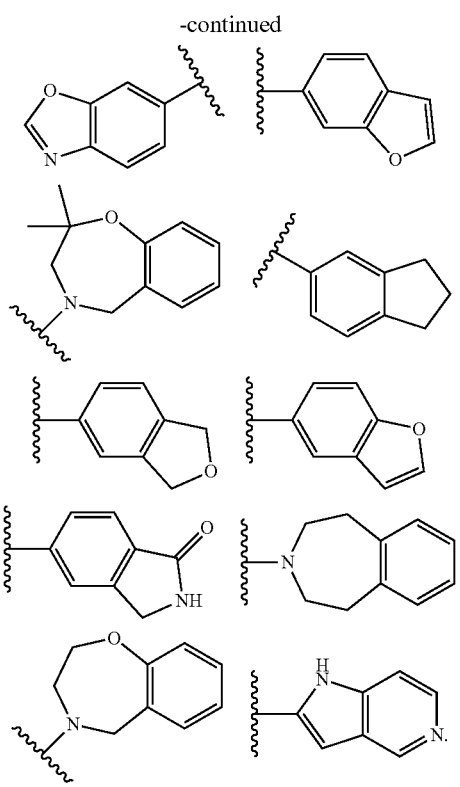
In certain embodiments of the compounds of the invention,
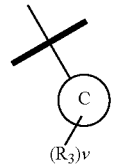
is represented by:
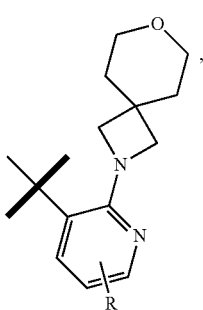

where R is hydrogen or methyl. For example,

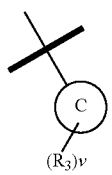

can be selected from the groups below:

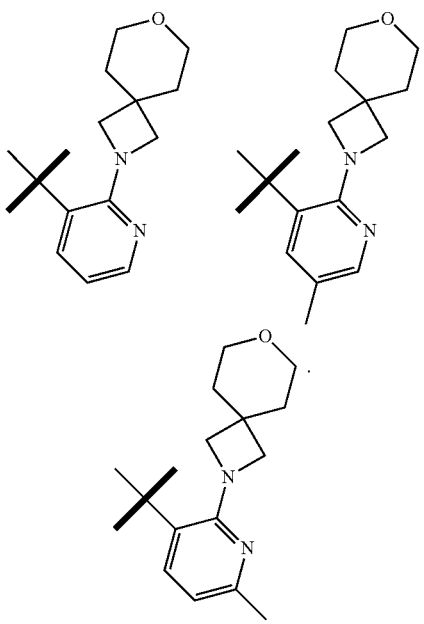

It will be appreciated that the description of the present invention herein should be construed in congruity with the laws and principles of chemical bonding. In some instances it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection in a subject in need thereof. The method comprises administering to the subject a therapeutically effective amount of a compound of formula (I).

The present invention also provides the use of a compound of formula (I) for the preparation of a medicament for the prevention or treatment of RSV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebuliser containing a medicament which comprises (a) a benzodiazepine derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above; or a pharmaceutically acceptable salt thereof, for use in a method of treating the human or animal body. The present invention also relates to a pharmaceutical composition comprising a novel compound as defined above and a pharmaceutically acceptable diluant or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral centre include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono-, bi-, or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono-, bi-, or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl" "$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]ocyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, protected hydroxy, —$NO_2$, —$N_3$, —CN, —$NH_2$, protected amino, oxo, thioxo, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2NH$—$C_1$-$C_{12}$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthio-methyl. It is understood that the aryls, heteroaryls, alkyls, cycloalkyls and the like can be further substituted.

In certain embodiments, a substituted alkyl, alkenyl or alkoxy group is substituted with one or more halogen atoms, preferably fluorine atoms. Such substituted alkyl groups include fluoromethyl, difluoromethyl and trifluoromethyl.

Such substituted alkoxy groups include fluoromethoxy, difluoromethoxy and trifluoromethoxy.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but are not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part*-2, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

In certain embodiments, the invention provides pharmaceutically acceptable prodrugs of the compounds disclosed herein. The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, J. of *Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound. For example, a compound of formula I wherein $R_1$ is an amino acid residue can also be esterified, for example at a hydroxyl group of the sugar residue, to form a compound with two groups that can be removed in vivo to yield the active compound.

The term "treating", as used herein, means relieving, lessening, reducing, eliminating, modulating, or ameliorating, i.e. causing regression of the disease state or condition. Treating can also include inhibiting, i.e. arresting the development, of a existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc. "Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example.

Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:

ACN for acetonitrile;

BME for 2-mercaptoethanol;

BOP for benzotriazol-1-yloxy-tris(dimethylamino)phosphonium hexafluorophosphate;

BTC for bis(trichloromethyl)carbonate; triphosgene;

BzCl for benzoyl chloride;

CDI for carbonyldiimidazole;

COD for cyclooctadiene;

DABCO for 1,4-diazabicyclo[2.2.2]octane;

DAST for diethylaminosulfur trifluoride;

DABCYL for 6-(N-4'-carboxy-4-(dimethylamino)azobenzene)-aminohexyl-;

1-O-(2-cyanoethyl)-(N,N-diisopropyl)-phosphoramidite;

DBU for 1, 8-Diazabicycloundec-7-ene;

DCC for N, N'-dicyclohexylcarbodiimide;

DCM for dichloromethane;

DIAD for diisopropyl azodicarboxylate;

DIBAL-H for diisobutylaluminum hydride;

DIPEA for diisopropyl ethylamine;

DMAP for N,N-dimethylaminopyridine;

DME for ethylene glycol dimethyl ether;

DMEM for Dulbecco's Modified Eagles Media;

DMF for N,N-dimethyl formamide;

DMSO for dimethylsulfoxide;

DPPA for diphenylphosphoryl azide or diphenyl phosphorylazidate;

DSC for N, N'-disuccinimidyl carbonate;
DUPHOS for

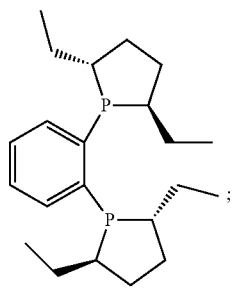 [SMILES: CC[C@@H]1CC[C@@H](CC)P1c1ccccc1P1[C@H](CC)CC[C@H]1CC]

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
EtOH for ethyl alcohol;
HATU for O (7-Azabenzotriazole-1-yl)-N,N,N',N'-tetramethyluronium hexafluorophosphate;
HCl for hydrochloric acid;
Hoveyda's Cat. for Dichloro(o-isopropoxyphenylmethylene)(tricyclohexylphosphine)ruthenium(II);
In for indium;
KHMDS is potassium bis(trimethylsilyl) amide;
Ms for mesyl;
NMM for N-4-methylmorpholine;
NMI for N-methylimidazole;
NMO for N-4-methylmorpholine-N-Oxide;
PyBrOP for Bromo-tri-pyrolidino-phosphonium hexafluorophosphate;
Ph for phenyl;
RCM for ring-closing metathesis;
RT for reverse transcription;
RT-PCR for reverse transcription-polymerase chain reaction;
TBME for tert-butyl methyl ether;
TCDI for 1,1'-thiocarbonyldiimidazole;
TEA for triethylamine;
Tf$_2$O for trifluoromethanesulfonic anhydride;
TFA for trifluoroacetic acid;
THF for tetrahydrofuran;
TLC for thin layer chromatography;
(TMS)$_2$NH for hexamethyldisilazane;
TMSOTf for trimethylsilyl trifluoromethanesulfonate;
TBS for t-Butyldimethylsilyl;
TMS for trimethylsilyl;
TPAP tetrapropylammonium perruthenate;
TPP or PPh$_3$ for triphenylphosphine;
TrCl for trityl chloride;
Ts for p-CH$_3$C$_6$H$_4$SO$_2$—
DMTrCl for 4,4'-dimethoxytrityl chloride;
tBOC or Boc for tert-butyloxy carbonyl;

Xantphos for 4,5-Bis-diphenylphosphanyl-9,9-dimethyl-9H-xanthene; and
Zhan 1 B for

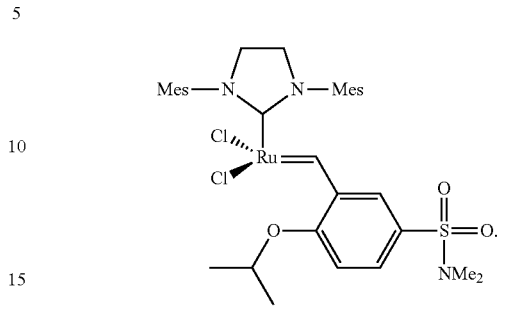

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Illustrated in Scheme 1, intermediate compound 7 for making novel RSV analogs is prepared starting from compound 1, wherein n, R$_1$ and ring A are defined as previously described. Substituted aryl fluoride 1 is reacted with diallylamine to yield diallylaniline 2. Subjection of 2 to elevated reaction temperatures furnished oxa-bridged benzazepine 3. The rate of this carbonyl-ene reaction can be improved with the addition of a Lewis acid such as, but not limited to, Cu(OTf)$_2$, Zn(OTf)$_2$, ZnCl$_2$ or Ti(O-iPr)$_2$Cl$_2$. Ring-opening cleavage of the C—O bond of 3 using, but not limited to, sulfuric acid, hydrochloric acid, or trifluoroacetic acid yields ketone 4. This procedure is well described in the literature, Zhang, Y.; Yang, F.; Zheng, L.; Dang, Q.; Bai, X. *Org. Lett.*, 2014, 16, 6041-6043. Carbaldehyde 5 is derived from 4 using, but not limited to, triphosgene or phosphorus(V) oxychloride in DMF. Thiophene 6 is formed by reacting ethyl 2-mercaptoacetate and a strong base, such as sodium ethoxide or sodium hydride, with 5. Allyl amine 6 is deprotected using palladium, a phosphine ligand, and an allyl sponge, such as 1,3-dimethyl-1,3-diazinane-2,4,6-trione, using amine 7.

Scheme 1

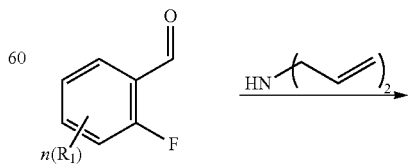

1

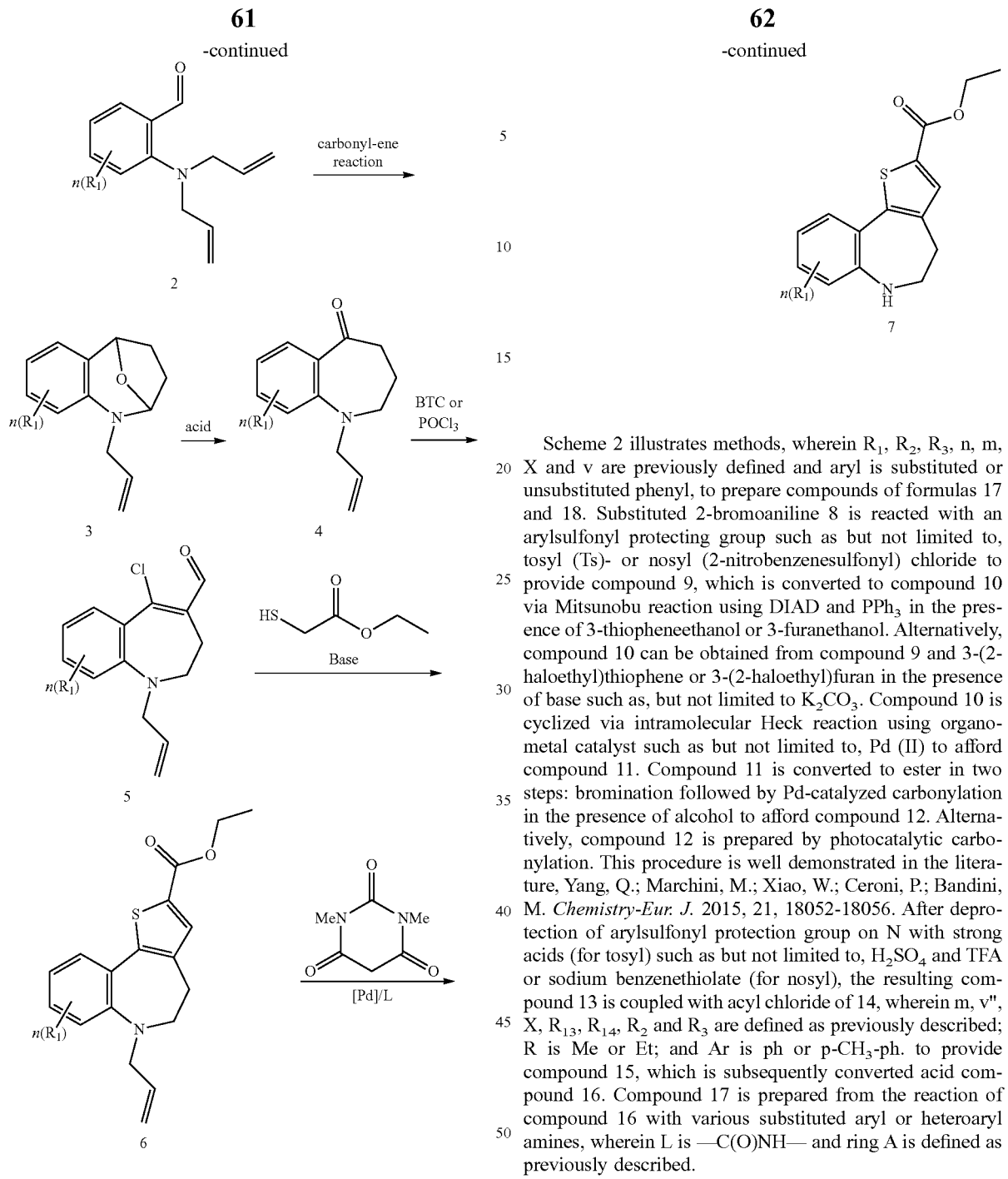

Scheme 2 illustrates methods, wherein $R_1$, $R_2$, $R_3$, n, m, X and v are previously defined and aryl is substituted or unsubstituted phenyl, to prepare compounds of formulas 17 and 18. Substituted 2-bromoaniline 8 is reacted with an arylsulfonyl protecting group such as but not limited to, tosyl (Ts)- or nosyl (2-nitrobenzenesulfonyl) chloride to provide compound 9, which is converted to compound 10 via Mitsunobu reaction using DIAD and $PPh_3$ in the presence of 3-thiopheneethanol or 3-furanethanol. Alternatively, compound 10 can be obtained from compound 9 and 3-(2-haloethyl)thiophene or 3-(2-haloethyl)furan in the presence of base such as, but not limited to $K_2CO_3$. Compound 10 is cyclized via intramolecular Heck reaction using organometal catalyst such as but not limited to, Pd (II) to afford compound 11. Compound 11 is converted to ester in two steps: bromination followed by Pd-catalyzed carbonylation in the presence of alcohol to afford compound 12. Alternatively, compound 12 is prepared by photocatalytic carbonylation. This procedure is well demonstrated in the literature, Yang, Q.; Marchini, M.; Xiao, W.; Ceroni, P.; Bandini, M. *Chemistry-Eur. J.* 2015, 21, 18052-18056. After deprotection of arylsulfonyl protection group on N with strong acids (for tosyl) such as but not limited to, $H_2SO_4$ and TFA or sodium benzenethiolate (for nosyl), the resulting compound 13 is coupled with acyl chloride of 14, wherein m, v'', X, $R_{13}$, $R_{14}$, $R_2$ and $R_3$ are defined as previously described; R is Me or Et; and Ar is ph or p-$CH_3$-ph. to provide compound 15, which is subsequently converted acid compound 16. Compound 17 is prepared from the reaction of compound 16 with various substituted aryl or heteroaryl amines, wherein L is —C(O)NH— and ring A is defined as previously described.

-continued
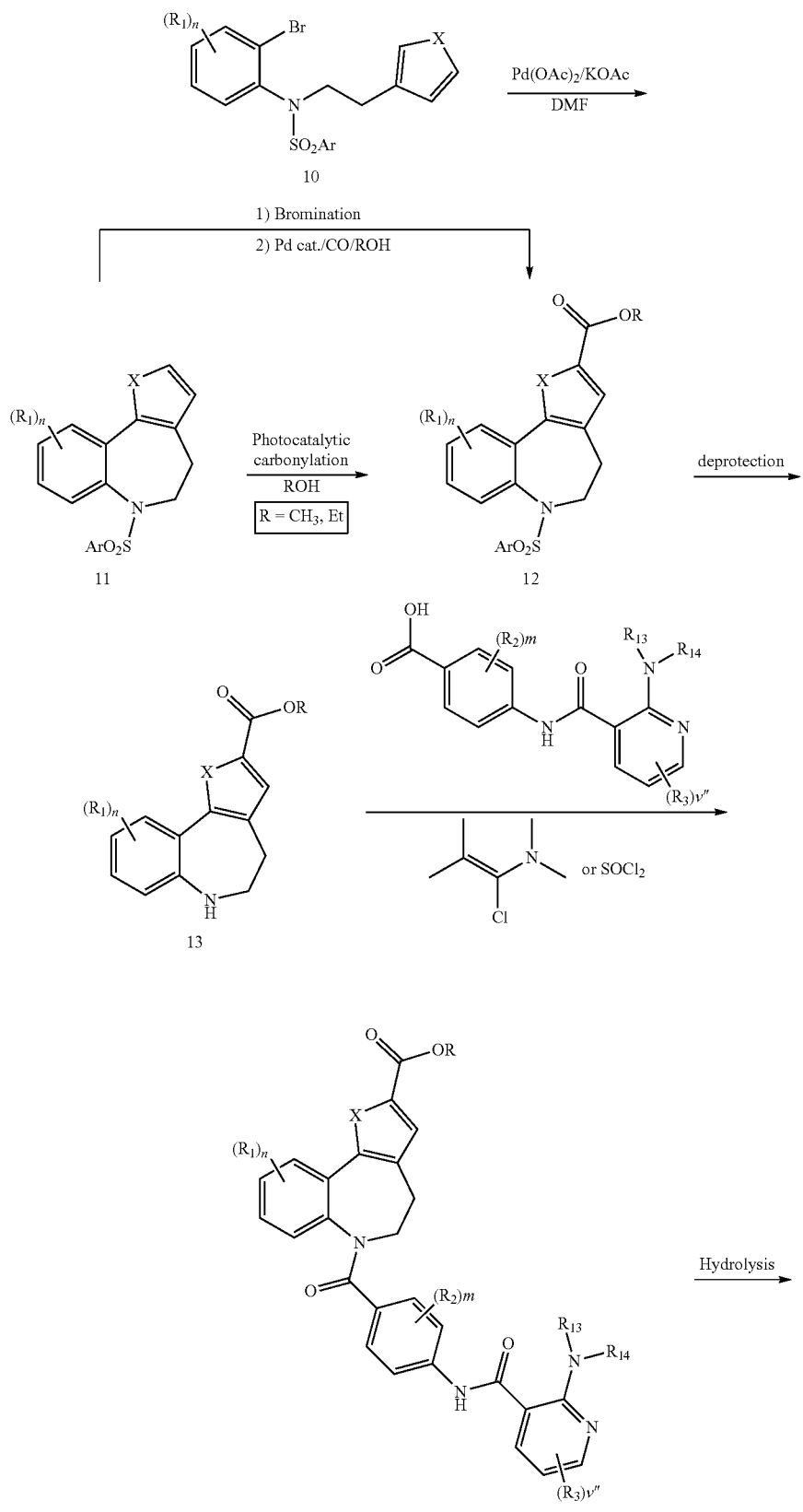

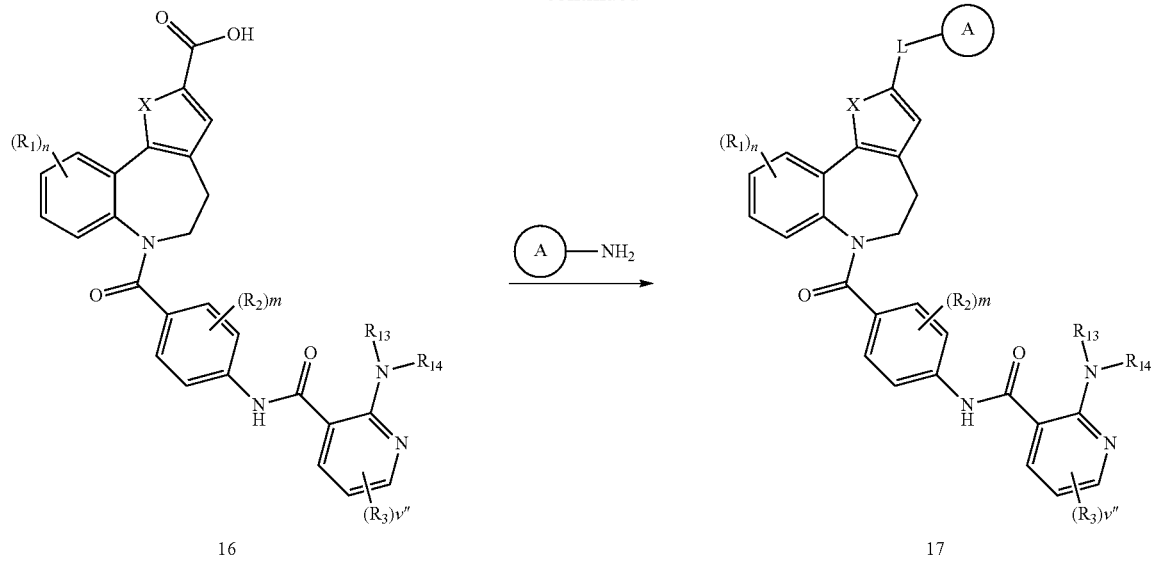

Scheme 3 illustrates methods, wherein L, X, n, R₁, m, R₂, v, v″, R₃, ring A and ring C are defined as previously described, to prepare compounds of formula 24. Compound 13 is coupled with substituted or unsubstituted 4-nitrobenzoyl chloride and subsequently reduced with reducing agent such as but not limited to, iron, to give compound 19. By reacting with functionalized compound 20, compound 19 is converted compound 15. On the other way, compound 19 is reacted with aryl acyl chloride 21 to provide compound 22.

Compound 22 is coupled with various boronic esters, boronic acids, organotin reagents, organozinc reagents, organomagnesium reagents, organic silicon reagents or the like catalyzed by appropriate Pd, Ni, Cu or the like catalyst to afford compounds of formula 23. Also, compound 22 is subjected to amination with various amines to provide compound 15. Both compound 15 and 23 are converted to compounds of formula 24 as described in scheme 3.

Scheme 3

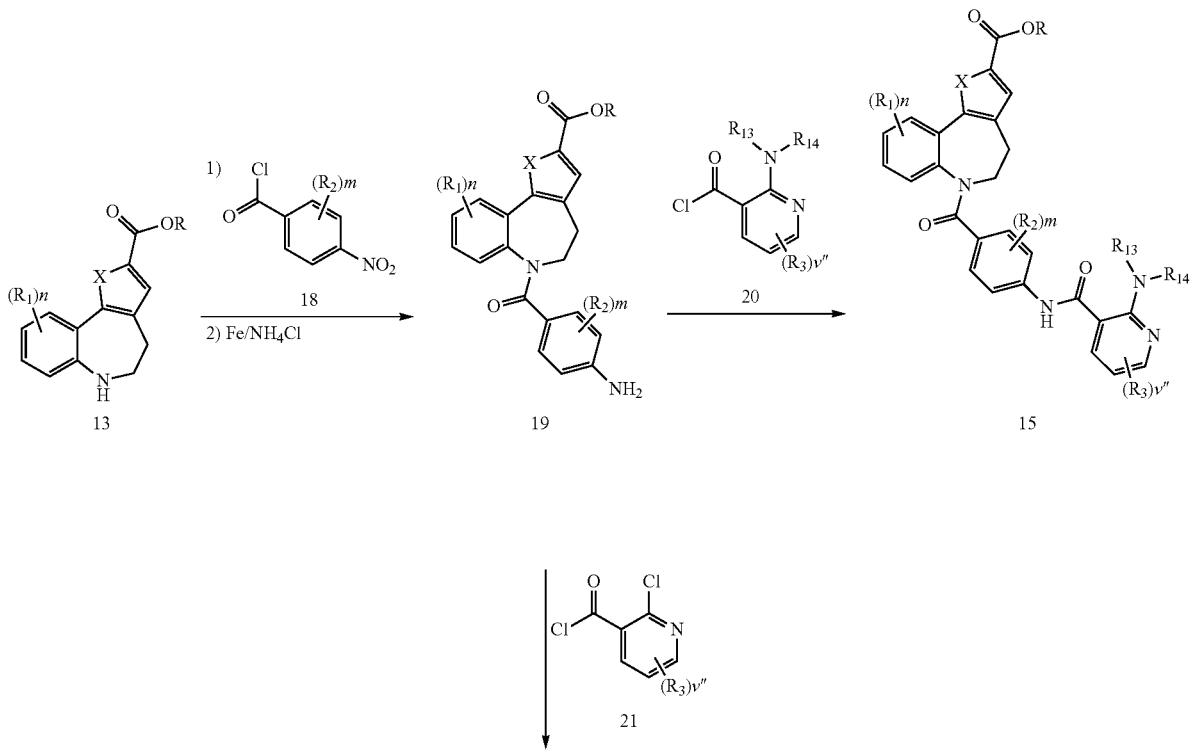

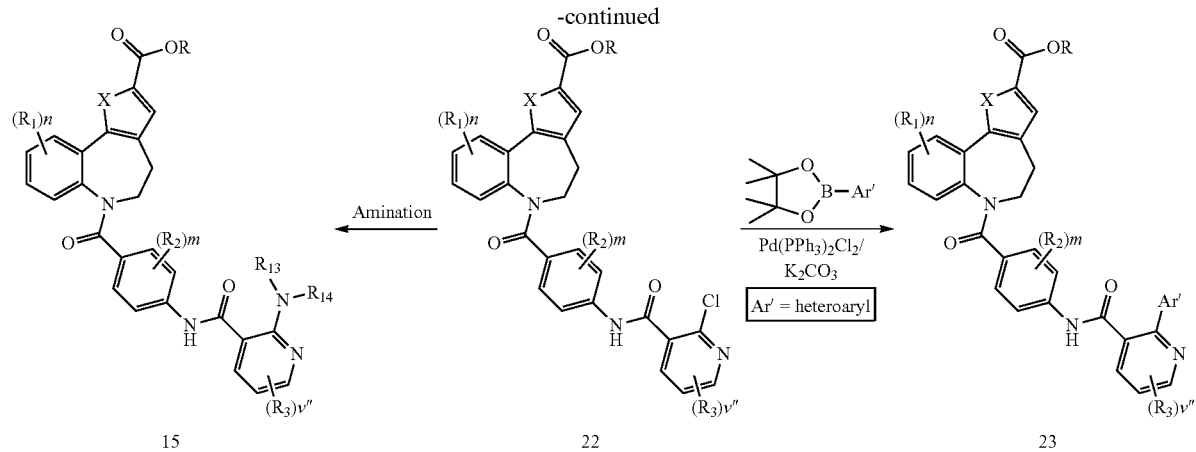
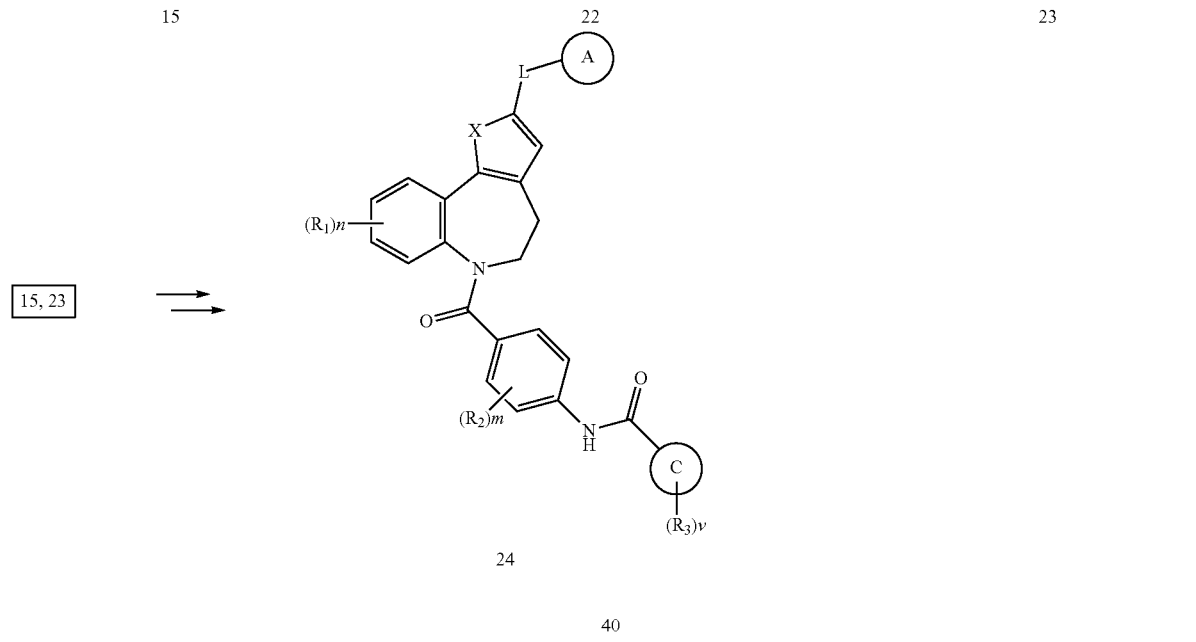
Scheme 4
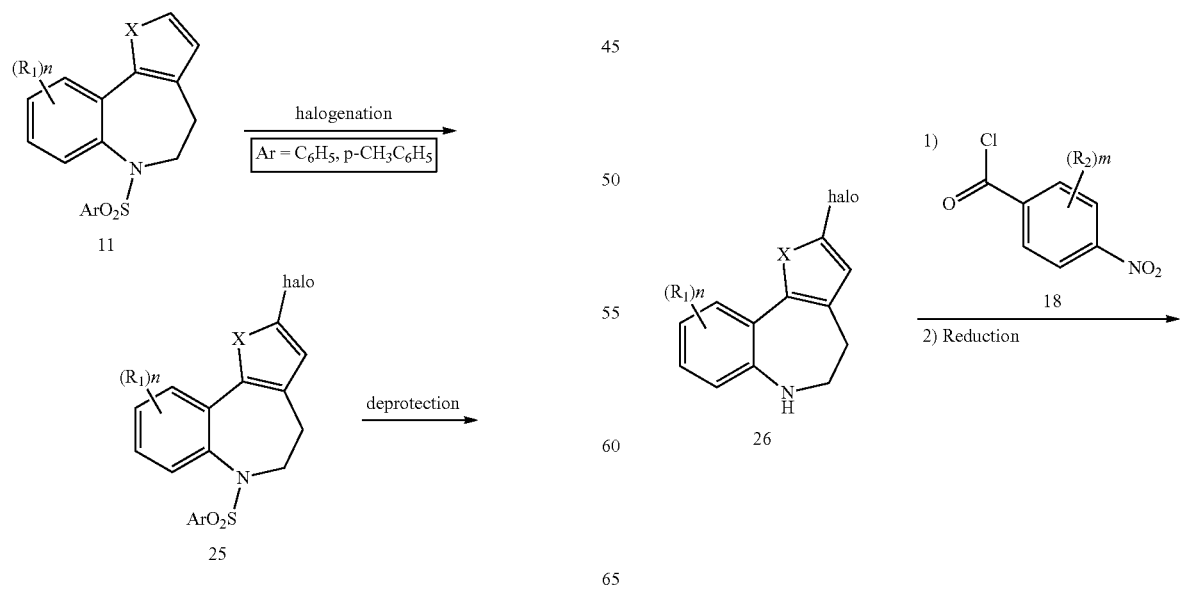

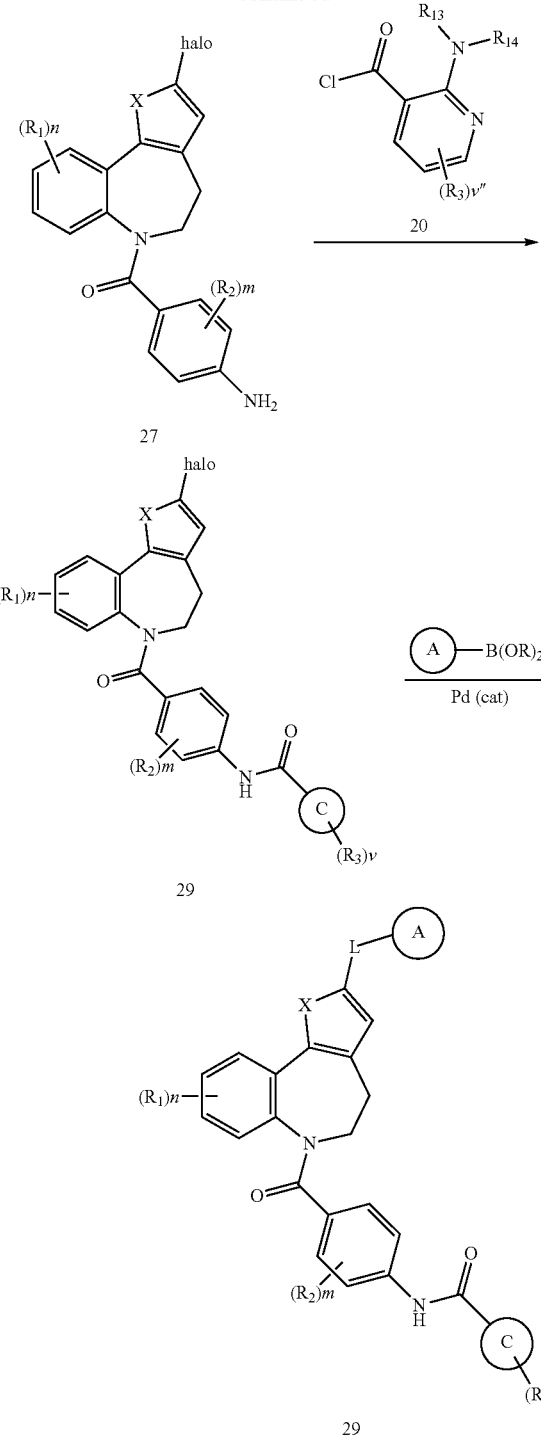

boronic esters, boronic acids, organotin reagents, organozinc reagents, organomagnesium reagents, organic silicon reagents or the like catalyzed by appropriate Pd, Ni, Cu or the like catalyst to afford compounds of formula 29.

Scheme 5 illustrates methods, wherein L, X, n, $R_1$, m, $R_2$, v, v", $R_3$ and A ring are defined as previously described, to prepare compounds of formula 36. N-protected compound 30 is hydrolyzed to provide compound 31, which is subjected to ortho lithiation followed by halogenation to afford compound 32. Lithiation is achieved by appropriate base such as but not limited to BuLi, LDA and LHMDS. After deprotection and esterification, compound 32 is converted to compound 36 as described in scheme 3.

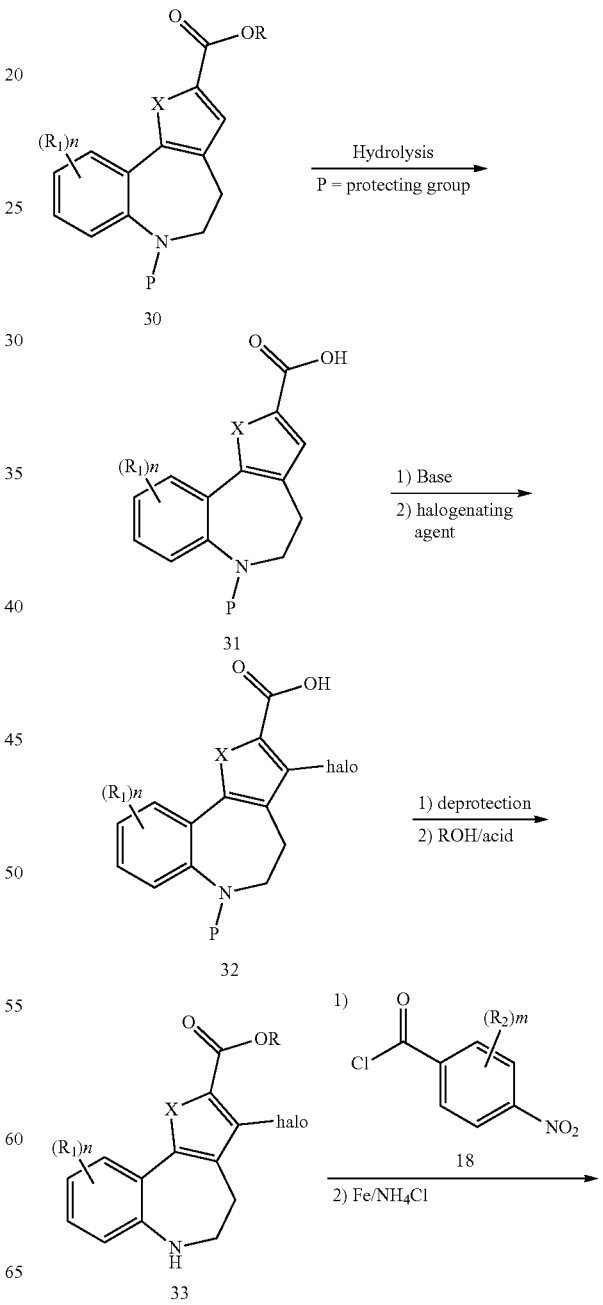

Scheme 4 illustrates methods, wherein L, X, n, $R_1$, m, $R_2$, v, v", $R_3$, ring A and ring C are defined as previously described; and Ar is phenyl or p-$CH_3$-phenyl, to prepare compounds of formula 29. Compound 11 is subjected to halogenation such as but not limited to, bromination and chlorination to give compound 25. Deprotection as described in scheme 2 followed by installation of substituted or unsubstituted 4-nitrobenzoyl group provides compound 27. After coupling with functionalized acyl chloride 20, compound 27 is converted 28, which is coupled with various

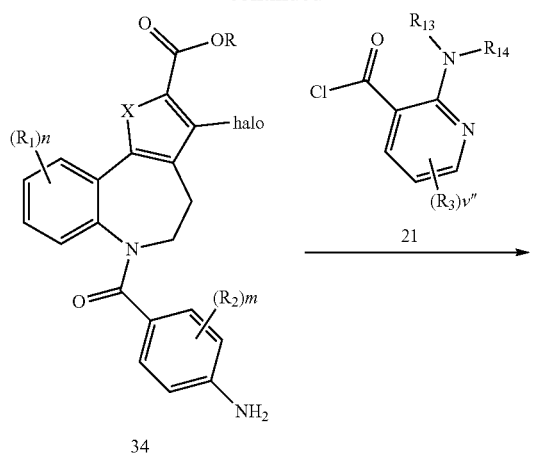
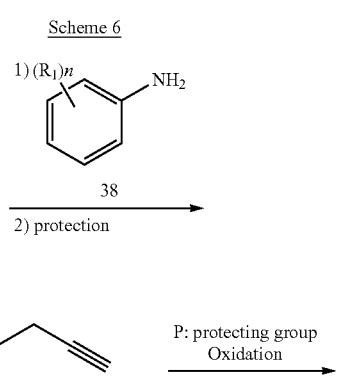
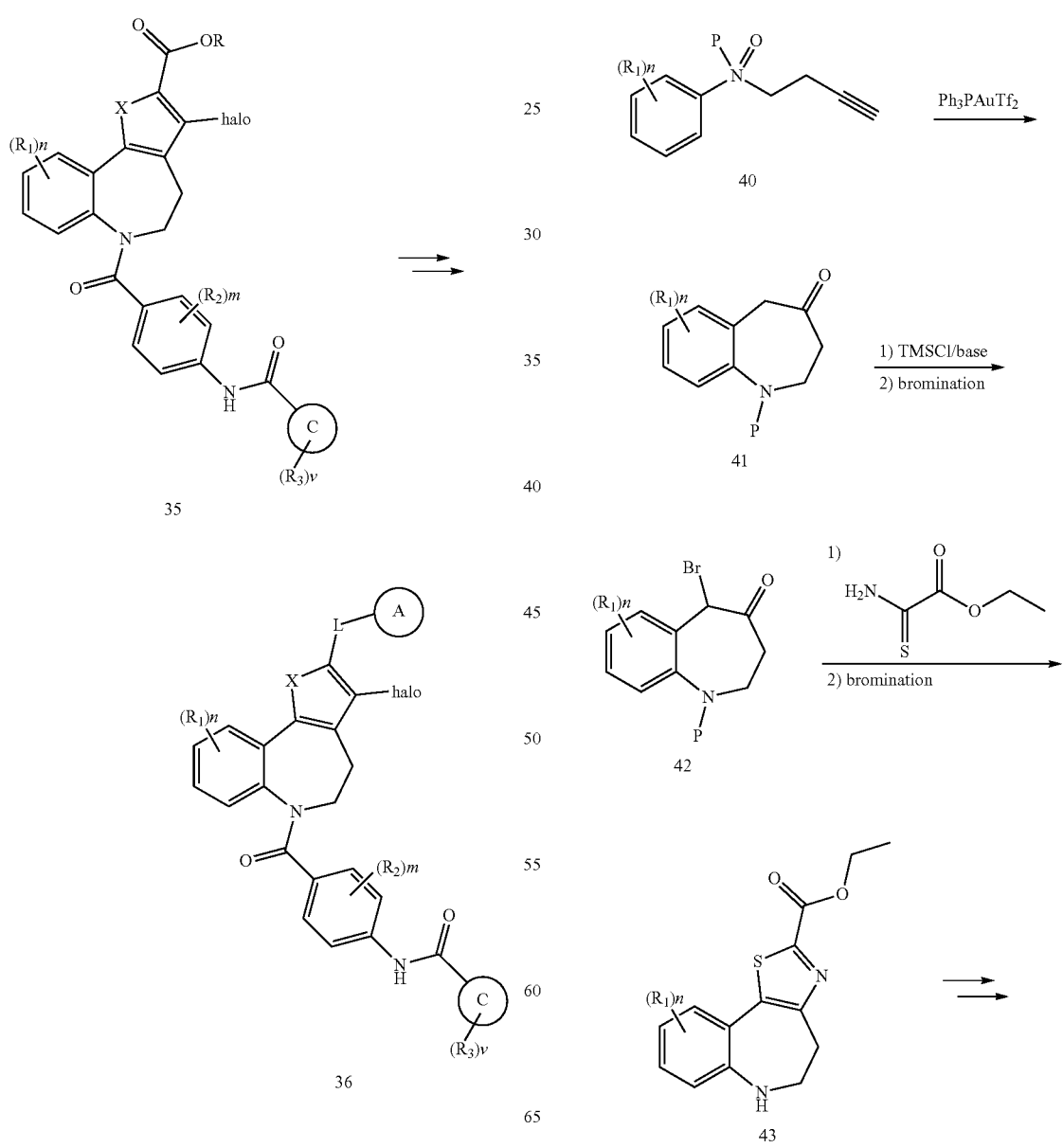
Scheme 6

73
-continued

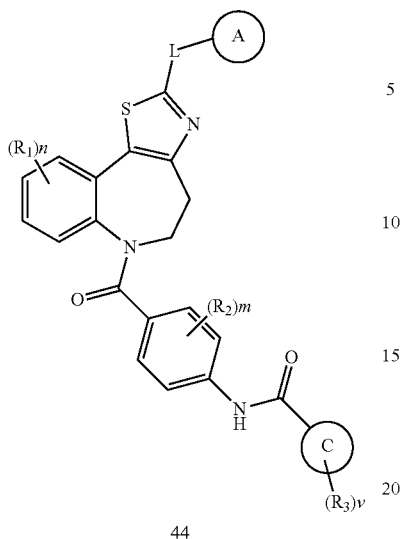
44

Scheme 6 illustrates methods, wherein L, X, n, R$_1$, m, R$_2$, v, R$_3$, ring A and C are defined as previously described to provide compound 44. Compound 37 which has a proper leaving group is reacted with substituted aniline in the presence of base to afford 39, which is converted to compound 41 via oxidation using oxidating agents such as but not limited to, m-CPBA, oxone and Au-catalyzed cyclization. This cyclization can be achieved by other metal catalysts such as but not limited to, AgBF$_4$, PtCl$_2$ and is also well described in the literature, Cui, L.; Zhang, G.; Peng, Y.; Zhang, L. *Org. Lett.*, 2009, 11, 1225-1228. Compound 41 is brominated at benzylic position in two steps: i) silyl enol ether formation using TMSCl and base such as but not limited to Et$_3$N, DIPEA; ii) bromination using Br$_2$ or N-bromosuccinimide to afford compound 42. Subsequently, compound 42 is reacted with carbamothioylformate in 2-propanol and converted to compound 43 after deprotection. Compounds of formula 44 are prepared from compound 43.

Scheme 7

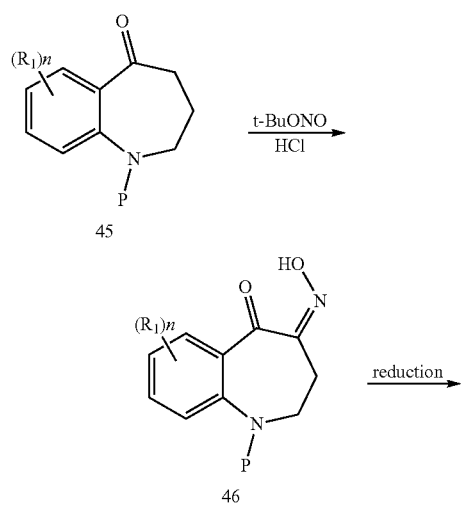
45

46

74
-continued

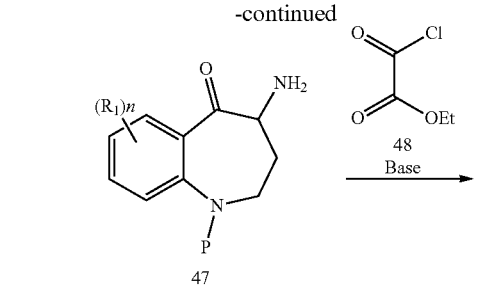
47

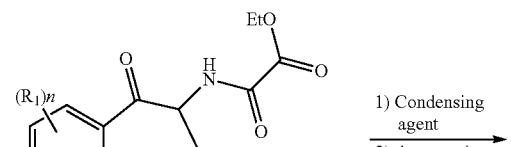
49

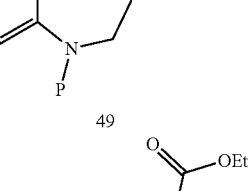
50

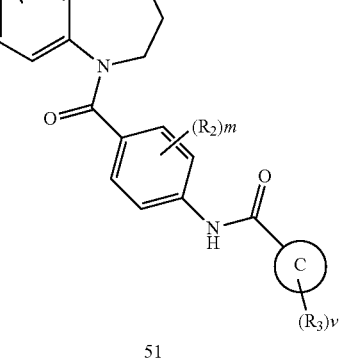
51

Scheme 7 illustrates methods, wherein L, X, n, R$_1$, m, R$_2$, v, R$_3$, ring A and C are defined as previously described to provide compound 51. N-protected compound 45 was subjected to oxime formation using nitrite such as but not limited to tert-butyl nitrite in the presence of HCl to afford compound 46. After reduction of compound 46 with reducing agent such as but not limited to, Zn, the obtained compound 47 is reacted with ethyl 2-chloro-2-oxoacetate in the presence of base such as but not limited to Et$_3$N and DIPEA to give compound 49. Condensation of compound 49 with POCl$_3$ or the like and deprotection provides compound 50, which is converted to compounds of formula 51.

Scheme 8 illustrates methods, wherein (R₁), (R₂), (R₃), n, m, and v are previously defined, to prepare for compounds of formula 54. Carboxylic acid 16 is converted to amine 53 via Curtius rearrangement. The key intermediate of Curtius rearrangement, acyl azide can be prepared using various conditions such as but not limited to, diphenylphosphoryl azide (DPPA), from the reaction of acid chlorides or anhydrides with sodium azide or trimethylsilyl azide. Acyl azide is reacted with nucleophilic alcohol such as but not limited to, tert-butanol and benzyl alcohol to afford to compound 52. After deprotection of amine protection group on nitrogen with acids (tert-butoxycarbonyl) or palladium-carbon (benzyloxycarbonyl) such as but not limited to, HCl and TFA or 10% Pd—C, the resulting compound 53 is coupled with arylacyl chloride to provide compounds of formula 31.

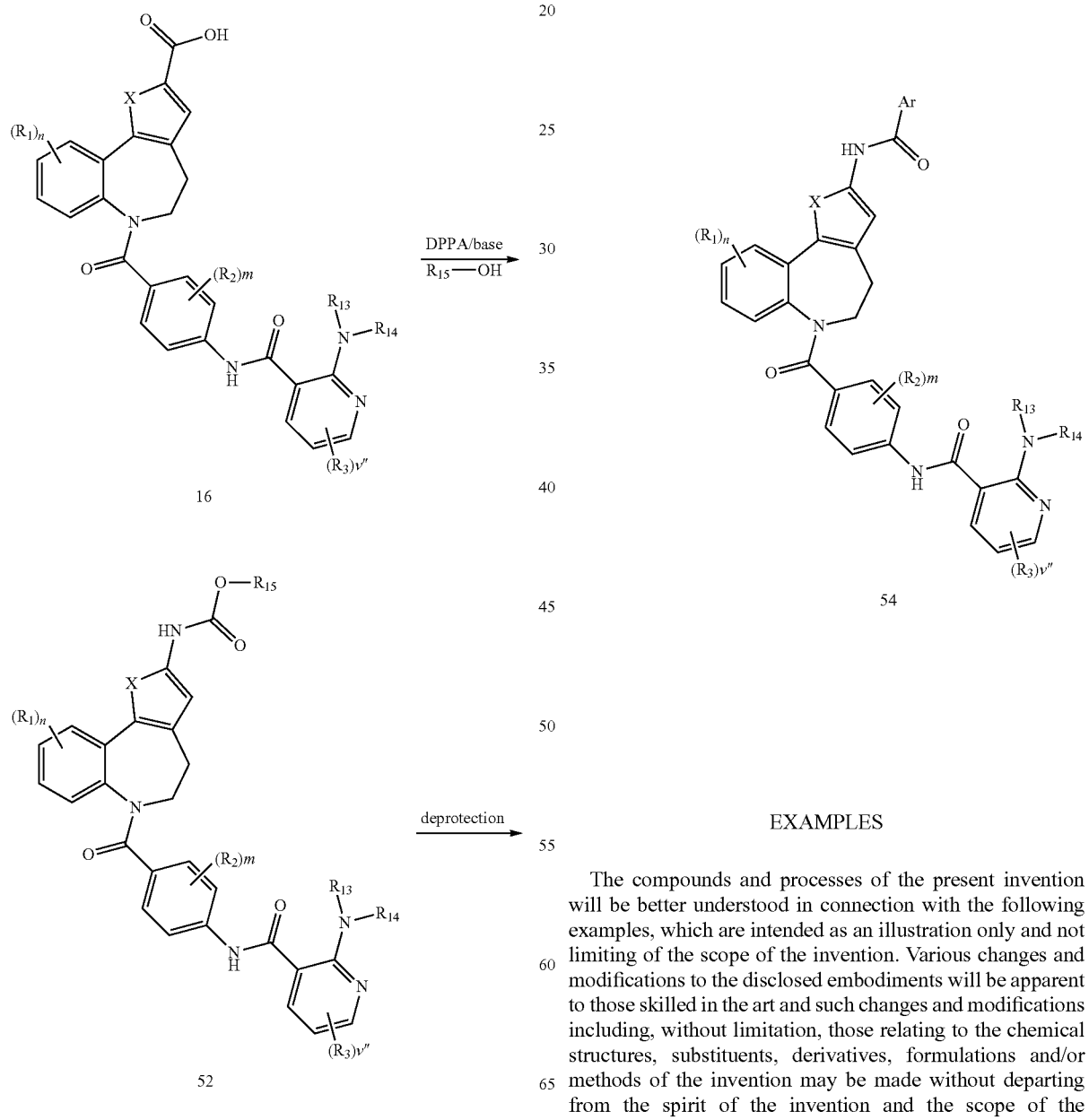

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Scheme 1

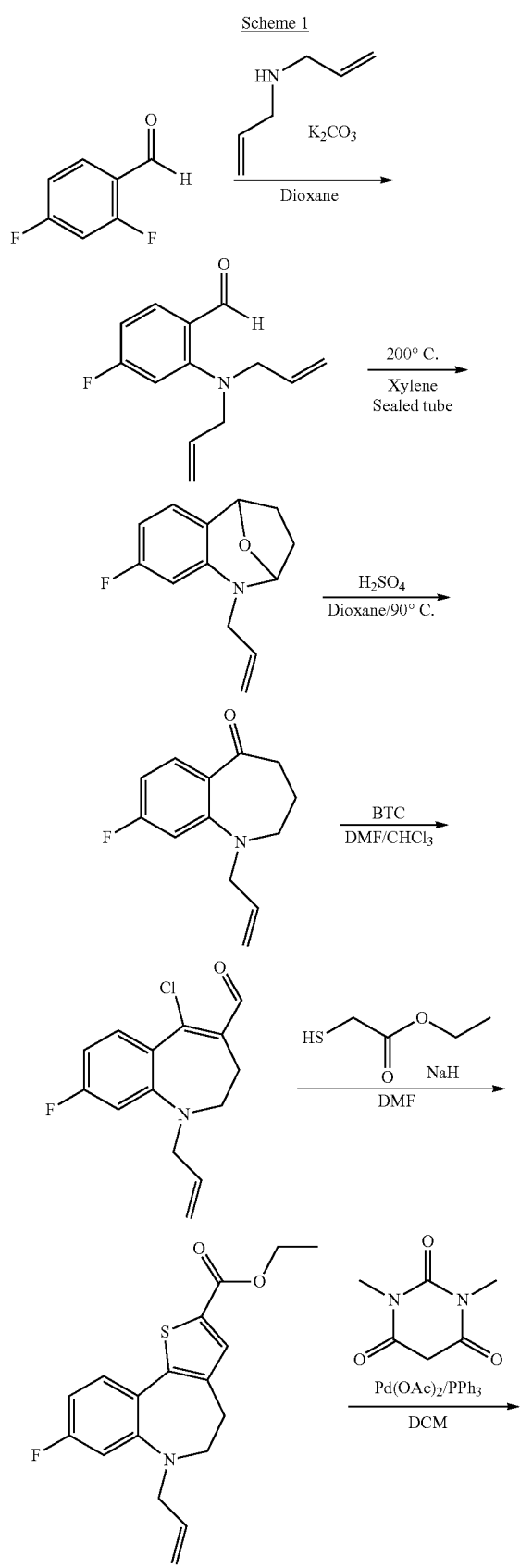

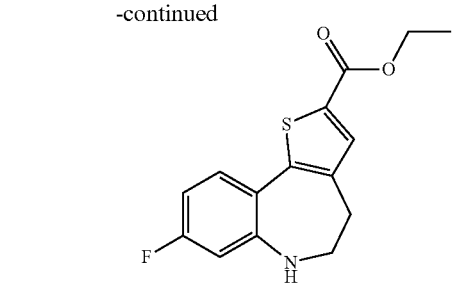

Intermediate 1

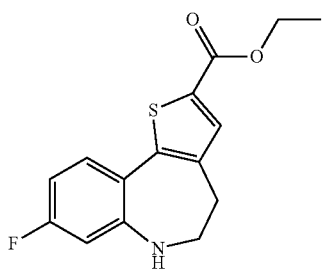 [SMILES: CCOC(=O)c1cc2c(s1)-c1ccc(F)cc1NCC2]

Intermediate 1 Step a

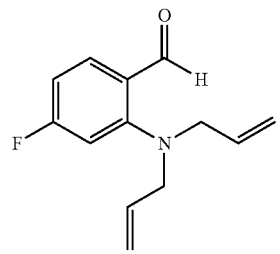 [SMILES: C=CCN(CC=C)c1cc(F)ccc1C=O]

Into a 20-L 4-necked round-bottom flask purged and maintained with an inert atmosphere of nitrogen, was placed a solution of 2,4-difluorobenzaldehyde (500 g, 3.52 mol, 1.00 equiv) in dioxane (10 L) at room temperature. This was followed by the addition of $K_2CO_3$ (728.8 g, 5.24 mol) at room temperature. To this was added bis(prop-2-en-1-yl) amine (375.7 g, 3.87 mol) at room temperature. The resulting solution was stirred for 6 days at 100° C. The reaction mixture was cooled to room temperature with a water bath. The resulting mixture was concentrated under vacuum. The resulting solution was diluted with of EA (5 L). The resulting mixture was washed with 3×2000 mL of brine. The mixture was dried over anhydrous sodium sulfate and concentrated under vacuum. The residue was purified by silica gel column chromatography eluting with ethyl acetate/petroleum ether (1:100) to provide the desired compound (1.1 kg) as yellow oil. ESI-MS m/z: 220.0 [M+H]$^+$.

Intermediate 1 Step b

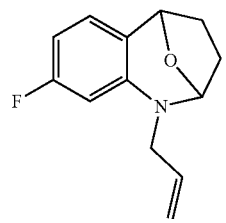 [SMILES: C=CCN1c2cc(F)ccc2C2CCC1O2]

Into a 10-L sealed tube purged and maintained with an inert atmosphere of nitrogen, was placed a solution of the compound from step a (600 g, 2.74 mol) in dimethylbenzene (6 L) at room temperature. The resulting solution was stirred for 3 days at 200° C. The mixture was cooled to room temperature. The resulting mixture was concentrated under vacuum to give the desired product (700 g) as yellow oil. ESI-MS m/z: 220.0 [M+H]$^+$.

Intermediate 1 Step c

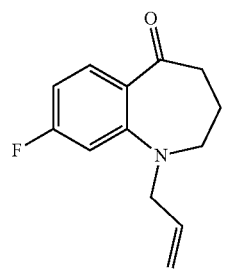 [SMILES: C=CCN1CCCC(=O)c2ccc(F)cc21]

Into a 20-L 4-necked round-bottom flask purged and maintained with an inert atmosphere of nitrogen, was placed a solution of the compound from step b (700 g, crude) in dioxane/10% sulfuric acid (1.4/7 L) at room temperature. The resulting solution was stirred overnight at 90° C. The reaction mixture was cooled to room temperature with a water bath. The resulting solution was extracted with ethyl acetate (3×2 L) and the organic layers combined. The resulting mixture was washed with brine. The mixture was dried over anhydrous sodium sulfate and concentrated under vacuum. The residue was purified by silica gel column chromatography eluting with ethyl acetate/petroleum ether (1:100) to give the desire product (345 g) as a yellow solid. ESI-MS m/z: 220.0 [M+H]$^+$.

Intermediate 1 Step d

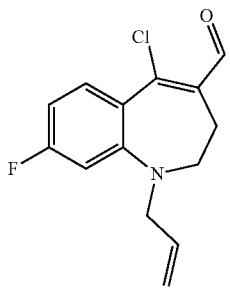 [SMILES: C=CCN1CCC(C=O)=C(Cl)c2ccc(F)cc21]

Into a 5-L 4-necked round-bottom flask purged and maintained with an inert atmosphere of nitrogen, was placed a solution of DMF (160 g, 2.19 mol) in chloroform (1 L) at room temperature. This was followed by the addition of a solution of BTC (217 g, 0.73 mol) in chloroform (1.5 L) dropwise with stirring at 0° C. The resulting solution was stirred for 1 h at room temperature. To this was added a solution of the compound form step c (160 g, 0.73 mol) in chloroform (1 L) dropwise with stirring at room temperature. The resulting solution was stirred overnight at 60° C. The reaction mixture was cooled to room temperature with a water bath. The reaction was then quenched by the addition of NaOAc(aq) (2 L). The resulting solution was extracted with of ethyl acetate (3×2 L) and the organic layers combined. The resulting mixture was washed with of brine (2×2 L). The mixture was dried over anhydrous sodium sulfate and concentrated under vacuum. The residue was purified by silica gel column chromatography eluting with ethyl acetate/petroleum ether (1:20) to give the desired product (83 g) as yellow oil. ESI-MS m/z: 266.1 [M+H]$^+$.

Intermediate 1 Step e

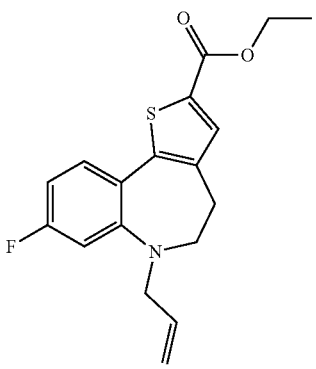 [SMILES: C=CCN1CCc2cc(C(=O)OCC)sc2-c2ccc(F)cc21]

Into a 2000-mL 4-necked round-bottom flask purged and maintained with an inert atmosphere of nitrogen, was placed a solution of ethyl 2-sulfanylacetate (70 g, 582.51 mmol,) in DMF (1 L) at room temperature. This was followed by the addition of sodium hydride (23 g, 582.5 mmol,) in several batches at 0° C. The resulting solution was stirred for 0.5 h at 0° C. To this was added a solution of the compound from step d (77 g, 289.79 mmol,) in N,N-dimethylformamide (500 mL) dropwise with stirring at 0° C. The resulting solution was stirred for 1 h at room temperature. The reaction was then quenched by the addition of 3000 mL of water/ice. The pH value of the solution was adjusted to 7 with hydrogen chloride (3 mol/L). The resulting solution was extracted with EtOAc (3×1 L) and the organic layers combined. The resulting mixture was washed with brine. The mixture was dried over anhydrous sodium sulfate and concentrated under vacuum. The residue was purified by silica gel column chromatography eluting with ethyl acetate/petroleum ether (1:20) to give the desired product (62 g) as a yellow solid. ESI-MS m/z: 332.1 [M+H]$^+$. 1H NMR (300 MHz, CDCl$_3$) δ 1.37-1.42 (m, 3H), 3.02-3.05 (m, 2H), 3.33-3.36 (m, 2H), 3.91-3.92 (m, 2H), 4.33-4.40 (m, 2H), 5.27-5.32 (m, 2H), 5.88-6.00 (m, 1H), 6.59-6.70 (m, 2H), 7.59 (s, 1H), 7.70-7.75 (m, 1H).

Intermediate 1 Step f

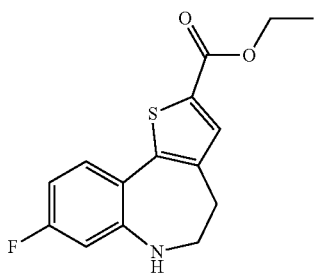 [SMILES: CCOC(=O)c1cc2c(s1)-c1ccc(F)cc1NCC2]

Into a 2000-mL 4-necked round-bottom flask purged and maintained with an inert atmosphere of nitrogen, was placed a solution of the compound from step e (74 g, 223.29 mmol) in dichloromethane (1.2 L) at room temperature. This was followed by the addition of 1,3-dimethyl-1,3-diazinane-2,4,6-trione (70 g, 448.32 mmol) at room temperature. To this was added triphenylphosphane (29 g, 110.57 mmol) at room temperature. To the mixture was added (acetyloxy)palladio acetate (5 g, 22.27 mmol) at room temperature. The resulting solution was stirred overnight at 35° C. The reaction was then quenched by the addition of water (1 L). The resulting solution was extracted with dichloromethane (3×500 mL) and the organic layers combined. The resulting mixture was washed with brine. The mixture was dried over anhydrous sodium sulfate and concentrated under vacuum. The residue was applied onto a silica gel column eluting with ethyl acetate/petroleum ether (1:30) to give the desired product (60 g) as a yellow solid. ESI-MS m/z: 292.0 [M+H]$^+$. $^1$H NMR (300 MHz, CDCl$_3$) δ 1.35-1.39 (m, 3H), 3.04-3.07 (m, 2H), 3.43-3.46 (m, 2H), 4.30-4.37 (m, 2H), 6.34-6.38 (m, 1H), 6.48-6.54 (m, 1H), 7.50 (s, 1H), 7.60-7.66 (m, 1H).

Intermediate 2

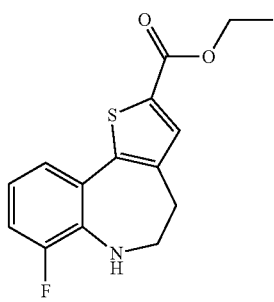 [SMILES: CCOC(=O)c1cc2c(s1)-c1cccc(F)c1NCC2]

Intermediate 2 was prepared using a procedure similar to that used to prepare the intermediate 1 where 2,3-difluorobenzaldehyde was used in place of 2,4-difluorobenzaldehyde. ESI-MS m/z: 292.1 [M+H]$^+$.

Scheme 2

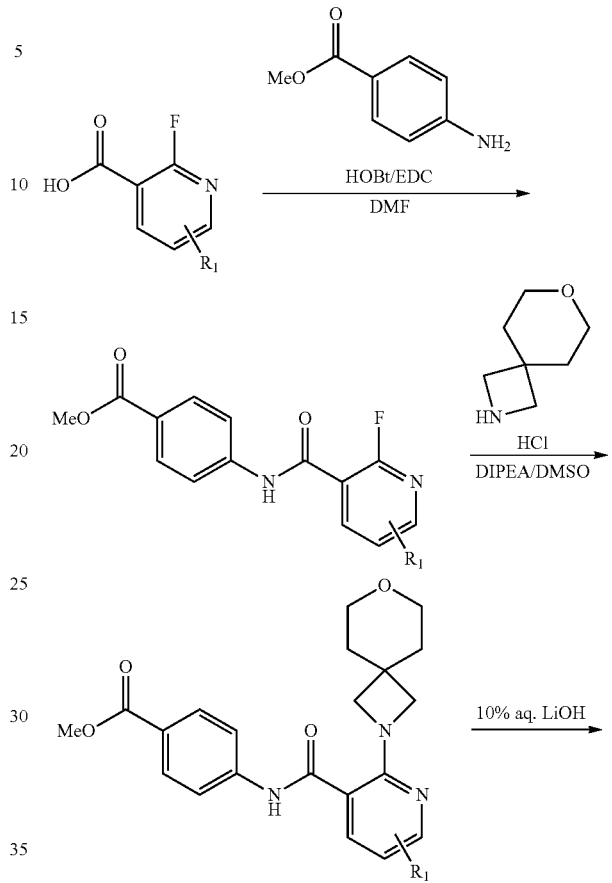

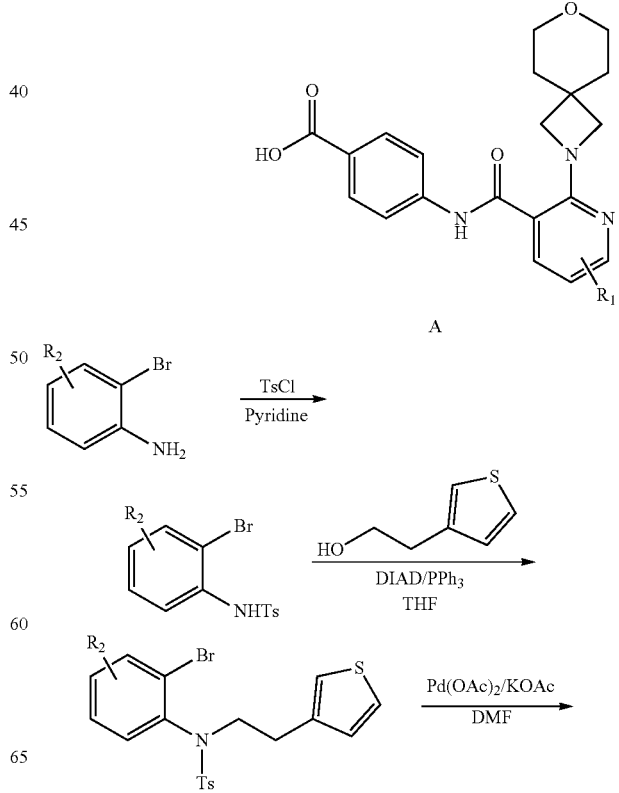

83
-continued

84
-continued

-continued

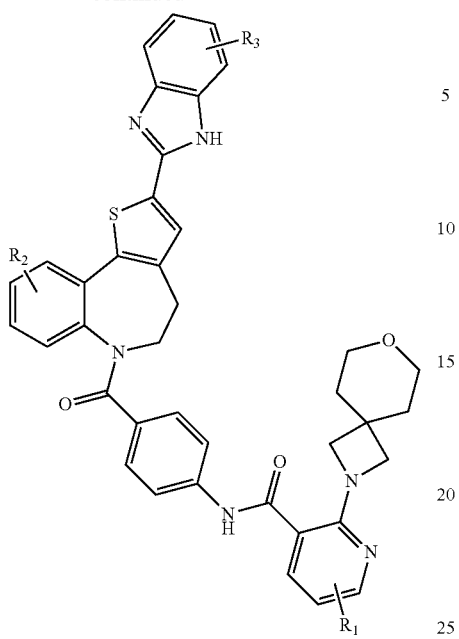

Example 3

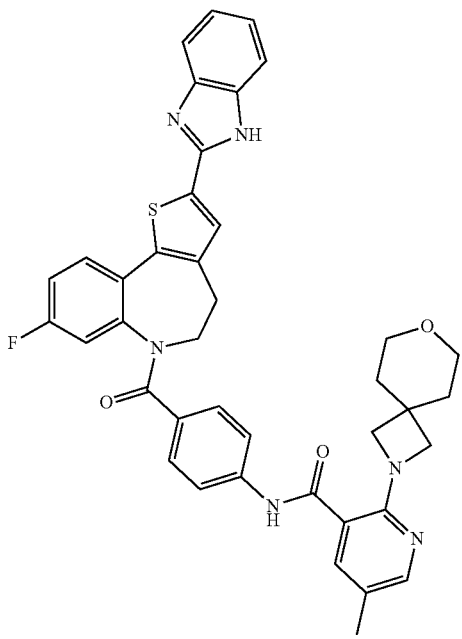 [SMILES: Cc1cnc(N2CC3(CCOCC3)C2)c(C(=O)Nc2ccc(C(=O)N3CCc4cc(-c5nc6ccccc6[nH]5)sc4-c4ccc(F)cc43)cc2)c1]

Example 3

Step a

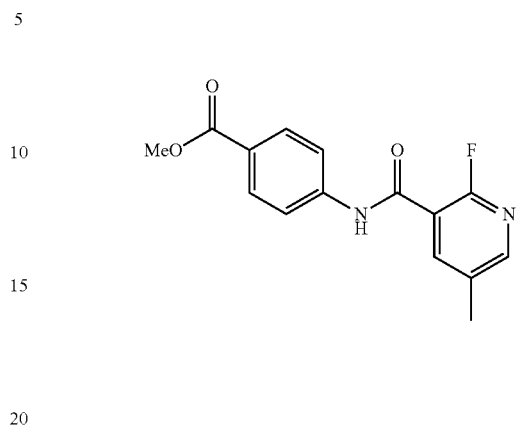

To a cooled to 0° C. mixture of 4-amino-benzoic acid methyl ester (0.930 g, 61.7 mmol) and 2-fluoro-5-methyl-nicotinic acid (10.0 g, 64.5 mmol) was added a solution of HOBt (10.0 g, 74.0 mmol) in dry DMF (100 mL). EDC (11.0 g, 70.9 mmol) was added and the reaction mass was stirred overnight at room temperature. The resulting mixture was poured into cold water (600 mL). The precipitated solid was collected by filtration, washed with water, and dried in vacuum to obtain methyl 4-(2-fluoro-5-methylnicotinamido)benzoate (14.2 g).

Example 3

Step b

A mixture of methyl 4-(2-fluoro-5-methylnicotinamido)benzoate (9.30 g, 32.3 mmol), 7-oxa-2-aza-spiro[3.5]nonane hydrochloride (5.60 g, 34.0 mmol), and DIPEA (7.20 g, 55.7 mmol) in DMSO (50 mL) was stirred at 90° C. for 24 hrs, cooled to room temperature, and diluted with water. The precipitated solid was collected by filtration, washed with water, 2-propanol, and hexane, and dried to obtain the desired product (12.0 g).

Example 3

Step c

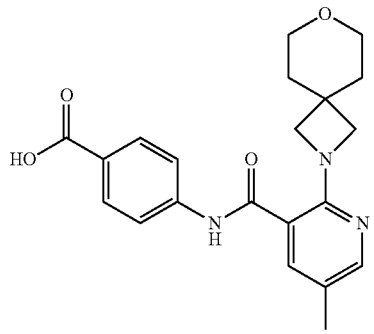 [SMILES: Cc1cnc(N2CC3(CCOCC3)C2)c(C(=O)Nc2ccc(C(=O)O)cc2)c1]

To a solution of methyl 4-(5-methyl-2-(7-oxa-2-azaspiro[3.5]nonan-2-yl)nicotinamido)benzoate (12.0 g, 30.3 mmol) in THF (100 mL), 10% aqueous LiOH (20 mL) was added and the reaction mass was stirred until TLC revealed completion of the reaction (approx. 48 h). The volatiles were evaporated and water (100 mL) was added to the residue. The mixture was acidified to pH 3 with 10% hydrochloric acid and filtered. The obtained solid was washed with water and dried in vacuum to obtain the desired product (9.60 g).

Example 3

Step d

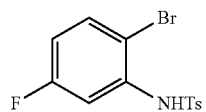

A mixture of 2-bromo-5-fluoroaniline (5.1 g, 26.8 mmol) and TsCl (5.1 g, 26.8 mmol) was stirred in pyridine (0.2 M) for 24 h. The reaction mixture was poured into 5 volumes of water. The product was filtered, washed with water, and dried to provide the desired product (8.78 g) as a white solid.

Example 3

Step e

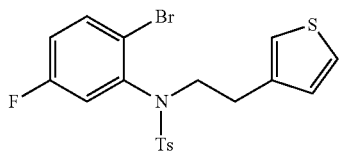 [SMILES: Cc1ccc(S(=O)(=O)N(CCc2ccsc2)c2cc(F)ccc2Br)cc1]

A mixture of N-(2-bromo-5-fluorophenyl)-4-methylbenzenesulfonamide (9.1 g, 26.4 mmol), triphenylphosphine (6.9 g, 26.4 mmol), and 2-(thiophen-3-yl)ethan-1-ol (3.4 g, 26.4 mmol) in dry THF (0.2 M) was stirred at 0° C. DIAD (5.14 mL, 26.4 mmol) was added slowly. Reaction mixture stirred at rt for 1 hour. THF was removed under reduced pressure, and residue was purified on silica gel with 0-100% ethyl acetate:hexanes to provide the desired product (12.0 g).

Example 3

Step f

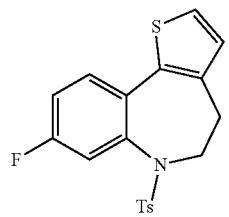 [SMILES: Cc1ccc(S(=O)(=O)N2CCc3ccsc3-c3ccc(F)cc32)cc1]

A mixture of the compound from step e (3.3 g, 7.26 mmol), KOAc (5.0 g, 50.8 mmol), and palladium (II) acetate (163 mg, 0.726 mmol) was heated in dry DMF (0.2 M) at 120° C. for 1 hour under nitrogen gas. After cooling to room temperature, the reaction mixture was poured into 10 volumes of water. The crude product was filtered over celite. The solids were dissolved in ethyl acetate, and concentrated onto solid silica gel. The silica cake was purified by silica gel column chromatography eluting with 0-100% ethyl acetate: hexanes to provide the desired product (2.3 g).

Example 3

Step g

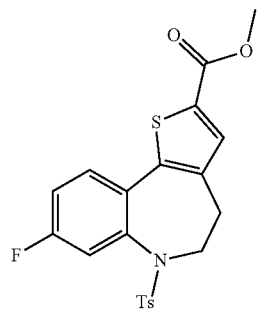 [SMILES: COC(=O)c1cc2c(s1)-c1ccc(F)cc1N(S(=O)(=O)c1ccc(C)cc1)CC2]

A mixture of the compound form f (100 mg, 0.268 mmol), Ru(bpy)$_3$Cl$_2$.6H$_2$O (4 mg, 0.005 mmol), CBr$_4$ (133 mg, 0.402 mmol), and diisopropylamine (54 mg, 0.536 mmol) was stirred in degassed MeOH (0.2 M). The reaction mixture was irradiated with 3W blue LEDs for 48 hours. The methanol was removed under reduced pressure and the product was purified by silica gel column chromatography eluting with 0-100% ethyl acetate:hexanes to provide the desired product (23 mg).

Example 3

Step h

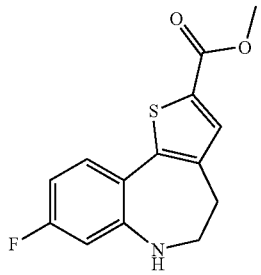 [SMILES: COC(=O)c1cc2c(s1)-c1ccc(F)cc1NCC2]

The compound form step g (110 mg, 0.255 mmol) was stirred in conc. H₂SO₄ (1 mL) at 50° C. for 30 min. The reaction mixture was diluted with 10 volumes of water. The pH was adjusted to 3 by addition of powdered NaOH. The product was extracted with ethyl acetate, concentrated, and the residue was purified by silica gel column chromatography eluting with 0-100% ethyl acetate:hexanes to provide the desired product (63 mg).

Example 3

Step i

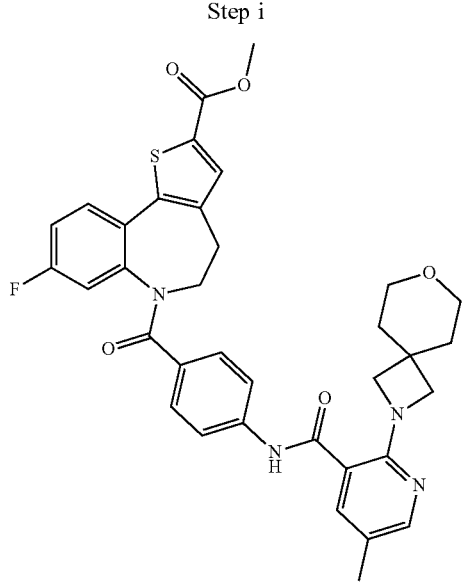

4-(2-(7-Oxa-2-azaspiro[3.5]nonan-2-yl)nicotinamido)benzoic acid (1.00 g, 2.62 mmol) was stirred in DCM (0.5 M). 1-chloro-N,N,2-trimethylprop-1-en-1-amine (1.041 mL, 7.87 mmol) was added at rt. Reaction was stirred for one hour. The DCM was removed under a stream of nitrogen gas and the crude residue was further dried on high vacuum. The crude mixture was dissolved in pyridine (0.2 M). The compound from step h (727 mg, 2.62 mmol) was added and the reaction mixture was stirred at 80° C. for 18 hrs. The pyridine was removed under a stream of nitrogen gas, and the crude residue was partitioned between water and ethyl acetate. The product was extracted with ethyl acetate, and concentrated. The residue was purified by silica gel column chromatography eluting with 0-100% ethyl acetate:hexanes to provide the desired product (1.68 g).

Example 3

Step j

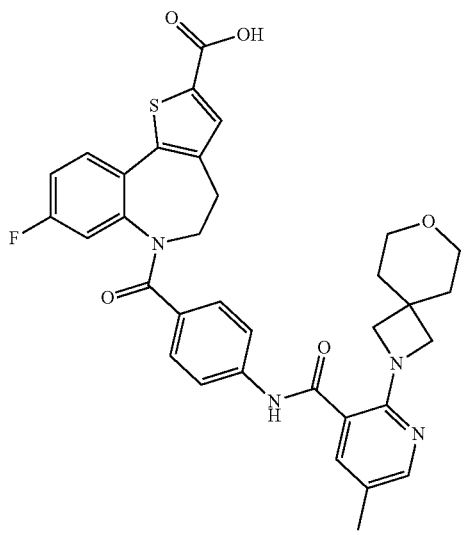

The compound from step i (750 mg, 1.145 mmol) was stirred in methanol (0.5 M). The mixture was diluted with water to a final concentration of 0.4 M. Powdered NaOH (916 mg, 22.91 mmol) was added. Reaction mixture stirred at 50° C. for 1 h. The majority of methanol was removed under a stream of nitrogen gas. The pH was adjusted to 3 by dropwise addition of 4 M aq. HCl. The product was extracted with ethyl acetate, concentrated, and taken on directly to the next step.

Example 3

Step k

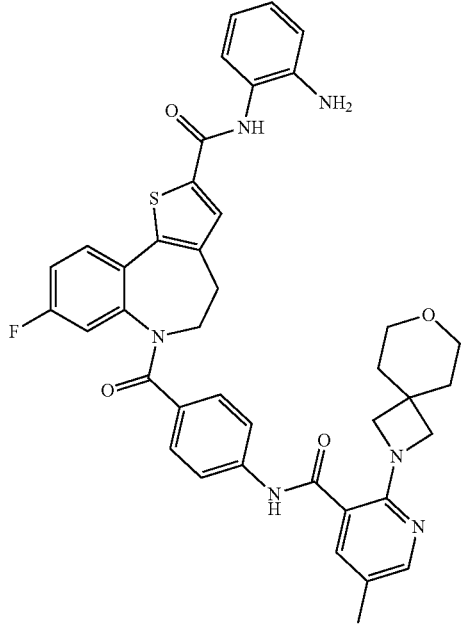 [SMILES: Cc1cnc(N2CC3(CCOCC3)C2)c(C(=O)Nc2ccc(C(=O)N3CCc4cc(C(=O)Nc5ccccc5N)sc4-c4ccc(F)cc43)cc2)c1]

The compound from step j (50 mg, 0.080 mmol) was dissolved in DMF (0.2 M). HATU (36 mg, 0.096 mmol) and DIPEA (0.042 mL, 0.239 mmol) were added, followed by benzene-1,2-diamine (8.6 mg, 0.080 mmol). The reaction mixture was stirred for 1 h at room temperature. The crude product was purified by RP-HPLC to provide the desired product (25 mg). ESI-MS m/z: 717.0 [M+H]$^+$.

Example 3

Step 1

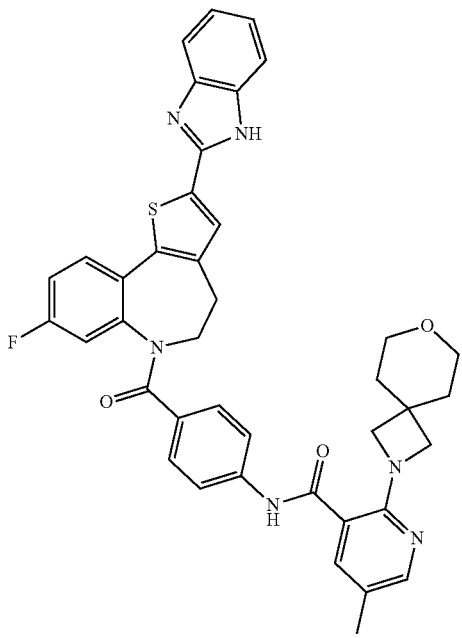 [SMILES: Cc1cnc(N2CC3(CCOCC3)C2)c(C(=O)Nc2ccc(C(=O)N3CCc4cc(-c5nc6ccccc6[nH]5)sc4-c4ccc(F)cc43)cc2)c1]

The compound from step k (25 mg, 0.035 mmol) was dissolved in acetic acid (5 mL). The mixture was heated at 110° C. for 1 h. The acetic acid was removed under a stream of nitrogen gas. The crude product was purified by RP-HPLC to provide the desired compound (31 mg). ESI-MS m/z: 699.0 [M+H]$^+$.

Example 4

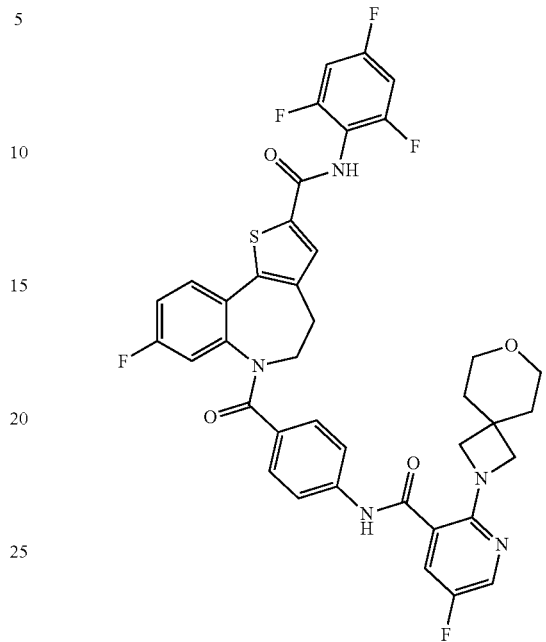

To a mixture of the compound from step j 8 (65 mg, 0.1 mmol) in DCM (0.2 mL) was added 1-chloro-N,N, 2-trimethylprop-1-en-1-amine (41.3 mg, 0.3 mmol) was added and stirred for one hour. After evaporated the solvent and dried in vacuo, the residue was dissolved in pyridine (0.5 mL), treated with 2,4,6-trifluoroaniline (22.7 mg, 0.15 mmol) and stirred at 80° C. for 18 hrs. The pyridine was removed under a stream of N$_2$, and the crude residue was partitioned between water and ethyl acetate. The aqueous layer was extracted with EtOAc. The combine organic layer was washed with water and brine, dried over anhydrous sodium sulfate, filtered and concentrated. The residue was purified by reverse phase prepHPLC to provide the desired compound (45 mg). ESI-MS m/z: 760.0 [M+H]$^+$.

Examples 5-18 shown in table 1 were prepared using the procedure similar to that of example 4 from the corresponding intermediates.

TABLE 1
| Example | Structure | ESI-MS m/z: [M + H]+ |
|---|---|---|
| 5 | 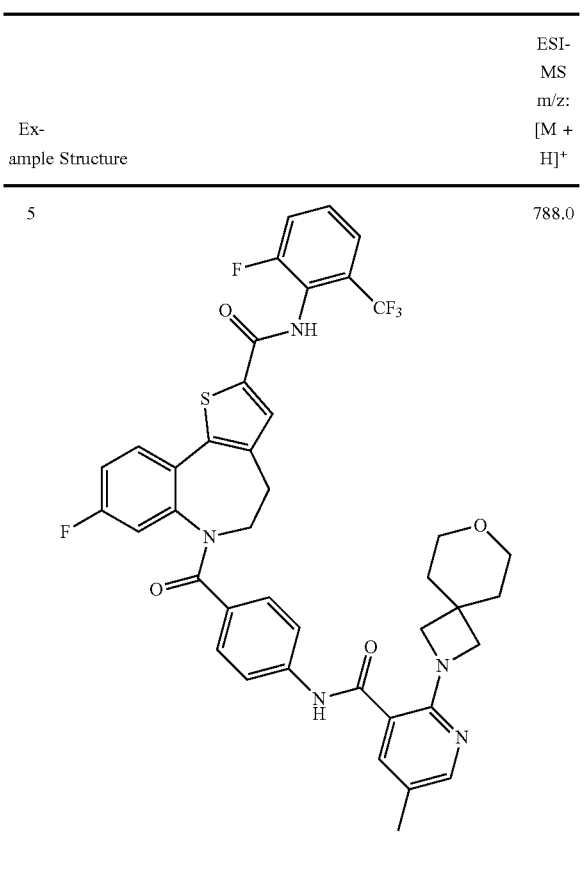 | 788.0 |
| 6 | 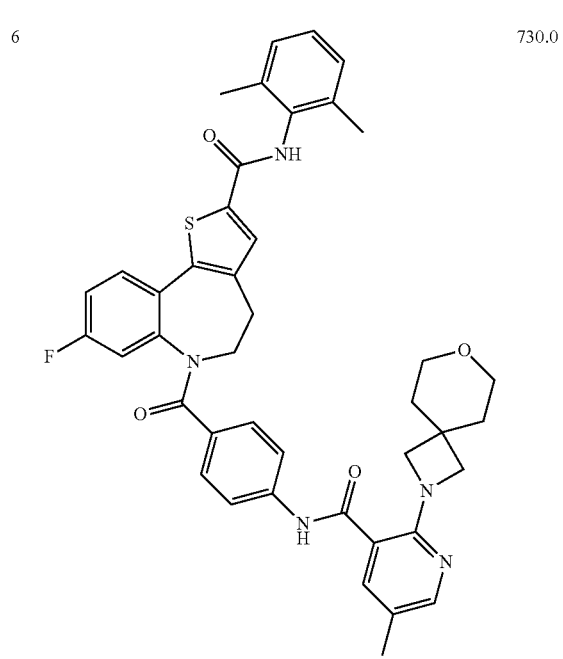 | 730.0 |
TABLE 1-continued
| Example | Structure | ESI-MS m/z: [M + H]+ |
|---|---|---|
| 7 | 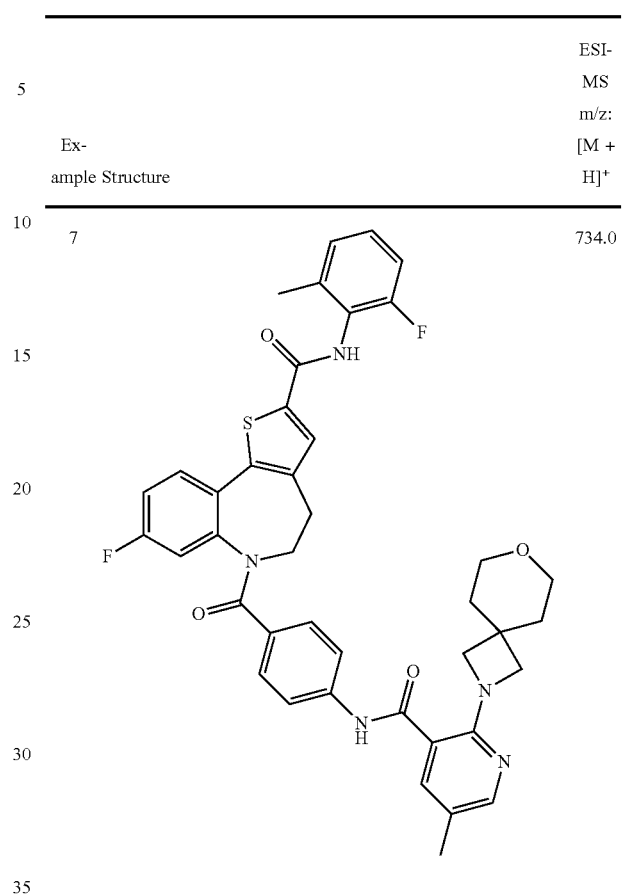 | 734.0 |
| 8 | 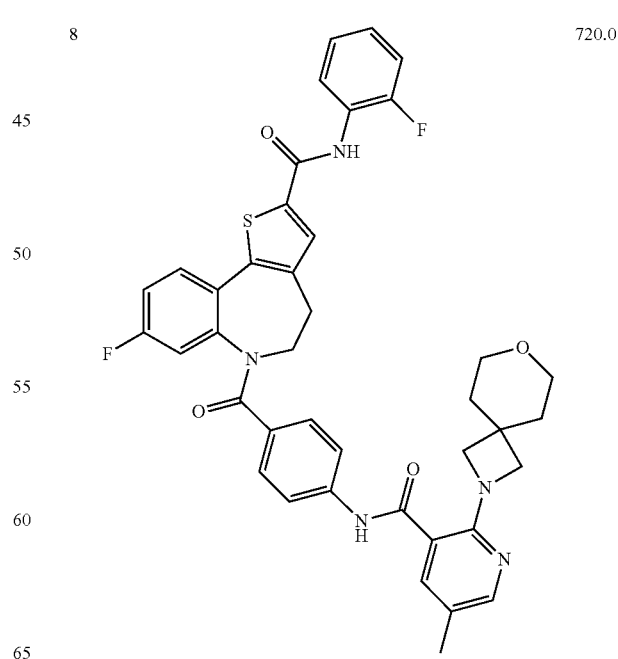 | 720.0 |

TABLE 1-continued
| Example | Structure | ESI-MS m/z: [M + H]+ |
|---|---|---|
| 9 | 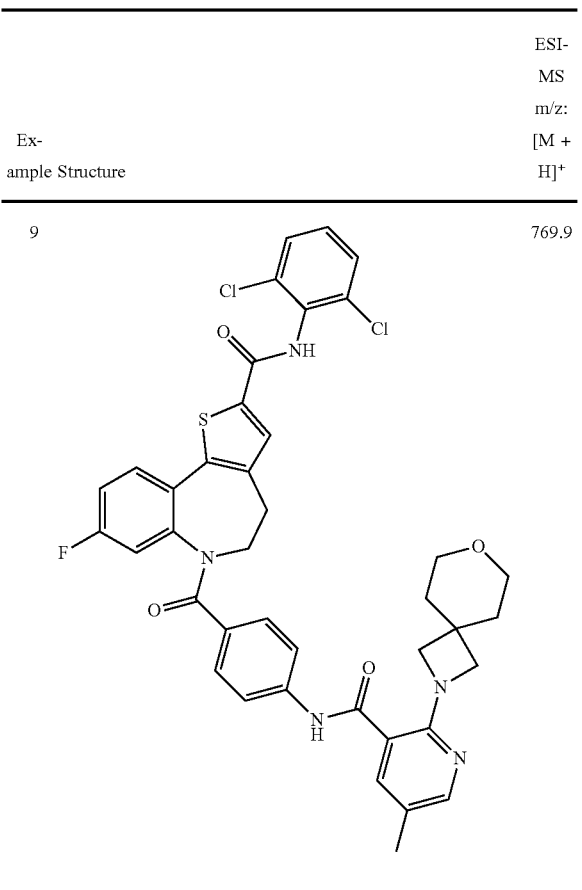 | 769.9 |
| 10 | 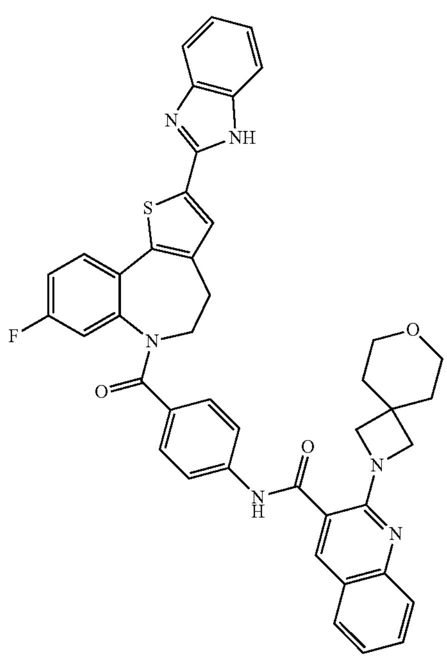 [SMILES: O=C(Nc1ccc(C(=O)N2CCc3cc(-c4nc5ccccc5[nH]4)sc3-c3ccc(F)cc32)cc1)c1cc2ccccc2nc1N1CC2(CCOCC2)C1] | 735.0 |
| 11 | 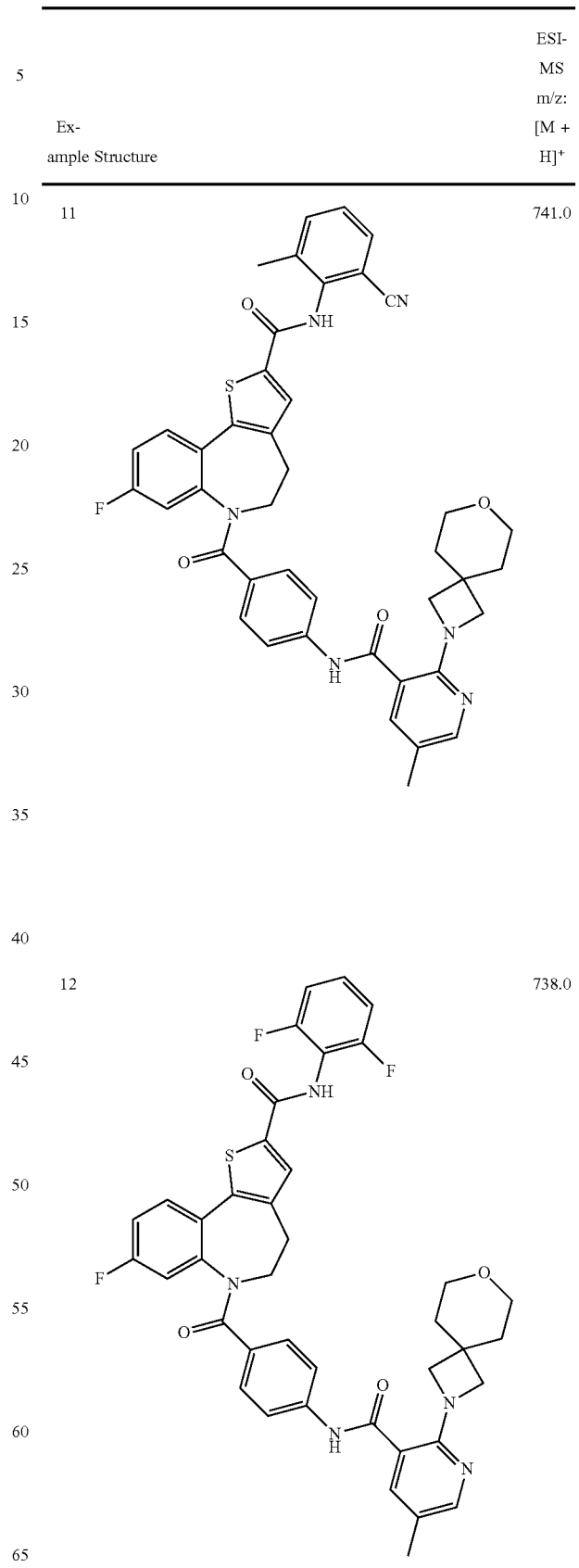 | 741.0 |
| 12 | | 738.0 |

TABLE 1-continued
| Example | Structure | ESI-MS m/z: [M + H]+ |
|---|---|---|
| 13 | 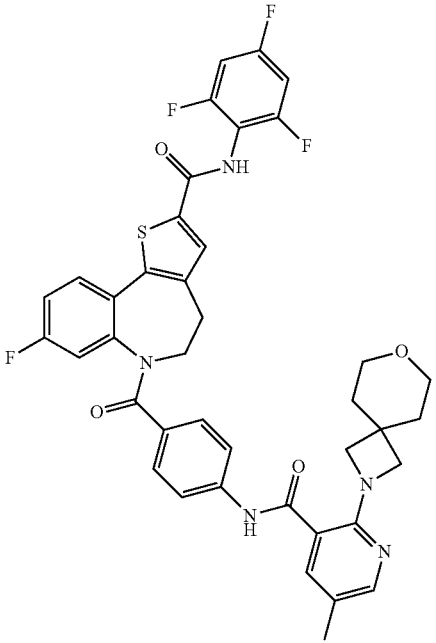 [SMILES: Cc1cnc(N2CC3(CCOCC3)C2)c(C(=O)Nc2ccc(C(=O)N3CCc4cc(C(=O)Nc5c(F)cc(F)cc5F)sc4-c4ccc(F)cc43)cc2)c1] | 756.0 |
| 14 | 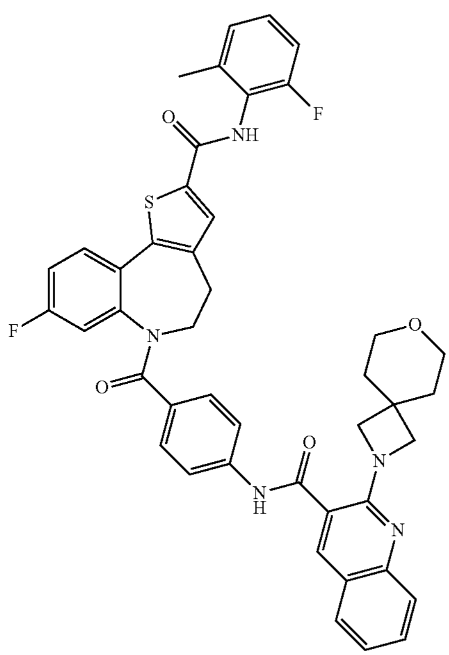 [SMILES: Cc1cccc(F)c1NC(=O)c1cc2c(s1)-c1ccc(F)cc1N(C(=O)c1ccc(NC(=O)c3cc4ccccc4nc3N3CC4(CCOCC4)C3)cc1)CC2] | 770.0 |
| 15 | | 792.0 |
| 16 | | 774.0 |

TABLE 1-continued
| Example | Structure | ESI-MS m/z: [M + H]+ |
|---|---|---|
| 17 | 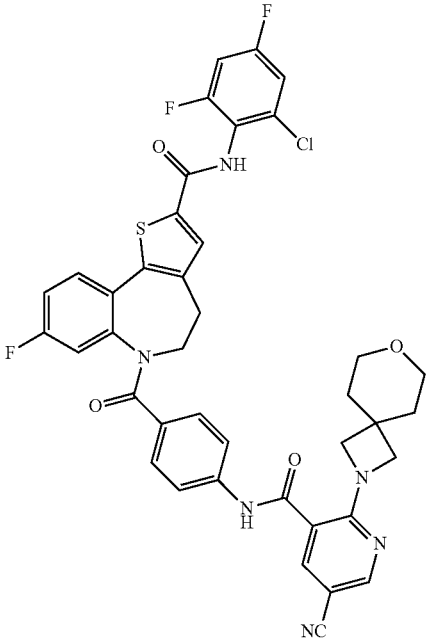 [SMILES: N#Cc1cnc(N2CC3(CCOCC3)C2)c(C(=O)Nc2ccc(C(=O)N3CCc4cc(C(=O)Nc5c(F)cc(F)cc5Cl)sc4-c4ccc(F)cc43)cc2)c1] | 783.0 |
| 18 | 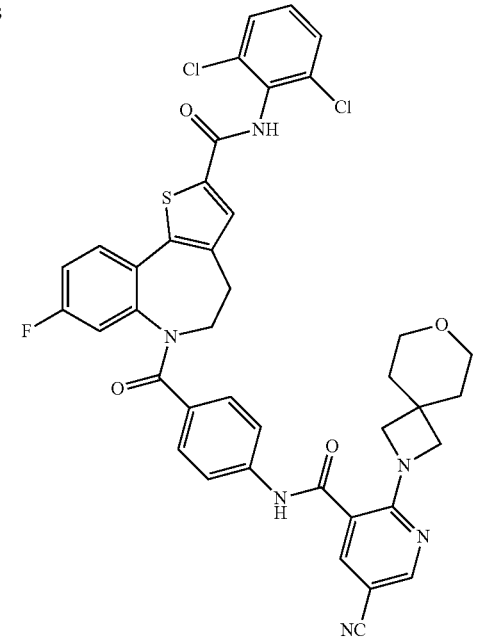 | 781.0 |
Scheme 3
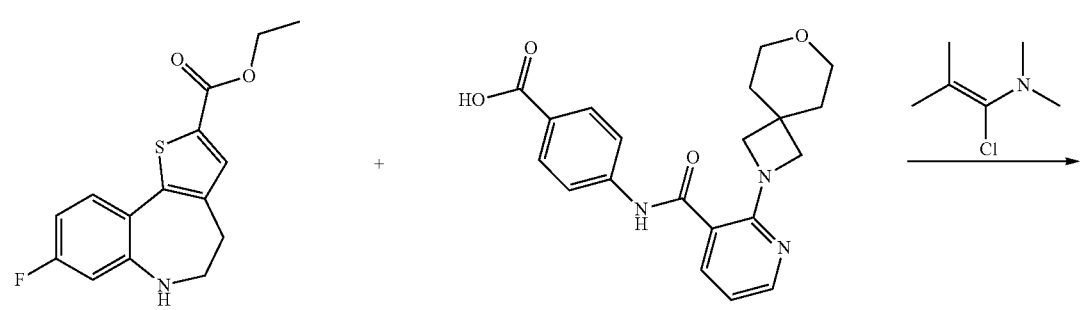

-continued
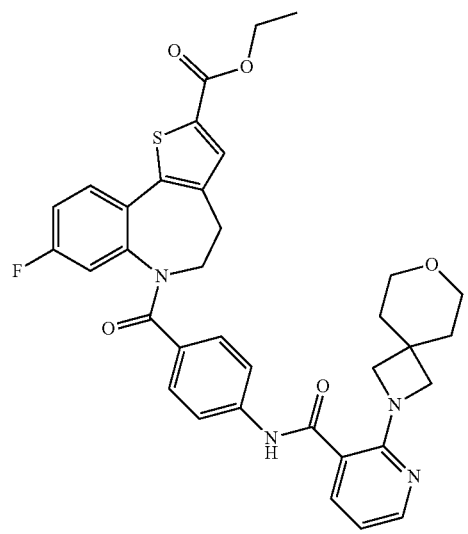
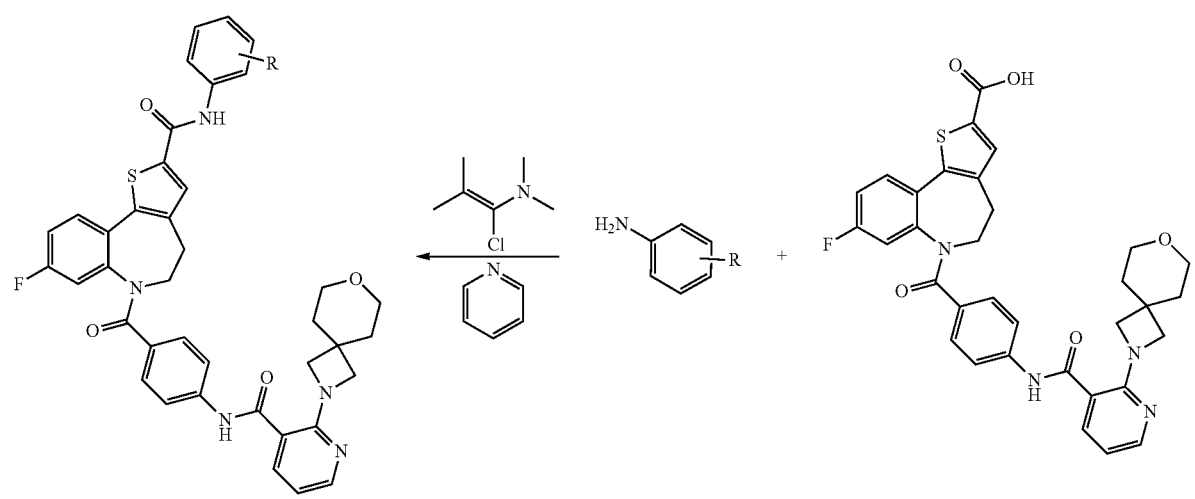

Example 19

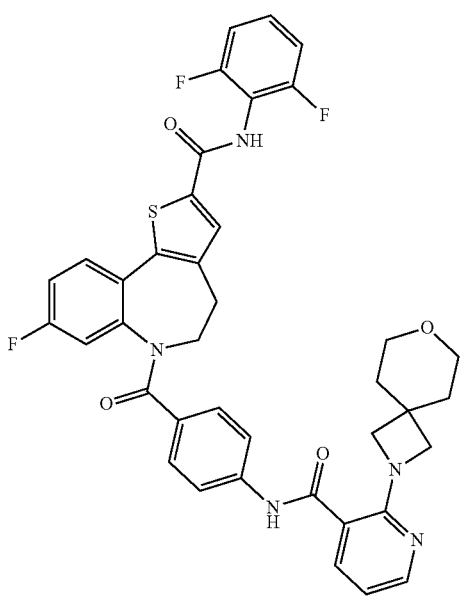 [SMILES: O=C(Nc1c(F)cccc1F)c1cc2c(s1)-c1ccc(F)cc1N(C(=O)c1ccc(NC(=O)c3cccnc3N3CC4(CCOCC4)C3)cc1)CC2]

Example 19

Step a

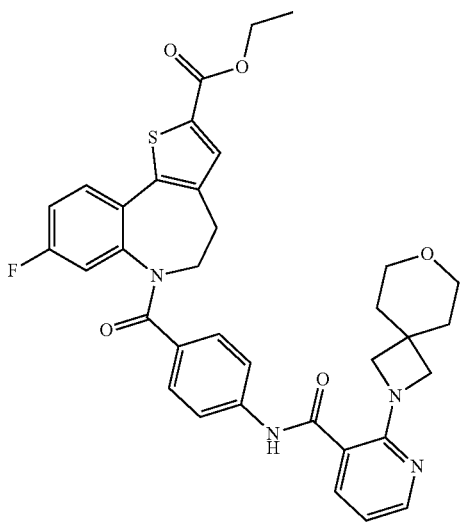 [SMILES: CCOC(=O)c1cc2c(s1)-c1ccc(F)cc1N(C(=O)c1ccc(NC(=O)c3cccnc3N3CC4(CCOCC4)C3)cc1)CC2]

To a solution of 4-(2-(7-oxa-2-azaspiro[3.5]nonan-2-yl)nicotinamido)benzoic acid (1.38 g, 3.78 mmol) in DCM (50 mL) was added 1-chloro-N,N, 2-trimethylprop-1-en-1-amine (0.92 g, 6.86 mmol). The reaction mixture was stirred at rt for 30 min and was then concentrated in vacuo. The resulting residue was taken into DCM (50 mL) and a solution of ethyl 8-fluoro-5,6-dihydro-4H-benzo[b]thieno[2,3-d]azepine-2-carboxylate (1.0 g, 3.43 mmol) in pyridine (2 mL) and DCM (5 mL) was added. After stirred at rt for 16 hrs, the mixture was partitioned between DCM (200 mL) and brine (50 mL). The organic layer was dried, filtered, evaporated, and purified by combiflash eluting with 0-4% DCM/MeOH to obtain the desired product (1.91 g) as a white solid. ESI-MS m/z: 641.2 [M+H]⁺.

Example 19

Step b

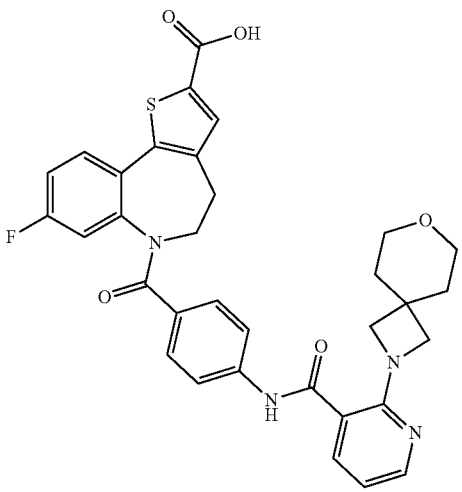

To a solution of compound from step a (120 mg, 0.187 mmol) in MeOH (1 mL) was added LiOH (44.8 mg, 1.87 mmol) in water (0.5 mL). The resulting mixture was stirred at 50° C. for 1 h. The mixture was adjusted to pH ~5 with 1N HCl. The white precipitated solid was filtered and dried in oven at 50° C. overnight to obtain the desired product (96 mg) as a white solid. ESI-MS m/z: 613.2 [M+H]⁺.

Example 19

Step c

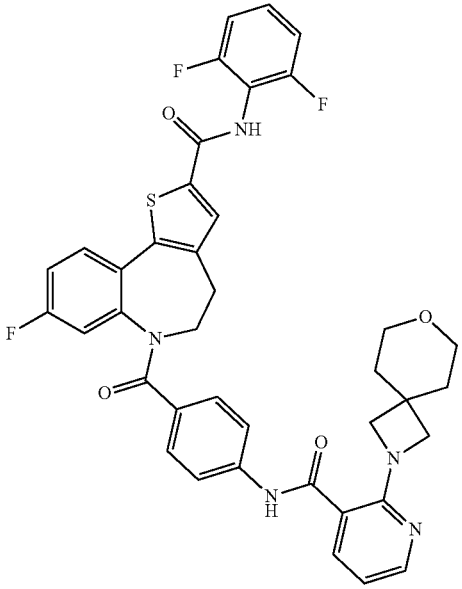 [SMILES: O=C(Nc1c(F)cccc1F)c1cc2c(s1)-c1ccc(F)cc1N(C(=O)c1ccc(NC(=O)c3cccnc3N3CC4(CCOCC4)C3)cc1)CC2]

To a solution of compound from step b (100 mg, 0.163 mmol) in DCM (10 mL), 1-chloro-N,N, 2-trimethylprop-1-en-1-amine (43.6 mg, 0.326 mmol) was added. The reaction mixture was stirred at rt for 30 min and was then concentrated in vacuo. The resulting residue was taken into DCM (6 mL) and a solution of 2,6-difluoroaniline (25.3 mg, 0.196 mmol) in pyrindine (0.5 mL) and DCM (2 mL) was added. After stirred at rt for 16 hrs, the mixture was partitioned between DCM (50 mL) and brine (20 mL). The organic layer was dried, filtered, evaporated, and purified by combiflash elurting with 0-4% DCM/MeOH to obtain the desired product (102 mg, 85%) as a white foam. ESI-MS m/z: 724.2 [M+H]$^+$.

Examples 20-22 shown in table 2 were prepared using the procedure similar to that of example 4 from the corresponding intermediates.

TABLE 2

| Example | Structure | ESI-MS m/z: [M + H]$^+$ |
|---|---|---|
| 20 | | 740.2 |
| 21 | 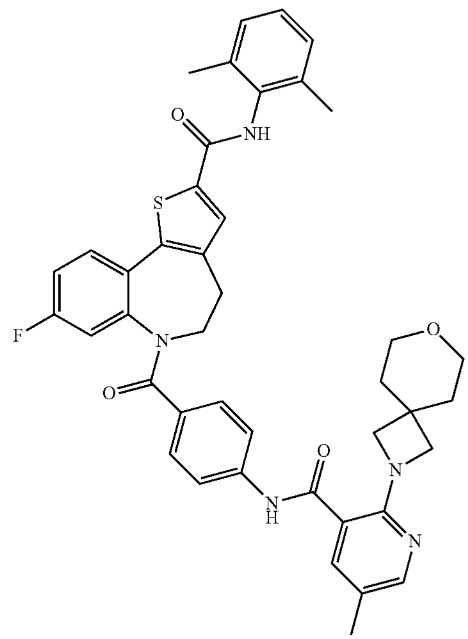 [SMILES: Cc1cnc(N2CC3(CCOCC3)C2)c(C(=O)Nc2ccc(C(=O)N3CCc4cc(C(=O)Nc5c(C)cccc5C)sc4-c4ccc(F)cc43)cc2)c1] | 758.2 |
| 22 | 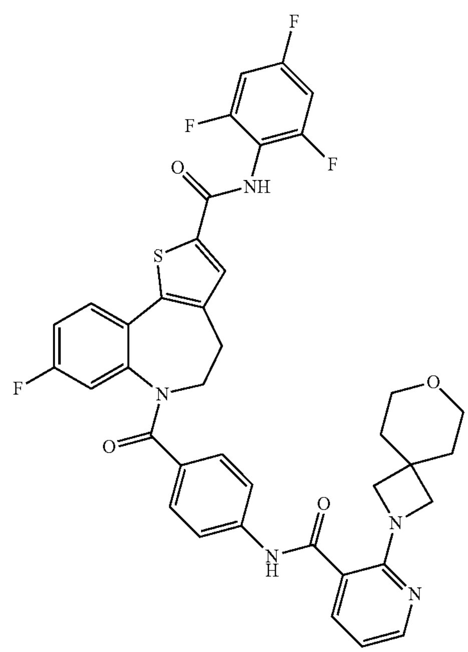 [SMILES: O=C(Nc1c(F)cc(F)cc1F)c1cc2c(s1)-c1ccc(F)cc1N(C(=O)c1ccc(NC(=O)c3cccnc3N3CC4(CCOCC4)C3)cc1)CC2] | 742.2 |

107
Scheme 4
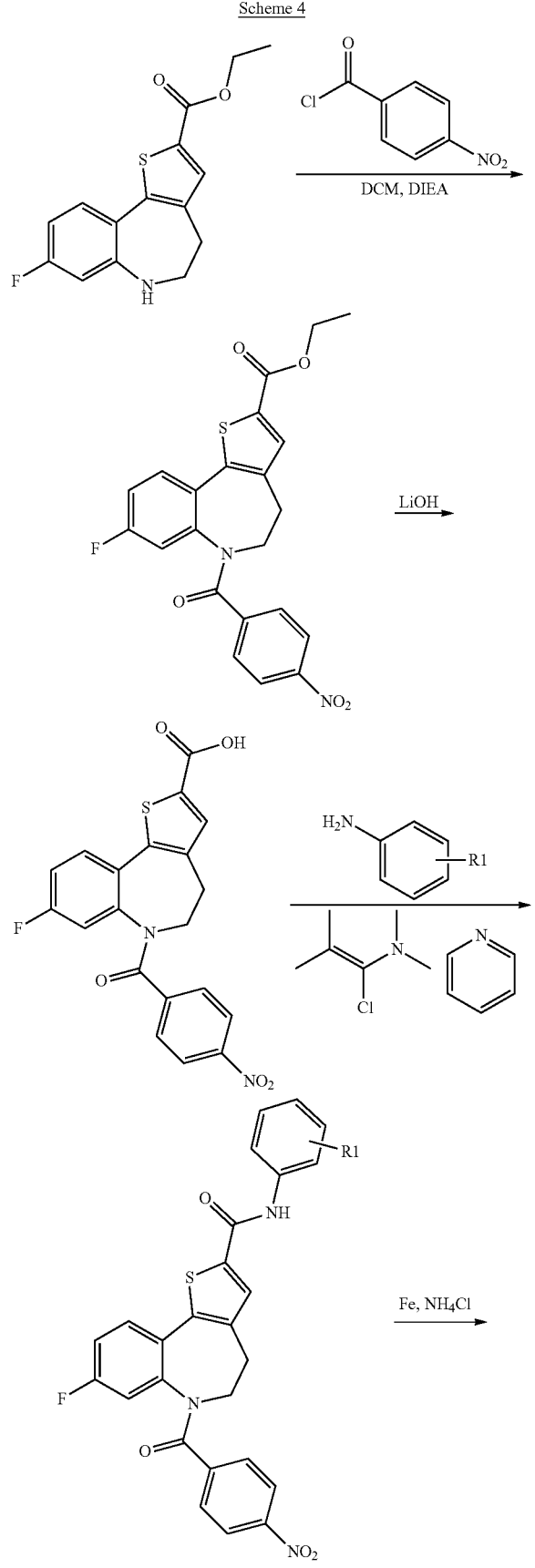
108
-continued
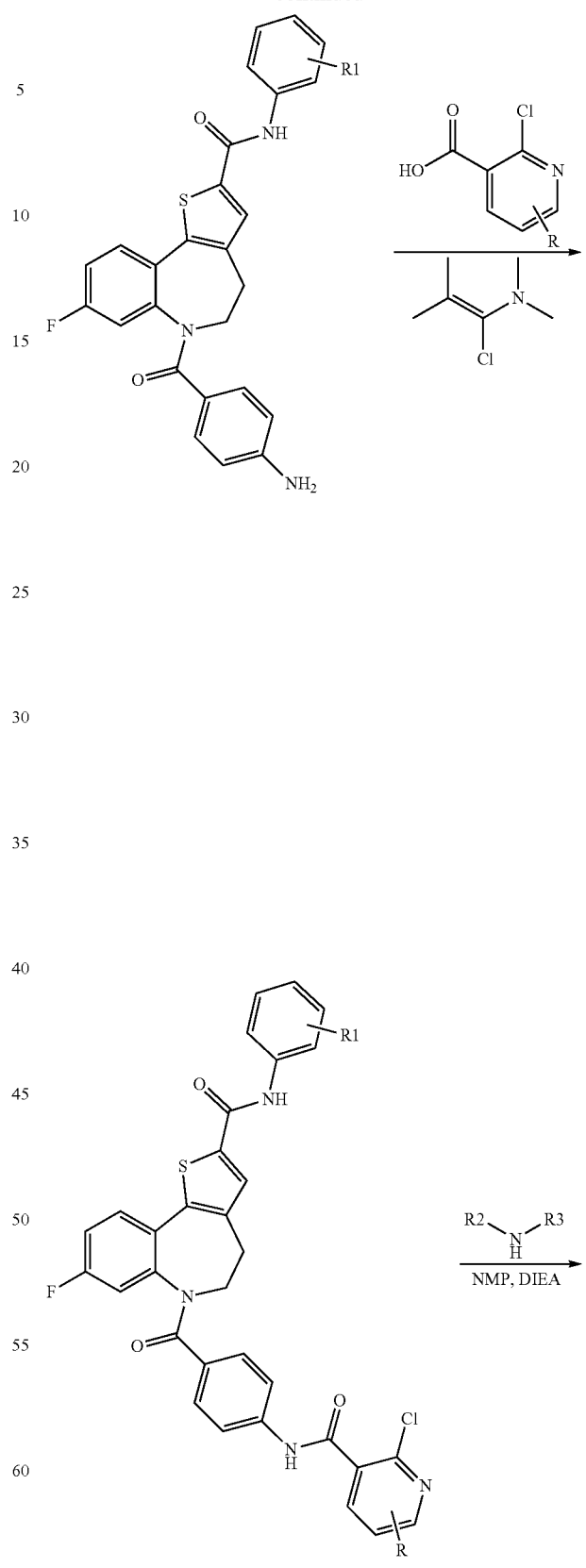

109
-continued

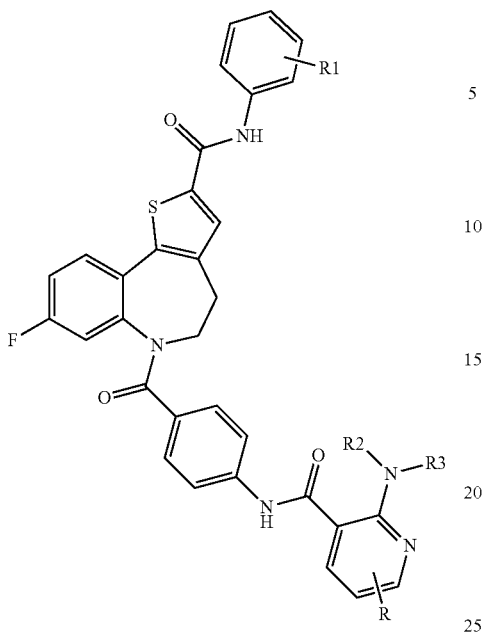

Example 23

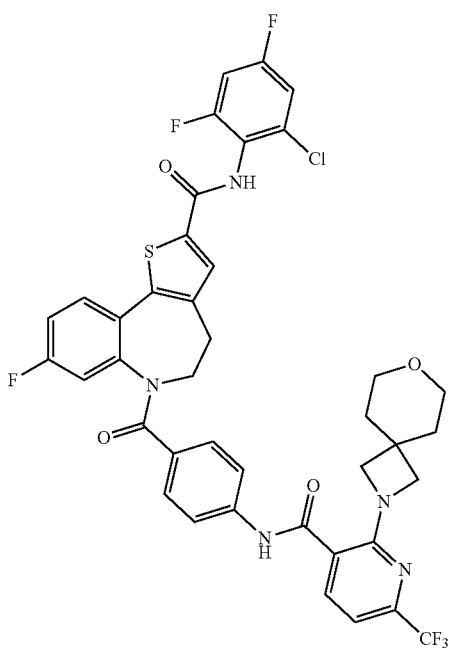 [SMILES: O=C(Nc1c(F)cc(F)cc1Cl)c1cc2c(s1)-c1ccc(F)cc1N(C(=O)c1ccc(NC(=O)c3ccc(C(F)(F)F)nc3N3CC4(CCOCC4)C3)cc1)CC2]

110

Example 23

Step a

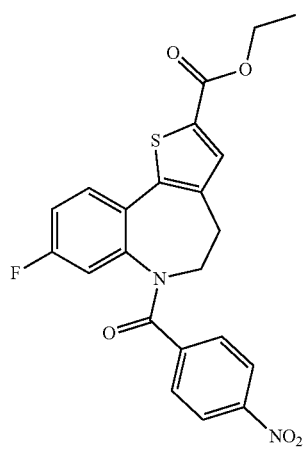 [SMILES: CCOC(=O)c1cc2c(s1)-c1ccc(F)cc1N(C(=O)c1ccc([N+](=O)[O-])cc1)CC2]

Ethyl 8-fluoro-5,6-dihydro-4H-benzo[b]thieno[2,3-d] azepine-2-carboxylate (800 mg, 2.75 mmol) and 4-nitrobenzoyl chloride (611 mg, 3.30 mmol) were dissolved in DCM (25 mL), then DIEA (1 mL) was slowly added. The reaction mixture was stirred at rt for 16 hrs. After being diluted with DCM (100 mL), the organic layer was washed with brine, dried and evaporated. The residue was purified by combi-flash eluting with 0-30% EtOAc/hexanes to obtain the desired product (1.17 g) as a pale yellow solid. ESI-MS m/z: 441.1 [M+H]$^+$.

Example 23

Step b

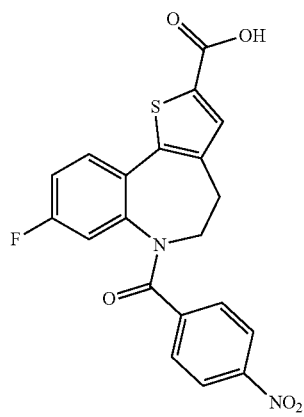 [SMILES: O=C(O)c1cc2c(s1)-c1ccc(F)cc1N(C(=O)c1ccc([N+](=O)[O-])cc1)CC2]

To a solution of compound from step (1.15 g, 2.61 mmol) a in MeOH (60 mL), LiOH (0.625 g, 26.1 mmol) in water (20 mL) was slowly added. The resulting mixture was heated at 55° C. and stirred for 3 hrs. After cooled down, the mixture was adjusted to pH ~5 with 1N HCl. The white precipitated solid was filtered and dried in oven at 55° C. overnight to obtain the desired product (1.0 g) as a pale yellow solid.

Example 23

Step c

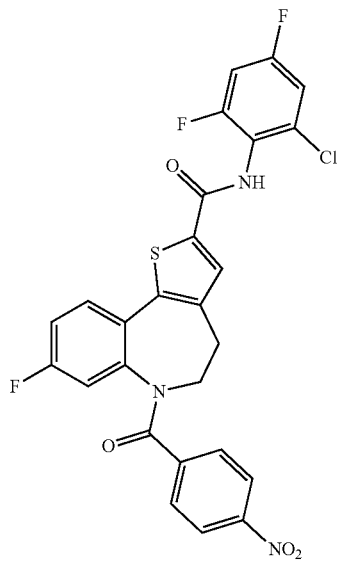 [SMILES: O=C(Nc1c(F)cc(F)cc1Cl)c1cc2c(s1)-c1ccc(F)cc1N(C(=O)c1ccc([N+](=O)[O-])cc1)CC2]

To a solution of compound from step b (500 mg, 1.21 mmol) in DCM (30 mL) was added 1-chloro-N,N, 2-trimethylprop-1-en-1-amine in DCM (2 mL). The reaction mixture was stirred at rt for 30 min and was then concentrated in vacuo. The resulting residue was taken into DCM (30 mL) and a solution of 2-chloro-4,6-difluoroaniline (297 mg, 1.82 mmol) in pyrindine (1.5 mL) and DCM (5 mL) was added. After stirred at rt for 16 hrs, the mixture was partitioned between DCM (100 mL) and brine (20 mL). The organic layer was separated, dried, evaporated, and purified by combiflash eluting with 0-45% EtOAc/hexanes to obtain the desired product (590 mg) as a colorless oil. ESI-MS m/z: 558.1 [M+H]$^+$.

Example 23

Step d

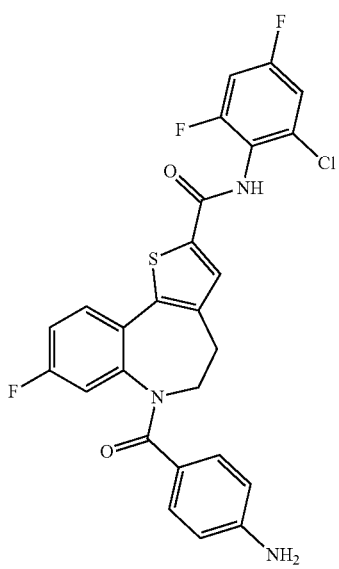

The compound from step c (1.50 g, 2.69 mmol) was dissolved in EtOH/water (150 mL, 2:1), then iron (0.75 g, 13.4 mmol) and ammonium chloride (1.44 g, 26.9 mmol) were added. The resulting mixture was heated at 80° C. for 2 hrs. After cooled to rt and filtered through a celite pad, the pad was washed with EtOAc (100 mL). The mixture was neutralized to pH 8 by adding sat NaHCO$_3$, the organic layer was separated and washed with brine, dried and concentrated to provide the desired product (1.4 g) as pale yellow foam. ESI-MS m/z: 528.1 [M+H]$^+$.

Example 23

Step e

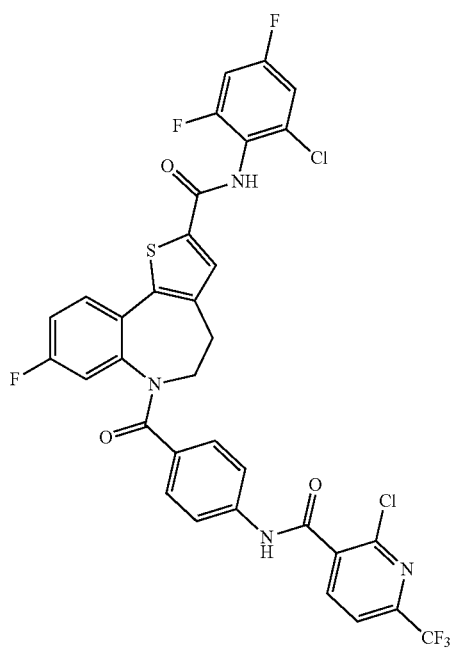 [SMILES: O=C(Nc1c(F)cc(F)cc1Cl)c1cc2c(s1)-c1ccc(F)cc1N(C(=O)c1ccc(NC(=O)c3ccc(C(F)(F)F)nc3Cl)cc1)CC2]

Example 23

Step f

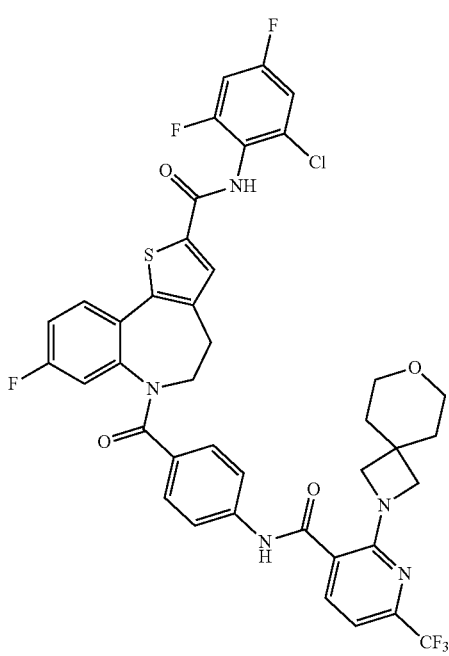 [SMILES: O=C(Nc1c(F)cc(F)cc1Cl)c1cc2c(s1)-c1ccc(F)cc1N(C(=O)c1ccc(NC(=O)c3ccc(C(F)(F)F)nc3N3CC4(CCOCC4)C3)cc1)CC2]

To a solution of 2-chloro-6-(trifluoromethyl)nicotinic acid (51.3 mg, 0.23 mmol) in DCM (5 mL) was added 1-chloro-N,N, 2-trimethylprop-1-en-1-amine (50.6 mg, 0.38 mmol). The reaction mixture was stirred at rt for 30 min and was then concentrated in vacuo. The resulting residue was taken into DCM (10 mL) and a solution of compound from step e (100 mg, 0.19 mmol) in pyridine (0.2 mL) and DCM (4 mL) was added. After stirred at rt for 16 hrs, the reaction mixture was diluted with DCM (150 mL). The Organic layer was washed with brine (50 mL), dried, filtered and evaporated. The residue was purified by combiflash eluting with 0-40% EtOAc/hexanes to obtain the desired product (77.2 mg) as white foam. ESI-MS m/z: 735.1 [M+H]$^+$.

The mixture of compound from step f (80 mg, 0.11 mmol), 7-oxa-2-azaspiro[3.5]nonane hydrochloride (53.4 mg, 0.33 mmol) and DIPEA (0.2 mL) was heated at 150° C. for 2 hrs. After cooled down and diluted with EtOAc (100 mL), the organic layer was washed with water (50 mL×3), brine (50 mL), dried, filtered and evaporated. The residue was purified by combiflash eluting with 0-3% MeOH/DCM to afford the desired product (17 mg) as a pale yellow solid. ESI-MS m/z: 826.2 [M+H]$^+$.

Examples 24-27 shown in table 3 were prepared using the procedure similar to that of Example 23 from the corresponding intermediates.

TABLE 3
| Example | Structure | ESI-MS m/z: [M + H]+ |
|---|---|---|
| 24 | 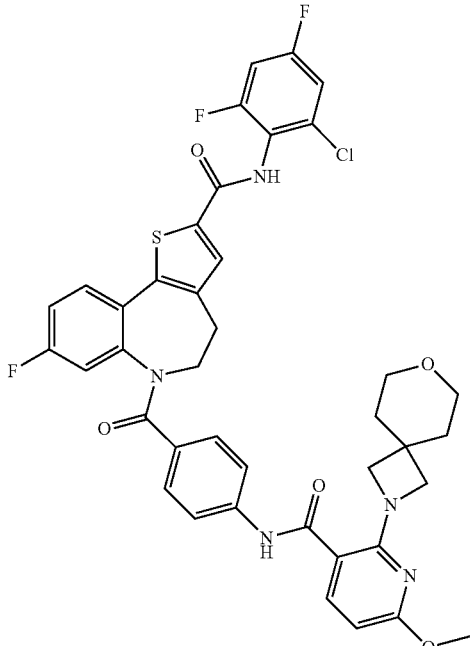 | 788.2 |
| 25 | 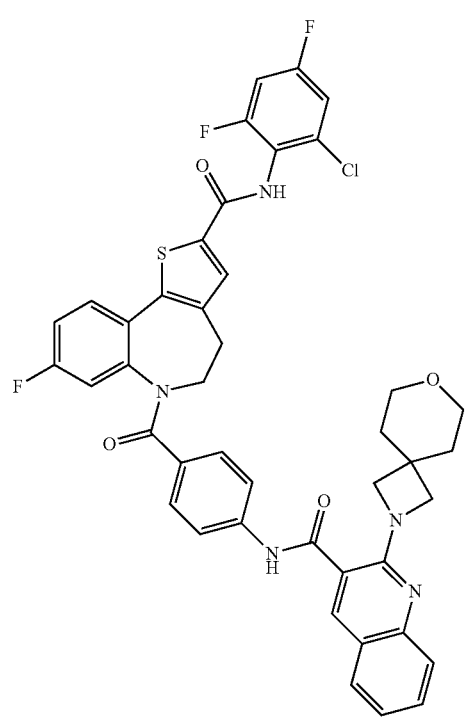 [SMILES: O=C(Nc1c(F)cc(F)cc1Cl)c1cc2c(s1)-c1ccc(F)cc1N(C(=O)c1ccc(NC(=O)c3cc4ccccc4nc3N3CC4(CCOCC4)C3)cc1)CC2] | 808.2 |

TABLE 3-continued
| Example | Structure | ESI-MS m/z: [M + H]+ |
|---|---|---|
| 26 | 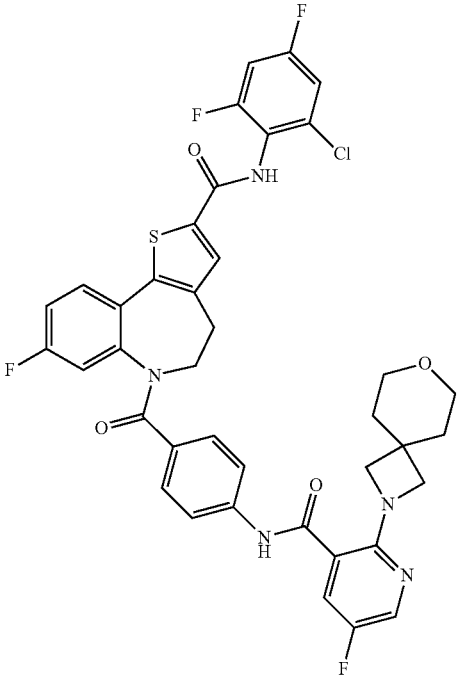 [SMILES: O=C(Nc1c(F)cc(F)cc1Cl)c1cc2c(s1)-c1ccc(F)cc1N(C(=O)c1ccc(NC(=O)c3cc(F)cnc3N3CC4(CCOCC4)C3)cc1)CC2] | 776.2 |
| 27 | 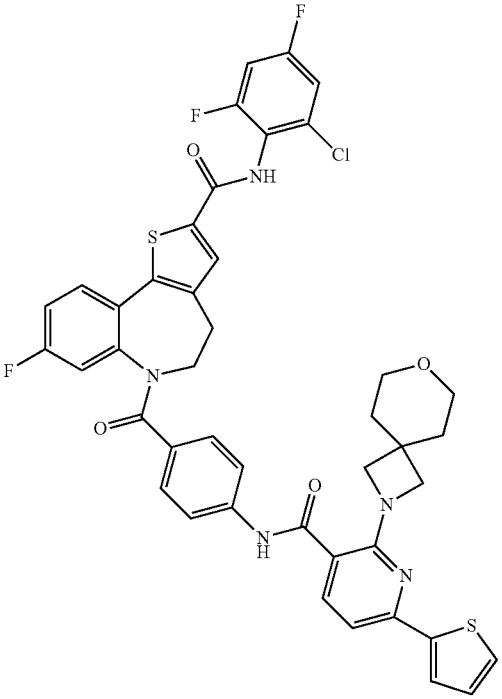 [SMILES: O=C(Nc1c(F)cc(F)cc1Cl)c1cc2c(s1)-c1ccc(F)cc1N(C(=O)c1ccc(NC(=O)c3ccc(-c4cccs4)nc3N3CC4(CCOCC4)C3)cc1)CC2] | 840.2 |

Example 28

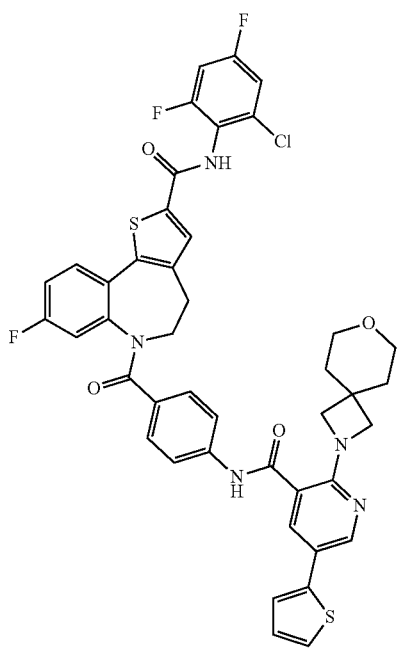 [SMILES: O=C(Nc1c(F)cc(F)cc1Cl)c1cc2c(s1)-c1ccc(F)cc1N(C(=O)c1ccc(NC(=O)c3cc(-c4cccs4)cnc3N3CC4(CCOCC4)C3)cc1)CC2]

Example 28

Example 28

Step a

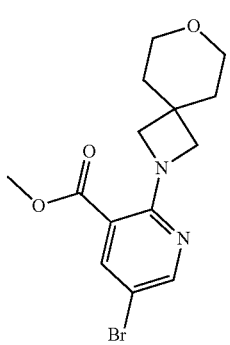 [SMILES: COC(=O)c1cc(Br)cnc1N1CC2(CCOCC2)C1]

To a suspension of methyl 5-bromo-2-chloronicotinate (300 mg, 1.2 mmol) and 7-oxa-2-azaspiro[3.5]nonane hydrochloride (392 mg, 2.4 mmol) was added DIPEA (1.6 mL), the resulting mixture was heated at 80° C. for 2 hrs. After cooled down, the mixture was poured into EtOAc (150 mL) which was washed with water, brine, dried and concentrated. The residue was purified by silica gel column chromatography eluting with 0-30% EtOAc/hexanes to obtain the desired product (360 mg) as yellowish oil. ESI-MS m/z: 341.0 [M+H]$^+$.

Example 28

Step b

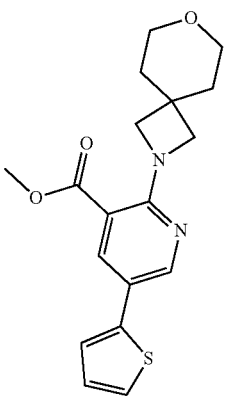 [SMILES: COC(=O)c1cc(-c2cccs2)cnc1N1CC2(CCOCC2)C1]

To a round-bottomed flask bottomed flask were charged with bromide from step a (250 mg, 0.733 mmol), 4,4,5,5-tetramethyl-2-(thiophen-2-yl)-1,3,2-dioxaborolane (169 mg, 0.806 mmol), Pd(PPh$_3$)$_2$Cl$_2$ (25.7 mg, 0.037 mmol) and potassium carbonate (506 mg, 3.66 mmol) in a mixed solvent [DME/EtOH/H$_2$O (2/2/1, 12.5 mL)]. The reaction mixture was degassed and heated at 85° C. with vigorous stirring. After 4 hrs, the reaction mixture was cooled to room temperature and diluted with ethyl acetate (50 mL). The organic layer was washed with brine, dried over Na$_2$SO$_4$, filtered and concentrated. The residue was purified by silica gel column chromatography eluting with 0-50% EtOAv/hexanes to give the desired compound (250 mg, 99%) as yellowish oil. ESI-MS m/z: 345.1 [M+H]+.

Example 28

Step c

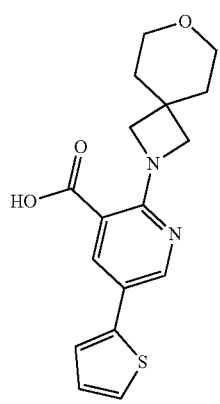 [SMILES: O=C(O)c1cc(-c2cccs2)cnc1N1CC2(CCOCC2)C1]

To suspension of methyl ester from step 2 (240 mg, 0.697 mmol) in THF/MeOH (1/1, 10 mL) was added LiOH (167 mg, 6.97 mmol) in water (5 mL). The resulting mixture was heated at 50° C. for 2 hrs and the reaction was completed. Evaporated most of THF and MeOH, diluted with 5 mL water, cooled down to 0° C., and neutralized to pH ~3 with aq. 1 M HCl. The mixture was extracted with DCM/MeOH (20:1, 100 mL×2), and the organic layers were dried and evaporated to afford the desired product (220 mg, 96%) as a yellowish foam. ESI-MS m/z: 331.1 [M+H]+.

Example 28

Step d

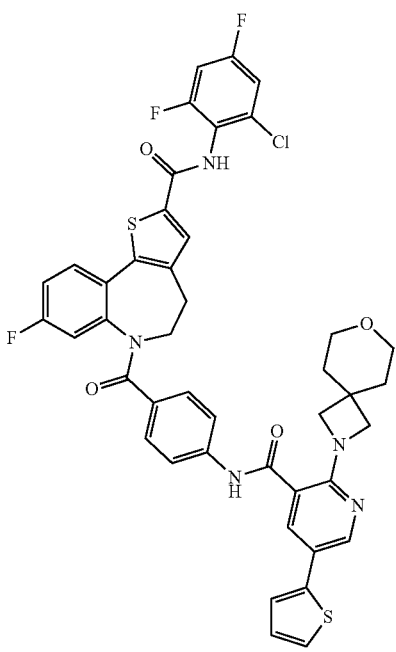 [SMILES: O=C(Nc1c(F)cc(F)cc1Cl)c1cc2c(s1)-c1ccc(F)cc1N(C(=O)c1ccc(NC(=O)c3cc(-c4cccs4)cnc3N3CC4(CCOCC4)C3)cc1)CC2]

To a mixture of 2-(7-oxa-2-azaspiro[3.5]nonan-2-yl)-5-(thiophen-2-yl)nicotinic acid (140 mg, 0.424 mmol) in DCM (5 mL) was added 1-chloro-N,N, 2-trimethylprop-1-en-1-amine (113 mg, 0.847 mmol) and stirred at rt for 1 hr and concentrated in vacuo. The resulting residue was taken into DCM (4 mL) and cooled to 0° C., then, a solution of 6-(4-aminobenzoyl)-N-(2-chloro-4,6-difluorophenyl)-8-fluoro-5,6-dihydro-4H-benzo[b]thieno[2,3-d]azepine-2-carboxamide (224 mg, 0.424 mmol) in pyridine (0.2 mL) and DCM (2 mL) was added. After being stirred at rt for 16 hrs, the mixture was evaporated and purified by combiflash eluting with 0-5% MeOH/DCM to provide the desired product (160 mg) as a brownish foam. ESI-MS m/z: 840.17 [M+H]$^+$.

Examples 29-37 shown in table 4 were prepared using the procedure similar to that of Example 28 from the corresponding intermediates.

TABLE 4

| Example | Structure | ESI-MS m/z: [M + H]$^+$ |
|---------|-----------|-------------------------|
| 29 | 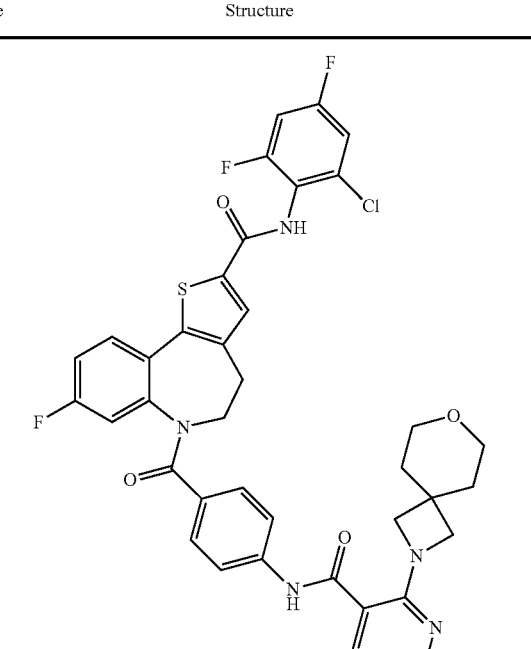 | 826.2 |

TABLE 4-continued
| Example | Structure | ESI-MS m/z: [M + H]+ |
|---|---|---|
| 30 | 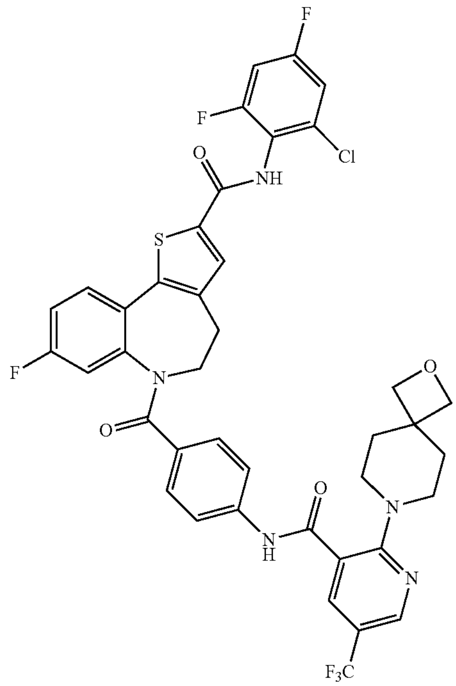 [SMILES: O=C(Nc1c(F)cc(F)cc1Cl)c1cc2c(s1)-c1ccc(F)cc1N(C(=O)c1ccc(NC(=O)c3cc(C(F)(F)F)cnc3N3CCC4(CC3)COC4)cc1)CC2] | 826.2 |
| 31 | 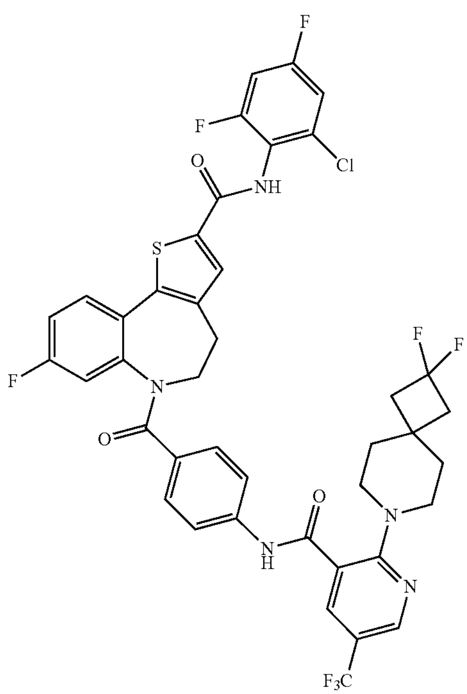 [SMILES: O=C(Nc1c(F)cc(F)cc1Cl)c1cc2c(s1)-c1ccc(F)cc1N(C(=O)c1ccc(NC(=O)c3cc(C(F)(F)F)cnc3N3CCC4(CC3)CC(F)(F)C4)cc1)CC2] | 842.2 |
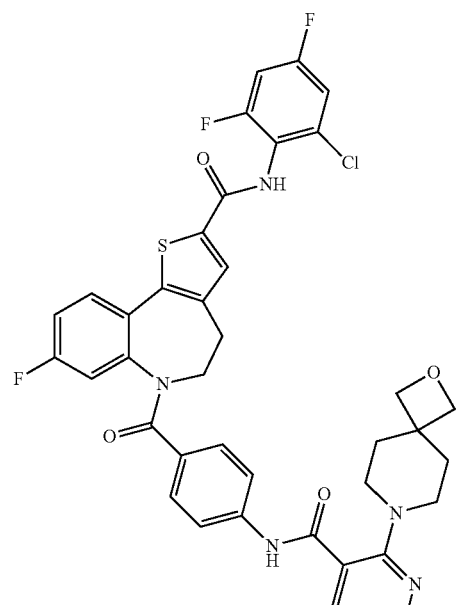

TABLE 4-continued
| Example | Structure | ESI-MS m/z: [M + H]+ |
|---|---|---|
| 32 | 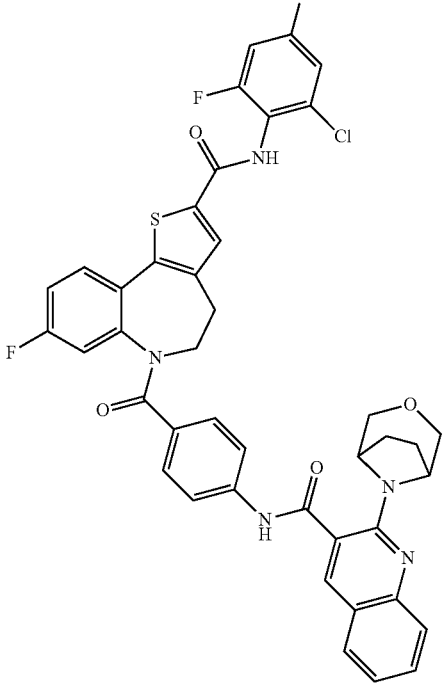 | 794.2 |
| 33 | 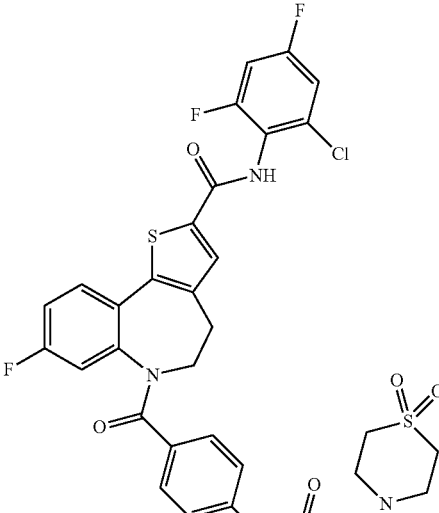 | 816.1 |

TABLE 4-continued

| Example | Structure | ESI-MS m/z: [M + H]+ |
|---------|-----------|----------------------|
| 34 | 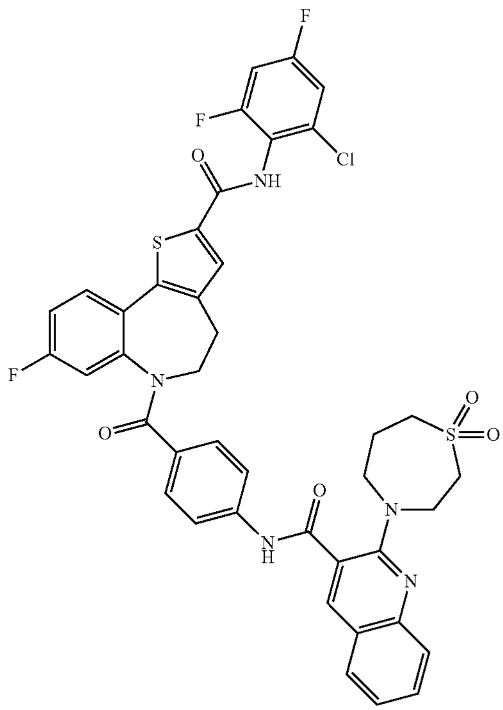 [SMILES: O=C(Nc1c(F)cc(F)cc1Cl)c1cc2c(s1)-c1ccc(F)cc1N(C(=O)c1ccc(NC(=O)c3cc4ccccc4nc3N3CCCS(=O)(=O)CC3)cc1)CC2] | 830.2 |
| 35 | 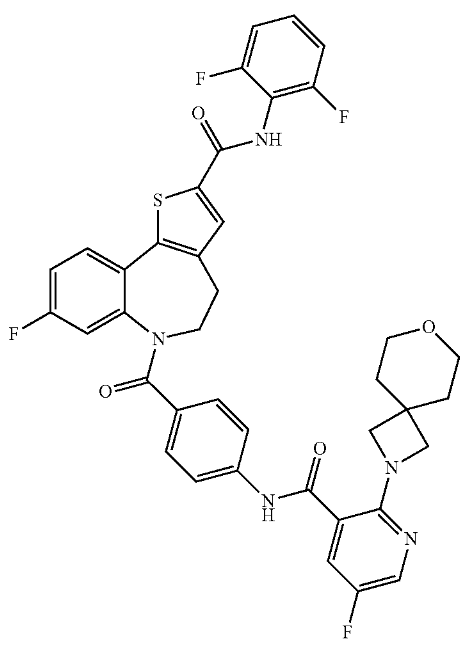 [SMILES: O=C(Nc1c(F)cccc1F)c1cc2c(s1)-c1ccc(F)cc1N(C(=O)c1ccc(NC(=O)c3cc(F)cnc3N3CC4(CCOCC4)C3)cc1)CC2] | 742.2 |

TABLE 4-continued
| Example | Structure | ESI-MS m/z: [M + H]+ |
|---|---|---|
| 36 | 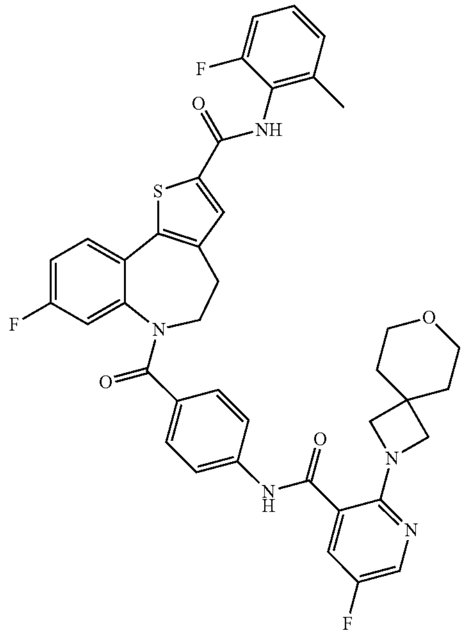 [SMILES: Cc1cccc(F)c1NC(=O)c1cc2c(s1)-c1ccc(F)cc1N(C(=O)c1ccc(NC(=O)c3cc(F)cnc3N3CC4(CCOCC4)C3)cc1)CC2] | 738.3 |
| 37 | 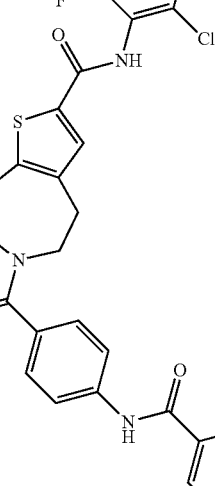 | 758.2 |
Examples 38-44 shown in table 5 were prepared using the procedure similar to that of example 3 (step k and l) from the corresponding intermediates.

TABLE 5

| Example | Structure | ESI-MS m/z: [M + H]+ |
|---|---|---|
| 38 | 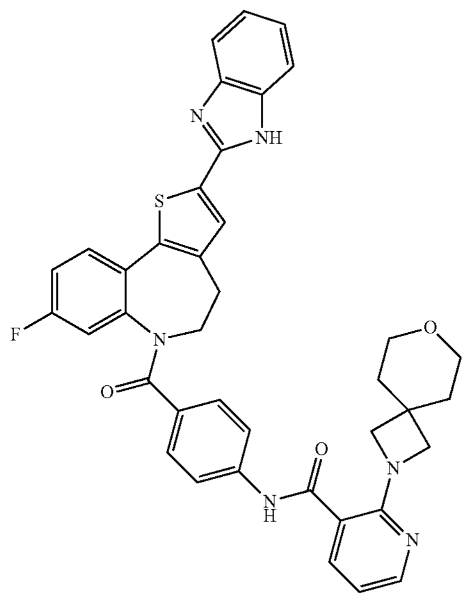 [SMILES: O=C(Nc1ccc(C(=O)N2CCc3cc(-c4nc5ccccc5[nH]4)sc3-c3ccc(F)cc32)cc1)c1cccnc1N1CC2(CCOCC2)C1] | 685.2.2 |
| 39 | 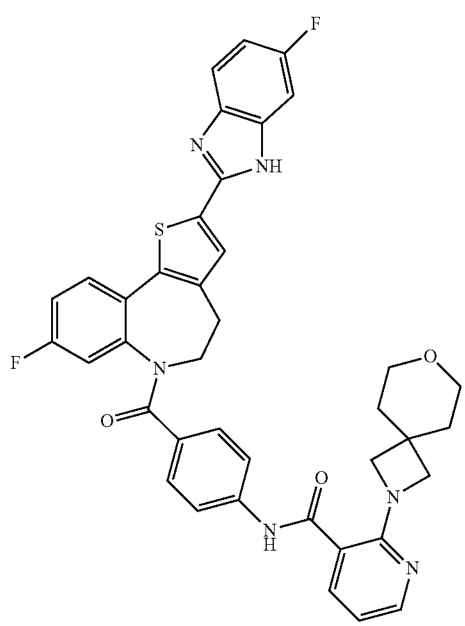 [SMILES: O=C(Nc1ccc(C(=O)N2CCc3cc(-c4nc5ccc(F)cc5[nH]4)sc3-c3ccc(F)cc32)cc1)c1cccnc1N1CC2(CCOCC2)C1] | 703.2 |

TABLE 5-continued

| Example | Structure | ESI-MS m/z: [M + H]+ |
|---|---|---|
| 40 | 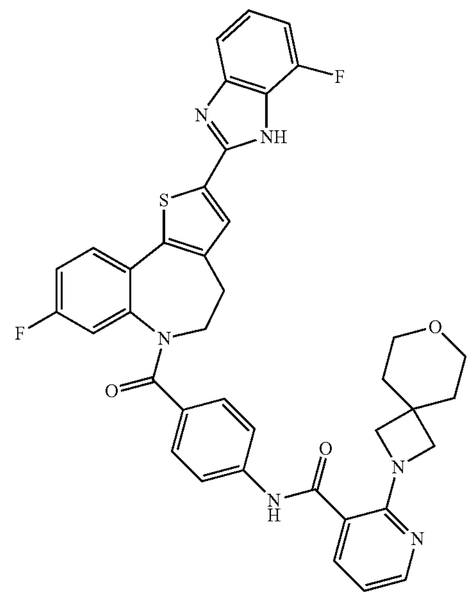 [SMILES: O=C(Nc1ccc(C(=O)N2CCc3cc(-c4nc5cccc(F)c5[nH]4)sc3-c3ccc(F)cc32)cc1)c1cccnc1N1CC2(CCOCC2)C1] | 703.2 |
| 41 | 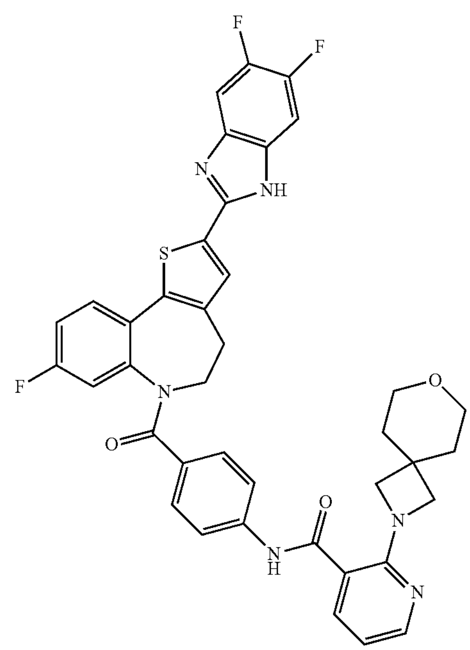 [SMILES: O=C(Nc1ccc(C(=O)N2CCc3cc(-c4nc5cc(F)c(F)cc5[nH]4)sc3-c3ccc(F)cc32)cc1)c1cccnc1N1CC2(CCOCC2)C1] | 721.2 |

TABLE 5-continued
| Example | Structure | ESI-MS m/z: [M + H]+ |
|---|---|---|
| 42 | 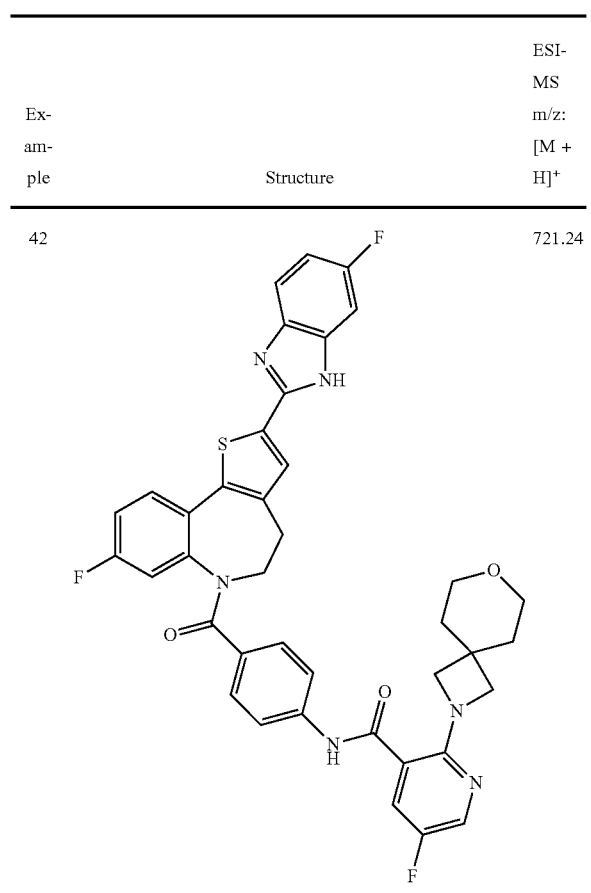 | 721.24 |
| 43 | 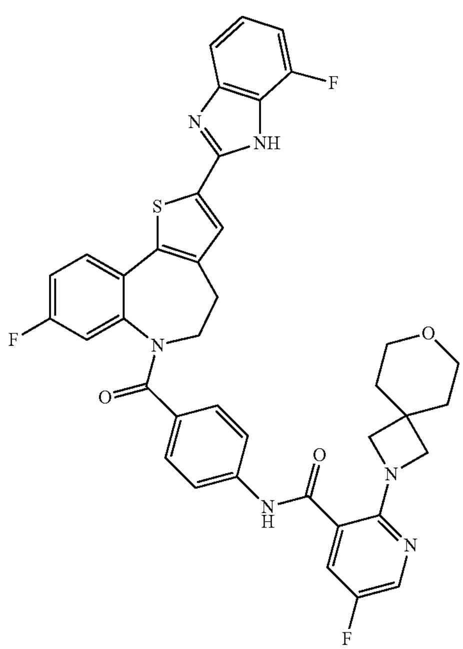 [SMILES: O=C(Nc1ccc(C(=O)N2CCc3cc(-c4nc5cccc(F)c5[nH]4)sc3-c3ccc(F)cc32)cc1)c1cc(F)cnc1N1CC2(CCOCC2)C1] | 721.24 |
| 44 | 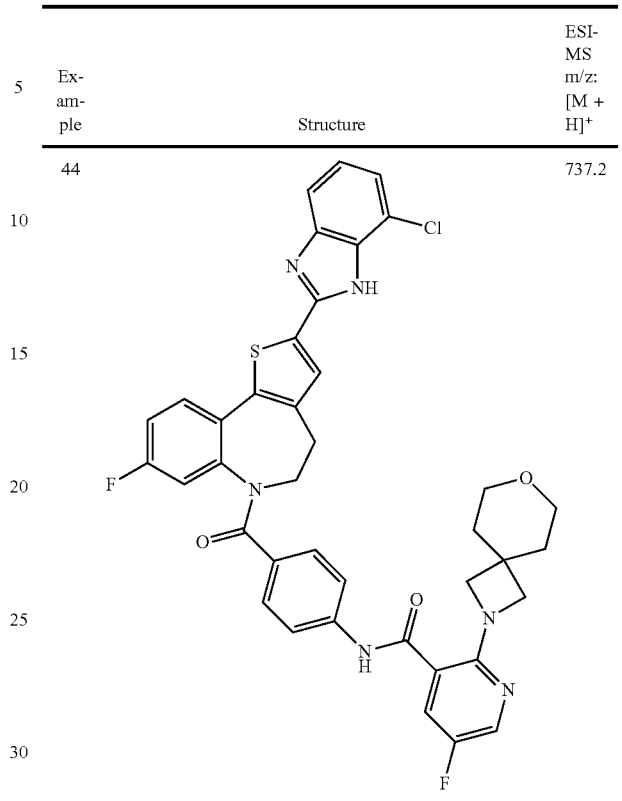 | 737.2 |
Scheme 4
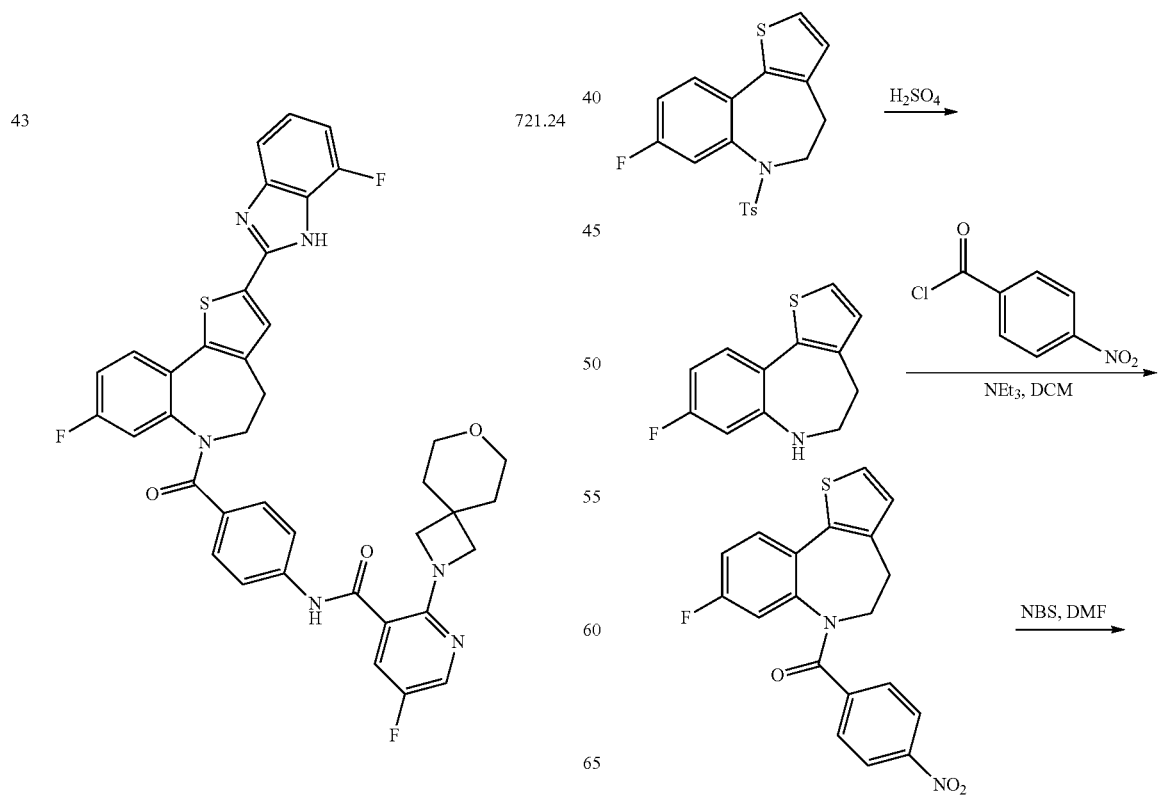

135

-continued

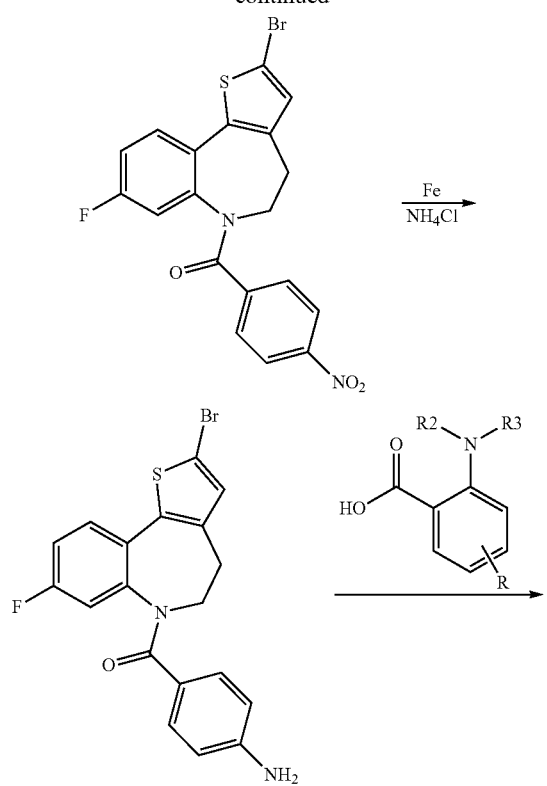

136

Example 45

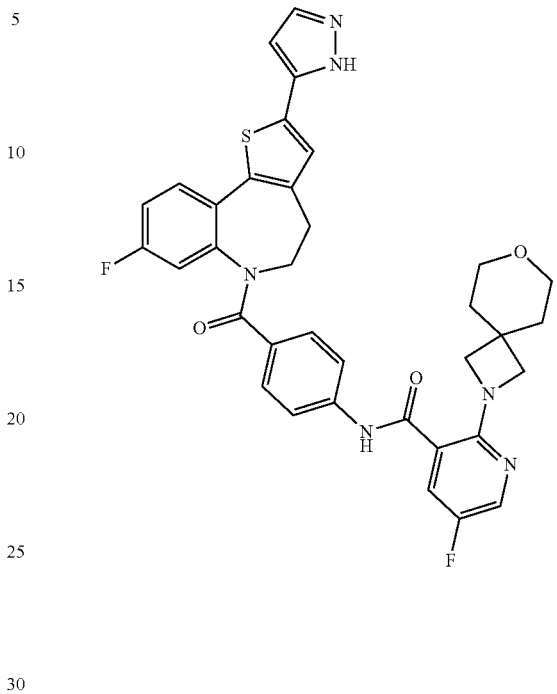

Example 45

Step a

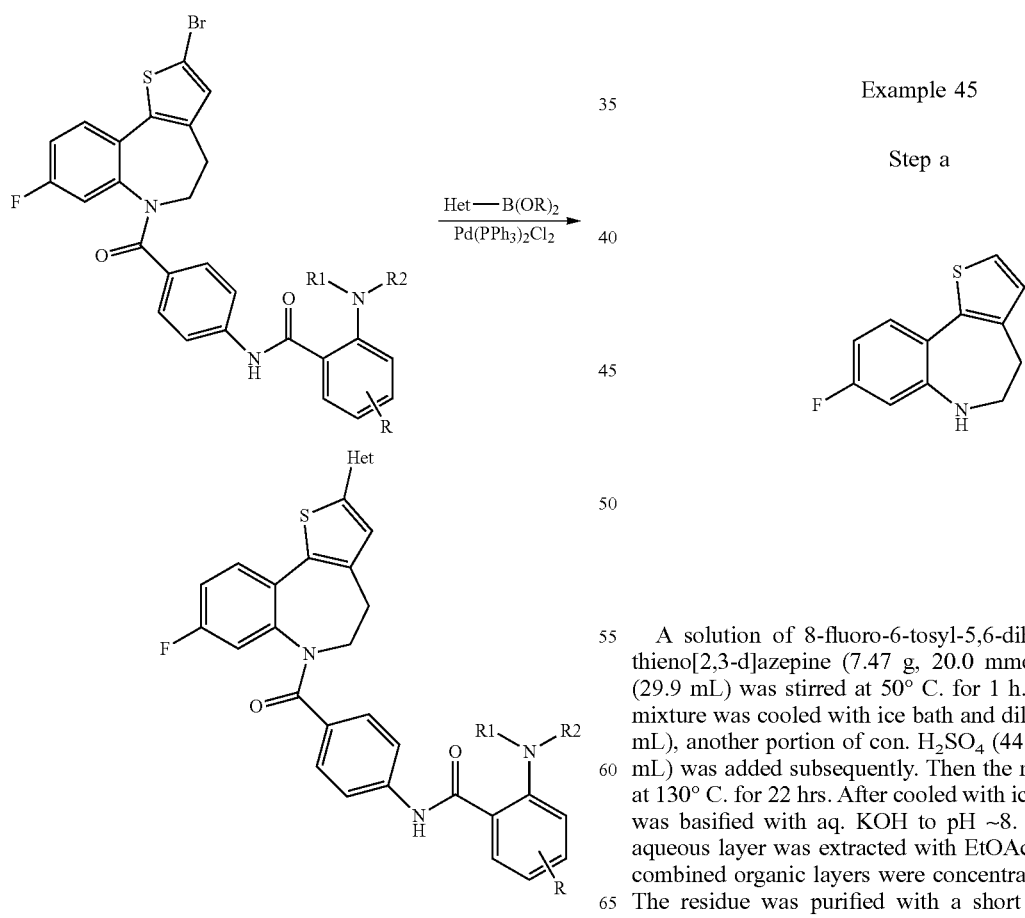

A solution of 8-fluoro-6-tosyl-5,6-dihydro-4H-benzo[b]thieno[2,3-d]azepine (7.47 g, 20.0 mmol) in H$_2$SO$_4$ con. (29.9 mL) was stirred at 50° C. for 1 h. After the reaction mixture was cooled with ice bath and diluted with H$_2$O (60 mL), another portion of con. H$_2$SO$_4$ (44.8 mL) in H$_2$O (90 mL) was added subsequently. Then the mixture was stirred at 130° C. for 22 hrs. After cooled with ice bath, the mixture was basified with aq. KOH to pH ~8. After filtrated, the aqueous layer was extracted with EtOAc (200 mL×5). The combined organic layers were concentrated under vacuum. The residue was purified with a short silica gel column chromatography eluting with EtOAc to get the desired product (3.54 g). ESI-MS m/z: 220.15 [M+H]$^+$.

Example 45

Step b

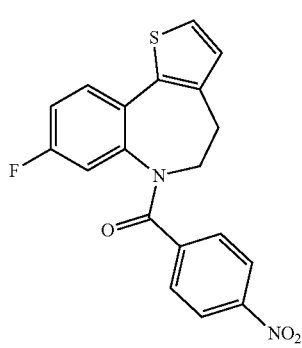

4-Nitrobenzoyl chloride (6.41 g, 34.6 mmol) was added to a solution of the compound from step a (3.79 g, 17.3 mmol) and Et$_3$N (12.1 mL, 86.4 mmol) in DCM (170 mL) at rt. The reaction was quenched by adding aq NaOH (0.6 M, 50 mL) after 2 hrs. The organic layer was washed with another aq NaOH (0.6 M, 50 mL) and H$_2$O (50 mL) subsequently. The combined aqueous layers were extracted with DCM (30 mL×3). The combined DCM layer was concentrated under vacuum. The residue was purified by silica gel column chromatography eluting with 0-20% EtOAc/DCM to get the desired product (5.29 g). ESI-MS m/z: 369.1 [M+H]$^+$.

Example 45

Step c

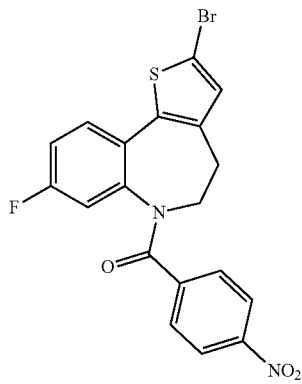 [SMILES: O=C(c1ccc([N+](=O)[O-])cc1)N1CCc2cc(Br)sc2-c2ccc(F)cc21]

To a solution of the compound from step b (5.34 g, 14.5 mmol) in DMF (50 mL) was added NBS (2.84 g, 15.9 mmol) at rt. After stirred for 15 hrs, the mixture was diluted with EtOAc (500 mL) which was washed with H$_2$O (100 mL×4). The combined aqueous layers was extracted with EA (50 mL×2). The combined organic layers were concentrated under vacuum. The residue was purified by silica gel column chromatography eluting with 0-80% EtOAc/hexanes to get the desired product (8.68 g). ESI-MS m/z: [M+H]$^+$.

Example 45

Step d

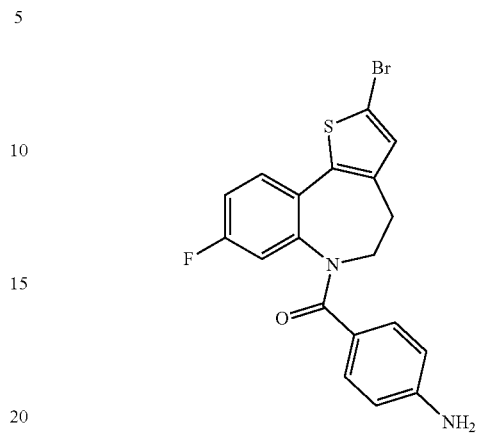

A solution of the crude compound from step c (9.0 g, 15.2 mmol) and Fe (2.56 g, 45.7 mmol) in 95% EtOH (228 mL) and aq. sat. NH$_4$Cl (30 mL) was stirred at 80° C. for 2 hrs. The mixture was passed through the celite and washed with H$_2$O (200 mL) and EA (200 mL×3). After removal most of organic solvents, the solution was adjusted to pH ~9. The mixture was extracted with 10% MeOH/DCM. The combined solvent was washed with brine, dried, filtered, and evaporated to get the crude product (6.59 g). ESI-MS m/z: 417.0 [M+H]$^+$.

Example 45

Step e

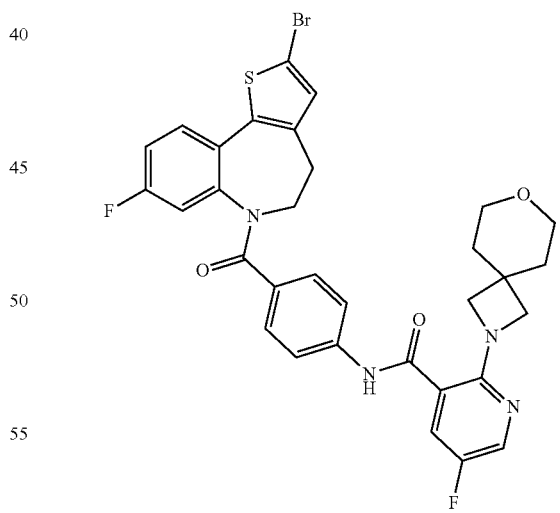

To a solution of compound from step d (200 mg, 0.75 mmol) in DCM (10 mL) was added 1-chloro-N,N, 2-trimethylprop-1-en-1-amine in DCM (201 mg, 1.50 mmol). The reaction mixture was stirred at rt for 30 min and was then concentrated in vacuo. The resulting residue was taken into DCM (15 mL) and a solution of 2-chloro-4,6-difluoroaniline (313 mg, 0.75 mmol) in pyrindine (1.0 mL) and DCM (4 mL) was added. After stirred at rt for 16 hrs, the mixture was partitioned between DCM (100 mL) and brine (20 mL). The organic layer was separated, dried, evaporated, and purified by combiflash eluting with 0-80% EtOAc/hexanes to obtain the desired product (420 mg) as colorless oil. ESI-MS m/z: 667.1 [M+H]⁺.

Example 45

Step f

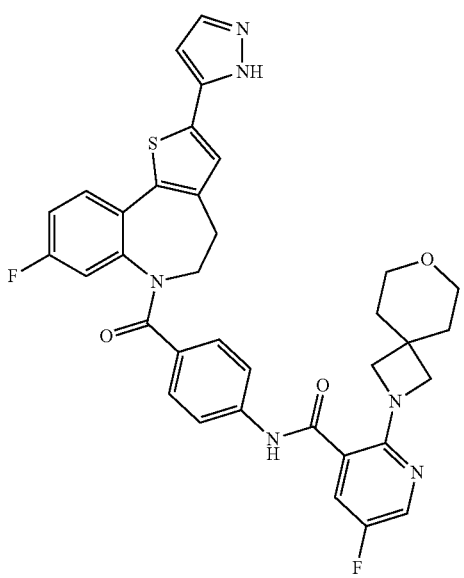 [SMILES: O=C(Nc1ccc(C(=O)N2CCc3cc(-c4ccn[nH]4)sc3-c3ccc(F)cc32)cc1)c1cc(F)cnc1N1CC2(CCOCC2)C1]

A mixture of the compound from step e (60 mg, 0.09 mmol), 5-(4,4,5,5-tetramethyl-1,3,2-dioxaborolan-2-yl)-1H-pyrazole (19.2 mmg, 0.099 mmol), Pd(Ph₃)₂Cl₂ (3.2 mg, 0.045 mmol) and K₂CO₃ (18.7 mg, 0.135 mmol) in DME/EtOH/H₂O (2.5 mL, 2/1/2) was heated at 100° C. for 16 hrs. After cooled down and evaporated, the residue was purified by silica gel column chromatograph eluting with 0-5% MeOH/DCM to obtain the desired product (20 mg). ESI-MS m/z: 653.2 [M+H]⁺.

Example 46

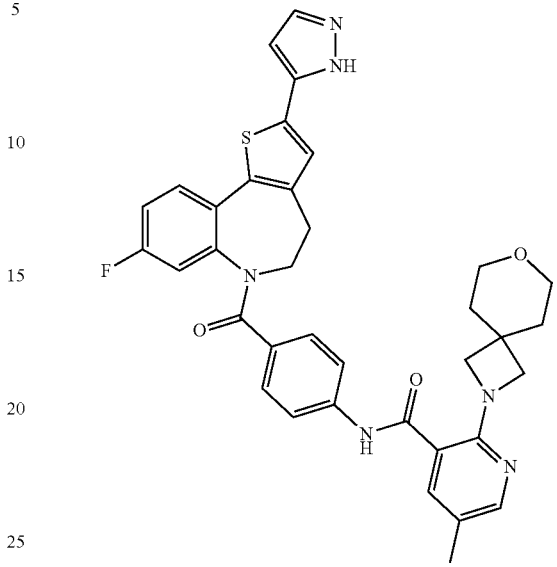

Example 46 was prepared using a procedure similar to that used to prepare example 27. ESI-MS m/z: 649.3 [M+H]⁺.

Scheme 5

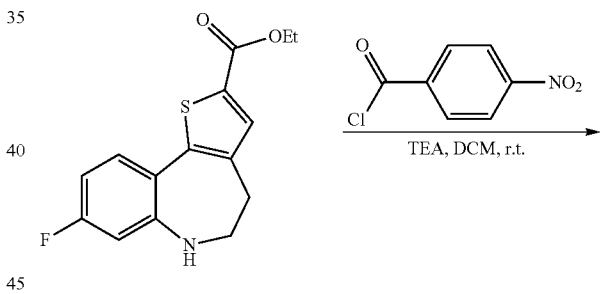

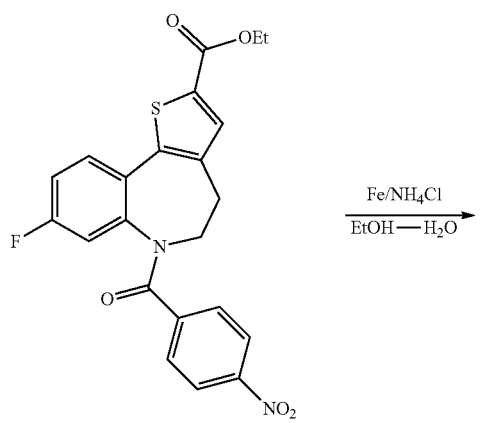

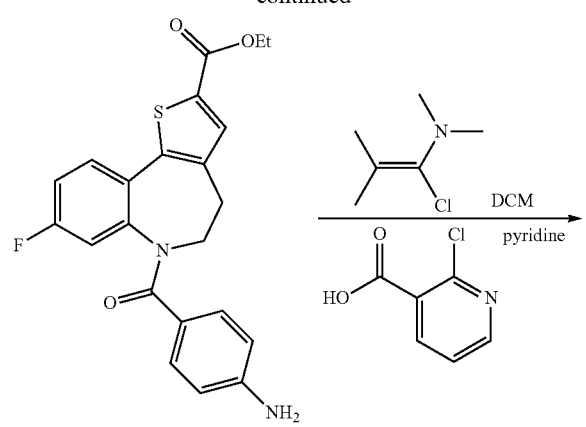
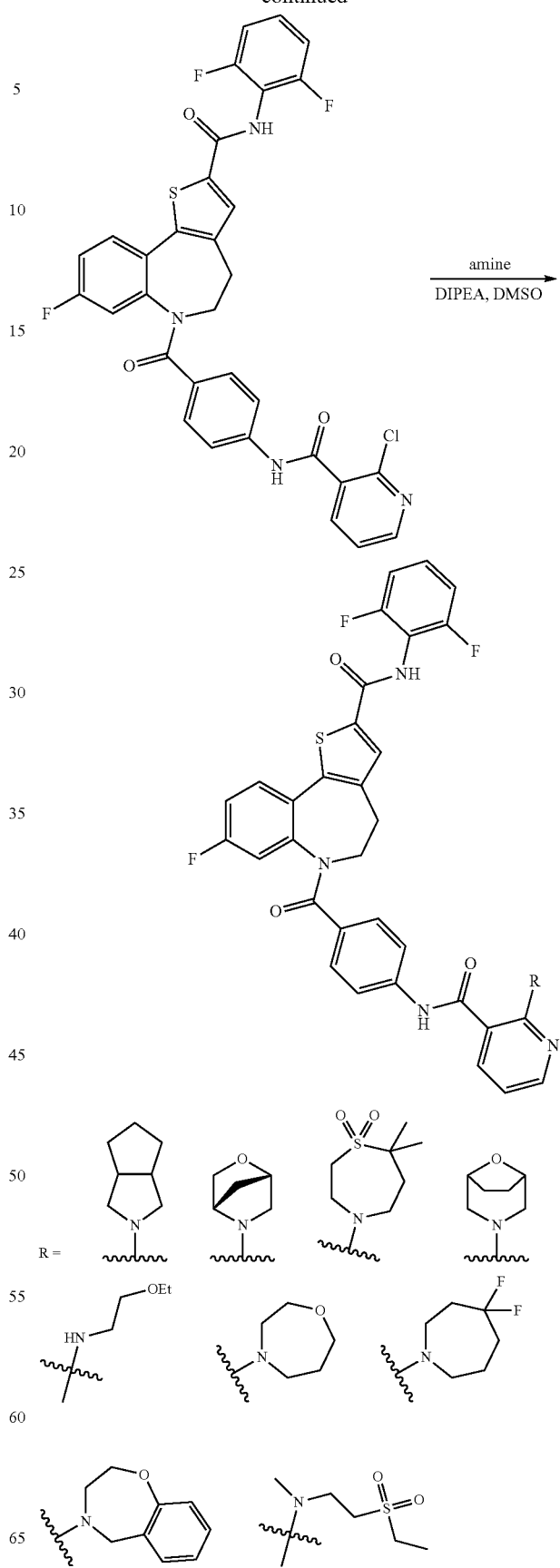

-continued

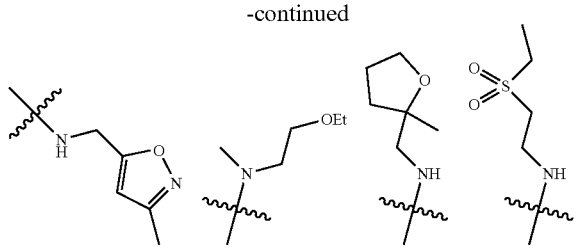

Example 47

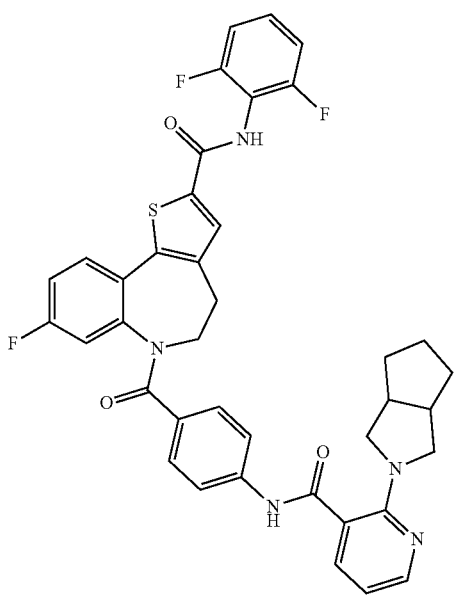 [SMILES: O=C(Nc1c(F)cccc1F)c1cc2c(s1)-c1ccc(F)cc1N(C(=O)c1ccc(NC(=O)c3cccnc3N3CC4CCCC4C3)cc1)CC2]

Example 47

Step a

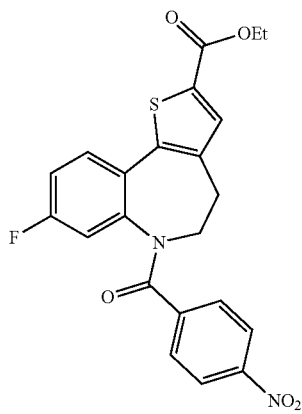

A solution of ethyl 8-fluoro-5,6-dihydro-4H-benzo[b]thieno[2,3-d]azepine-2-carboxylate (6 g, 21 mmol), 4-nitrobenzoyl chloride (7.63 g, 41 mmol), TEA (5 mL) in DCM (100 mL) was stirred for 1 h. The solution was concentrated and purified by silica gel column chromatography eluting with 0-60% EtOAc/hexanes to give the desired compound as a yellow solid (3.1 g). ESI-MS m/z: 441.1 [M+H]$^+$.

Example 47

Step b

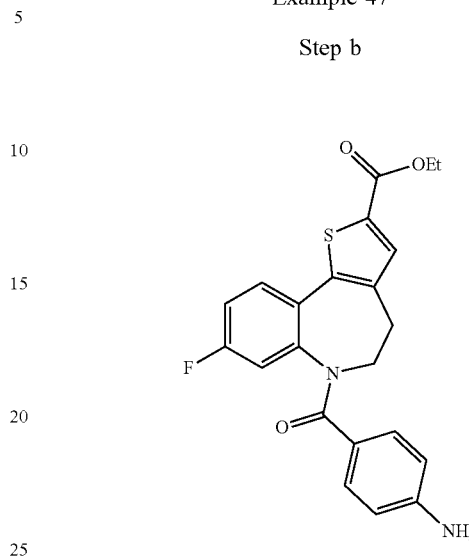

A solution of the compound from step a (3.1 g, 7 mmol), NH$_4$Cl (1.86 g, 35 mmol), Fe (1.97 g, 35 mmol) in EtOH (50 mL) and water (20 mL) was stirred at 80° C. for 1 h. The mixture was passed through the celite and washed with H$_2$O (200 mL) and EA (200 mL×3). After removal most of organic solvents, the solution was adjusted to pH ~9. The mixture was extracted with 10% MeOH/DCM. The combined solvent was washed with brine, dried, filtered, and evaporated to get the desired product as a yellowish solid (2.5 g). ESI-MS m/z: 410.8 [M+H]$^+$.

Example 47

Step c

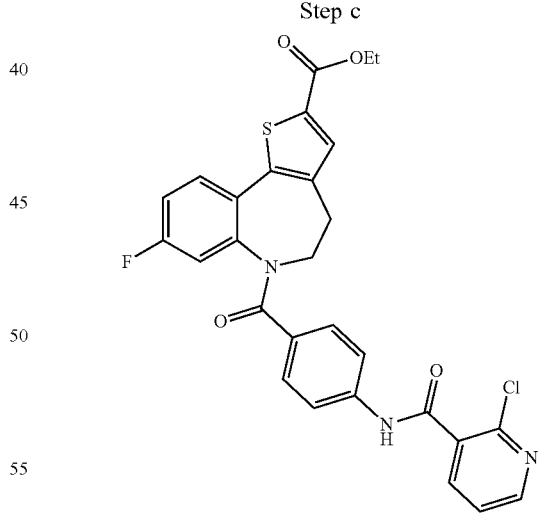

To a solution of 2-chloronicotinic acid (766 mg, 4.9 mmol) in DCM (50 mL) was added 1-chloro-N,N, 2-trimethylprop-1-en-1-amine (1.3 g, 9.8 mmol). The mixture was stirred for 1 h before being concentrated. The compound from step b (2 g, 4.9 mmol) was dissolved in pyridine (1 mL) in DCM (50 mL) and stirred for 1 h. The solution was diluted with DCM, washed with brine. The organic layer was dried and evaporated to give the crude desired compound as yellow solid (2.69 g), which was used directly for the next step. ESI-MS m/z: 550.1 [M+H]$^+$.

Example 47

Step d

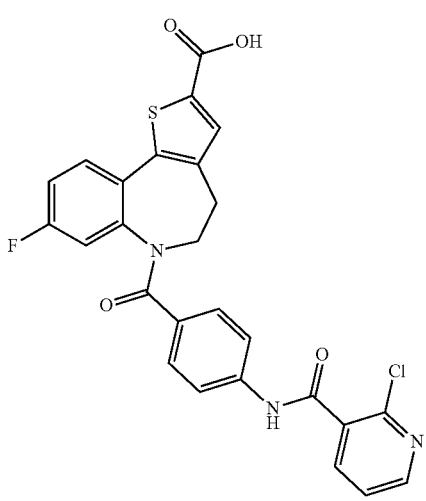 [SMILES: O=C(O)c1cc2c(s1)-c1ccc(F)cc1N(C(=O)c1ccc(NC(=O)c3cccnc3Cl)cc1)CC2]

A solution of the compound from step c (2.69 g, 4.9 mmol), LiOH (1.18 g, 49 mmol) in THF (50 mL) and water (50 mL) was stirred for 1 h at 50° C. The mixture was concentrated and adjusted pH ~2 with 1M HCl. The precipitate was filtered to give the desired compound as a pink solid (2.5 g). ESI-MS m/z: 522.0 [M+H]$^+$.

Example 47

Step e

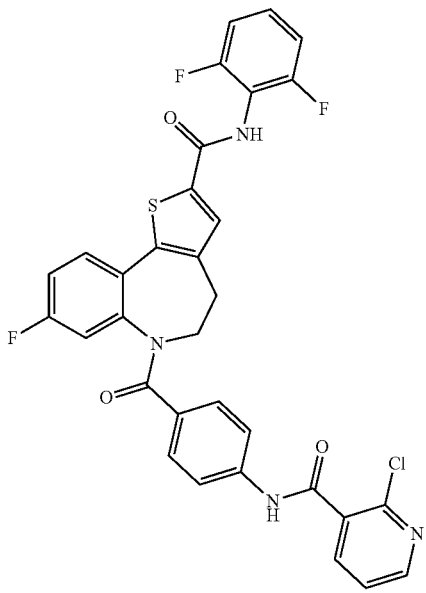 [SMILES: O=C(Nc1c(F)cccc1F)c1cc2c(s1)-c1ccc(F)cc1N(C(=O)c1ccc(NC(=O)c3cccnc3Cl)cc1)CC2]

1-Chloro-N,N, 2-trimethylprop-1-en-1-amine (1.38 g, 10 mmol) was added to the solution of the compound from step d (2.7 g, 5.2 mmol) in DCM (50 mL). The mixture was stirred for 1 h before being concentrated. 2,6-Difluoroaniline (671 mg, 5.2 mmol) and pyridine (2 mL) was dropwise added to a solution of the reaction mixture in DCM (10 mL). The mixture was stirred for 1 h. The solution was evaporated and purified by Prep-HPLC(MeCN/H$_2$O) and silica gel column chromatography (DCM-MeOH) to give the desired compound as a yellow solid (2.13 g). ESI-MS m/z: 633.0 [M+H]$^+$.

Example 47

Step f

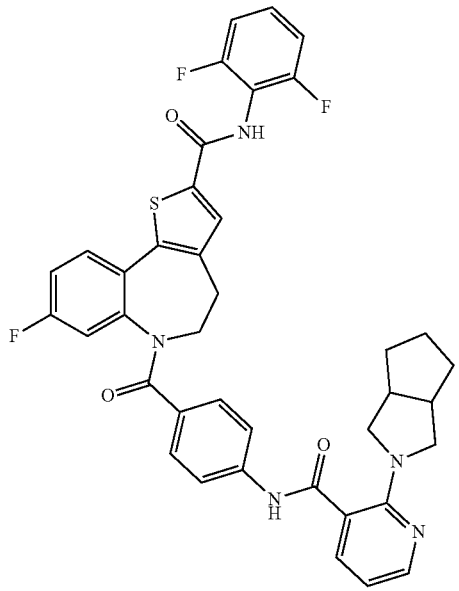 [SMILES: O=C(Nc1c(F)cccc1F)c1cc2c(s1)-c1ccc(F)cc1N(C(=O)c1ccc(NC(=O)c3cccnc3N3CC4CCCC4C3)cc1)CC2]

A solution of the compound from step e (100 mg, 0.158 mmol), octahydrocyclopenta[c]-pyrrole hydrochloride (47 mg, 0.316 mmol), DIPEA (0.5 mL) in DMSO (1 mL) was stirred at 120° C. for overnight. The crude product was purified by prep-HPLC(MeCN/H$_2$O/10 mmol/L NH$_4$HCO$_3$) to give the title compound as a light yellowish solid (47.9 mg). ESI-MS m/z: 707.70 [M+H]$^+$. $^1$H NMR (400 MHz, DMSO-d$_6$) δ 1.27 (m, 2H), 1.45 (m, 1H), 1.64 (m, 3H), 2.51 (m, 2H), 2.57 (m, 2H), 3.14 (m, 3H), 3.46 (m, 2H), 4.90 (s, 1H), 6.67 (m, 1H), 6.84 (d, J=9.3 Hz, 1H), 7.02 (d, J=7.9 Hz, 2H), 7.10-7.29 (m, 3H), 7.41 (m, 1H), 7.48-7.70 (m, 3H), 7.83 (m, 1H), 7.94 (s, 1H), 8.16 (m, 1H), 10.27 (s, 1H), 10.47 (s, 1H).

Examples 48-59 shown in table 6 were prepared using the procedure similar to that of example 47 from the corresponding intermediates.

TABLE 6
| Example | Structure | ESI-MS m/z: [M + H]+ |
|---|---|---|
| 48 | 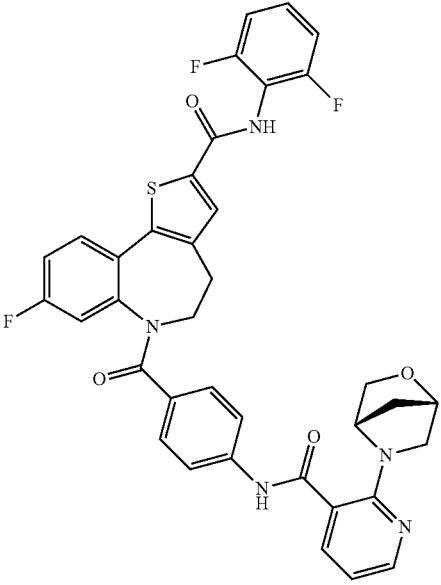 [SMILES: O=C(Nc1c(F)cccc1F)c1cc2c(s1)-c1ccc(F)cc1N(C(=O)c1ccc(NC(=O)c3cccnc3N3C[C@@H]4C[C@H]3CO4)cc1)CC2] | 696.10 |
| 49 | 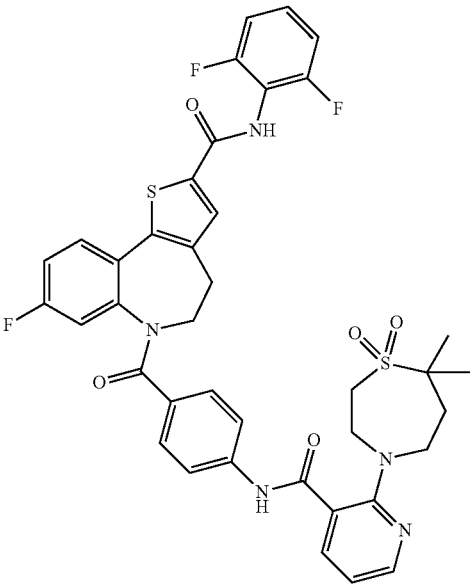 [SMILES: CC1(C)CCN(c2ncccc2C(=O)Nc2ccc(C(=O)N3CCc4cc(C(=O)Nc5c(F)cccc5F)sc4-c4ccc(F)cc43)cc2)CCS1(=O)=O] | 773.70 |

TABLE 6-continued
| Example | Structure | ESI-MS m/z: [M + H]+ |
|---------|-----------|----------------------|
| 50 | 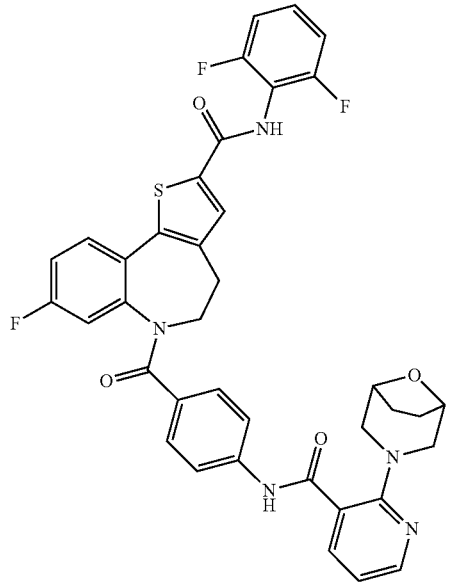 [SMILES: O=C(Nc1c(F)cccc1F)c1cc2c(s1)-c1ccc(F)cc1N(C(=O)c1ccc(NC(=O)c3cccnc3N3CC4CCC(C3)O4)cc1)CC2] | 710.10 |
| 51 | 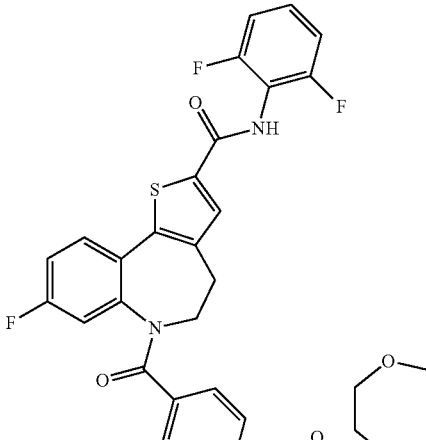 | 697.70 |

TABLE 6-continued
| Example | Structure | ESI-MS m/z: [M + H]+ |
|---------|-----------|----------------------|
| 52 | 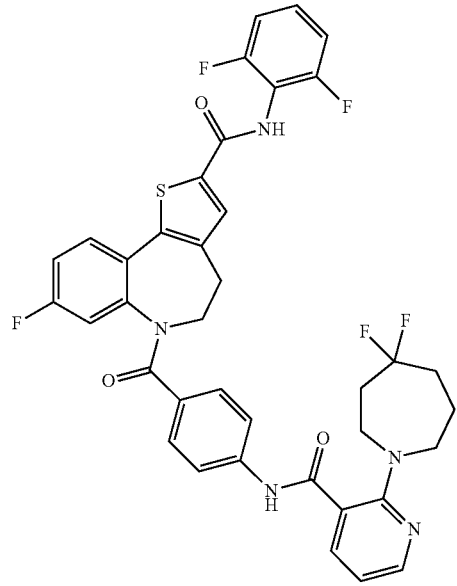 [SMILES: O=C(Nc1c(F)cccc1F)c1cc2c(s1)-c1ccc(F)cc1N(C(=O)c1ccc(NC(=O)c3cccnc3N3CCCC(F)(F)CC3)cc1)CC2] | 731.70 |
| 53 | 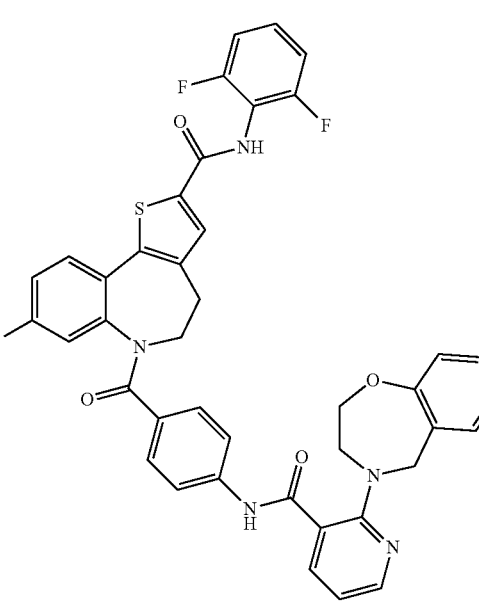 | 746.05 |

TABLE 6-continued
| Example | Structure | ESI-MS m/z: [M + H]+ |
|---|---|---|
| 54 | 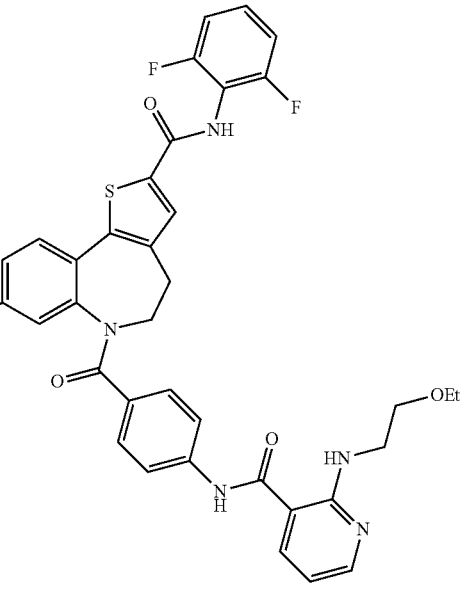 | 686.05 |
| 55 | 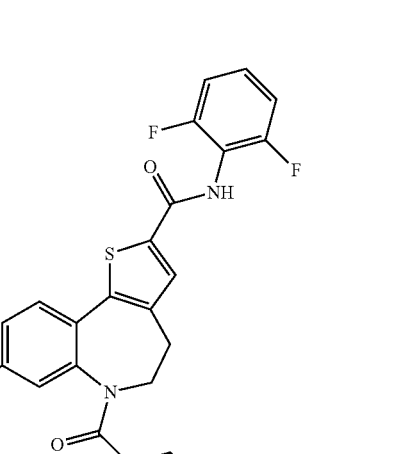 | 700.25 |

TABLE 6-continued
| Example | Structure | ESI-MS m/z: [M + H]+ |
|---------|-----------|----------------------|
| 56 | 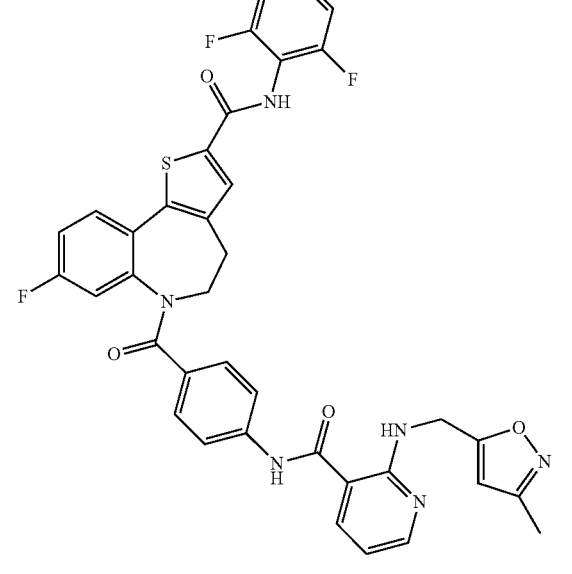 | 709.30 |
| 57 | 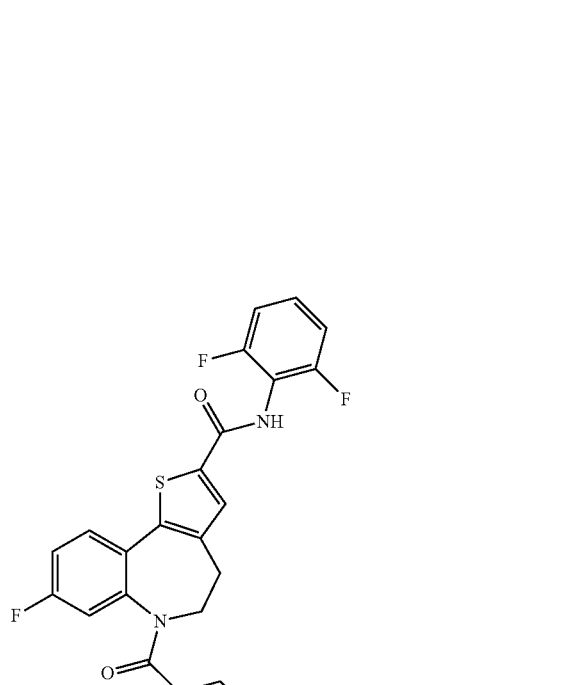 | 748.15 |

TABLE 6-continued
| Example | Structure | ESI-MS m/z: [M + H]+ |
|---|---|---|
| 58 | 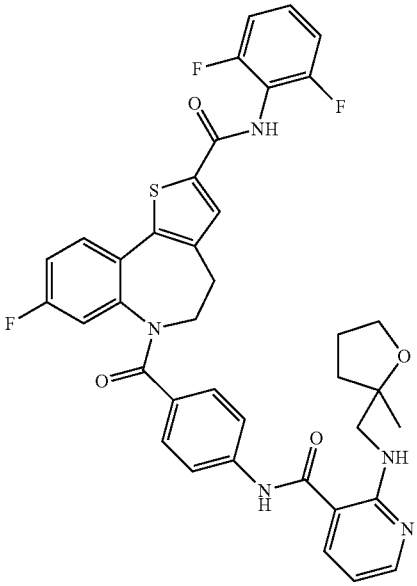 [SMILES: CC1(CNc2ncccc2C(=O)Nc2ccc(C(=O)N3CCc4cc(C(=O)Nc5c(F)cccc5F)sc4-c4ccc(F)cc43)cc2)CCCO1] | 712.35 |
| 59 | 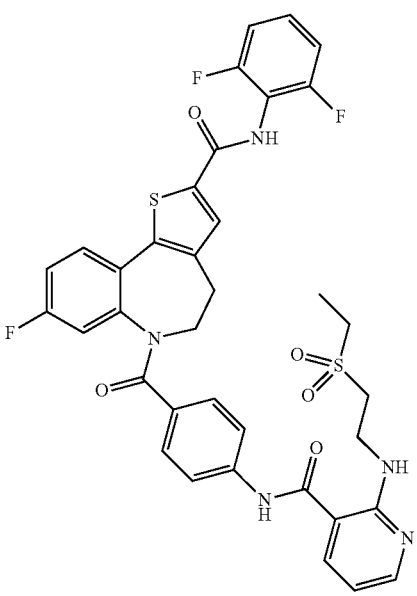 [SMILES: CCS(=O)(=O)CCNc1ncccc1C(=O)Nc1ccc(C(=O)N2CCc3cc(C(=O)Nc4c(F)cccc4F)sc3-c3ccc(F)cc32)cc1] | 735.25 |

Scheme 6

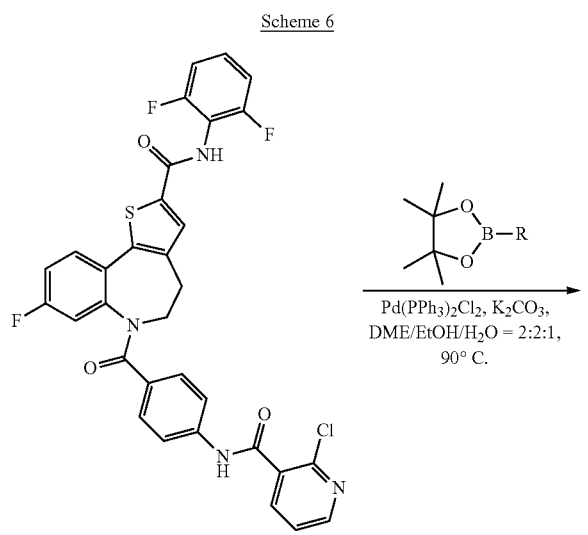

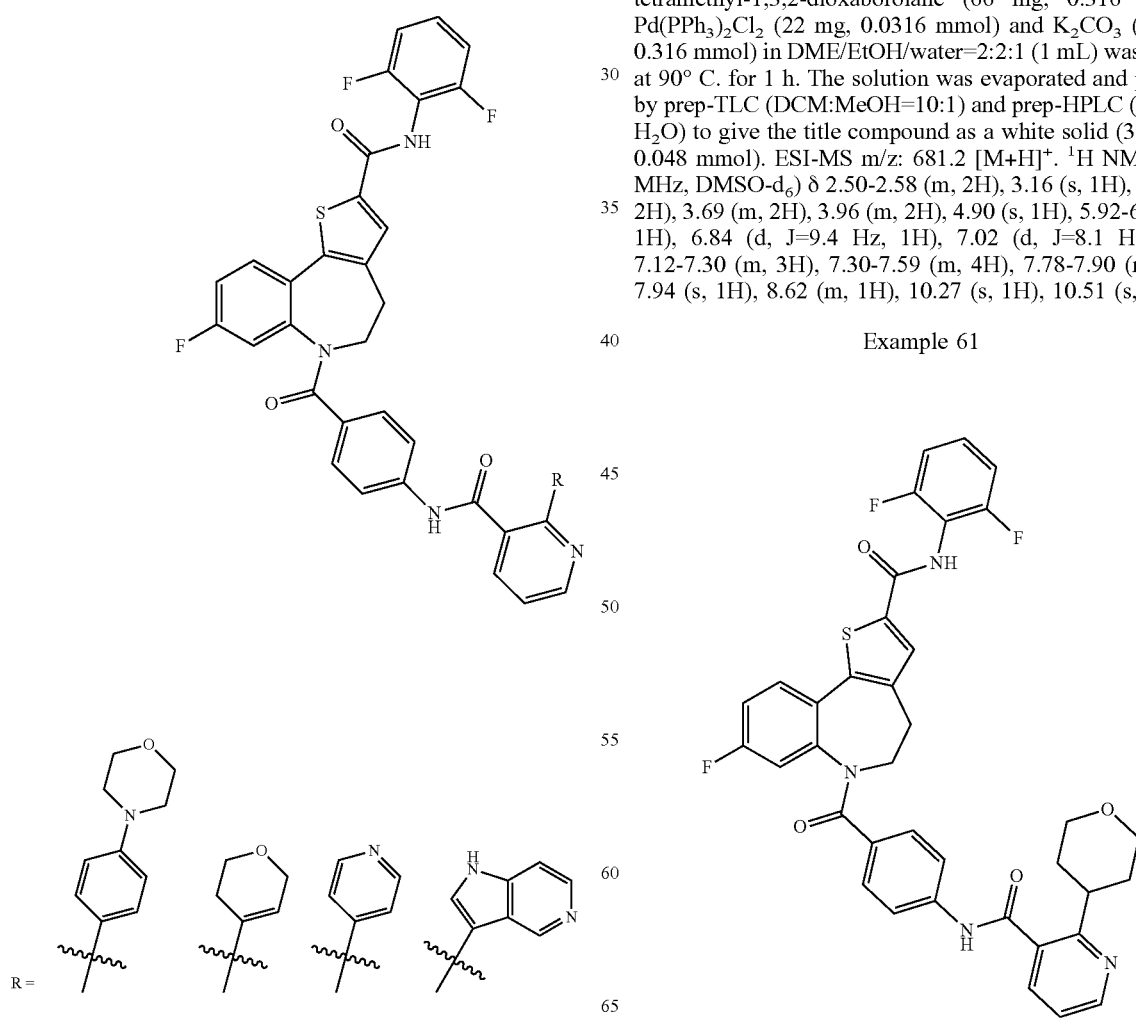

Example 60

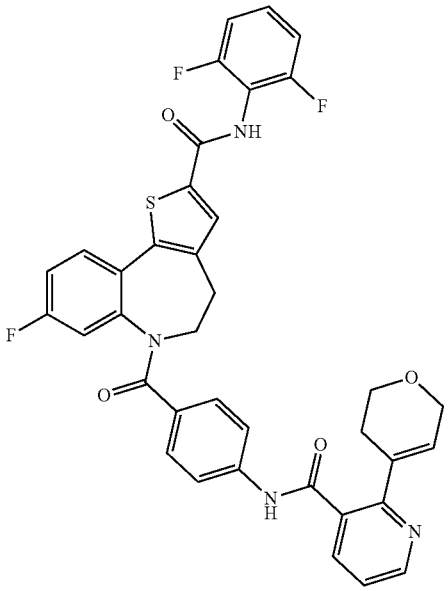 [SMILES: O=C(Nc1c(F)cccc1F)c1cc2c(s1)-c1ccc(F)cc1N(C(=O)c1ccc(NC(=O)c3cccnc3C3=CCOCC3)cc1)CC2]

A solution of the compound from example 47 step e (100 mg, 0.158 mmol), 2-(3,6-dihydro-2H-pyran-4-yl)-4,4,5,5-tetramethyl-1,3,2-dioxaborolane (66 mg, 0.316 mmol), Pd(PPh$_3$)$_2$Cl$_2$ (22 mg, 0.0316 mmol) and K$_2$CO$_3$ (44 mg, 0.316 mmol) in DME/EtOH/water=2:2:1 (1 mL) was heated at 90° C. for 1 h. The solution was evaporated and purified by prep-TLC (DCM:MeOH=10:1) and prep-HPLC (MeCN/H$_2$O) to give the title compound as a white solid (32.8 mg, 0.048 mmol). ESI-MS m/z: 681.2 [M+H]$^+$. $^1$H NMR (400 MHz, DMSO-d$_6$) δ 2.50-2.58 (m, 2H), 3.16 (s, 1H), 3.28 (s, 2H), 3.69 (m, 2H), 3.96 (m, 2H), 4.90 (s, 1H), 5.92-6.04 (m, 1H), 6.84 (d, J=9.4 Hz, 1H), 7.02 (d, J=8.1 Hz, 2H), 7.12-7.30 (m, 3H), 7.30-7.59 (m, 4H), 7.78-7.90 (m, 2H), 7.94 (s, 1H), 8.62 (m, 1H), 10.27 (s, 1H), 10.51 (s, 1H).

Example 61

A mixture of the compound of the compound from example 60 (100 mg, 0.147 mmol), Pd/C (100 mg) in MeOH (10 mL) was stirred for 1 hr under $H_2$. The reaction mixture was filtrated, evaporated, purified by prep-TLC (DCM:MeOH=10:1) and prep-HPLC (MeCN/$H_2O$) to give the title compound as a white solid (12.5 mg, 0.018 mmol). ESI-MS m/z: 683.2 [M+H]$^+$. $^1$H NMR (400 MHz, DMSO-d$_6$) δ 1.62 (m, 2H), 1.88 (m, 2H), 3.17 (m, 2H), 3.28 (s, 3H), 3.79-3.92 (m, 2H), 4.90 (s, 1H), 6.87 (d, J=9.2 Hz, 1H), 7.05 (d, J=8.7 Hz, 2H), 7.13-7.26 (m, 3H), 7.32 (m, 1H), 7.41 (m, 1H), 7.56 (d, J=8.2 Hz, 2H), 7.80-7.88 (m, 2H), 7.94 (s, 1H), 8.62 (m, 1H), 10.27 (s, 1H), 10.62 (s, 1H).

Examples 62-64 shown in table 7 were prepared using the procedure similar to that of example 60 from the corresponding intermediates.

TABLE 7

| Example | Structure | ESI-MS m/z: [M + H]$^+$ |
|---|---|---|
| 62 | 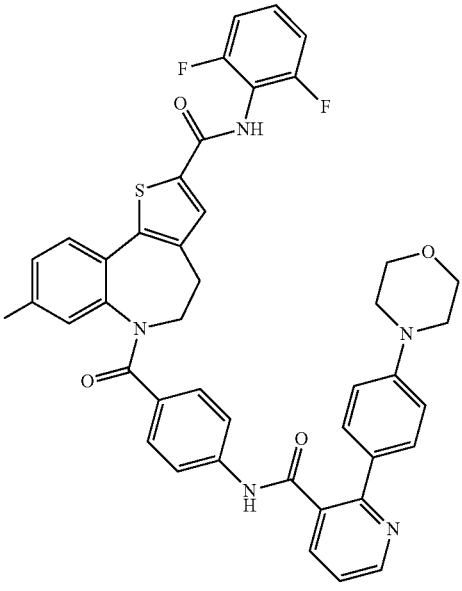 | 760.10 |
| 63 | 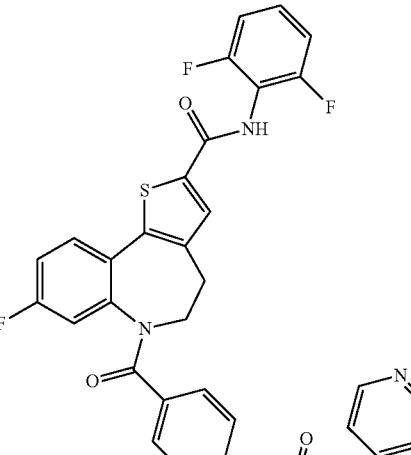 | 676.15 |

TABLE 7-continued
| Example | Structure | ESI-MS m/z: [M + H]+ |
|---|---|---|
| 64 | 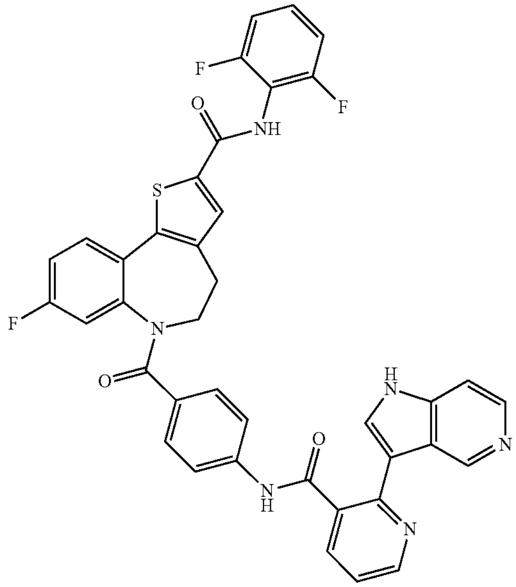 [SMILES: O=C(Nc1c(F)cccc1F)c1cc2c(s1)-c1ccc(F)cc1N(C(=O)c1ccc(NC(=O)c3cccnc3-c3c[nH]c4ccncc34)cc1)CC2] | 715.15 |
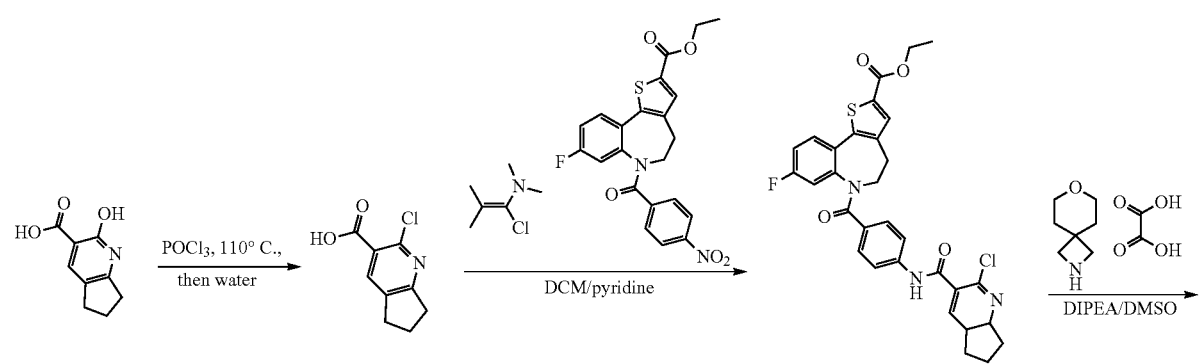
Scheme 7

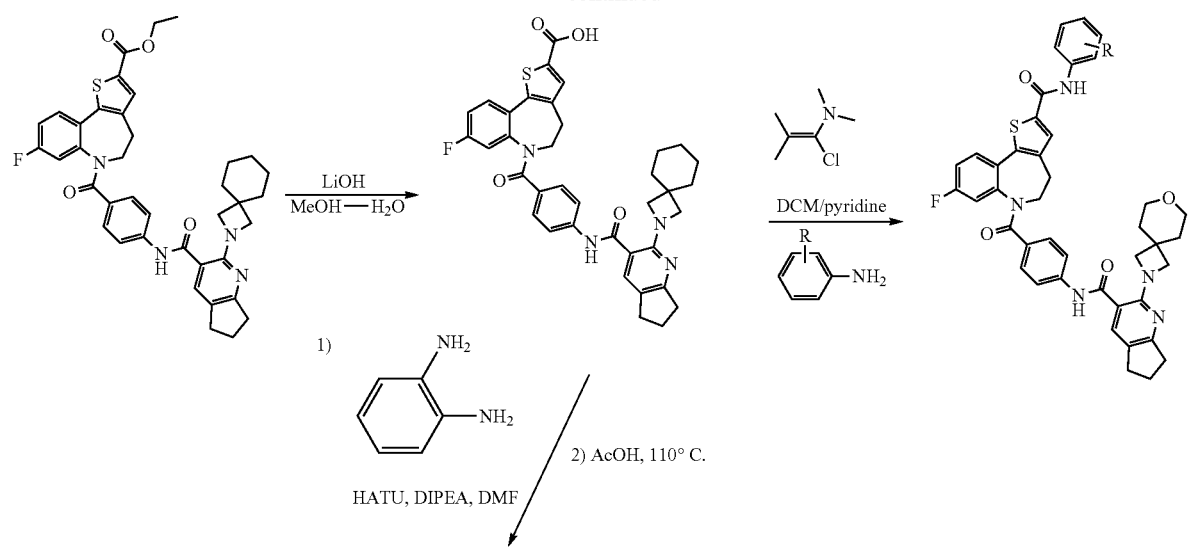
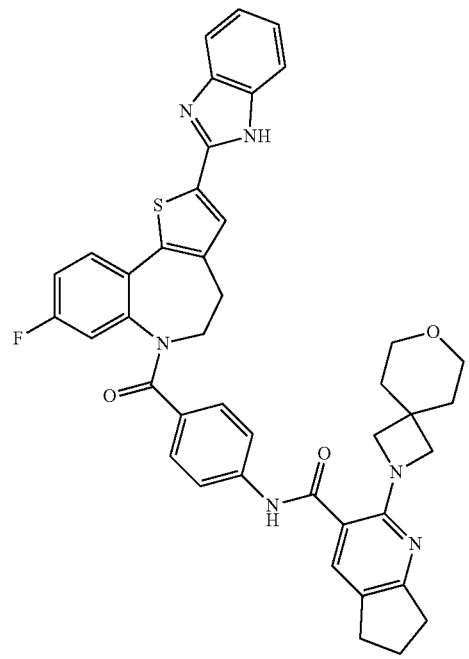

Example 65

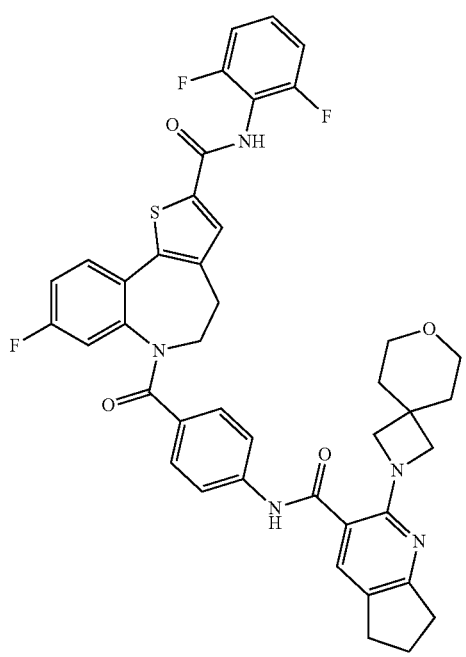 [SMILES: O=C(Nc1c(F)cccc1F)c1cc2c(s1)-c1ccc(F)cc1N(C(=O)c1ccc(NC(=O)c3cc4c(nc3N3CC5(CCOCC5)C3)CCC4)cc1)CC2]

Example 65

Step b

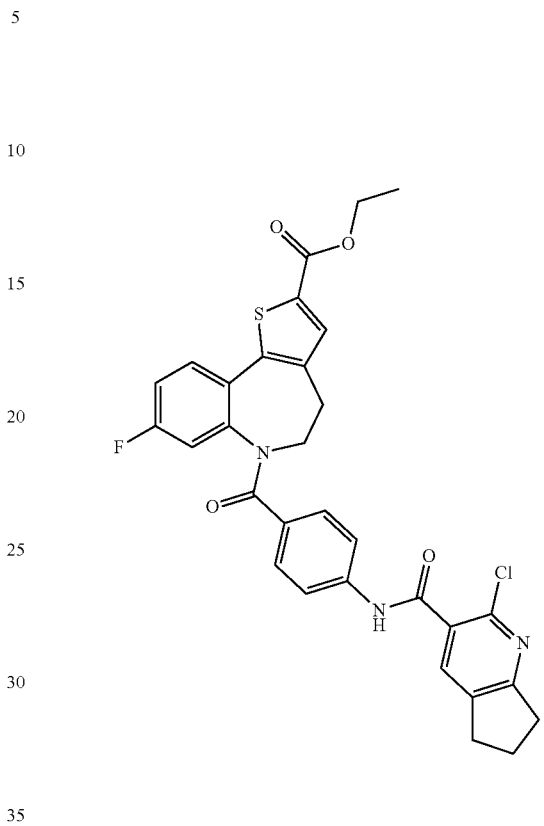

Example 65

Step a

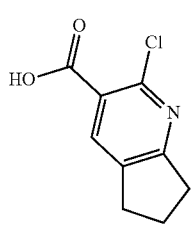

A solution of 2-hydroxy-6, 7-dihydro-5H-cyclopenta[b]pyridine-3-carboxylic acid (1.0 g, 5.58 mmol) in POCl$_3$ (10 mL) was stirred at 110° C. for 4 hrs. The solution was diluted with KOAc Sat solution at 0° C. and extracted with EA then dried over Na$_2$SO$_4$, filtered, and purified by column chromatography (MeCN/H$_2$O) to give desired compound as a yellowish solid (500 mg). ESI-MS m/z: 197.1 [M+H]$^+$.

A solution of the compound from step a (306 mg, 1.55 mmol), 1-chloro-N, N, 2-trimethylprop-1-en-1-amine (412 mg, 3.10 mmol) in DCM (10 mL) was stirred for 1 h at rt. The solution was concentrated, dissolved in DCM (10 mL), treated with ethyl 6-(4aminobenzoyl)-8-fluoro-5,6-dihydro-4H-benzo[b]thieno[2,3-d]azepine-2-carboxylate (530 mg, 1.29 mmol) and pyridine (0.5 mL). The solution was stirred at rt for 1 h and concentrated and purified by silica gel column (PE/EA) to give the desired compound as a light yellowish solid (710 mg). ESI-MS m/z: 590.2 [M+H]$^+$.

Example 65

Step c

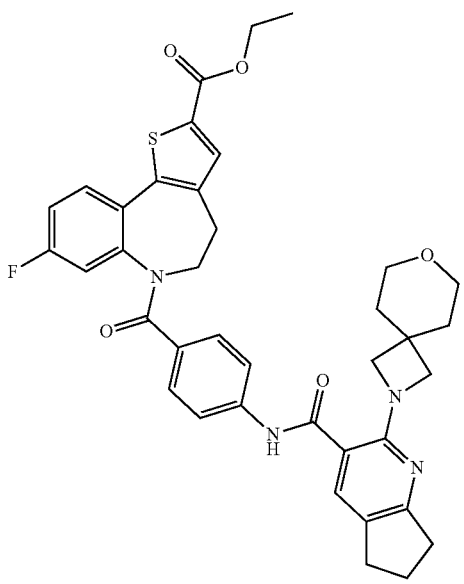 [SMILES: CCOC(=O)c1cc2c(s1)-c1ccc(F)cc1N(C(=O)c1ccc(NC(=O)c3cc4c(nc3N3CC5(CCOCC5)C3)CCC4)cc1)CC2]

A mixture of the compound from step b (700 mg, 1.18 mmol), 7-oxa-2-azaspiro[3.5]nonane hemioxalate (613 mg, 3.56 mmol)), DIPEA (2 mL) in DMSO (20 mL) was stirred overnight at 120° C. The solution was purified by column chromatography (MeCN/H$_2$O) to give the desired compound as a yellowish solid (650 mg). ESI-MS m/z: 681.3 [M+H]$^+$.

Example 65

Step d

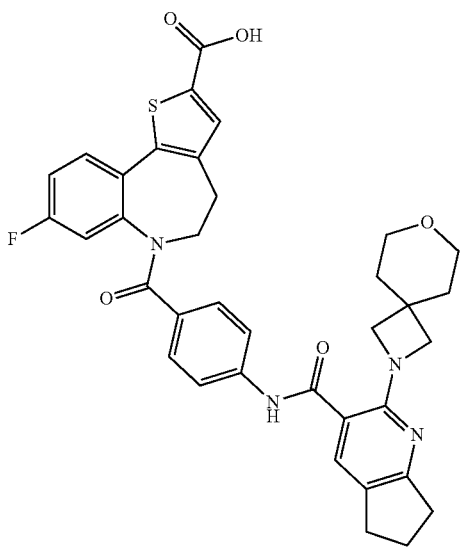 [SMILES: O=C(O)c1cc2c(s1)-c1ccc(F)cc1N(C(=O)c1ccc(NC(=O)c3cc4c(nc3N3CC5(CCOCC5)C3)CCC4)cc1)CC2]

A mixture of the compound from step c (650 mg, 0.95 mmol), LiOH (230 mg, 9.5 mmol) in MeOH (15 mL) and H$_2$O (10 mL) was stirred at rt for 2 hrs. The solution was removed solvent and adjusted PH value to 4 with HCl (12M), filtered and dried to give the desired compound as a yellow solid (460 mg). ESI-MS m/z: 653.3 [M+H]$^+$.

Example 65

Step e

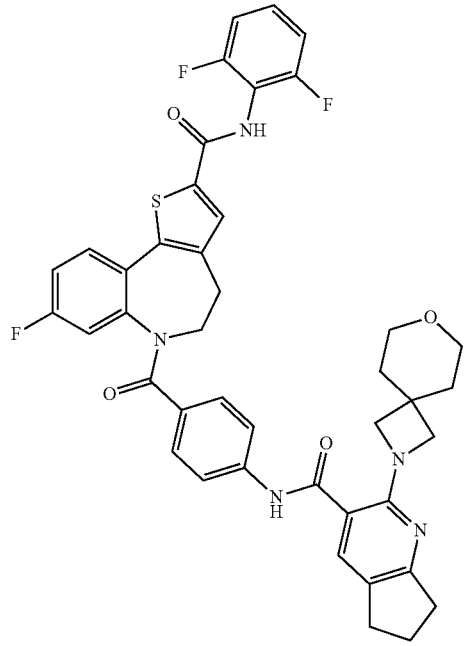 [SMILES: O=C(Nc1c(F)cccc1F)c1cc2c(s1)-c1ccc(F)cc1N(C(=O)c1ccc(NC(=O)c3cc4c(nc3N3CC5(CCOCC5)C3)CCC4)cc1)CC2]

A mixture of the compound from step d (110 mg, 0.17 mmol), 1-chloro-N, N, 2-trimethylprop-1-en-1-amine (67 mg, 0.51 mmol) in DCM (10 mL) was stirred at room temperature for 1 h. The reaction mixture was concentrated, dissolved in DCM (5 mL), treated with 2,6-difluoroaniline (13 mg, 0.10 mmol) and pyridine (0.5 mL) and stirred at rt for 3 hrs, then it was concentrated and purified by prep-HPLC (MeCN/H$_2$O) to give title compound as an off-white solid (47.9 mg). ESI-MS m/z: 764.3 [M+H]$^+$. $^1$H NMR (300 MHz, DMSO-d$_6$) δ 1.63 (s, 4H), 2.01-2.06 (m, 2H), 2.75-2.84 (m, 4H), 3.28-3.67 (m, 11H), 4.91 (s, 1H), 6.85-6.92 (m, 1H), 7.03-7.26 (m, 5H), 7.38-7.96 (m, 6H), 10.29-10.39 (m, 2H).

Examples 66-67 shown in table 8 were prepared using the procedure similar to that of example 65 from the corresponding intermediates.

TABLE 8
| Example | Structure | ESI-MS m/z: [M + H]+ |
|---|---|---|
| 66 | 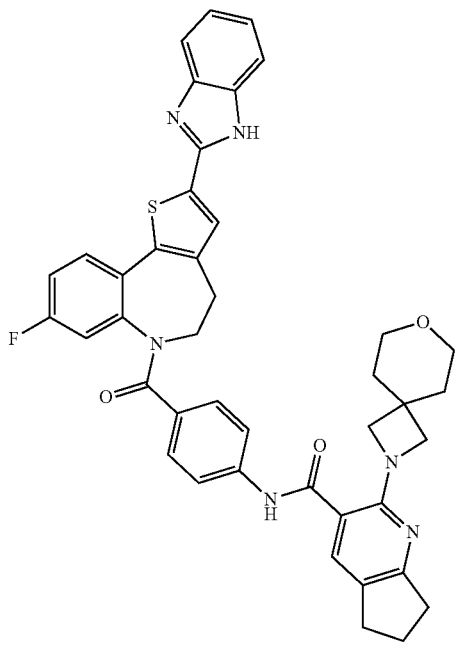 [SMILES: O=C(Nc1ccc(C(=O)N2CCc3cc(-c4nc5ccccc5[nH]4)sc3-c3ccc(F)cc32)cc1)c1cc2c(nc1N1CC3(CCOCC3)C1)CCC2] | 798.20 |
| 67 | 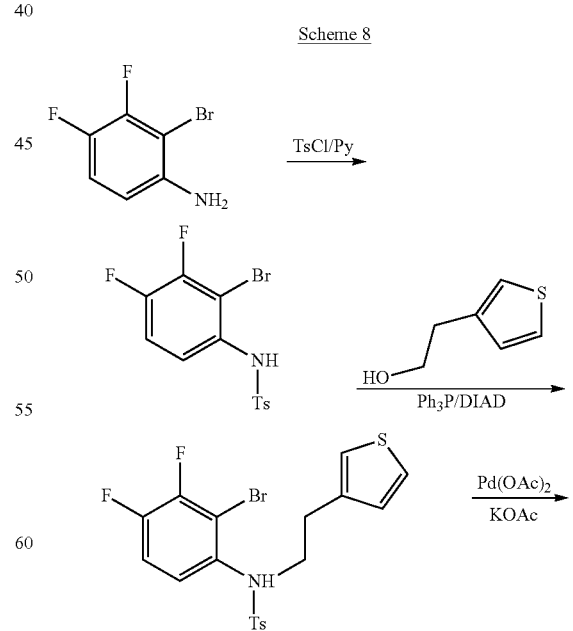 | 782.20 |
Example 68
Example 68 was prepared using the procedure similar to that of example 3 (step k and l) from the corresponding intermediates. ESI-MS m/z: 725.25 [M+H]+. $^1$H NMR (300 MHz, DMSO-d$_6$) δ 1.60-1.62 (m, 4H), 1.90-2.10 (m, 2H), 2.74-2.79 (m, 4H), 3.29-3.60 (m, 11H), 4.94 (m, 1H), 6.52-6.87 (m, 1H), 7.03-7.26 (m, 5H), 7.46-7.90 (m, 7H), 10.31 (s, 1H), 13.05 (s, 1H).
Scheme 8

173
-continued
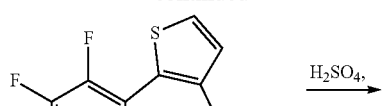
174
-continued
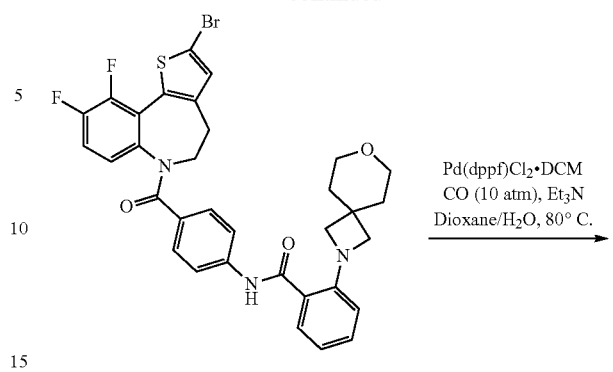
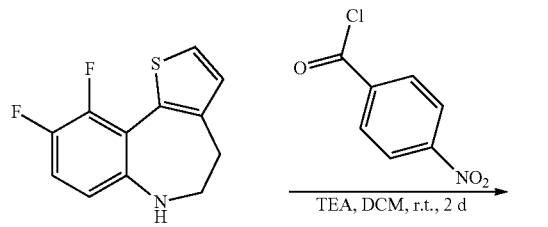
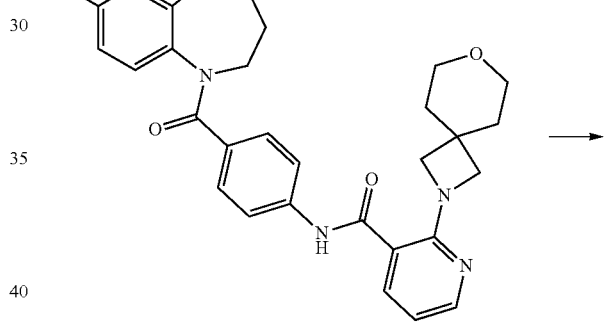
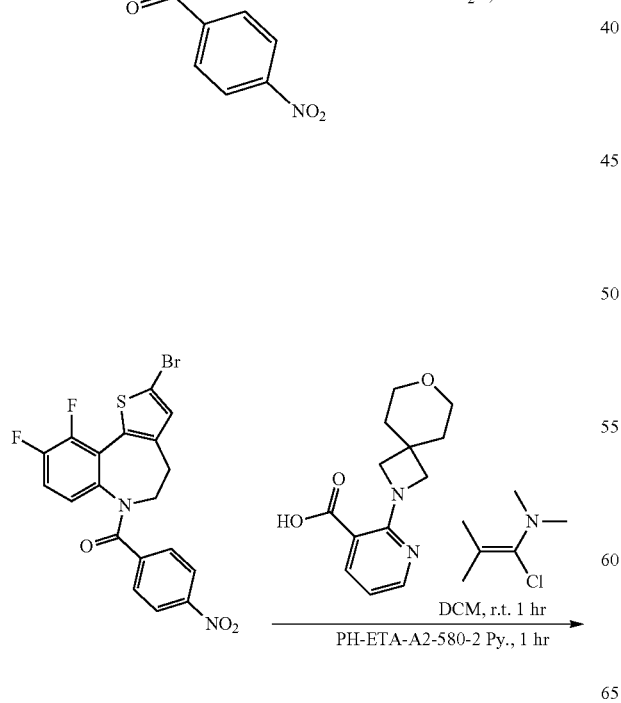
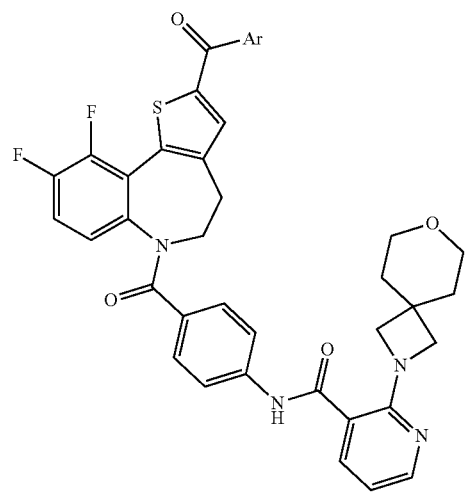

Example 69

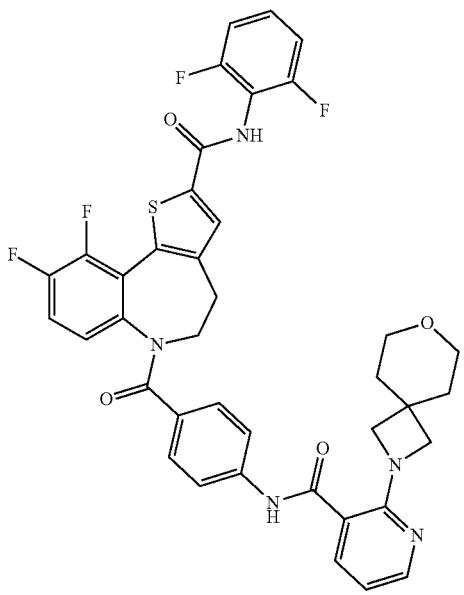 [SMILES: O=C(Nc1c(F)cccc1F)c1cc2c(s1)-c1c(ccc(F)c1F)N(C(=O)c1ccc(NC(=O)c3cccnc3N3CC4(CCOCC4)C3)cc1)CC2]

Example 69

Step a

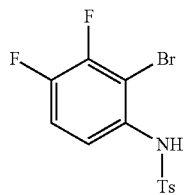 [SMILES: Cc1ccc(S(=O)(=O)Nc2ccc(F)c(F)c2Br)cc1]

To a solution of 2-bromo-3,4-difluoroaniline (7.0 g, 33.65 mmol) in pyridine was added TsCl (6.72 g, 35.3 mmol) at <30° C. in 20 min. After being stirred at rt for overnight, ice-cold water (400 mL) was added to the reaction mixture. Then the mixture was filtrated and washed with H₂O (3×100 mL). The filter cake was dissolved in EA, dried over Na₂SO₄ for 30 min, concentrated under vacuum to provide the title compound (11.6 g).

Example 69

Step b

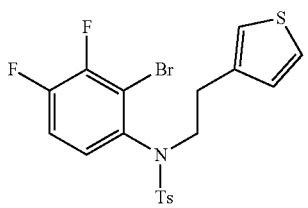 [SMILES: Cc1ccc(S(=O)(=O)N(CCc2ccsc2)c2ccc(F)c(F)c2Br)cc1]

A solution of the compound from step a (11.6 g, 31.9 mmol), 2-(thiophen-3-yl)ethan-1-ol (4.3 mL), PPh₃ (12.4 g, 47.8 mmol) in THF (62 mL) was cooled to 0° C. Then, DIAD (9.5 mL, 44.8 mmol) was dropwise added to the reaction mixture. After being stirred at 0° C. for 10 min, the reaction mixture was allowed to warm to rt and stirred for additional 1 hr. The solvent was evaporated under vacuum. The residue was purified by silica gel column chromatography (PE:EtOAc=10:1 to PE:EtOAc=5:1) to give the desired compound (15.69 g). ESI-MS m/z: 472.0 [M+H]⁺.

Example 69

Step c

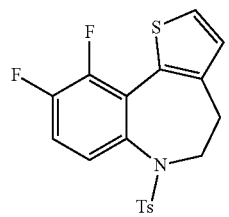

A mixture of the compound from step b (15.69 g, 33.2 mmol), Pd(OAc)₂ (0.75 g, 3.32 mmol), KOAc (19.6 g, 199.0 mmol) in DMF (72 mL) was stirred at 120° C. for 1 h under N₂ atmosphere. After being cooled to rt, the mixture was filtered through silica gel pad and washed with EA (5×100 mL). The filtrate was washed with H₂O (4×70 mL). The combined aqueous layers were extracted with EtOAc (3×50 mL). The combined organic layers was washed with brine, dried over Na₂SO₄, filtered and concentrated under vacuum. The residue was purified by silica gel column chromatography (PE:DCM=1:1) to give the desired product (8.89 g). ESI-MS m/z:=409.1 [M+NH₄]⁺.

Example 69

Step d

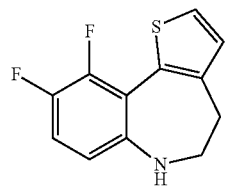

A solution of the compound from step c (7.87 g, 20.1 mmol) in con. H₂SO₄ (30 mL) was stirred at 50° C. for 1 h. Then the reaction mixture was cooled with ice bath and 60 mL H₂O, con. H₂SO₄ (45 mL) in H₂O (90 mL) was added to the mixture subsequently. Then, the mixture was stirred at 130° C. for 13 hrs and 140° C. for 8 hrs. After being cooled with ice bath, the mixture was basified with con. NaOH aq. (controlled the internal temperature below 30° C.). The obtained solid-liquid mixture was filtered and the aqueous layer was extracted with EtOAc (4×300 mL). The combined organic layer was washed with brine, dried over Na₂SO₄, filtered and concentrated under vacuum. The residue was purified by silica gel column chromatography eluting with EtOAc to afford the desired product (3.15 g). ESI-MS m/z: 238.1 [M+H]⁺.

Example 69

Step e

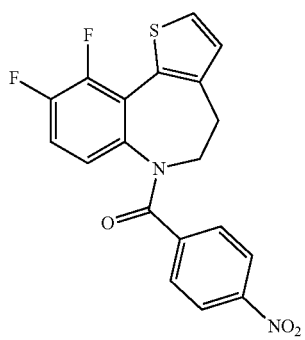 [SMILES: O=C(c1ccc([N+](=O)[O-])cc1)N1CCc2ccsc2-c2c1ccc(F)c2F]

To a mixture of the compound from step d (3.15 g, 13.3 mmol) and Et₃N (9.4 mL, 66.5 mmol) in DCM (50 mL) was added 4-nitrobenzoyl chloride (4.94 g, 26.6 mmol) at the temperature <30° C. in portions. The reaction mixture was stirred at rt for 16 hrs and concentrated. Then, the residue was diluted with DCM (200 mL) and the organic layer was washed with aq. NaOH (2×50 mL) and H₂O (50 mL) subsequently. The combined aqueous layers were extracted with DCM (30 mL). The combined organic layer was washed with brine, dried over Na₂SO₄, filtered and concentrated under vacuum. The residue was purified by silica gel column chromatography (DCM/EtOAc) to provide the desired product (5.0 g). ESI-MS m/z: 387.1 [M+H]⁺.

Example 69

Step f

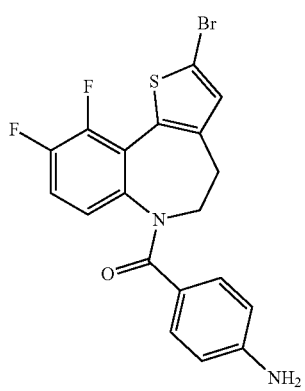 [SMILES: Nc1ccc(C(=O)N2CCc3cc(Br)sc3-c3c2ccc(F)c3F)cc1]

N-Bromosuccimide (2.76 g, 15.5 mmol) was added to the solution of the compound from step example 51 step e (5.0 g, 12.9 mmol) in DMF (40 mL) at rt for one time. The reaction mixture as stirred for 16 hrs and diluted with EtOAc (200 mL), washed with H₂O (4×50 mL). The aqueous layer was extracted with EtOAc (2×30 mL). The combined organic layer was washed with brine, dried over Na₂SO₄, filtered and concentrated under vacuum. The residue was purified by short silica gel pad (EtOAc) to give the crude product and used for next reaction without further purification. ESI-MS m/z: 464.9 [M+H]⁺. A solution of the crude product and Fe (2.17 g, 38.7 mmol) in 95% EtOH (240 mL) and sat. NH₄Cl aq. (60 mL) was stirred at 80° C. for 3.5 hrs. The mixture was concentrated under vacuum until about 100 mL remained, filtrated through celite, washed with H₂O (40 mL) and EA (5×100 mL). The combined organic layer was washed with brine, dried over Na₂SO₄, filtered and concentrated under vacuum. The residue was purified by short silica gel column chromatography (EtOAc) to provide the desired product (7.3 g). ESI-MS m/z: 434.9 [M+H]⁺.

Example 69

Step g

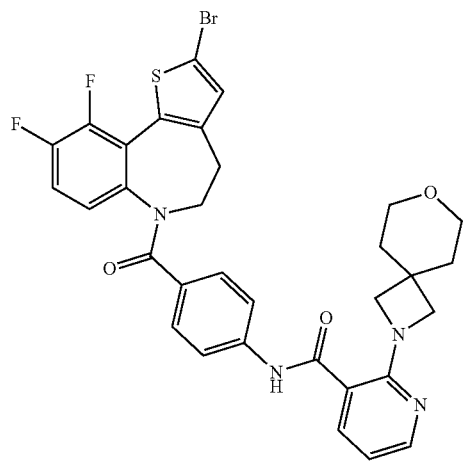 [SMILES: O=C(Nc1ccc(C(=O)N2CCc3cc(Br)sc3-c3c2ccc(F)c3F)cc1)c1cccnc1N1CC2(CCOCC2)C1]

A solution of the 1-chloro-N,N, 2-trimethylprop-1-en-1-amine (2.03 g, 15.2 mmol) and 2-(7-oxa-2-azaspiro[3.5]nonan-2-yl)nicotinic acid (1.37 g, 5.51 mmol) in DCM (20 mL) was stirred at rt for 60 min before being concentrated under vacuum. Then, the residue was dissolved in DCM (20 mL), a solution of the compound from step f (2.0 g, 4.59 mmol) and pyridine (1.1 mL, 13.8 mmol) in DCM (60 mL) was dropwise added to acyl chloride solution at rt and stirred for one day. The reaction was quenched by addition of aq. NaOH (100 mL) and separated. The organic layer was washed with aq. NaOH (100 mL) and 50 mL H₂O subsequently. The combined aqueous layer was extracted with DCM (2×30 mL). The combined organic layer was washed with brine, dried over Na₂SO₄, filtered and concentrated under vacuum. The residue was purified by silica gel column chromatography to give the desired product (1.45 g). ESI-MS m/z: 665.1 [M+H]⁺.

Example 69

Step h

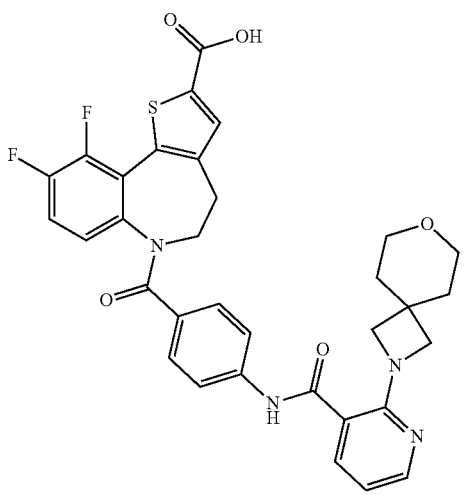 [SMILES: O=C(O)c1cc2c(s1)-c1c(ccc(F)c1F)N(C(=O)c1ccc(NC(=O)c3cccnc3N3CC4(CCOCC4)C3)cc1)CC2]

A solution of the compound from step g (1.01 g, 1.5 mmol), Pd(dppf)Cl$_2$.DCM (245 mg, 0.301 mmol), Et$_3$N (2.1 mL, 15.0 mmol) in dioxane/H$_2$O (8/4 mL) was stirred at 80° C. for 4 hrs under CO atmosphere (10 atm). After being cooled to rt, the reaction mixture was concentrated under vacuum. The residue was purified by silica gel column chromatography (EA to DCM:MeOH=10:1 to 5:1) to provide the desired product (660 mg). ESI-MS m/z: 631.1 [M+H]$^+$.

Example 69

Step i

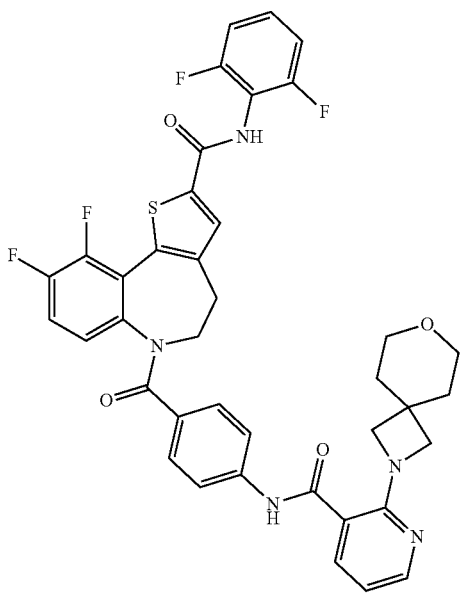 [SMILES: O=C(Nc1c(F)cccc1F)c1cc2c(s1)-c1c(ccc(F)c1F)N(C(=O)c1ccc(NC(=O)c3cccnc3N3CC4(CCOCC4)C3)cc1)CC2]

A solution of 1-chloro-N,N, 2-trimethylprop-1-en-1-amine (33 mg, 0.2445 mmol) and carboxylic acid from step h (50 mg, 0.0815 mmol) in DCM (1 mL) was stirred at rt for 90 min. Then, 2,6-difluoroaniline (53 mg, 0.407 mmol) and pyridine (64 mg, 0.815 mmol) in DCM (1 mL) was added to the above mixture in one portion. The reaction mixture was stirred at rt for 5 hrs. After being concentrated under vacuum, the residue was purified by prep-HPLC to give the product as a white solid (15.8 mg). ESI-MS m/z: 742.05 [M+H]$^+$. $^1$H NMR (400 MHz, DMSO-d$_6$) δ 1.64 (t, J=5.2 Hz, 2H), 2.89-3.05 (m, 1H), 3.16-3.26 (m, 1H), 3.44-3.53 (m, 3H), 3.66 (s, 5H), 4.80 (ws, 1H), 6.89-7.07 (m, 3H), 7.11-7.36 (m, 3H), 7.39-7.49 (m, 1H), 7.56 (d, J=8.3 Hz, 2H), 7.64 (dd, J=7.5, 1.9 Hz, 1H), 8.05 (s, 1H), 8.19 (dd, J=4.8, 1.8 Hz, 1H), 8.46-8.30 (m, 1H), 10.41 (s, 1H).

Example 70

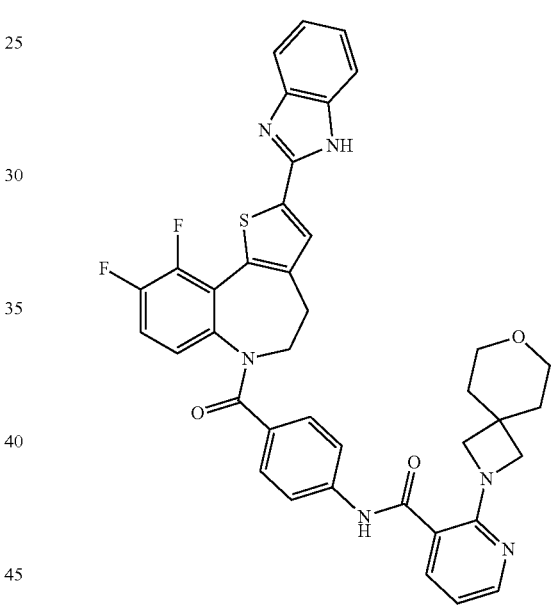

Example 70 was prepared using the procedure similar to that of example 3 (step k and l) from the corresponding intermediates. ESI-MS m/z: 703.05 [M+H]$^+$.

Examples 71-81 shown in table 9 were prepared using the procedure similar to those of example 3 (step k and l) from the corresponding intermediates.

TABLE 9

| Example | Structure | ESI-MS m/z: [M+H]+ |
|---|---|---|
| 71 | 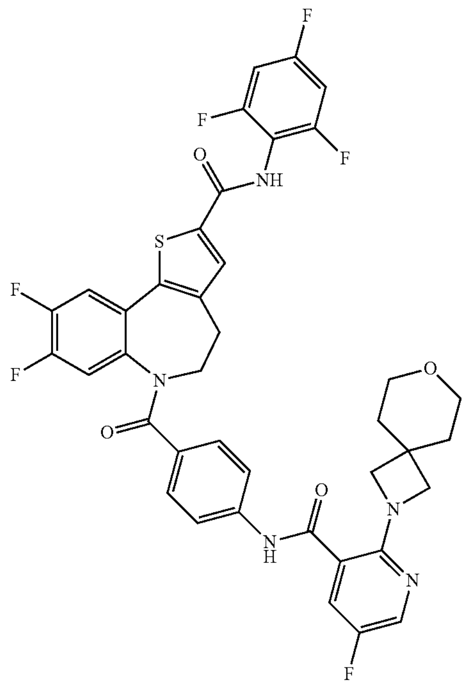 [SMILES: O=C(Nc1c(F)cc(F)cc1F)c1cc2c(s1)-c1cc(F)c(F)cc1N(C(=O)c1ccc(NC(=O)c3cc(F)cnc3N3CC4(CCOCC4)C3)cc1)CC2] | 778.0 |
| 72 | 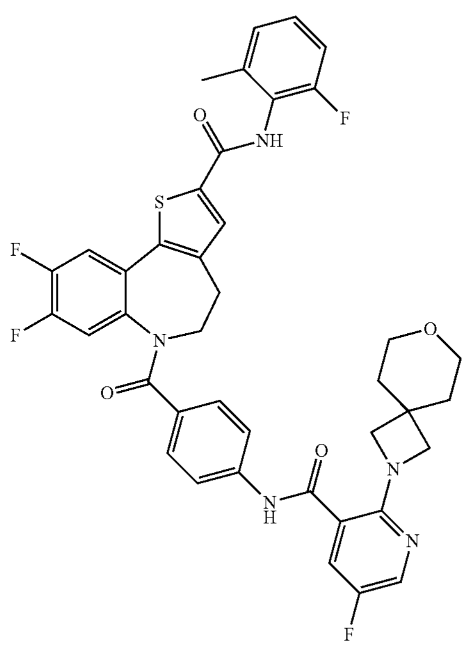 [SMILES: O=C(Nc1c(F)cccc1F)c1cc2c(s1)-c1cc(F)c(F)cc1N(C(=O)c1ccc(NC(=O)c3cc(F)cnc3N3CC4(CCOCC4)C3)cc1)CC2] | 756.0 |
| 73 | | 760.0 |
| 74 | | 776.0 |

TABLE 9-continued

| Example | Structure | ESI-MS m/z: [M + H]+ |
|---|---|---|
| 75 | 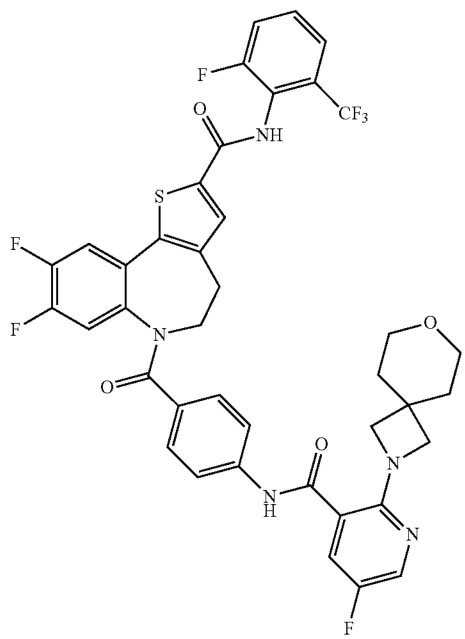 [SMILES: O=C(Nc1c(F)cccc1Cl)c1cc2c(s1)-c1cc(F)c(F)cc1N(C(=O)c1ccc(NC(=O)c3cc(F)cnc3N3CC4(CCOCC4)C3)cc1)CC2] | 810.0 |
| 76 | 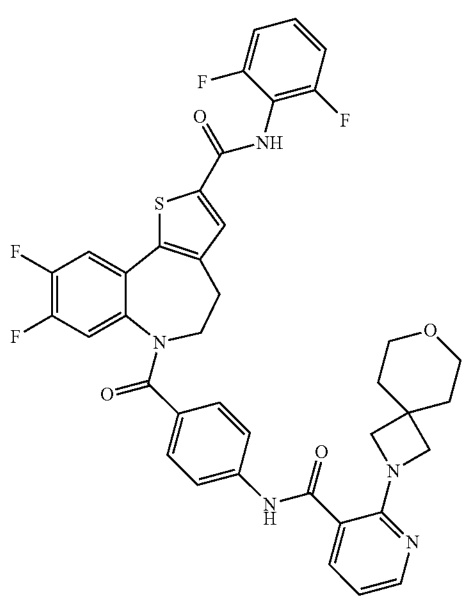 [SMILES: O=C(Nc1c(F)cccc1F)c1cc2c(s1)-c1cc(F)c(F)cc1N(C(=O)c1ccc(NC(=O)c3cccnc3N3CC4(CCOCC4)C3)cc1)CC2] | 742.0 |
| 77 | | 719.05 |
| 78 | | 760.05 |

TABLE 9-continued

| Example | Structure | ESI-MS m/z: [M + H]+ |
|---|---|---|
| 79 | 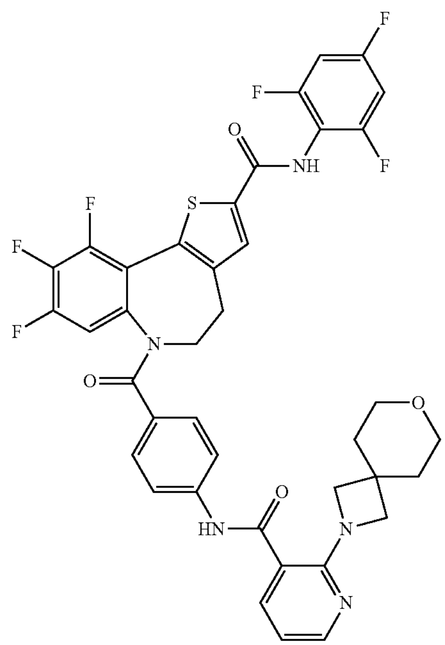 [SMILES: O=C(Nc1c(F)cc(F)cc1F)c1cc2c(s1)-c1c(cc(F)c(F)c1F)N(C(=O)c1ccc(NC(=O)c3cccnc3N3CC4(CCOCC4)C3)cc1)CC2] | 778.05 |
| 80 | 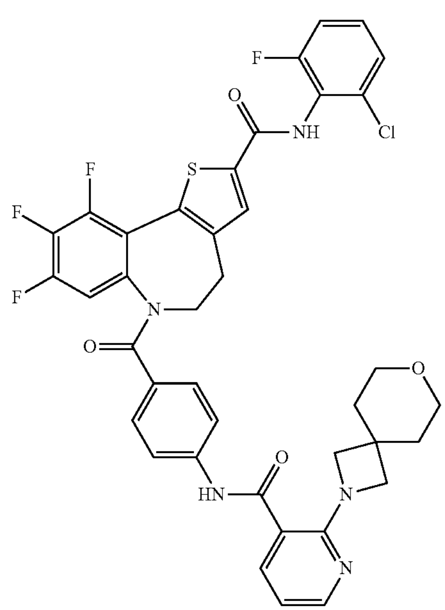 [SMILES: O=C(Nc1c(F)cccc1Cl)c1cc2c(s1)-c1c(cc(F)c(F)c1F)N(C(=O)c1ccc(NC(=O)c3cccnc3N3CC4(CCOCC4)C3)cc1)CC2] | 775.95 |
| 81 | 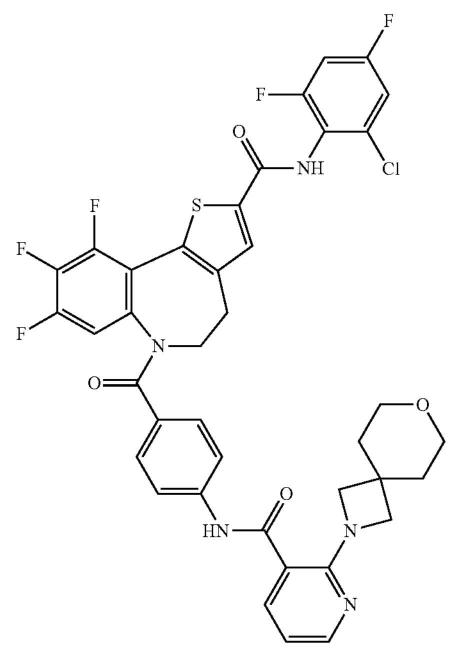 [SMILES: O=C(Nc1c(F)cc(F)cc1Cl)c1cc2c(s1)-c1c(cc(F)c(F)c1F)N(C(=O)c1ccc(NC(=O)c3cccnc3N3CC4(CCOCC4)C3)cc1)CC2] | 793.95 |

Scheme 9
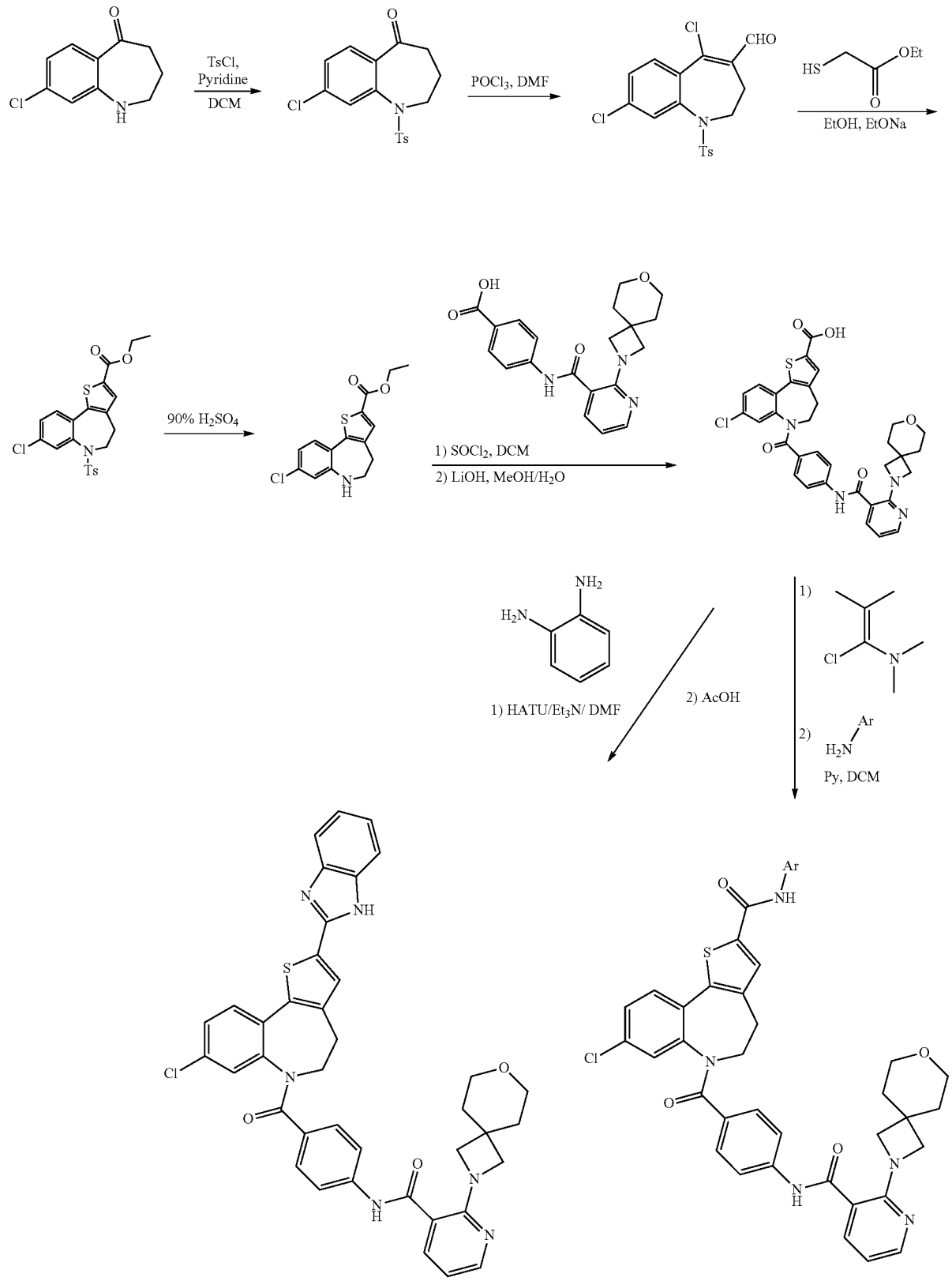

Example 82

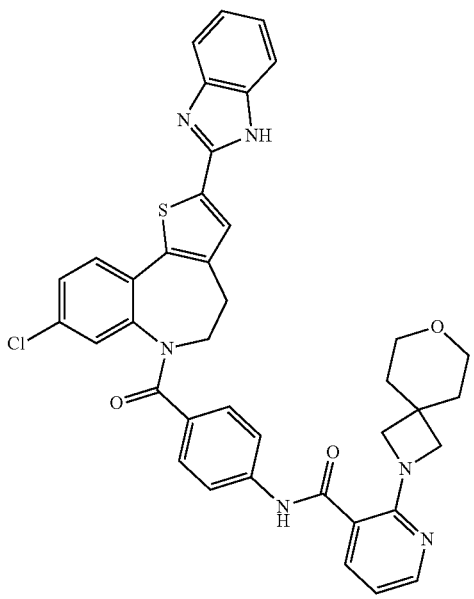 [SMILES: O=C(Nc1ccc(C(=O)N2CCc3cc(-c4nc5ccccc5[nH]4)sc3-c3ccc(Cl)cc32)cc1)c1cccnc1N1CC2(CCOCC2)C1]

Example 82

Step a

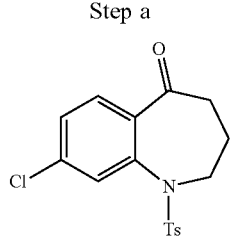

To a mixture of 8-chloro-1,2,3,4-tetrahydro-5H-benzo[b]azepin-5-one (5.0 g, 25.5 mmol) in DCM (25 mL) and pyridine (5 mL) was added TsCl (5.8 g, 30.6 mmol) at 0° C. and stirred at rt for overnight. The reaction was quenched by addition of water (75 mL) and extracted with DCM (30 mL×3). The combined organic phase was washed with water, brine, dried over anhydrous Na$_2$SO$_4$ and concentrated under reduced pressure. The residue was washed with mixed solvent (PE:EtOAc=20:1) to give the desired product as a light yellow solid (7.1 g).

Example 82

Step b

POCl$_3$ (6.6 g, 42.9 mmol) was dropwise added to DMF (20 mL) at 0° C. under N$_2$. Then, a solution of the compound from step a (5.0 g, 14.3 mol) in DMF (5 mL) was added. The reaction mixture was then warmed to room temperature and heated at 80° C. for 3 hrs. The mixture was poured into cooled. Saturated aq. AcONa solution (100 mL) was added and the mixture was extracted with EtOAc (100 mL×3). The combined organic phase was washed with water, saturated NaHCO$_3$ aqueous solution, brine, dried over anhydrous Na$_2$SO$_4$ and concentrated under reduced pressure. The residue was purified by silica gel column chromatography (PE:EtOAc=3:1) to give the desired product as a yellow solid (3.0 g). ESI-MS m/z: 396.00 [M+H]$^+$.

Example 82

Step c

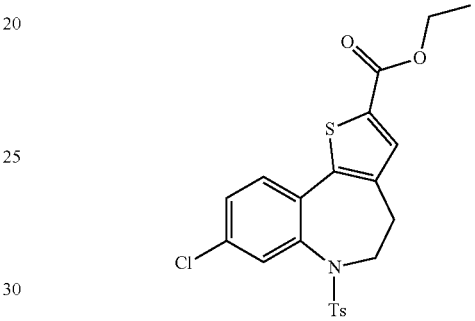

A solution of EtONa/EtOH (21%, 6.5 mL, 17.5 mmol) was added to a solution of ethyl-2-mercaptoacetate (1.9 mL, 17.5 mmol) in EtOH (30 mL) cooled with ice bath under N$_2$. The mixture was stirred for 30 min and then the compound from step b (2.3 g, 5.82 mmol) was added. The reaction mixture was stirred at this temperature for 30 min and then refluxed for 2.5 hrs. The mixture was then cooled to rt, adjusted pH to 7 with 2 N HCl, extracted with EA (50 mL×3) and the combined organic phase was washed with water, sat. aq. NaHCO$_3$ solution, brine, dried over anhydrous Na$_2$SO$_4$ and concentrated under reduced pressure. The residue was purified by silica gel column chromatography (PE: EtOAc=2:1) to give the desired product as a yellow solid (2.0 g). ESI-MS m/z: 484.00 [M+H]$^+$.

Example 82

Step d

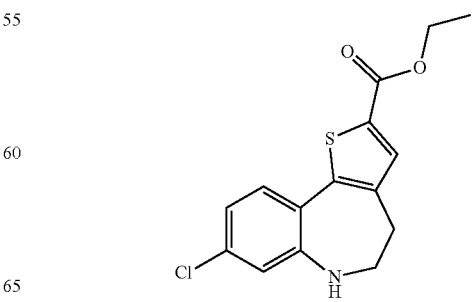

The compound from example 82 step c (1.8 g, 3.9 mmol) was added to 90% H$_2$SO$_4$ (20 mL) at 0° C. and stirred at rt for 4 hrs. The reaction mixture was poured into ice water and the precipitate was filtered, washed with water, dried under vacuum to give the desired product as a yellow solid (1.1 g). ESI-MS m/z: 308.00 [M+H]$^+$.

Example 82

Step e

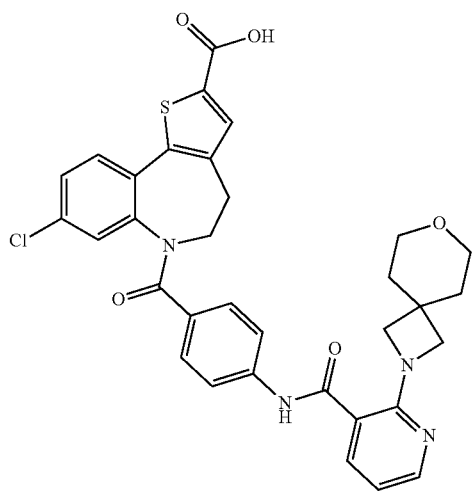 [SMILES: O=C(O)c1cc2c(s1)-c1ccc(Cl)cc1N(C(=O)c1ccc(NC(=O)c3cccnc3N3CC4(CCOCC4)C3)cc1)CC2]

To a mixture of 4-(2-(7-oxa-azaspiro[3.5]nonan-2-yl)nicotinamido)benzoic acid (500 mg, 1.36 mmol) in DCM (20 mL) was dropwise added SOCl$_2$ (2.0 mL) and heated at 45° C. for 1 hr and concentrated. Compound from example 82 step d (627 m g, 2.04 mmol) in DCM (20 mL) and pyridine (1 mL) were added. The reaction mixture was stirred at rt for 1 hr and concentrated and purified by column chromatography (MeCN/H$_2$O) to give the desired compound as a red solid (850 mg), which was dissolved in MeOH (20 mL)/H$_2$O (10 mL), treated with LiOH (311 mg, 12.9 mmol) and stirred at rt for 1 hr. The reaction mixture was adjusted to pH 4 with HCl (12M) and the solids were filtered to provide the desired compound as a yellow solid (790 mg). ESI MS m/z=629.20 [M+H]$^+$.

Example 82 was prepared using the procedure similar to that of example 3 (step k and l) from the acid in step e. ESI-MS m/z: 701.20 [M+H]$^+$.

Examples 83-87 shown in table 10 were prepared using the procedure similar to those of example 4 from the corresponding intermediates.

TABLE 10

| Example | Structure | ESI-MS m/z: [M + H]$^+$ |
|---|---|---|
| 83 | 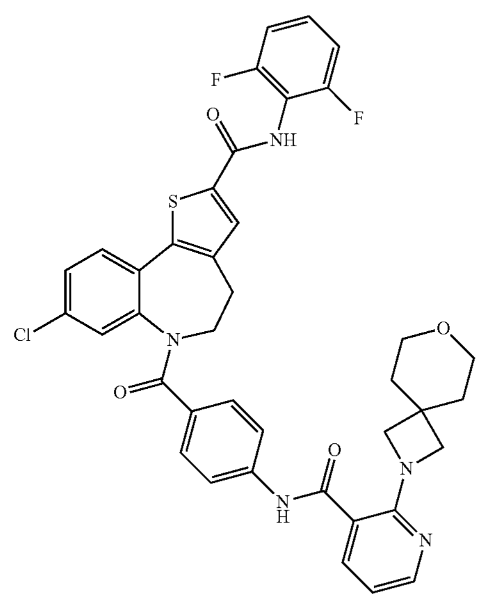 [SMILES: O=C(Nc1c(F)cccc1F)c1cc2c(s1)-c1ccc(Cl)cc1N(C(=O)c1ccc(NC(=O)c3cccnc3N3CC4(CCOCC4)C3)cc1)CC2] | 740.20 |

TABLE 10-continued

| Example | Structure | ESI-MS m/z: [M + H]+ |
|---|---|---|
| 84 | 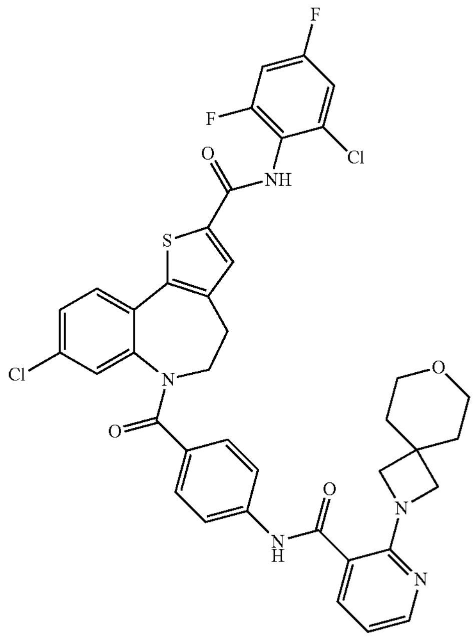 [SMILES: O=C(Nc1c(F)cc(F)cc1Cl)c1cc2c(s1)-c1ccc(Cl)cc1N(C(=O)c1ccc(NC(=O)c3cccnc3N3CC4(CCOCC4)C3)cc1)CC2] | 774.15 |
| 85 | 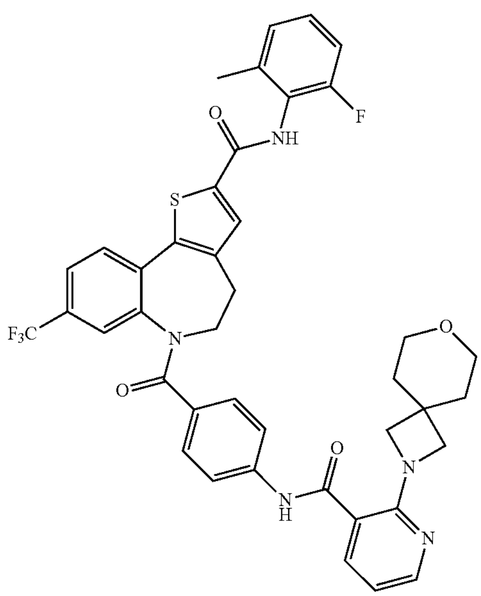 [SMILES: Cc1cccc(F)c1NC(=O)c1cc2c(s1)-c1ccc(C(F)(F)F)cc1N(C(=O)c1ccc(NC(=O)c3cccnc3N3CC4(CCOCC4)C3)cc1)CC2] | 770.0 |

TABLE 10-continued

| Example | Structure | ESI-MS m/z: [M + H]+ |
|---|---|---|
| 86 | 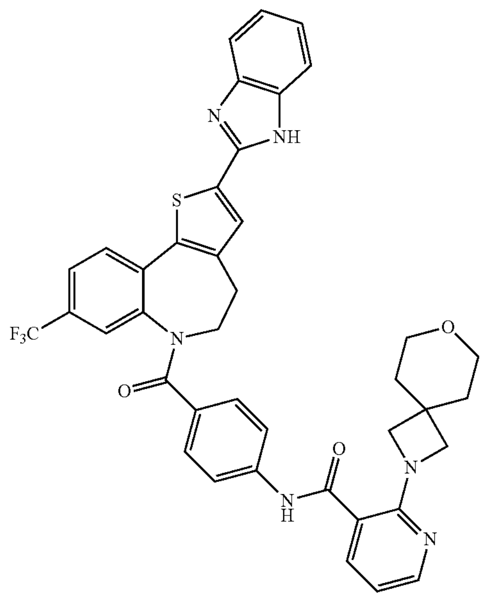 [SMILES: O=C(Nc1ccc(C(=O)N2CCc3cc(-c4nc5ccccc5[nH]4)sc3-c3ccc(C(F)(F)F)cc32)cc1)c1cccnc1N1CC2(CCOCC2)C1] | 735.0 |
| 87 | 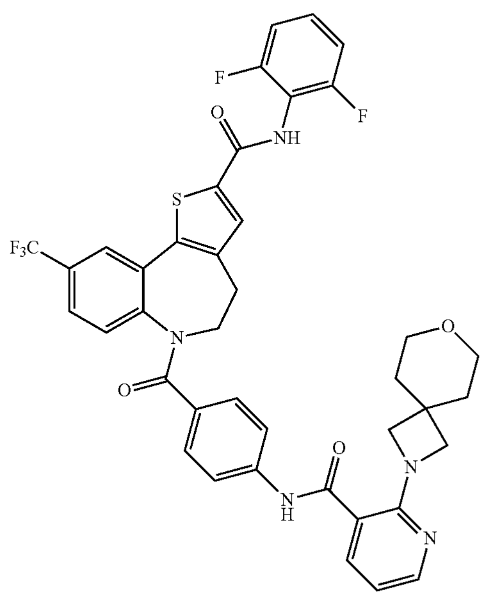 [SMILES: O=C(Nc1c(F)cccc1F)c1cc2c(s1)-c1cc(C(F)(F)F)ccc1N(C(=O)c1ccc(NC(=O)c3cccnc3N3CC4(CCOCC4)C3)cc1)CC2] | 774.0 |

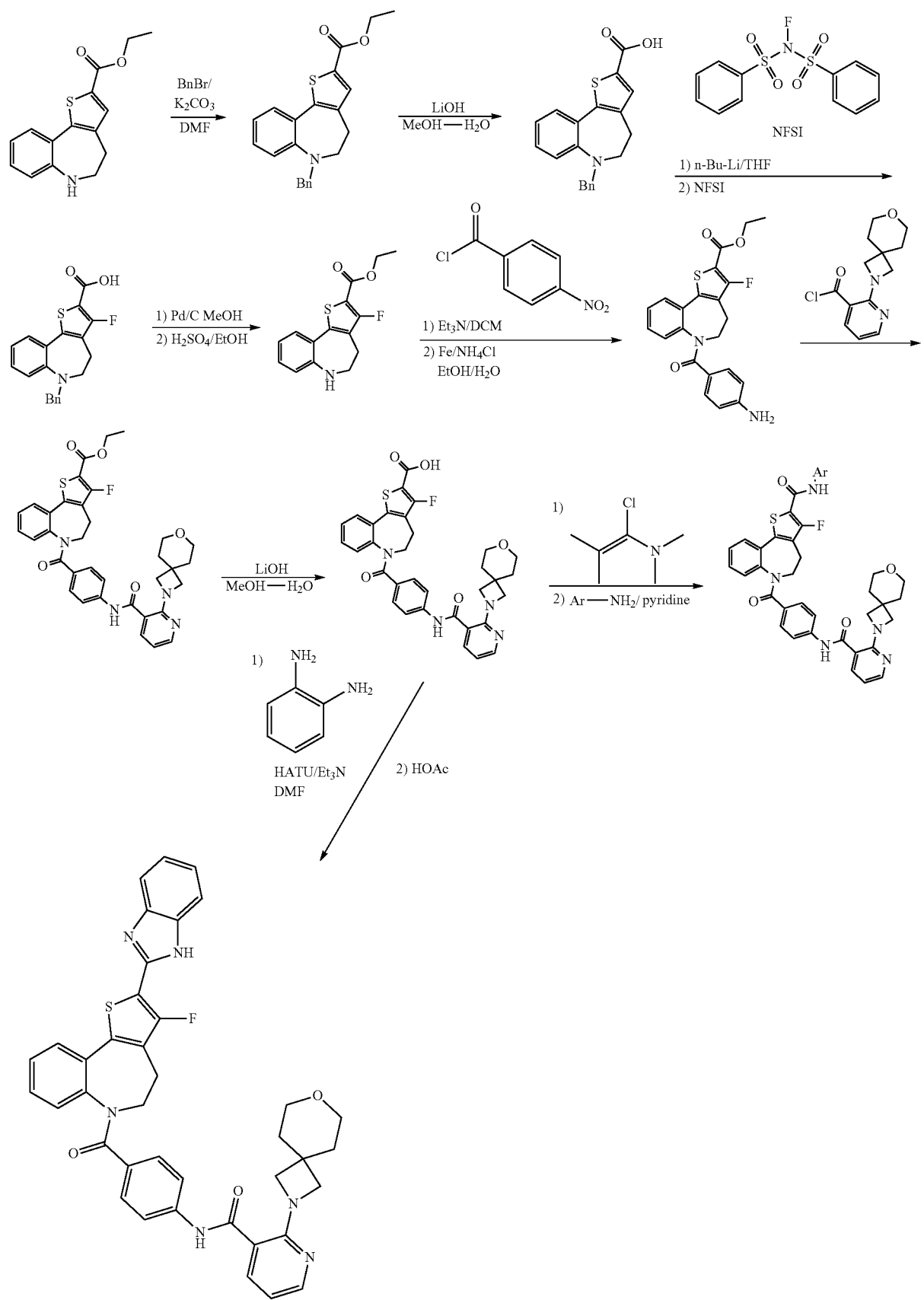
Scheme 10

Example 88

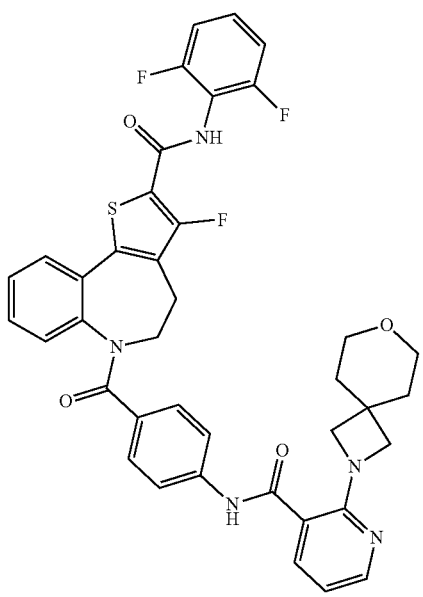 [SMILES: O=C(Nc1ccc(C(=O)N2CCc3c(sc(C(=O)Nc4c(F)cccc4F)c3F)-c3ccccc32)cc1)c1cccnc1N1CC2(CCOCC2)C1]

Example 88

Step a

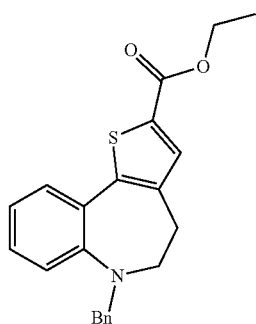 [SMILES: CCOC(=O)c1cc2c(s1)-c1ccccc1N(Cc1ccccc1)CC2]

To a mixture of ethyl 5,6-dihydro-4H-benzo[b]thieno[2,3-d]azepine-2-carboxylate (4.0 g, 14.65 mmol) DMF (50 mL) were added BnBr (12.4 g, 72.94 mmol) and K$_2$CO$_3$ (6.06 g, 43.91 mmol) and heated at 100° C. for 3 hrs. The reaction mixture was diluted with water and extracted with EtOAc (3 times). The combined organic layer was washed with brine, dried over Na$_2$SO$_4$, filtered and concentrated under vacuum to give the crude product (4.3 g), which was used for next step directly. ESI-MS m/z: 364.10 [M+H]$^+$.

Example 88

Step b

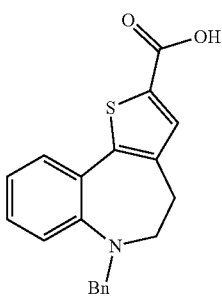 [SMILES: O=C(O)c1cc2c(s1)-c1ccccc1N(Cc1ccccc1)CC2]

To a mixture of the compound from step a (4.3 g, crude) in THF-MeOH—H$_2$O (2:1:1, 40 mL) was added NaOH (2.0 g, 50 mmol) and heated at 50° C. for 3 hrs. The reaction mixture was adjusted to pH=4 with 2 N HCl, and extracted with EtOAc. The organic layer was washed with brine, dried over Na$_2$SO$_4$, filtered and concentrated. The crude product was purified by silica gel column chromatography (0 t-60% CH$_3$CN in H$_2$O) to afford the desired compound (3.9 g) as a light yellow solid. ESI-MS m/z: 336.10 [M+H]$^+$.

Example 88

Step c

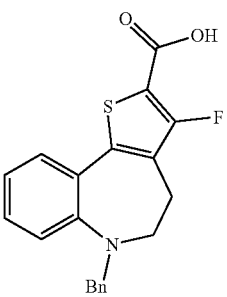 [SMILES: O=C(O)c1sc2c(c1F)CCN(Cc1ccccc1)c1ccccc1-2]

To a mixture of the compound from step b (3.1 g, 9.25 mmol) in THF was dropwise added n-BuLi (2.5 M, 9 mL, 22.5 mmol) at −78° C. and stirred for 2 hrs. Then, N-fluorobenzene-sulfonimide (7.1 g, 22.5 mmol) in THF was dropwise added to the reaction mixture at −78° C. and stirred for 10 min before being allowed to warm to rt and stirred for 2 hrs. The reaction mixture was adjusted to pH=4 with 2 N HCl, and then extracted with EtOAc. The organic layer was washed with brine, dried over Na$_2$SO$_4$, filtered and concentrated under vacuum. The crude product was purified by silica gel column chromatography eluting with 0-5% MeOH/DCM to afford the desired product (1.5 g) as a yellowish solid. ESI-MS m/z: 354.05 [M+H]$^+$.

Example 88

Step d

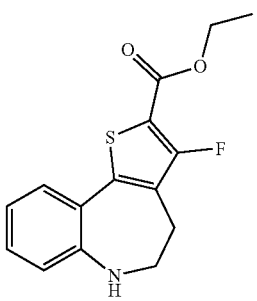 [SMILES: CCOC(=O)c1sc2c(c1F)CCNc1ccccc1-2]

A mixture of the compound from step c (900 mg, 2.55 mmol) and Pd/C (2.5 g) in MeOH (65 mL) was stirred at rt for 5 hrs under H$_2$ atmosphere. The solids were filtered and evaporated to afford crude product (635 mg), which dissolved in EtOH (50 mL) and con. H$_2$SO$_4$ (3 mL) and heated at 85° C. for overnight. The reaction mixture was concentrated, diluted with H$_2$O and adjusted pH to 10 with NaHCO$_3$, extracted with EtOAc and washed with brine, dried over Na$_2$SO$_4$ filtered and concentrated to afford the desired product (580 mg) as a red oil. ESI-MS m/z: 292.10 [M+H]$^+$.

Example 88

Step e

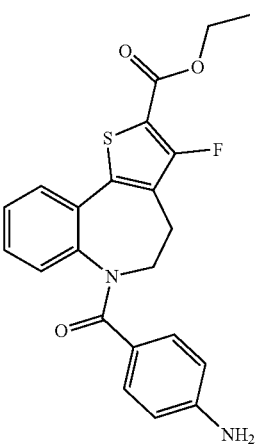 [SMILES: CCOC(=O)c1sc2c(c1F)CCN(C(=O)c1ccc(N)cc1)c1ccccc1-2]

To a mixture of the compound from step d (580 mg, 1.99 mmol) and Et$_3$N (1 mL) in DCM (20 mL) was added 4-nitrobenzoyl chloride (736 mg, 3.98 mmol) and stirred at rt for 3 hrs. The reaction mixture was concentrated and purified by silica gel column chromatography to afford the desired product (610 mg) as a yellow solid. ESI MS m/z: 441.05 [M+H]$^+$. A mixture of previously obtained compound (580 mg, 1.38 mmol), Fe (1.53 g, 27.27 mmol) and NH$_4$Cl (1.46 g, 27.27 mmol) in EtOH (20 mL)-H$_2$O (10 mL) was heated at 80° C. for 3 hrs. The reaction mixture was filtered. Then, the filtrate was diluted with water and extracted with EtOAc (3 times). The combined organic layer was washed with brine, dried over Na$_2$SO$_4$, filtered and concentrated under vacuum. The crude product was purified by column chromatography to afford the desired product (450 mg) as a yellowish solid. ESI-MS m/z: 411.10 [M+H]$^+$.

Example 88

Step f

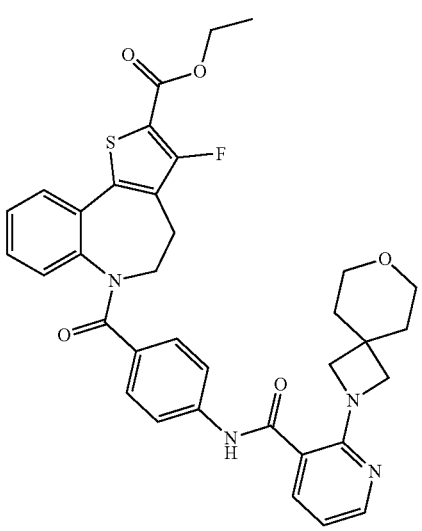 [SMILES: CCOC(=O)c1sc2c(c1F)CCN(C(=O)c1ccc(NC(=O)c3cccnc3N3CC4(CCOCC4)C3)cc1)c1ccccc1-2]

To a mixture of 2-(7-oxa-2-azaspiro[3.5]nonan-2-yl)nicotinic acid (300 mg, 1.20 mmol) in DCM (10 mL) was added 1-chloro-N,N-2-trimethylprop-1-en-1-amine (320 mg, 2.40 mmol) and stirred at rt for 1 h and concentrated. the compound from step e (410 mg, 1.0 mmol) in DCM (5 mL) and pyridine (0.5 mL) were added to the reaction mixture. The reaction was stirred at rt for 3 hrs and concentrated. The crude product was purified by silica gel column chromatography to afford the desired product (520 mg) as a yellowish solid. ESI-MS m/z: 641.20 [M+H]$^+$.

Example 88

Step g

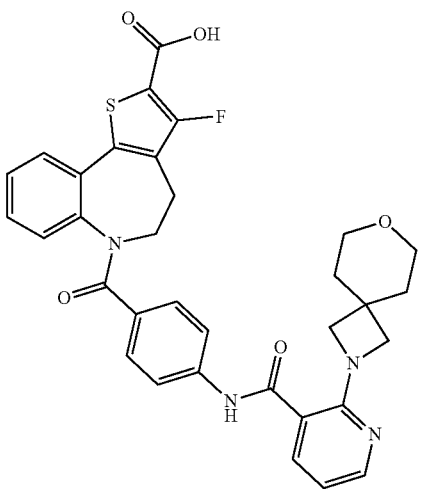 [SMILES: O=C(Nc1ccc(C(=O)N2CCc3c(sc(C(=O)O)c3F)-c3ccccc32)cc1)c1cccnc1N1CC2(CCOCC2)C1]

To a mixture of the compound from step e (490 mg, 0.76 mmol) in MeOH—H$_2$O (2:1, 15 mL) was added LiOH (184 mg, 7.65 mmol) and stirred at rt for 1 hr. The reaction mixture was adjusted pH to 4 with HCl (12 M) and filtered to afford the desired product (455 mg) as a yellowish solid. ESI-MS m/z: 613.00 [M+H]$^+$.

Example 88

Step h

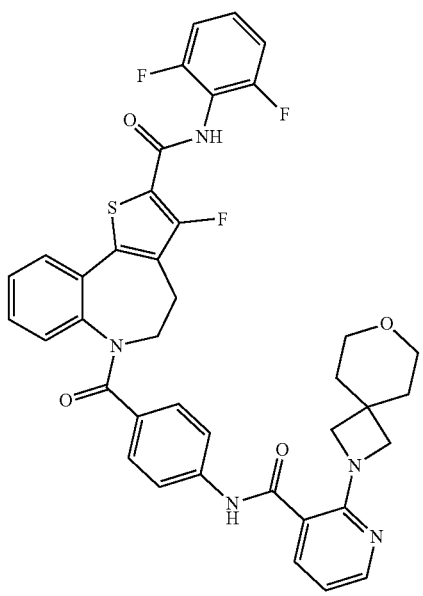 [SMILES: O=C(Nc1ccc(C(=O)N2CCc3c(sc(C(=O)Nc4c(F)cccc4F)c3F)-c3ccccc32)cc1)c1cccnc1N1CC2(CCOCC2)C1]

Example 88 was prepared using the procedure similar to those of example 4 from the corresponding intermediates. ESI-MS m/z: 724.20 [M+H]$^+$. $^1$H NMR (300 MHz, DMSO-d$_6$) δ 1.61-1.65 (m, 4H), 3.07-3.64 (m, 11H), 4.90-5.10 (m, 1H), 6.54-6.91 (m, 4H), 7.02-7.34 (m, 5H), 7.41-7.88 (m, 4H), 8.17-8.19 (m, 1H), 9.74 (s, 1H), 12.40 (s, 1H).

Examples 89-98 shown in table 11 were prepared using the procedure similar to those of example 3 (step k and l) and example 4 from the corresponding intermediates.

TABLE 11

| Example | Structure | ESI-MS m/z: [M + H]$^+$ |
|---------|-----------|------------------------|
| 89 | 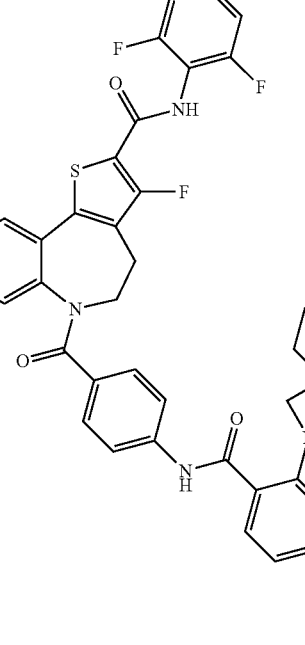 | 740.20 |
| 90 | 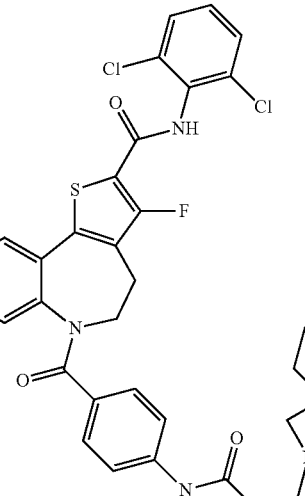 | 756.15 |

TABLE 11-continued

| Example | Structure | ESI-MS m/z: [M + H]+ |
|---|---|---|
| 91 | 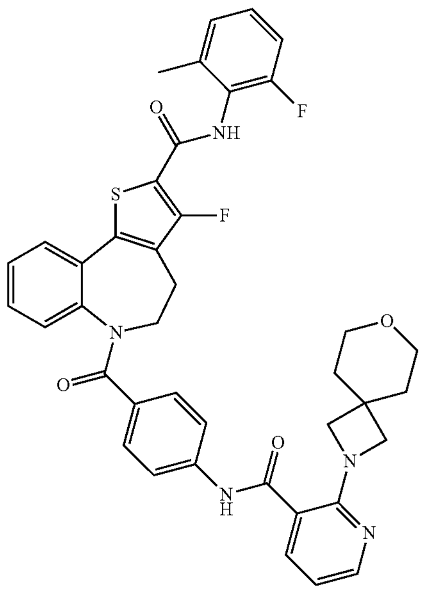 [SMILES: Cc1cccc(F)c1NC(=O)c1sc2c(c1F)CCN(C(=O)c1ccc(NC(=O)c3cccnc3N3CC4(CCOCC4)C3)cc1)c1ccccc1-2] | 720.25 |
| 92 | 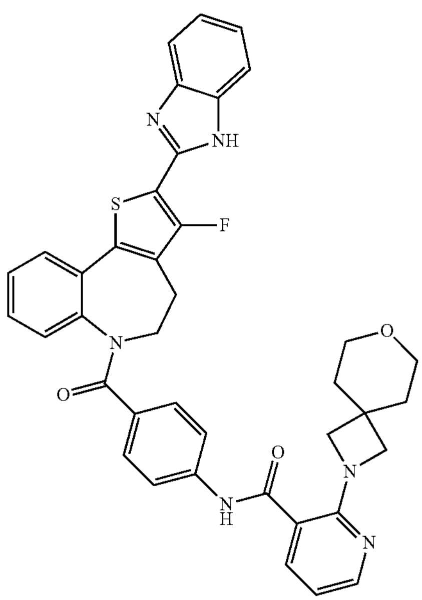 [SMILES: O=C(Nc1ccc(C(=O)N2CCc3c(sc(-c4nc5ccccc5[nH]4)c3F)-c3ccccc32)cc1)c1cccnc1N1CC2(CCOCC2)C1] | 685.30 |
| 93 | | 738.20 |
| 94 | | 756.25 |

TABLE 11-continued

| Example | Structure | ESI-MS m/z: [M + H]+ |
|---------|-----------|----------------------|
| 95 | 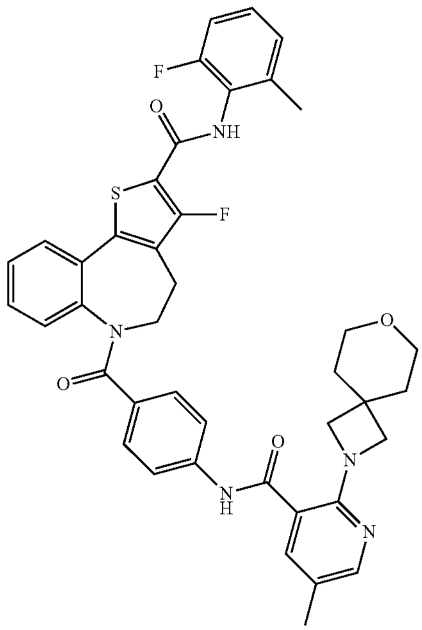 [SMILES: Cc1cnc(N2CC3(CCOCC3)C2)c(C(=O)Nc2ccc(C(=O)N3CCc4c(sc(C(=O)Nc5c(C)cccc5F)c4F)-c4ccccc43)cc2)c1] | 734.30 |
| 96 | 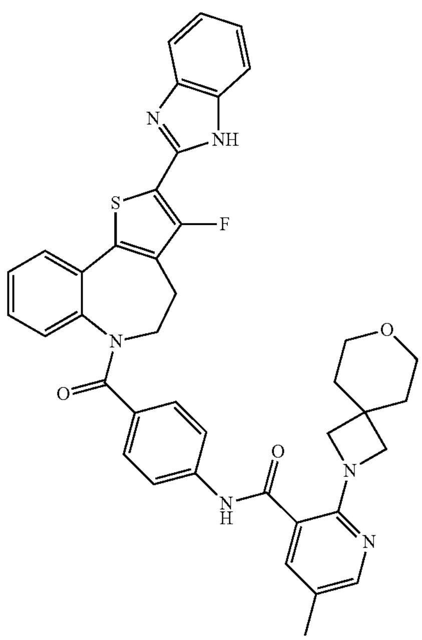 [SMILES: Cc1cnc(N2CC3(CCOCC3)C2)c(C(=O)Nc2ccc(C(=O)N3CCc4c(sc(-c5nc6ccccc6[nH]5)c4F)-c4ccccc43)cc2)c1] | 699.10 |
| 97 | | 733.05 |
| 98 | | 767.05 |

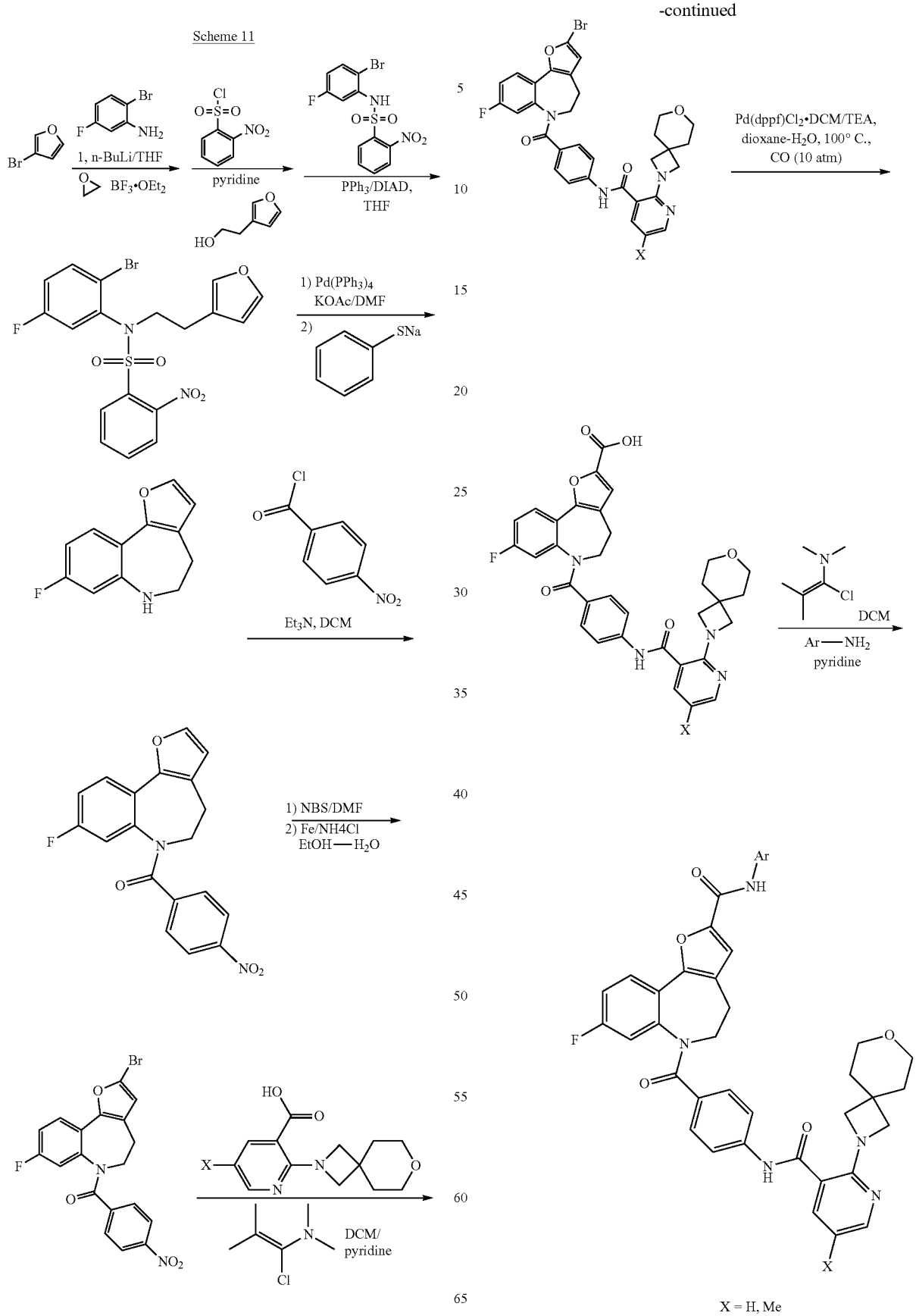
X = H, Me

Example 99

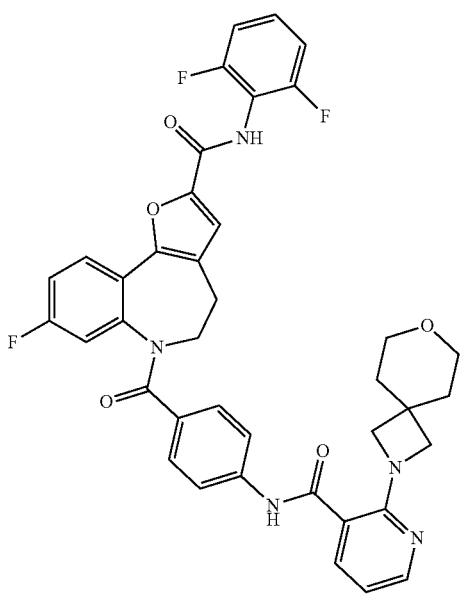 [SMILES: O=C(Nc1c(F)cccc1F)c1cc2c(o1)-c1ccc(F)cc1N(C(=O)c1ccc(NC(=O)c3cccnc3N3CC4(CCOCC4)C3)cc1)CC2]

Example 99

Step a

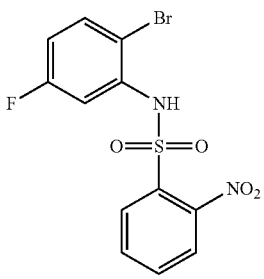 [SMILES: O=[N+]([O-])c1ccccc1S(=O)(=O)Nc1cc(F)ccc1Br]

To a mixture of 2-bromo-5-fluorobenzenamine (30 g, 158.7 mmol) in pyridine (300 mL) was added 2-nitrobenzene-1-sulfonyl chloride (38.6 g, 174.6 mmol) at rt. The reaction mixture was stirred for overnight. The reaction mixture was diluted with water and extracted with EtOAc. The organic layer was washed with brine, dried over Na₂SO₄, filtered and concentrated under vacuum. The residue was purified by silica gel column chromatography to afford the desired product as a yellow solid (51 g). ESI-MS m/z: 372.85 [M+H]⁺.

Example 99

Step b

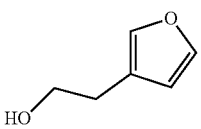

To a mixture of 3-bromofuran (9 g, 61.37 mmol, 1 equiv) in THF was dropwise added n-BuLi (24.7 mL, 61.37 mmol) at −78° C. for 1 h under nitrogen atmosphere followed by the slow addition of oxirane (3.24 g, 73.65 mmol) and BF₃.Et₂O (10.45 g, 73.65 mmol) at −78° C. The resulting mixture was stirred at −78° C. for 2 hrs. The reaction was quenched by addition of saturated NaHCO₃. The resulting mixture was extracted with EtOAc (3×200 mL). The combined organic layers were dried over Na₂SO₄, filtered and concentrated under vacuum to afford the desired product (9 g, crude) as a yellow oil. The crude product was used in the next step directly without further purification.

Example 99

Step c

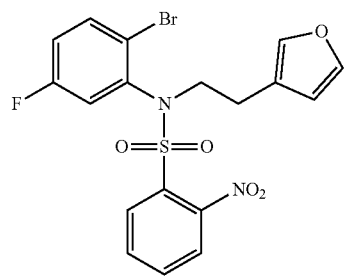 [SMILES: O=[N+]([O-])c1ccccc1S(=O)(=O)N(CCc1ccoc1)c1cc(F)ccc1Br]

To a mixture of the compound from step b (9 g, crude, 80.4 mmol), PPh₃ (21.06 g, 80.4 mmol), and the compound from step a (15.03 g, 40.2 mmol) in THF was dropwise added DIAD (16.2 g) at 0° C. under N₂. The reaction mixture was stirred at rt for 2 hrs, then it was purified by silica gel column chromatography (15 g crude obtained). The crude product (7 g) was further purified by column chromatography (MeCN/H₂O) to afford the desired product (3 g). ESI-MS m/z: 486.00 [M+H]⁺.

Example 99

Step d

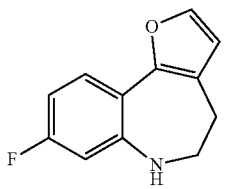 [SMILES: Fc1ccc2c(c1)NCCc1ccoc1-2]

A mixture of the compound from step c (3.0 g, 6.4 mmol), Pd(PPh₃)₄ (738 mg, 0.64 mmol) and KOAc (1.25 g, 12.8 mmol) in DMF was heated at 110° C. overnight under N₂. The reaction mixture was allowed to cool to rt, diluted with water, extracted with EtOAc (3 times). The combined organic layer was washed with brine, dried over Na₂SO₄, filtered and concentrated. The crude product was purified by column chromatography (MeCN/H₂O) to afford the desired product (1.4 g), which was dissolved in MeCN (10 mL), treated with sodium benzenethiolate (953 mg, 7.2 mmol) and stirred for 1 h. Then, the reaction mixture was filtered, concentrated and purified by column chromatography (MeCN/H₂O) to afford the desired compound as an orange solid (460 mg). ESI-MS m/z: 204.10 [M+H]⁺.

Example 99

Step e

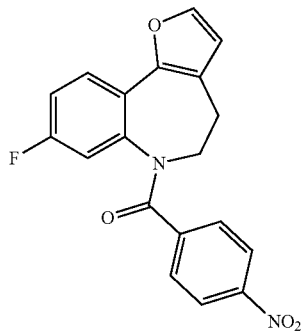 [SMILES: O=C(c1ccc([N+](=O)[O-])cc1)N1CCc2ccoc2-c2ccc(F)cc21]

To a mixture of the compound from step d (460 mg, 2.27 mmol) and TEA (1 mL) in DCM (5 mL) was added 4-nitrobenzoyl chloride (838 mg, 4.53 mmol) at rt and stirred for 1 h. Then, the reaction was concentrated and purified by prep-TLC (PE/EtOAc) to afford the desired compound as an orange solid (660 mg). ESI-MS m/z: 353.10 [M+H]⁺.

Example 99

Step f

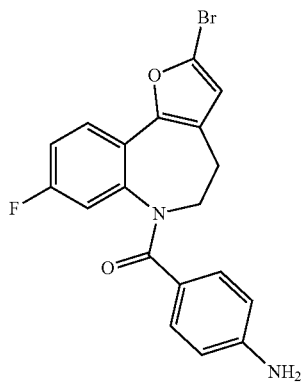

The title compound was prepared from the compound in step e using a procedure similar to that used to prepare the compound in example 69 step f. ESI-MS m/z: 401.05 [M+H]⁺.

Example 99

Step g

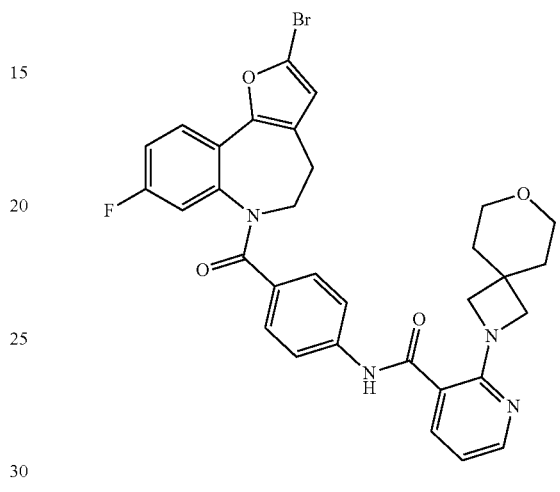

The title compound was prepared from the compound in step f using a procedure similar to that used to prepare the compound in example 69 step g. ESI-MS m/z: 631.15 [M+H]⁺.

Example 99

Step h

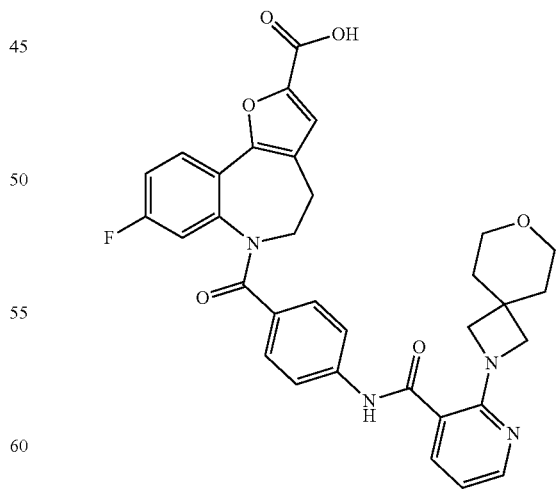

The title compound was prepared from the compound in step g using a procedure similar to that used to prepare the compound in example 69 step h. ESI-MS m/z: 597.30 [M+H]⁺.

Example 99
Step i
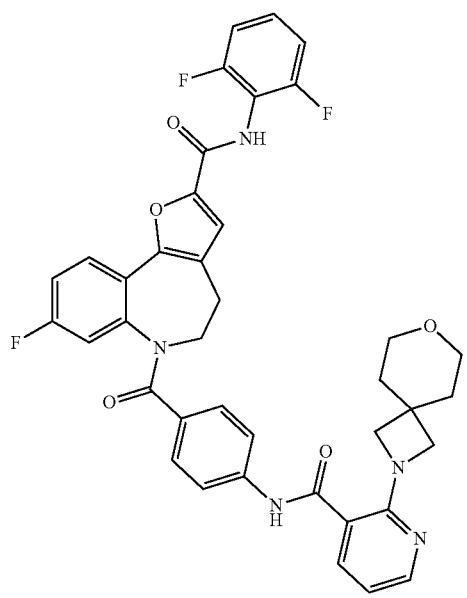 [SMILES: O=C(Nc1c(F)cccc1F)c1cc2c(o1)-c1ccc(F)cc1N(C(=O)c1ccc(NC(=O)c3cccnc3N3CC4(CCOCC4)C3)cc1)CC2]
The title compound was prepared using the procedure similar to those of example 4. ESI-MS m/z: 708.15 [M+H]⁺.
Examples 100-103 shown in table 12 were prepared using the procedure similar to that of example 4 from the corresponding intermediates.
TABLE 12
| Example | Structure | ESI-MS m/z: [M + H]⁺ |
|---|---|---|
| 100 | | 726.15 |
| 101 | 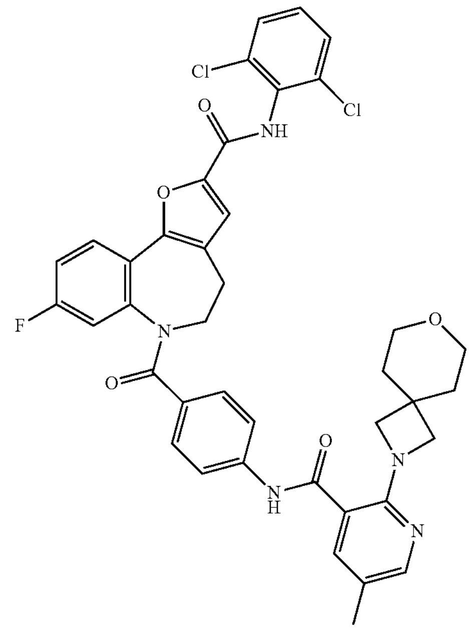 [SMILES: Cc1cnc(N2CC3(CCOCC3)C2)c(C(=O)Nc2ccc(C(=O)N3CCc4cc(C(=O)Nc5c(Cl)cccc5Cl)oc4-c4ccc(F)cc43)cc2)c1] | 755.0 |
| 102 | 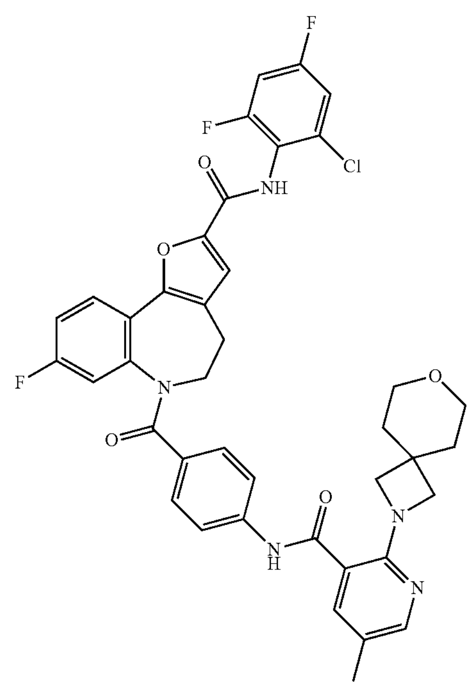 [SMILES: Cc1cnc(N2CC3(CCOCC3)C2)c(C(=O)Nc2ccc(C(=O)N3CCc4cc(C(=O)Nc5c(F)cc(F)cc5Cl)oc4-c4ccc(F)cc43)cc2)c1] | 757.0 |

TABLE 12-continued
| Example | Structure | ESI-MS m/z: [M + H]+ |
|---|---|---|
| 103 | 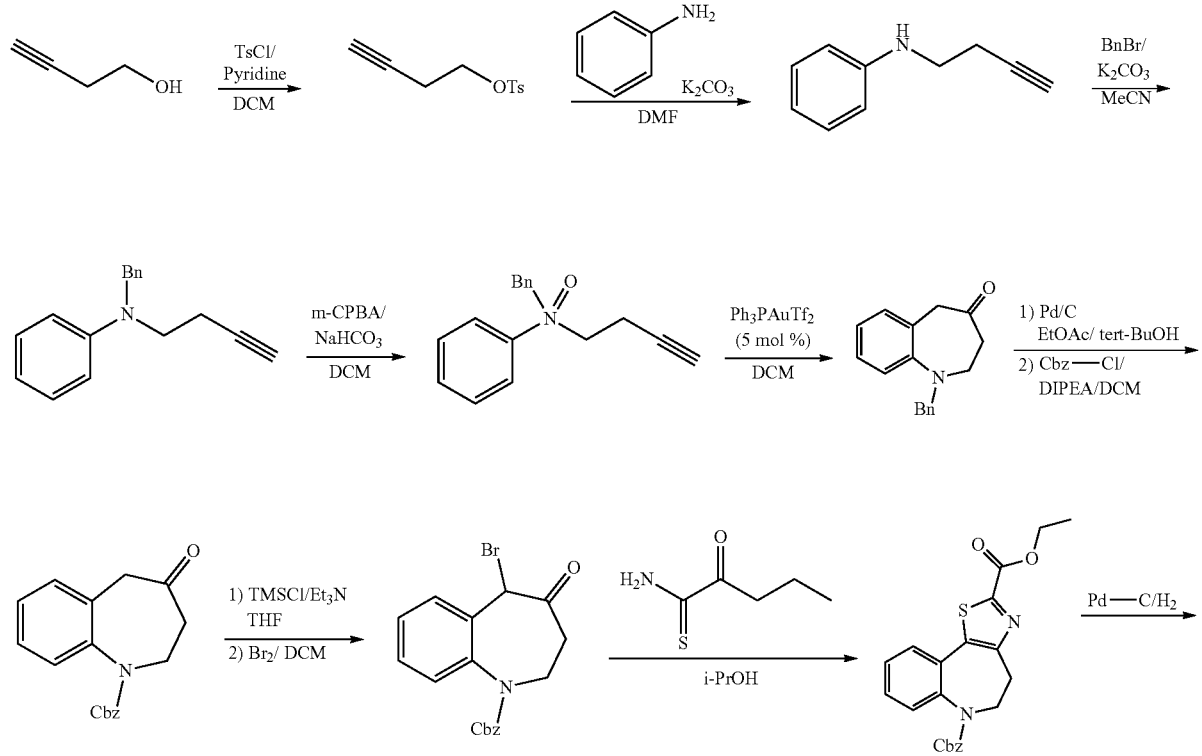 | 722.0 |

219 220

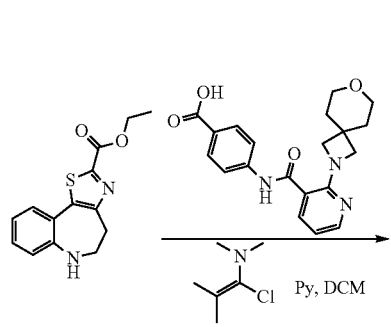
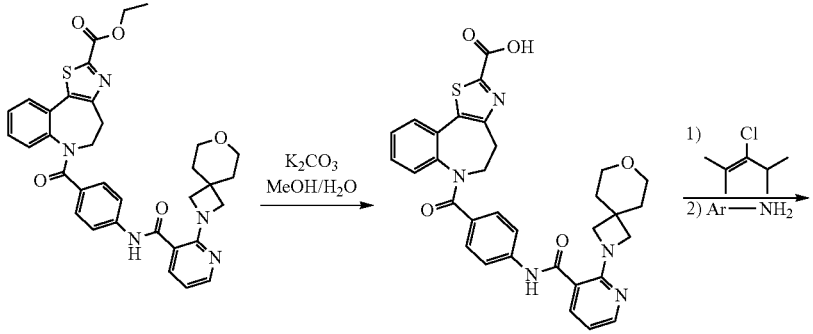

-continued

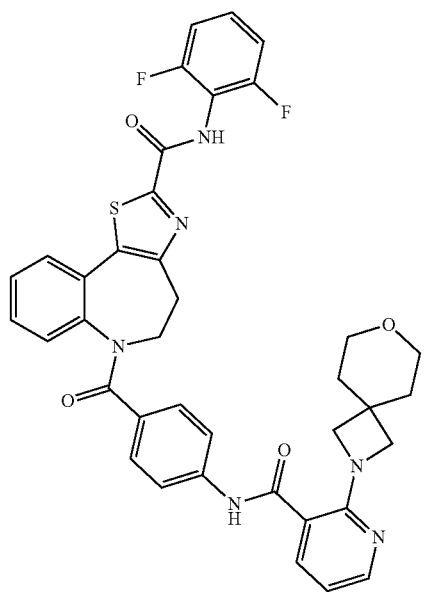 [SMILES: O=C(Nc1c(F)cccc1F)c1nc2c(s1)-c1ccccc1N(C(=O)c1ccc(NC(=O)c3cccnc3N3CC4(CCOCC4)C3)cc1)CC2]

Example 104

Example 104

Step a

To a mixture of but-3-yn-1-ol (100 g, 1.43 mol) and pyridine (169.2 g, 2.14 mol) in DCM (1 L) was added p-toluenesulfonyl chloride (298.6 g, 1.57 mol) in portions at 0° C. The resulting solution was stirred at room temperature for overnight. The reaction was then quenched by the addition of water (500 mL). The resulting solution was extracted with dichloromethane (2×500 mL), washed with brine (3×500 mL). The mixture was dried over anhydrous sodium sulfate, filtered and concentrated under vacuum to provide the title compound (120 g) as a colorless oil.

Example 104

Step b

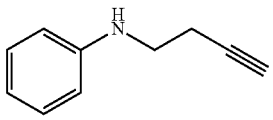

To a mixture of the compound from step a (120 g, 535.06 mmol) in DMF (1.5 L) was added potassium carbonate (88.6 g, 636.43 mmol) and aniline (49.8 g, 534.76 mmol) and heated at 100° C. for overnight. The reaction was then quenched by the addition of water (1.5 L). The resulting solution was extracted with ethyl acetate (3×500 mL) and the organic layers combined. The resulting mixture was washed with of brine (3×500 mL). The mixture was dried over anhydrous sodium sulfate, filtered concentrated under vacuum. The residue was purified by silica gel column chromatography eluting with 0-10% EtOAc/PE to afford the desired compound (60 g) as a colorless oil. ESI-MS m/z: 146.20 $[M+H]^+$.

Example 104

Step c

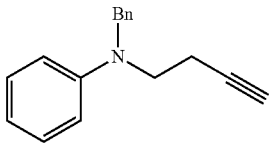 [SMILES: C#CCCN(Cc1ccccc1)c1ccccc1]

To a mixture of the compound from example 104 step b (60 g, 413.22 mmol) in $CH_3CN$ (600 mL) were added $K_2CO_3$ (68 g, 488.46 mmol) and benzylbromide (69.8 g, 408.11 mmol) and heated at 70° C. for overnight. The resulting mixture was concentrated under vacuum. The residue was purified by silica gel column chromatography eluting with 0-50% EtOAc/PE to give the desired compound (60 g) as colorless oil. ESI-MS m/z: 236.32 $[M+H]^+$.

Example 104

Step d

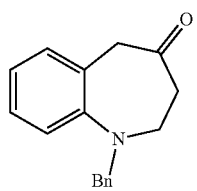 [SMILES: O=C1CCN(Cc2ccccc2)c2ccccc2C1]

To a mixture of the compound from step c (40 g, 169.98 mmol) in dichloromethane (1 L) was added m-CPBA (58.5 g, 338.99 mmol) in portions at 0° C. under $N_2$. To this was added sodium methaneperoxoate (28.6 g, 340.45 mmol, 2.00 equiv), in portions at 0° C. The resulting solution was stirred for 30 min at 0° C. which was used for the next step directly. To a mixture of the compound above (40 g, 159.16 mmol) in dichloromethane (1 L) was added $Ph_3PAuTf_2$ (5 g) in portions at −20° C. under N2 stream. The resulting solution was stirred for 2 hrs at room temperature. The reaction was then quenched by the addition of water (500 mL), extracted with dichloromethane (2×500 mL). The combined organic layer was washed with brine (2×500 mL). The mixture was dried over anhydrous sodium sulfate, filtered and concentrated under vacuum. The residue was purified by silica gel column chromatography eluting with 0-10% EtOAc/PE to provide the title compound (15 g) as a light yellow oil. ESI-MS m/z: 252.32 $[M+H]^+$.

Example 104

Step e

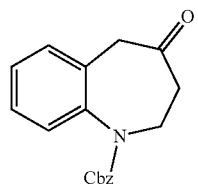 [SMILES: O=C1CCN(C(=O)OCc2ccccc2)c2ccccc2C1]

To a mixture of the compound from step d (10 g, 39.79 mmol) in EA/t-BuOH (90/10 mL) was added palladium charcol (2 g) and stirred under $H_2$ atmosphere at room temperature for overnight. The reaction mixture was filtered out and the resulting mixture was concentrated under vacuum to give 2,3,4,5-tetrahydro-1H-1-benzazepin-4-one (4 g) as a colorless oil, which was dissolved in DCM (50 mL), treated with DIPEA (4.8 g, 37.14 mmol), cooled to 0° C. treated with CbzCl (5.1 g, 29.90 mmol) and stirred at rt for overnight. The reaction was then quenched by the addition of water (30 mL) and extracted with DCM (2×50 mL). The combined organic layer was washed with brine (2×50 mL). The mixture was dried over anhydrous sodium sulfate, filtered and concentrated under vacuum. The residue was purified by silica gel column chromatography eluting with 0-10% EtOAc/PE to give the desired compound (4 g) as a colorless oil. ESI-MS m/z: 296.33 $[M+H]^+$.

Example 104

Step f

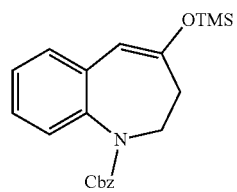

To a mixture of the compound from step e (4.0 g, 13.54 mmol) and triethylamine (2.05 g, 20.26 mmol) in tetrahydrofuran (50 mL) was dropwise added chlorotrimethylsilane (1.76 g, 16.20 mmol) at 0° C. and stirred at rt for overnight. The reaction mixture was then quenched by the addition of water (30 mL), extracted with ethyl acetate (2×50 mL). The combined organic layer was washed with brine (2×50 mL). The mixture was dried over anhydrous sodium sulfate, filtered and concentrated under vacuum to afford the title compound (4.0 g) as a colorless oil. ESI-MS m/z: 368.51 [M+H]⁺.

Example 104

Step g

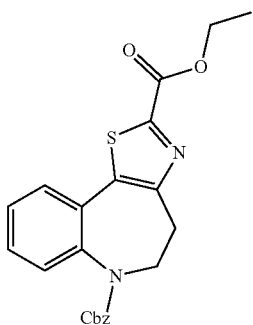 [SMILES: CCOC(=O)c1nc2c(s1)-c1ccccc1N(C(=O)OCc1ccccc1)CC2]

To a mixture of the compound from step f (4.0 g, 10.88 mmol) in dichloromethane (40 mL) was dropwise added Br₂ (1.7 g, 10.64 mmol) at 0° C. The resulting solution was stirred at rt for 30 min, concentrated under vacuum to provide bromide, which was used for the next step directly.

To a solution of bromide (4.0 g, 10.69 mmol) in propan-2-ol (200 mL) was added ethyl carbamothioylformate (2.9 g, 21.78 mmol). The resulting solution was stirred at rt for overnight. The resulting mixture was concentrated under vacuum. The residue was purified by silica gel column chromatography eluting with 0-10% EtOAc/PE to afford the desired compound (1.0 g) as a yellow solid. ESI-MS m/z: 409.47 [M+H]⁺. ¹H NMR (300 MHz, DMSO-d₆): δ 1.33 (t, J=6.9 Hz, 3H), 3.17-3.34 (m, 2H), 4.36-4.51 (m, 2H), 5.01-5.17 (br, 2H), 7.23-7.49 (m, 8H), 7.79-7.77 (d, J=7.5 Hz, 1H).

Example 104

Step h

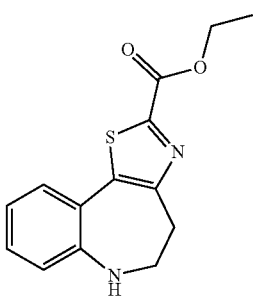 [SMILES: CCOC(=O)c1nc2c(s1)-c1ccccc1NCC2]

The compound from step g (0.8 g, 1.96 mmol) was deprotected using 33% HBr in HOAc (10 mL) at 70° C. for 30 min to provide the desired compound (450 mg) as a yellow solid. ESI-MS m/z: 275.00 [M+H]⁺.

Example 104

Step i

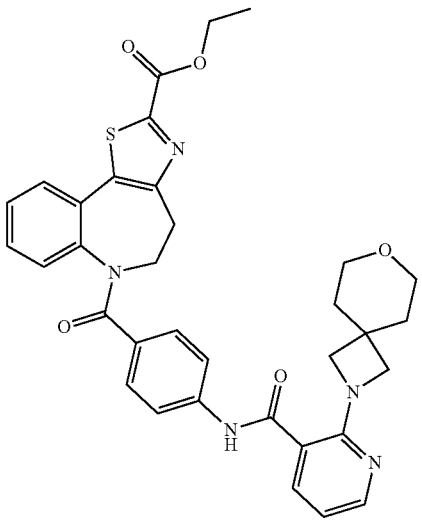 [SMILES: CCOC(=O)c1nc2c(s1)-c1ccccc1N(C(=O)c1ccc(NC(=O)c3cccnc3N3CC4(CCOCC4)C3)cc1)CC2]

The title compound was prepared from the compound step h using a procedure similar to that used to prepare the compound in example 53 step h. ESI-MS m/z: 624.45 [M+H]⁺.

Example 104

Step j

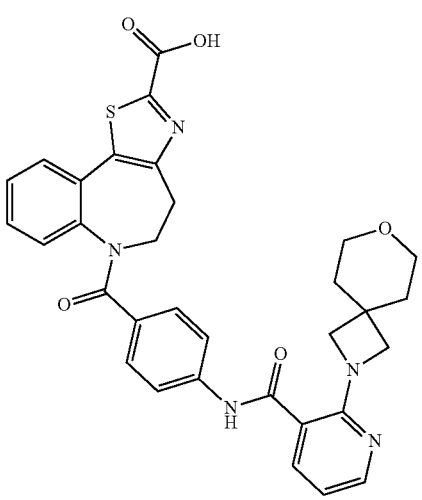 [SMILES: O=C(O)c1nc2c(s1)-c1ccccc1N(C(=O)c1ccc(NC(=O)c3cccnc3N3CC4(CCOCC4)C3)cc1)CC2]

To a mixture of the compound from step i (450 mg, 0.72 mmol) in MeOH (20 mL)/H₂O (10 mL) was added K₂CO₃ (997 mg, 7.20 mmol) and stirred at rt for 1 h. The reaction mixture was adjusted pH to 4 with 4 M HCl, concentrated and purified by column chromatography (MeCN/H₂O) to give the desired compound as a yellow solid (385 mg). ESI-MS m/z: 596.20 [M+H]⁺.

Examples 104-107 shown in table 13 were prepared using the procedure similar to those of example 3 (step k and l) and example 4 from the corresponding intermediates.

TABLE 13

| Example | Structure | ESI-MS m/z: [M + H]+ |
|---|---|---|
| 104 | 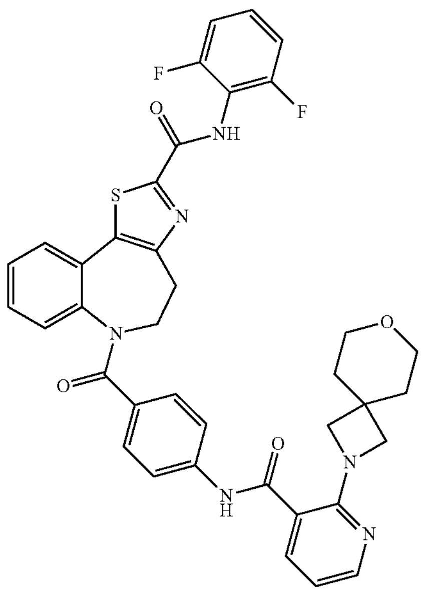 [SMILES: O=C(Nc1c(F)cccc1F)c1nc2c(s1)-c1ccccc1N(C(=O)c1ccc(NC(=O)c3cccnc3N3CC4(CCOCC4)C3)cc1)CC2] | 707.15 |
| 105 | 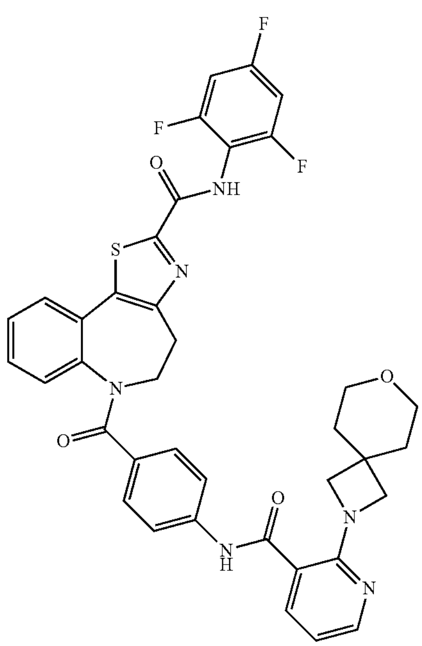 [SMILES: O=C(Nc1c(F)cc(F)cc1F)c1nc2c(s1)-c1ccccc1N(C(=O)c1ccc(NC(=O)c3cccnc3N3CC4(CCOCC4)C3)cc1)CC2] | 725.15 |
| 106 | | 741.15 |
| 107 | | 668.25 |

Scheme 13
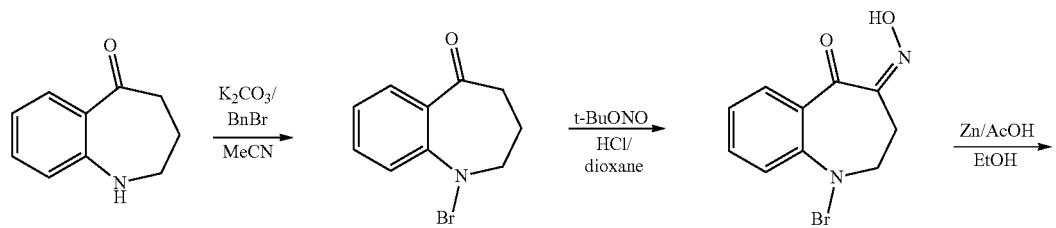
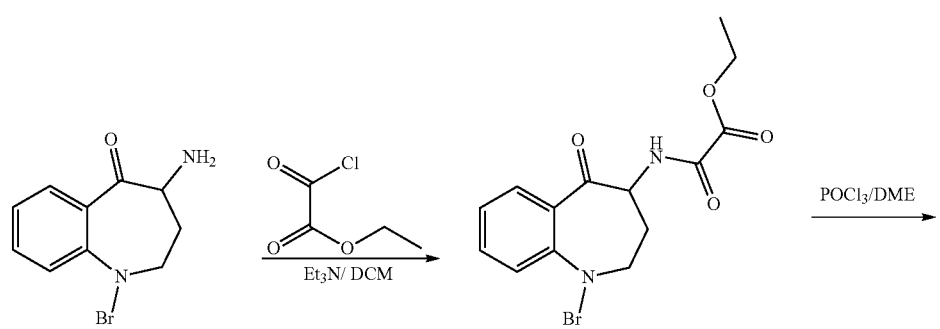
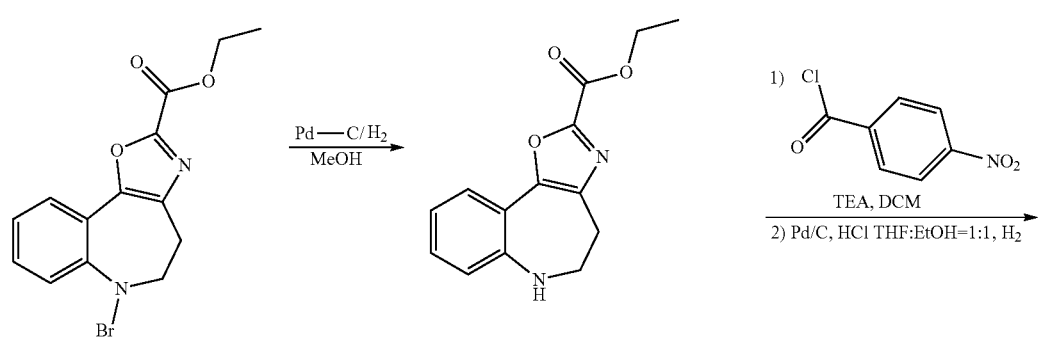
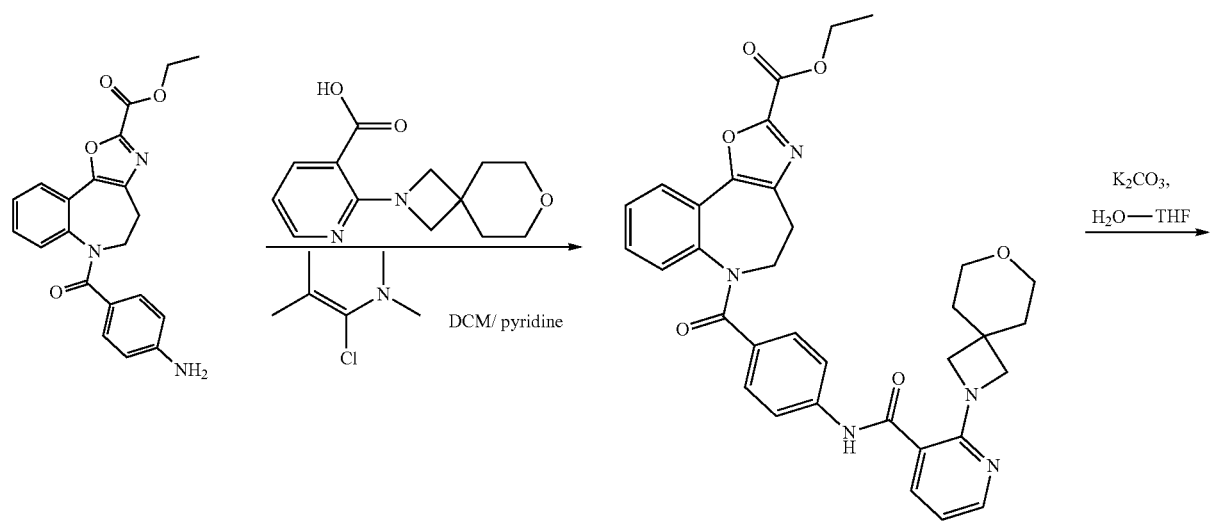

-continued
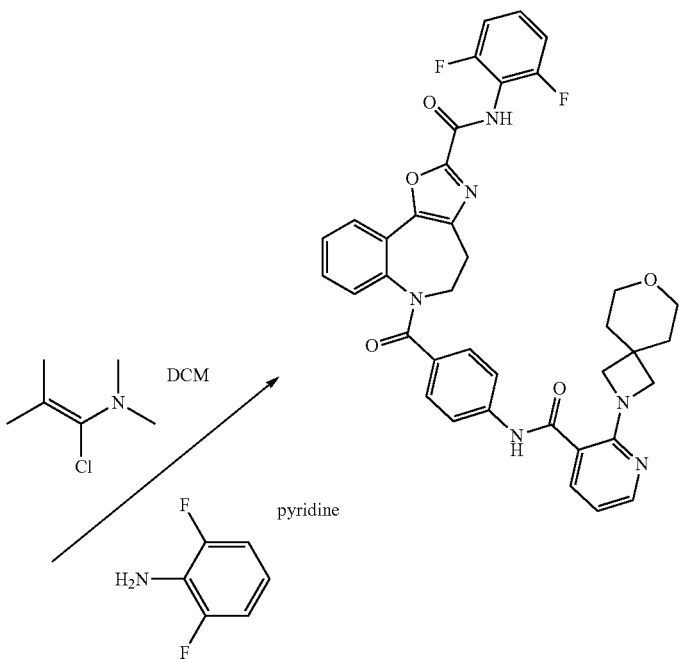
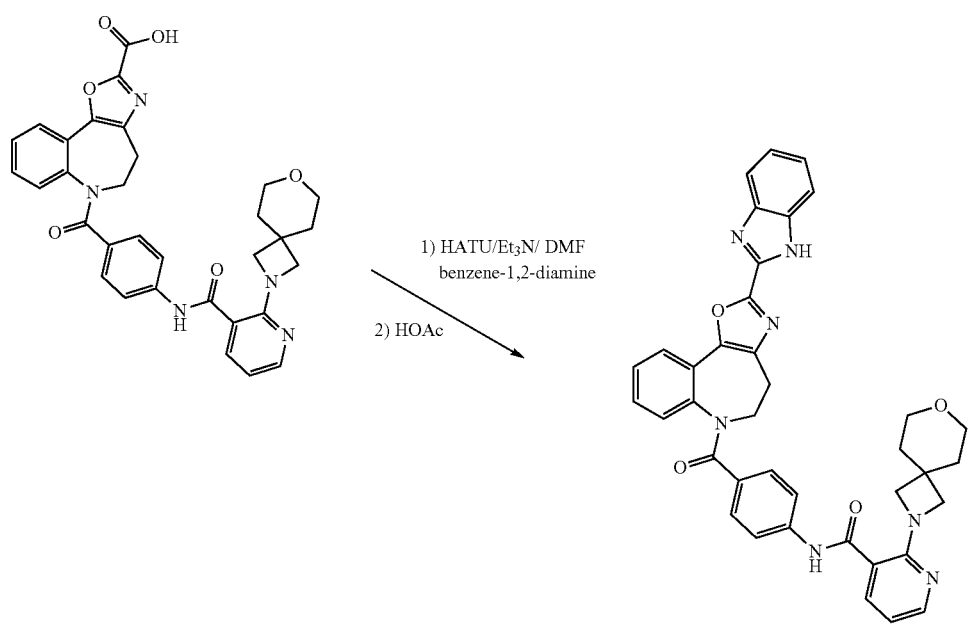

231

Example 108

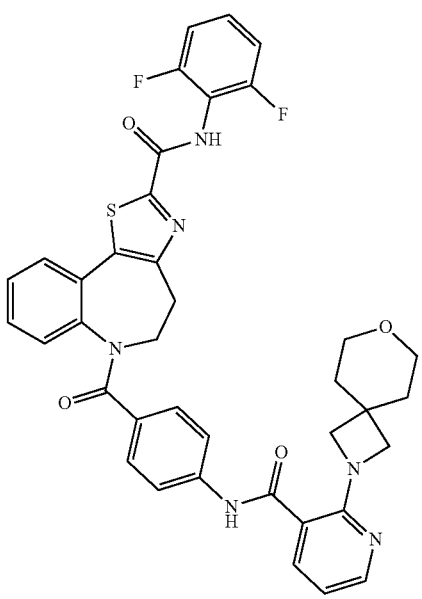

Example 108

Step a

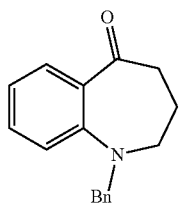 [SMILES: O=C1CCCN(Cc2ccccc2)c2ccccc21]

To a mixture of 2,3,4,5-tetrahydro-1H-1-benzazepin-5-one (25 g, 155.09 mmol) in CH$_3$CN (500 mL), K$_2$CO$_3$ (64.2 g, 461.16 mmol), benzyl bromide (52.8 g, 308.71 mmol). The resulting solution was stirred overnight at 90° C. The solids were filtered and the filtrate was concentrated under vacuum. The residue was purified by silica gel column chromatography eluting with 0-10% EtOAc/PE to provide the desired compound (25 g) as a colorless oil. ESI-MS m/z: 252.32 [M+H]$^+$.

232

Example 108

Step b

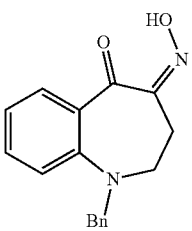 [SMILES: O=C1/C(=N\O)CCN(Cc2ccccc2)c2ccccc21]

To a mixture of the compound from step a (25 g, 99.47 mmol) in THF (500 ml) was added t-BuONO (20.6 g, 200.0 mmol). This was followed by the addition of HCl/dioxane (4 M) (62.5 mL) dropwise with stirring at 0° C. The resulting solution was stirred at 0° C. for 30 min. The reaction was then quenched by the addition of water (500 mL). The resulting solution was extracted with EtOAc (500 mL). The combined organic layer was washed with brine, dried over Na$_2$SO$_4$, filtered and concentrated under vacuum. The residue was purified by silica gel column chromatography eluting with 0-10% EtOAc/PE to give the desired compound (9 g) as a colorless oil. ESI-MS m/z: 281.32 [M+H]$^+$.

Example 108

Step c

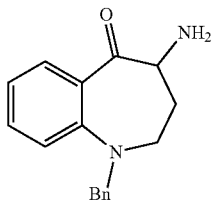 [SMILES: NC1CCN(Cc2ccccc2)c2ccccc2C1=O]

A mixture of the compound from step b (9 g) in ethanol/HOAc (90/10 mL) was added Zn (10.45 g). The reaction mixture was stirred at rt for overnight. After filtered through celite, the filtrate was concentrated under vacuum, which was used for the next step directly.

Example 108

Step d

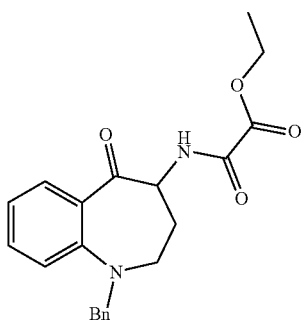 [SMILES: CCOC(=O)C(=O)NC1CCN(Cc2ccccc2)c2ccccc2C1=O]

To a mixture of the compound from step c (8.6 g, 32.29 mmol) in DCM (200 mL) was added triethylamine (31.6 g, 312.28 mmol) and degassed. The reaction was treated with ethyl 2-chloro-2-oxoacetate (5.27 g, 38.60 mmol) with stirring at 0° C. The resulting solution was stirred for 30 min at rt and then quenched by the addition of water (100 mL). The resulting solution was extracted with DCM (2×100 mL) and the combined organic layer was washed with brine, dried, filtered and concentrated under vacuum. The residue was purified by silica gel column chromatography eluting with 0-10% EtOAc/PE to give the title compound (3.2 g) as a colorless oil. ESI-MS m/z: 367.41 [M+H]$^+$.

Example 108

Step e

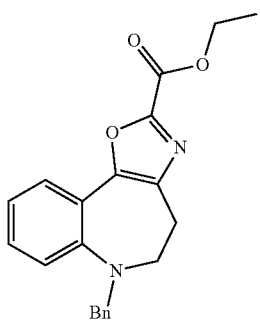 [SMILES: CCOC(=O)c1nc2c(o1)-c1ccccc1N(Cc1ccccc1)CC2]

To a solution of the compound from step d (3.2 g, 8.73 mmol) in DME (500 mL) was added POCl$_3$ (13.2 g, 86.09 mmol). The resulting solution was heated at 90° C. for overnight. After cooling, the reaction was then quenched by the addition of water (500 mL), extracted with ethyl acetate (500 mL). The combined organic layer was washed with brine (2×500 mL). The mixture was dried over anhydrous sodium sulfate, filtered and concentrated under vacuum. The residue was purified by silica gel column chromatography eluting with 0-10% EtOAc/PE to afford the desired compound (2.01 g) as a yellow solid. ESI-MS m/z: 349.40 [M+H]$^+$. $^1$H NMR (300 MHz, CDCl$_3$): δ 1.43-1.48 (t, J=7.2 Hz, 3H), 2.90-2.93 (t, J=5.4 Hz, 2H), 3.34-3.37 (t, J=5.4 Hz, 2H), 4.46-4.53 (t, J=7.2 Hz, 3H), 4.57 (s, 1H), 6.99-7.04 (m, 2H), 7.19-7.37 (m, 6H), 7.98-8.01 (m, 1H).

Example 108

Step f

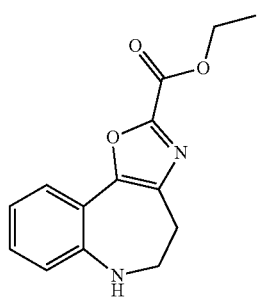 [SMILES: CCOC(=O)c1nc2c(o1)-c1ccccc1NCC2]

A mixture of the compound from step e (800 mg, 2.3 mmol), Pd/C (1 g) in MeOH (3 mL) was stirred for 5 hrs under H$_2$ atmosphere. The reaction mixture was filtered and concentrated to afford the desired compound (490 mg) as a yellow sold. ESI-MS m/z: 259.00 [M+H]$^+$.

Example 108

Step g

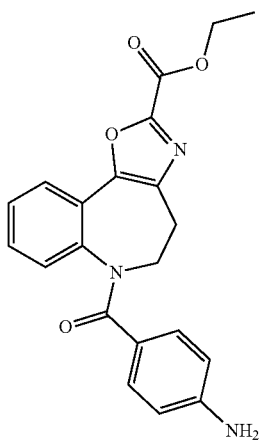 [SMILES: CCOC(=O)c1nc2c(o1)-c1ccccc1N(C(=O)c1ccc(N)cc1)CC2]

The title compound was prepared from the compound step f using a procedure similar to that used to prepare for the compound in example 99 step f. ESI-MS m/z: 378.00 [M+H]$^+$.

Example 108

Step h

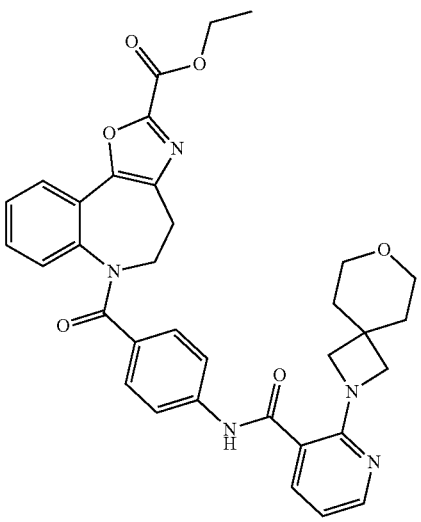 [SMILES: CCOC(=O)c1nc2c(o1)-c1ccccc1N(C(=O)c1ccc(NC(=O)c3cccnc3N3CC4(CCOCC4)C3)cc1)CC2]

The title compound was prepared from the compound step g using a procedure similar to that used to prepare the compound in example 99 step g. ESI-MS m/z: 608.45 [M+H]$^+$.

Example 108

Step i

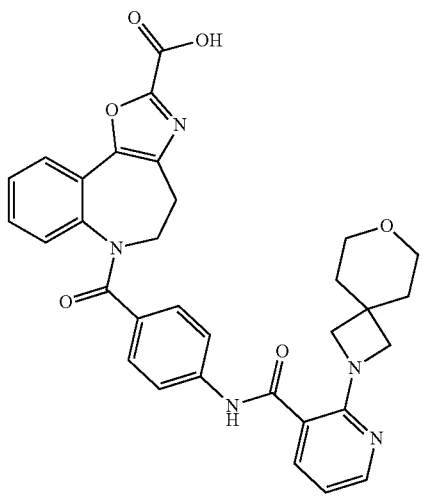 [SMILES: O=C(O)c1nc2c(o1)-c1ccccc1N(C(=O)c1ccc(NC(=O)c3cccnc3N3CC4(CCOCC4)C3)cc1)CC2]

The title compound was prepared from the compound step h using a procedure similar to that used to prepare the compound in example 104 step j. ESI-MS m/z: 580.10 [M+H]⁺.

Example 108

Step j

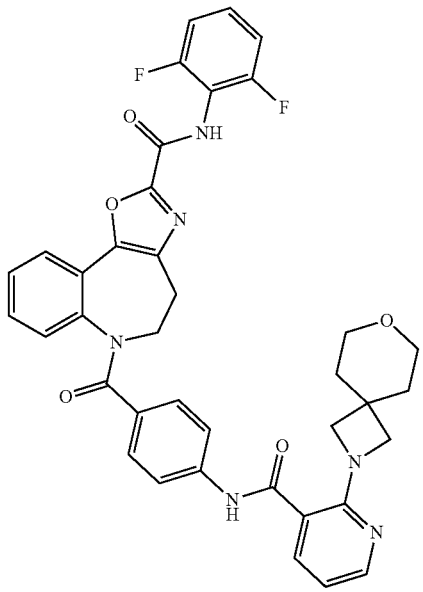 [SMILES: O=C(Nc1c(F)cccc1F)c1nc2c(o1)-c1ccccc1N(C(=O)c1ccc(NC(=O)c3cccnc3N3CC4(CCOCC4)C3)cc1)CC2]

The title compound was prepared from the compound step i using a procedure similar to that used to prepare the compound in example 4. ESI-MS m/z: 690.80 [M+H]⁺.

Example 109

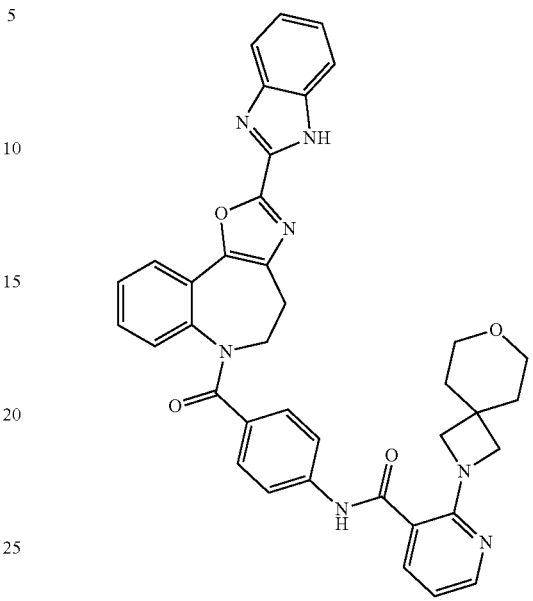

Example 109 was prepared using a procedure similar to that used to prepare the compound in example 3 step k and l. ESI-MS m/z: 652.20 [M+H]⁺.

Examples 110-140 shown in table 14 were prepared using the procedure similar to that of example 4 from the corresponding intermediates.

TABLE 14

| Example | Structure | ESI-MS m/z: [M + H]⁺ |
|---|---|---|
| 110 | (structure shown) | 738.2 |

TABLE 14-continued
| Example | Structure | ESI-MS m/z: [M + H]+ |
|---|---|---|
| 111 | 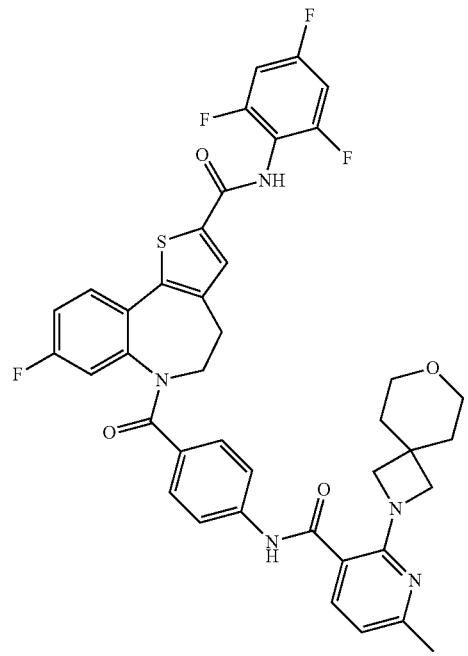 [SMILES: Cc1ccc(C(=O)Nc2ccc(C(=O)N3CCc4cc(C(=O)Nc5c(F)cc(F)cc5F)sc4-c4ccc(F)cc43)cc2)c(N2CC3(CCOCC3)C2)n1] | 756.2 |
| 112 | 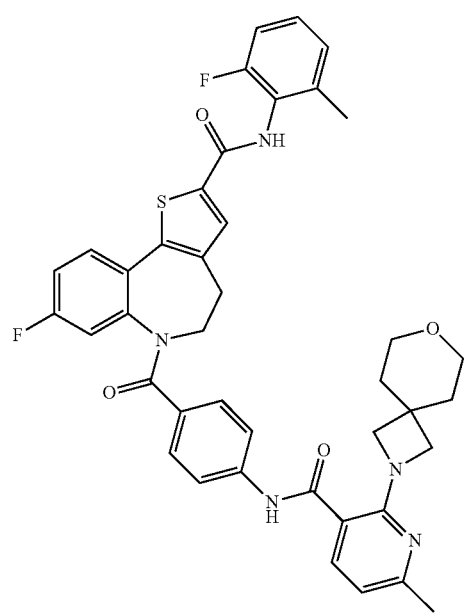 | 734.4 |
| 113 | 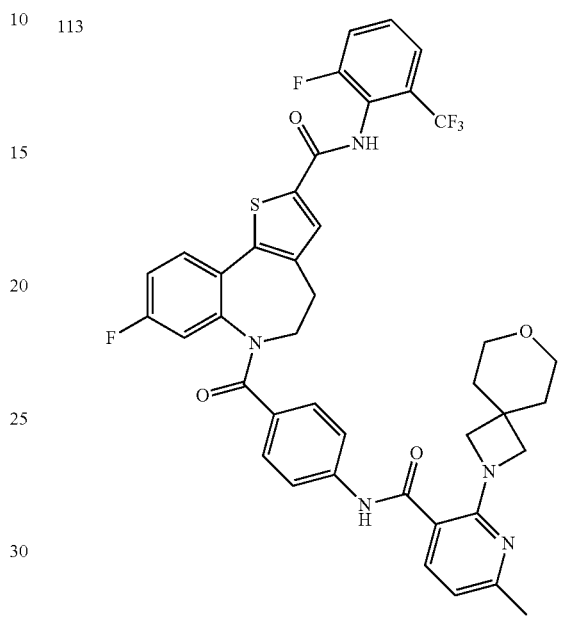 | 788.2 |
| 114 | 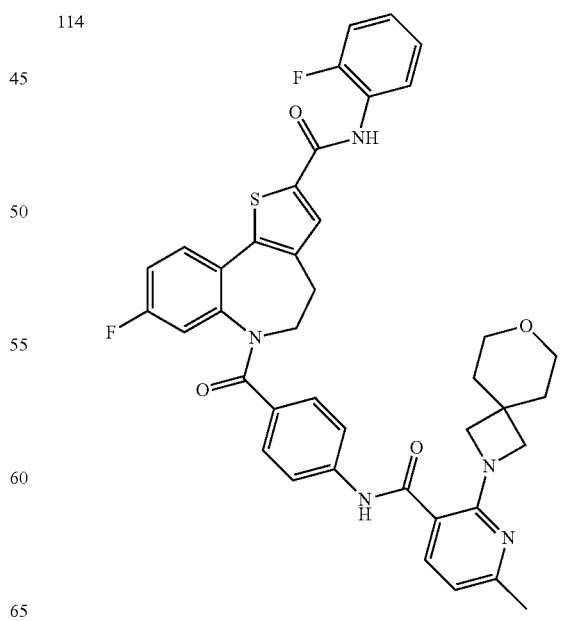 | 720.2 |

TABLE 14-continued

| Example | Structure | ESI-MS m/z: [M + H]+ |
|---------|-----------|----------------------|
| 115 | 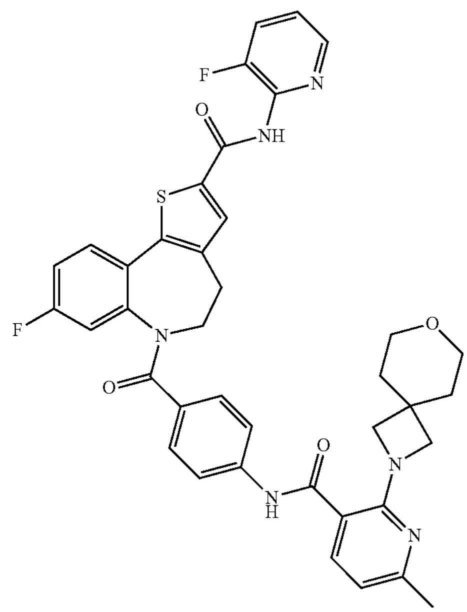 [SMILES: Cc1ccc(C(=O)Nc2ccc(C(=O)N3CCc4cc(C(=O)Nc5ncccc5F)sc4-c4ccc(F)cc43)cc2)c(N2CC3(CCOCC3)C2)n1] | 721.2 |
| 116 | 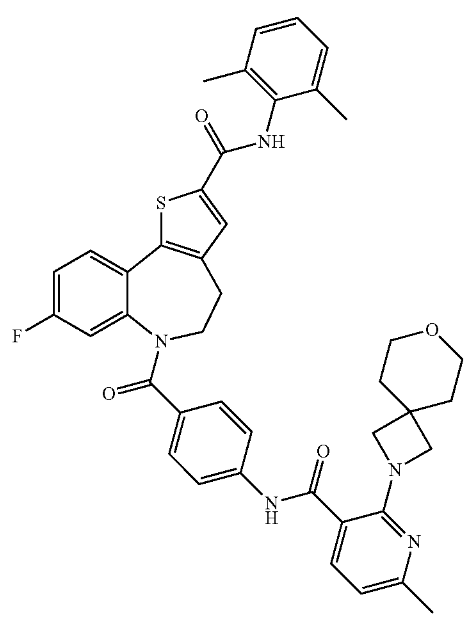 [SMILES: Cc1ccc(C(=O)Nc2ccc(C(=O)N3CCc4cc(C(=O)Nc5c(C)cccc5C)sc4-c4ccc(F)cc43)cc2)c(N2CC3(CCOCC3)C2)n1] | 730.0 |
| 117 | | 739.7 |
| 118 | | 67.3 |

TABLE 14-continued

| Example | Structure | ESI-MS m/z: [M+H]+ |
|---|---|---|
| 119 | 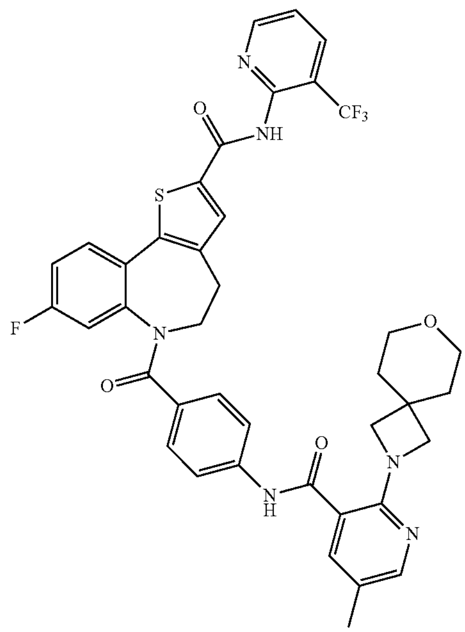 [SMILES: Cc1cnc(N2CC3(CCOCC3)C2)c(C(=O)Nc2ccc(C(=O)N3CCc4cc(C(=O)Nc5ncccc5C(F)(F)F)sc4-c4ccc(F)cc43)cc2)c1] | 771.3 |
| 120 | 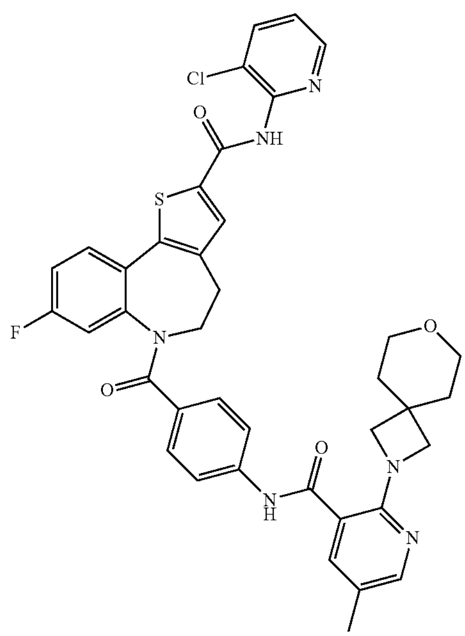 [SMILES: Cc1cnc(N2CC3(CCOCC3)C2)c(C(=O)Nc2ccc(C(=O)N3CCc4cc(C(=O)Nc5ncccc5Cl)sc4-c4ccc(F)cc43)cc2)c1] | 738.3 |
| 121 | 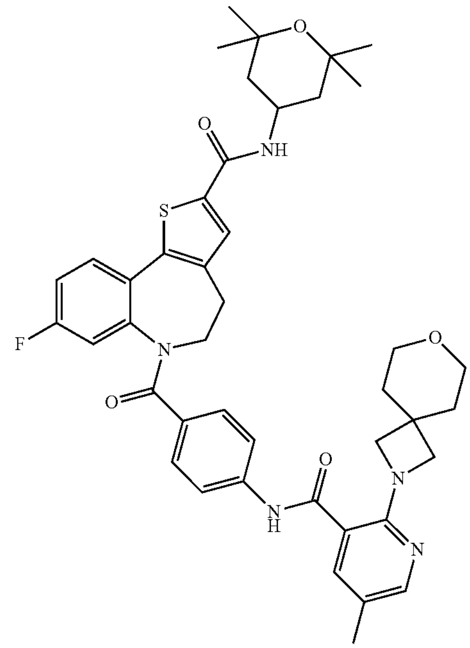 [SMILES: Cc1cnc(N2CC3(CCOCC3)C2)c(C(=O)Nc2ccc(C(=O)N3CCc4cc(C(=O)NC5CC(C)(C)OC(C)(C)C5)sc4-c4ccc(F)cc43)cc2)c1] | 766.4 |
| 122 | 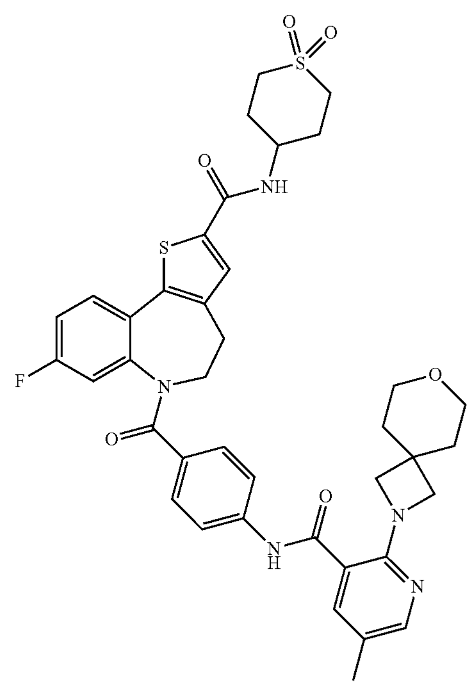 [SMILES: Cc1cnc(N2CC3(CCOCC3)C2)c(C(=O)Nc2ccc(C(=O)N3CCc4cc(C(=O)NC5CCS(=O)(=O)CC5)sc4-c4ccc(F)cc43)cc2)c1] | 758.3 |

TABLE 14-continued
| Example | Structure | ESI-MS m/z: [M + H]+ |
|---|---|---|
| 123 | 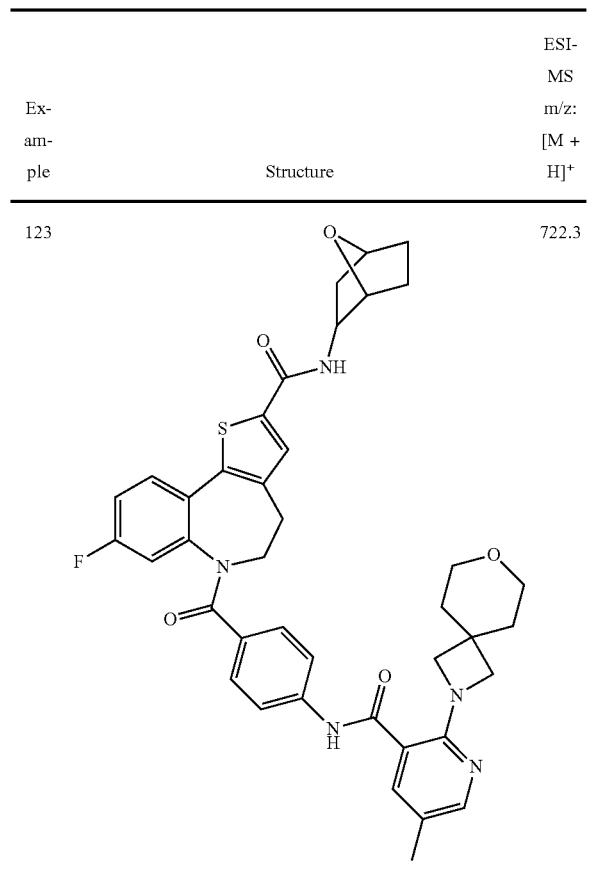 | 722.3 |
| 124 | 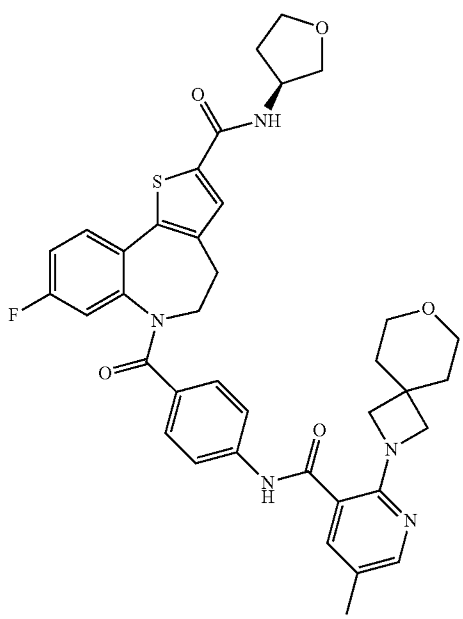 [SMILES: Cc1cnc(N2CC3(CCOCC3)C2)c(C(=O)Nc2ccc(C(=O)N3CCc4cc(C(=O)N[C@H]5CCOC5)sc4-c4ccc(F)cc43)cc2)c1] | 696.0 |
| 125 | 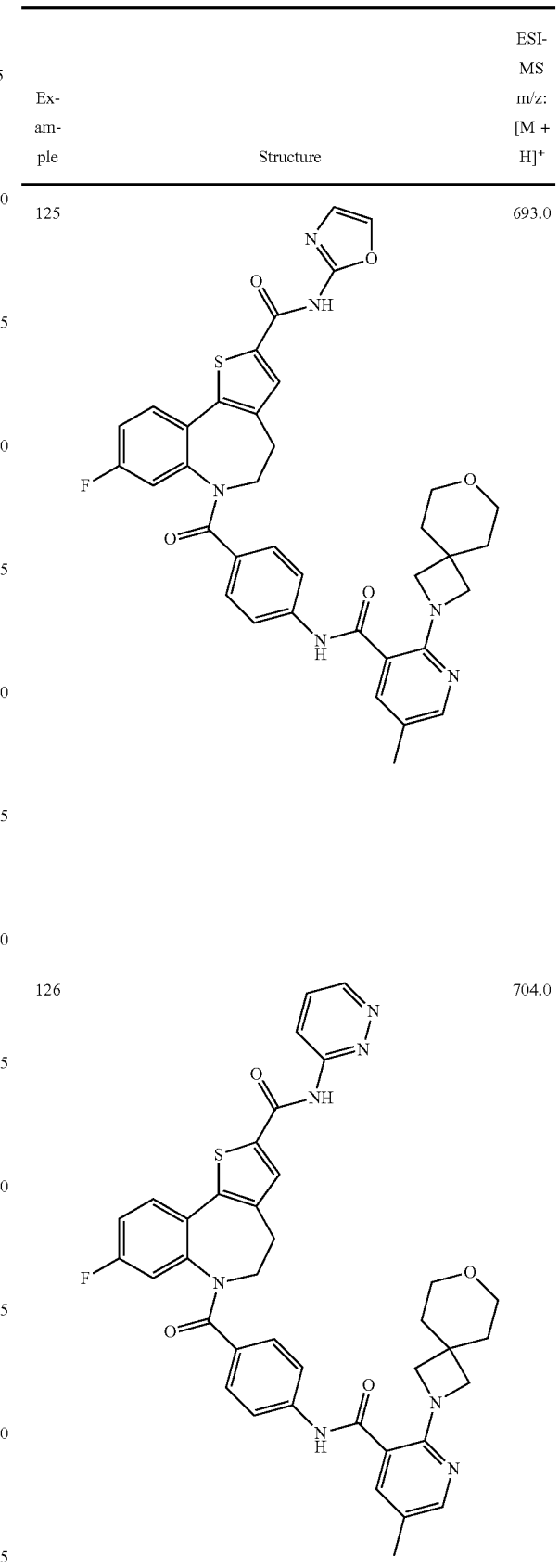 | 693.0 |
| 126 | | 704.0 |

TABLE 14-continued
| Example | Structure | ESI-MS m/z: [M + H]+ |
|---|---|---|
| 127 | 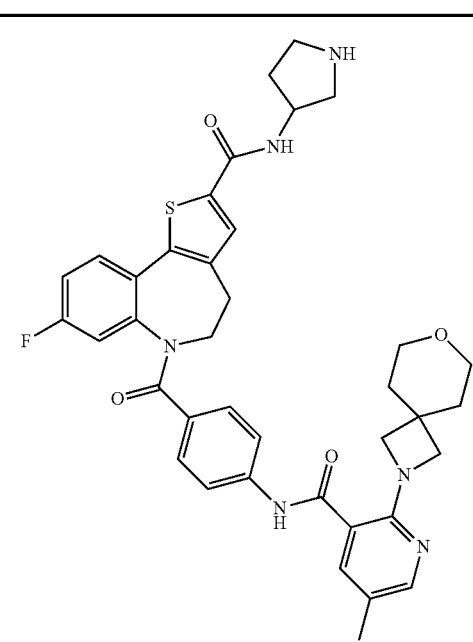 | 704.0 |
| 128 | 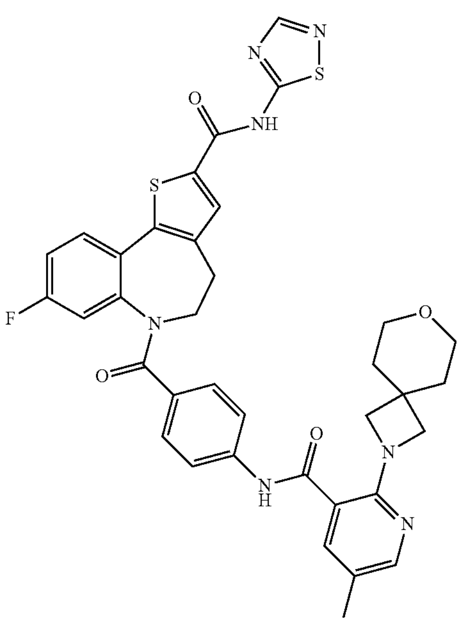 [SMILES: Cc1cnc(N2CC3(CCOCC3)C2)c(C(=O)Nc2ccc(C(=O)N3CCc4cc(C(=O)Nc5ncco5)sc4-c4ccc(F)cc43)cc2)c1] | 710.0 |
| 129 | 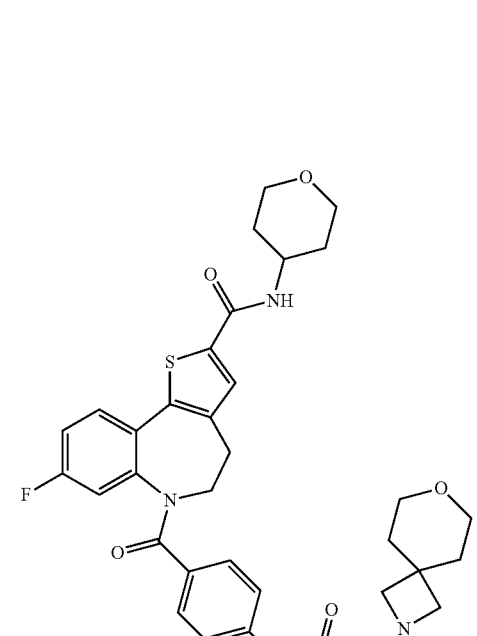 | 695.0 |
| 130 | 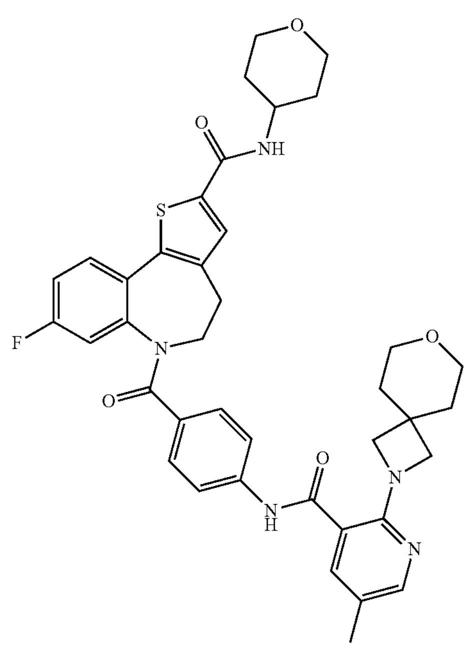 [SMILES: Cc1cnc(N2CC3(CCOCC3)C2)c(C(=O)Nc2ccc(C(=O)N3CCc4cc(C(=O)NC5CCOCC5)sc4-c4ccc(F)cc43)cc2)c1] | 710.0 |

TABLE 14-continued

| Example | Structure | ESI-MS m/z: [M + H]+ |
|---|---|---|
| 131 | 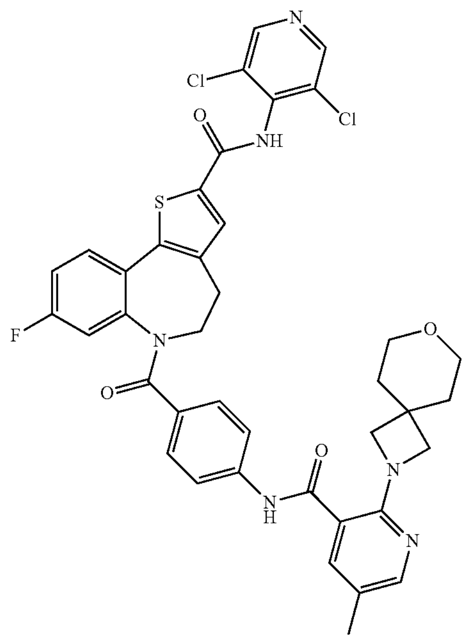 [SMILES: Cc1cnc(N2CC3(CCOCC3)C2)c(C(=O)Nc2ccc(C(=O)N3CCc4cc(C(=O)Nc5c(Cl)cncc5Cl)sc4-c4ccc(F)cc43)cc2)c1] | 772.0 |
| 132 | 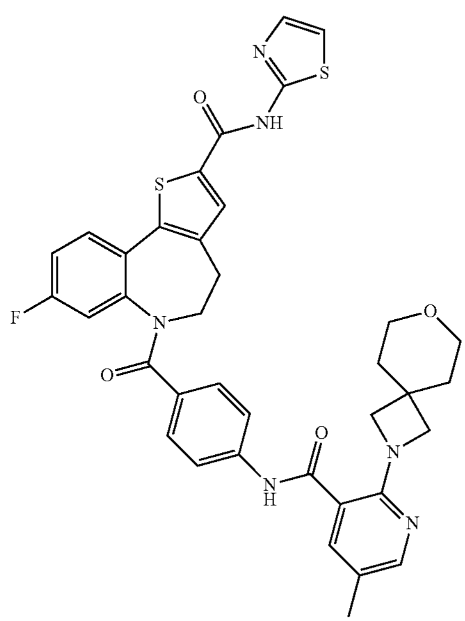 | 709.0 |
| 133 | | 724.0 |
| 134 | | 707.0 |

TABLE 14-continued
| Example | Structure | ESI-MS m/z: [M + H]+ |
|---|---|---|
| 135 | 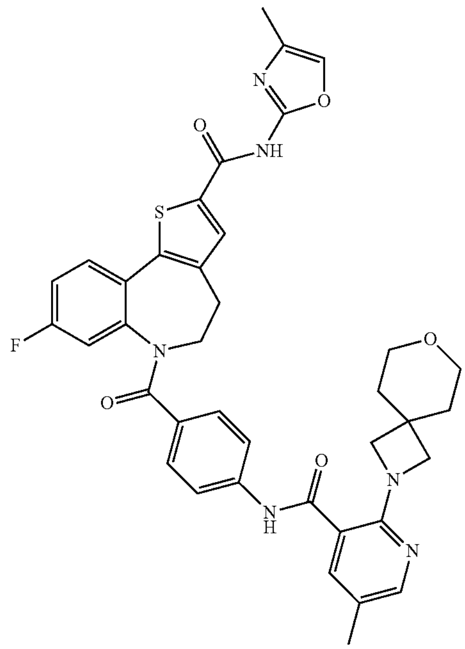 [SMILES: Cc1cnc(N2CC3(CCOCC3)C2)c(C(=O)Nc2ccc(C(=O)N3CCc4cc(C(=O)Nc5nc(C)co5)sc4-c4ccc(F)cc43)cc2)c1] | 707.0 |
| 136 | 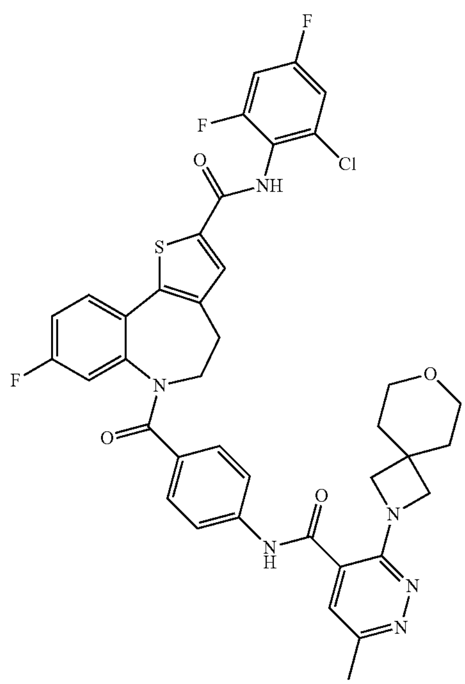 [SMILES: Cc1cc(C(=O)Nc2ccc(C(=O)N3CCc4cc(C(=O)Nc5c(F)cc(F)cc5Cl)sc4-c4ccc(F)cc43)cc2)c(N2CC3(CCOCC3)C2)nn1] | 774.0 |
| 137 | | 796.3 |
| 138 | | 780.2 |
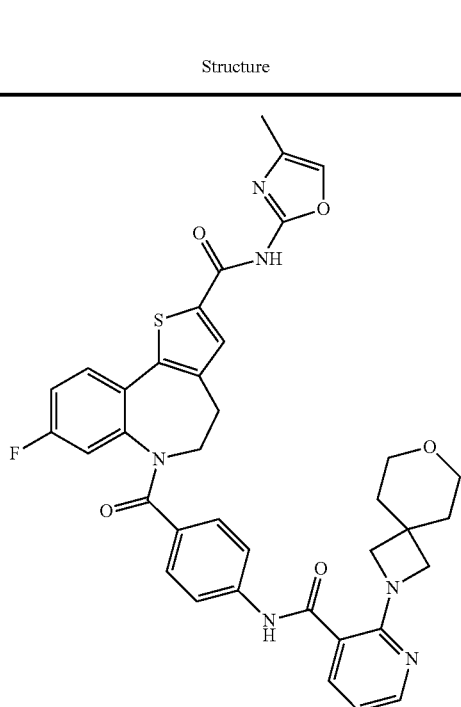

251

TABLE 14-continued

| Example | Structure | ESI-MS m/z: [M + H]+ |
|---|---|---|
| 139 | 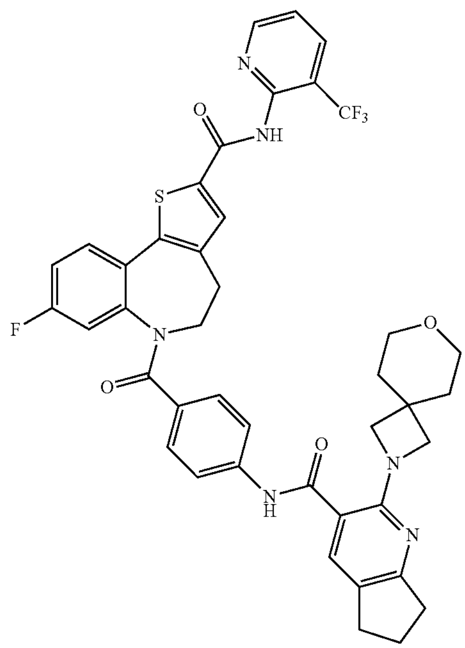 [SMILES: O=C(Nc1ncccc1C(F)(F)F)c1cc2c(s1)-c1ccc(F)cc1N(C(=O)c1ccc(NC(=O)c3cc4c(nc3N3CC5(CCOCC5)C3)CCC4)cc1)CC2] | 797.3 |
| 140 | 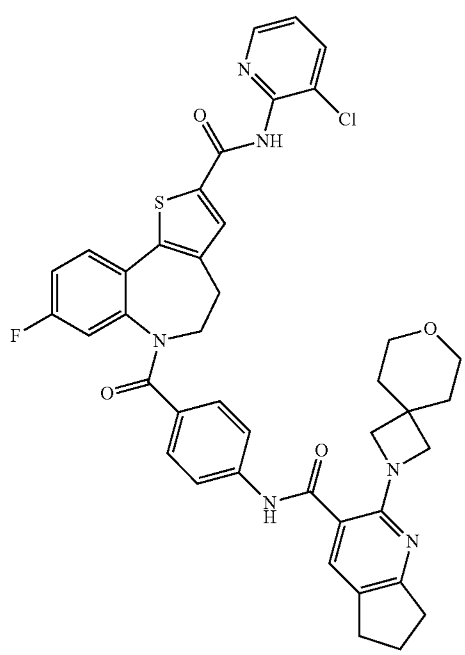 [SMILES: O=C(Nc1ncccc1Cl)c1cc2c(s1)-c1ccc(F)cc1N(C(=O)c1ccc(NC(=O)c3cc4c(nc3N3CC5(CCOCC5)C3)CCC4)cc1)CC2] | 763.3 |

252

Example 141

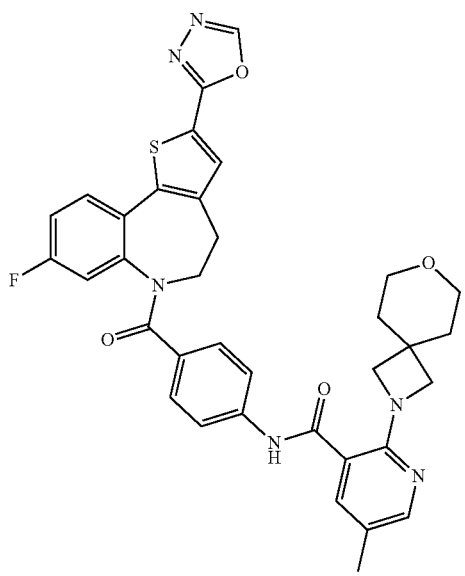 [SMILES: Cc1cnc(N2CC3(CCOCC3)C2)c(C(=O)Nc2ccc(C(=O)N3CCc4cc(-c5nnco5)sc4-c4ccc(F)cc43)cc2)c1]

Example 141

Step a

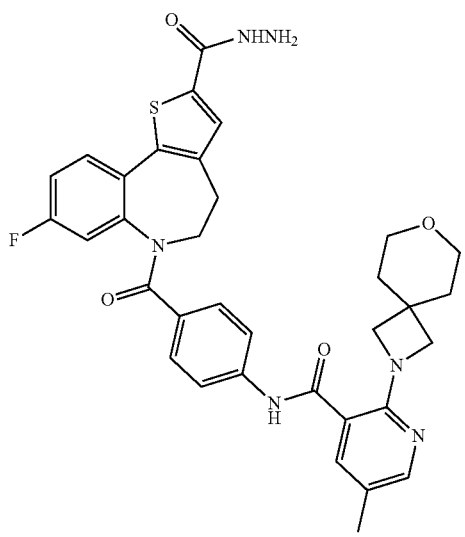 [SMILES: Cc1cnc(N2CC3(CCOCC3)C2)c(C(=O)Nc2ccc(C(=O)N3CCc4cc(C(=O)NN)sc4-c4ccc(F)cc43)cc2)c1]

A mixture of the compound from Example 3 step i (200 mg, 0.305 mmol) and hydrazine hydrate (1 mL) in MeOH (5 mL) was heated at 80° C. for 12 hrs and then diluted with DCM (100 mL) and water (10 mL). The organic layer was washed with brine (20 mL×3), dried and evaporated to obtain the desired crude product (280 mg) as yellowish oil. The crude residue was used directly for the next step. ESI-MS m/z: 641.25 [M+H]+.

Example 141

Step b

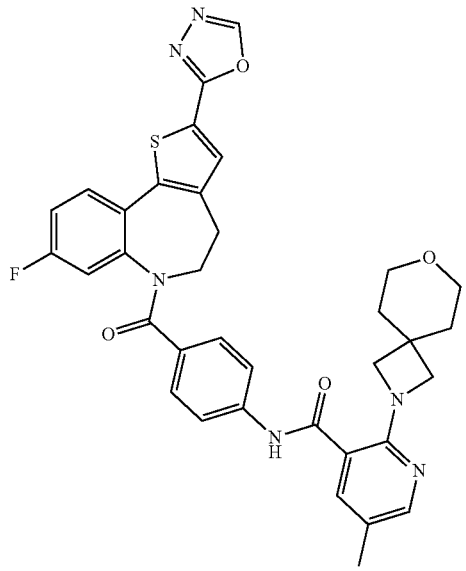 [SMILES: Cc1cnc(N2CC3(CCOCC3)C2)c(C(=O)Nc2ccc(C(=O)N3CCc4cc(-c5nnco5)sc4-c4ccc(F)cc43)cc2)c1]

A mixture of the compound from step a (200 mg, 0.312 mmol) and trimethoxymethane (2 mL) was heated at 120° C. for 30 hrs and then diluted with DCM (100 mL) and water (10 mL). The organic layer was washed with brine (20 mL×3), dried and evaporated. The crude residue was purified by silica gel column chromatography eluting with 0-3% MeOH/DCM to obtain the desired product (80 mg, 39%) as a pale yellow solid. ESI-MS m/z: 651.23 [M+H]$^+$.

Example 142

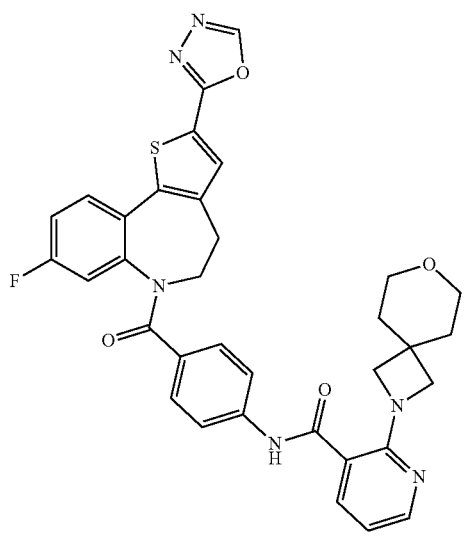 [SMILES: O=C(Nc1ccc(C(=O)N2CCc3cc(-c4nnco4)sc3-c3ccc(F)cc32)cc1)c1cccnc1N1CC2(CCOCC2)C1]

Example 142 was prepared using the procedure similar to that of example 141 from the corresponding intermediate. ESI-MS m/z: 637.21 [M+H]$^+$.

Example 143

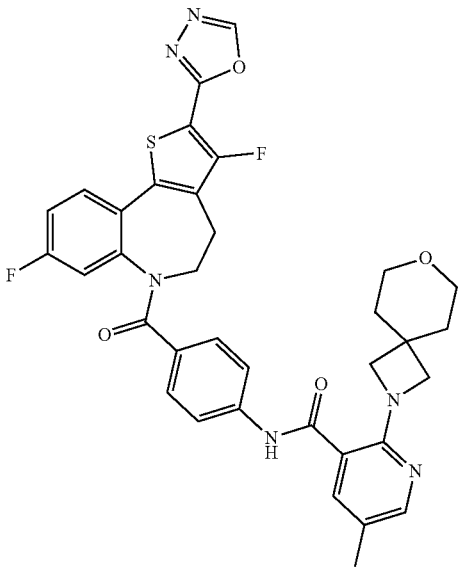 [SMILES: Cc1cnc(N2CC3(CCOCC3)C2)c(C(=O)Nc2ccc(C(=O)N3CCc4c(sc(-c5nnco5)c4F)-c4ccc(F)cc43)cc2)c1]

Example 143 was prepared using the procedure similar to that of example 141 from the corresponding intermediate. ESI-MS m/z: 651.21 [M+H]$^+$.

Example 144

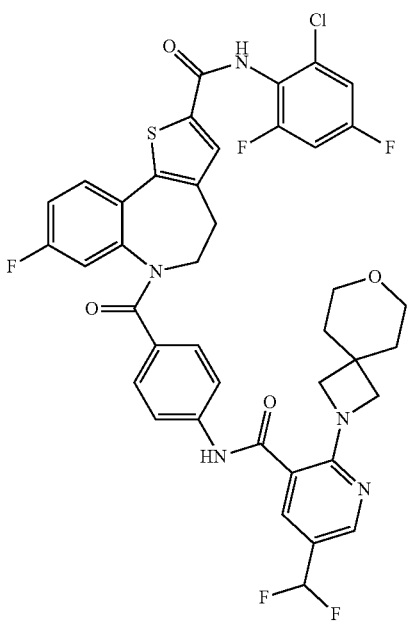 [SMILES: O=C(Nc1c(F)cc(F)cc1Cl)c1cc2c(s1)-c1ccc(F)cc1N(C(=O)c1ccc(NC(=O)c3cc(C(F)F)cnc3N3CC4(CCOCC4)C3)cc1)CC2]

Example 144

Step a

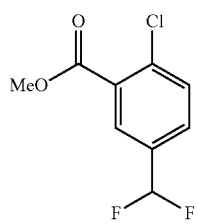 [SMILES: COC(=O)c1cc(C(F)F)ccc1Cl]

To a solution of methyl 2-chloro-5-formylbenzoate (1.0 g, 5.01 mmol) in DCM (50 mL) was added diethylaminosulfur trifluoride (DAST) (2.42 g, 15.03 mmol). The resulting mixture was stirred at rt for 2 hrs. Then the reaction was quenched with aq. NaHCO$_3$ and adjusted the pH ~8. After extracted with DCM (50 mL×3), the organic layer was dried, filtered and evaporated. The residue was purified by silica gel column chromatography eluting with 0-20% EtOAc/hexanes to obtain the desired product (530 mg, 48%) as colorless oil. ESI-MS m/z: 222.23 [M+H]$^+$.

Example 144

Step b

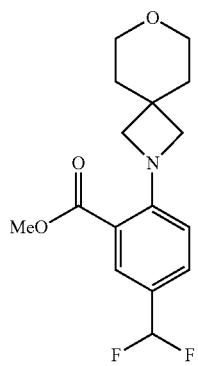 [SMILES: COC(=O)c1cc(C(F)F)ccc1N1CC2(CCOCC2)C1]

The mixture of the compound form step a (530 mg, 2.38 mmol), 7-oxa-2-azaspiro[3.5]nonane hydrochloride (783 mg, 4.78 mmol) and DIPEA (0.5 mL) in DMSO (1 mL) was heated at 80° C. for 4 hrs and then diluted with EtOAc (100 mL). The mixture was washed with water (20 mL×3) and brine (20 mL). The organic layer was dried and evaporated. The residue was purified by silica gel column chromatography eluting with 0-30% EtOAc/hexanes to obtain the desired product (710 mg, 95%) as colorless oil. ESI-MS m/z: 313.22 [M+H]$^+$.

Example 144

Step c

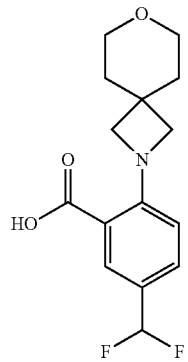 [SMILES: O=C(O)c1cc(C(F)F)ccc1N1CC2(CCOCC2)C1]

To a solution of the compound from step c (710 mg, 2.27 mmol) in MeOH/THF (20 mL, 1:1) was added LiOH (554 mg, 22.73 mmol) in water (4 mL). The resulting mixture was stirred at 50° C. for 2 hrs. The mixture was adjusted to pH ~5 with 1M HCl. The mixture was extracted with 10% MeOH/DCM (50 mL×3). The combined organic layer was dried and evaporated to obtain the desired product (500 mg, 80%) as off-white solid. ESI-MS m/z: 277.21 [M+H]$^+$.

Example 144

Step d

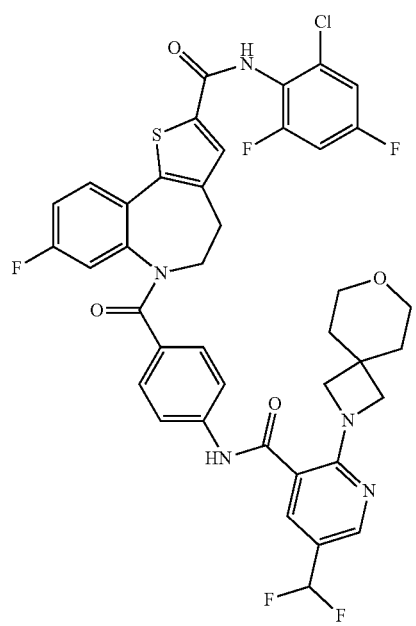 [SMILES: O=C(Nc1c(F)cc(F)cc1Cl)c1cc2c(s1)-c1ccc(F)cc1N(C(=O)c1ccc(NC(=O)c3cc(C(F)F)cnc3N3CC4(CCOCC4)C3)cc1)CC2]

To a solution of the compound from step c (56.5 mg, 0.19 mmol) in DCM (5 mL), 1-chloro-N,N, 2-trimethylprop-1-en-1-amine (50.6 mg, 0.38 mmol) was added. The reaction mixture was stirred at rt for 1 h and was then concentrated in vacuo. The resulting residue was taken into DCM (6 mL) and a solution of 6-(4-aminobenzoyl)-N-(2-chloro-4,6-difluorophenyl)-8-fluoro-5,6-dihydro-4H-benzo[b]thieno[2,3-d]azepine-2-carboxamide (100 mg, 0.199 mmol) in pyridine (0.2 mL) and DCM (2 mL) was added. After stirred at rt for 16 hrs, the mixture was partitioned between DCM (50 mL) and brine (20 mL). The organic layer was dried, filtered, evaporated, and purified by silica gel column chromatography eluting with 0-4% MeOH/DCM to obtain the desired product (100 mg, 65.3%) as white foam. ESI-MS m/z: 808.22 [M+H]$^+$.

Example 145

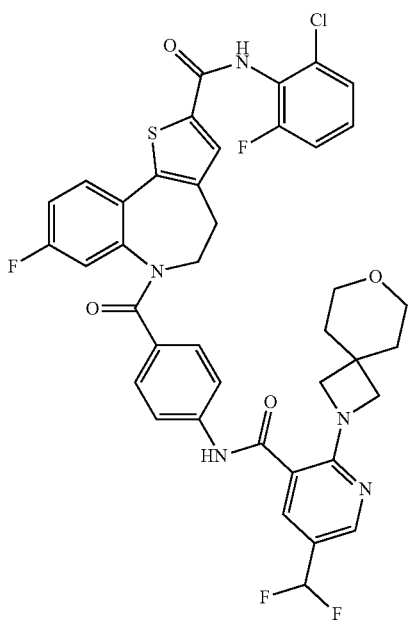

Example 145 was prepared using the procedure similar to that of example 144 from the corresponding intermediate. ESI-MS m/z: 790.22 [M+H]$^+$.

Example 146

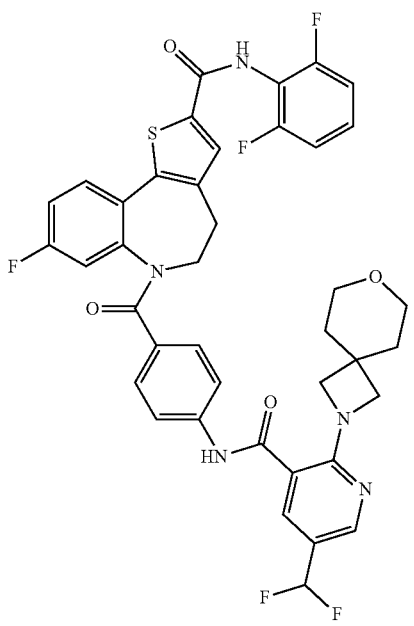 [SMILES: O=C(Nc1c(F)cccc1F)c1cc2c(s1)-c1ccc(F)cc1N(C(=O)c1ccc(NC(=O)c3cc(C(F)F)cnc3N3CC4(CCOCC4)C3)cc1)CC2]

Example 146 was prepared using the procedure similar to that of example 144 from the corresponding intermediate. ESI-MS m/z: 774.25 [M+H]$^+$.

Examples 147-149 shown in table 15 were prepared using the procedure similar to that of example 3 from the corresponding intermediates.

TABLE 15

| Example | Structure | ESI-MS m/z: [M + H]$^+$ |
|---|---|---|
| 147 | 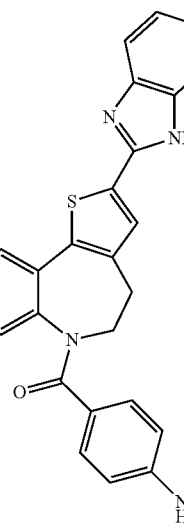 | 699.2 |
| 148 | 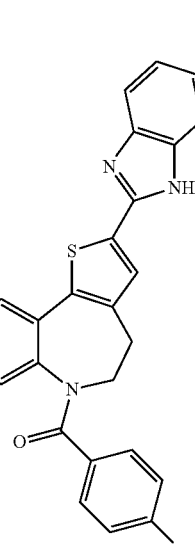 | 733.2 |

TABLE 15-continued

| Example | Structure | ESI-MS m/z: [M + H]+ |
|---|---|---|
| 149 | 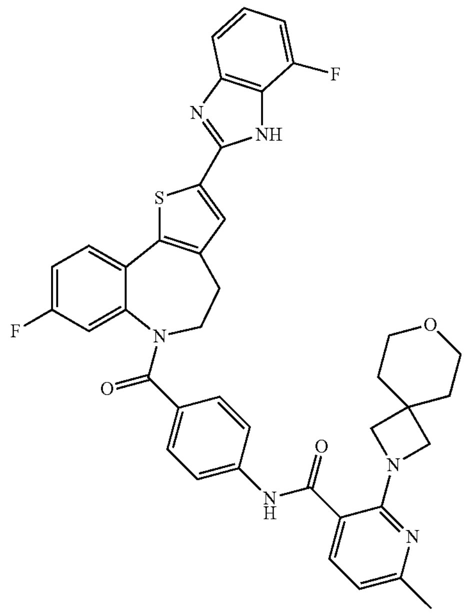 [SMILES: Cc1ccc(C(=O)Nc2ccc(C(=O)N3CCc4cc(-c5nc6cccc(F)c6[nH]5)sc4-c4ccc(F)cc43)cc2)c(N2CC3(CCOCC3)C2)n1] | 717.2 |

Examples 150-193 shown in table 16 were prepared using the procedure similar to that of example 45 from the corresponding intermediates.

TABLE 16

| Example | Structure | ESI-MS m/z: [M + H]+ |
|---|---|---|
| 150 | | 681.2 |
| 151 | 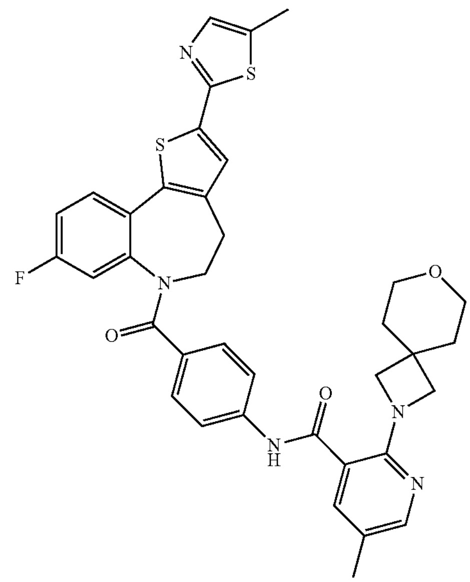 | 680.2 |
| 152 | 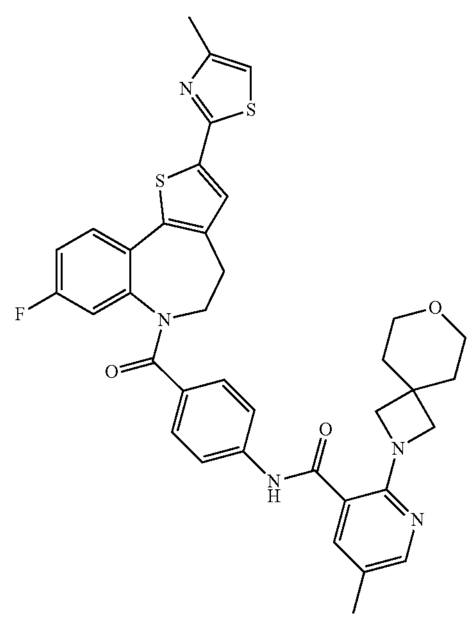 | 680.2 |

TABLE 16-continued
| Example | Structure | ESI-MS m/z: [M + H]+ |
|---|---|---|
| 153 | 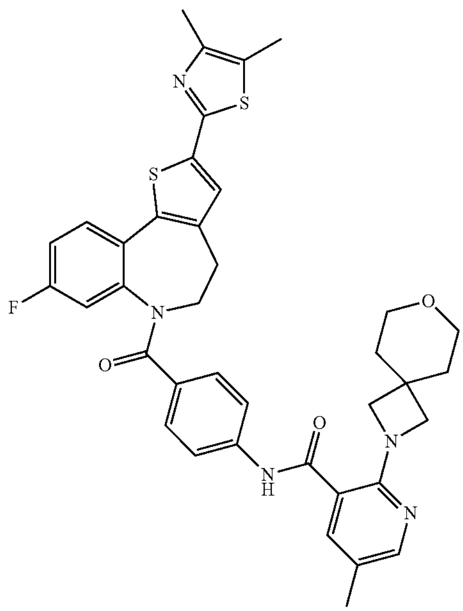 [SMILES: Cc1cnc(N2CC3(CCOCC3)C2)c(C(=O)Nc2ccc(C(=O)N3CCc4cc(-c5nc(C)c(C)s5)sc4-c4ccc(F)cc43)cc2)c1] | 694.3 |
| 154 | 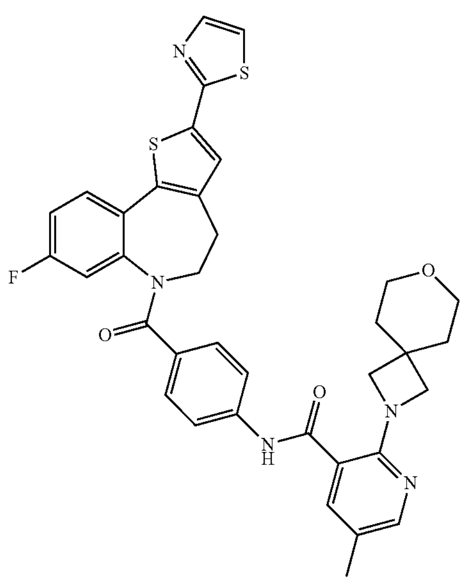 [SMILES: Cc1cnc(N2CC3(CCOCC3)C2)c(C(=O)Nc2ccc(C(=O)N3CCc4cc(-c5nccs5)sc4-c4ccc(F)cc43)cc2)c1] | 666.2 |
| 155 | | 667.3 |
| 156 | | 664.3 |
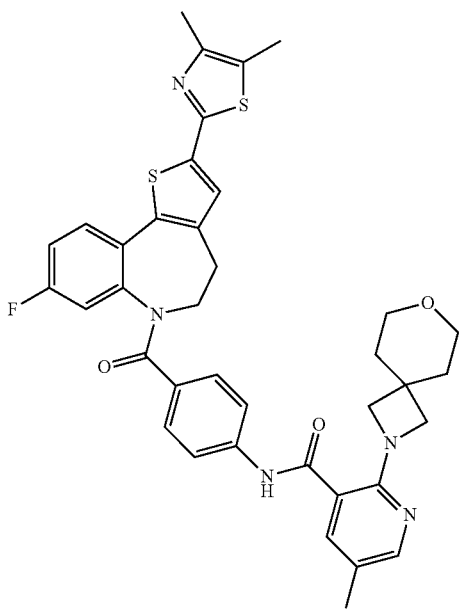

TABLE 16-continued

| Example | Structure | ESI-MS m/z: [M + H]+ |
|---|---|---|
| 157 | 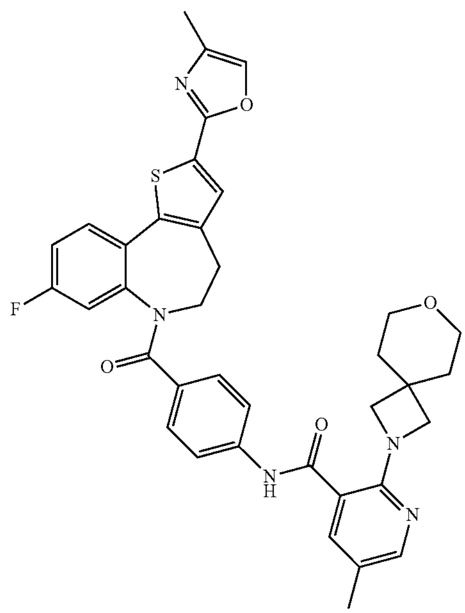 [SMILES: Cc1cnc(N2CC3(CCOCC3)C2)c(C(=O)Nc2ccc(C(=O)N3CCc4cc(-c5nc(C)co5)sc4-c4ccc(F)cc43)cc2)c1] | 664.3 |
| 158 | 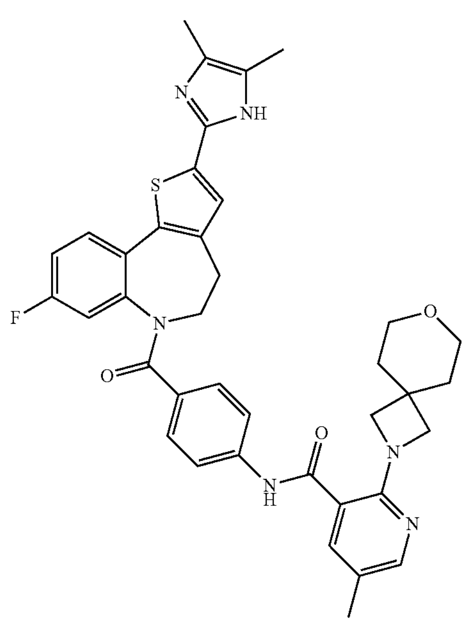 [SMILES: Cc1cnc(N2CC3(CCOCC3)C2)c(C(=O)Nc2ccc(C(=O)N3CCc4cc(-c5nc(C)c(C)[nH]5)sc4-c4ccc(F)cc43)cc2)c1] | 677.3 |
| 159 | 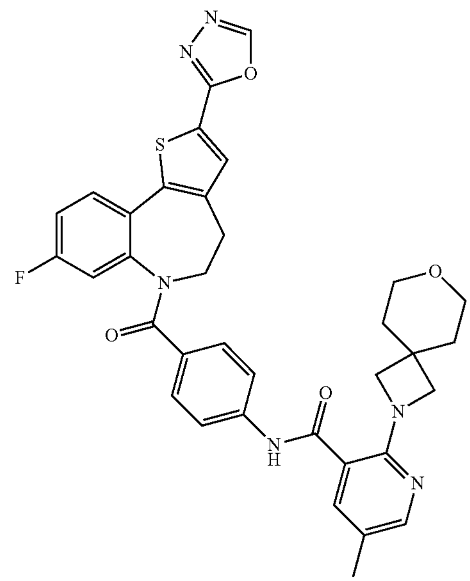 [SMILES: Cc1cnc(N2CC3(CCOCC3)C2)c(C(=O)Nc2ccc(C(=O)N3CCc4cc(-c5nnco5)sc4-c4ccc(F)cc43)cc2)c1] | 651.2 |
| 160 | 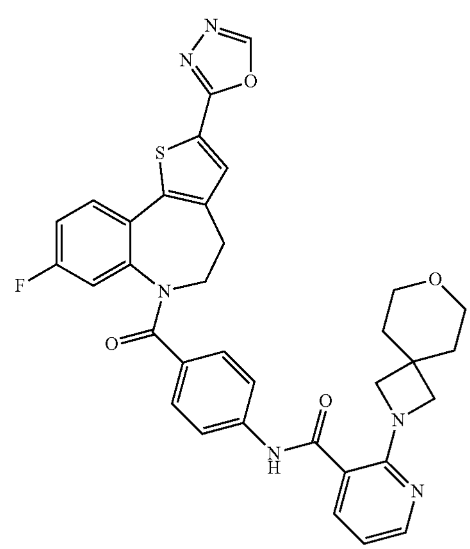 [SMILES: O=C(Nc1ccc(C(=O)N2CCc3cc(-c4nnco4)sc3-c3ccc(F)cc32)cc1)c1cccnc1N1CC2(CCOCC2)C1] | 637.2 |

TABLE 16-continued
| Example | Structure | ESI-MS m/z: [M + H]+ |
|---|---|---|
| 161 | 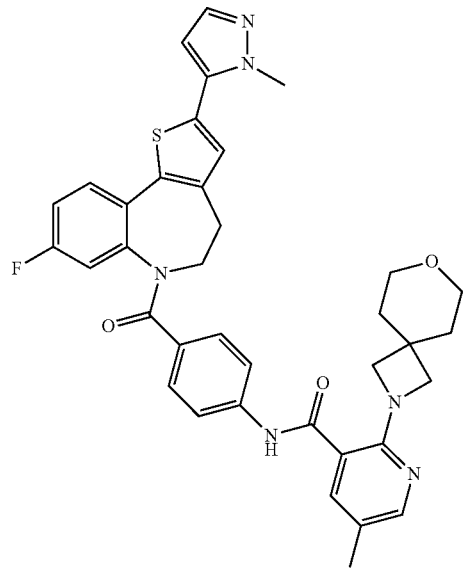 [SMILES: Cc1cnc(N2CC3(CCOCC3)C2)c(C(=O)Nc2ccc(C(=O)N3CCc4cc(-c5ccnn5C)sc4-c4ccc(F)cc43)cc2)c1] | 663.3 |
| 162 | 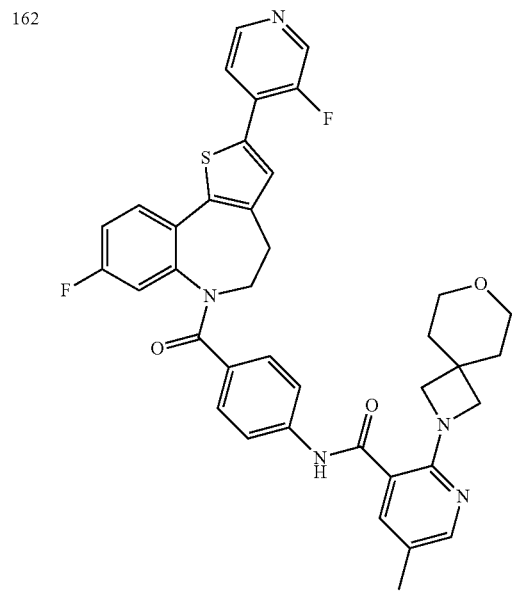 | 678.3 |
| 163 | 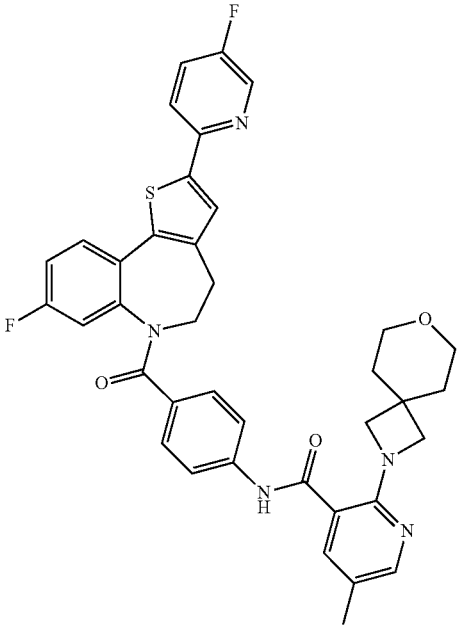 [SMILES: Cc1cnc(N2CC3(CCOCC3)C2)c(C(=O)Nc2ccc(C(=O)N3CCc4cc(-c5ccc(F)cn5)sc4-c4ccc(F)cc43)cc2)c1] | 678.3 |
| 164 | 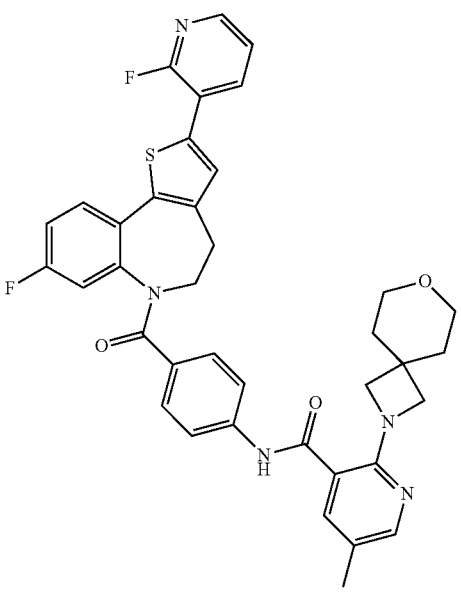 [SMILES: Cc1cnc(N2CC3(CCOCC3)C2)c(C(=O)Nc2ccc(C(=O)N3CCc4cc(-c5cccnc5F)sc4-c4ccc(F)cc43)cc2)c1] | 678.3 |

TABLE 16-continued
| Example | Structure | ESI-MS m/z: [M + H]+ |
|---|---|---|
| 165 | 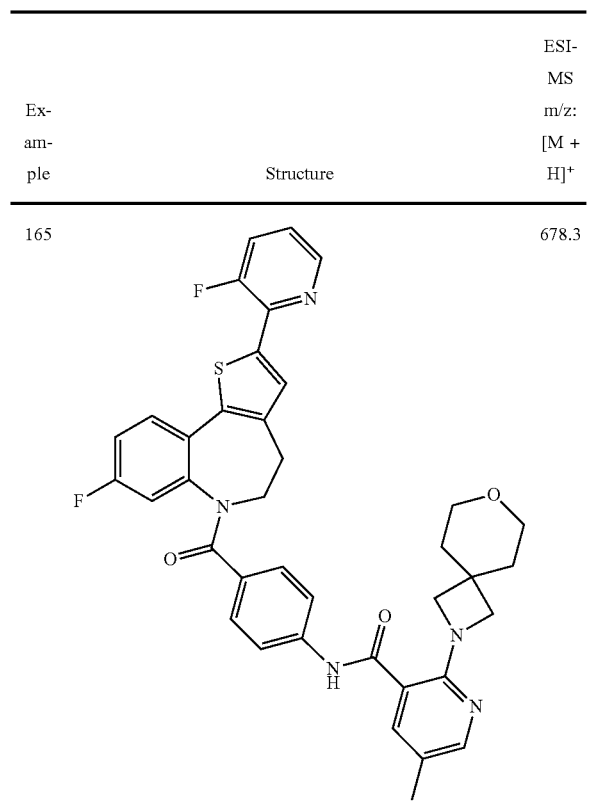 | 678.3 |
| 166 | 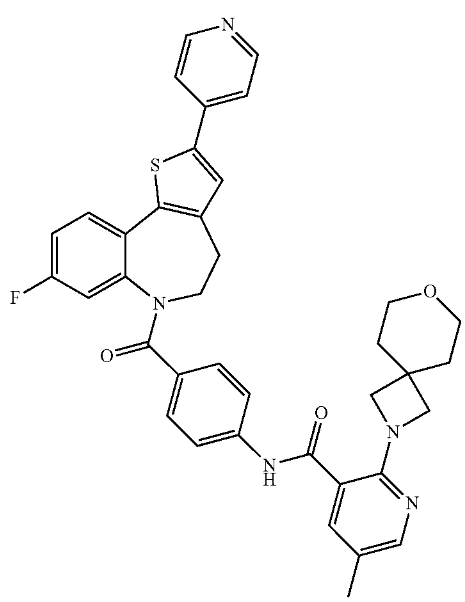 [SMILES: Cc1cnc(N2CC3(CCOCC3)C2)c(C(=O)Nc2ccc(C(=O)N3CCc4cc(-c5ccncc5)sc4-c4ccc(F)cc43)cc2)c1] | 660.3 |
| 167 | 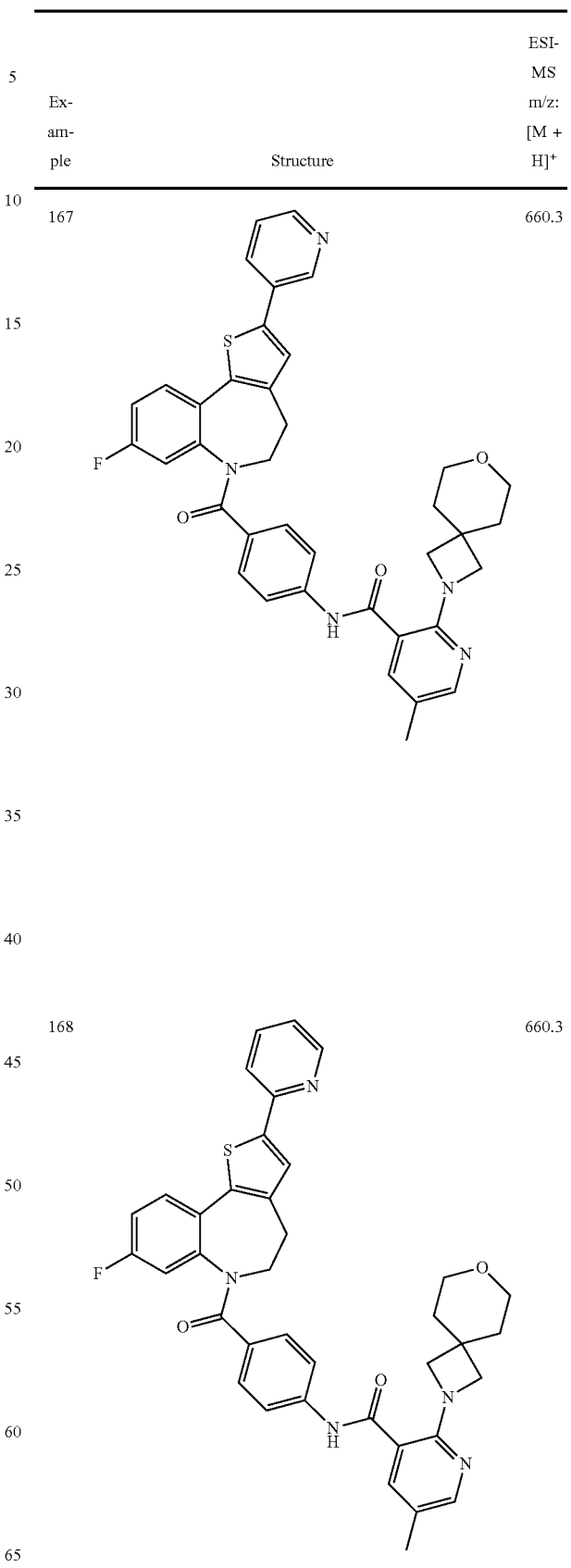 | 660.3 |
| 168 | 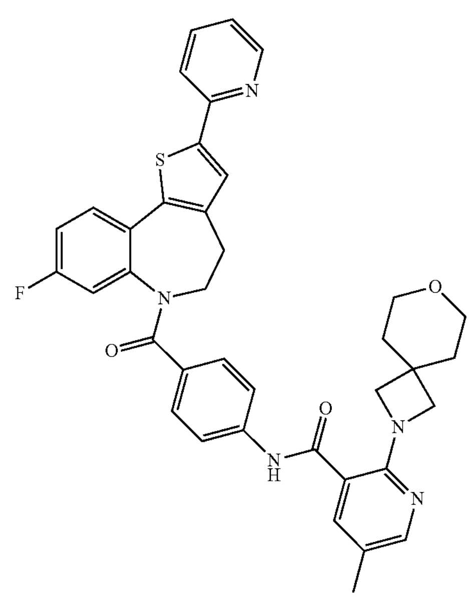 [SMILES: Cc1cnc(N2CC3(CCOCC3)C2)c(C(=O)Nc2ccc(C(=O)N3CCc4cc(-c5ccccn5)sc4-c4ccc(F)cc43)cc2)c1] | 660.3 |

TABLE 16-continued
| Example | Structure | ESI-MS m/z: [M + H]+ |
|---|---|---|
| 169 | 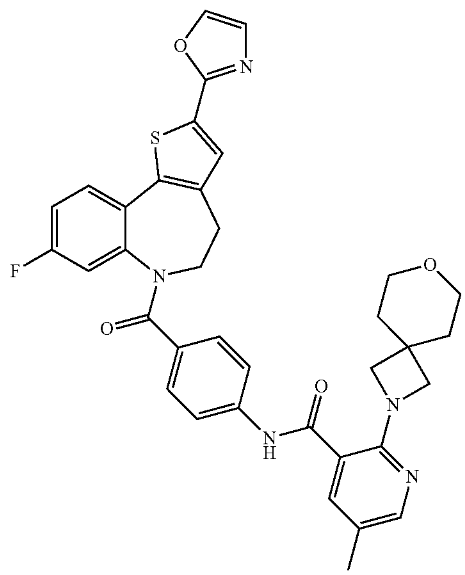 [SMILES: Cc1cnc(N2CC3(CCOCC3)C2)c(C(=O)Nc2ccc(C(=O)N3CCc4cc(-c5ncco5)sc4-c4ccc(F)cc43)cc2)c1] | 650.2 |
| 170 | 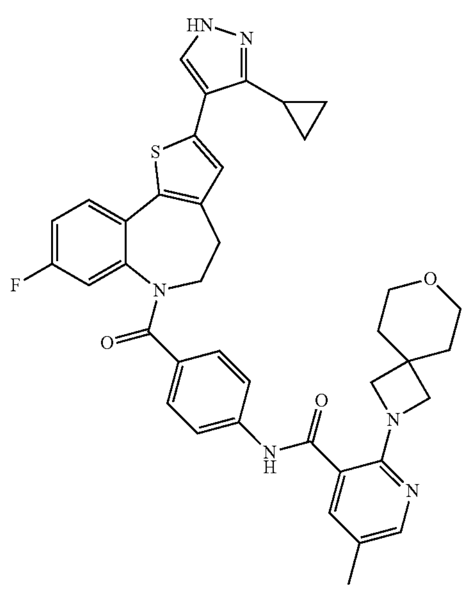 [SMILES: Cc1cnc(N2CC3(CCOCC3)C2)c(C(=O)Nc2ccc(C(=O)N3CCc4cc(-c5c[nH]nc5C5CC5)sc4-c4ccc(F)cc43)cc2)c1] | 689.2 |
| 171 | | 677.3 |
| 172 | | 678.2 |
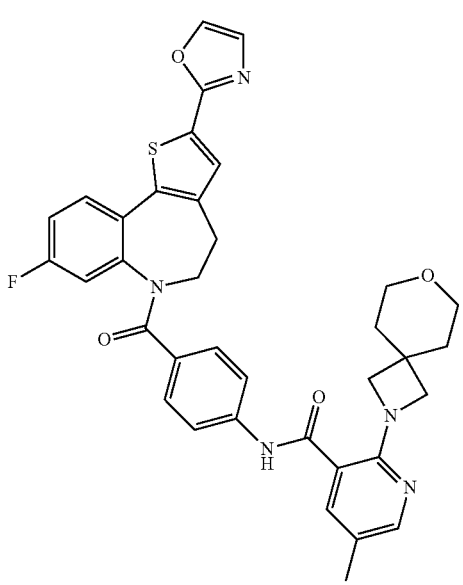

TABLE 16-continued

| Example | Structure | ESI-MS m/z: [M+H]+ |
|---|---|---|
| 173 | 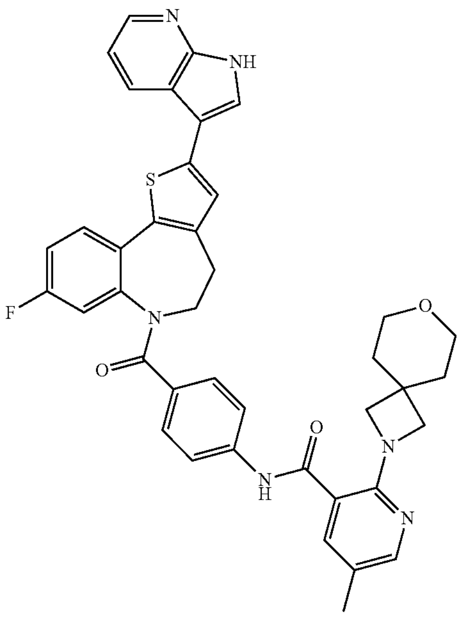 [SMILES: Cc1cnc(N2CC3(CCOCC3)C2)c(C(=O)Nc2ccc(C(=O)N3CCc4cc(-c5c[nH]c6ncccc56)sc4-c4ccc(F)cc43)cc2)c1] | 699.2 |
| 174 | 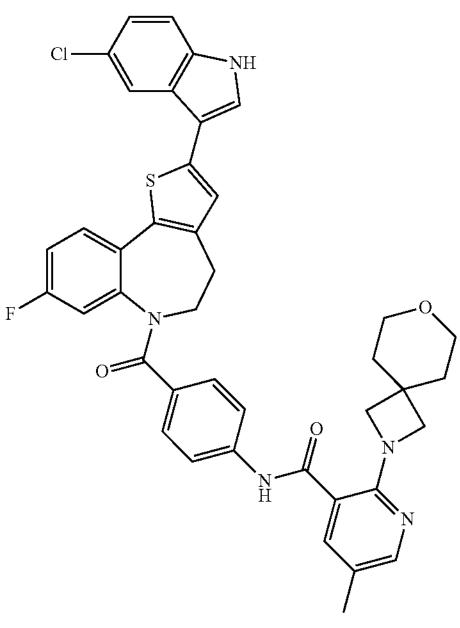 | 732.2 |
| 175 | | 732.2 |
| 176 | | 712.3 |

TABLE 16-continued

| Example | Structure | ESI-MS m/z: [M + H]+ |
|---|---|---|
| 177 | 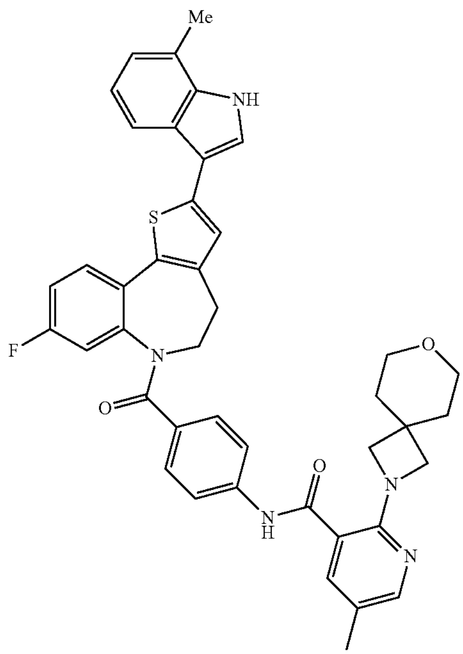 | 712.3 |
| 178 | 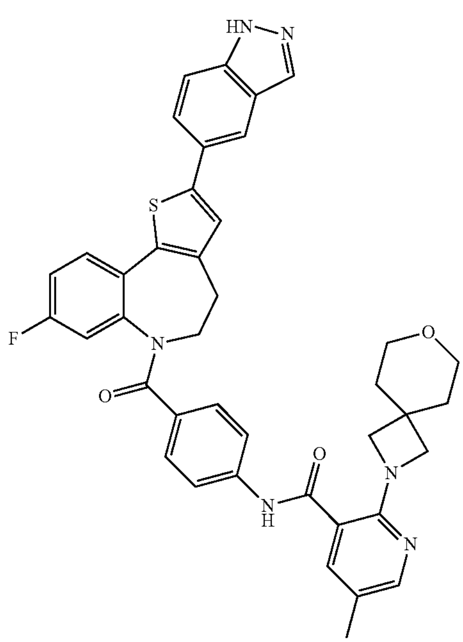 [SMILES: Cc1cnc(N2CC3(CCOCC3)C2)c(C(=O)Nc2ccc(C(=O)N3CCc4cc(-c5ccc6[nH]ncc6c5)sc4-c4ccc(F)cc43)cc2)c1] | 699.3 |
| 179 | | 700.3 |
| 180 | | 699.3 |

TABLE 16-continued

| Example | Structure | ESI-MS m/z: [M+H]+ |
|---|---|---|
| 181 | 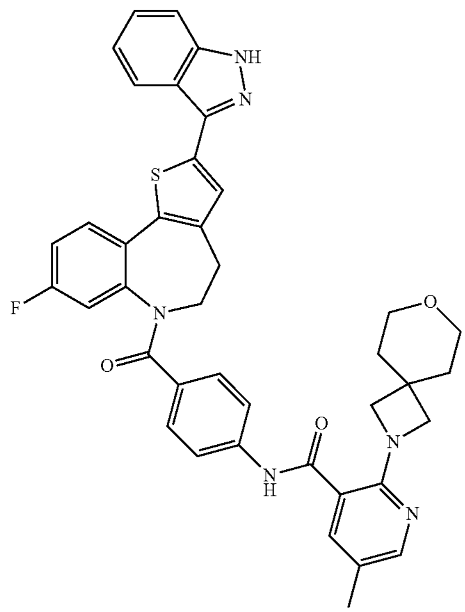 [SMILES: Cc1cnc(N2CC3(CCOCC3)C2)c(C(=O)Nc2ccc(C(=O)N3CCc4cc(-c5n[nH]c6ccccc56)sc4-c4ccc(F)cc43)cc2)c1] | 699.3 |
| 182 | 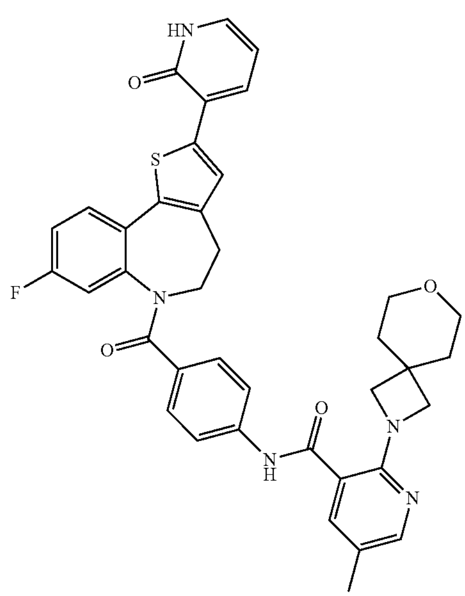 [SMILES: Cc1cnc(N2CC3(CCOCC3)C2)c(C(=O)Nc2ccc(C(=O)N3CCc4cc(-c5ccc[nH]c5=O)sc4-c4ccc(F)cc43)cc2)c1] | 676.3 |
| 183 | | 676.3 |
| 184 | | 676.3 |

TABLE 16-continued

| Example | Structure | ESI-MS m/z: [M + H]+ |
|---|---|---|
| 185 | 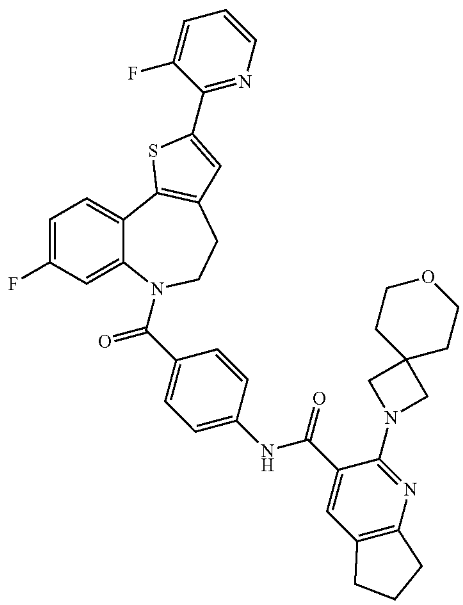 [SMILES: O=C(Nc1ccc(C(=O)N2CCc3cc(-c4ncccc4F)sc3-c3ccc(F)cc32)cc1)c1cc2c(nc1N1CC3(CCOCC3)C1)CCC2] | 747.3 |
| 186 | 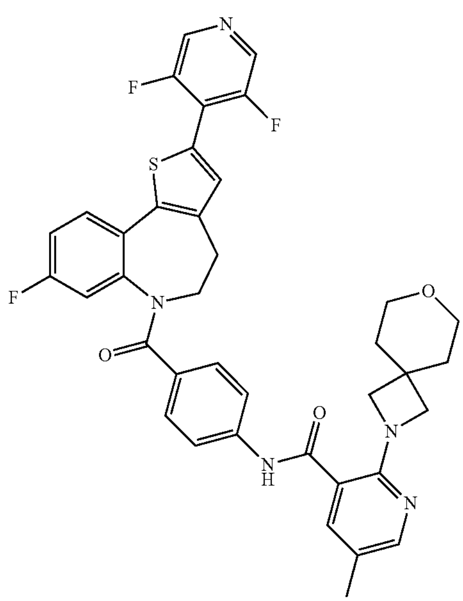 [SMILES: Cc1cnc(N2CC3(CCOCC3)C2)c(C(=O)Nc2ccc(C(=O)N3CCc4cc(-c5c(F)cncc5F)sc4-c4ccc(F)cc43)cc2)c1] | 696.3 |
| 187 | | 663.0 |
| 188 | | 740.0 |

TABLE 16-continued

| Example | Structure | ESI-MS m/z: [M+H]+ |
|---|---|---|
| 189 | 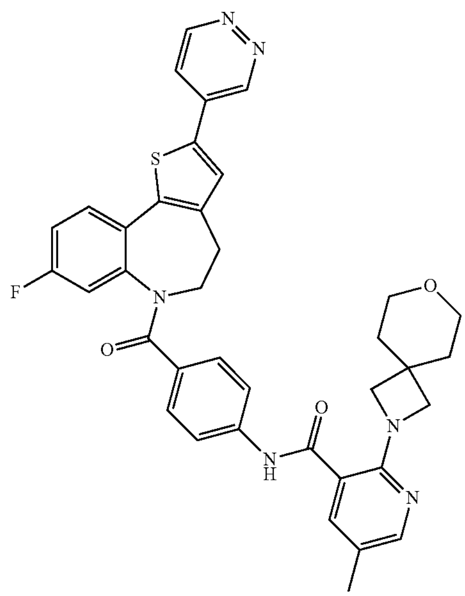 | 661.0 |
| 190 | 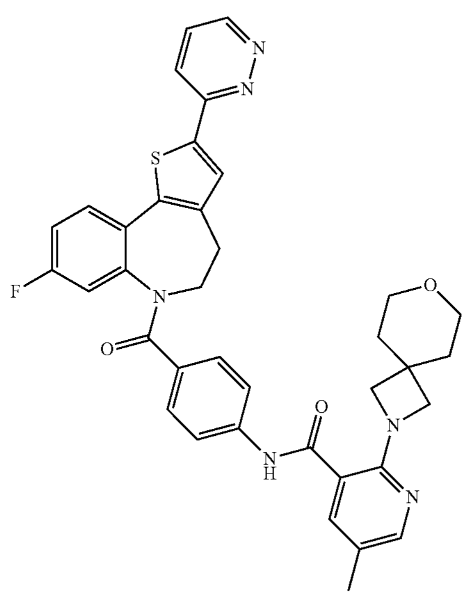 | 661.0 |
| 191 | 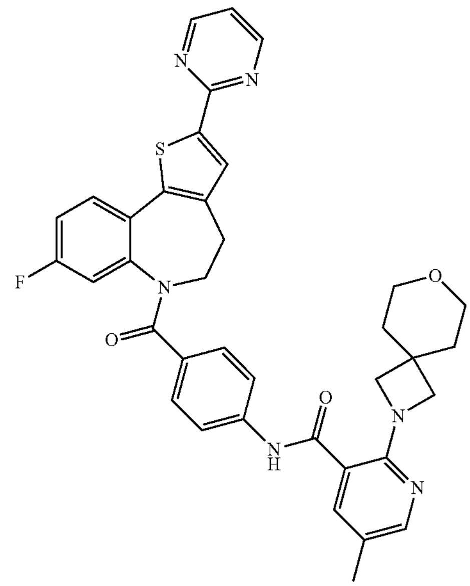 | 661.0 |
| 192 | 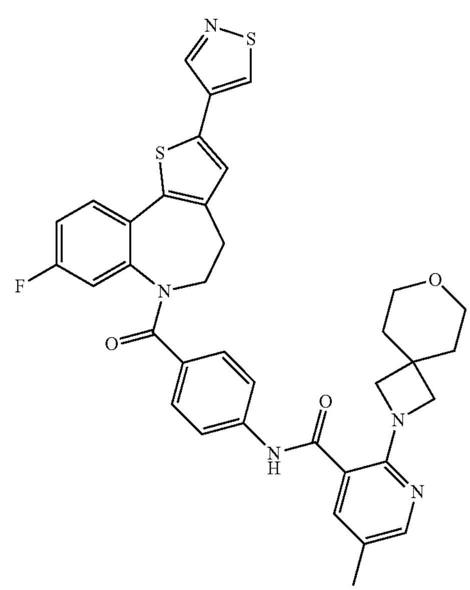 [SMILES: Cc1cnc(N2CC3(CCOCC3)C2)c(C(=O)Nc2ccc(C(=O)N3CCc4cc(-c5cnsc5)sc4-c4ccc(F)cc43)cc2)c1] | 666.0 |

281
TABLE 16-continued

| Example | Structure | ESI-MS m/z: [M + H]+ |
|---|---|---|
| 193 | 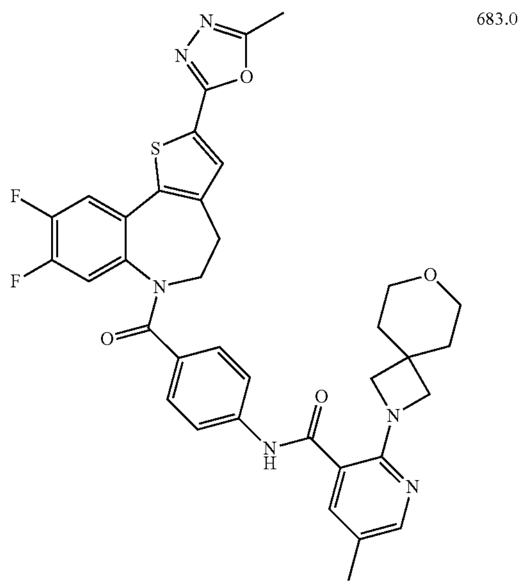 | 683.0 |

Example 194

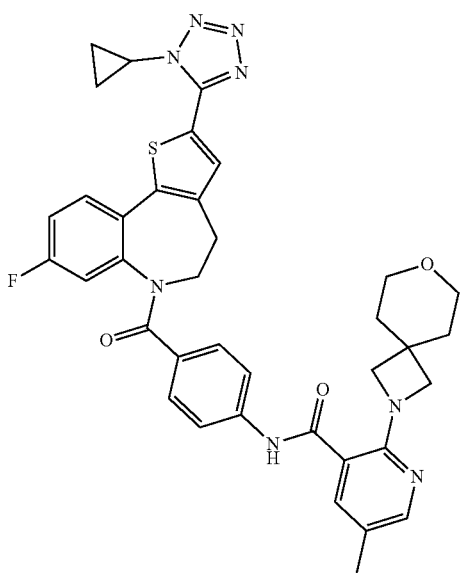 [SMILES: Cc1cnc(N2CC3(CCOCC3)C2)c(C(=O)Nc2ccc(C(=O)N3CCc4cc(-c5nnnn5C5CC5)sc4-c4ccc(F)cc43)cc2)c1]

282

Example 194

Step a

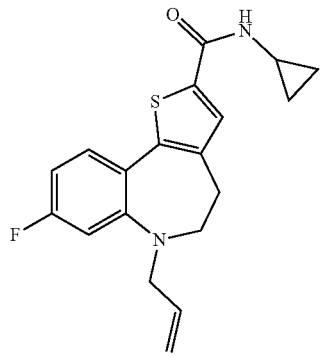 [SMILES: C=CCN1CCc2cc(C(=O)NC3CC3)sc2-c2ccc(F)cc21]

To a stirring solution of 6-allyl-8-fluoro-5,6-dihydro-4H-benzo[b]thieno[2,3-d]azepine-2-carboxylic acid (500 mg, 1.65 mmol) was added 1-chloro-N,N, 2-trimethylprop-1-en-1-amine (454 μL, 3.30 mmol), the mixture was stirred at room temperature for 1 h and was then concentrated under vacuum. The residue was taken in DCM (8.2 mL) and a solution of cyclopropanamine (457 μL, 6.59 mmol) in pyridine (1600 μL, 19.78 mmol) was added. The resulting solution was stirred overnight. The resulting mixture was concentrated under vacuum. The crude product purified through a silica gel column chromatography eluting with 0-60% EtOAc/hexanes to afford the desired product (307.9 mg, 55% yield) as a white solid. ESI-MS m/z: 342.8 [M+H]+.

Example 194

Step b

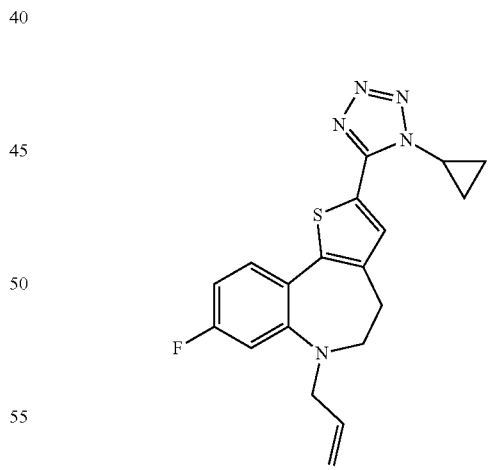

To a stirring solution of compound from step a (0.31 g, 0.90 mmol) and 2-(diphenylphosphanyl)pyridine (0.973 g, 3.59 mmol) in THF (4.5 mL) was added DIAD (0.74 mL, 3.59 mmol) followed by the dropwise addition of diphenyl phosphorazidate (0.80 mL, 3.59 mmol). The solution was left to stir at 45° C. for 24 hrs. The reaction mixture was diluted with ethyl acetate and washed with saturated aqueous sodium bicarbonate solution. The organic layer was dried over anhydrous Na₂SO₄ and concentrated in vacuo.

The crude product purified through a silica gel column eluenting 0-60% EtOAc/hexanes to give the desired product (203 mg, 62% yield) as a white solid. ESI-MS m/z: 367.8 [M+H]⁺.

Example 194

Step c

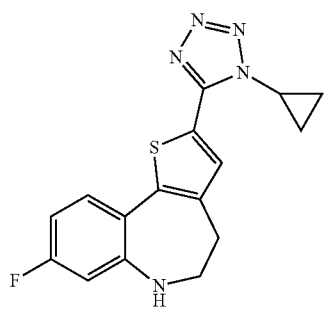 [SMILES: Fc1ccc2c(c1)NCCc1cc(-c3nnnn3C3CC3)sc1-2]

To a dried round bottom flash were added compound from step b (0.20 g, 0.544 mmol), Pd(OAc)₂ (0.012 g, 0.054 mmol), triphenylphosphine (0.072 g, 0.272 mmol) and 1,3-dimethylpyrimidine-2,4,6(1H,3H,5H)-trione (0.258 g, 1.633 mmol) in DCM (5.4 mL). After degassed, the reaction mixture was heated at 35° C. overnight. After cooling to rt, saturated sodium bicarbonate solution was added to the reaction mixture adjust the pH to 9-10 and extracted with DCM (3×10 mL). The combined organic extracts were washed with brine, dried over anhydrous Na₂SO₄ and concentrated in vacuo. The residue was purified by flash column chromatography eluting with 0-75% EtOAc in hexanes to afford the desired product (115.4 mg, 65% yield) as an orange-yellow solid. ESI-MS m/z: 327.8 [M+H]⁺.

Example 194

Step d

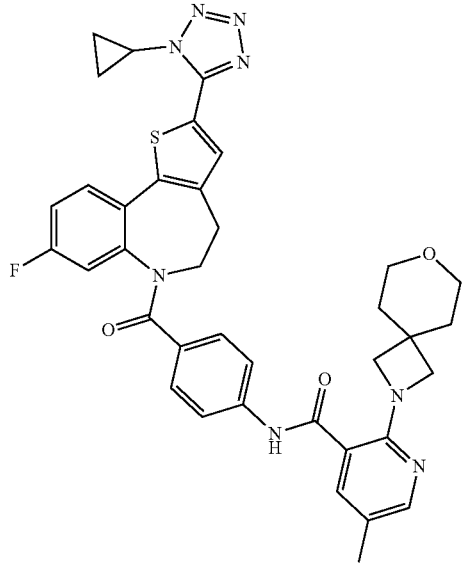 [SMILES: Cc1cnc(N2CC3(CCOCC3)C2)c(C(=O)Nc2ccc(C(=O)N3CCc4cc(-c5nnnn5C5CC5)sc4-c4ccc(F)cc43)cc2)c1]

To solution of 4-(5-methyl-2-(7-oxa-2-azaspiro[3.5]nonan-2-yl)nicotinamido)benzoic acid (98 mg, 0.244 mmol) in DCM (1.2 mL) under N₂ atmosphere at rt was added 1-chloro-N,N, 2-trimethylprop-1-en-1-amine (67 µL, 0.489 mmol). The mixture was stirred at room temperature for 1 hour and was then concentrated under vacuum. The crude acid chloride was redissolved in pyridine (1.2 mL) and compound from step c (40 mg, 0.122 mmol) was added and the reaction mixture stirred overnight at 80° C. After cooling to room temperature, the solvent was removed under reduced pressure and the crude residue was purified by reverse phase prep-HPLC (MeCN/H₂O) to obtain the desired product (17 mg, 20% yield) as a white solid. ESI-MS m/z: 691.0 [M+H]⁺.

Examples 195 and 196 shown in table 17 were prepared using the procedure similar to that of example 194 from the corresponding intermediates.

TABLE 17

| Example | Structure | ESI-MS m/z: [M+H]⁺ |
|---|---|---|
| 195 | 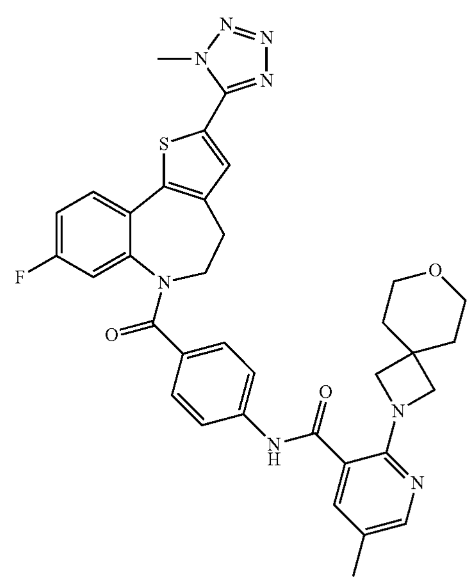 [SMILES: Cc1cnc(N2CC3(CCOCC3)C2)c(C(=O)Nc2ccc(C(=O)N3CCc4cc(-c5nnnn5C)sc4-c4ccc(F)cc43)cc2)c1] | 665.0 |

TABLE 17-continued
| Example | Structure | ESI-MS m/z: [M + H]+ |
|---|---|---|
| 196 | 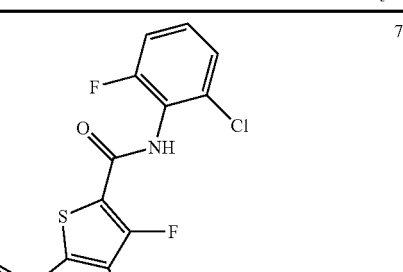 | 651.0 |
Examples 197-233 shown in table 18 were prepared using the procedure similar to that of example 93 and example 96 from the corresponding intermediates.
TABLE 18
| Example | Structure | ESI-MS m/z: [M + H]+ |
|---|---|---|
| 197 | | 754.2 |
| 198 | 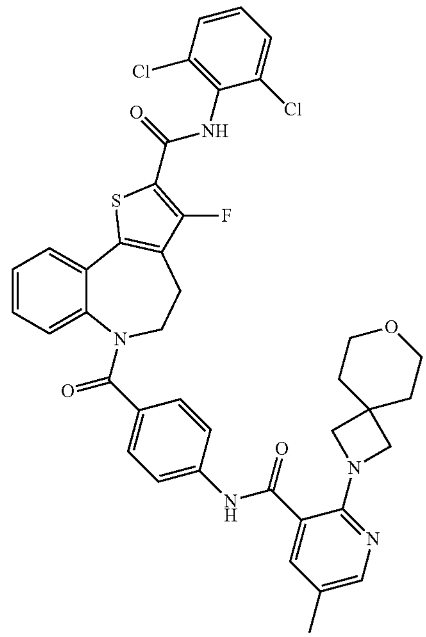 [SMILES: Cc1cnc(N2CC3(CCOCC3)C2)c(C(=O)Nc2ccc(C(=O)N3CCc4c(sc(C(=O)Nc5c(Cl)cccc5Cl)c4F)-c4ccccc43)cc2)c1] | 777.0 |
| 199 | 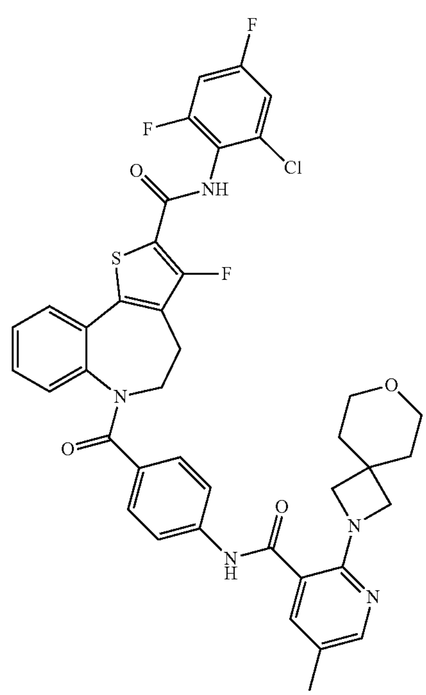 [SMILES: Cc1cnc(N2CC3(CCOCC3)C2)c(C(=O)Nc2ccc(C(=O)N3CCc4c(sc(C(=O)Nc5c(F)cc(F)cc5Cl)c4F)-c4ccccc43)cc2)c1] | 772.1 |
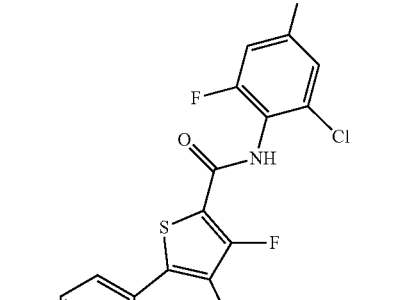

TABLE 18-continued
| Example | Structure | ESI-MS m/z: [M + H]+ |
|---------|-----------|----------------------|
| 200 | 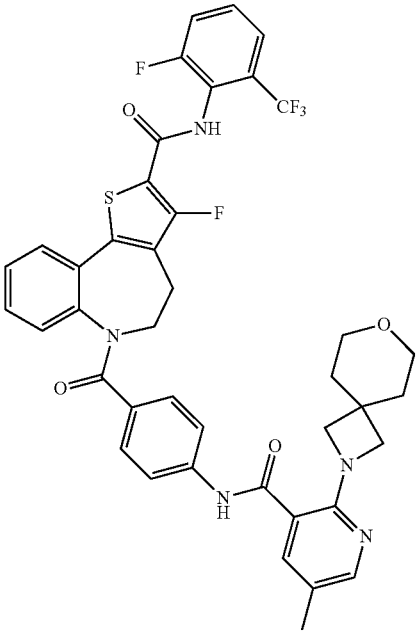 | 788.1 |
| 201 | 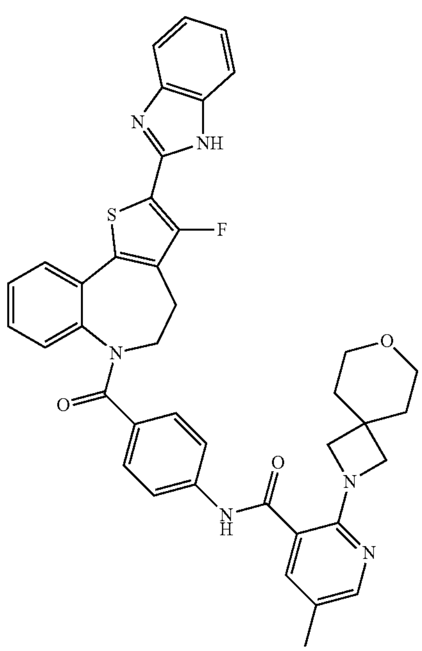 [SMILES: Cc1cnc(N2CC3(CCOCC3)C2)c(C(=O)Nc2ccc(C(=O)N3CCc4c(sc(-c5nc6ccccc6[nH]5)c4F)-c4ccccc43)cc2)c1] | 699.1 |
| 202 | 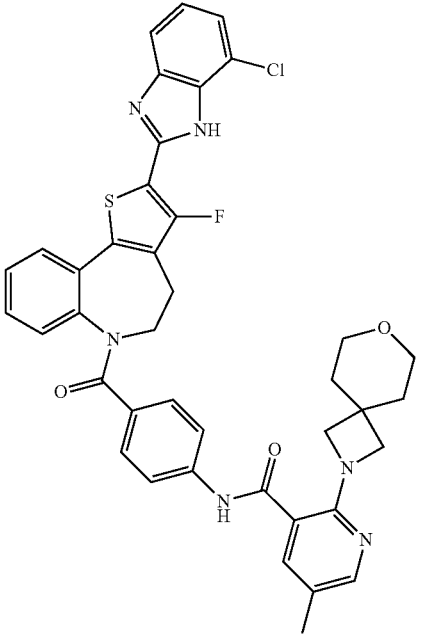 [SMILES: Cc1cnc(N2CC3(CCOCC3)C2)c(C(=O)Nc2ccc(C(=O)N3CCc4c(sc(-c5nc6cccc(Cl)c6[nH]5)c4F)-c4ccccc43)cc2)c1] | 733.1 |
| 203 | 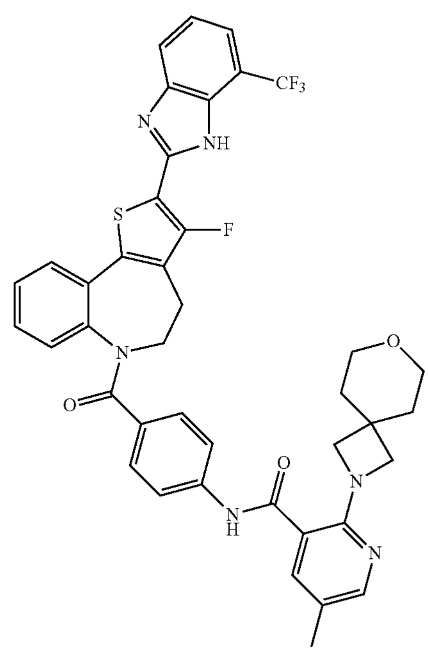 | 767.1 |

TABLE 18-continued

| Example | Structure | ESI-MS m/z: [M + H]+ |
|---|---|---|
| 204 | 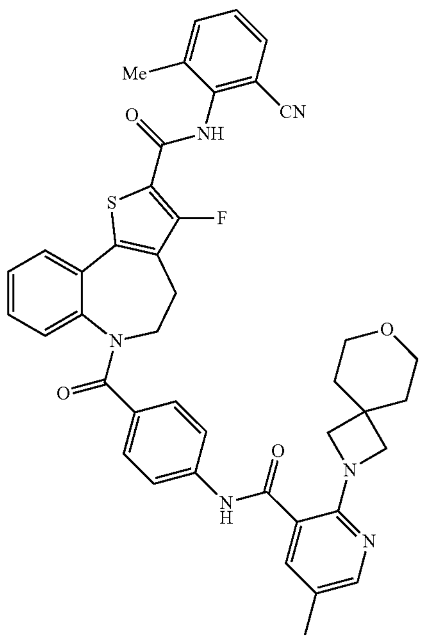 [SMILES: Cc1cnc(N2CC3(CCOCC3)C2)c(C(=O)Nc2ccc(C(=O)N3CCc4c(sc(C(=O)Nc5c(C)cccc5C#N)c4F)-c4ccccc43)cc2)c1] | 741.0 |
| 205 | 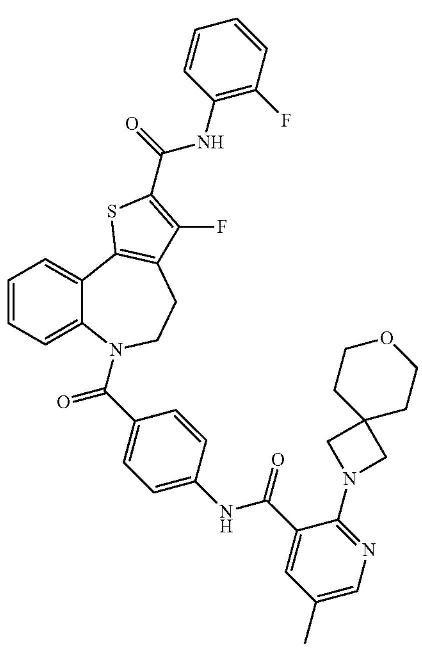 [SMILES: Cc1cnc(N2CC3(CCOCC3)C2)c(C(=O)Nc2ccc(C(=O)N3CCc4c(sc(C(=O)Nc5ccccc5F)c4F)-c4ccccc43)cc2)c1] | 720.0 |
| 206 | | 717.0 |
| 207 | | 717.0 |

TABLE 18-continued
| Example | Structure | ESI-MS m/z: [M + H]+ |
|---|---|---|
| 208 | 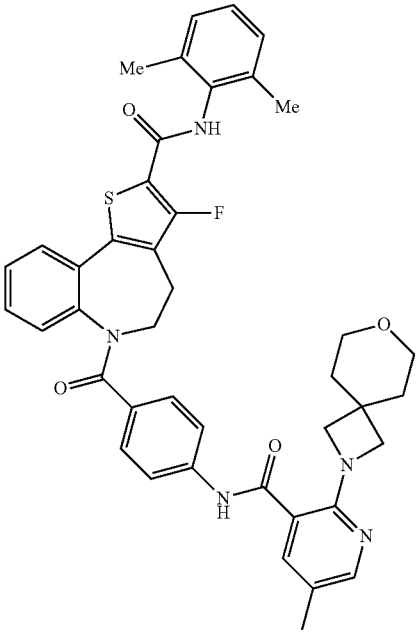 [SMILES: Cc1cnc(N2CC3(CCOCC3)C2)c(C(=O)Nc2ccc(C(=O)N3CCc4c(sc(C(=O)Nc5c(C)cccc5C)c4F)-c4ccccc43)cc2)c1] | 730.0 |
| 209 | 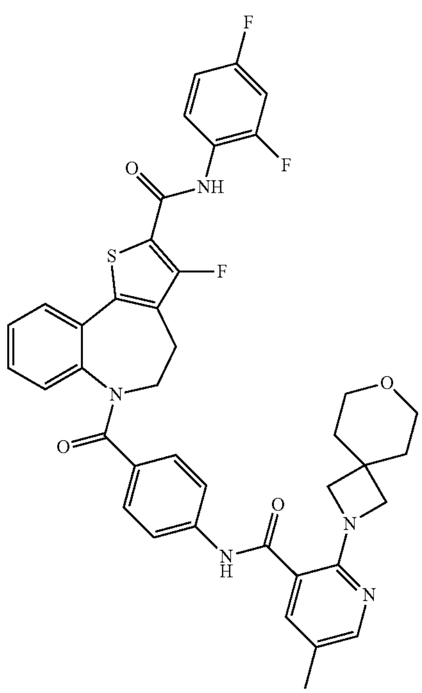 [SMILES: Cc1cnc(N2CC3(CCOCC3)C2)c(C(=O)Nc2ccc(C(=O)N3CCc4c(sc(C(=O)Nc5ccc(F)cc5F)c4F)-c4ccccc43)cc2)c1] | 738.0 |
TABLE 18-continued
| Example | Structure | ESI-MS m/z: [M + H]+ |
|---|---|---|
| 210 | 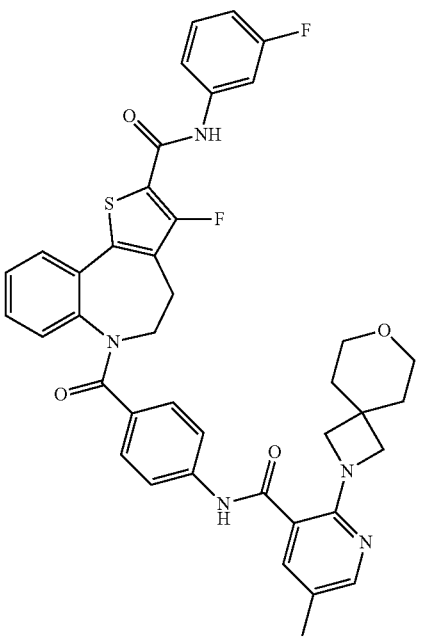 [SMILES: Cc1cnc(N2CC3(CCOCC3)C2)c(C(=O)Nc2ccc(C(=O)N3CCc4c(sc(C(=O)Nc5cccc(F)c5)c4F)-c4ccccc43)cc2)c1] | 720.0 |
| 211 | | 702.0 |

TABLE 18-continued

| Example | Structure | ESI-MS m/z: [M + H]+ |
|---|---|---|
| 212 | 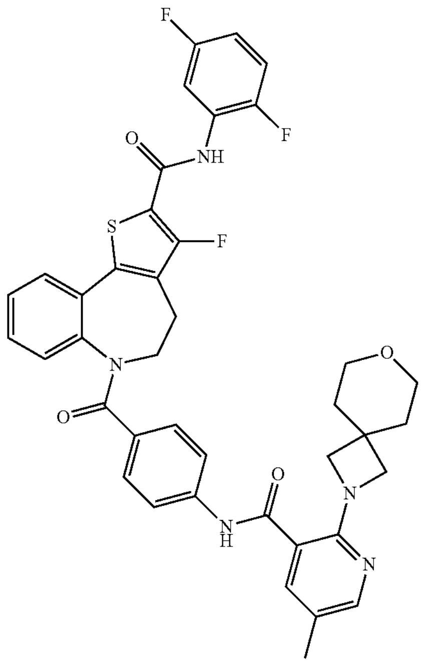 [SMILES: Cc1cnc(N2CC3(CCOCC3)C2)c(C(=O)Nc2ccc(C(=O)N3CCc4c(sc(C(=O)Nc5cc(F)ccc5F)c4F)-c4ccccc43)cc2)c1] | 738.0 |
| 213 | 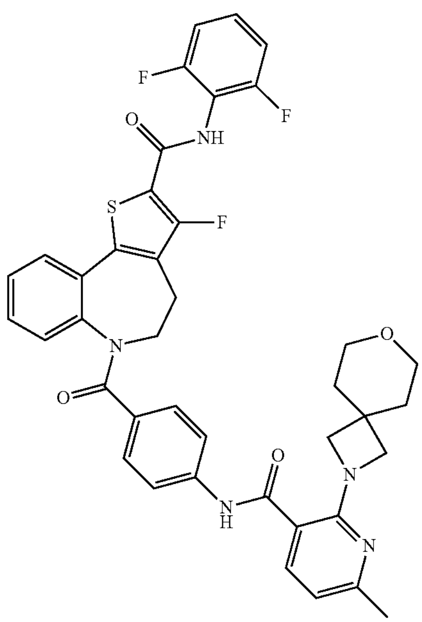 [SMILES: Cc1ccc(C(=O)Nc2ccc(C(=O)N3CCc4c(sc(C(=O)Nc5c(F)cccc5F)c4F)-c4ccccc43)cc2)c(N2CC3(CCOCC3)C2)n1] | 738.0 |
| 214 | | 717.0 |
| 215 | | 721.0 |

TABLE 18-continued
| Example | Structure | ESI-MS m/z: [M + H]+ |
|---|---|---|
| 216 | 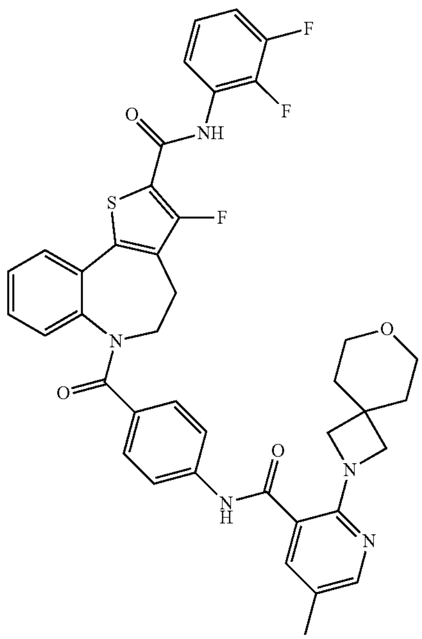 [SMILES: Cc1cnc(N2CC3(CCOCC3)C2)c(C(=O)Nc2ccc(C(=O)N3CCc4c(sc(C(=O)Nc5cccc(F)c5F)c4F)-c4ccccc43)cc2)c1] | 738.0 |
| 217 | 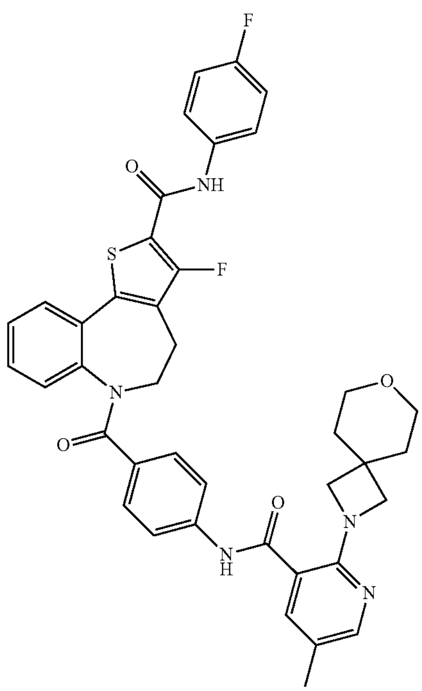 [SMILES: Cc1cnc(N2CC3(CCOCC3)C2)c(C(=O)Nc2ccc(C(=O)N3CCc4c(sc(C(=O)Nc5ccc(F)cc5)c4F)-c4ccccc43)cc2)c1] | 720.0 |
TABLE 18-continued
| Example | Structure | ESI-MS m/z: [M + H]+ |
|---|---|---|
| 218 | | 721.2 |
| 219 | | 735.0 |
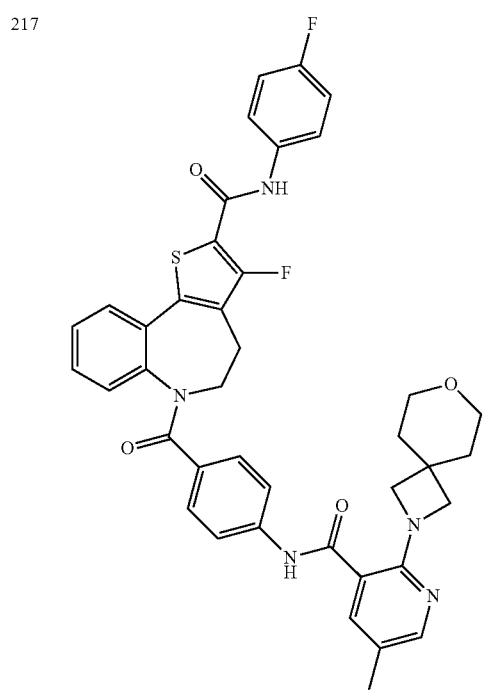
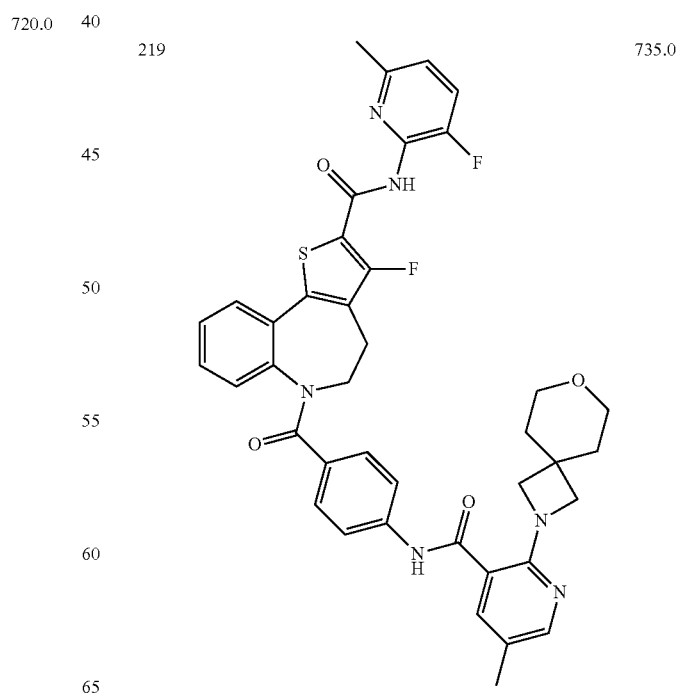

TABLE 18-continued
| Example | Structure | ESI-MS m/z: [M + H]+ |
|---------|-----------|----------------------|
| 220 | 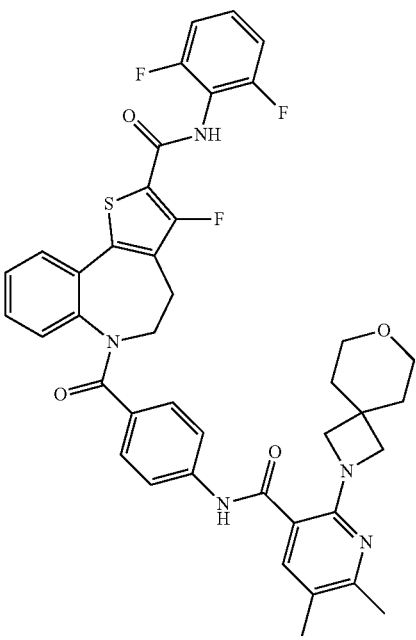 [SMILES: Cc1cc(C(=O)Nc2ccc(C(=O)N3CCc4c(sc(C(=O)Nc5c(F)cccc5F)c4F)-c4ccccc43)cc2)c(N2CC3(CCOCC3)C2)nc1C] | 752.1 |
| 221 | 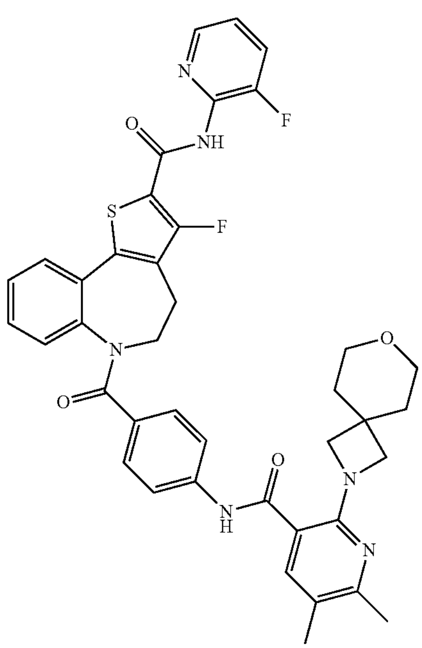 [SMILES: Cc1cc(C(=O)Nc2ccc(C(=O)N3CCc4c(sc(C(=O)Nc5ncccc5F)c4F)-c4ccccc43)cc2)c(N2CC3(CCOCC3)C2)nc1C] | 735.0 |
TABLE 18-continued
| Example | Structure | ESI-MS m/z: [M + H]+ |
|---------|-----------|----------------------|
| 222 | 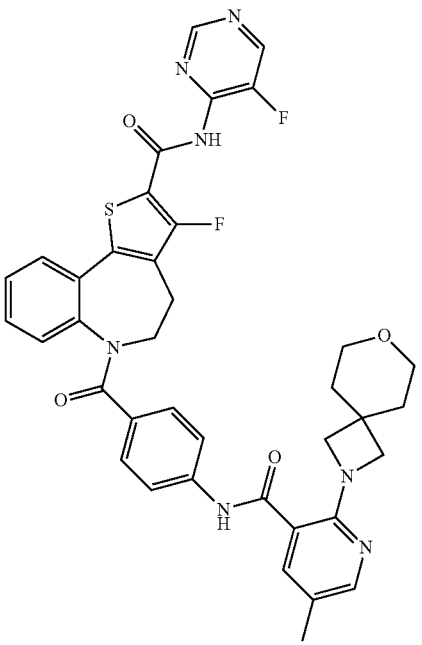 [SMILES: Cc1cnc(N2CC3(CCOCC3)C2)c(C(=O)Nc2ccc(C(=O)N3CCc4c(sc(C(=O)Nc5ncncc5F)c4F)-c4ccccc43)cc2)c1] | 722.0 |
| 223 | 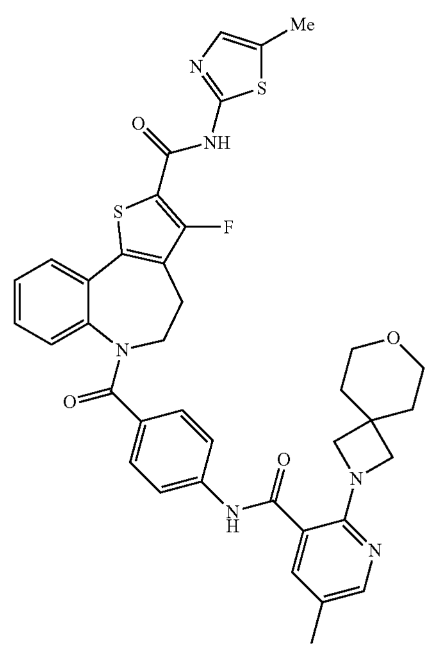 [SMILES: Cc1cnc(N2CC3(CCOCC3)C2)c(C(=O)Nc2ccc(C(=O)N3CCc4c(sc(C(=O)Nc5ncc(C)s5)c4F)-c4ccccc43)cc2)c1] | 723.0 |

TABLE 18-continued

| Example | Structure | ESI-MS m/z: [M + H]+ |
|---------|-----------|----------------------|
| 224 | 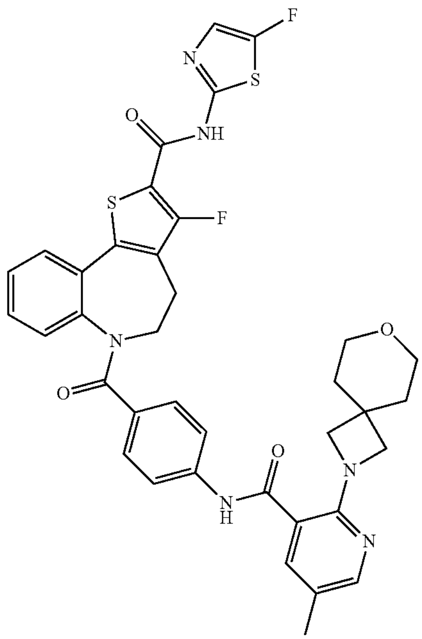 [SMILES: Cc1cnc(N2CC3(CCOCC3)C2)c(C(=O)Nc2ccc(C(=O)N3CCc4c(sc(C(=O)Nc5ncc(F)s5)c4F)-c4ccccc43)cc2)c1] | 727.0 |
| 225 | 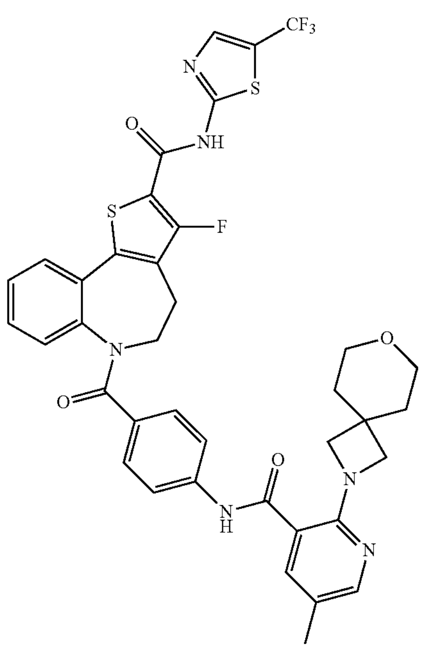 [SMILES: Cc1cnc(N2CC3(CCOCC3)C2)c(C(=O)Nc2ccc(C(=O)N3CCc4c(sc(C(=O)Nc5ncc(C(F)(F)F)s5)c4F)-c4ccccc43)cc2)c1] | 777.0 |
| 226 | 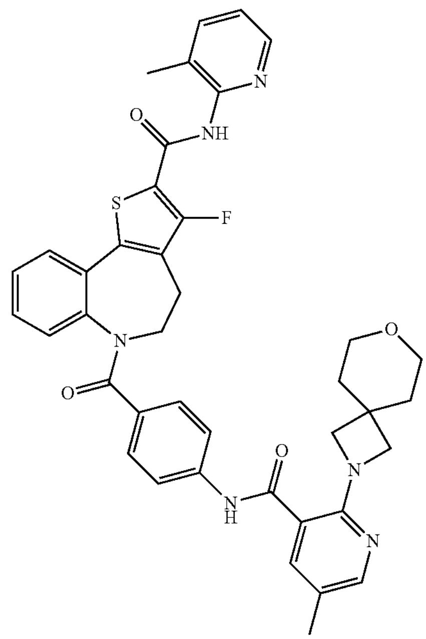 [SMILES: Cc1cnc(N2CC3(CCOCC3)C2)c(C(=O)Nc2ccc(C(=O)N3CCc4c(sc(C(=O)Nc5ncccc5C)c4F)-c4ccccc43)cc2)c1] | 717.2 |
| 227 | 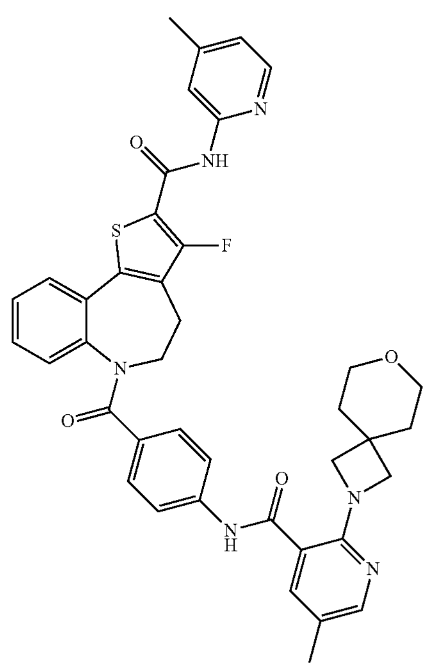 [SMILES: Cc1ccnc(NC(=O)c2sc3c(c2F)CCN(C(=O)c2ccc(NC(=O)c4cc(C)cnc4N4CC5(CCOCC5)C4)cc2)c2ccccc2-3)c1] | 717.2 |

TABLE 18-continued

| Example | Structure | ESI-MS m/z: [M + H]+ |
|---|---|---|
| 228 | 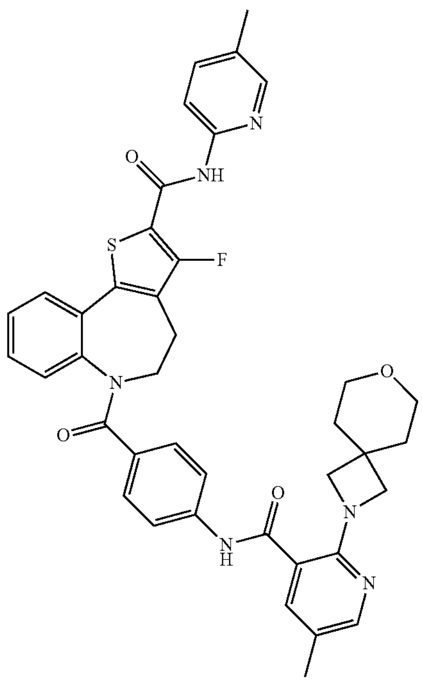 [SMILES: Cc1ccc(NC(=O)c2sc3c(c2F)CCN(C(=O)c2ccc(NC(=O)c4cc(C)cnc4N4CC5(CCOCC5)C4)cc2)c2ccccc2-3)nc1] | 717.2 |
| 229 | 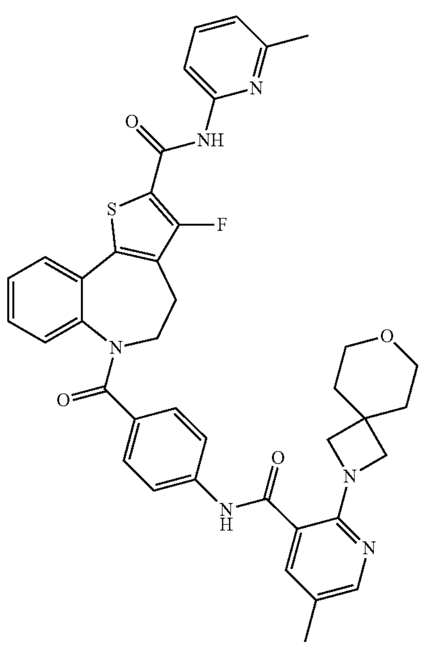 [SMILES: Cc1cnc(N2CC3(CCOCC3)C2)c(C(=O)Nc2ccc(C(=O)N3CCc4c(sc(C(=O)Nc5cccc(C)n5)c4F)-c4ccccc43)cc2)c1] | 717.2 |
| 230 | 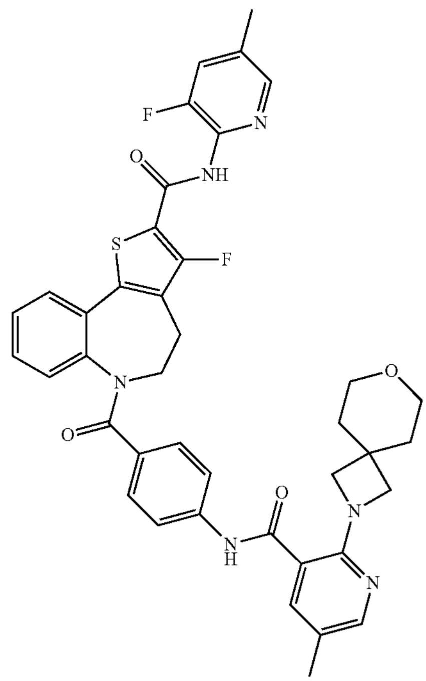 [SMILES: Cc1cnc(NC(=O)c2sc3c(c2F)CCN(C(=O)c2ccc(NC(=O)c4cc(C)cnc4N4CC5(CCOCC5)C4)cc2)c2ccccc2-3)c(F)c1] | 735.2 |
| 231 | 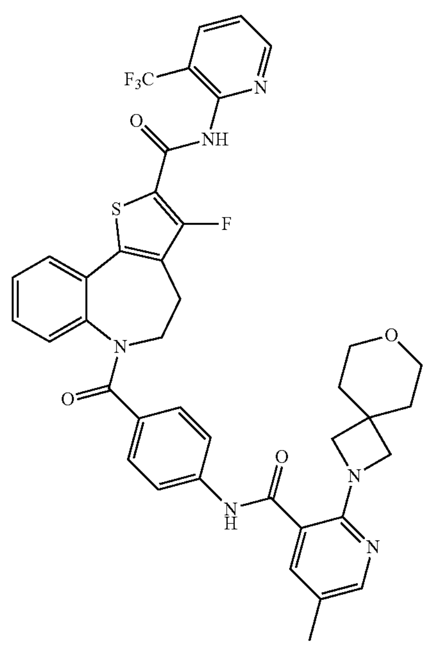 [SMILES: Cc1cnc(N2CC3(CCOCC3)C2)c(C(=O)Nc2ccc(C(=O)N3CCc4c(sc(C(=O)Nc5ncccc5C(F)(F)F)c4F)-c4ccccc43)cc2)c1] | 771.2 |

TABLE 18-continued
| Example | Structure | ESI-MS m/z: [M + H]+ |
|---|---|---|
| 232 | 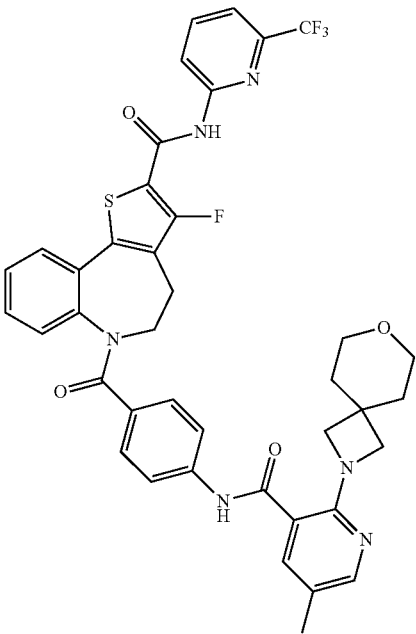 [SMILES: Cc1cnc(N2CC3(CCOCC3)C2)c(C(=O)Nc2ccc(C(=O)N3CCc4c(sc(C(=O)Nc5cccc(C(F)(F)F)n5)c4F)-c4ccccc43)cc2)c1] | 771.2 |
| 233 | 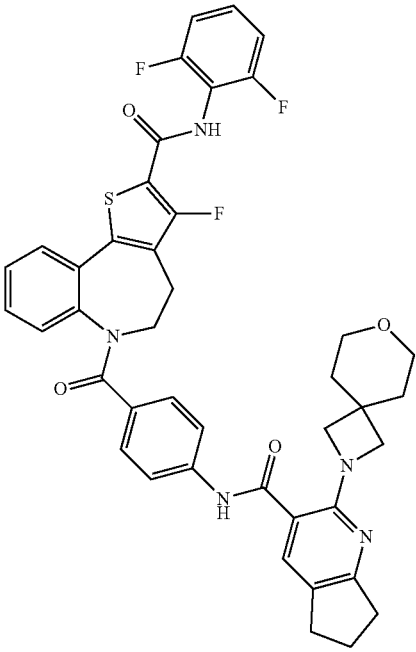 [SMILES: O=C(Nc1ccc(C(=O)N2CCc3c(sc(C(=O)Nc4c(F)cccc4F)c3F)-c3ccccc32)cc1)c1cc2c(nc1N1CC3(CCOCC3)C1)CCC2] | 764.3 |
TABLE 19
| Example | Structure | ESI-MS m/z: [M + H]+ |
|---|---|---|
| 234 | 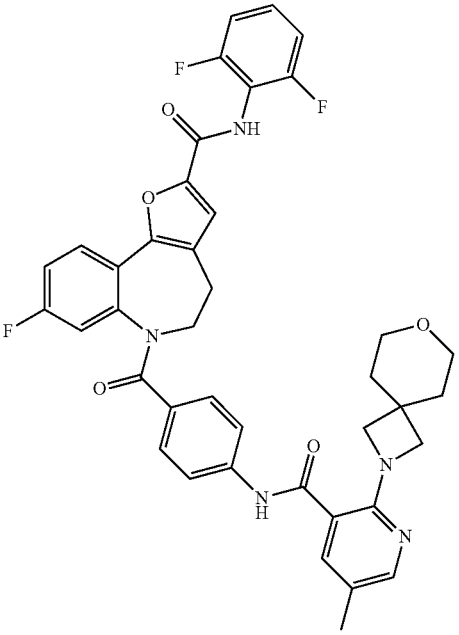 [SMILES: Cc1cnc(N2CC3(CCOCC3)C2)c(C(=O)Nc2ccc(C(=O)N3CCc4cc(C(=O)Nc5c(F)cccc5F)oc4-c4ccc(F)cc43)cc2)c1] | 722.0 |
| 235 | 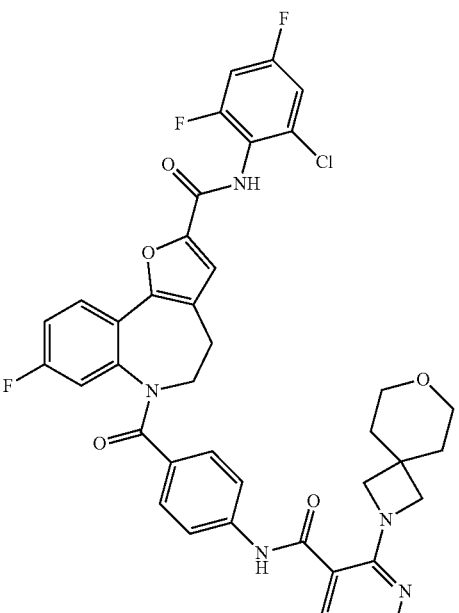 | 757.0 |
Examples 234-242 shown in table 19 were prepared using the procedure similar to that of example 100 from the corresponding intermediates.

TABLE 19-continued

| Example | Structure | ESI-MS m/z: [M + H]+ |
|---|---|---|
| 236 | 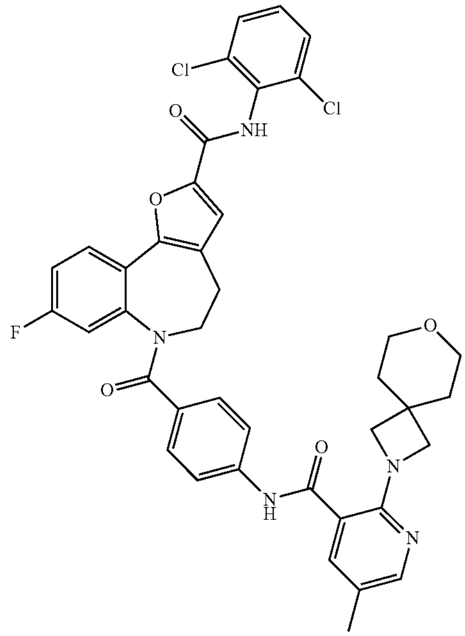 [SMILES: Cc1cnc(N2CC3(CCOCC3)C2)c(C(=O)Nc2ccc(C(=O)N3CCc4cc(C(=O)Nc5c(Cl)cccc5Cl)oc4-c4ccc(F)cc43)cc2)c1] | 755.0 |
| 237 | 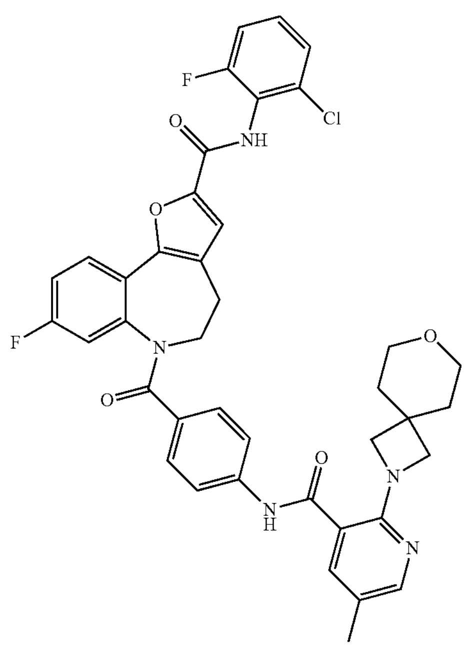 | 738.3 |
| 238 | | 777.3 |
| 239 | | 748.1 |

TABLE 19-continued

| Example | Structure | ESI-MS m/z: [M + H]+ |
|---|---|---|
| 240 | 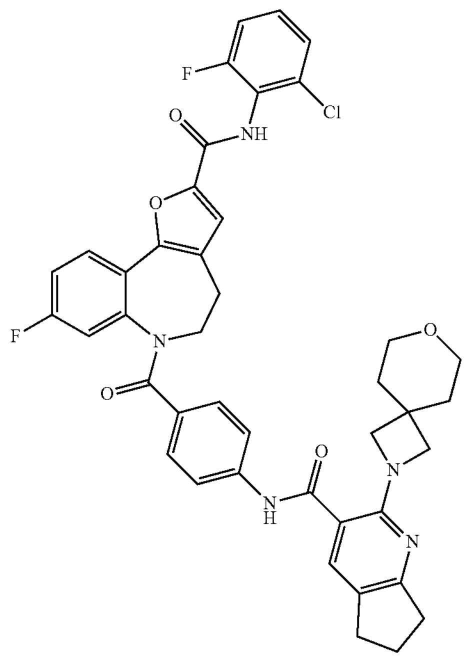 | 764.2 |
| 241 | 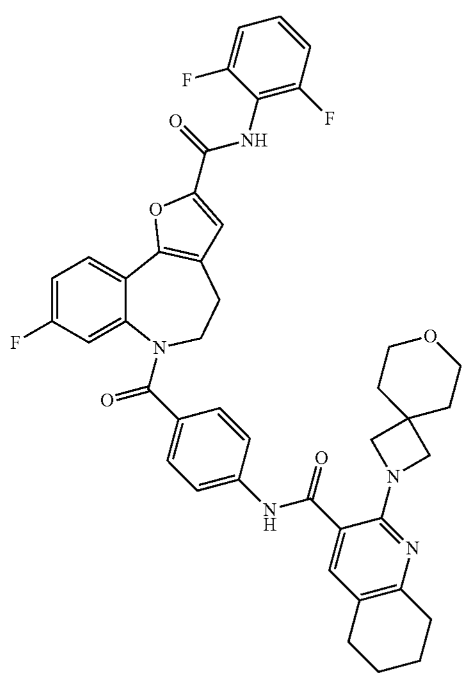 [SMILES: O=C(Nc1c(F)cccc1F)c1cc2c(o1)-c1ccc(F)cc1N(C(=O)c1ccc(NC(=O)c3cc4c(nc3N3CC5(CCOCC5)C3)CCCC4)cc1)CC2] | 762.4 |
| 242 | 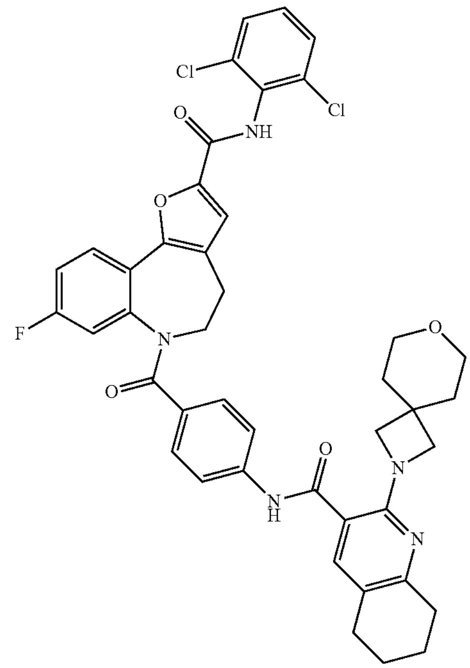 | 794.2 |

Example 243

Example 243

Step a

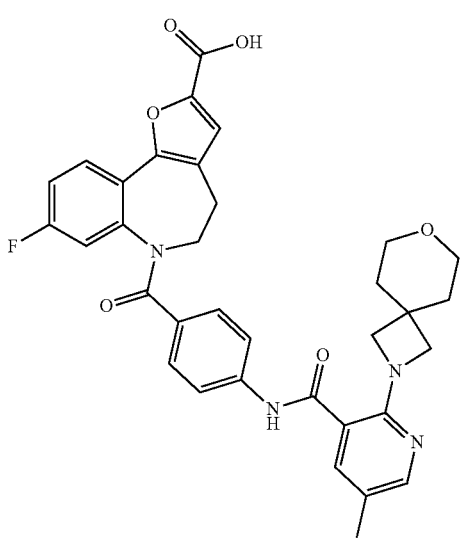

The title compound was prepared using a procedure similar to that used to prepare the compound in example 99 step h. ESI-MS m/z: 611.3 [M+H]$^+$.

Example 243

Step b

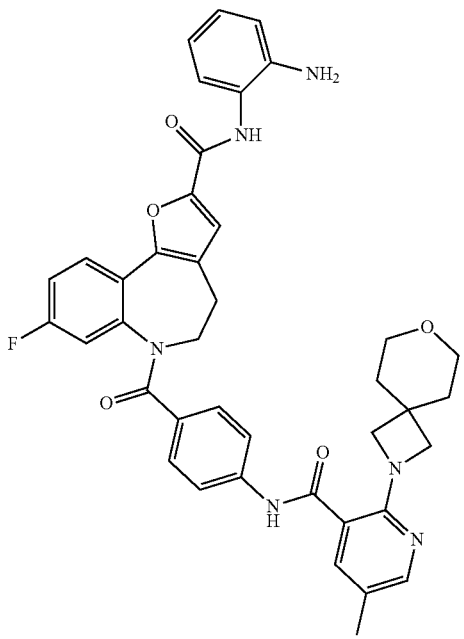 [SMILES: Cc1cnc(N2CC3(CCOCC3)C2)c(C(=O)Nc2ccc(C(=O)N3CCc4cc(C(=O)Nc5ccccc5N)oc4-c4ccc(F)cc43)cc2)c1]

A solution of the compound from step a (100 mg, 0.164 mmol), benzene-1,2-diamine (53 mg, 0.492 mmol), HATU (123 mg, 0.328 mmol) and TEA (0.5 mL) in DMF (1 mL) was stirred for 1 h. The solution was purified by reverse phase C18 column chromatography (MeCN/H$_2$O) to give the desired compound (100 mg, 87%) as a yellow solid. ESI-MS m/z: 701.4 [M+H]$^+$.

Example 243

Step c

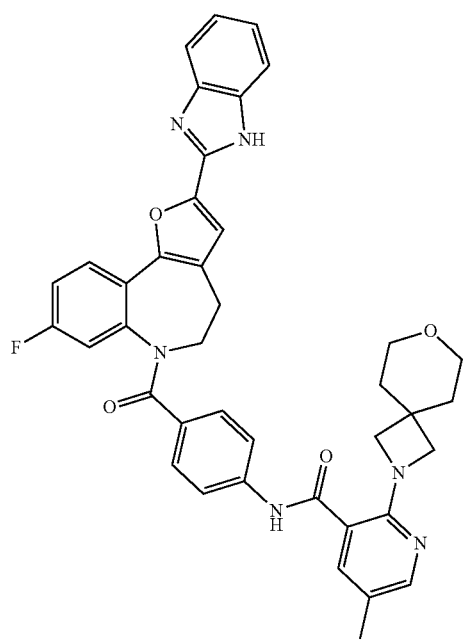 [SMILES: Cc1cnc(N2CC3(CCOCC3)C2)c(C(=O)Nc2ccc(C(=O)N3CCc4cc(-c5nc6ccccc6[nH]5)oc4-c4ccc(F)cc43)cc2)c1]

A solution of the compound from step b (100 mg, 0.14 mmol) in HOAc (3 mL) was stirred at 90° C. for 1 h. The solution was evaporated and adjusted PH=8 with saturated NaHCO$_3$ (a.q.), extracted with EtOAc (20 mL×3), the organic layer was concentrated. The crude product was purified by Prep-HPLC (MeCN/H$_2$O/0.1% FA) to give the title compound as a white solid (40.2 mg, 41.2%). ESI-MS m/z: 683.1 [M+H]$^+$.

Example 244
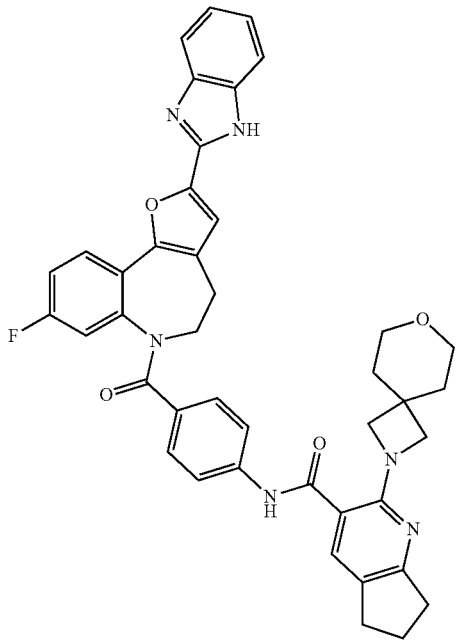 [SMILES: O=C(Nc1ccc(C(=O)N2CCc3cc(-c4nc5ccccc5[nH]4)oc3-c3ccc(F)cc32)cc1)c1cc2c(nc1N1CC3(CCOCC3)C1)CCC2]
The title compound was prepared using a procedure similar to that used to prepare the compound in example 243. ESI-MS m/z: 709.3 [M+H]+.
Example 245
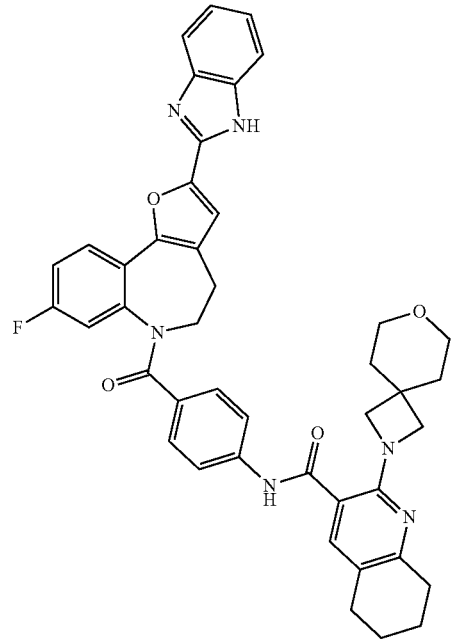 [SMILES: O=C(Nc1ccc(C(=O)N2CCc3cc(-c4nc5ccccc5[nH]4)oc3-c3ccc(F)cc32)cc1)c1cc2c(nc1N1CC3(CCOCC3)C1)CCCC2]
The title compound was prepared using a procedure similar to that used to prepare the compound in example 243. ESI-MS m/z: 723.3 [M+H]+.
Scheme 14
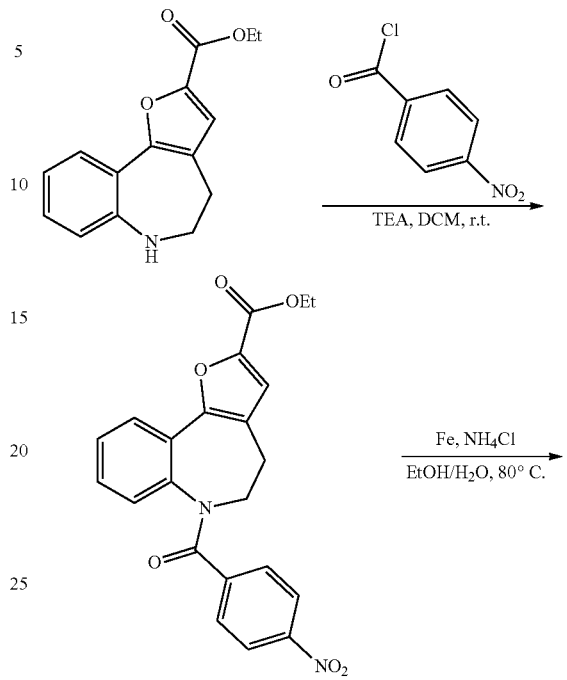
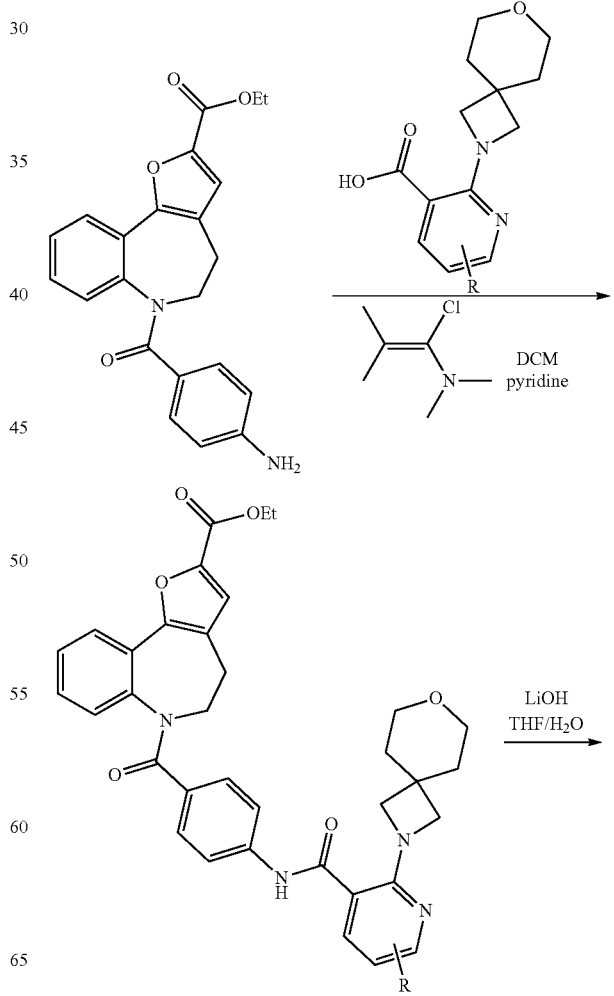

313
-continued

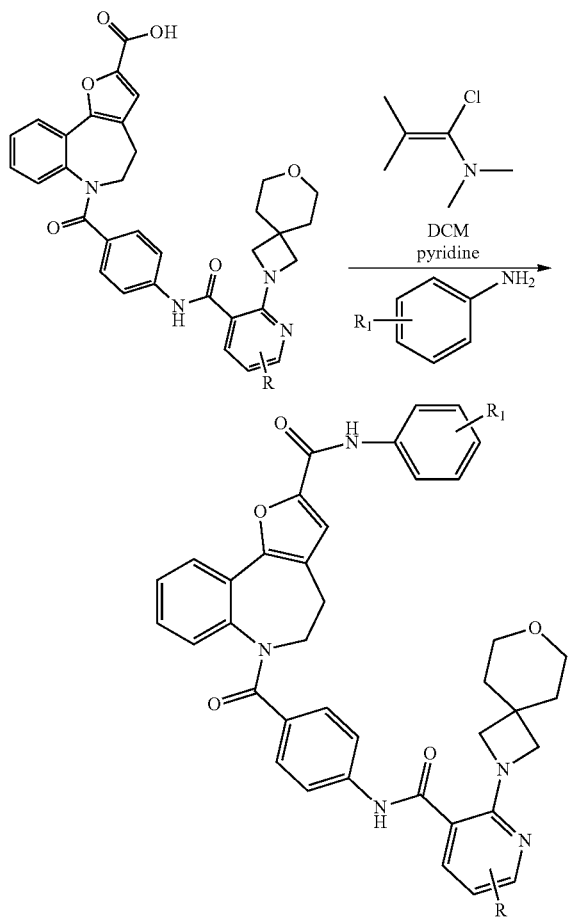

Example 246

314
Example 246

Step a

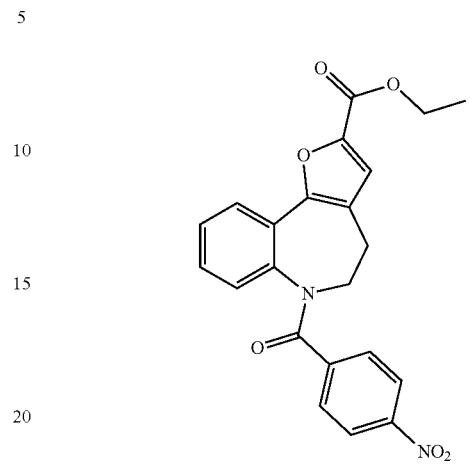

To a round-bottom flask (50 mL) were added the compound ethyl 6-(4-nitrobenzoyl)-5,6-dihydro-4H-benzo[b]furo[2,3-d]azepine-2-carboxylate (1.0 g, 3.89 mmol) which was prepared using the similar method to that of intermediate 1, $Et_3N$ (2.1 g, 20.59 mmol), 4-nitrobenzoyl chloride (0.79 g, 4.28 mmol) and DCM (25 mL) at room temperature. The resulting mixture was stirred for 10 hrs at room temperature. After removed most of solvent, the residue was purified by silica gel column chromatography eluting with 0-40% EtOAc/hexanes to obtain the desired product (1.15 g, 72.8%) as a pale yellowish solid which was used directly for the next step.

Example 246

Step b

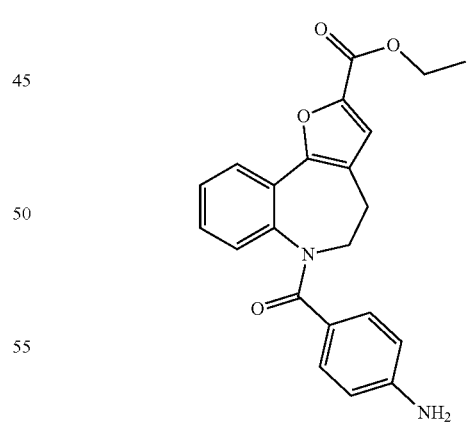

To a 250 mL round-bottom flask were added the compound from step a (1.15 g, 2.83 mmol), EtOH (80 mL), Fe (0.79 g, 14.15 mmol) and $NH_4Cl$ (1.51 g, 28.30 mmol) in $H_2O$ (20 mL) solution at rt. The resulting mixture was stirred at 80° C. for 4 hrs. After filtered through the Celite, the filtrate was neutralized to pH ~8. The mixture was extracted with 10% MeOH/DCM (4×100 mL). The combined organic layer was dried, filtered and evaporated to obtain the desired crude product (1.0 g, 94%) as yellowish foam which was used directly for the next step. ESI-MS m/z: 377.13 [M+H]$^+$.

Example 246

Step c

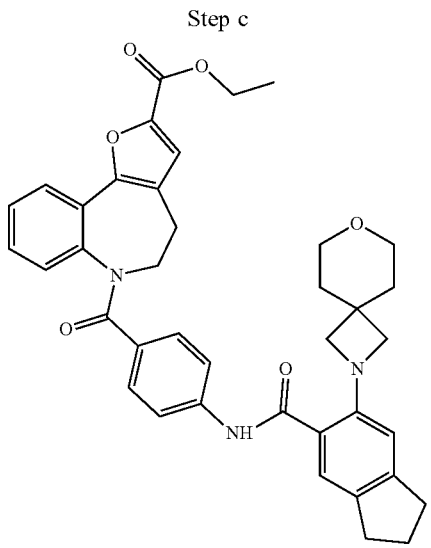

To a round-bottom flask (100 mL) were added 6-(7-oxa-2-azaspiro[3.5]nonan-2-yl)-2,3-dihydro-1H-indene-5-carboxylic acid (383 mg, 1.33 mmol), DCM (20 mL) and (1-chloro-2-methylprop-1-en-1-yl)dimethylamine (355 mg, 2.66 mmol) at room temperature. The resulting mixture was stirred for 1 h at room temperature under N$_2$ atmosphere. The resulting mixture was concentrated under vacuum. After dried for 2 hrs, the residue was dissolved in DCM (25 mL) and then the compound from step b (500 mg, 1.33 mmol) and pyridine (0.5 mL) were added. The resulting mixture was stirred for 12 hrs at room temperature and then concentrated under vacuum. The residue was purified by silica gel column chromatography eluting with 0-4% MeOH/DCM to afford the desired product (630 mg, 73.3%) as white foam. ESI-MS m/z: 647.30 [M+H]$^+$.

Example 246

Step d

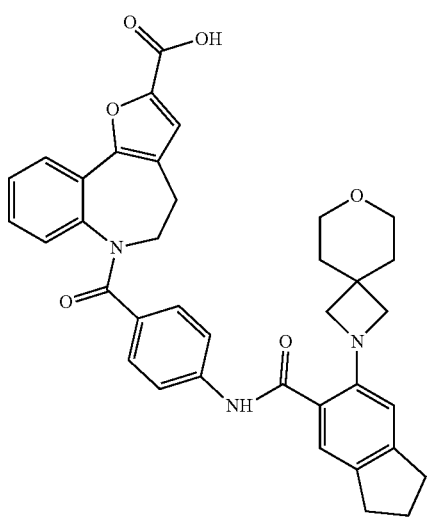 [SMILES: O=C(O)c1cc2c(o1)-c1ccccc1N(C(=O)c1ccc(NC(=O)c3cc4c(cc3N3CC5(CCOCC5)C3)CCC4)cc1)CC2]

To a solution of compound from step c (630 mg, 0.974 mmol) in MeOH/THF (20 mL, 1:1) was added LiOH (233 mg, 9.74 mmol) in water (0.5 mL). The resulting mixture was stirred at 50° C. for 2 hrs. The mixture was adjusted to pH ~5 with 1N HCl. The white precipitated solid was filtered and dried in oven to obtain the desired product (600 mg, 100%) as a white solid. ESI-MS m/z: 619.20 [M+H]$^+$.

Example 246

Step e

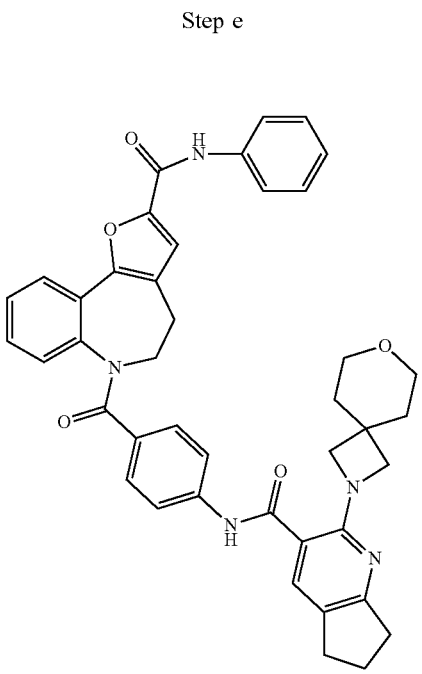

To a solution of compound from step d (80 mg, 0.129 mmol) in DCM (10 mL), 1-chloro-N,N, 2-trimethylprop-1-en-1-amine (34.6 mg, 0.259 mmol) was added. The reaction mixture was stirred at rt for 1 h and was then concentrated in vacuo. The resulting residue was taken into DCM (6 mL) and a solution of aniline (48.2 mg, 0.517 mmol) in pyridine (0.5 mL) and DCM (2 mL) was added. After stirred at rt for 16 hrs, the mixture was partitioned between DCM (50 mL) and brine (20 mL). The organic layer was dried, filtered, evaporated, and purified by silica gel column chromatography eluting with 0-4% DCM/MeOH to obtain the desired product (41 mg, 45.7%) as white foam. ESI-MS m/z: 694.32 [M+H]$^+$.

Examples 247-260 shown in table 20 were prepared using the procedure similar to that of example 243 and 246 from the corresponding intermediates.

TABLE 20

| Example | Structure | ESI-MS m/z: [M + H]+ |
|---|---|---|
| 247 | 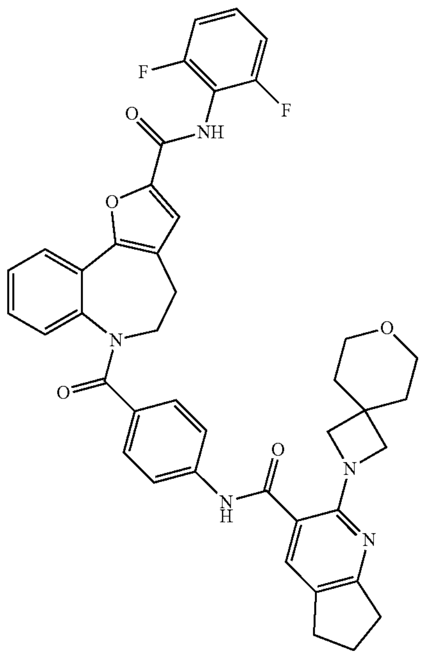 | 730.3 |
| 248 | 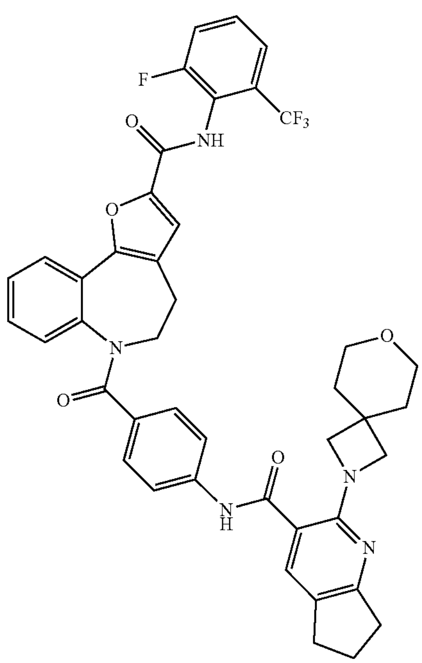 | 780.3 |

TABLE 20-continued

| Example | Structure | ESI-MS m/z: [M + H]+ |
|---|---|---|
| 249 | 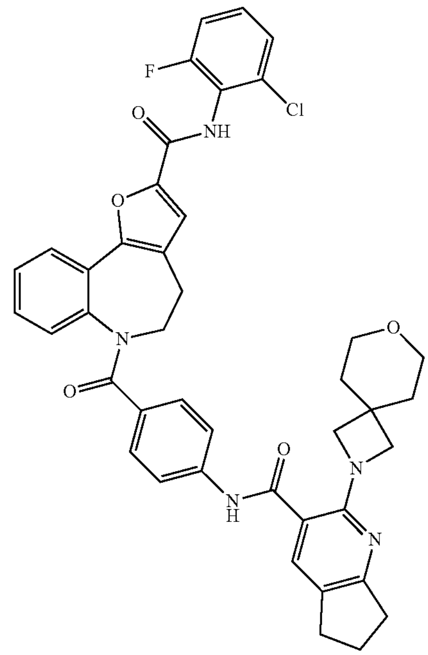 | 746.3 |
| 250 | 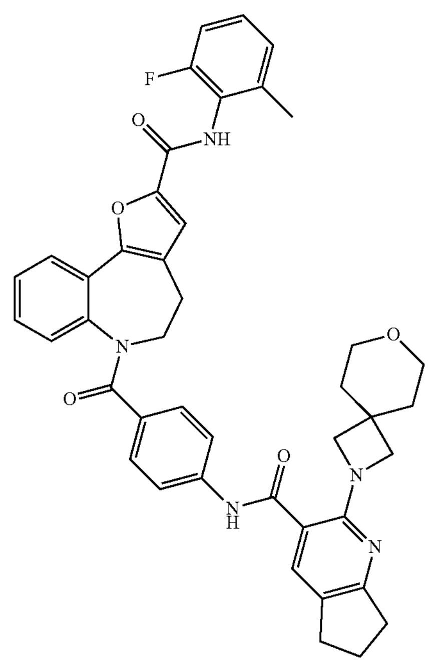 | 726.4 |

TABLE 20-continued
| Example | Structure | ESI-MS m/z: [M + H]+ |
|---|---|---|
| 251 | 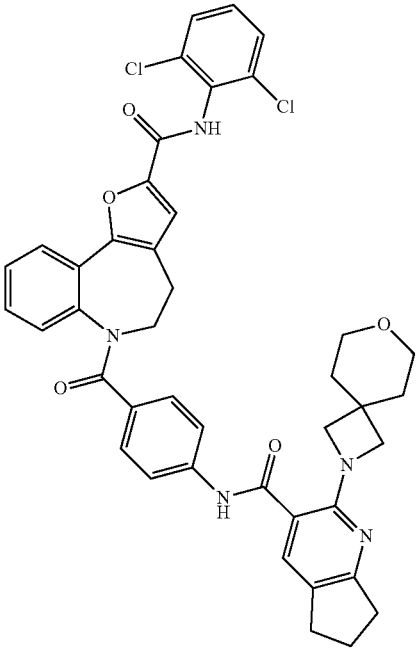 [SMILES: O=C(Nc1c(Cl)cccc1Cl)c1cc2c(o1)-c1ccccc1N(C(=O)c1ccc(NC(=O)c3cc4c(nc3N3CC5(CCOCC5)C3)CCC4)cc1)CC2] | 762.3 |
| 252 | 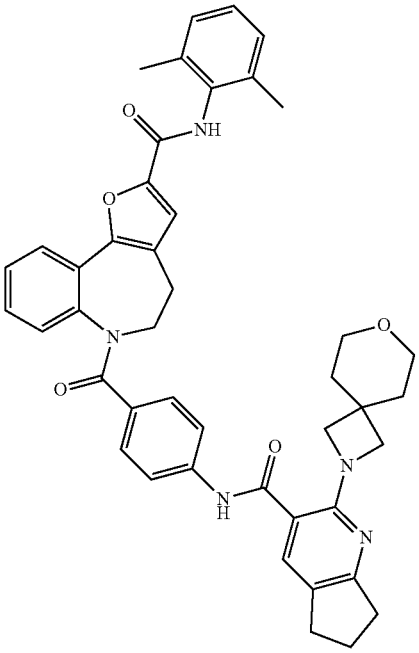 | 722.4 |
TABLE 20-continued
| Example | Structure | ESI-MS m/z: [M + H]+ |
|---|---|---|
| 253 | 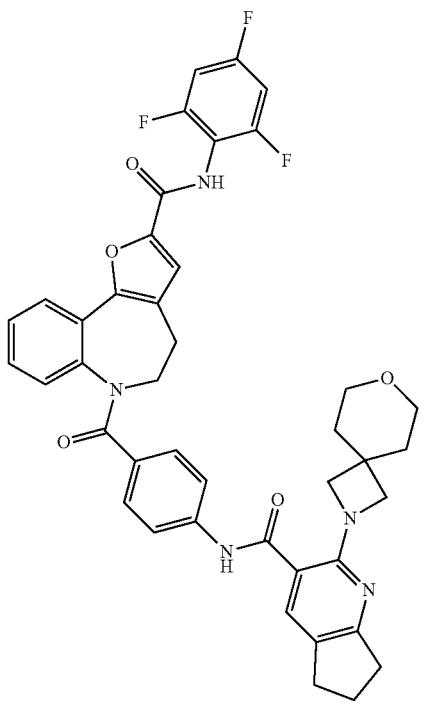 [SMILES: O=C(Nc1c(F)cc(F)cc1F)c1cc2c(o1)-c1ccccc1N(C(=O)c1ccc(NC(=O)c3cc4c(nc3N3CC5(CCOCC5)C3)CCC4)cc1)CC2] | 748.3 |
| 254 | 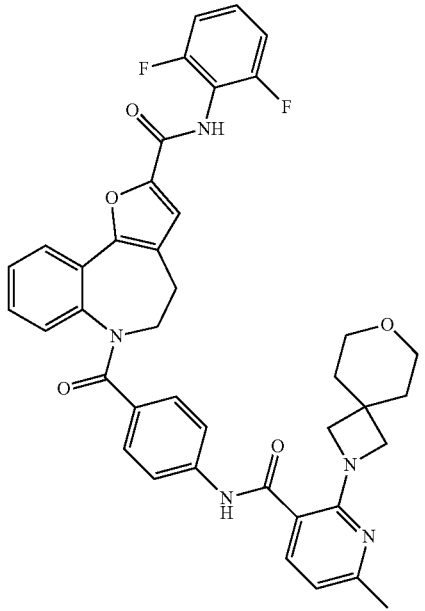 | 704.3 |

TABLE 20-continued

| Example | Structure | ESI-MS m/z: [M + H]+ |
|---|---|---|
| 255 | 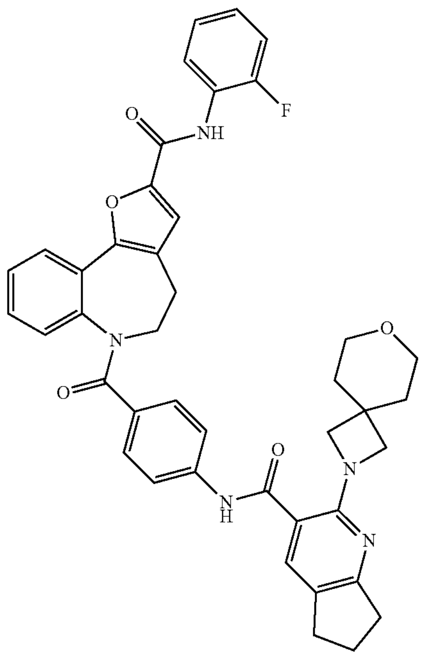 [SMILES: O=C(Nc1ccccc1F)c1cc2c(o1)-c1ccccc1N(C(=O)c1ccc(NC(=O)c3cc4c(nc3N3CC5(CCOCC5)C3)CCC4)cc1)CC2] | 712.3 |
| 256 | 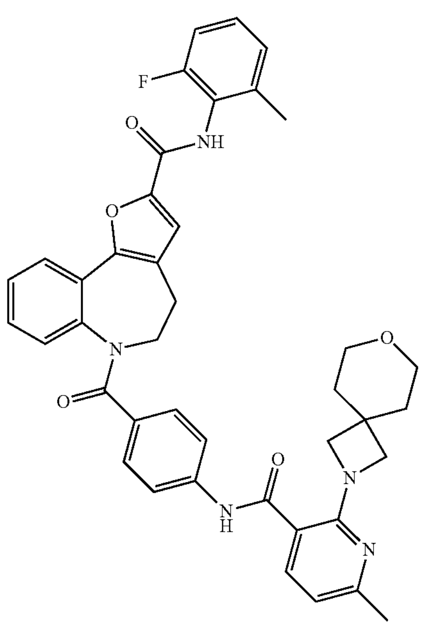 [SMILES: Cc1ccc(C(=O)Nc2ccc(C(=O)N3CCc4cc(C(=O)Nc5c(C)cccc5F)oc4-c4ccccc43)cc2)c(N2CC3(CCOCC3)C2)n1] | 700.3 |
| 257 | | 722.3 |
| 258 | | 686.3 |

TABLE 20-continued

| Example | Structure | ESI-MS m/z: [M + H]+ |
|---|---|---|
| 259 | 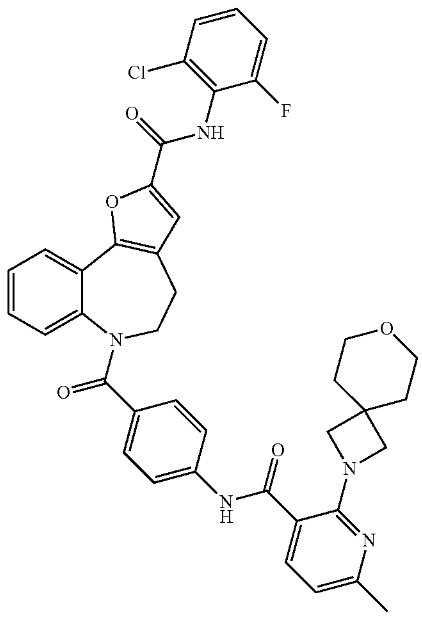 | 721.3 |
| 260 | 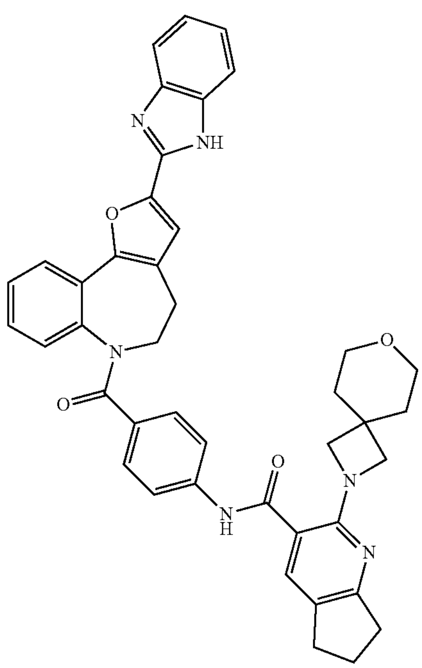 [SMILES: O=C(Nc1ccc(C(=O)N2CCc3cc(-c4nc5ccccc5[nH]4)oc3-c3ccccc32)cc1)c1cc2c(nc1N1CC3(CCOCC3)C1)CCC2] | 691.3 |

Example 261

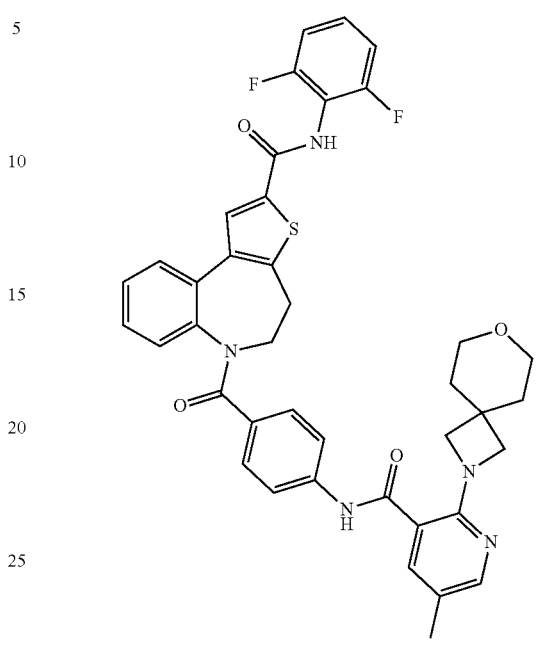

Example 261

Step a

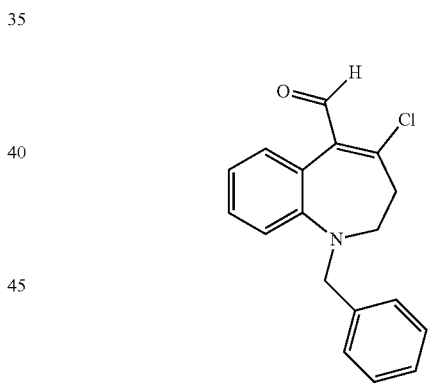

To DMF (3.08 mL) previously cooled to 0° C., POCl₃ (2.78 ml, 29.8 mmol) was added dropwise with continuous stirring and in an inert atmosphere, while maintaining the reaction temperature below 10° C. DCM (9.37 mL) was added and the resulting mixture was stirred at room temperature for 2 hrs. Then, a solution of 1-benzyl-1,2,3,5-tetrahydro-4H-benzo[b]azepin-4-one (5 g, 19.89 mmol) in DCM (45.0 mL) was added dropwise and the reaction mixture was stirred at room temperature for 24 hrs. Crushed ice was added and the mixture was stirred until ice had melted. Then, solid sodium acetate (3 g) was added and the mixture was stirred for additional 5 min. The organic phase was separated and the aqueous portion was extracted with dichloromethane (2×35 mL). The combined organic extracts were washed with sat. aq. sodium hydrogen carbonate and brine, dried (sodium sulfate), and solvent evaporated. The crude product was added to a silica gel column and was eluting with 0-50% EtOAc/hexanes to give the desired product (1.59 g, 26.8% yield) as a yellow oil. ESI-MS m/z: 297.6 [M+H]⁺.

Example 261

Step b

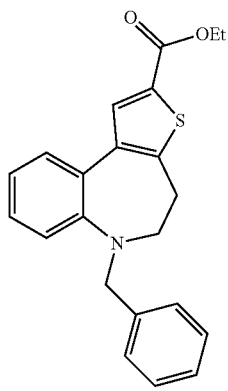 [SMILES: CCOC(=O)c1cc2c(s1)CCN(Cc1ccccc1)c1ccccc1-2]

To the solution of compound from step a (1.59 g, 5.34 mmol) in pyridine (13.35 mL), ethyl 2-mercaptoacetate (1.124 mL, 10.25 mmol) and triethylamine (4.47 mL, 32.0 mmol) were added. The reaction mixture was stirred at 70° C. overnight. Solvents were removed under reduced pressure and the residue was partitioned between water and ethyl acetate. The aqueous phase was extracted with ethyl acetate (2×25 mL). The organic layer was dried, filter and concentrated. The crude product was purified by silica gel column chromatography eluting with 0-50% EtOAc/hexanes to give the desired product (1.17 g, 60.3% yield) as a yellow solid.

Example 261

Step c

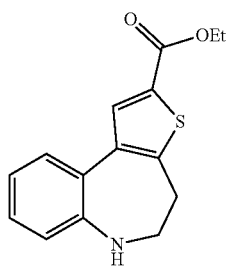 [SMILES: CCOC(=O)c1cc2c(s1)CCNc1ccccc1-2]

To a mixture of compound from step b (1.17 g, 3.22 mmol) in ethanol (27.6 mL) and DCM (4.60 mL) was added palladium on carbon (0.206 g, 1.931 mmol) and stirred under H₂ atmosphere at room temperature overnight. The reaction mixture was filtered over celite and washed with EtOAc. The resulting mixture was concentrated under vacuum. The crude product was purified by silica gel column chromatography eluting with 0-100% EtOAc/ hexanes to give the desired product (0.44 g, 50.0% yield) as a solid.

Example 261

Step d

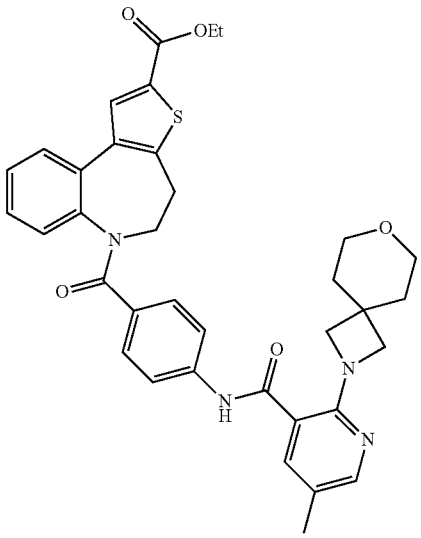 [SMILES: Cc1cnc(N2CC3(CCOCC3)C2)c(C(=O)Nc2ccc(C(=O)N3CCc4sc(C(=O)O)cc4-c4ccccc43)cc2)c1]

To a oven-dried vial, 4-(5-methyl-2-(7-oxa-2-azaspiro [3.5]nonan-2-yl)nicotinamido)benzoic acid (0.675 g, 1.771 mmol) was dissolved in DCM (8.0 mL). Then 1-chloro-N,N, 2-trimethylprop-1-en-1-amine (0.426 mL, 3.22 mmol) was added dropwise and stirred for 1 h at room temperature. The reaction mixture was concentrated and compound from step c (0.44 g, 1.610 mmol) and pyridine (6.51 ml, 80 mmol) were added. The reaction mixture was heated to 80° C. overnight. The reaction mixture was cooled to room temperature and concentrated on the rotovap. The crude product was purified by silica gel column chromatography eluting with 0-100% EtOAc/hexanes to give the desired product (271 mg, 26.4% yield) as a white solid. ESI-MS m/z: 637.0 [M+H]⁺.

Example 261

Step e

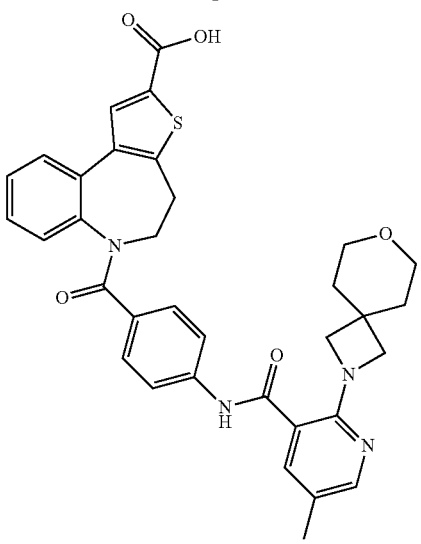

In a vial, compound form step d (271 mg, 0.426 mmol) was dissolved in THF (4.0 mL), MeOH (0.5 mL), and water (0.5 mL). LiOH (102 mg, 4.26 mmol) was added and the reaction was allowed to stir at rt overnight. Water and 4M HCl were added to adjust to pH=2-3. The aqueous layer was washed with DCM. The organic layer was dried over MgSO₄ and concentrated to give the desired product (251 mg, 97% yield) as a light yellow solid. ESI-MS m/z: 609.0 [M+H]⁺.

Example 261

Step f

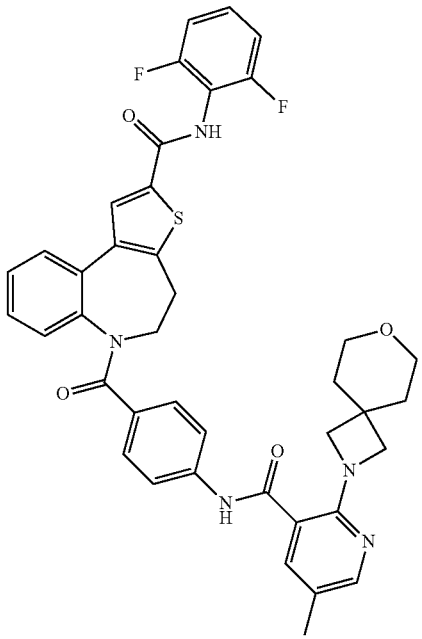 [SMILES: Cc1cnc(N2CC3(CCOCC3)C2)c(C(=O)Nc2ccc(C(=O)N3CCc4sc(C(=O)Nc5c(F)cccc5F)cc4-c4ccccc43)cc2)c1]

To a oven-dried vial, compound from step e (40 mg, 0.066 mmol) in DCM (0.5 mL) was added 1-chloro-N,N, 2-trimethylprop-1-en-1-amine (130 µl, 0.131 mmol) dropwise and the reaction mixture was stirred for 2 hrs and concentrated. To the residue, 2,6-difluoroaniline (219 µl, 0.263 mmol), DCM (329 µl) and pyridine (269 µl, 0.263 mmol) were added. The reaction mixture was stirred at room temperature overnight at which the solvent was concentrated. The crude product was purified by silica gel column chromatography eluting with 0-10% MeOH/DCM to give the desired product (42 mg, 89% yield) as a white solid. ESI-MS m/z: 720.0 [M+H]⁺.

Example 262

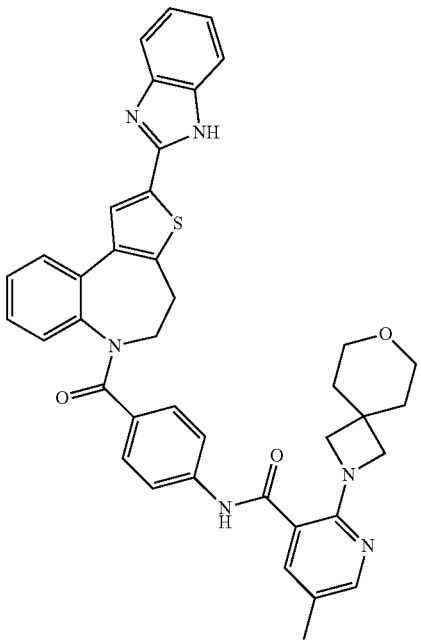 [SMILES: Cc1cnc(N2CC3(CCOCC3)C2)c(C(=O)Nc2ccc(C(=O)N3CCc4sc(-c5nc6ccccc6[nH]5)cc4-c4ccccc43)cc2)c1]

Example 262

Step a

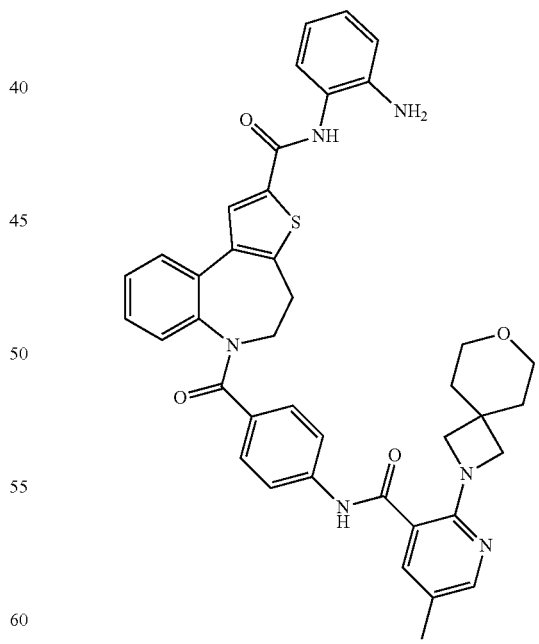

To a solution of compound from Example 252 step e (40 mg, 0.066 mmol), EDC (15.12 mg, 0.079 mmol), and HOBt (12.08 mg, 0.079 mmol) in DMF (0.5 mL) was added benzene-1,2-diamine (10.66 mg, 0.099 mmol), and the mixture was stirred at room temperature for 24 hrs. The reaction mixture was poured into water and extracted with EtOAc. The organic layer was separated, washed with saturated NaHCO$_3$ and brine, and dried over Na$_2$SO$_4$. Filtration, concentration in vacuo, and purification of the residue by silica gel flash column chromatography eluting with 10-100% EtOAc/hexanes to obtain the desired product (31 mg, 67.5% yield). ESI-MS m/z: 699.0 [M+H]$^+$.

Example 262

Step b

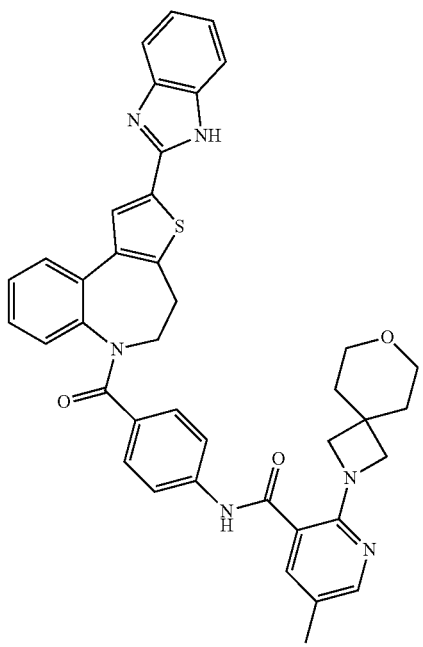 [SMILES: Cc1cnc(N2CC3(CCOCC3)C2)c(C(=O)Nc2ccc(C(=O)N3CCc4sc(-c5nc6ccccc6[nH]5)cc4-c4ccccc43)cc2)c1]

In a vial, compound from step a (31 mg, 0.044 mmol) was dissolved in acetic acid (1.2 mL). The vial was sealed and heated to 100° C. for 2 hrs. The vial was cooled to room temperature and concentrated. Saturated aq. NaHCO$_3$ and DCM were added. The aqueous layer was extracted with DCM. Combined organic layer was dried over MgSO$_4$ and concentrated. The was purified by silica gel column chromatography eluting with 0-10% MeOH/DCM to give the desired product (19 mg, 62.9% yield) as a pale yellow solid. ESI-MS m/z: 681.0 [M+H]$^+$.

Example 263-266 shown in table 21 were prepared using the procedure similar to that of example 261 and 262 from the corresponding intermediates.

TABLE 21

| Example | Structure | ESI-MS m/z: [M + H]$^+$ |
|---|---|---|
| 263 | 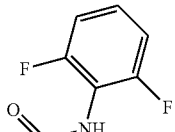 | 746.0 |
| 264 | 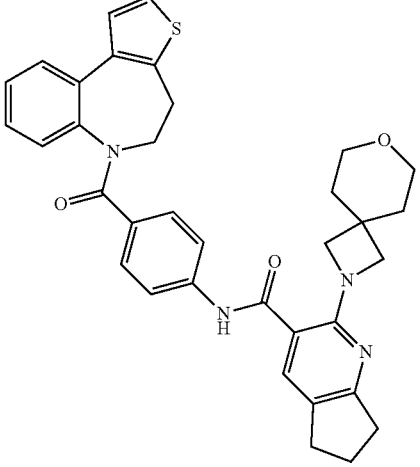 | 707.0 |

TABLE 21-continued
| Example | Structure | ESI-MS m/z: [M + H]+ |
|---|---|---|
| 265 | 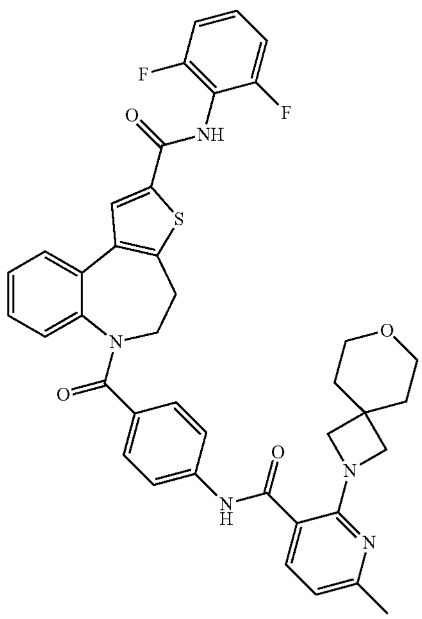 [SMILES: Cc1ccc(C(=O)Nc2ccc(C(=O)N3CCc4sc(C(=O)Nc5c(F)cccc5F)cc4-c4ccccc43)cc2)c(N2CC3(CCOCC3)C2)n1] | 720.0 |
| 266 | 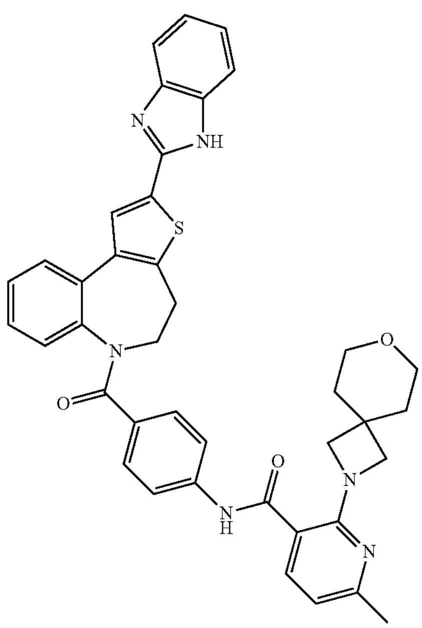 [SMILES: Cc1ccc(C(=O)Nc2ccc(C(=O)N3CCc4sc(-c5nc6ccccc6[nH]5)cc4-c4ccccc43)cc2)c(N2CC3(CCOCC3)C2)n1] | 681.0 |
Scheme 15
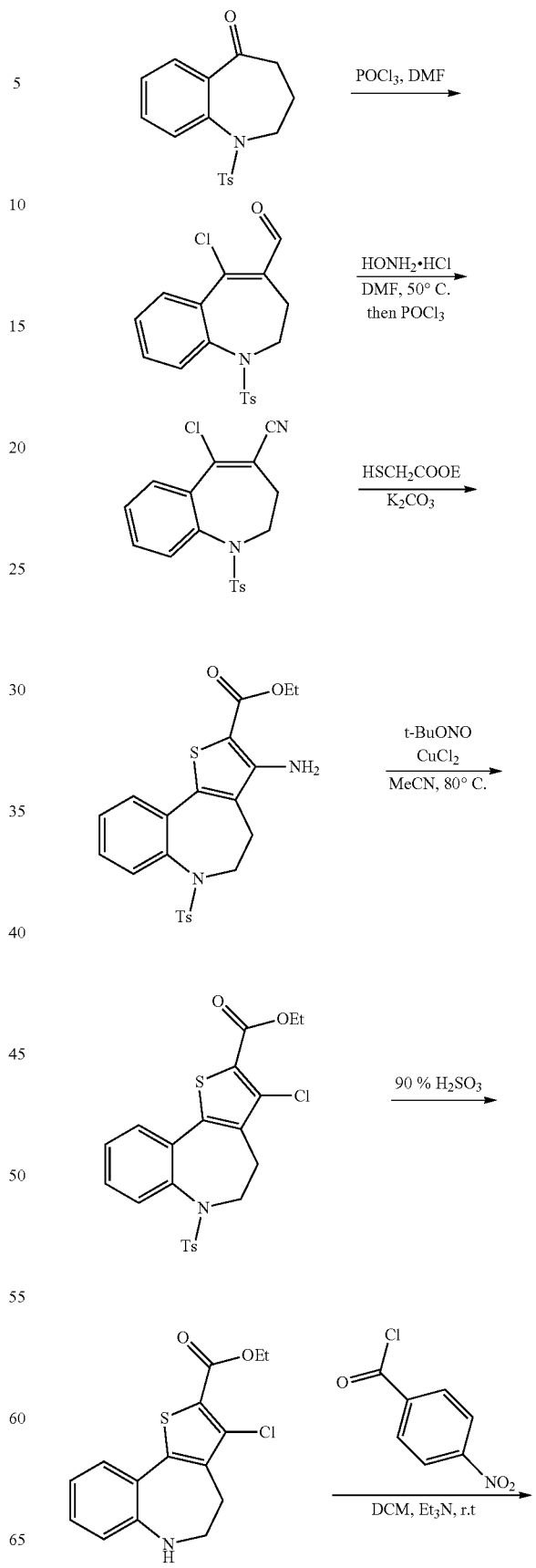

333
-continued
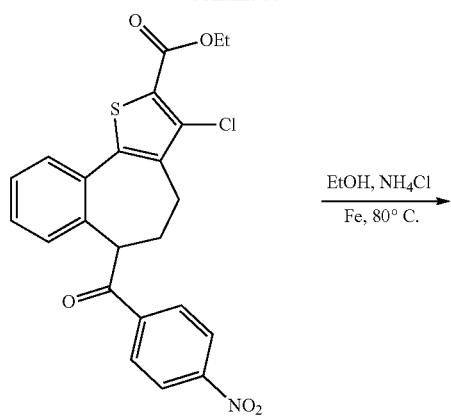
EtOH, NH₄Cl
Fe, 80° C.
334
-continued
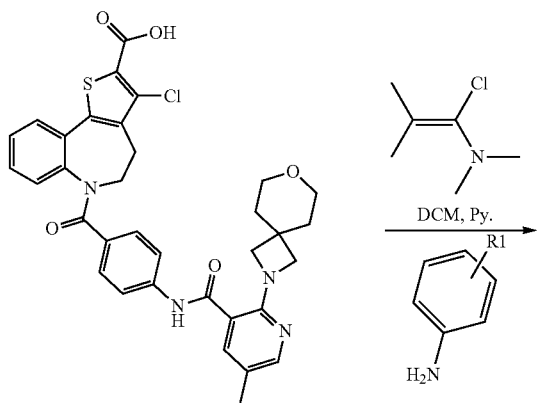
DCM, Py.
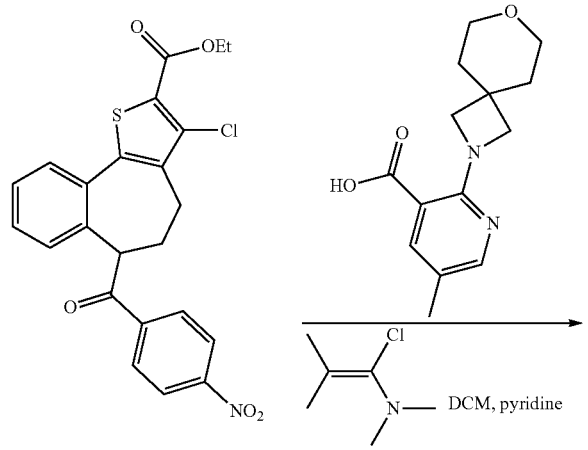
DCM, pyridine
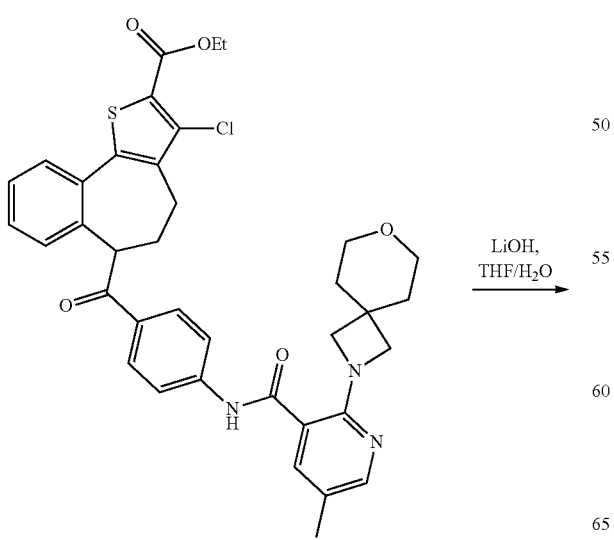
LiOH,
THF/H₂O
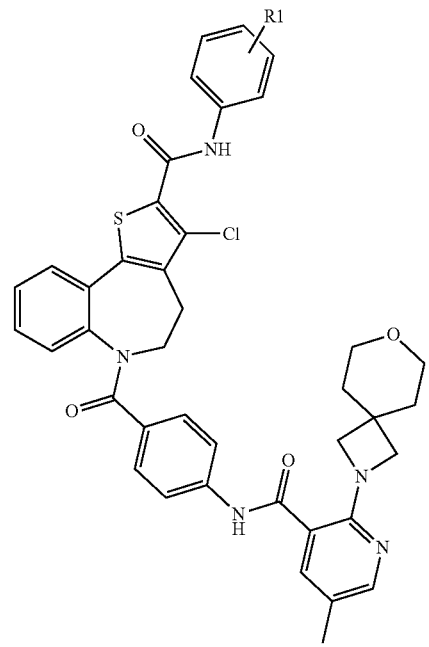

Example 267

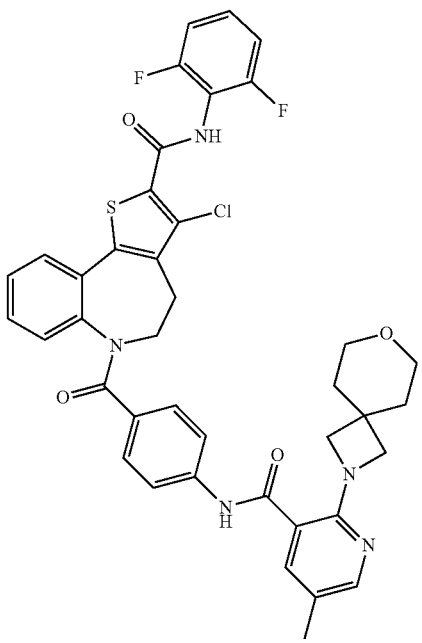 [SMILES: Cc1cnc(N2CC3(CCOCC3)C2)c(C(=O)Nc2ccc(C(=O)N3CCc4c(sc(C(=O)Nc5c(F)cccc5F)c4Cl)-c4ccccc43)cc2)c1]

Example 267

Step a

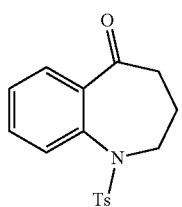 [SMILES: Cc1ccc(S(=O)(=O)N2CCCC(=O)c3ccccc32)cc1]

To a stirring solution of 2,3,4,5-tetrahydro-1H-1-benzazepin-5-one (50 g, 310.17 mmol) in DCM (250 mL) was added pyridine (175 mL). The mixture was cooled with ice bath and TsCl (84.0 g, 440.76 mmol) was added. The mixture was warmed to room temperature and stirred 2 hrs. Water (750 mL) was added and the mixture was extracted with DCM (4×300 mL). The combined organic phase was washed with brine, dried and concentrated under reduced pressure. The residue was washed with mixed solvent (PE:EA=50:1) to give the desired compound (95.7 g, 97.8%) as an off-white solid. ESI-MS m/z: 333.15 [M+NH$_4$]$^+$.

Example 267

Step b

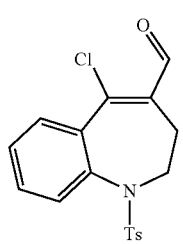 [SMILES: Cc1ccc(S(=O)(=O)N2CCC(C=O)=C(Cl)c3ccccc32)cc1]

POCl$_3$ (66.0 mL, 430.67 mmol) was added dropwise to DMF (250 mL) at 0° C. under N$_2$. Then a solution of the compound from step a (76 g, 240.97 mmol) in DMF (100 mL) was added. The mixture was then warmed to room temperature and heated to 80° C. for 3 hrs. The mixture was poured into ice cooled sat. aq. AcONa (1 L) and extracted with EA. The combined organic phase was washed with water, brine, dried over anhydrous Na$_2$SO$_4$ and concentrated under reduced pressure. The residue was washed with mixed solvent (PE:EA=30:1) to afford the desired product (75 g, 86.0%) as a yellow solid. ESI-MS m/z: 361.95 [M+H]$^+$.

Example 267

Step c

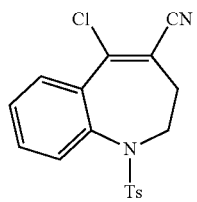 [SMILES: Cc1ccc(S(=O)(=O)N2CCC(C#N)=C(Cl)c3ccccc32)cc1]

A solution of the compound from step b (13.0 g, 35.93 mmol) in DMF (100 mL) and NH$_2$OH.HCl (12.5 g, 179.88 mmol) was added slowly. The resulting mixture was stirred for 4 hrs at 50° C. under N$_2$. After cooled to room temperature, POCl$_3$ (15 mL, 160.93 mmol) was added and then heated to 50° C. The reaction was quenched with sat. aq. NaOAc (400 mL) at 0° C. After extracted with EtOAc (4×300 mL), the organic layer was separated, dried and concentrated under vacuum. The residue was purified by silica gel column chromatography eluting with PE/EtOAc (7:3) to give the desired compound (11.7 g, 90.8%) as an off-white solid. ESI-MS m/z: 376.10 [M+NH$_4$]$^+$.

Example 267

Step d

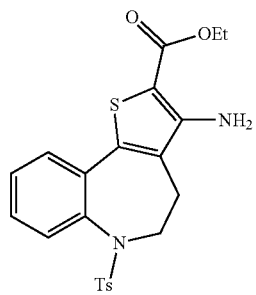 [SMILES: CCOC(=O)c1sc2c(c1N)CCN(S(=O)(=O)c1ccc(C)cc1)c1ccccc1-2]

To a stirred solution of the compound from step c (11.2 g, 31.21 mmol) and K$_2$CO$_3$ (4.3 g, 31.21 mmol) in EtOH/THF (160 mL, 7:1) were added ethyl 2-sulfanylacetate (5.6 g, 46.82 mmol) dropwise at 0° C. The resulting mixture was stirred for 12 hrs at 80° C. under N$_2$. Water (400 mL) was added and the mixture was extracted with EtOAc. The organic layer was separated, dried and concentrated. The residue was washed with a mixed solvent (PE:EA=25:1) to give the desired product (13.59 g, 98.4%) as a yellow solid. ESI-MS m/z: 443.10 [M+H]$^+$.

Example 267

Step e

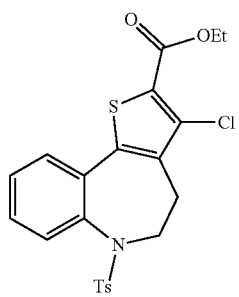 [SMILES: CCOC(=O)c1sc2c(c1Cl)CCN(S(=O)(=O)c1ccc(C)cc1)c1ccccc1-2]

The compound from step d (5 g, 11.30 mmol) in MeCN (110 mL) was dropwised to the solution of t-BuNO$_2$ (4.66 g, 45.19 mmol) and CuCl$_2$ (6.08 g, 45.19 mmol) in MeCN (40 mL) at 0-5° C. The solution was stirred for 20 min at the same temperature and 2 hrs at 80° C. The mixture was diluted with water (100 mL), and then extracted with EtOAc. The combined organic layers were dried, concentrated and purified by silica gel column with PE/EtOAc (5:1) to afford the desired compound (4.239 g, 81.21%) as yellow solid. ESI-MS m/z: 462.10 [M+H]$^+$.

Example 267

Step f

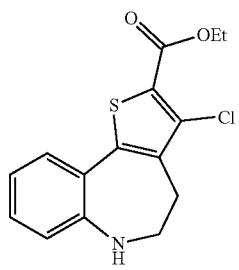 [SMILES: CCOC(=O)c1sc2c(c1Cl)CCNc1ccccc1-2]

A solution of the compound from step e (4.239 g, 9.18 mmol) and 90% H$_2$SO$_4$ (15 mL) was stirred for 4 hrs at 50° C. and then cooled down to room temperature. The mixture was acidified to pH=4 with sat. aq. NaHCO$_3$, extracted with EtOAc. The combined organic layers were dried and concentrated to give the crude compound (2.624 g, 92.91%) as brown solid. ESI-MS m/z: 308.05 [M+H]+.

Example 267

Step g

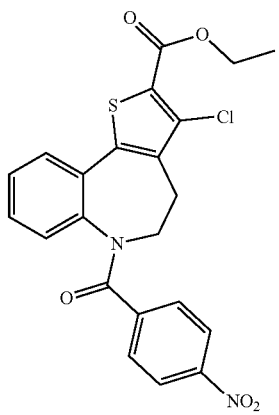 [SMILES: CCOC(=O)c1sc2c(c1Cl)CCN(C(=O)c1ccc([N+](=O)[O-])cc1)c1ccccc1-2]

A solution of the compound from step f (2.624 g, 8.53 mmol), 4-nitrobenzoyl chloride (4.746 g, 25.58 mmol) and Et$_3$N (3 mL) in DCM (20 ml) was stirred for 12 hrs at rt. The mixture was concentrated and diluted with water (100 mL), extracted with EtOAc (×3), washed with brine, dried and concentrated to give the crude desired compound (2.517 g, 64.62%) as a brown solid. ESI-MS m/z: 457.10 [M+H]$^+$.

Example 267

Step h

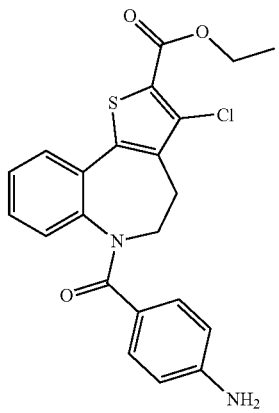 [SMILES: CCOC(=O)c1sc2c(c1Cl)CCN(C(=O)c1ccc(N)cc1)c1ccccc1-2]

A mixture of the compound from step g (2.517 g, 5.51 mmol), Fe (3.085 g, 55.24 mmol) and sat. aq. NH$_4$Cl (15 mL) in EtOH (15 mL) was stirred at 80° C. for 2 hrs. The resulting mixture was filtered, the filter cake was washed with EtOH. The filtrate was concentrated and diluted the mixture with water, extracted with EtOAc, washed with brine, dried over concentrated and purified by silica gel column chromatography eluting with PE/EtOAc (2:1) to afford the desired compound (2.15 g, 91.42%) as a yellow solid. ESI-MS m/z: 427.00 [M+H]$^+$.

Example 267

Step i

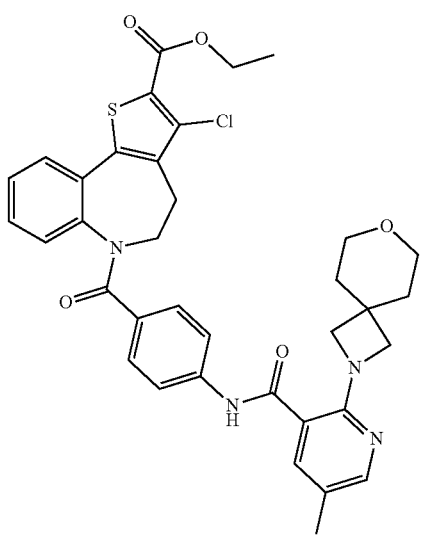 [SMILES: CCOC(=O)c1sc2c(c1Cl)CCN(C(=O)c1ccc(NC(=O)c3cc(C)cnc3N3CC4(CCOCC4)C3)cc1)c1ccccc1-2]

A solution of 5-methyl-2-(7-oxa-2-azaspiro[3.5]nonan-2-yl)nicotinic acid (1.59 g, 6.04 mmol) and (1-chloro-2-methylprop-1-en-1-yl)dimethylamine (1.35 g, 10.07 mmol) in DCM (10 mL) was stirred for 1 h under $N_2$. After evaporated, the residue was dissolved in DCM (10 mL), and then the compound from step h (2.15 g, 5.04 mmol) and pyridine (1 mL) in DCM (10 mL) were added dropwise. The resulting mixture was stirred for additional 1 h. The resulting mixture was concentrated and purified by reverse phase column chromatography (MeCN/$H_2O$) to give the desired compound (2.7 g, 79.88%) as a yellow solid. ESI-MS m/z: 671.15[M+H]$^+$.

Example 267

Step j

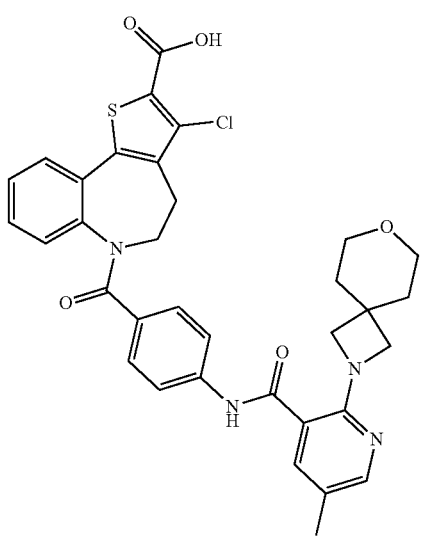 [SMILES: Cc1cnc(N2CC3(CCOCC3)C2)c(C(=O)Nc2ccc(C(=O)N3CCc4c(sc(C(=O)O)c4Cl)-c4ccccc43)cc2)c1]

A solution of the compound from step i (2.7 g, 4.02 mmol) and LiOH (963.3 mg, 40.23 mmol), THF/$H_2O$ (10 mL, 1:1) was stirred overnight. The resulting mixture was concentrated and acidified to pH=2 with 1 M HCl. The precipitated solids were collected by filtration and washed with water to afford the desired compound (2.58 g, 100%) as a white solid. ESI-MS m/z: 643.20 [M+H]+.

Example 267

Step k

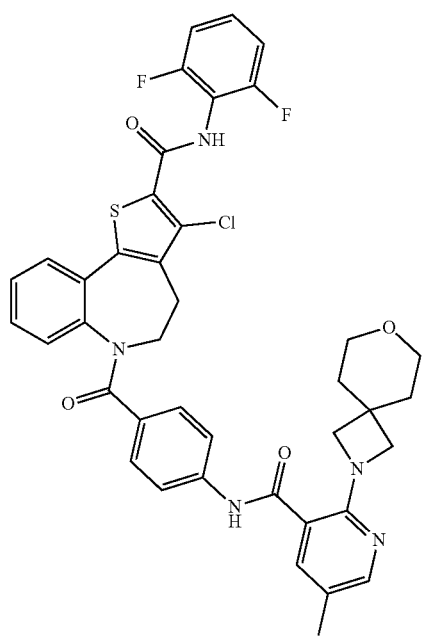 [SMILES: Cc1cnc(N2CC3(CCOCC3)C2)c(C(=O)Nc2ccc(C(=O)N3CCc4c(sc(C(=O)Nc5c(F)cccc5F)c4Cl)-c4ccccc43)cc2)c1]

A solution of the compound from step j (90 mg, 0.14 mmol) and (1-chloro-2-methylprop-1-en-1-yl)-dimethylamine (37.4 mg, 0.28 mmol) in DCM (5 mL) was stirred for 1 h under $N_2$. To the above mixture was added 2,6-difluoroaniline (54.2 mg, 0.42 mmol), pyridine (0.1 mL) in DCM (1 mL) dropwise. The resulting mixture was stirred for additional 1 h. The resulting mixture was concentrated, purified by Prep-TLC (DCM/MeOH 10:1) and Prep-HPLC (MeCN/$H_2O$/0.1% TFA) to afford the desired compound (46.0 mg, 26%) as a white solid. ESI-MS m/z: 754.20 [M+H]$^+$.

Example 268-271 shown in table 22 were prepared using the procedure similar to that of example 267 from the corresponding intermediates.

TABLE 22

| Example | Structure | ESI-MS m/z: [M + H]+ |
|---|---|---|
| 268 | 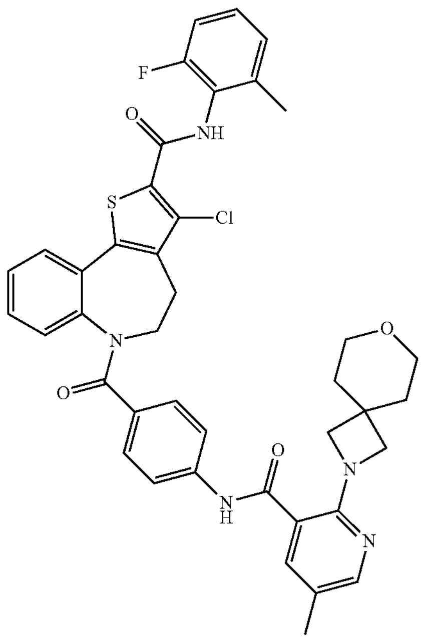 [SMILES: Cc1cnc(N2CC3(CCOCC3)C2)c(C(=O)Nc2ccc(C(=O)N3CCc4c(sc(C(=O)Nc5c(C)cccc5F)c4Cl)-c4ccccc43)cc2)c1] | 750.2 |
| 269 | 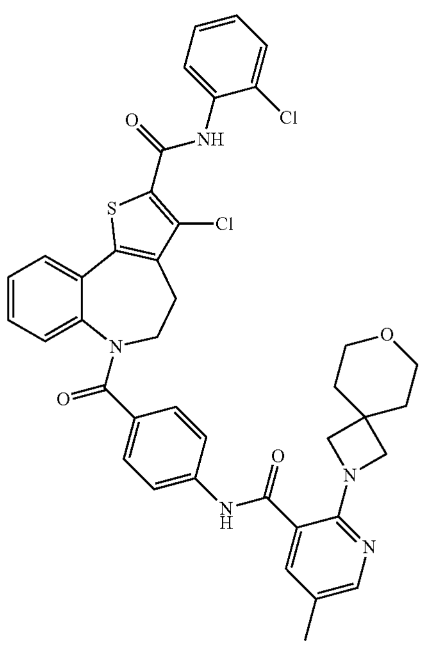 [SMILES: Cc1cnc(N2CC3(CCOCC3)C2)c(C(=O)Nc2ccc(C(=O)N3CCc4c(sc(C(=O)Nc5ccccc5Cl)c4Cl)-c4ccccc43)cc2)c1] | 752.3 |

TABLE 22-continued

| Example | Structure | ESI-MS m/z: [M + H]+ |
|---|---|---|
| 270 | 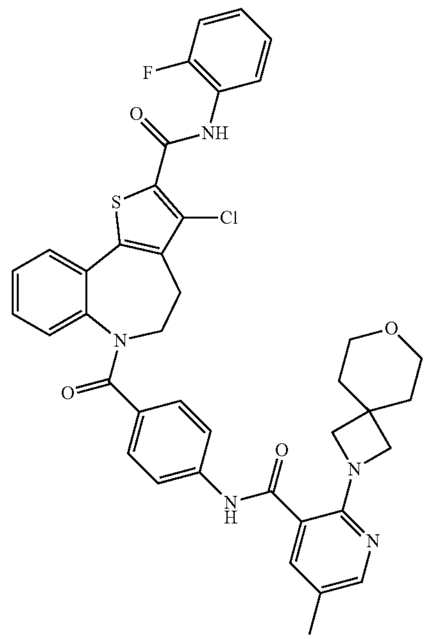 [SMILES: Cc1cnc(N2CC3(CCOCC3)C2)c(C(=O)Nc2ccc(C(=O)N3CCc4c(sc(C(=O)Nc5ccccc5F)c4Cl)-c4ccccc43)cc2)c1] | 736.2 |
| 271 | 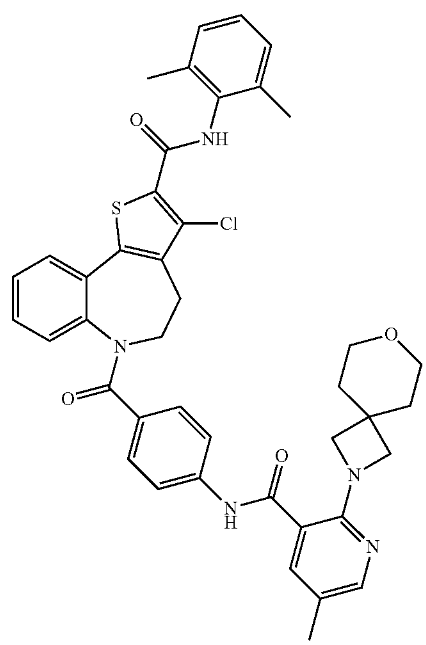 [SMILES: Cc1cnc(N2CC3(CCOCC3)C2)c(C(=O)Nc2ccc(C(=O)N3CCc4c(sc(C(=O)Nc5c(C)cccc5C)c4Cl)-c4ccccc43)cc2)c1] | 746.2 |

Example 272

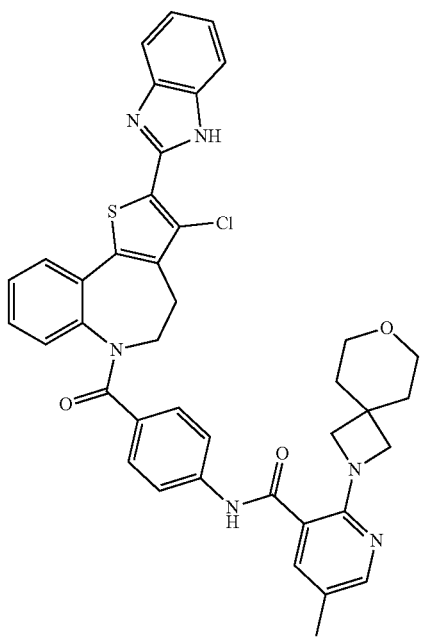 [SMILES: Cc1cnc(N2CC3(CCOCC3)C2)c(C(=O)Nc2ccc(C(=O)N3CCc4c(sc(-c5nc6ccccc6[nH]5)c4Cl)-c4ccccc43)cc2)c1]

Example 272

Step a

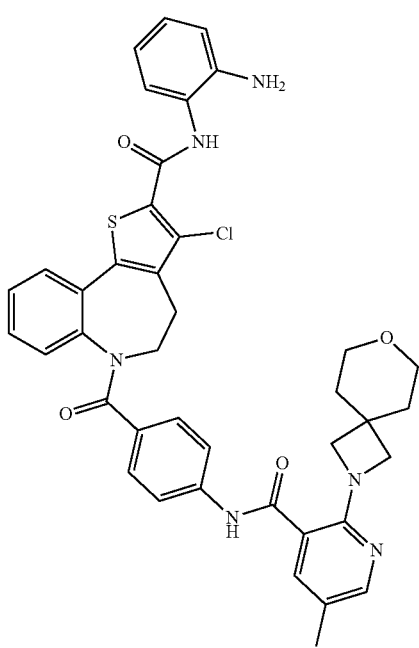 [SMILES: Cc1cnc(N2CC3(CCOCC3)C2)c(C(=O)Nc2ccc(C(=O)N3CCc4c(sc(C(=O)Nc5ccccc5N)c4Cl)-c4ccccc43)cc2)c1]

A solution of benzene-1,2-diamine (50.4 mg, 0.47 mmol), the compound from example 267 step j (100 mg, 0.16 mmol) and HATU (118.2 mg, 0.31 mmol), TEA (0.2 mL) in DMF (1 mL) was stirred for 1 h. The crude product was purified by reverse phase flash column chromatography (MeCN/H$_2$O) to give the desired product (90 mg, 78.94%) as a yellow solid. ESI-MS m/z: 733.25 [M+H]$^+$.

Example 272

Step b

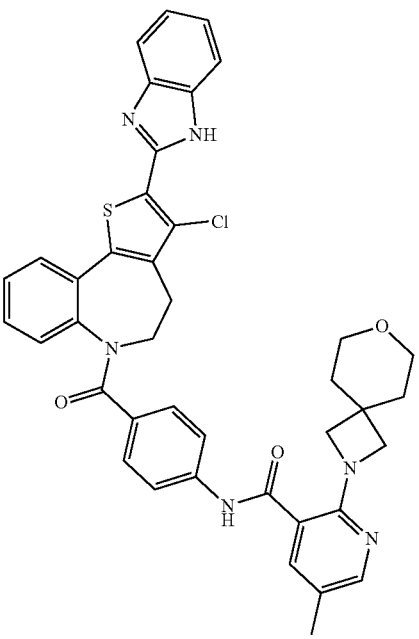 [SMILES: Cc1cnc(N2CC3(CCOCC3)C2)c(C(=O)Nc2ccc(C(=O)N3CCc4c(sc(-c5nc6ccccc6[nH]5)c4Cl)-c4ccccc43)cc2)c1]

A solution of the compound from step a (90 mg, 0.12 mmol) and AcOH (2 mL) was heated at 90° C. in a sealed vessel for 1 h. The resulting mixture was concentrated and adjusted the pH=8 with sat. aq. NaHCO$_3$. The residue was diluted with DCM (20 mL) and water (20 mL). The organic layer was separated and washed with brine, dried and evaporated. The residue was purified by Prep-HPLC (MeCN/H$_2$O/10 mmol/L NH$_4$HCO$_3$) to afford the desired product (44.7 mg, 50.9%) as a white solid. ESI-MS m/z: 715.20 [M+H]$^+$.

Scheme 16
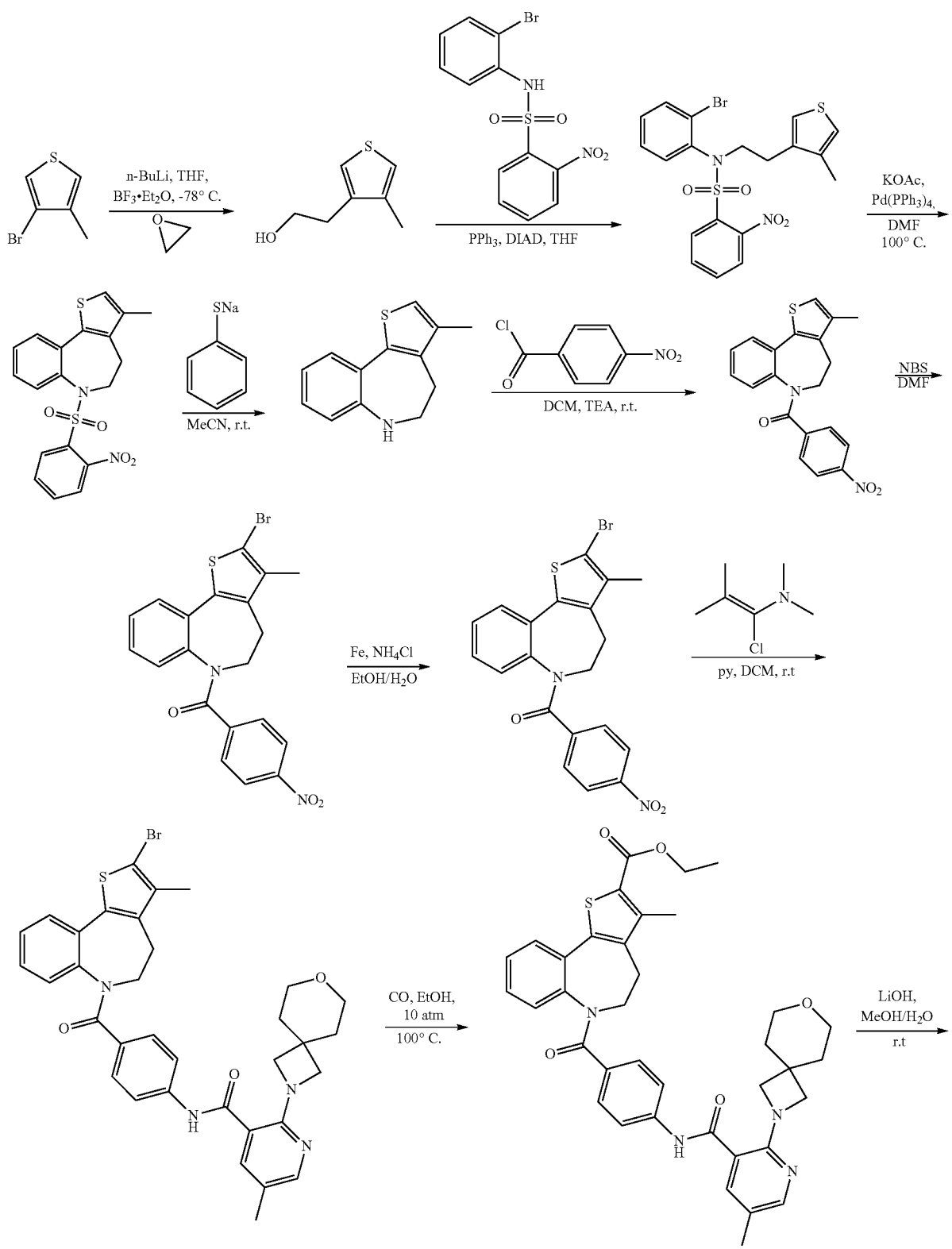

-continued
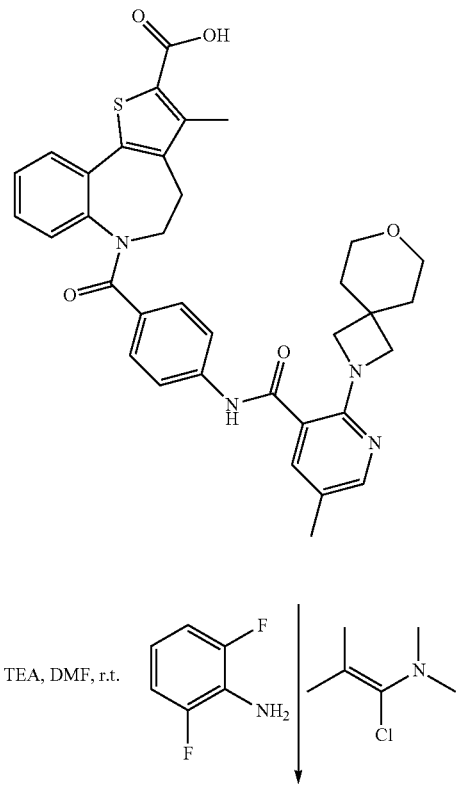
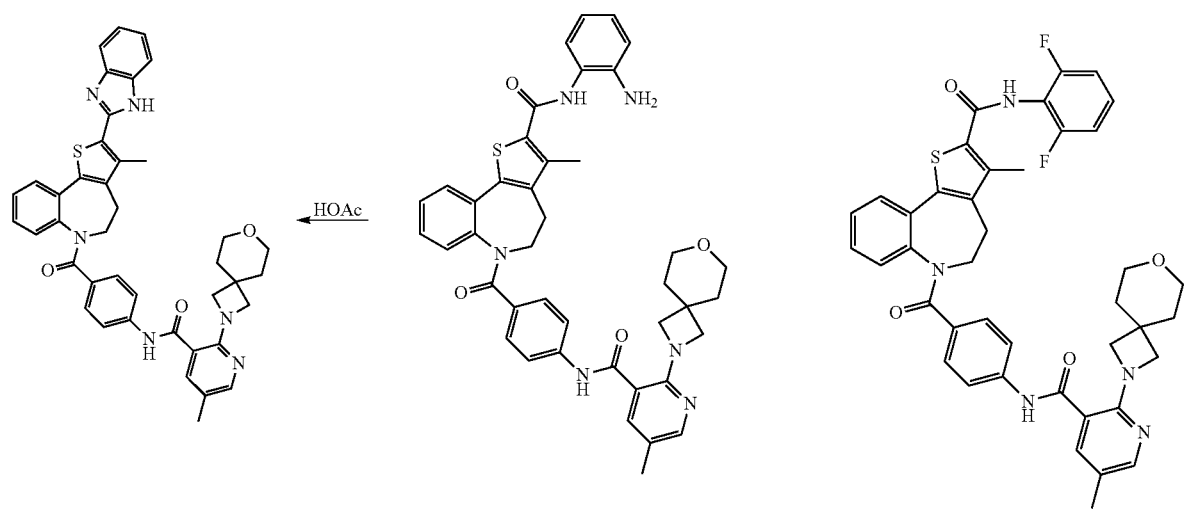

Example 273

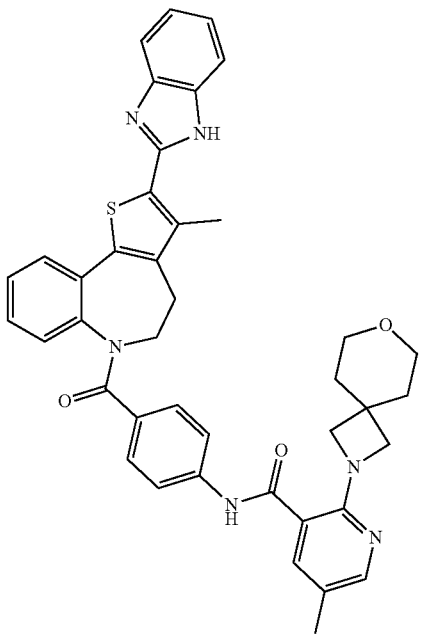 [SMILES: Cc1cnc(N2CC3(CCOCC3)C2)c(C(=O)Nc2ccc(C(=O)N3CCc4c(sc(-c5nc6ccccc6[nH]5)c4C)-c4ccccc43)cc2)c1]

Example 273

Step a

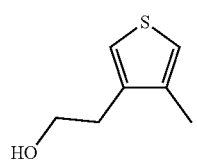

n-BuLi (41 mL, 101.66 mol, 2.5 m in hexanes) was added to the solution of 3-bromo-4-methylthiophene (15 g, 84.72 mol) in THF (150 mL) dropwise at −78° C. under N₂. The resulting mixture was stirred for 1 h at −78° C. under N₂. To the above mixture was added oxirane (7.5 g, 169.43 mol), followed by BF₃.Et₂O (18.0 g, 127.07 mol) dropwised over 35 min at −78° C. The resulting mixture was stirred for additional 2 hrs at −78° C. The reaction was quenched by the addition of sat. aq. NaHCO₃ (250 mL). The resulting mixture was extracted with EtOAc. The combined organic layers were washed with brine and dried over anhydrous Na₂SO₄. After filtrated, the filtrate was concentrated to give the desired compound (11 g, 90%) as red oil.

Example 273

Step b

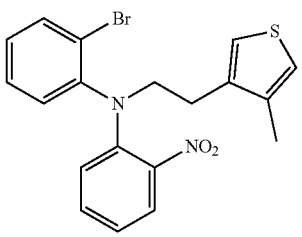 [SMILES: Cc1cscc1CCN(c1ccccc1Br)c1ccccc1[N+](=O)[O-]]

A solution of the compound from step a (6.1 g, 53.44 mmol), N-(2-bromophenyl)-2-nitrobenzene-1-sulfonamide (7.6 g, 21.28 mmol), PPh₃ (8.4 g, 53.44 mmol) and DIAD (6.5 g, 53.44 mmol) in THF (200 mL) was stirred for 2 hrs at room temperature. The mixture was concentrated and purified by reverse phase flash chromatography (MeCN/H₂O) to give the desired compound (11.6 g, 45%) as yellow oil. ESI-MS m/z: 481.15 [M+H]⁺.

Example 273

Step c

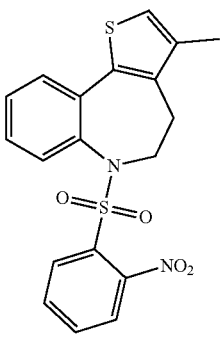 [SMILES: Cc1csc2c1CCN(S(=O)(=O)c1ccccc1[N+](=O)[O-])c1ccccc1-2]

Potassium acetate (3.0 g, 31.58 mmol) and Pd(PPh₃)₄ (3.6 g, 3.16 mmol) were added to the solution of the compound from step b (7.6 g, 15.79 mmol) in DMF (50 mL). The mixture was stirred for 2 hrs at 110° C. The mixture was allowed to cool down to rt. The resulting mixture was diluted with EtOAc. The separated organic layer was washed with brine and dried over anhydrous Na₂SO₄. After filtration, the filtrate was concentrated and purified by silica gel column chromatography to give the desired compound (5.5 g, 87%) as a brown solid. ESI-MS m/z: 401.05 [M+H]⁺.

Example 273

Step d

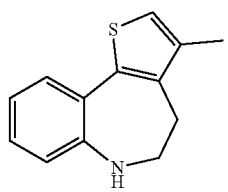

A solution of the compound from step c (2.2 g, 5.49 mmol) and (sodiosulfanyl)benzene (1.1 g, 8.24 mmol) in acetonitrile (20 mL) was stirred at rt overnight. The solution was concentrated and the residue was purified by silica gel column chromatography to give the desired compound (720 mg, 61%) as a yellow solid.

Example 273

Step e

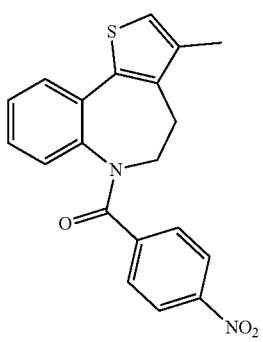 [SMILES: Cc1csc2c1CCN(C(=O)c1ccc([N+](=O)[O-])cc1)c1ccccc1-2]

A solution of the compound from step d (720 mg, 3.34 mmol), 4-nitrobenzoyl chloride (1.2 g, 6.69 mmol) and TEA (1 mL, 7.19 mmol) in DCM (10 mL) was stirred for 2 hrs at rt. The resulting mixture was concentrated and purified by silica gel column chromatography to give the desired compound (800 mg, 65%) as a yellow solid.

Example 273

Step f

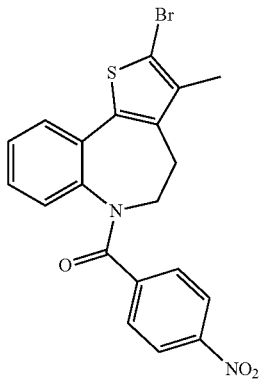 [SMILES: Cc1c(Br)sc2c1CCN(C(=O)c1ccc([N+](=O)[O-])cc1)c1ccccc1-2]

A solution of the compound from step e (800 mg, 2.20 mmol), NBS (391 mg, 2.20 mmol) in DMF (10 mL) was stirred for 2 hrs at rt. The resulting mixture was concentrated and purified by reverse phase flash chromatography (MeCN/H$_2$O) to give the desired compound (600 mg, 61%) as a yellow solid. ESI-MS m/z: 442.95 [M+H]$^+$.

Example 273

Step g

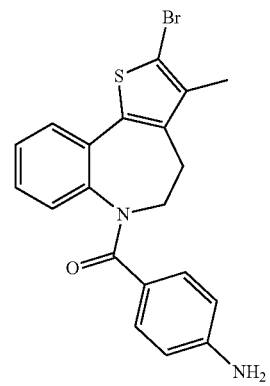 [SMILES: Cc1c(Br)sc2c1CCN(C(=O)c1ccc(N)cc1)c1ccccc1-2]

A solution of the compound from step f (600 mg, 1.35 mmol), Fe (756 mg, 13.53 mmol) and NH$_4$Cl (724 mg, 13.53 mmol) in EtOH/H$_2$O (15 mL, 2:1) was stirred at 80° C. for 2 hrs. After cooled down, the reaction mixture was filtered. The filtrate was concentrated and purified by silica gel column chromatography to give the desired compound (460 mg, 82%) as a yellow solid. ESI-MS m/z: 413.00 [M+H]$^+$.

Example 273

Step h

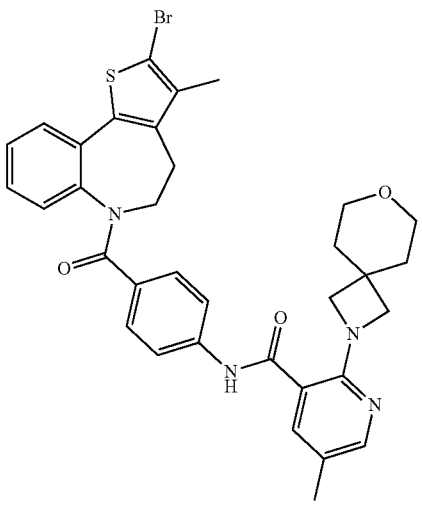 [SMILES: Cc1cnc(N2CC3(CCOCC3)C2)c(C(=O)Nc2ccc(C(=O)N3CCc4c(sc(Br)c4C)-c4ccccc43)cc2)c1]

1-Chloro-N,N, 2-trimethylprop-1-en-1-amine (666 mg, 5.01 mmol) was added to the solution of 5-methyl-2-(7-oxa-2-azaspiro[3.5]nonan-2-yl)nicotinic acid (439 mg, 1.67 mmol) in DCM (5 mL). The mixture was stirred for 1 h and then concentrated. The residue was dissolved in DCM (5 mL), and the compound from step g (460 mg, 1.11 mmol) and pyridine (2 mL) were added dropwise. After stirred for 1 h, the solution was evaporated and purified by reverse phase column chromatography (MeCN/H₂O) to give the desired compound (604 mg, 83%) as a yellow solid. ESI-MS m/z: 657.10 [M+H]⁺.

Example 273

Step i

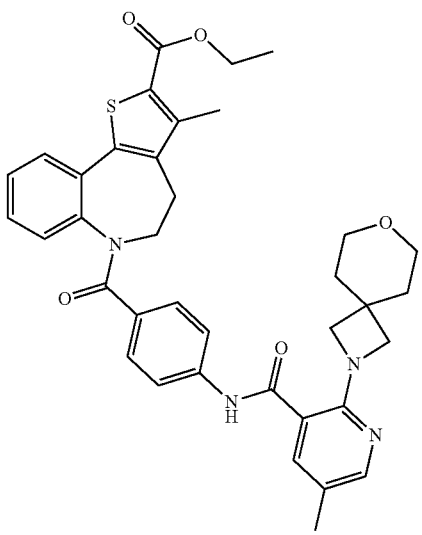 [SMILES: CCOC(=O)c1sc2c(c1C)CCN(C(=O)c1ccc(NC(=O)c3cc(C)cnc3N3CC4(CCOCC4)C3)cc1)c1ccccc1-2]

A solution of the compound from step h (604 mg, 0.92 mmol), Pd(dppf)Cl₂CH₂Cl₂ (86.9 mg, 0.11 mmol,) and TEA (0.5 mL) in EtOH (5 mL) was stirred at 100° C. for 2 hrs under CO atmosphere. The resulting mixture was concentrated and the residue was purified by silica gel column chromatography to give the desired compound (580 mg, 96%) as a yellow solid. ESI-MS m/z: 651.30 [M+H]⁺.

Example 273

Step j

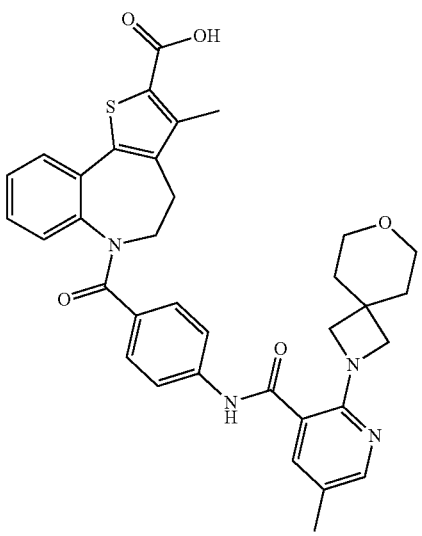 [SMILES: Cc1cnc(N2CC3(CCOCC3)C2)c(C(=O)Nc2ccc(C(=O)N3CCc4c(sc(C(=O)O)c4C)-c4ccccc43)cc2)c1]

A solution of the compound from step i (580 mg, 0.89 mmol), LiOH (214 mg, 8.92 mmol) in MeOH (5 mL), H₂O (5 mL) was stirred for 2 hrs at rt. The mixture was concentrated and adjusted PH=2 with 1M HCl. After evaporated, the residue was purified by reverse phase column chromatography (MeCN/H₂O) to give the desired compound (498 mg, 90%) as a yellow solid. ESI-MS m/z: 623.30 [M+H]⁺.

Example 273

Step k

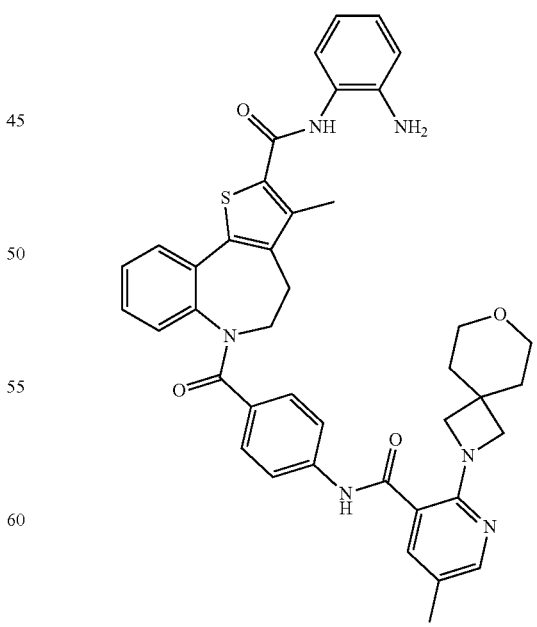

A solution of the compound from step j (100 mg, 0.16 mmol), benzene-1,2-diamine (52.3 mg, 0.48 mmol), HATU (122 mg, 0.32 mmol) and TEA (0.2 mL) in DMF (1 mL) was stirred for 1 h. After evaporated, the residue was purified by reverse phase column chromatography (MeCN/H₂O) to give the desired compound (55 mg, 50%) as a yellow solid. ESI-MS m/z: 713.35 [M+H]⁺.

Example 273

Step 1

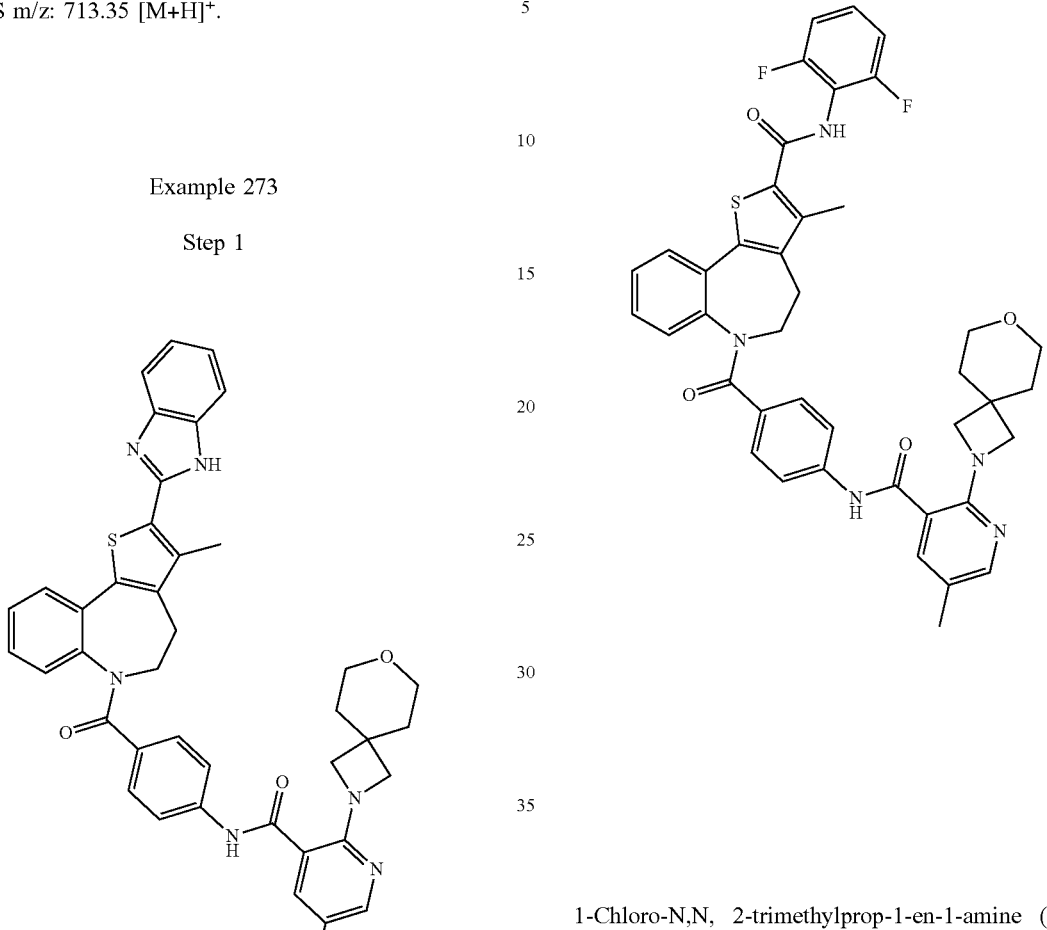

Example 274

A solution of the compound from step k (55 mg, 0.08 mmol) in HOAc (3 mL) was stirred at 90° C. for 1 h. The mixture was concentrated, adjusted PH=8 with sat. aq. NaHCO₃. After extracted with EA, the organic layer was dried, filtered and concentrated. The crude product was purified by Prep-HPLC (MeCN/H₂O/0.05% FA) to give the desired product (10.4 mg, 19.40%) as an off-white solid. ESI-MS m/z: 695.15 [M+H]⁺.

1-Chloro-N,N, 2-trimethylprop-1-en-1-amine (42 mg, 0.32 mmol) was added to the solution of the compound from step j (60 mg, 0.09 mmol) in DCM (5 mL). The mixture was stirred for 1 h at room temperature and evaporated. The residue was dissolved in DCM (5 mL) and 2,6-difluoroaniline (62 mg, 0.48 mmol) and pyridine (0.1 mL) were added dropwise. The mixture was stirred for 1 h and then evaporated. The residue was purified by Prep-TLC (DCM: MeOH=20:1) and then Prep-HPLC(MeCN/H₂O/0.1% TFA) to give the desired compound (8.6 mg, 8.3%) as a white solid. ESI-MS m/z: 734.20 [M+H]⁺.

Scheme 17

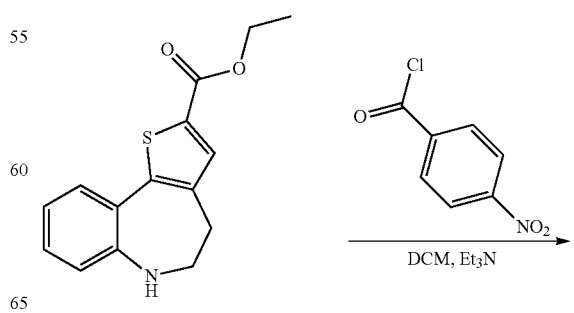

357
-continued
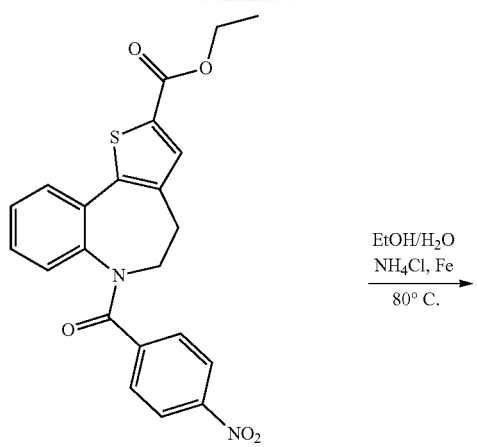
358
-continued
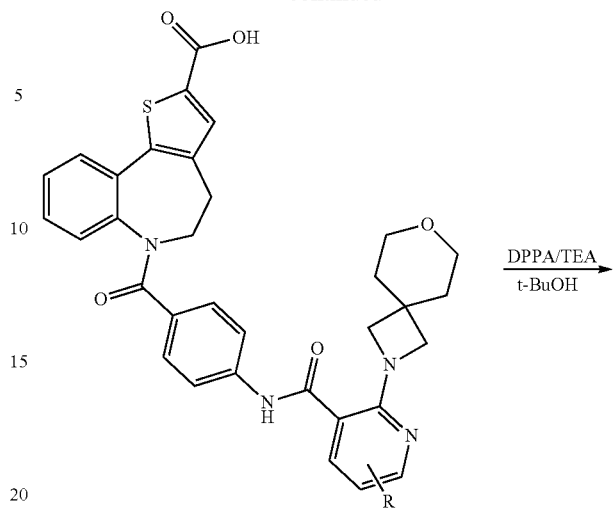
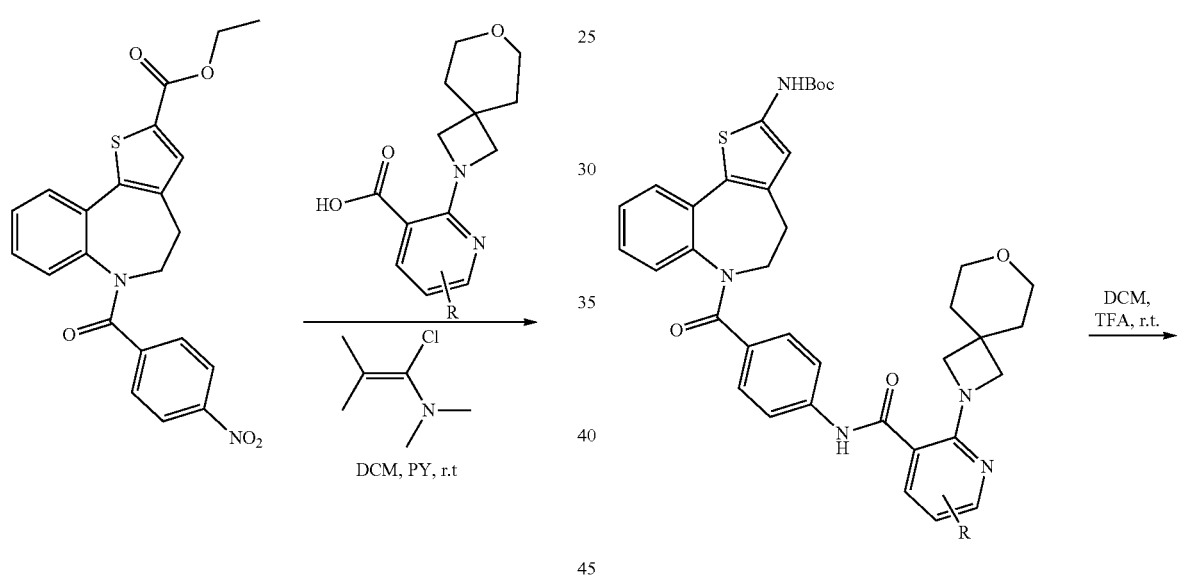
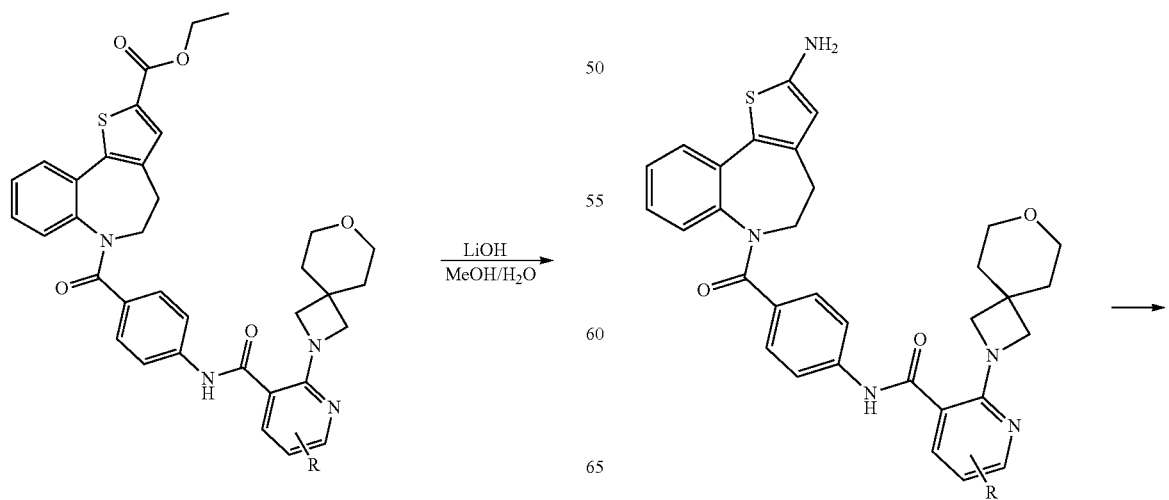

359
-continued

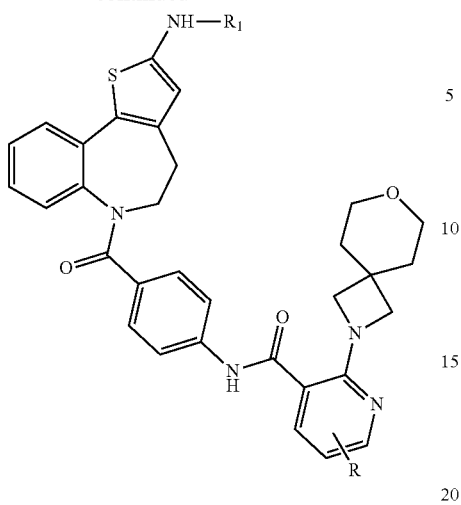

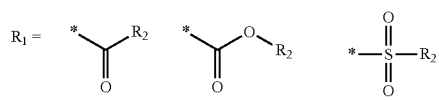

Example 275

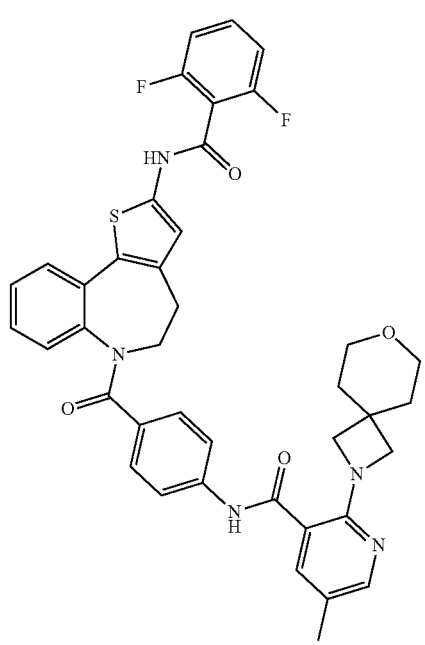 [SMILES: Cc1cnc(N2CC3(CCOCC3)C2)c(C(=O)Nc2ccc(C(=O)N3CCc4cc(NC(=O)c5c(F)cccc5F)sc4-c4ccccc43)cc2)c1]

360

Example 275

Step a

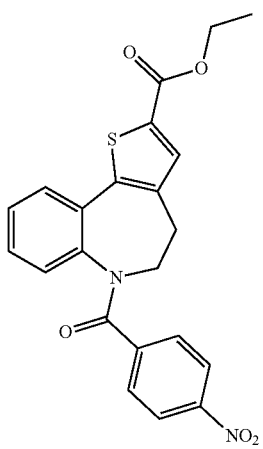 [SMILES: CCOC(=O)c1cc2c(s1)-c1ccccc1N(C(=O)c1ccc([N+](=O)[O-])cc1)CC2]

Into a 500 mL round-bottom flask were added ethyl 5,6-dihydro-4H-benzo[b]thieno[2,3-d]azepine-2-carboxylate (8 g, 29.267 mmol), Et$_3$N (8.88 g, 87.800 mmol) and 4-nitrobenzoyl chloride (5.97 g, 32.193 mmol) in DCM (250 mL) at rt. The resulting mixture was concentrated under vacuum. The residue was purified by silica gel column chromatography to afford the desired compound (11.6 g, 93.82%) as a yellow solid. ESI-MS m/z: 423.15 [M+H]$^+$.

Example 275

Step b

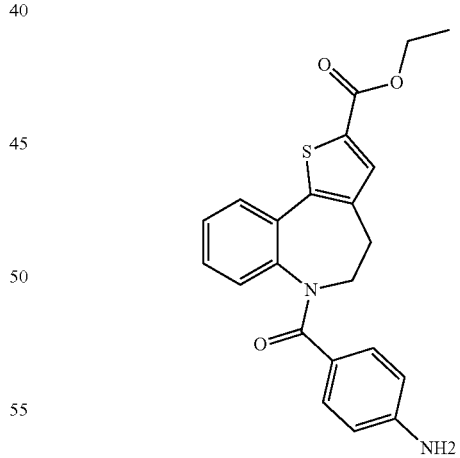

Into a 500 mL round-bottom flask were added the compound from step a (11.6 g, 27.458 mmol), EtOH (120 mL), Fe (15.33 g, 274.582 mmol), NH$_4$Cl (14.69 g, 274.582 mmol) and H$_2$O (50 mL) at rt. The resulting mixture was stirred at 80° C. for 2 hrs. After cooled down, the reaction mixture was filtered. The filtrate was concentrated and purified by purified by silica gel column chromatography to afford the desired compound (10.23 g, 95%) as a yellow solid. ESI-MS m/z: 393.05 [M+H]$^+$.

Example 275

Step c

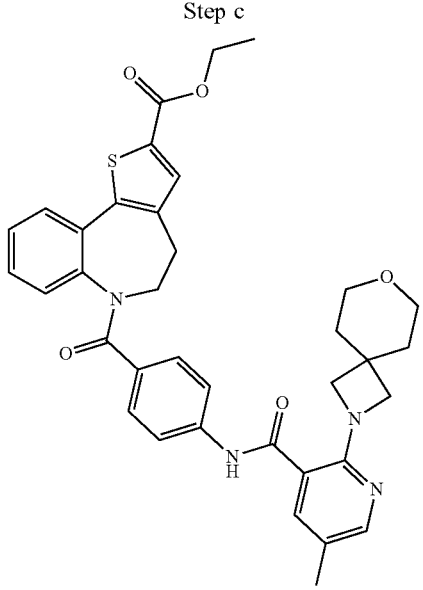

Into a 250 mL round-bottom flask were added 5-methyl-2-(7-oxa-2-azaspiro[3.5]nonan-2-yl)-nicotinic acid (4.81 g, 18.345 mmol), (1-chloro-2-methylprop-1-en-1-yl)dimethylamine (6.13 g, 45.863 mmol) and DCM (100 mL) at room temperature. The resulting mixture was stirred for 1 h at rt. The resulting mixture was concentrated under vacuum. The residue was dissolved in DCM (100 mL) and the compound from step b (6 g, 15.288 mmol) and pyridine (3 mL) were added slowly at room temperature. After stirred 2 hrs at room temperature, the resulting mixture was concentrated under reduced pressure and purified by reverse phase column chromatography to afford the desired compound (8.5 g, 87.3%) as a yellow solid. ESI-MS m/z: 637.20 [M+H]$^+$.

Example 275

Step d

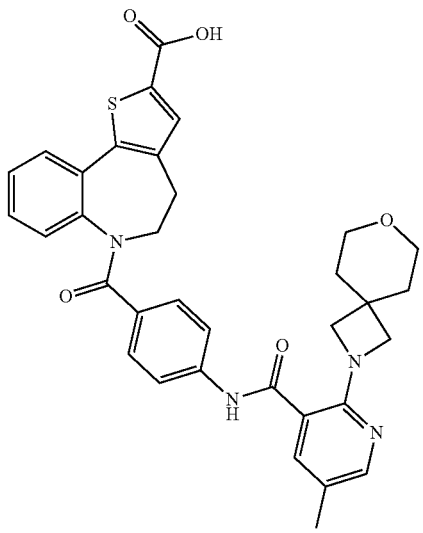 [SMILES: Cc1cnc(N2CC3(CCOCC3)C2)c(C(=O)Nc2ccc(C(=O)N3CCc4cc(C(=O)O)sc4-c4ccccc43)cc2)c1]

Into a 250 mL round-bottom flask were added the compound from step c (1.8 g, 2.83 mmol), MeOH (15 mL), LiOH (0.7 g, 28.27 mmol) and H$_2$O (7 mL) at rt. The mixture was stirred for 2 hrs at rt. The mixture was acidified to pH=5 with 2 M HCl (aq.) and concentrated under vacuum. The crude product was purified by reverse phase column chromatography to afford the desired compound (1.6 g, 92.99%) as a yellow solid. ESI-MS m/z: 609.02 [M+H]$^+$.

Example 275

Step e

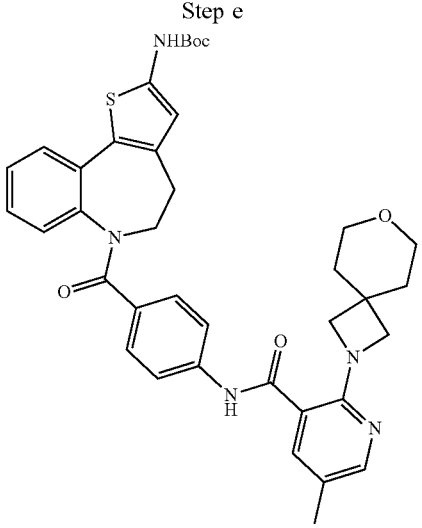

To a 100 mL round-bottom flask were added the compound from step d (1 g, 1.64 mmol), DPPA (904.2 mg, 3.29 mmol), TEA (392.6 mg, 4.88 mmol), and t-BuOH (10 mL) at rt. The mixture was stirred for overnight at 80° C. under N$_2$. The resulting mixture was extracted with CH$_2$Cl$_2$ (3×200 mL). The combined organic layer was concentrated under reduced pressure and purified by reverse phase column chromatography to afford the desired compound (1.2 g, 107.44%) as a yellow solid. ESI-MS m/z: 680.30 [M+H]$^+$.

Example 275

Step f

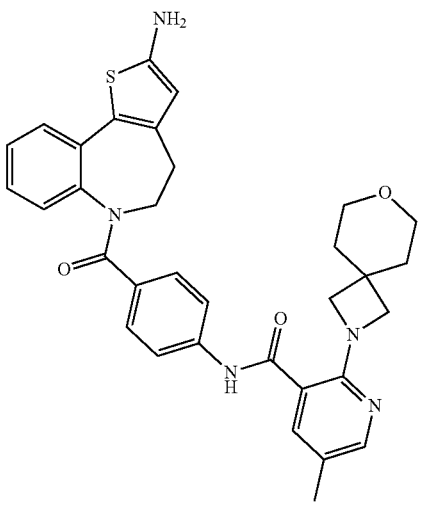 [SMILES: Cc1cnc(N2CC3(CCOCC3)C2)c(C(=O)Nc2ccc(C(=O)N3CCc4cc(N)sc4-c4ccccc43)cc2)c1]

To a 100 mL round-bottom flask were added the compound from step e (1.2 g, 1.765 mmol) into DCM (20 mL) and TFA (5 mL) at rt. The resulting mixture was stirred for 4 hrs at rt. The mixture was neutralized to pH=8 with sat. aq. Na$_2$CO$_3$ and concentrated under reduced pressure. The crude product was purified by reverse phase column chromatography to afford the desired compound (410 mg, 40.07%) as a brown yellow solid. ESI-MS m/z: 580.25 [M+H]$^+$.

Example 275

Step g

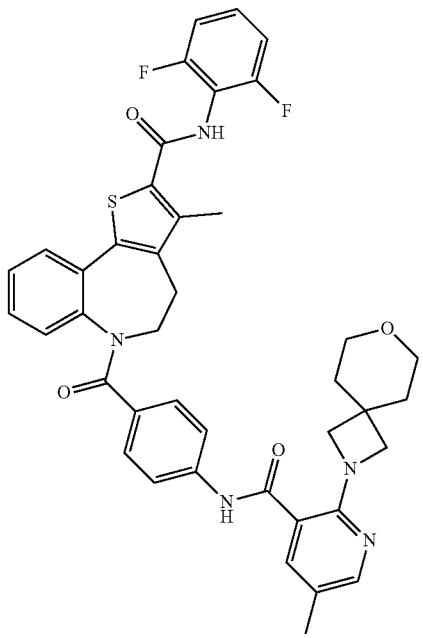 [SMILES: Cc1cnc(N2CC3(CCOCC3)C2)c(C(=O)Nc2ccc(C(=O)N3CCc4c(sc(C(=O)Nc5c(F)cccc5F)c4C)-c4ccccc43)cc2)c1]

To a 25 mL round-bottom flask were added 2,6-difluorobenzoic acid (54.54 mg, 0.345 mmol) and (1-chloro-2-methylprop-1-en-1-yl)dimethylamine (138.29 mg, 1.035 mmol) in DCM (5 mL) at room temperature. The resulting mixture was stirred for 1 h at rt under nitrogen atmosphere. The resulting mixture was concentrated under vacuum. The residue was dissolved in DCM (5 mL) and the compound from step f (100 mg, 0.172 mmol) and pyridine (0.1 mL) were added in at room temperature. The resulting mixture was stirred for 2 hrs at room temperature. The resulting mixture was concentrated under vacuum. The crude product was purified by Prep-HPLC to afford the desired compound (38 mg, 30.6%) as a white solid. ESI-MS m/z: 720.20 [M+H]$^+$.

Example 276-302 shown in table 23 were prepared using the procedure similar to that of example 275 from the corresponding intermediates.

TABLE 23

| Example | Structure | ESI-MS m/z: [M + H]$^+$ |
|---|---|---|
| 276 | 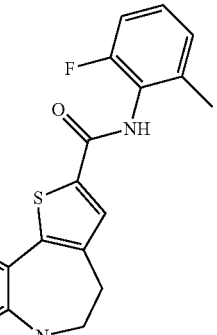 | 716.2 |
| 277 | 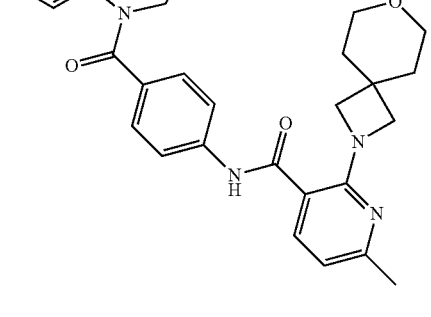 | 736.2 |

TABLE 23-continued
| Example | Structure | ESI-MS m/z: [M + H]+ |
|---|---|---|
| 278 | 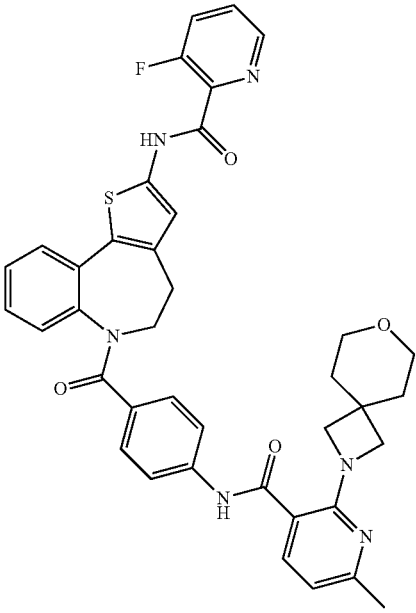 [SMILES: Cc1ccc(C(=O)Nc2ccc(C(=O)N3CCc4cc(NC(=O)c5ncccc5F)sc4-c4ccccc43)cc2)c(N2CC3(CCOCC3)C2)n1] | 703.4 |
| 279 | 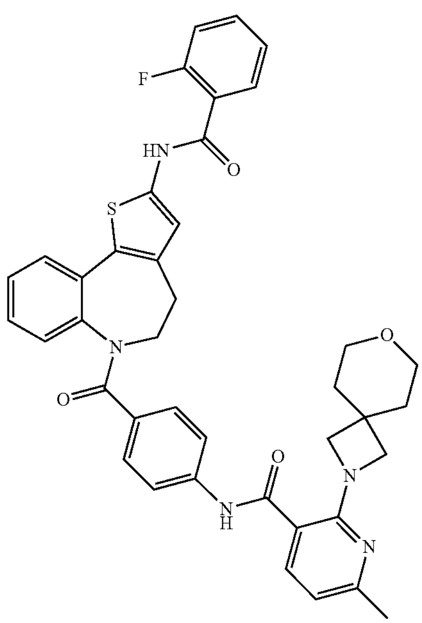 [SMILES: Cc1ccc(C(=O)Nc2ccc(C(=O)N3CCc4cc(NC(=O)c5ccccc5F)sc4-c4ccccc43)cc2)c(N2CC3(CCOCC3)C2)n1] | 720.3 |
TABLE 23-continued
| Example | Structure | ESI-MS m/z: [M + H]+ |
|---|---|---|
| 280 | 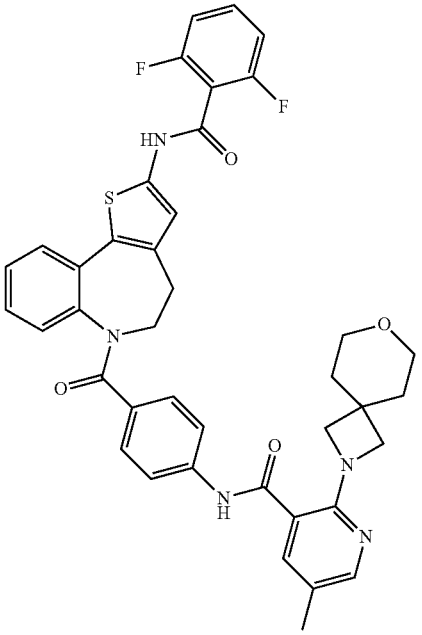 | 720.2 |
| 281 | 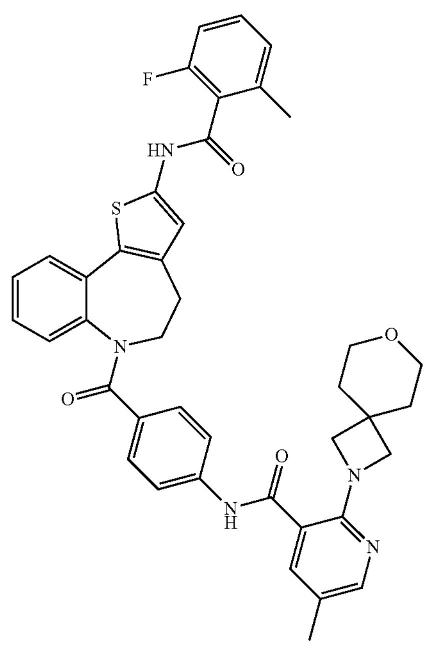 [SMILES: Cc1cnc(N2CC3(CCOCC3)C2)c(C(=O)Nc2ccc(C(=O)N3CCc4cc(NC(=O)c5c(C)cccc5F)sc4-c4ccccc43)cc2)c1] | 716.3 |

TABLE 23-continued

| Example | Structure | ESI-MS m/z: [M + H]+ |
|---|---|---|
| 282 | 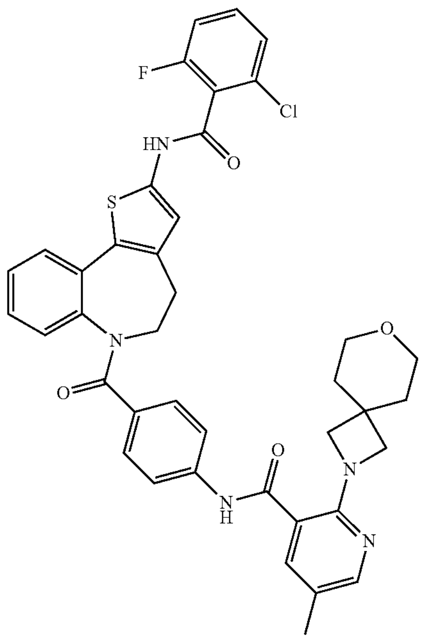 [SMILES: Cc1cnc(N2CC3(CCOCC3)C2)c(C(=O)Nc2ccc(C(=O)N3CCc4cc(NC(=O)c5c(F)cccc5Cl)sc4-c4ccccc43)cc2)c1] | 736.3 |
| 283 | 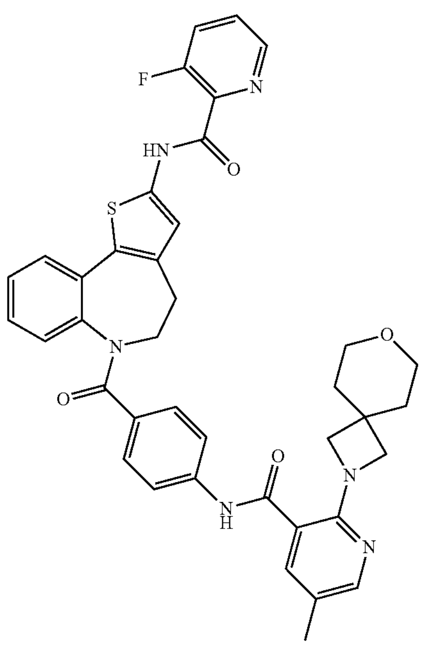 [SMILES: Cc1cnc(N2CC3(CCOCC3)C2)c(C(=O)Nc2ccc(C(=O)N3CCc4cc(NC(=O)c5ncccc5F)sc4-c4ccccc43)cc2)c1] | 703.3 |
| 284 | 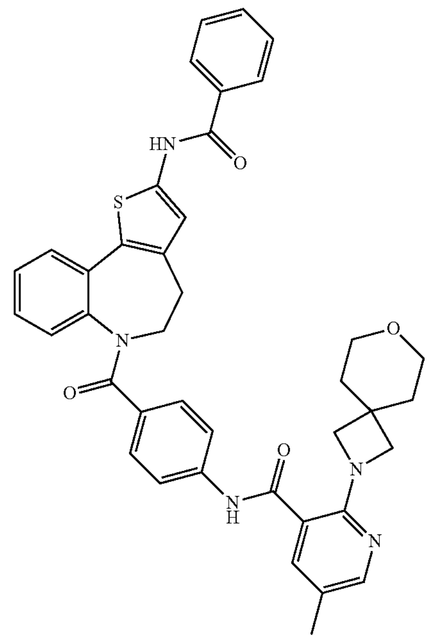 [SMILES: Cc1cnc(N2CC3(CCOCC3)C2)c(C(=O)Nc2ccc(C(=O)N3CCc4cc(NC(=O)c5ccccc5)sc4-c4ccccc43)cc2)c1] | 684.3 |
| 285 | 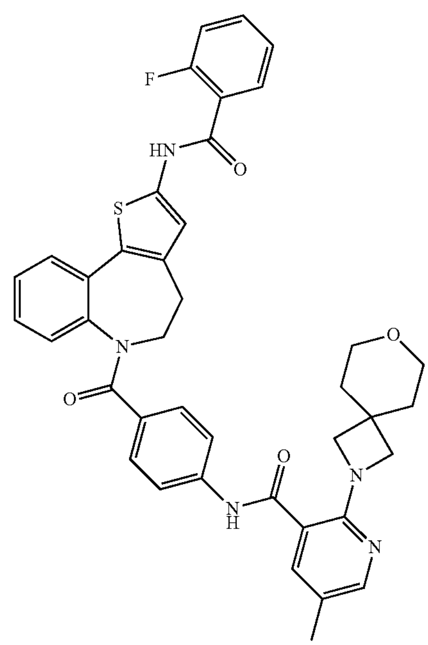 [SMILES: Cc1cnc(N2CC3(CCOCC3)C2)c(C(=O)Nc2ccc(C(=O)N3CCc4cc(NC(=O)c5ccccc5F)sc4-c4ccccc43)cc2)c1] | 702.4 |

TABLE 23-continued

| Example | Structure | ESI-MS m/z: [M + H]+ |
|---|---|---|
| 286 | 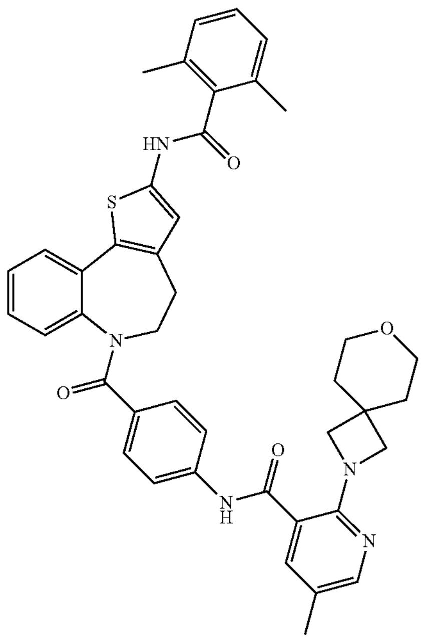 [SMILES: Cc1cnc(N2CC3(CCOCC3)C2)c(C(=O)Nc2ccc(C(=O)N3CCc4cc(NC(=O)c5c(C)cccc5C)sc4-c4ccccc43)cc2)c1] | 712.4 |
| 287 | 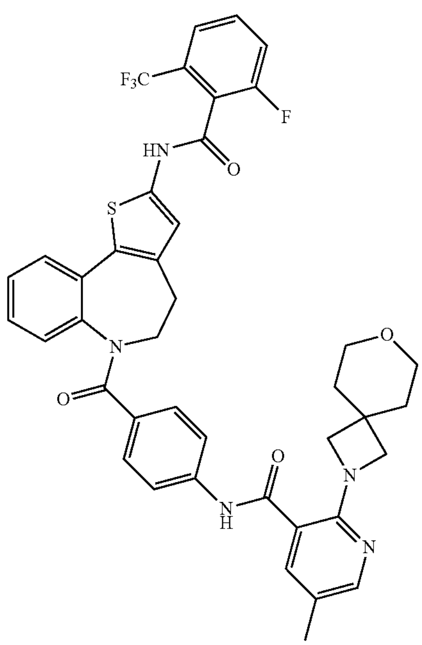 [SMILES: Cc1cnc(N2CC3(CCOCC3)C2)c(C(=O)Nc2ccc(C(=O)N3CCc4cc(NC(=O)c5c(F)cccc5C(F)(F)F)sc4-c4ccccc43)cc2)c1] | 770.4 |
| 288 | | 756.3 |
| 289 | | 752.2 |

TABLE 23-continued
| Example | Structure | ESI-MS m/z: [M + H]+ |
|---------|-----------|----------------------|
| 290 | 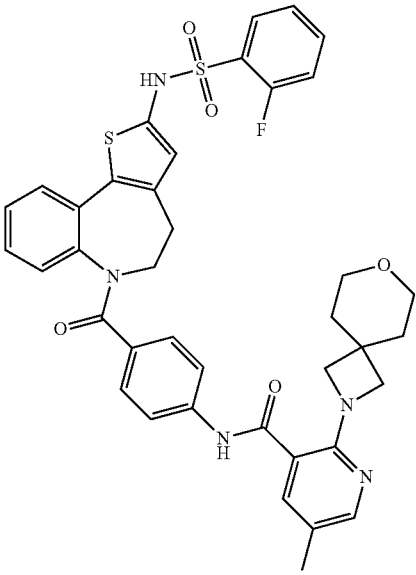 [SMILES: Cc1cnc(N2CC3(CCOCC3)C2)c(C(=O)Nc2ccc(C(=O)N3CCc4cc(NS(=O)(=O)c5ccccc5F)sc4-c4ccccc43)cc2)c1] | 738.2 |
| 291 | 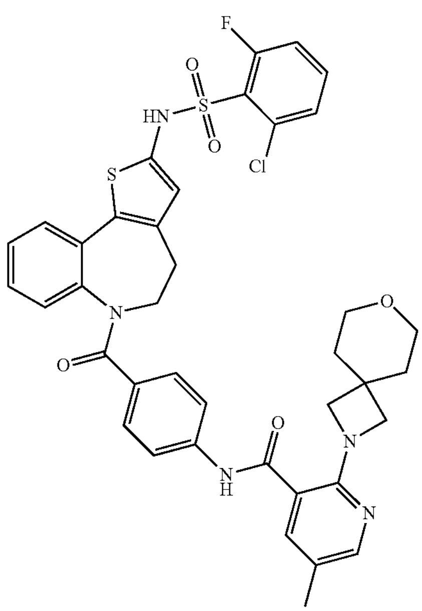 [SMILES: Cc1cnc(N2CC3(CCOCC3)C2)c(C(=O)Nc2ccc(C(=O)N3CCc4cc(NS(=O)(=O)c5c(F)cccc5Cl)sc4-c4ccccc43)cc2)c1] | 772.2 |
| 292 | 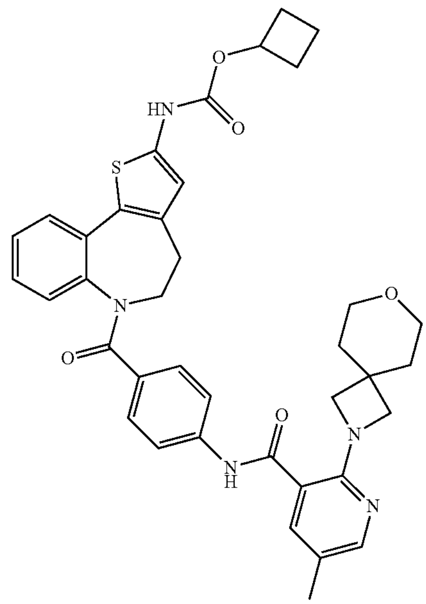 [SMILES: Cc1cnc(N2CC3(CCOCC3)C2)c(C(=O)Nc2ccc(C(=O)N3CCc4cc(NC(=O)OC5CCC5)sc4-c4ccccc43)cc2)c1] | 678.3 |
| 293 | 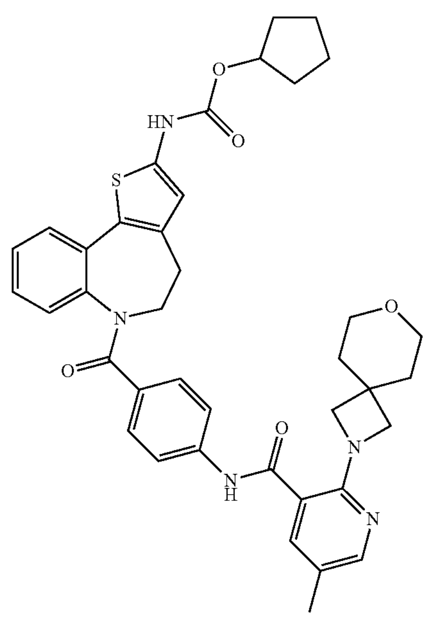 [SMILES: Cc1cnc(N2CC3(CCOCC3)C2)c(C(=O)Nc2ccc(C(=O)N3CCc4cc(NC(=O)OC5CCCC5)sc4-c4ccccc43)cc2)c1] | 692.3 |

TABLE 23-continued

| Example | Structure | ESI-MS m/z: [M + H]+ |
|---|---|---|
| 294 | 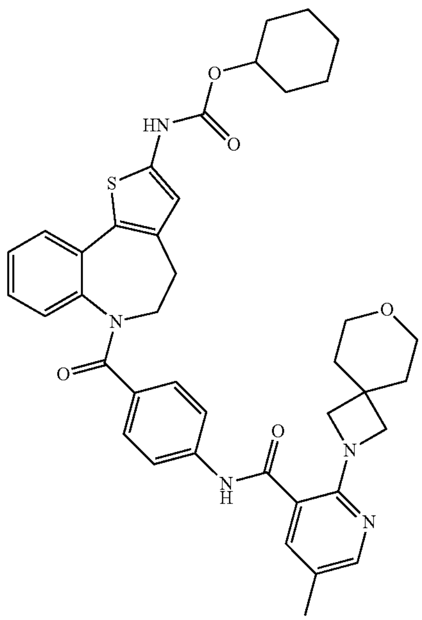 [SMILES: Cc1cnc(N2CC3(CCOCC3)C2)c(C(=O)Nc2ccc(C(=O)N3CCc4cc(NC(=O)OC5CCCCC5)sc4-c4ccccc43)cc2)c1] | 706.4 |
| 295 | 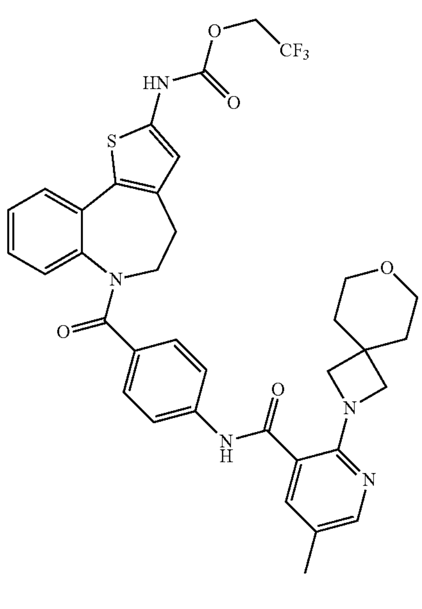 [SMILES: Cc1cnc(N2CC3(CCOCC3)C2)c(C(=O)Nc2ccc(C(=O)N3CCc4cc(NC(=O)OCC(F)(F)F)sc4-c4ccccc43)cc2)c1] | 706.2 |
| 296 | 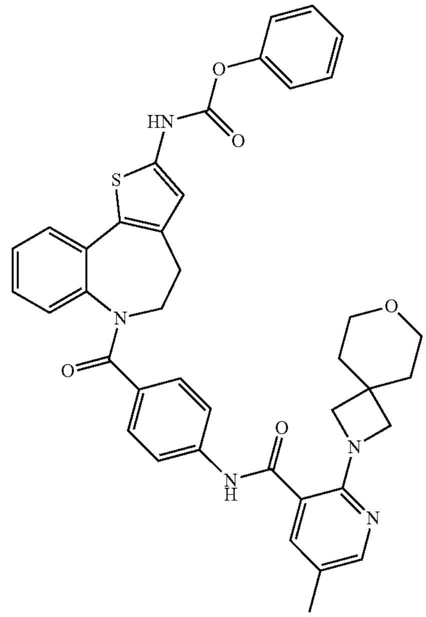 [SMILES: Cc1cnc(N2CC3(CCOCC3)C2)c(C(=O)Nc2ccc(C(=O)N3CCc4cc(NC(=O)Oc5ccccc5)sc4-c4ccccc43)cc2)c1] | 700.2 |
| 297 | 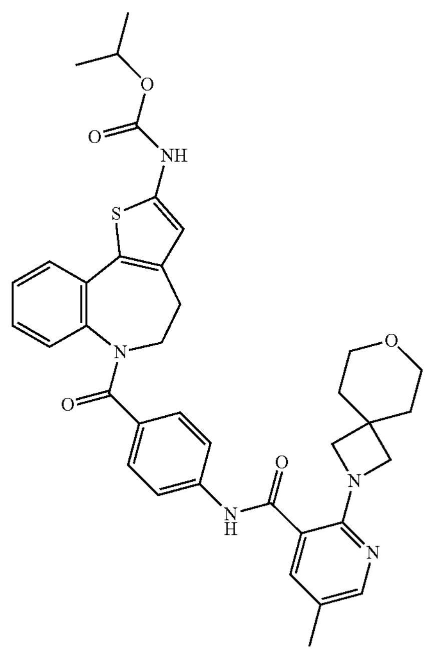 [SMILES: Cc1cnc(N2CC3(CCOCC3)C2)c(C(=O)Nc2ccc(C(=O)N3CCc4cc(NC(=O)OC(C)C)sc4-c4ccccc43)cc2)c1] | 666.3 |

TABLE 23-continued
| Example | Structure | ESI-MS m/z: [M + H]+ |
|---|---|---|
| 298 | 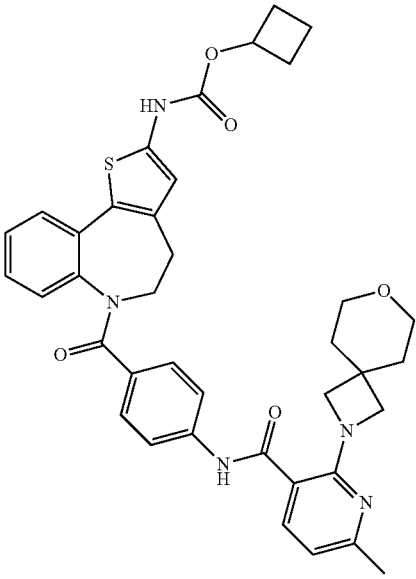 [SMILES: Cc1ccc(C(=O)Nc2ccc(C(=O)N3CCc4cc(NC(=O)OC5CCC5)sc4-c4ccccc43)cc2)c(N2CC3(CCOCC3)C2)n1] | 678.3 |
| 299 | 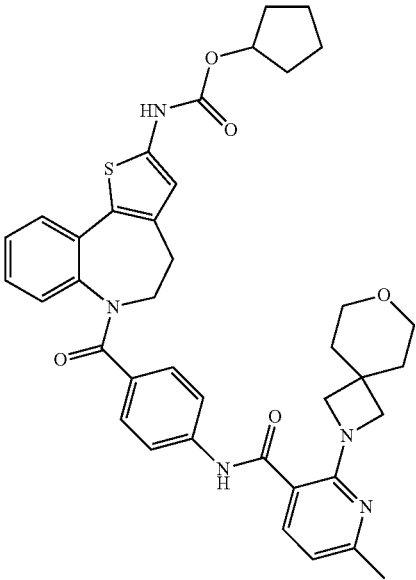 [SMILES: Cc1ccc(C(=O)Nc2ccc(C(=O)N3CCc4cc(NC(=O)OC5CCCC5)sc4-c4ccccc43)cc2)c(N2CC3(CCOCC3)C2)n1] | 692.3 |
| 300 | 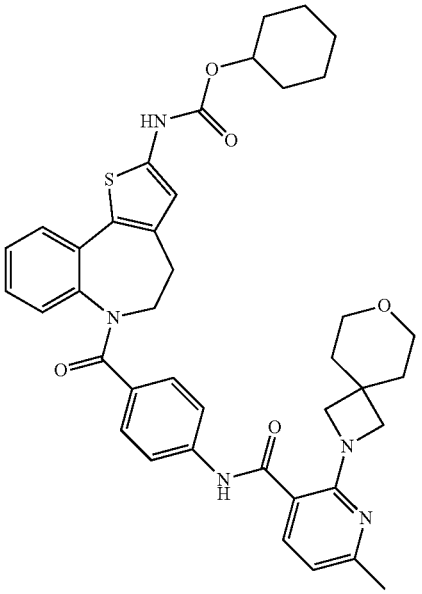 [SMILES: Cc1ccc(C(=O)Nc2ccc(C(=O)N3CCc4cc(NC(=O)OC5CCCCC5)sc4-c4ccccc43)cc2)c(N2CC3(CCOCC3)C2)n1] | 706.3 |
| 301 | 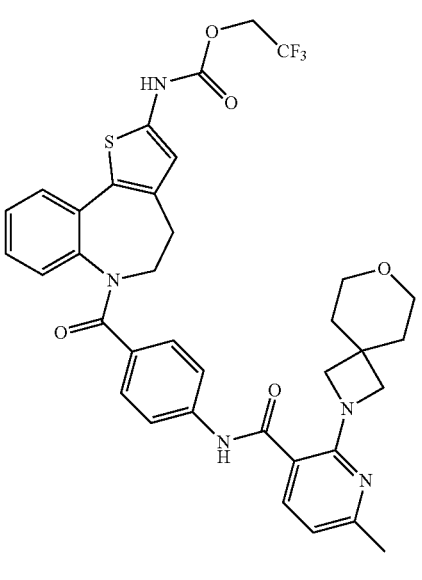 [SMILES: Cc1ccc(C(=O)Nc2ccc(C(=O)N3CCc4cc(NC(=O)OCC(F)(F)F)sc4-c4ccccc43)cc2)c(N2CC3(CCOCC3)C2)n1] | 706.2 |

TABLE 23-continued
| Example | Structure | ESI-MS m/z: [M + H]+ |
|---------|-----------|----------------------|
| 302 | 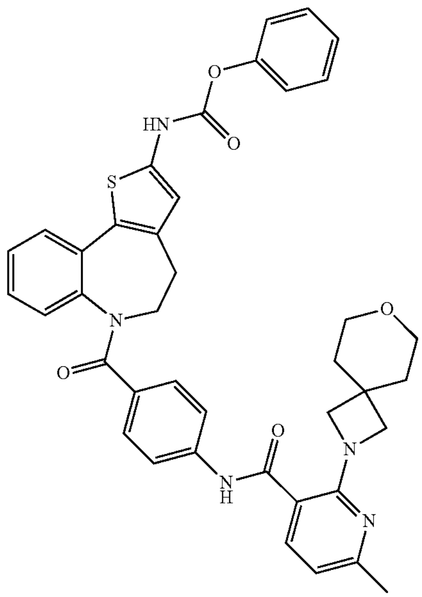 [SMILES: Cc1ccc(C(=O)Nc2ccc(C(=O)N3CCc4cc(NC(=O)Oc5ccccc5)sc4-c4ccccc43)cc2)c(N2CC3(CCOCC3)C2)n1] | 700.2 |
Scheme 18
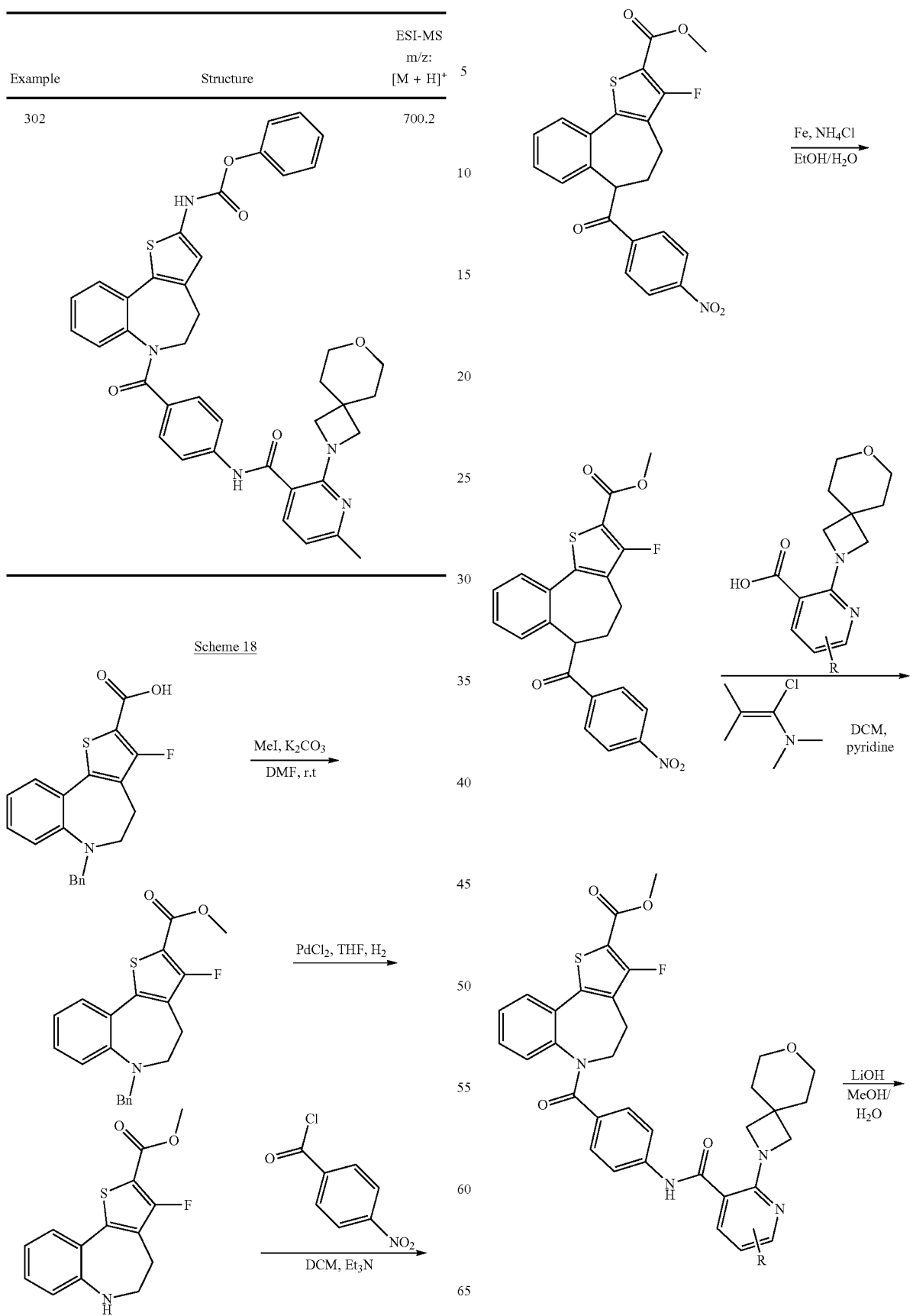

379
-continued
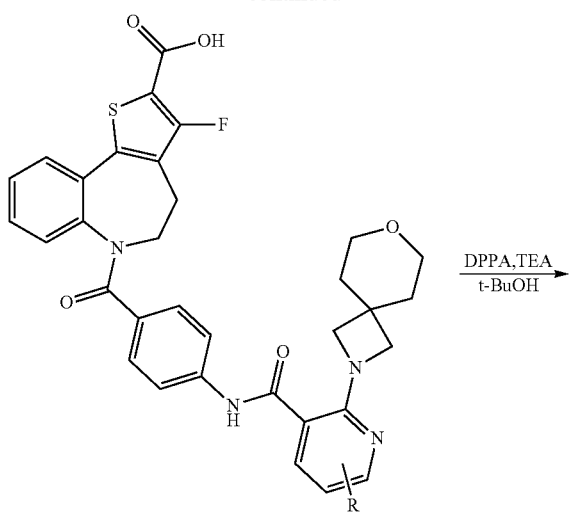
380
-continued
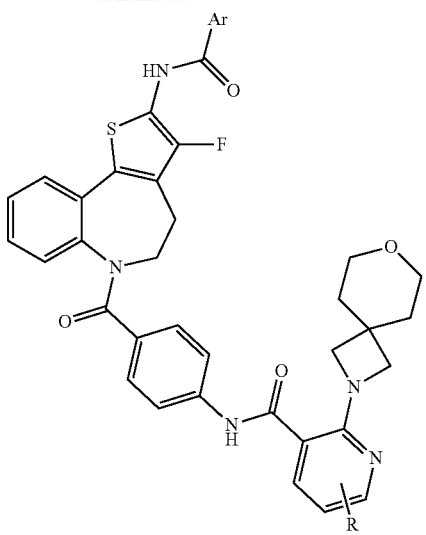
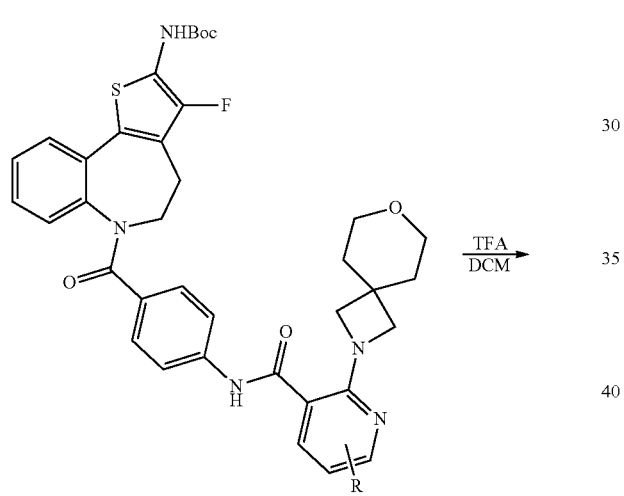
Example 303
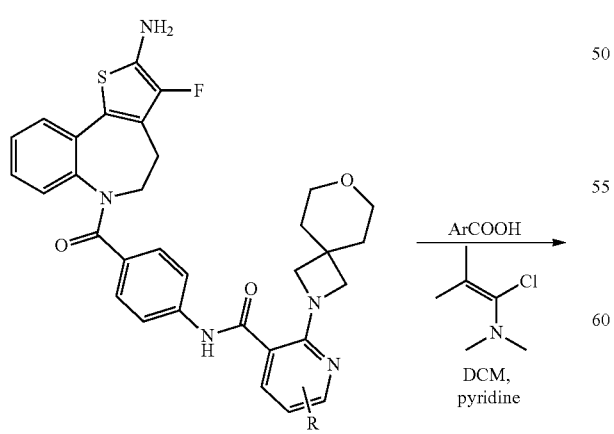
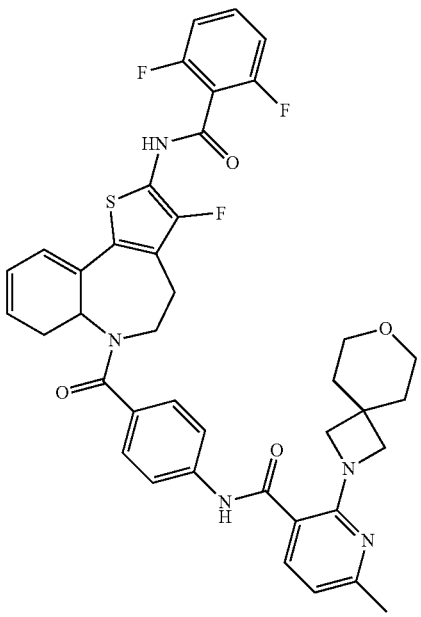 [SMILES: Cc1ccc(C(=O)Nc2ccc(C(=O)N3CCc4c(sc(NC(=O)c5c(F)cccc5F)c4F)C4=CC=CCC43)cc2)c(N2CC3(CCOCC3)C2)n1]

Example 303

Step a

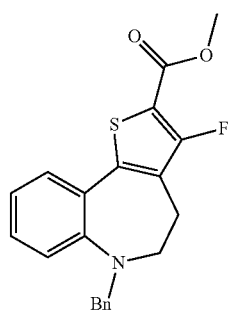 [SMILES: COC(=O)c1sc2c(c1F)CCN(Cc1ccccc1)c1ccccc1-2]

To a stirred mixture the compound from example 88 step c (1.1 g, 3.113 mmol) and MeI (0.88 g, 6.225 mmol) in DMF (100 mL) was added $K_2CO_3$ (0.86 g, 6.225 mmol) in portions and stirred for 4 hrs at rt. The resulting mixture was poured into water (100 mL) and extracted with EtOAc (3×300 mL). The organic layer was separated, dried and concentrated under reduced pressure. The residue was purified by reverse phase column chromatography to afford the desired compound (1.2 g, 104.9%) as a white solid. ESI-MS m/z: 368.10 [M+H]$^+$.

Example 303

Step b

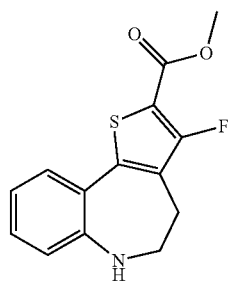 [SMILES: COC(=O)c1sc2c(c1F)CCNc1ccccc1-2]

To a 100 mL round-bottom flask were added the compound from step a (1.2 g, 3.266 mmol) and $PdCl_2$ (0.12 g, 0.653 mmol) in THF (50 mL) at room temperature. After degassed, the resulting mixture was stirred for 3 hrs at rt under hydrogen atmosphere. After filtered, the filter cake was washed with MeOH and EtOAc. The filtrate was concentrated under reduced pressure to afford the desired compound (1.0 g, crude) as a brown solid. ESI-MS m/z: 278.05 [M+H]$^+$.

Example 303

Step c

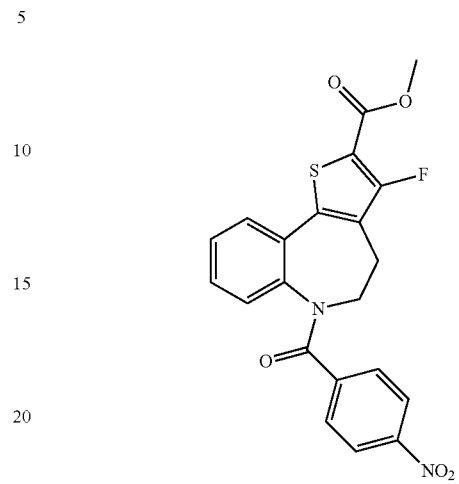

To a 100 mL round-bottom flask were added the compound from step b (1.0 g, 3.606 mmol), 4-nitrobenzoyl chloride (1.34 g, 7.212 mmol) and $Et_3N$ (3.65 g, 36.061 mmol) in DCM (50 mL) at rt. The resulting mixture was stirred for overnight at rt under nitrogen atmosphere. After evaporated the solvent, the residue was purified by silica gel column chromatography to afford the desired compound (1.3 g, 84.5%) as a yellow solid. ESI-MS m/z: 427.10 [M+H]$^+$.

Example 303

Step d

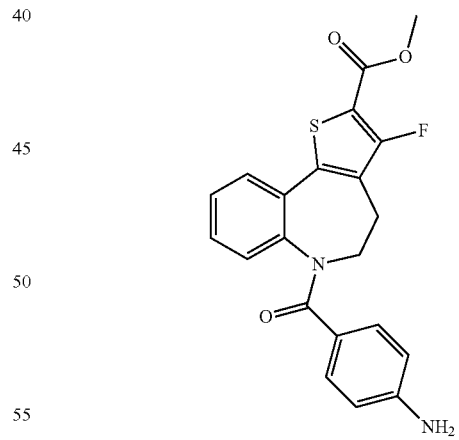

To a 250 mL round-bottom flask were added the compound from step c (1.3 g, 3.049 mmol), Fe (1.70 g, 30.486 mmol), EtOH (60 mL), $NH_4Cl$ (1.63 g, 30.486 mmol) and $H_2O$ (30 mL) at rt. The resulting mixture was stirred for 3 h at 80° C. The resulting mixture was filtered, the filter cake was washed with $CH_2Cl_2$. The filtrate was concentrated under reduced pressure. The residue was purified by reverse phase column chromatography to afford the desired compound (1.2 g, 99.3%) as a yellow solid. ESI-MS m/z: 397.15 [M+H]$^+$.

Example 303

Step e

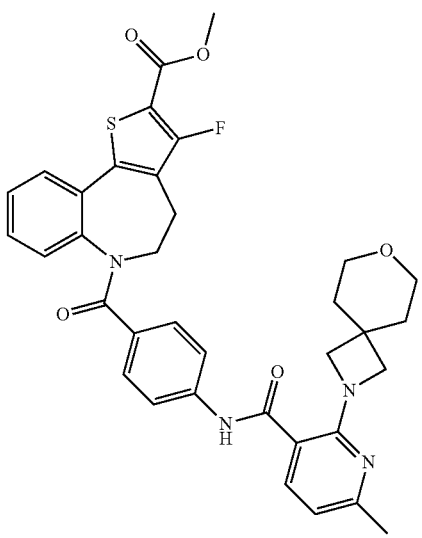 [SMILES: COC(=O)c1sc2c(c1F)CCN(C(=O)c1ccc(NC(=O)c3ccc(C)nc3N3CC4(CCOCC4)C3)cc1)c1ccccc1-2]

To a 100 mL round-bottom flask were added 6-methyl-2-(7-oxa-2-azaspiro[3.5]nonan-2-yl)-nicotinic acid (0.87 g, 3.330 mmol), (1-chloro-2-methylprop-1-en-1-yl)dimethylamine (1.21 g, 9.081 mmol) and DCM (30 mL) at rt. The mixture was stirred for 1 h at rt. The resulting mixture was concentrated under vacuum. To the above mixture were added the compound from step d (1.2 g, 3.027 mmol), DCM (20 mL) and pyridine (5 mL) in portions. The resulting mixture was stirred for additional 2 hrs at rt. The resulting mixture was concentrated under reduced pressure. The residue was purified by reverse phase column chromatography to afford the desired compound (1.6 g, 82.50%) as a yellow solid. ESI-MS m/z: 641.30 [M+H]$^+$.

Example 303

Step f

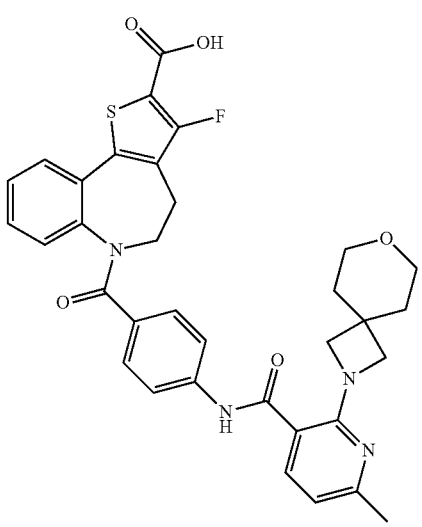 [SMILES: Cc1ccc(C(=O)Nc2ccc(C(=O)N3CCc4c(sc(C(=O)O)c4F)-c4ccccc43)cc2)c(N2CC3(CCOCC3)C2)n1]

To a 250 mL round-bottom flask were added the compound from step e (1.6 g, 2.497 mmol), MeOH (60 mL), LiOH (0.60 g, 24.972 mmol) and H$_2$O (20 mL) at rt. The mixture was stirred for 2 hrs at rt. The mixture was acidified to pH=5 with 2 M HCl (aq.) and concentrated under vacuum. The crude product was purified by reverse phase column chromatography to afford the desired compound (1.3 g, 83.1%) as an off-white solid. ESI-MS m/z: 627.30 [M+H]$^+$.

Example 303

Step g

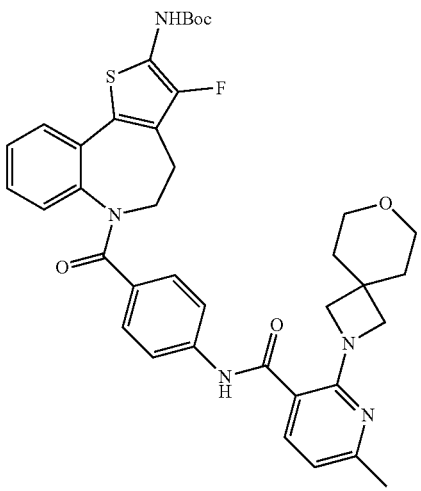 [SMILES: Cc1ccc(C(=O)Nc2ccc(C(=O)N3CCc4c(sc(NC(=O)OC(C)(C)C)c4F)-c4ccccc43)cc2)c(N2CC3(CCOCC3)C2)n1]

To a 100 mL round-bottom flask were added the compound from step f (600 mg, 0.957 mmol), DPPA (526.95 mg, 1.915 mmol), TEA (193.76 mg, 1.915 mmol), and t-BuOH (20 mL) at room temperature. The mixture was stirred for 3 hrs at 80° C. under N$_2$. The resulting mixture was extracted with EtOAc (3×200 mL). The organic layer was separated, dried and concentrated under reduced pressure. The residue was purified by reverse phase column chromatography to afford the desired compound (530 mg, 80.7%) as a red solid. ESI-MS m/z: 698.25 [M+H]$^+$.

Example 303

Step h

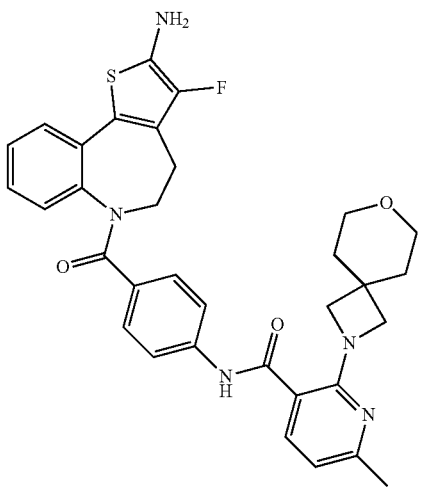 [SMILES: Cc1ccc(C(=O)Nc2ccc(C(=O)N3CCc4c(sc(N)c4F)-c4ccccc43)cc2)c(N2CC3(CCOCC3)C2)n1]

To a 100 mL round-bottom flask were added the compound from step g (530 mg, 0.759 mmol), DCM (15 mL) and TFA (7 mL) at room temperature. The resulting mixture was stirred for 4 h at room temperature. The mixture was neutralized to pH=8 with saturated $Na_2CO_3$ (aq.) and concentrated under reduced pressure. The crude product was purified by reverse phase column chromatography to afford the desired compound (430 mg, 94.7%) as a red solid. ESI-MS m/z: 598.20 [M+H]+.

Example 303

Step i

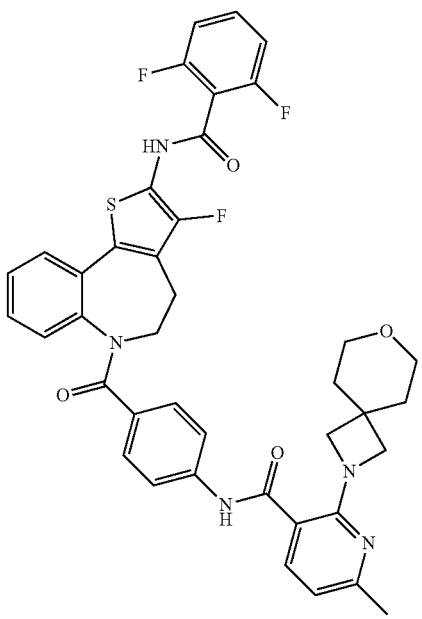 [SMILES: Cc1ccc(C(=O)Nc2ccc(C(=O)N3CCc4c(sc(NC(=O)c5c(F)cccc5F)c4F)-c4ccccc43)cc2)c(N2CC3(CCOCC3)C2)n1]

To a sealed tube were added 2,6-difluorobenzoic acid (23.81 mg, 0.151 mmol), (1-chloro-2-methylprop-1-en-1-yl) dimethylamine (40.24 mg, 0.301 mmol) and DCM (2 mL, 62.920 mmol). The mixture was stirred 1 h at rt and then concentrated under vacuum. To the residue were added the compound from step h (60 mg, 0.100 mmol), pyridine (0.3 mL) and DCM (2 mL) at rt. The reaction mixture was stirred 2 hrs at rt and then concentrated. The residue was purified by Prep-TLC ($CH_2Cl_2$/MeOH=15:1) and followed by Prep-HPLC to afford the desired compound (29.4 mg, 39.7%) as a red solid. ESI-MS m/z: 738.25 [M+H]+.

Example 304-311 shown in table 24 were prepared using the procedure similar to that of example 303 from the corresponding intermediates.

TABLE 24

| Example | Structure | ESI-MS m/z: [M + H]+ |
|---|---|---|
| 304 | 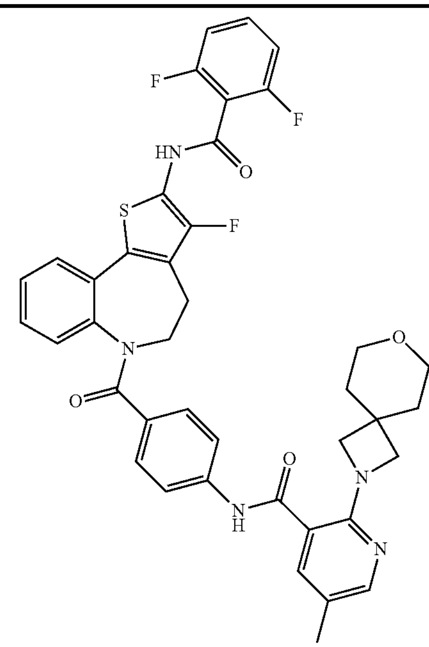 | 738.3 |
| 305 | 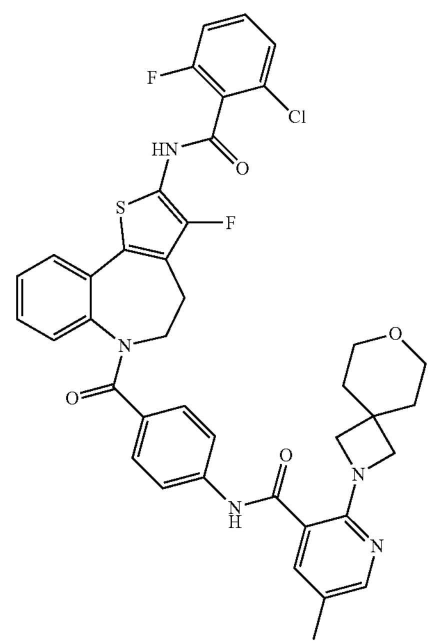 [SMILES: Cc1cnc(N2CC3(CCOCC3)C2)c(C(=O)Nc2ccc(C(=O)N3CCc4c(sc(NC(=O)c5c(F)cccc5Cl)c4F)-c4ccccc43)cc2)c1] | 754.2 |

TABLE 24-continued
| Example | Structure | ESI-MS m/z: [M + H]+ |
|---|---|---|
| 306 | 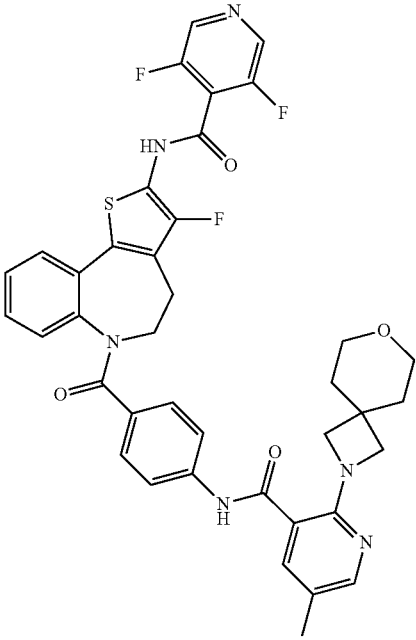 [SMILES: Cc1cnc(N2CC3(CCOCC3)C2)c(C(=O)Nc2ccc(C(=O)N3CCc4c(sc(NC(=O)c5c(F)cncc5F)c4F)-c4ccccc43)cc2)c1] | 739.2 |
| 307 | 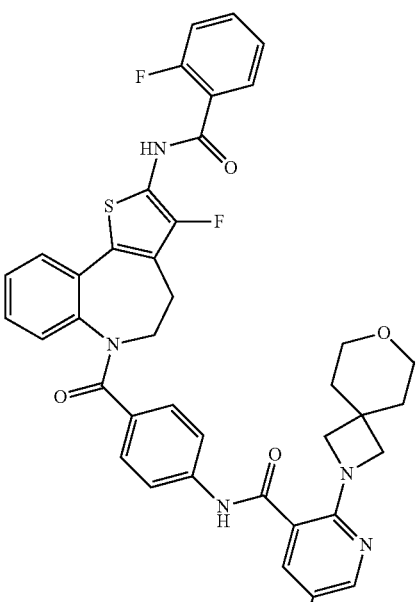 | 720.3 |
TABLE 24-continued
| Example | Structure | ESI-MS m/z: [M + H]+ |
|---|---|---|
| 308 | 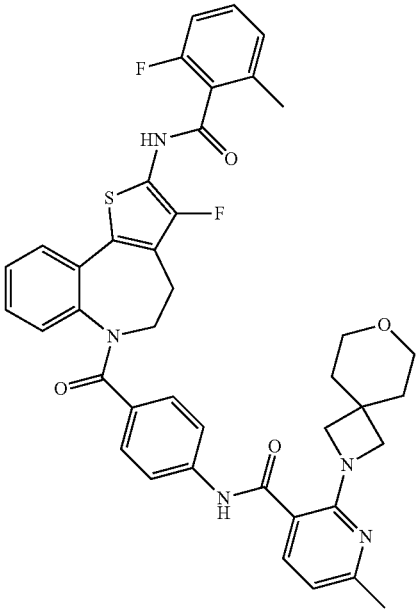 [SMILES: Cc1ccc(C(=O)Nc2ccc(C(=O)N3CCc4c(sc(NC(=O)c5c(C)cccc5F)c4F)-c4ccccc43)cc2)c(N2CC3(CCOCC3)C2)n1] | 734.3 |
| 309 | 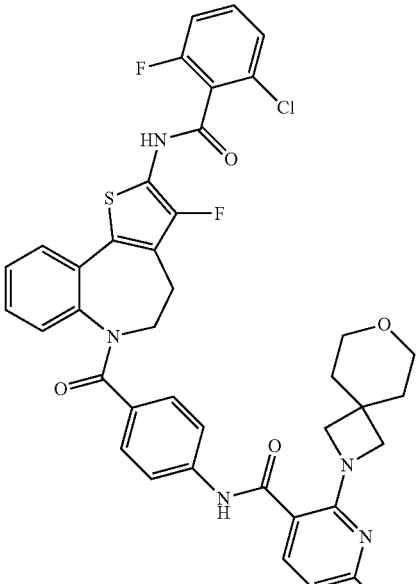 | 754.2 |

TABLE 24-continued

| Example | Structure | ESI-MS m/z: [M + H]+ |
|---|---|---|
| 310 | 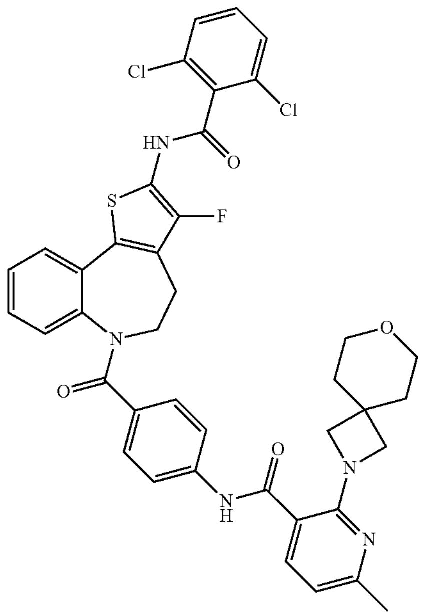 [SMILES: Cc1ccc(C(=O)Nc2ccc(C(=O)N3CCc4c(sc(NC(=O)c5c(Cl)cccc5Cl)c4F)-c4ccccc43)cc2)c(N2CC3(CCOCC3)C2)n1] | 770.2 |
| 311 | 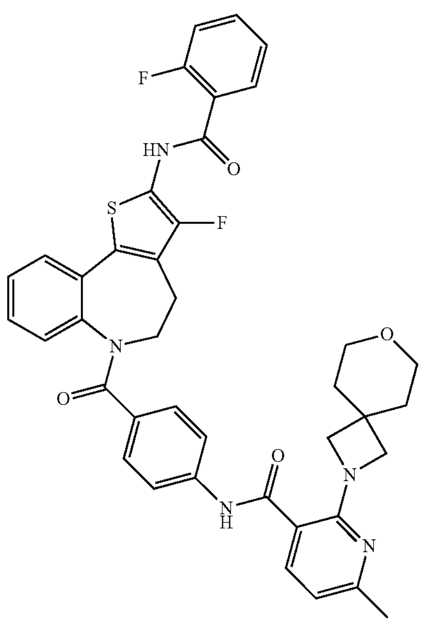 [SMILES: Cc1ccc(C(=O)Nc2ccc(C(=O)N3CCc4c(sc(NC(=O)c5ccccc5F)c4F)-c4ccccc43)cc2)c(N2CC3(CCOCC3)C2)n1] | 720.3 |

Assays
Introduction

RSV is a single stranded negative sense RNA virus that causes respiratory tract infections which can be dangerous to infants, the elderly, and immunosuppressed individuals. Currently there is no vaccine, and therapeutic options are both costly and of limited effectiveness. These approved treatments are Ribavirin, and Palivizumab/Synagis (a monoclonal antibody). RSV has two genotypes, A and B, which differ primarily in the structure of the virus' surface "G" attachment protein. Our current primary screen focuses on RSV-A and uses an in vitro cytoprotection assay where compounds are added in 2-fold dilutions to cells which are then subjected to fully replicative viral particles. Cell viability is measured several days later along with separate measurements of compound cytotoxicity. This report focuses on the results of our most recent screening of compounds.

Methods

HEp-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 3-fold viral dilutions across a 96-well plate, cultured for 4 days.

The control compound currently used in the RSV assay is RSV-604, a ~2.4 µM $EC_{50}$ nucleocapsid inhibitor previously developed by Novartis. Following extensive parameter testing, the final assay is run as follows: HEp-2 cells are seeded into the inner 60 wells of a 96-well plate at 8,000 cells per well in a volume of 50 µL using Growth Media (DMEM without phenol red, 1% L-Glut, 1% Penn/Strep, 1% nonessential amino acids, 10% FBS). 2-Fold serial dilutions of control and test compounds are added to the wells in duplicate in a total volume of 25 µL. Viral stock is then added to the wells in a volume of 25 bringing the total volume of each well to 100 µL. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 uL of growth media containing an equal quantity of sucrose as those wells receiving the viral stock in order to keep consistent in media and volume conditions. The outer wells of the plate are filled with 125 µL of growth media to act as a thermal and evaporative moat around the test wells. Following a 4-day incubation period, the plates are read using ATPlite (50 uL added per well), which quantifies the amount of ATP (a measure of cell health) present in each well. Assay plates are read using the Envision luminometer. In parallel, cytotoxicity is examined on an additional 96-well plate treated in an identical manner, but substituting the 25 µL of viral stock for 25 µL of growth media. These data are used to calculate the $EC_{50}$ of each compound. $EC_{50}$ ranges are as follows: A<0.01 µM; B 0.01-0.05 µM; C>0.05 µM.

TABLE 25

Summary of Activities

| Example | Human RSV-A ("Long" strain) $EC_{50}$ | Example | Human RSV-A ("Long" strain) $EC_{50}$ |
|---|---|---|---|
| 3 | A | 4 | C |
| 5 | A | 6 | A |
| 7 | A | 8 | A |
| 9 | A | 10 | B |
| 11 | A | 12 | A |
| 13 | A | 14 | A |
| 15 | A | 16 | A |
| 17 | B | 18 | B |
| 19 | A | 20 | A |
| 21 | A | 22 | A |

TABLE 25-continued

Summary of Activities

| Example | Human RSV-A ("Long" strain) EC$_{50}$ | Example | Human RSV-A ("Long" strain) EC$_{50}$ | Example | Human RSV-A ("Long" strain) EC$_{50}$ | Example | Human RSV-A ("Long" strain) EC$_{50}$ |
|---|---|---|---|---|---|---|---|
| 23 | B | 24 | B | 171 | A | 172 | A |
| 25 | B | 26 | A | 173 | A | 174 | C |
| 27 | B | 28 | B | 175 | C | 176 | C |
| 29 | B | 30 | B | 177 | B | 178 | A |
| 31 | B | 32 | C | 179 | A | 180 | B |
| 33 | C | 34 | C | 181 | A | 182 | A |
| 35 | A | 36 | A | 183 | A | 184 | A |
| 37 | A | 38 | B | 185 | A | 186 | B |
| 39 | B | 40 | B | 187 | A | 188 | B |
| 41 | C | 42 | B | 189 | A | 190 | A |
| 43 | B | 44 | B | 191 | B | 192 | A |
| 45 | B | 46 | B | 193 | A | 194 | B |
| 47 | B | 48 | B | 195 | B | 196 | C |
| 49 | C | 50 | B | 197 | A | 198 | A |
| 51 | C | 52 | C | 199 | A | 200 | A |
| 53 | C | 54 | C | 201 | A | 202 | B |
| 55 | C | 56 | C | 203 | B | 204 | A |
| 57 | C | 58 | C | 205 | A | 206 | A |
| 59 | C | 60 | C | 207 | A | 208 | A |
| 61 | B | 62 | C | 209 | A | 210 | A |
| 63 | C | 64 | C | 211 | A | 212 | B |
| 65 | A | 66 | A | 213 | A | 214 | A |
| 67 | A | 68 | B | 215 | A | 216 | A |
| 69 | B | 70 | B | 217 | A | 218 | A |
| 71 | B | 72 | B | 219 | A | 220 | A |
| 73 | B | 74 | B | 221 | A | 222 | A |
| 75 | B | 76 | A | 223 | B | 224 | B |
| 77 | B | 78 | A | 225 | C | 226 | A |
| 79 | B | 80 | B | 227 | B | 228 | B |
| 81 | B | 82 | B | 229 | B | 230 | A |
| 83 | A | 84 | B | 231 | A | 232 | C |
| 85 | C | 86 | C | 233 | A | 234 | A |
| 87 | B | 88 | A | 235 | A | 236 | A |
| 89 | A | 90 | B | 237 | A | 238 | B |
| 91 | A | 92 | A | 239 | A | 240 | A |
| 93 | A | 94 | A | 241 | A | 242 | A |
| 95 | A | 96 | A | 243 | A | 244 | A |
| 97 | B | 98 | B | 245 | B | 246 | A |
| 99 | A | 100 | A | 247 | A | 248 | A |
| 101 | A | 102 | A | 249 | A | 250 | A |
| 103 | A | 104 | A | 251 | A | 252 | A |
| 105 | B | 106 | B | 253 | A | 254 | A |
| 107 | B | 108 | B | 255 | A | 256 | A |
| 109 | B | 110 | A | 257 | A | 258 | A |
| 111 | A | 112 | A | 259 | A | 260 | A |
| 113 | A | 114 | A | 261 | A | 262 | B |
| 115 | A | 116 | A | 263 | B | 264 | B |
| 117 | A | 118 | A | 265 | C | 266 | A |
| 119 | A | 120 | A | 267 | A | 268 | A |
| 121 | A | 122 | C | 269 | B | 270 | A |
| 123 | A | 124 | A | 271 | B | 272 | A |
| 125 | B | 126 | A | 273 | B | 274 | A |
| 127 | B | 128 | B | 275 | A | 276 | B |
| 129 | C | 130 | A | 277 | B | 278 | A |
| 131 | A | 132 | A | 279 | A | 280 | A |
| 133 | B | 134 | A | 281 | B | 282 | A |
| 135 | A | 136 | B | 283 | A | 284 | A |
| 137 | A | 138 | A | 285 | A | 286 | B |
| 139 | A | 140 | A | 287 | B | 288 | C |
| 141 | A | 142 | C | 289 | C | 290 | C |
| 143 | A | 144 | B | 291 | C | 292 | A |
| 145 | B | 146 | B | 293 | B | 294 | B |
| 147 | A | 148 | B | 295 | A | 296 | B |
| 149 | A | 150 | A | 297 | A | 298 | B |
| 151 | A | 152 | B | 299 | B | 300 | C |
| 153 | B | 154 | A | 301 | B | 302 | C |
| 155 | A | 156 | B | 303 | B | 304 | A |
| 157 | B | 158 | A | 305 | A | 306 | A |
| 159 | A | 160 | C | 307 | A | 308 | B |
| 161 | A | 162 | A | 309 | B | 310 | B |
| 163 | A | 164 | A | 311 | B | | |
| 165 | A | 166 | A | | | | |
| 167 | A | 168 | A | | | | |
| 169 | A | 170 | A | | | | |

While this invention has been particularly shown and described with references to preferred embodiments thereof, it will be understood by those skilled in the art that various changes in form and details may be made therein without departing from the scope of the invention encompassed by the appended claims.

What is claimed:
1. A compound represented by Formula (I):

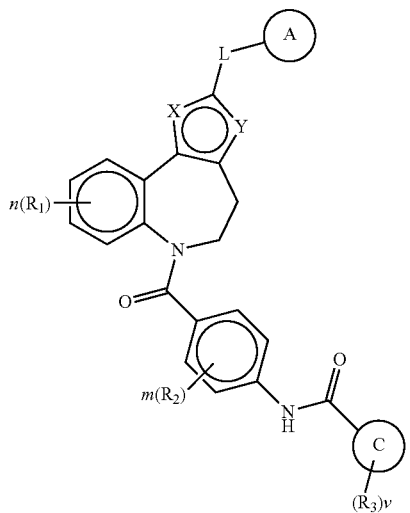

or a pharmaceutically acceptable salt thereof, wherein:
Ⓐ is selected from the group consisting of:
1) optionally substituted aryl;
2) optionally substituted heteroaryl;
3) optionally substituted arylalkyl;
4) optionally substituted heteroarylalkyl;
5) optionally substituted-$C_3$-$C_{12}$ cycloalkyl-$C_1$-$C_6$ alkyl; and
6) optionally substituted-$C_3$-$C_{12}$ cycloalkenyl-$C_1$-$C_6$ alkyl;
Ⓒ is aryl or heteroaryl;
L is —CONH—, —NHCO—, —NHCO$_2$—, or —NHS(O)$_2$—;
One of X and Y is selected from O, S, and NR$_4$, and the other is N or CR$_5$;
Each R$_1$ and R$_2$ is independently selected from the group consisting of: halogen, cyano, nitro, hydroxyl, protected hydroxyl, amino, protected amino, optionally substituted —$C_1$-$C_8$ alkyl, and optionally substituted —$C_1$-$C_8$ alkoxy;
Each R$_3$ is selected from the group consisting of:
1) halogen;
2) optionally substituted —$C_1$-$C_8$ alkoxy;
3) optionally substituted —$C_1$-$C_8$ alkyl;
4) optionally substituted —$C_2$-$C_8$ alkenyl;
5) optionally substituted —$C_2$-$C_8$ alkynyl;
6) optionally substituted —$C_3$-$C_{12}$ cycloalkyl;
7) optionally substituted —$C_3$-$C_{12}$ cycloalkenyl;
8) optionally substituted 3- to 12-membered heterocycloalkyl;
9) optionally substituted aryl;
10) optionally substituted heteroaryl;
11) optionally substituted arylalkyl;
12) optionally substituted aryloxy;
13) —C(O)R$_{12}$;
14) —C(O)NR$_{13}$R$_{14}$;
15) —C(O)NR$_{11}$S(O)$_2$R$_{12}$;
16) —S(O)$_2$NR$_{13}$R$_{14}$;
17) —NR$_{13}$R$_{14}$;
18) —NR$_{11}$S(O)$_2$R$_{12}$;
19) —NR$_{11}$C(O)R$_{12}$;
20) —NR$_{11}$C(O)NR$_{13}$R$_{14}$; and
21) —NR$_{11}$C(O)NHS(O)$_2$R$_{12}$;
n is 0, 1, 2, 3 or 4;
m is 0, 1, 2, 3 or 4;
v is 0, 1, 2, or 3;
R$_4$ is hydrogen or optionally substituted —$C_1$-$C_8$ alkyl;
R$_5$ is halogen or optionally substituted —$C_1$-$C_8$ alkoxy;
R$_{12}$ at each occurrence is independently selected from the group consisting of:
1) Hydrogen;
2) Halogen;
3) Hydroxyl;
4) optionally substituted —$C_1$-$C_8$ alkoxy;
5) optionally substituted —$C_1$-$C_8$ alkyl;
6) optionally substituted —$C_2$-$C_8$ alkenyl;
7) optionally substituted —$C_2$-$C_8$ alkynyl;
8) optionally substituted —$C_3$-$C_8$ cycloalkyl;
9) optionally substituted —$C_3$-$C_8$ cycloalkenyl;
10) optionally substituted 3- to 8-membered heterocycloalkyl;
11) optionally substituted aryl;
12) optionally substituted arylalkyl;
13) optionally substituted heteroaryl; and
14) optionally substituted heteroarylalkyl; and
R$_{11}$, R$_{13}$ and R$_{14}$ are each independently selected from hydrogen, optionally substituted —$C_1$-$C_8$-alkyl, optionally substituted —$C_2$-$C_8$-alkenyl, optionally substituted —$C_2$-$C_8$-alkynyl; optionally substituted —$C_3$-$C_8$-cycloalkyl, optionally substituted 3- to 8-membered heterocyclic, optionally substituted aryl, optionally substituted arylalkyl, optionally substituted heteroaryl, and optionally substituted heteroarylalkyl; alternatively R$_{13}$ and R$_{14}$ are taken together with the nitrogen atom to which they are attached to form an optionally substituted heterocyclic ring.

2. The compound of claim 1, wherein L is —CONH— or —NHCO—.

3. The compound of claim 1, wherein Ⓐ is selected from the groups

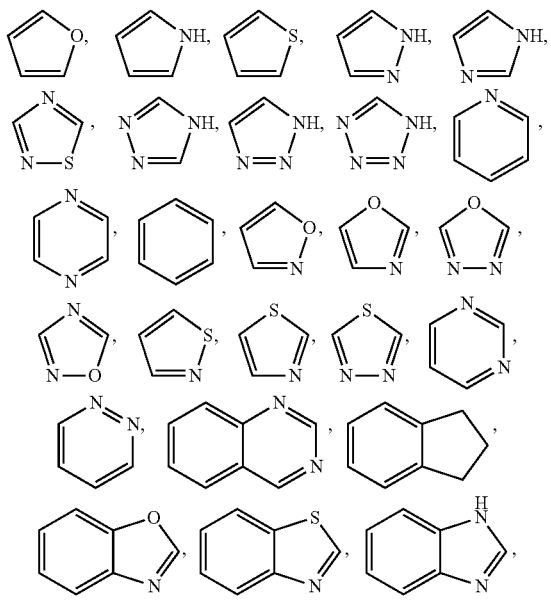

-continued

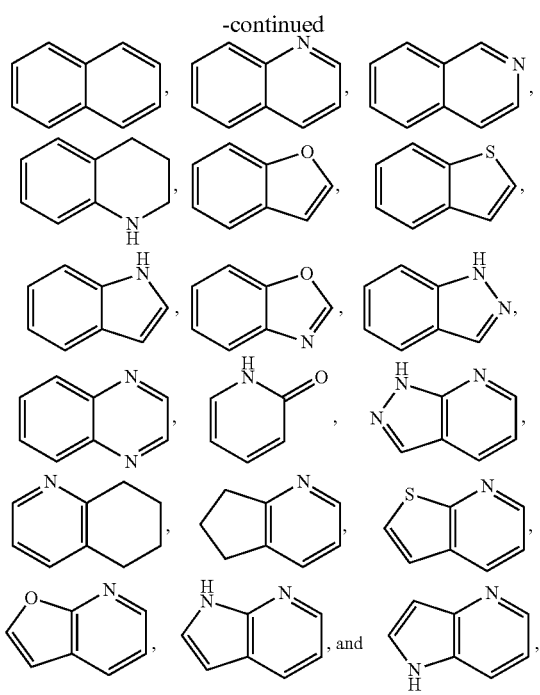

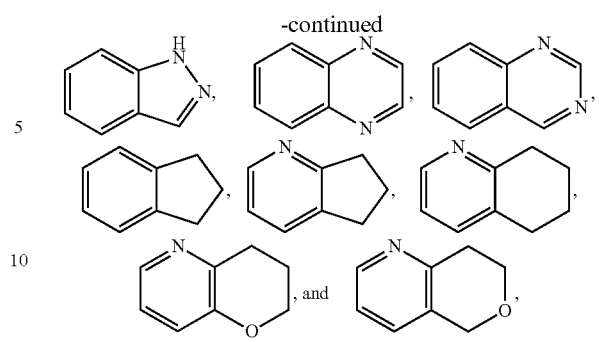

by removal of one hydrogen atom, wherein each of the groups is optionally substituted.

5. The compound of claim 1, wherein $R_3$ is selected from the following groups

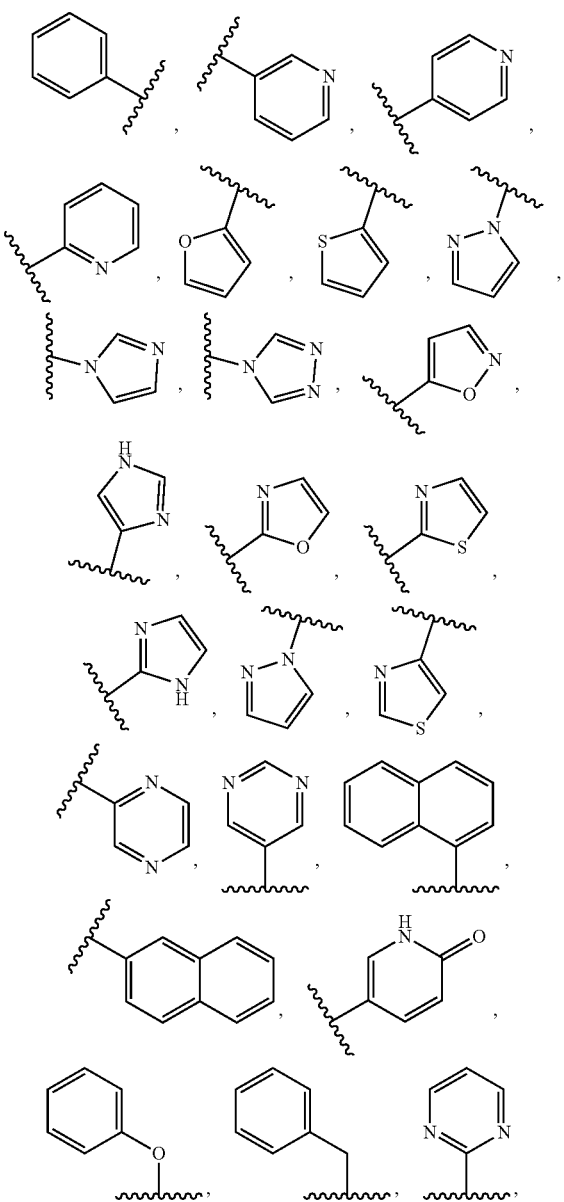

by removal of one hydrogen atom, wherein each of the groups is optionally substituted.

4. The compound of claim 1, wherein Ⓒ is selected from one of the following groups by removal of one hydrogen atom, wherein each of the groups is optionally substituted:

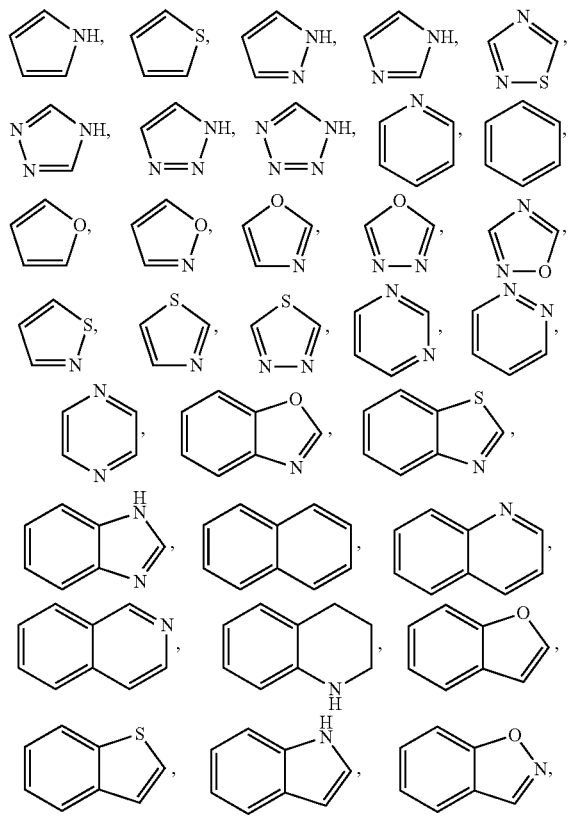

-continued
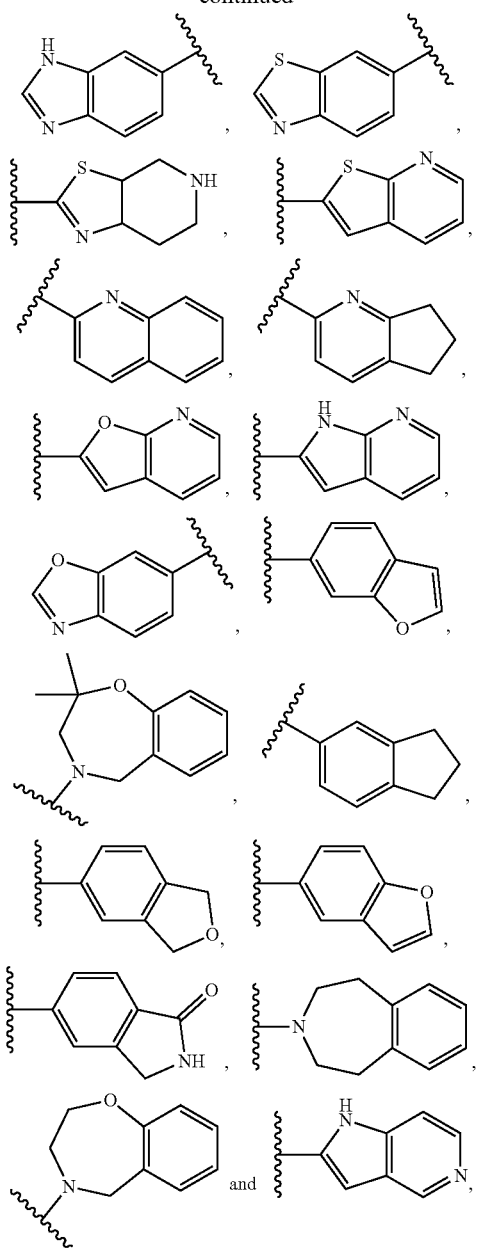
wherein each group is optionally substituted.
6. The compound of claim 1, wherein
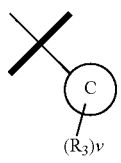
is represented by
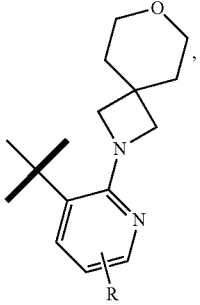
where R is hydrogen or methyl.
7. The compound of claim 1, represented by one of Formulas:
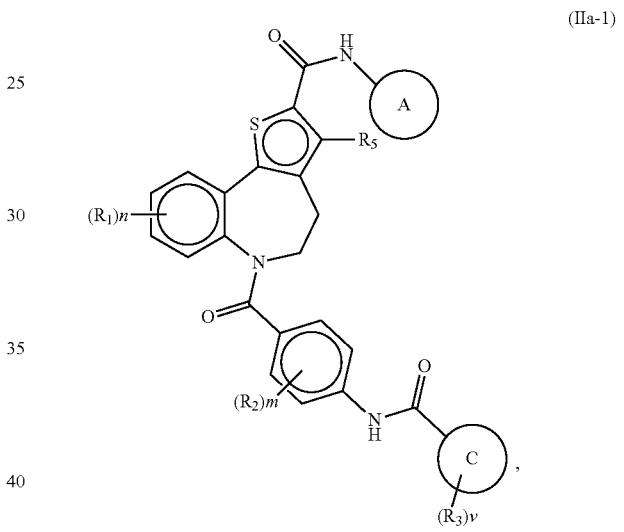
(IIa-1)
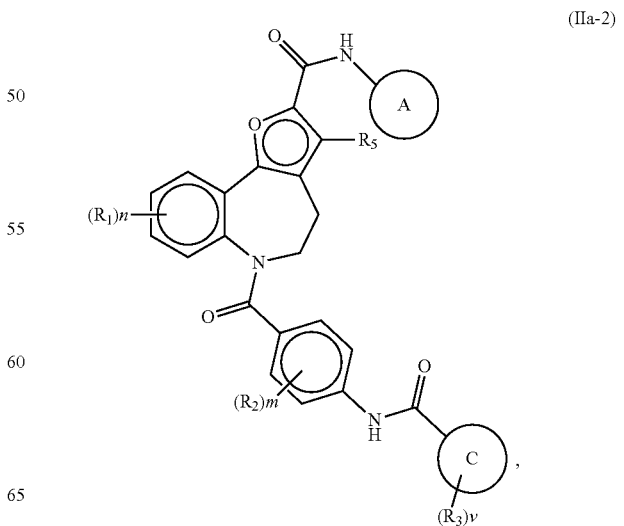
(IIa-2)

(IIa-3) 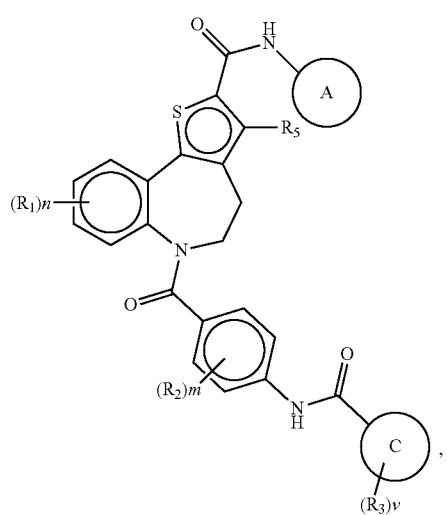
(IIa-4) 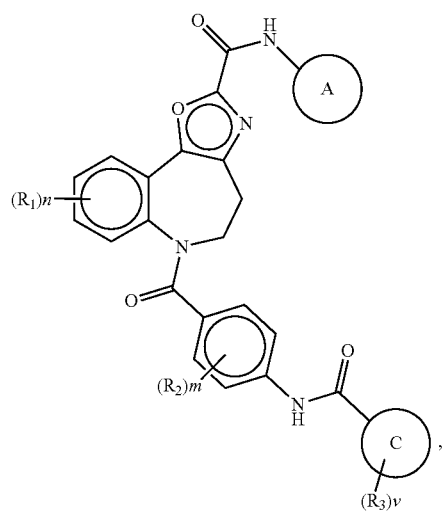
(IIc-1)
(IIc-2) 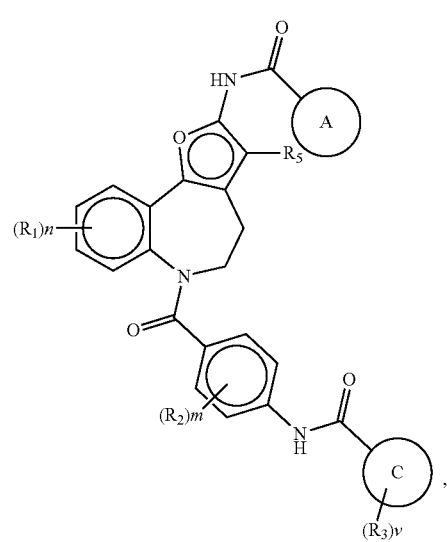
(IIc-3)
(IIc-4)
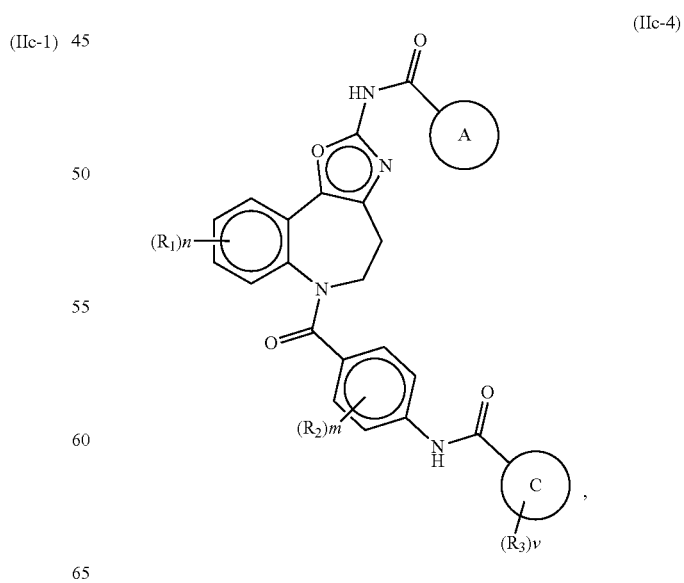
or a pharmaceutically acceptable salt thereof, wherein Ⓐ, Ⓒ, $R_1$, $R_2$, $R_3$, $R_5$, n, m, and v are as defined in claim 1.

8. The compound of claim 1, represented by one of Formulas

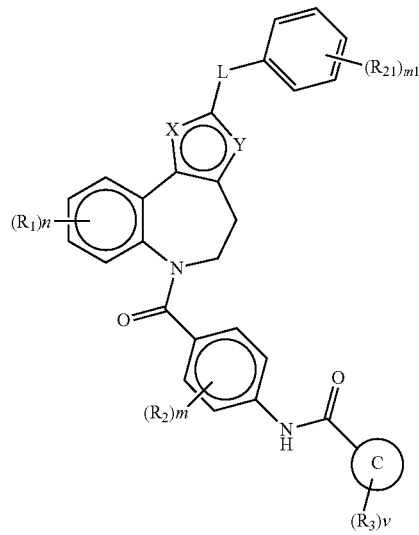
(IIIa)

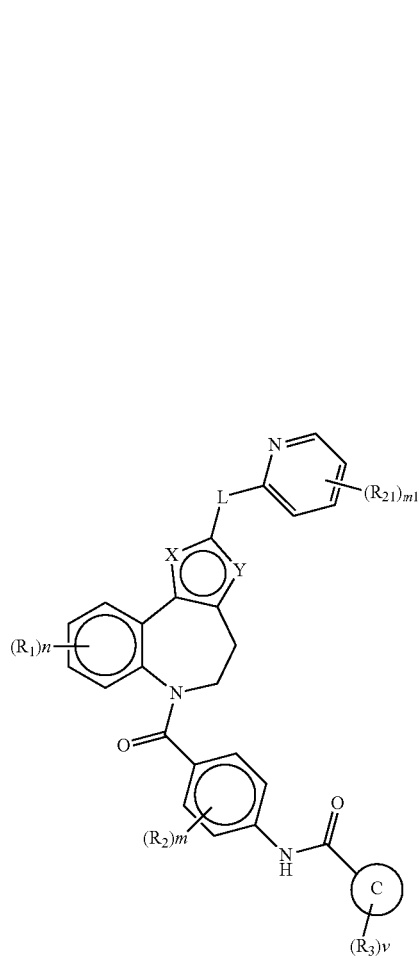
(IIIb)

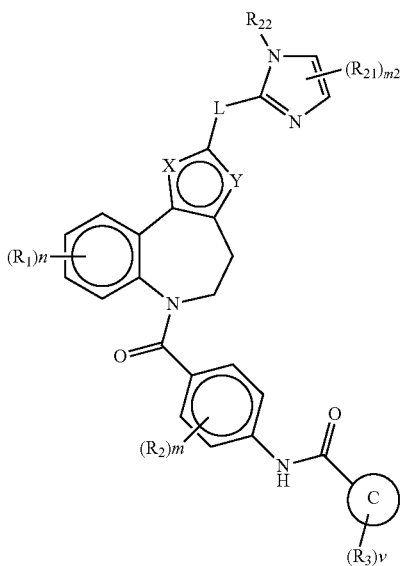
(IIIc)

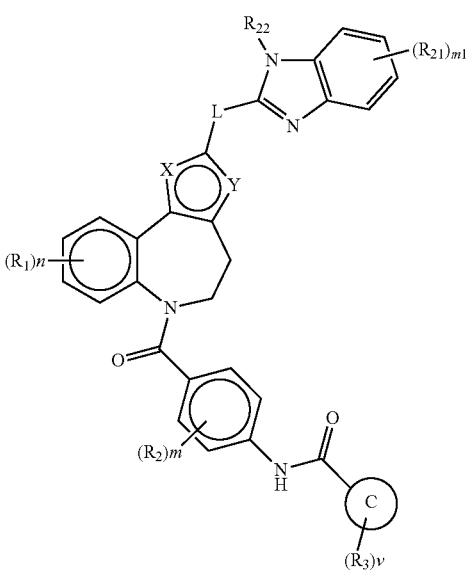
(IIId)

or a pharmaceutically acceptable salt thereof, wherein C, L, X, Y, $R_1$, $R_2$, $R_3$, n, m, and v are as defined in claim 1; m1 is 0, 1, 2, 3 or 4; m2 is 0, 1 or 2; $R_{22}$ is selected from hydrogen and —$CH_3$; and each $R_{21}$ is independently selected from halogen, —$NH_2$, optionally substituted —$C_1$-$C_3$ alkyl, and optionally substituted —$C_1$-$C_3$ alkoxy.

9. The compound of claim 1, represented by one of the Formulas

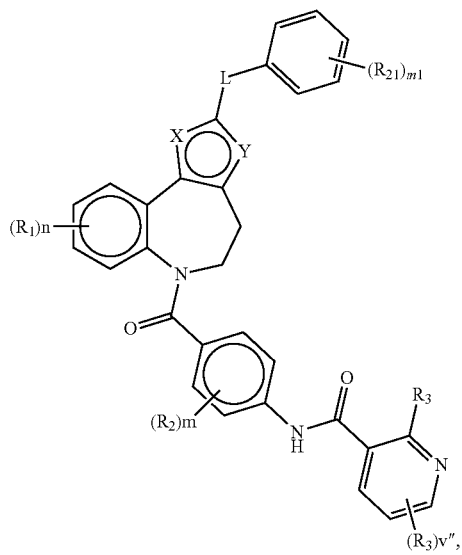
(IVa-1)
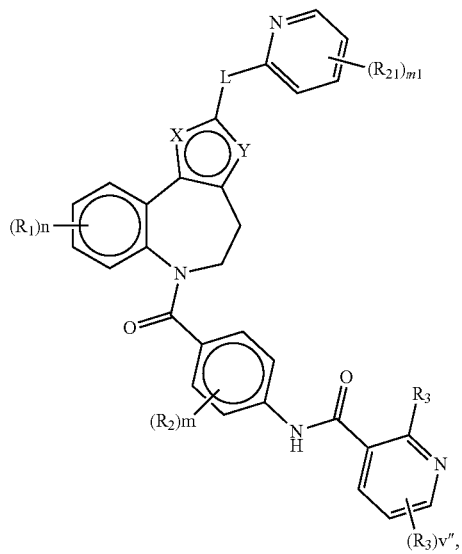
(IVb-1)
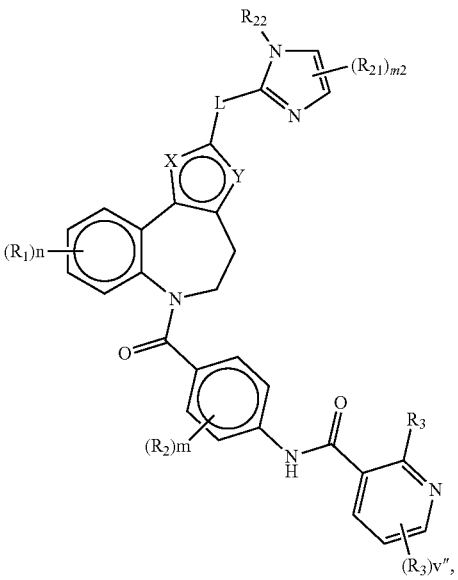
(IVc-1)
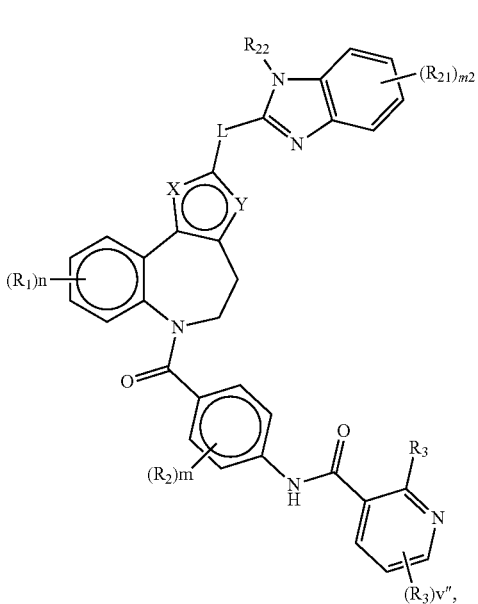
(IVd-1)

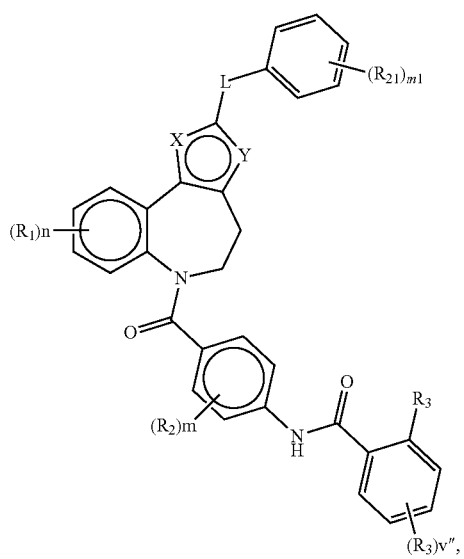
(IVa-2)
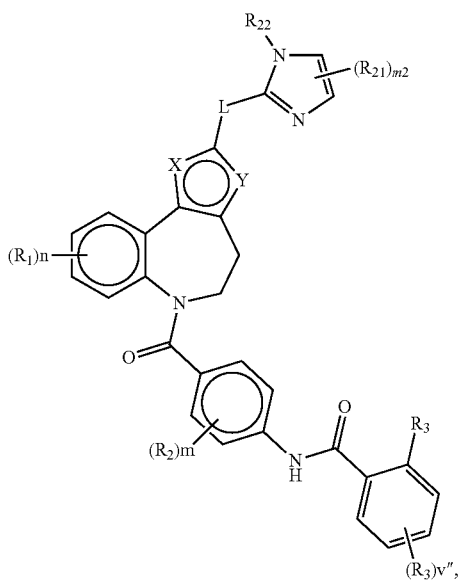
(IVc-2)
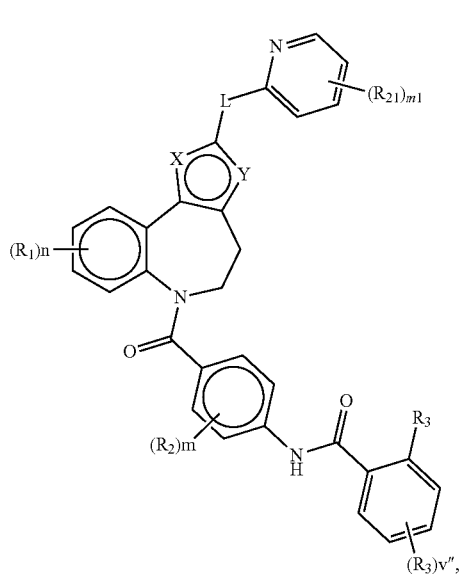
(IVb-2)
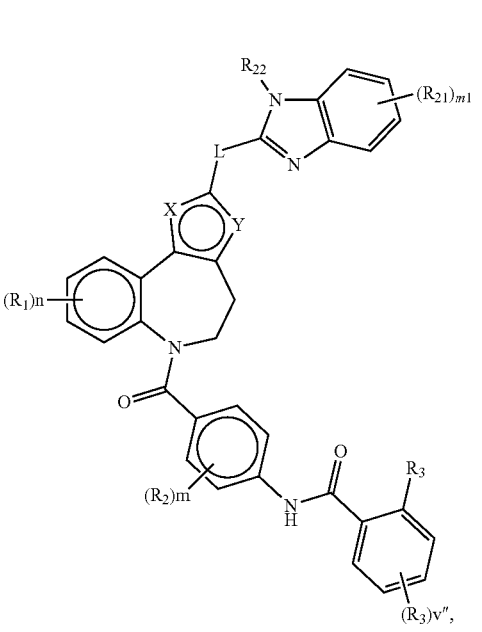
(IVd-2)

-continued
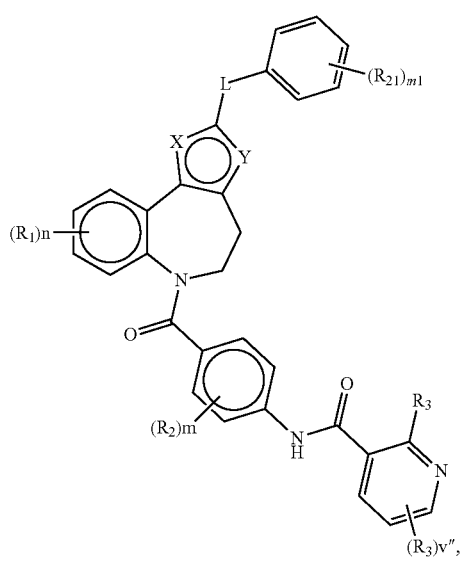
(IVa-1)
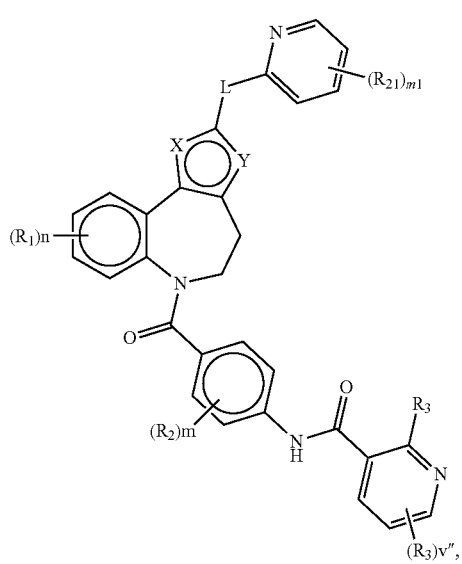
(IVb-1)
-continued
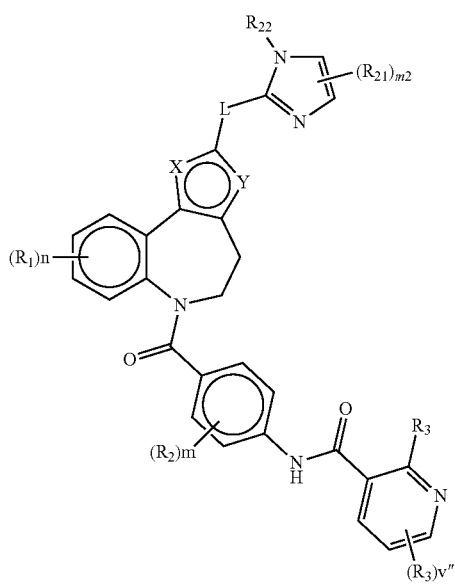
(IVc-1)
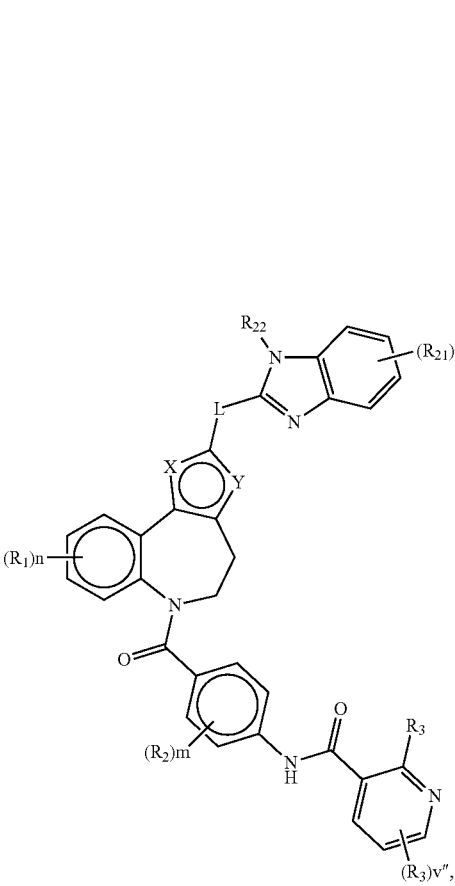
(IVd-1)

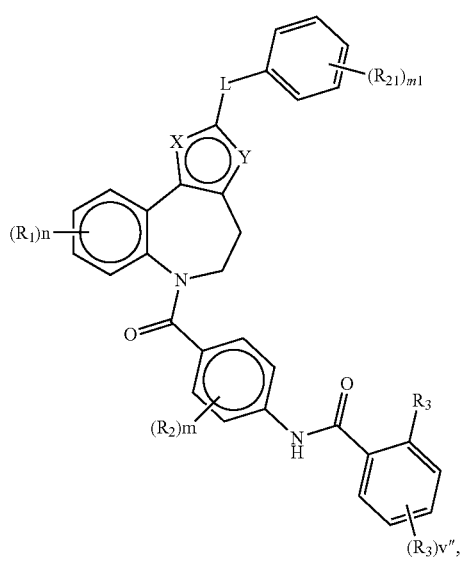
(IVa-2)
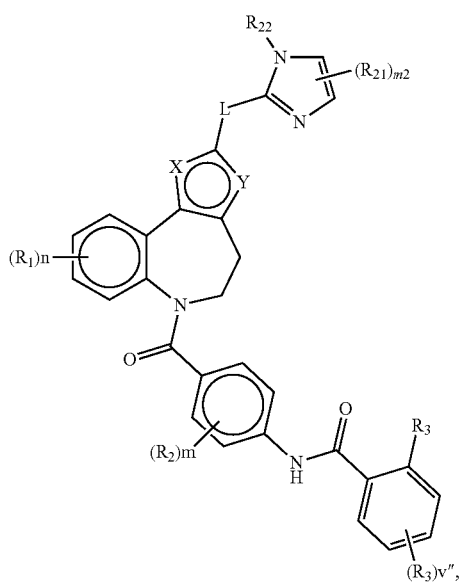
(IVc-2)
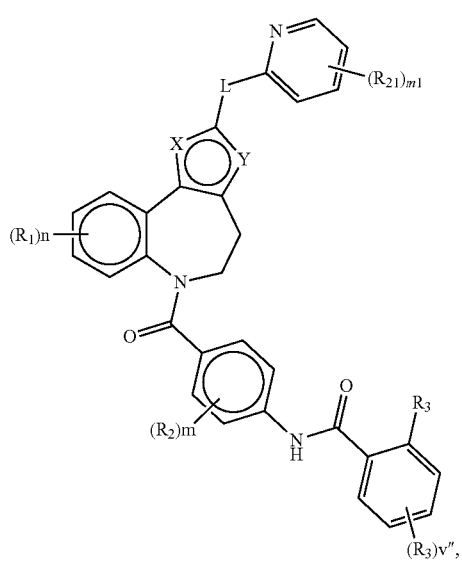
(IVb-2)
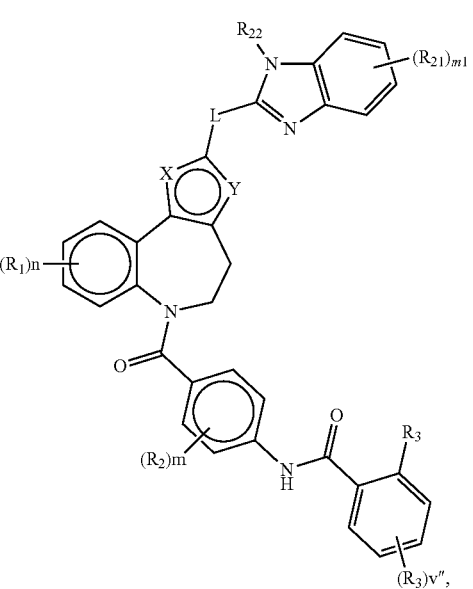
(IVd-2)

-continued
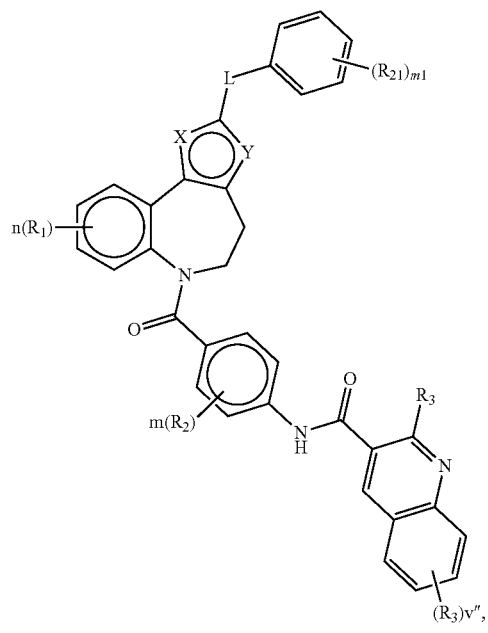
(IVa-3)
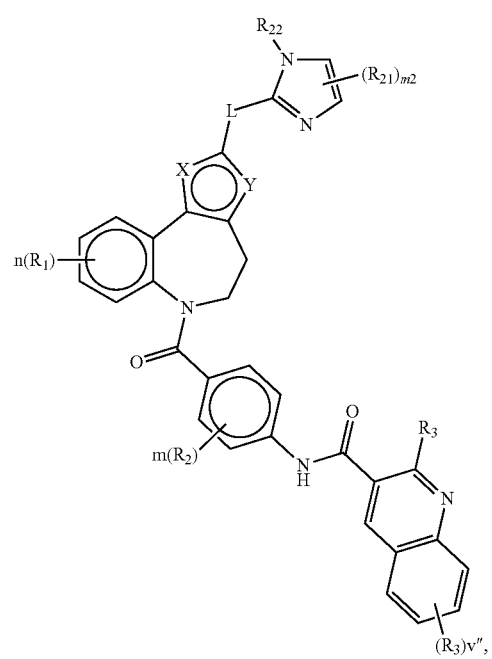
(IVc-3)
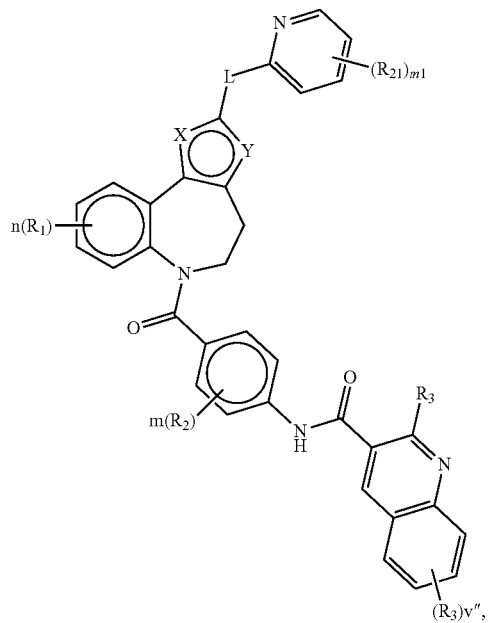
(IVb-3)
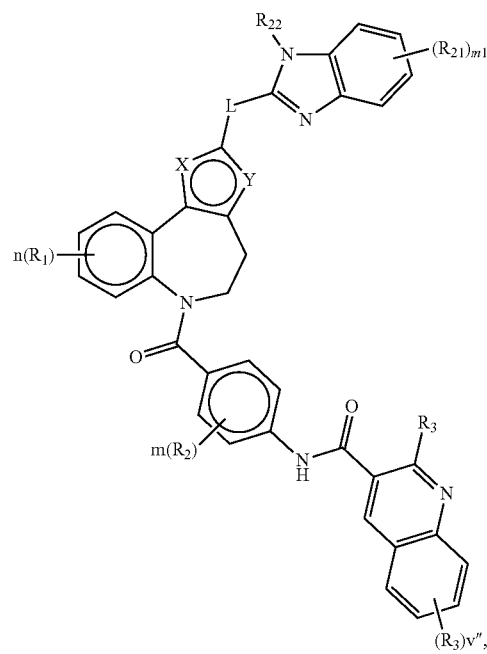
(IVd-3)

413
-continued

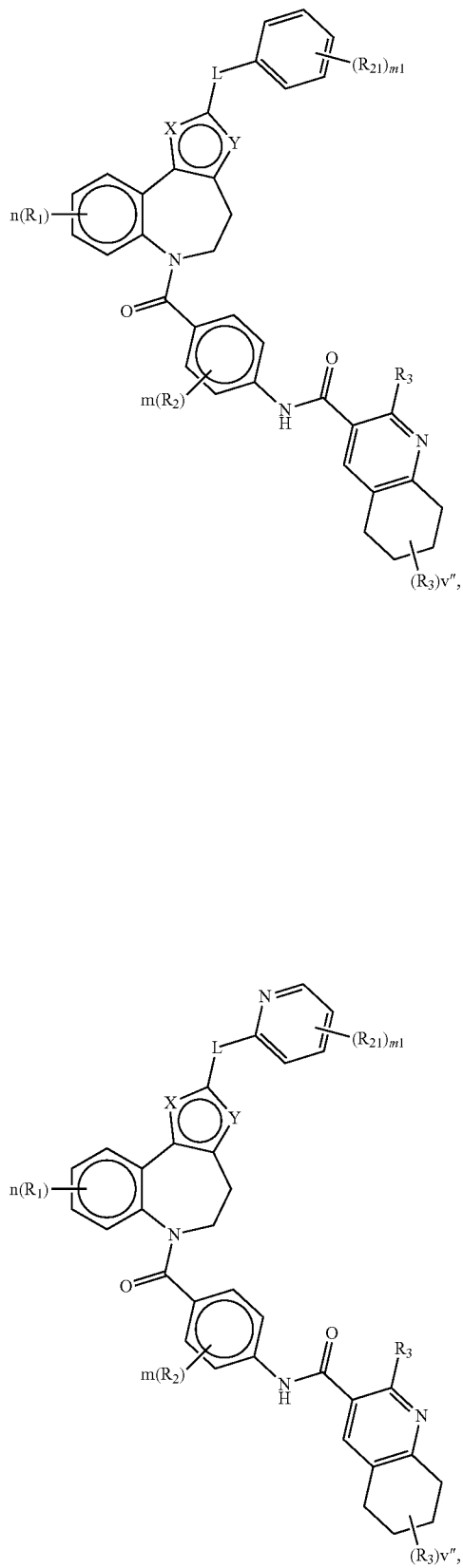

(IVa-4)

(IVb-4)

414
-continued

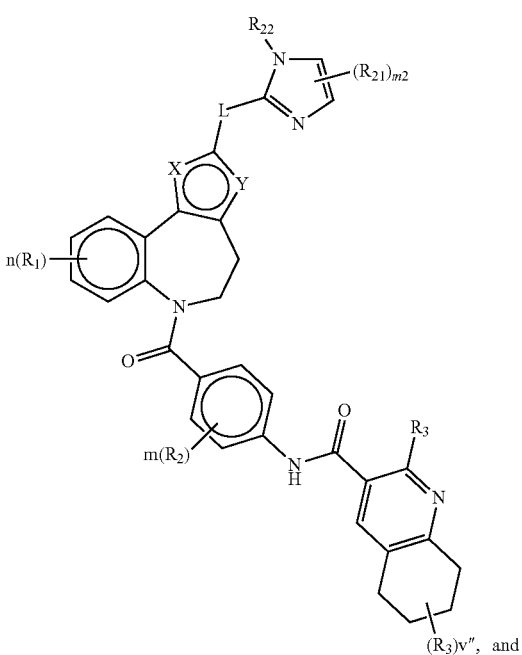

(IVc-4)

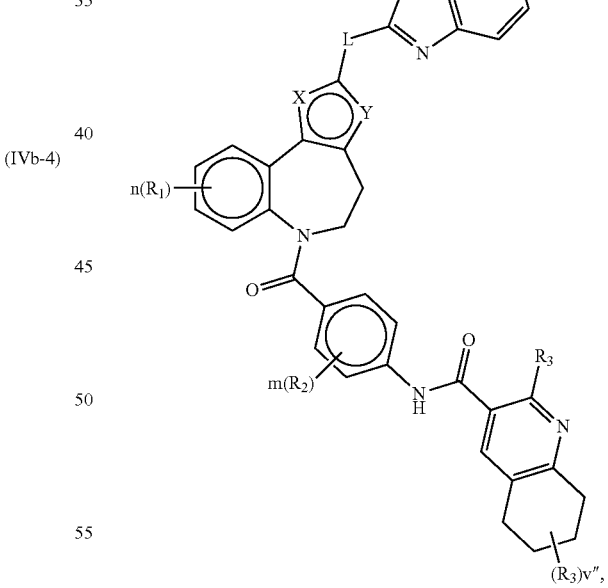

(IVd-4)

or a pharmaceutically acceptable salt thereof, wherein X, Y, L, R$_1$, R$_2$, R$_3$, n and m are as defined in claim 1; m1 is 0, 1, 2, 3 or 4; m2 is 0, 1 or 2; v' is 0, 1, 2, or 3; v" is 0, 1, or 2; R$_{22}$ is selected from hydrogen and —CH$_3$; and each R$_{21}$ is independently selected from halogen, —NH$_2$, optionally substituted —C$_1$-C$_3$ alkyl, and optionally substituted —C$_1$-C$_3$ alkoxy.

10. A compound selected from the compounds set forth below, or a pharmaceutically acceptable salt thereof:

| Compound | Structure |
|---|---|
| 3 | 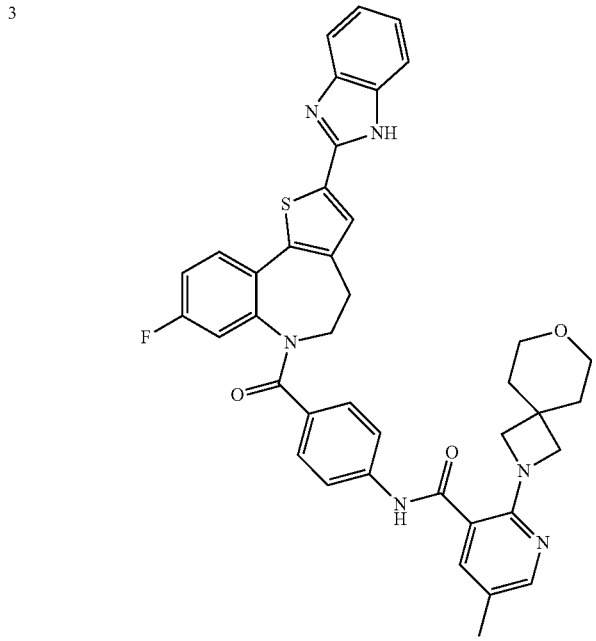 |
| 4 | 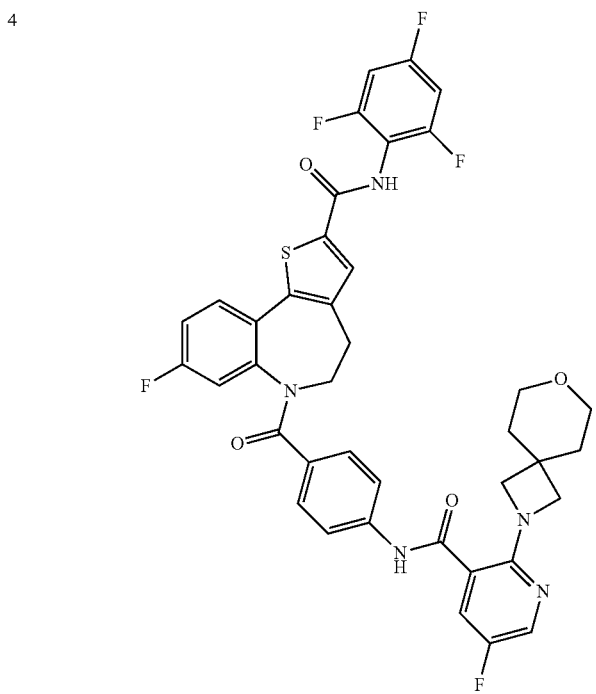 |

-continued
| Compound | Structure |
|---|---|
| 5 | 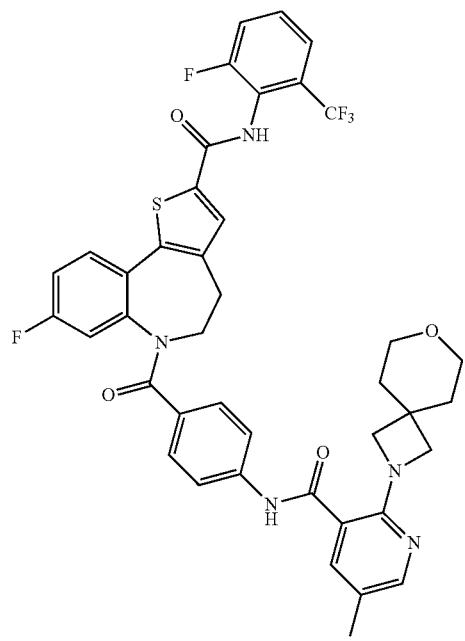 |
| 6 | 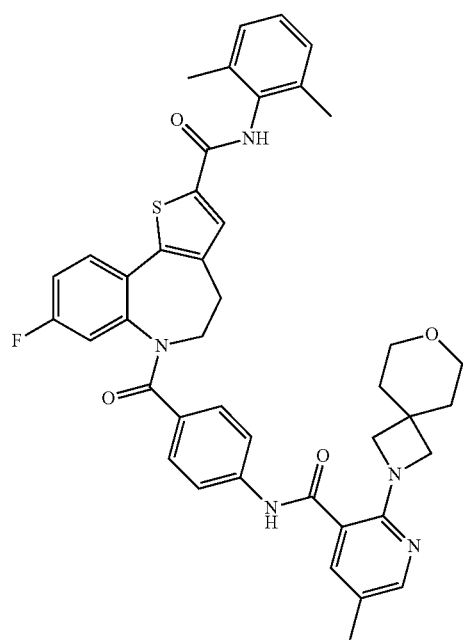 |

-continued
| Compound | Structure |
|---|---|
| 7 | 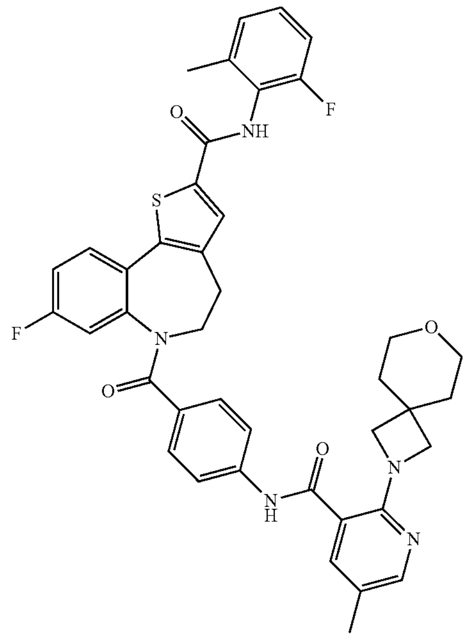 |
| 8 | 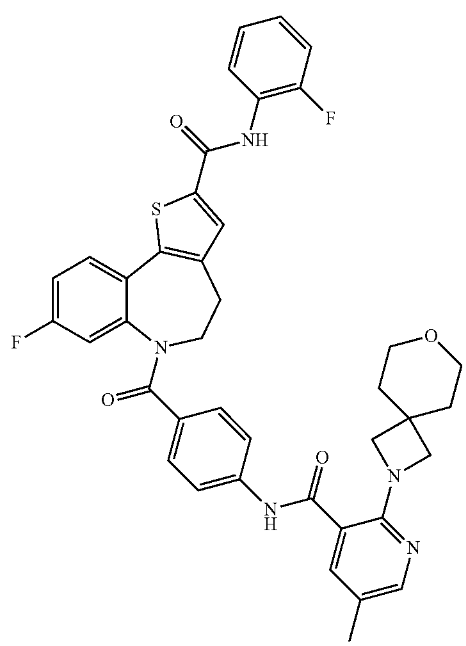 [SMILES: Cc1cnc(N2CC3(CCOCC3)C2)c(C(=O)Nc2ccc(C(=O)N3CCc4cc(C(=O)Nc5ccccc5F)sc4-c4ccc(F)cc43)cc2)c1] |

-continued
| Compound | Structure |
|---|---|
| 9 | 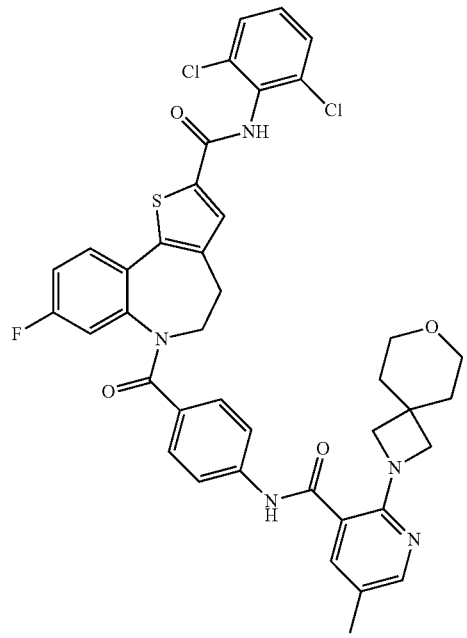 |
| 10 | 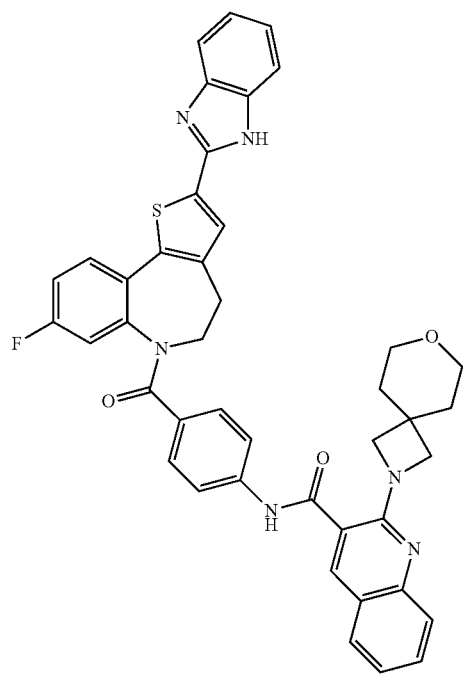 [SMILES: O=C(Nc1ccc(C(=O)N2CCc3cc(-c4nc5ccccc5[nH]4)sc3-c3ccc(F)cc32)cc1)c1cc2ccccc2nc1N1CC2(CCOCC2)C1] |

| Compound | Structure |
|---|---|
| 11 | 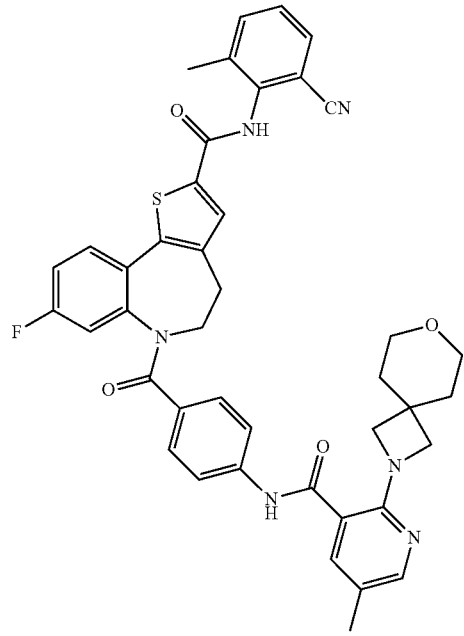 |
| 12 | 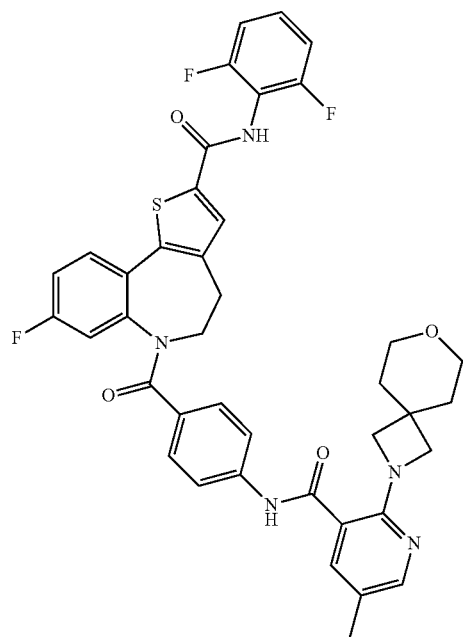 |

-continued
| Compound | Structure |
|---|---|
| 13 | 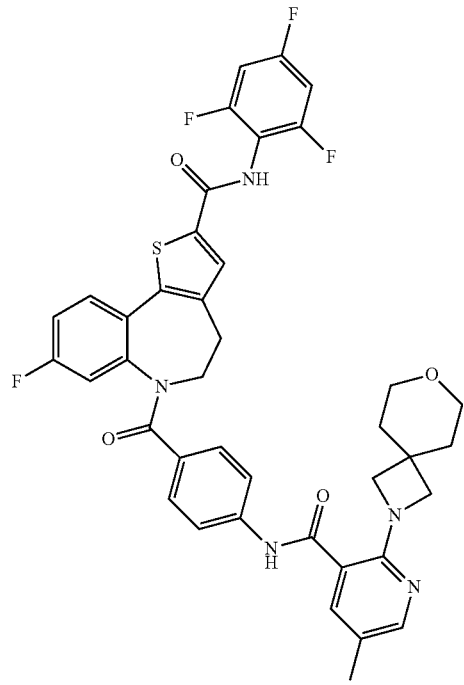 [SMILES: Cc1cnc(N2CC3(CCOCC3)C2)c(C(=O)Nc2ccc(C(=O)N3CCc4cc(C(=O)Nc5c(F)cc(F)cc5F)sc4-c4ccc(F)cc43)cc2)c1] |
| 14 | 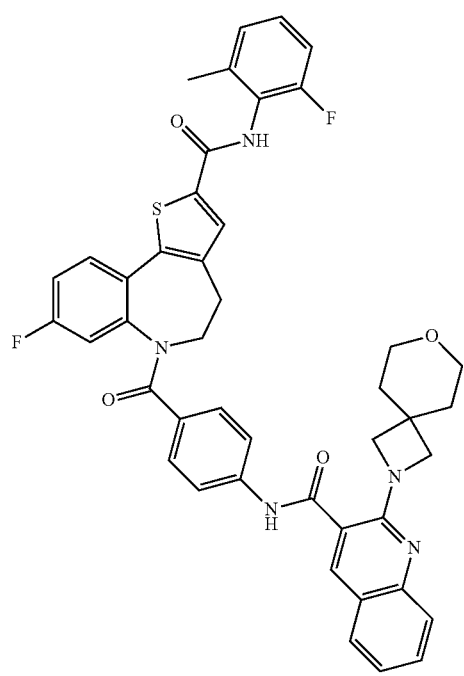 |

-continued
| Compound | Structure |
|---|---|
| 15 | 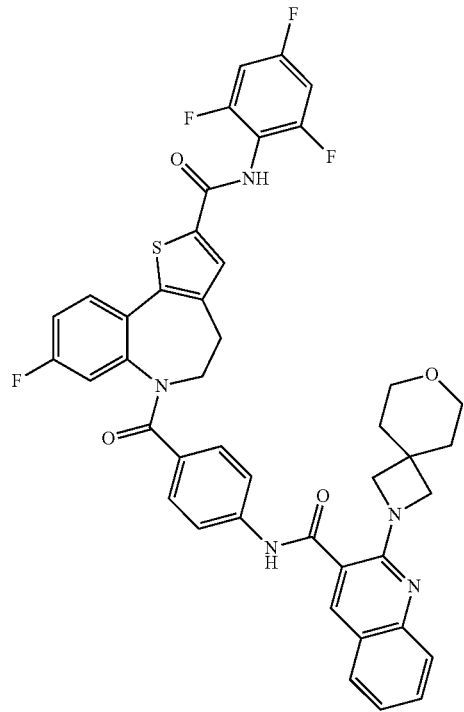 [SMILES: O=C(Nc1c(F)cc(F)cc1F)c1cc2c(s1)-c1ccc(F)cc1N(C(=O)c1ccc(NC(=O)c3cc4ccccc4nc3N3CC4(CCOCC4)C3)cc1)CC2] |
| 16 | 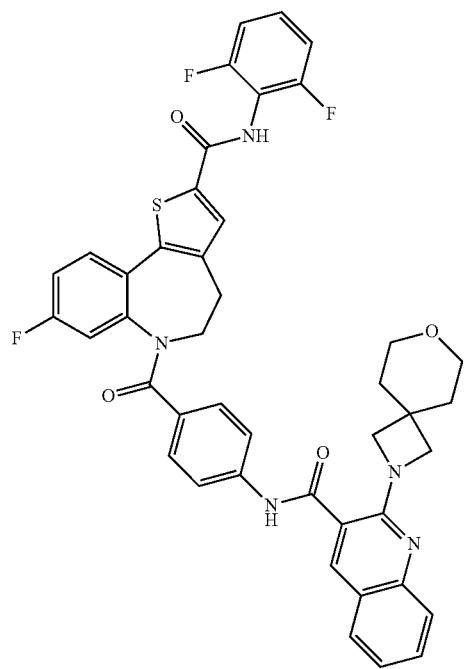 |

| Compound | Structure |
|---|---|
| 17 | 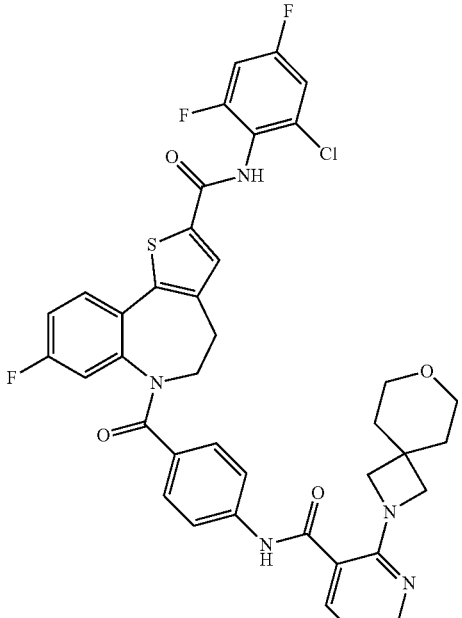 |
| 18 | 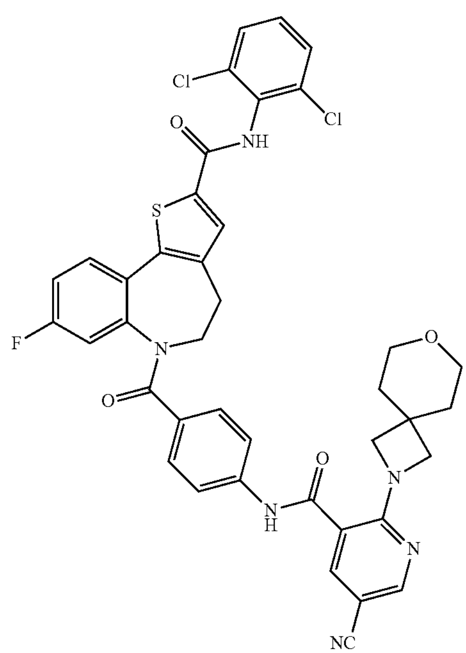 [SMILES: N#Cc1cnc(N2CC3(CCOCC3)C2)c(C(=O)Nc2ccc(C(=O)N3CCc4cc(C(=O)Nc5c(Cl)cccc5Cl)sc4-c4ccc(F)cc43)cc2)c1] |

-continued

| Compound | Structure |
|---|---|
| 19 | 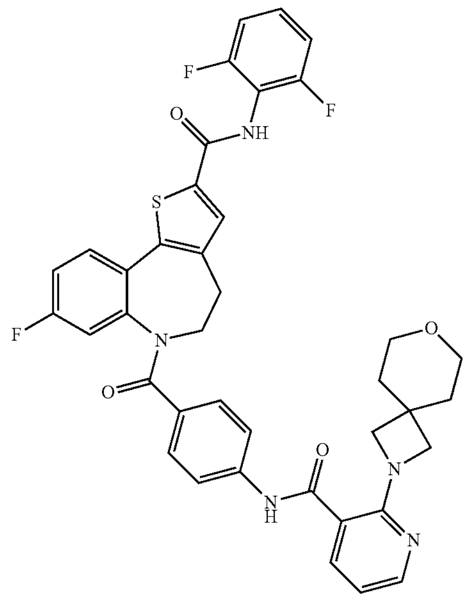 |
| 20 | 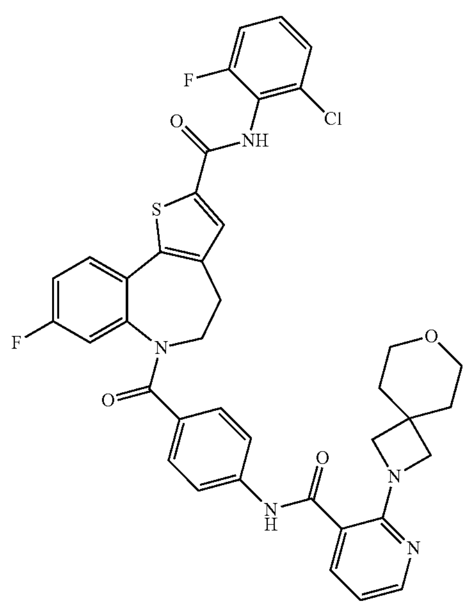 |

| Compound | Structure |
|---|---|
| 21 | 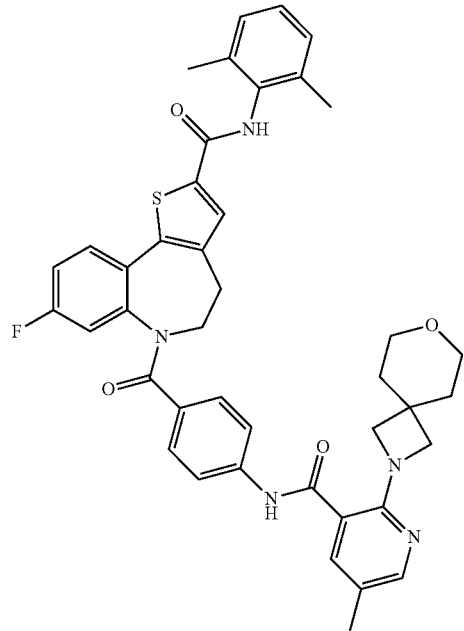 |
| 22 | 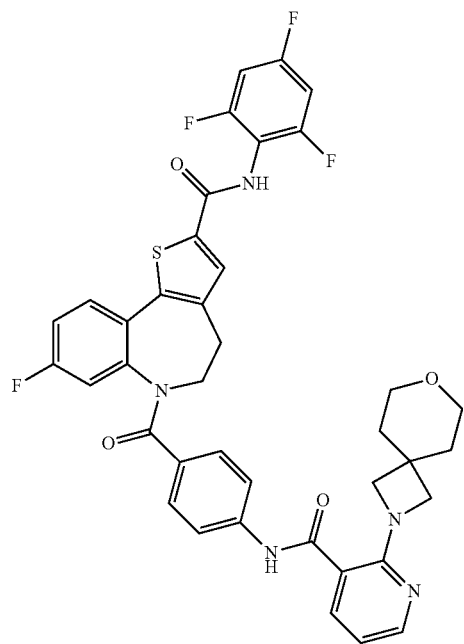 [SMILES: O=C(Nc1c(F)cc(F)cc1F)c1cc2c(s1)-c1ccc(F)cc1N(C(=O)c1ccc(NC(=O)c3cccnc3N3CC4(CCOCC4)C3)cc1)CC2] |

-continued
| Compound | Structure |
|---|---|
| 23 | 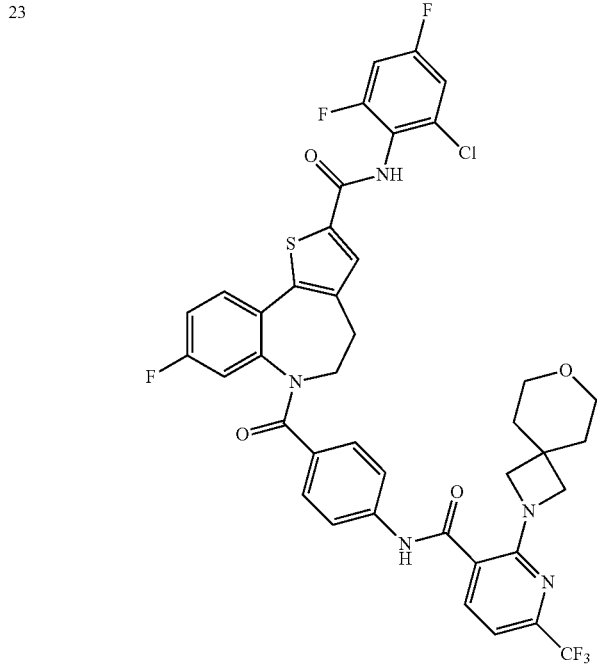 |
| 24 | 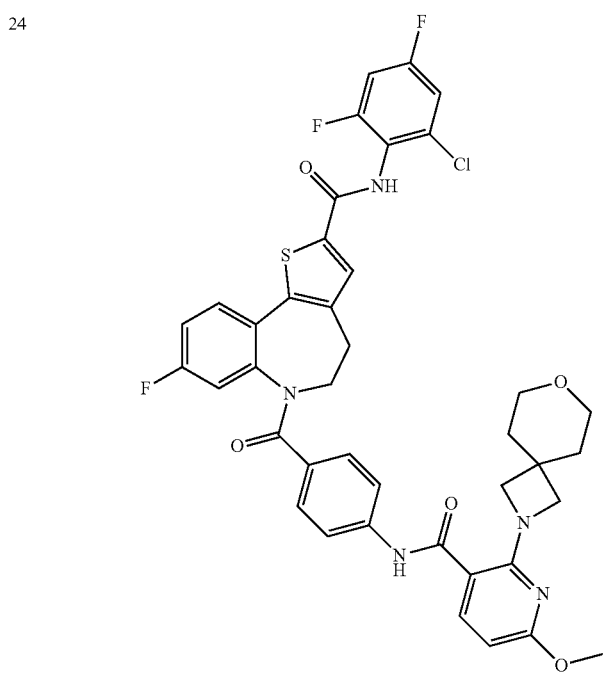 |

| Compound | Structure |
|---|---|
| 25 | 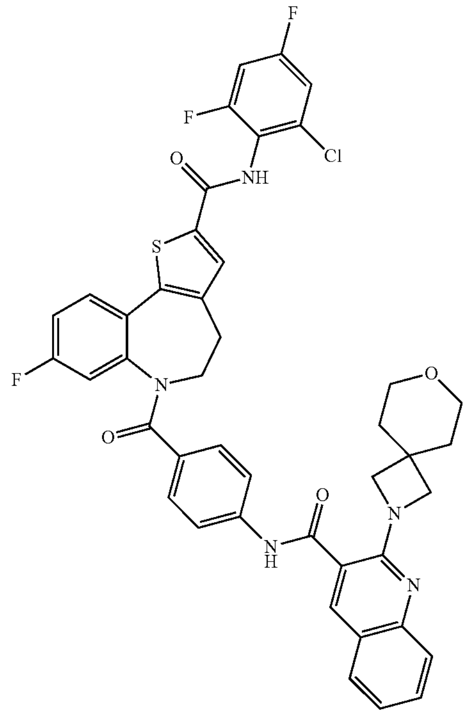 |
| 26 | 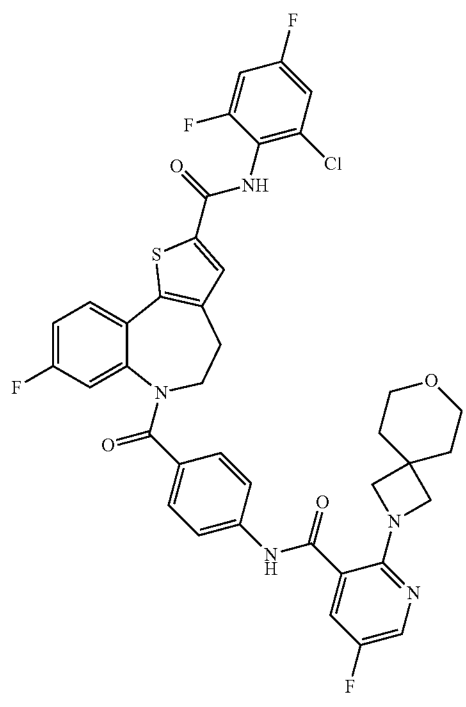 |

| Compound | Structure |
|---|---|
| 27 | 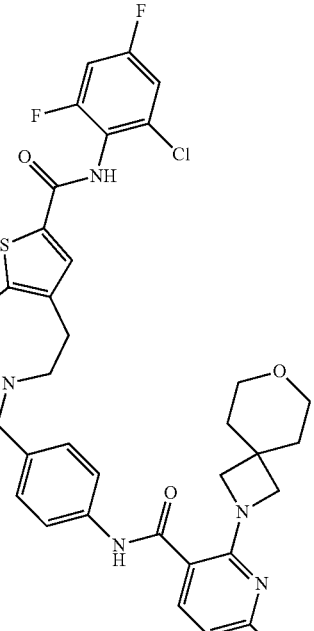 |
| 28 | 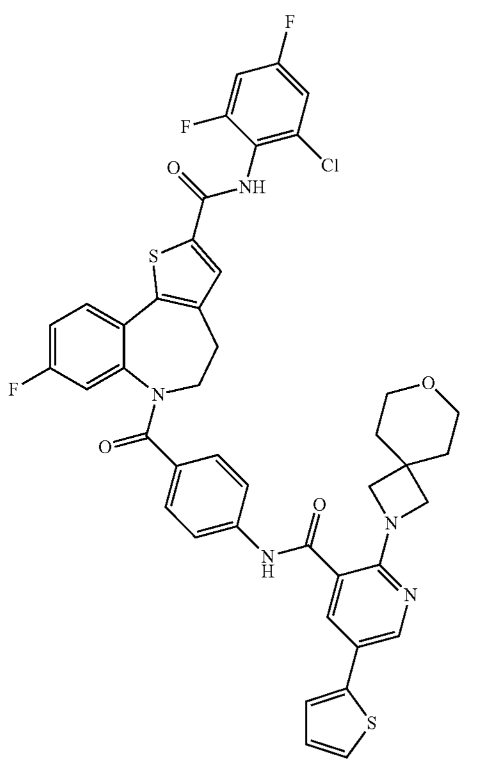 [SMILES: O=C(Nc1c(F)cc(F)cc1Cl)c1cc2c(s1)-c1ccc(F)cc1N(C(=O)c1ccc(NC(=O)c3cc(-c4cccs4)cnc3N3CC4(CCOCC4)C3)cc1)CC2] |

| Compound | Structure |
|---|---|
| 29 | 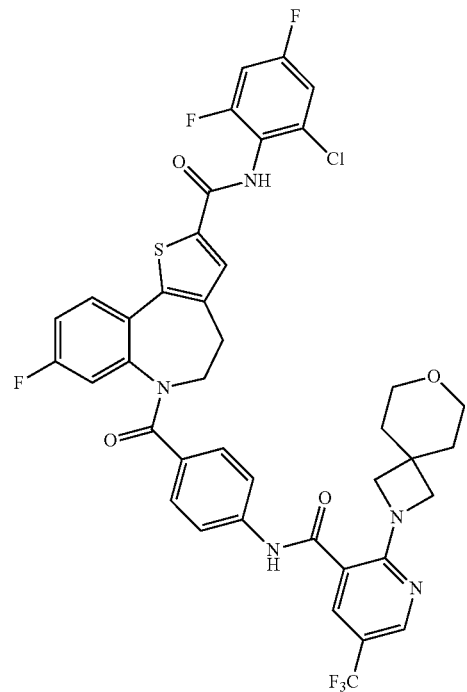 [SMILES: O=C(Nc1c(F)cc(F)cc1Cl)c1cc2c(s1)-c1ccc(F)cc1N(C(=O)c1ccc(NC(=O)c3cc(C(F)(F)F)cnc3N3CC4(CCOCC4)C3)cc1)CC2] |
| 30 | 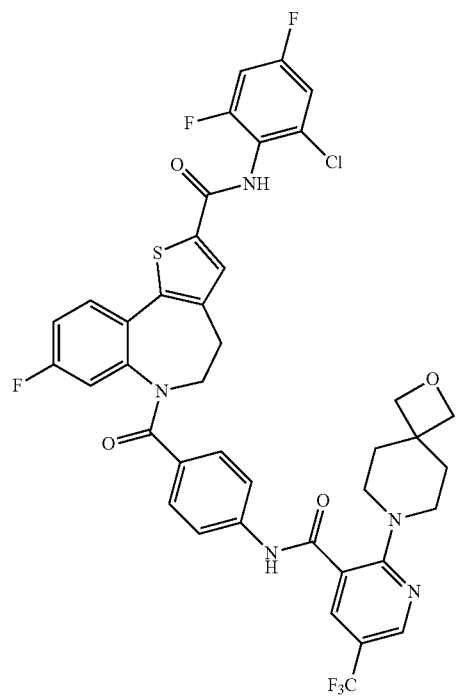 [SMILES: O=C(Nc1c(F)cc(F)cc1Cl)c1cc2c(s1)-c1ccc(F)cc1N(C(=O)c1ccc(NC(=O)c3cc(C(F)(F)F)cnc3N3CCC4(CC3)COC4)cc1)CC2] |

| Compound | Structure |
|---|---|
| 31 | 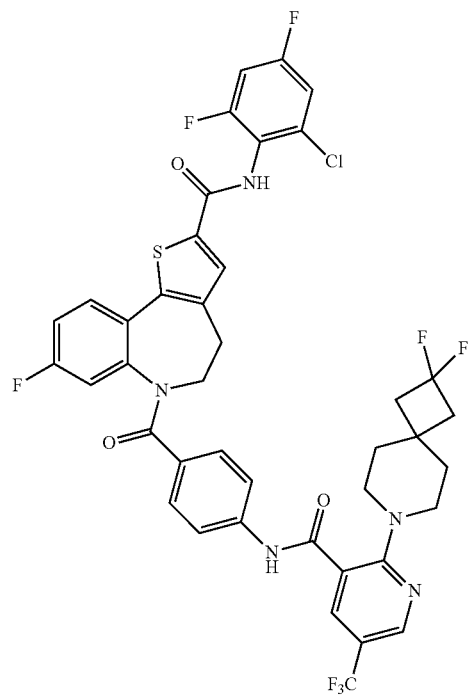 [SMILES: O=C(Nc1c(F)cc(F)cc1Cl)c1cc2c(s1)-c1ccc(F)cc1N(C(=O)c1ccc(NC(=O)c3cc(C(F)(F)F)cnc3N3CCC4(CC3)CC(F)(F)C4)cc1)CC2] |
| 32 | 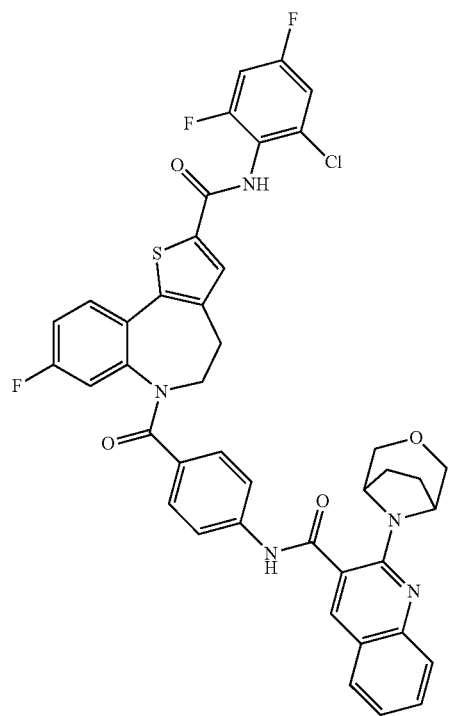 [SMILES: O=C(Nc1c(F)cc(F)cc1Cl)c1cc2c(s1)-c1ccc(F)cc1N(C(=O)c1ccc(NC(=O)c3cc4ccccc4nc3N3C4CCC3COC4)cc1)CC2] |

-continued
| Compound | Structure |
|---|---|
| 33 | 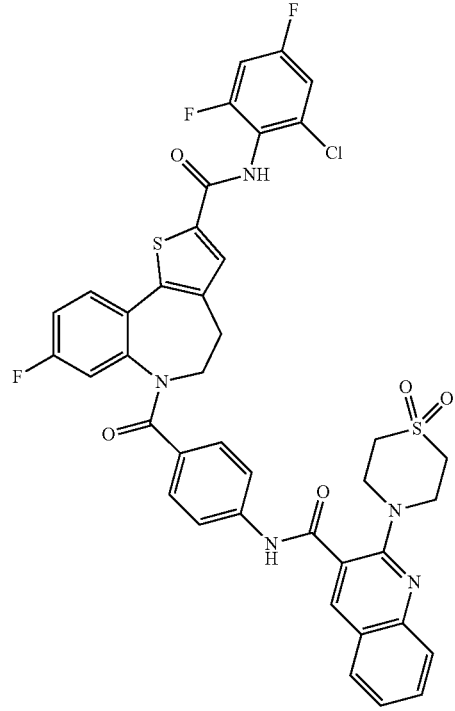 [SMILES: O=C(Nc1c(F)cc(F)cc1Cl)c1cc2c(s1)-c1ccc(F)cc1N(C(=O)c1ccc(NC(=O)c3cc4ccccc4nc3N3CCS(=O)(=O)CC3)cc1)CC2] |
| 34 | 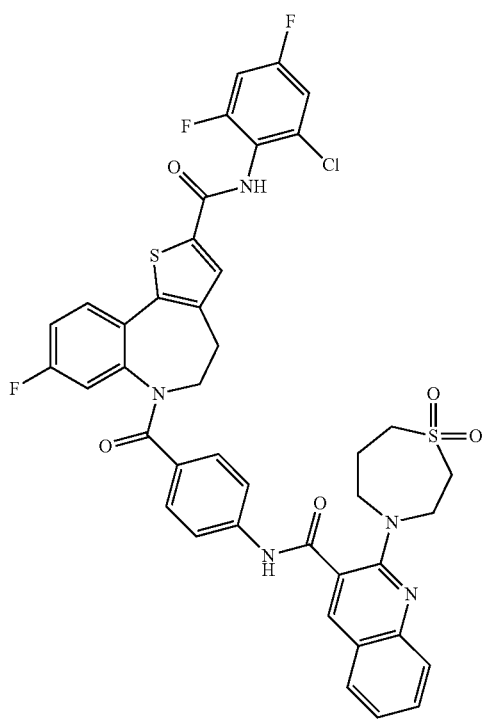 [SMILES: O=C(Nc1c(F)cc(F)cc1Cl)c1cc2c(s1)-c1ccc(F)cc1N(C(=O)c1ccc(NC(=O)c3cc4ccccc4nc3N3CCCS(=O)(=O)CC3)cc1)CC2] |

| Compound | Structure |
|---|---|
| 35 | 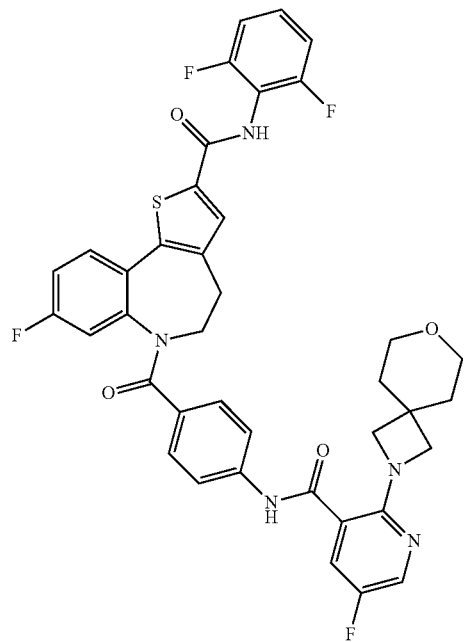 [SMILES: O=C(Nc1c(F)cccc1F)c1cc2c(s1)-c1ccc(F)cc1N(C(=O)c1ccc(NC(=O)c3cc(F)cnc3N3CC4(CCOCC4)C3)cc1)CC2] |
| 36 | 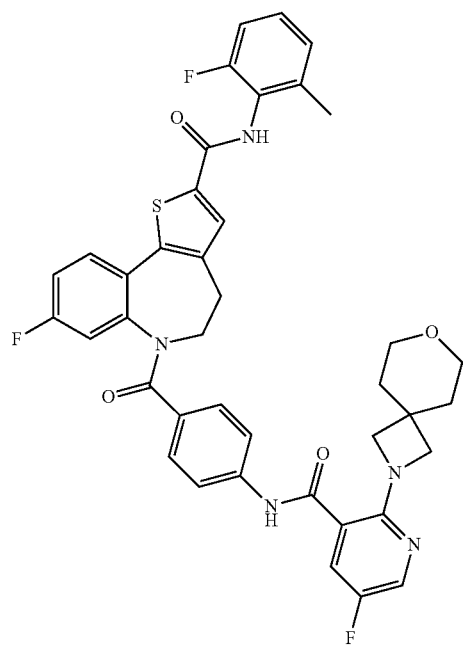 [SMILES: Cc1cccc(F)c1NC(=O)c1cc2c(s1)-c1ccc(F)cc1N(C(=O)c1ccc(NC(=O)c3cc(F)cnc3N3CC4(CCOCC4)C3)cc1)CC2] |

| Compound | Structure |
|---|---|
| 37 | 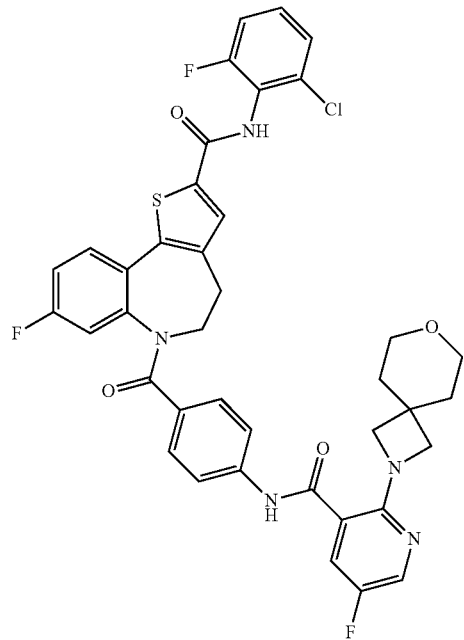 [SMILES: O=C(Nc1c(F)cccc1Cl)c1cc2c(s1)-c1ccc(F)cc1N(C(=O)c1ccc(NC(=O)c3cc(F)cnc3N3CC4(CCOCC4)C3)cc1)CC2] |
| 38 | 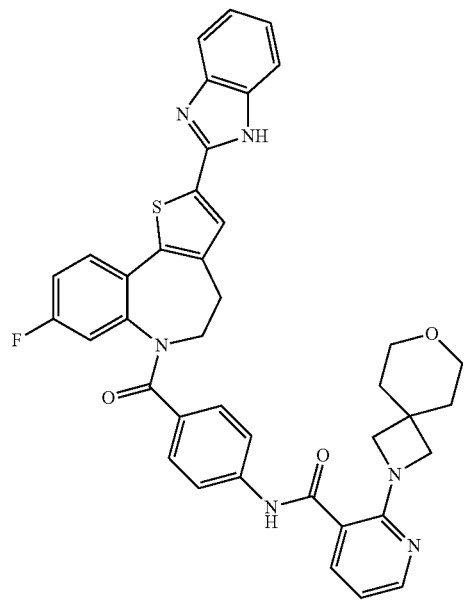 [SMILES: O=C(Nc1ccc(C(=O)N2CCc3cc(-c4nc5ccccc5[nH]4)sc3-c3ccc(F)cc32)cc1)c1cccnc1N1CC2(CCOCC2)C1] |

| Compound | Structure |
|---|---|
| 39 | 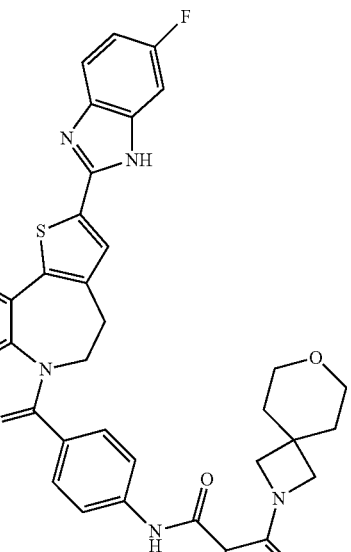 |
| 40 | 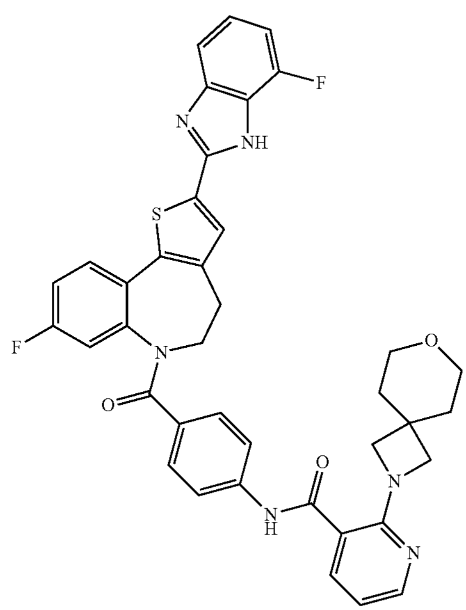 [SMILES: O=C(Nc1ccc(C(=O)N2CCc3cc(-c4nc5cccc(F)c5[nH]4)sc3-c3ccc(F)cc32)cc1)c1cccnc1N1CC2(CCOCC2)C1] |

-continued
| Compound | Structure |
|---|---|
| 41 | 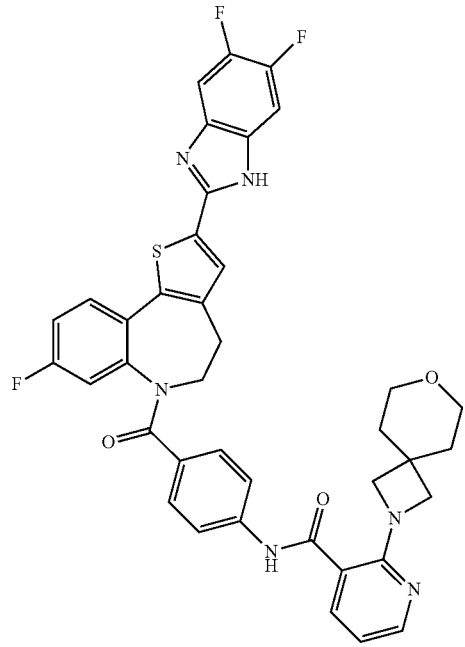 [SMILES: O=C(Nc1ccc(C(=O)N2CCc3cc(-c4nc5cc(F)c(F)cc5[nH]4)sc3-c3ccc(F)cc32)cc1)c1cccnc1N1CC2(CCOCC2)C1] |
| 42 | 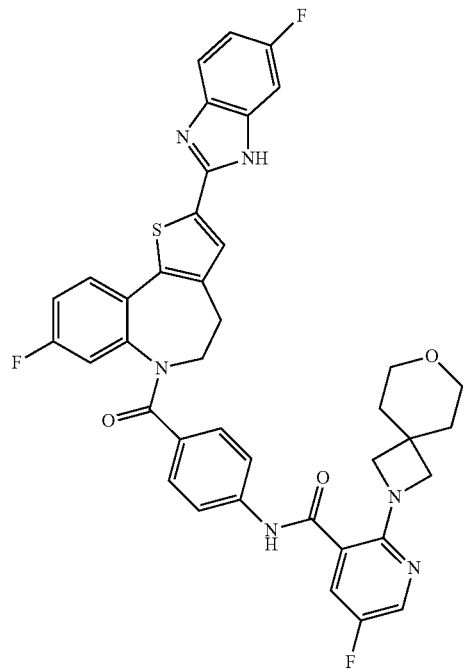 [SMILES: O=C(Nc1ccc(C(=O)N2CCc3cc(-c4nc5ccc(F)cc5[nH]4)sc3-c3ccc(F)cc32)cc1)c1cc(F)cnc1N1CC2(CCOCC2)C1] |

| Compound | Structure |
|---|---|
| 43 | 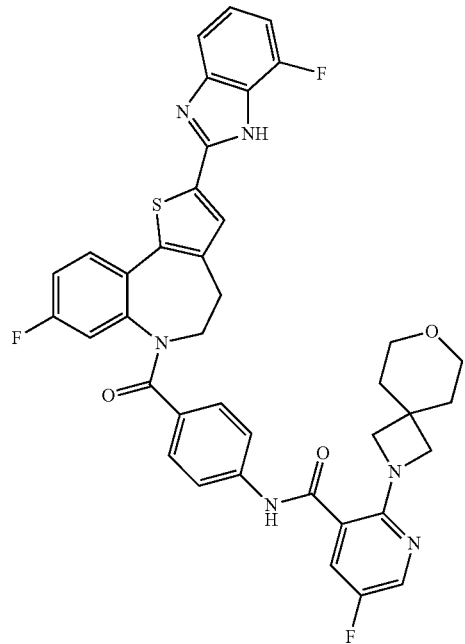 |
| 44 | 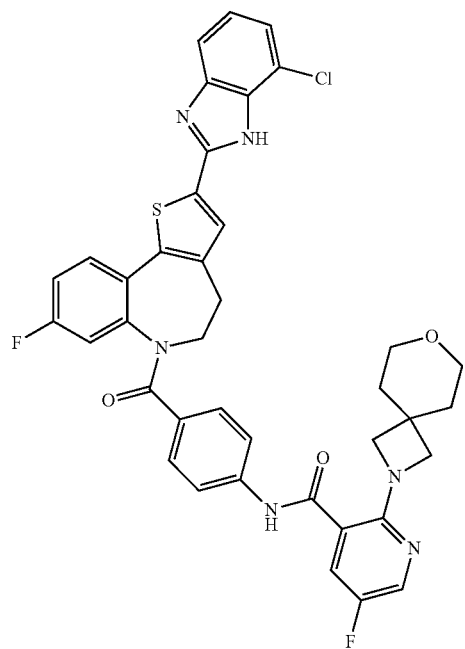 [SMILES: O=C(Nc1ccc(C(=O)N2CCc3cc(-c4nc5cccc(F)c5[nH]4)sc3-c3ccc(F)cc32)cc1)c1cc(F)cnc1N1CC2(CCOCC2)C1] |

| Compound | Structure |
|---|---|
| 45 | 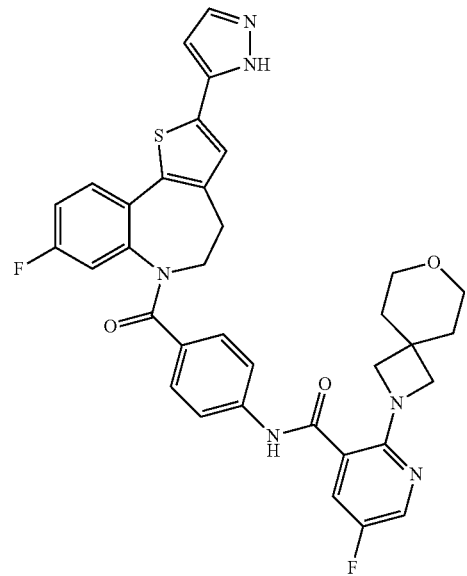 [SMILES: O=C(Nc1ccc(C(=O)N2CCc3cc(-c4ccn[nH]4)sc3-c3ccc(F)cc32)cc1)c1cc(F)cnc1N1CC2(CCOCC2)C1] |
| 46 | 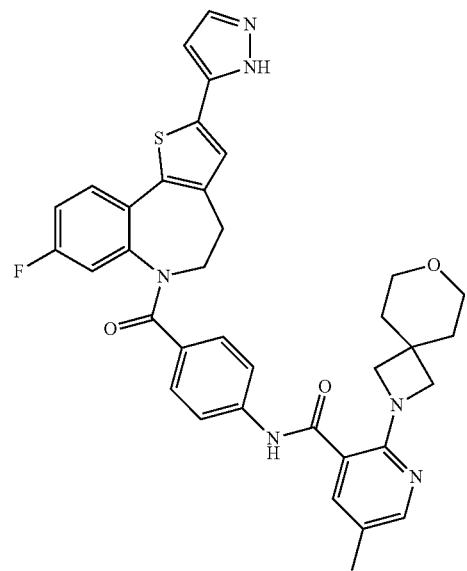 [SMILES: Cc1cnc(N2CC3(CCOCC3)C2)c(C(=O)Nc2ccc(C(=O)N3CCc4cc(-c5ccn[nH]5)sc4-c4ccc(F)cc43)cc2)c1] |

-continued
| Compound | Structure |
|---|---|
| 47 | 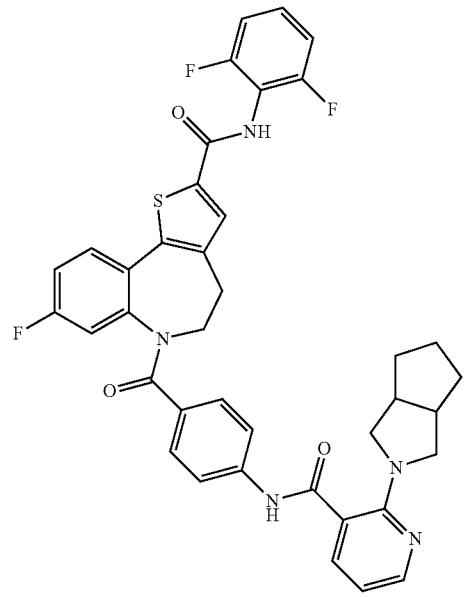 [SMILES: O=C(Nc1c(F)cccc1F)c1cc2c(s1)-c1ccc(F)cc1N(C(=O)c1ccc(NC(=O)c3cccnc3N3CC4CCCC4C3)cc1)CC2] |
| 48 | 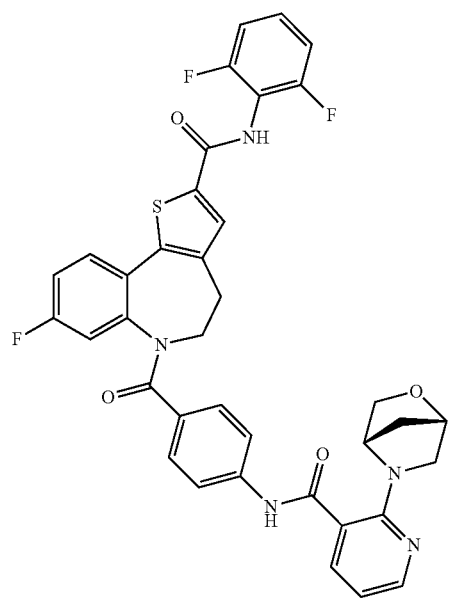 [SMILES: O=C(Nc1c(F)cccc1F)c1cc2c(s1)-c1ccc(F)cc1N(C(=O)c1ccc(NC(=O)c3cccnc3N3C[C@@H]4C[C@H]3CO4)cc1)CC2] |

| Compound | Structure |
|---|---|
| 49 | 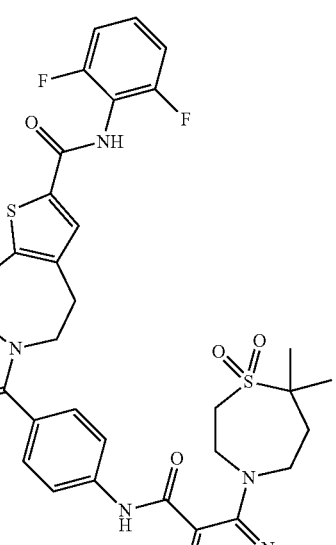 |
| 50 | 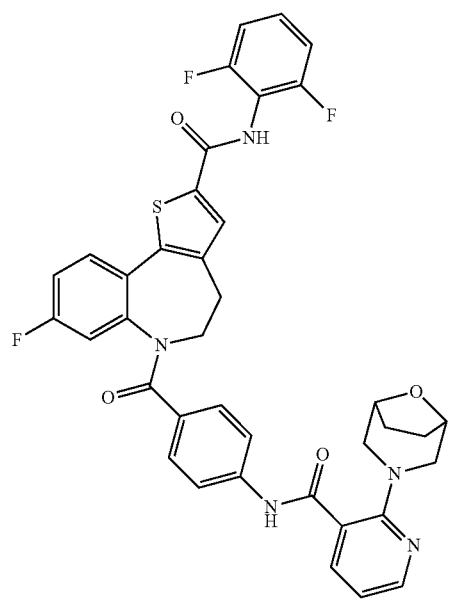 [SMILES: O=C(Nc1c(F)cccc1F)c1cc2c(s1)-c1ccc(F)cc1N(C(=O)c1ccc(NC(=O)c3cccnc3N3CC4CCC(C3)O4)cc1)CC2] |

-continued
| Compound | Structure |
|---|---|
| 51 | 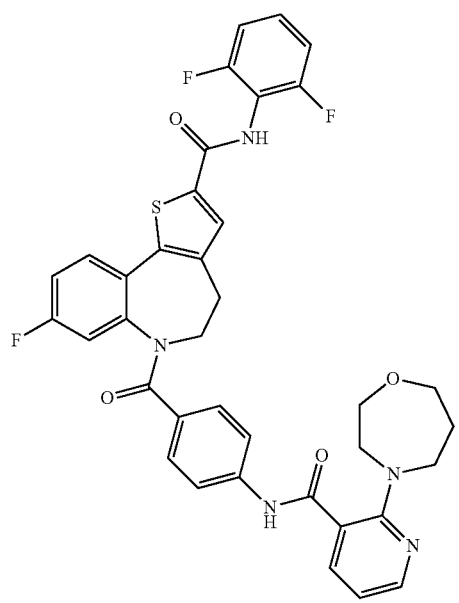 [SMILES: O=C(Nc1c(F)cccc1F)c1cc2c(s1)-c1ccc(F)cc1N(C(=O)c1ccc(NC(=O)c3cccnc3N3CCCOCC3)cc1)CC2] |
| 52 | 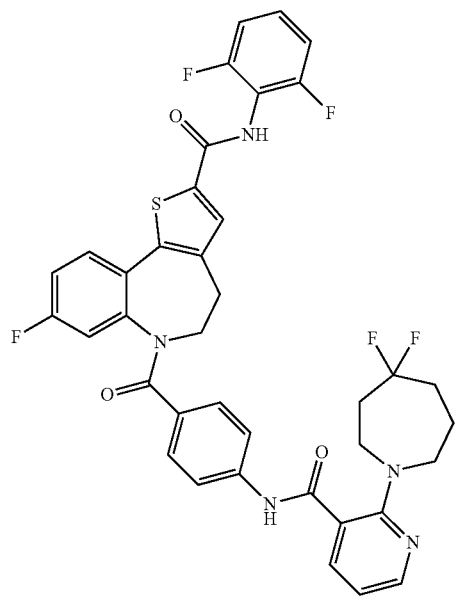 [SMILES: O=C(Nc1c(F)cccc1F)c1cc2c(s1)-c1ccc(F)cc1N(C(=O)c1ccc(NC(=O)c3cccnc3N3CCCC(F)(F)CC3)cc1)CC2] |

| Compound | Structure |
|---|---|
| 53 | 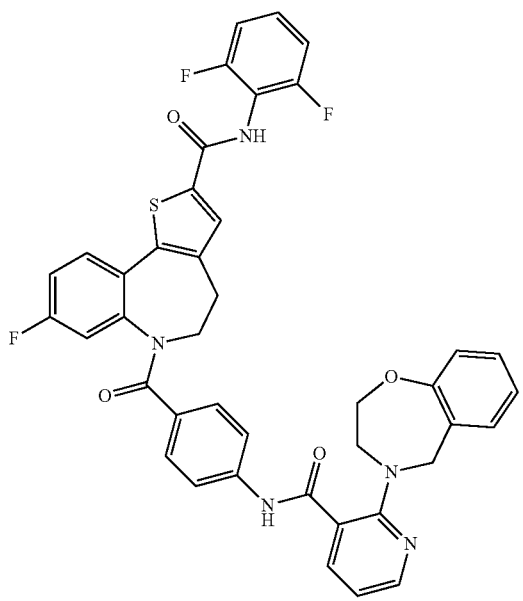 [SMILES: O=C(Nc1c(F)cccc1F)c1cc2c(s1)-c1ccc(F)cc1N(C(=O)c1ccc(NC(=O)c3cccnc3N3CCOc4ccccc4C3)cc1)CC2] |
| 54 | 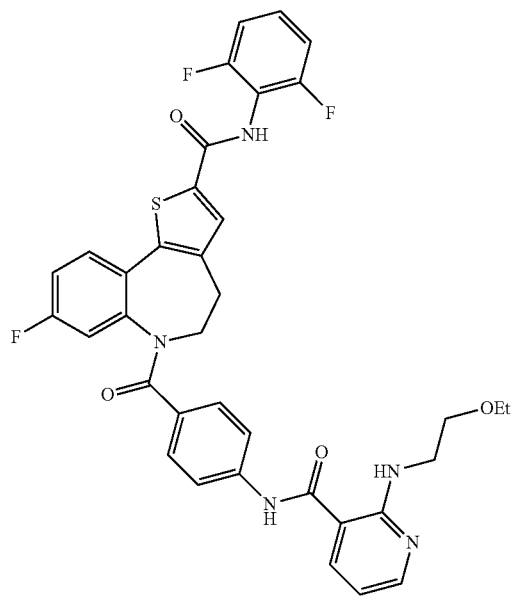 [SMILES: CCOCCNc1ncccc1C(=O)Nc1ccc(C(=O)N2CCc3cc(C(=O)Nc4c(F)cccc4F)sc3-c3ccc(F)cc32)cc1] |

-continued
| Compound | Structure |
|---|---|
| 55 | 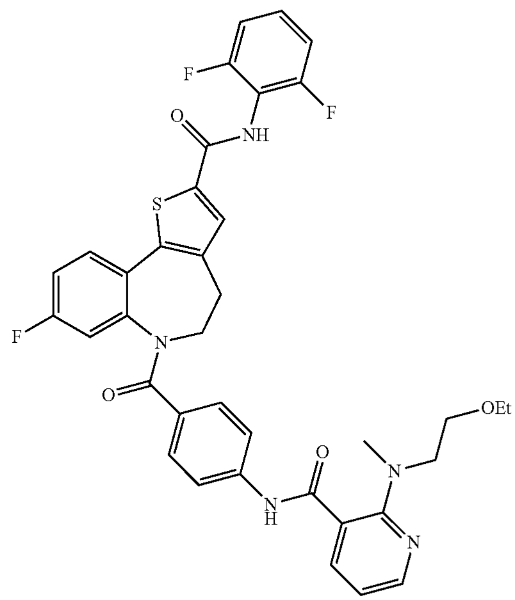 [SMILES: CCOCCN(C)c1ncccc1C(=O)Nc1ccc(C(=O)N2CCc3cc(C(=O)Nc4c(F)cccc4F)sc3-c3ccc(F)cc32)cc1] |
| 56 | 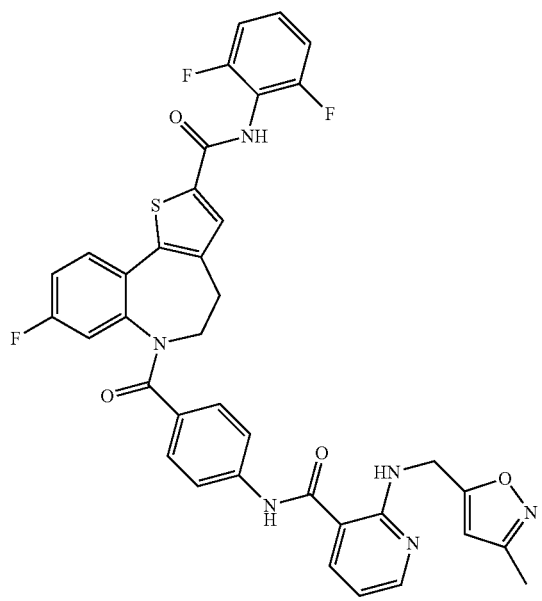 [SMILES: Cc1cc(CNc2ncccc2C(=O)Nc2ccc(C(=O)N3CCc4cc(C(=O)Nc5c(F)cccc5F)sc4-c4ccc(F)cc43)cc2)on1] |

-continued
| Compound | Structure |
|---|---|
| 57 | 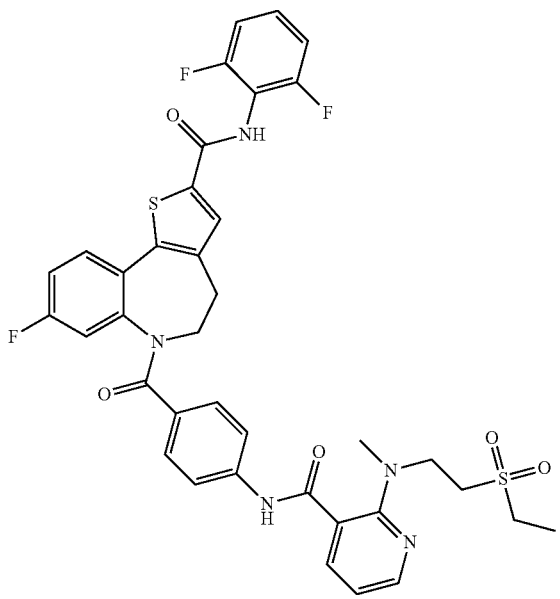 [SMILES: CCS(=O)(=O)CCN(C)c1ncccc1C(=O)Nc1ccc(C(=O)N2CCc3cc(C(=O)Nc4c(F)cccc4F)sc3-c3ccc(F)cc32)cc1] |
| 58 | 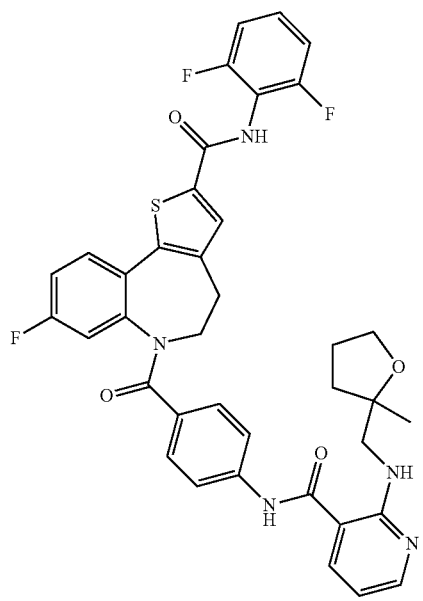 [SMILES: CC1(CNc2ncccc2C(=O)Nc2ccc(C(=O)N3CCc4cc(C(=O)Nc5c(F)cccc5F)sc4-c4ccc(F)cc43)cc2)CCCO1] |

-continued
| Compound | Structure |
|---|---|
| 59 | 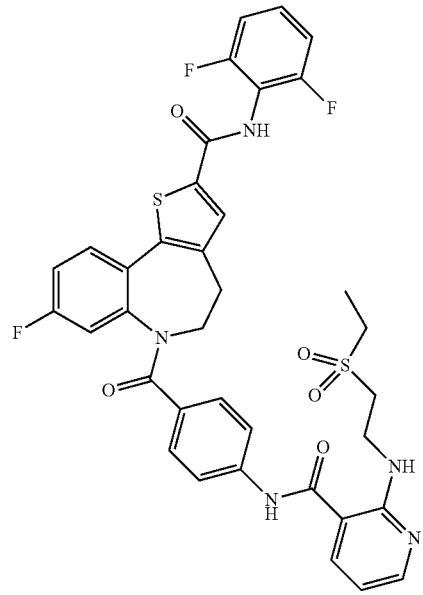 [SMILES: CCS(=O)(=O)CCNc1ncccc1C(=O)Nc1ccc(C(=O)N2CCc3cc(C(=O)Nc4c(F)cccc4F)sc3-c3ccc(F)cc32)cc1] |
| 60 | 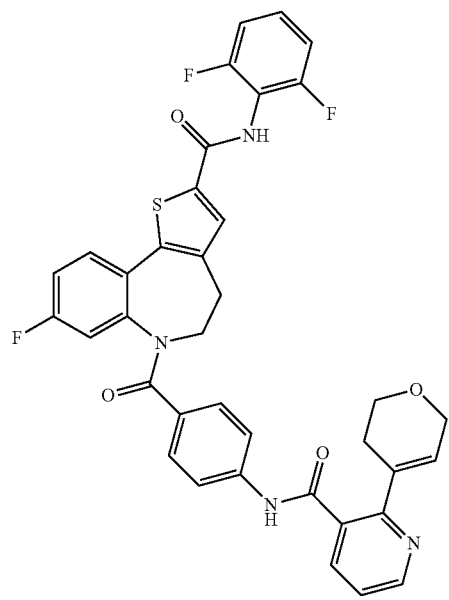 [SMILES: O=C(Nc1c(F)cccc1F)c1cc2c(s1)-c1ccc(F)cc1N(C(=O)c1ccc(NC(=O)c3cccnc3C3=CCOCC3)cc1)CC2] |

-continued
| Compound | Structure |
|---|---|
| 61 | 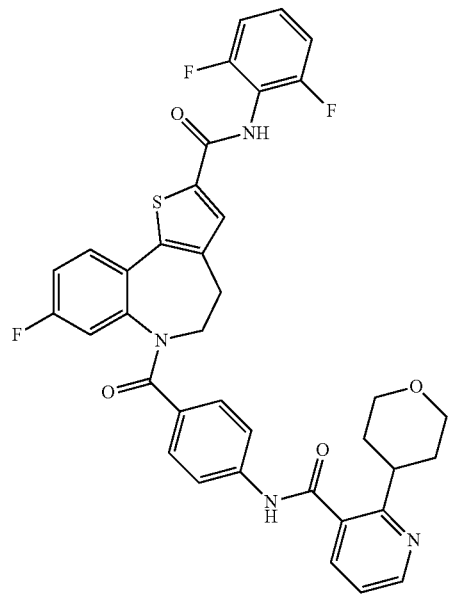 [SMILES: O=C(Nc1c(F)cccc1F)c1cc2c(s1)-c1ccc(F)cc1N(C(=O)c1ccc(NC(=O)c3cccnc3C3CCOCC3)cc1)CC2] |
| 62 | 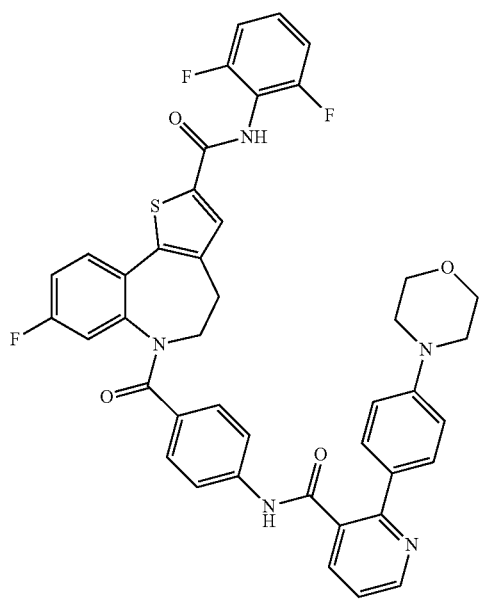 [SMILES: O=C(Nc1c(F)cccc1F)c1cc2c(s1)-c1ccc(F)cc1N(C(=O)c1ccc(NC(=O)c3cccnc3-c3ccc(N4CCOCC4)cc3)cc1)CC2] |

-continued

| Compound | Structure |
|---|---|
| 63 | 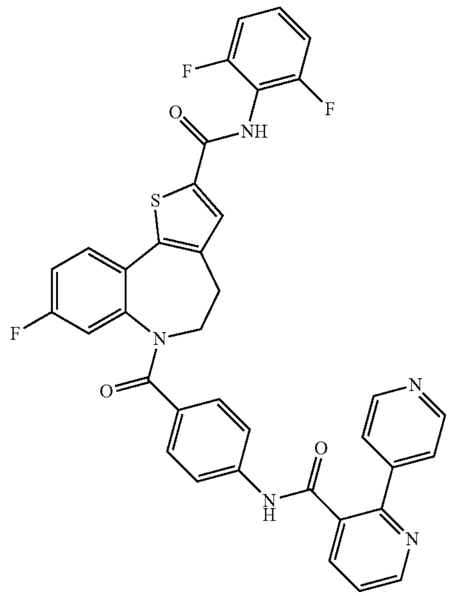 [SMILES: O=C(Nc1c(F)cccc1F)c1cc2c(s1)-c1ccc(F)cc1N(C(=O)c1ccc(NC(=O)c3cccnc3-c3ccncc3)cc1)CC2] |
| 64 | 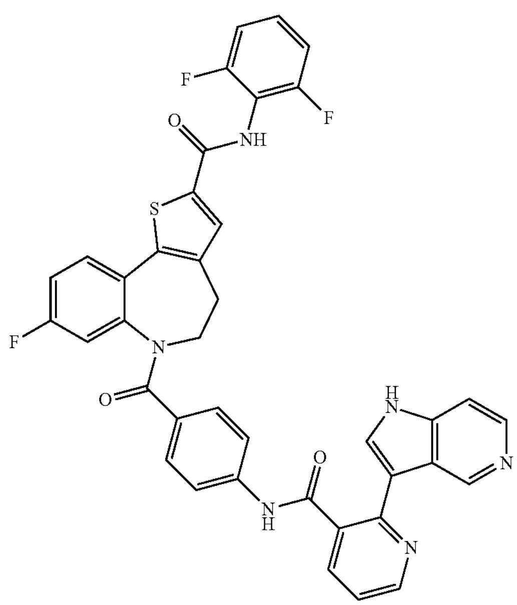 [SMILES: O=C(Nc1c(F)cccc1F)c1cc2c(s1)-c1ccc(F)cc1N(C(=O)c1ccc(NC(=O)c3cccnc3-c3c[nH]c4ccncc34)cc1)CC2] |

-continued
| Compound | Structure |
|---|---|
| 65 | 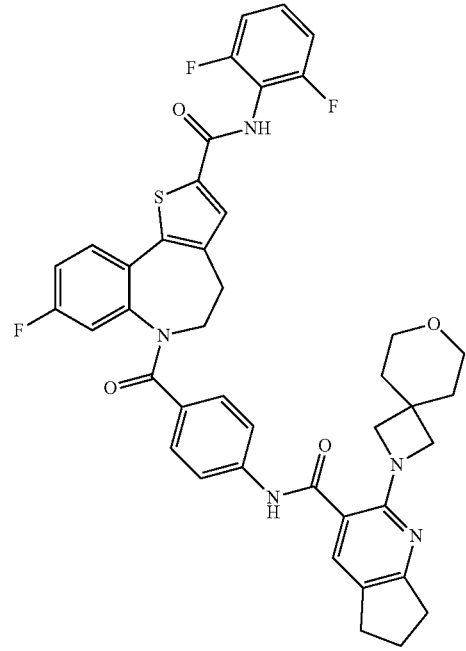 |
| 66 | 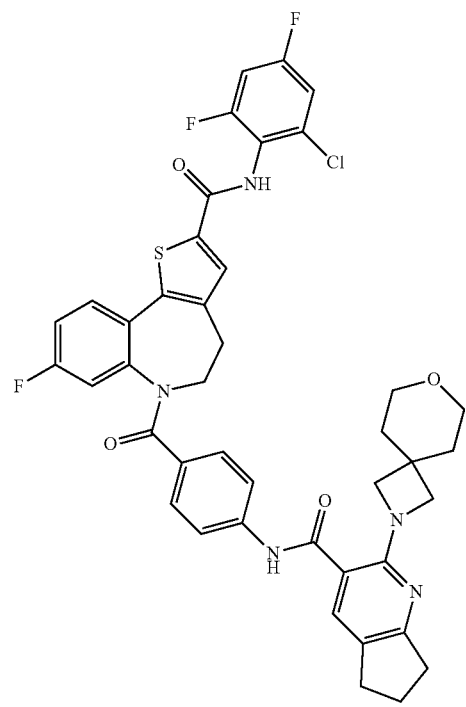 [SMILES: O=C(Nc1c(F)cc(F)cc1Cl)c1cc2c(s1)-c1ccc(F)cc1N(C(=O)c1ccc(NC(=O)c3cc4c(nc3N3CC5(CCOCC5)C3)CCC4)cc1)CC2] |

| Compound | Structure |
|---|---|
| 67 | 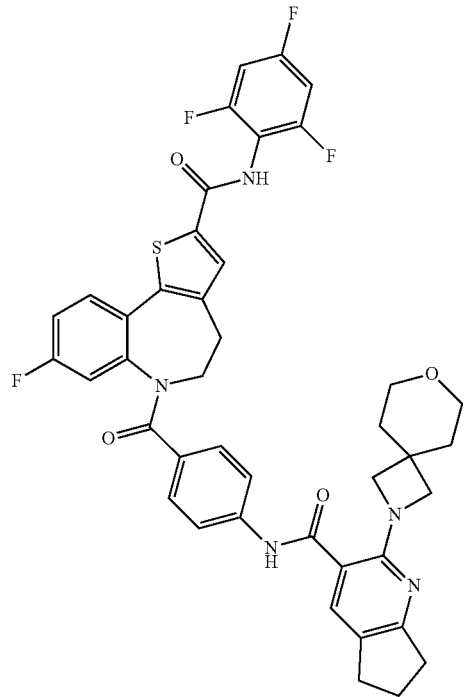 [SMILES: O=C(Nc1c(F)cc(F)cc1F)c1cc2c(s1)-c1ccc(F)cc1N(C(=O)c1ccc(NC(=O)c3cc4c(nc3N3CC5(CCOCC5)C3)CCC4)cc1)CC2] |
| 68 | 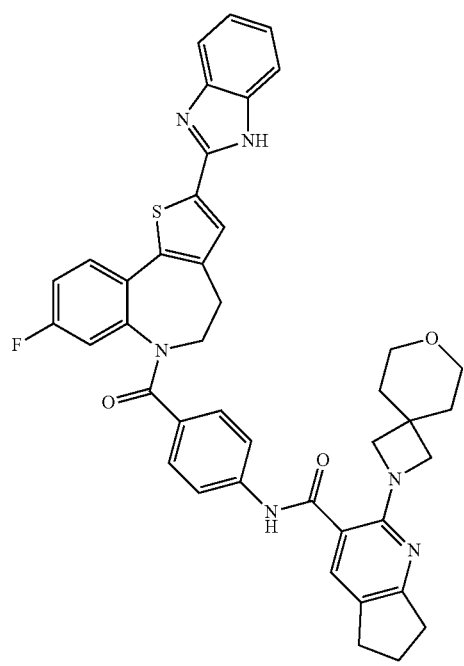 [SMILES: O=C(Nc1ccc(C(=O)N2CCc3cc(-c4nc5ccccc5[nH]4)sc3-c3ccc(F)cc32)cc1)c1cc2c(nc1N1CC3(CCOCC3)C1)CCC2] |

| Compound | Structure |
|---|---|
| 69 | 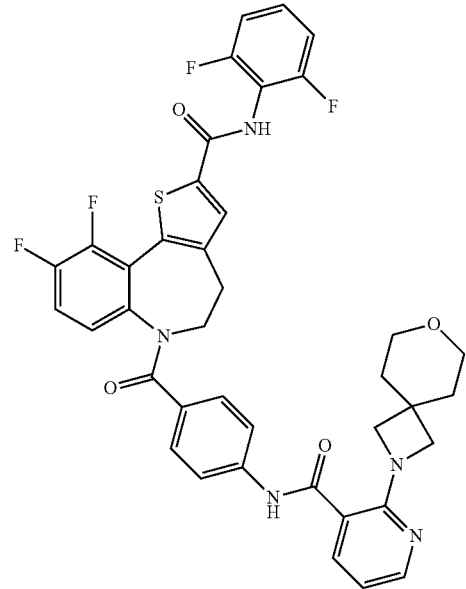 [SMILES: O=C(Nc1c(F)cccc1F)c1cc2c(s1)-c1c(ccc(F)c1F)N(C(=O)c1ccc(NC(=O)c3cccnc3N3CC4(CCOCC4)C3)cc1)CC2] |
| 70 | 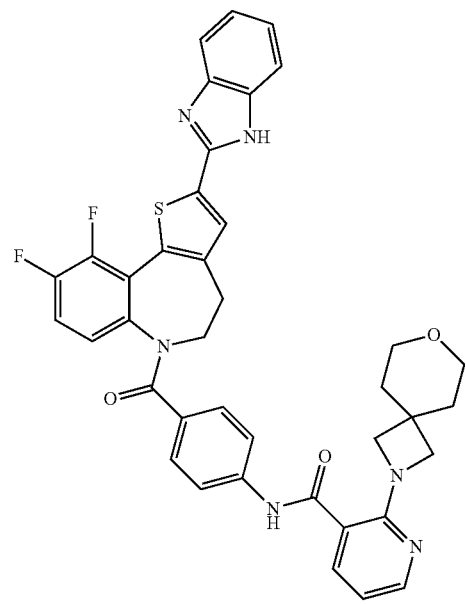 [SMILES: O=C(Nc1ccc(C(=O)N2CCc3cc(-c4nc5ccccc5[nH]4)sc3-c3c2ccc(F)c3F)cc1)c1cccnc1N1CC2(CCOCC2)C1] |

| Compound | Structure |
|---|---|
| 71 | 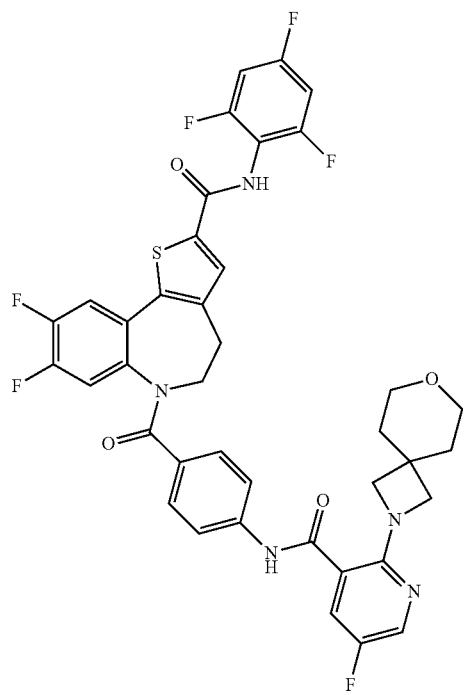 [SMILES: O=C(Nc1c(F)cc(F)cc1F)c1cc2c(s1)-c1cc(F)c(F)cc1N(C(=O)c1ccc(NC(=O)c3cc(F)cnc3N3CC4(CCOCC4)C3)cc1)CC2] |
| 72 | 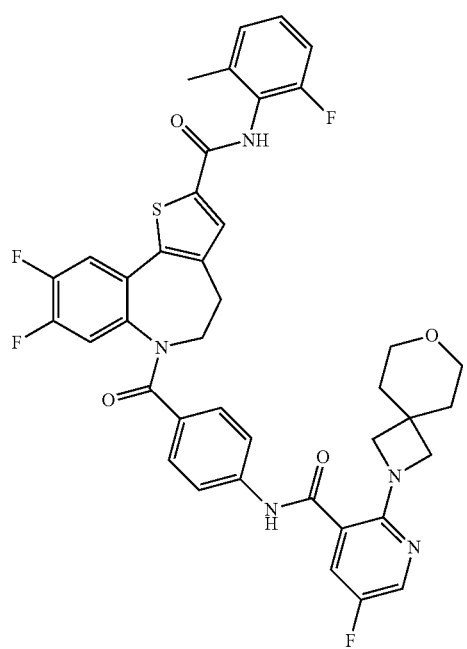 [SMILES: Cc1cccc(F)c1NC(=O)c1cc2c(s1)-c1cc(F)c(F)cc1N(C(=O)c1ccc(NC(=O)c3cc(F)cnc3N3CC4(CCOCC4)C3)cc1)CC2] |

| Compound | Structure |
|---|---|
| 73 | 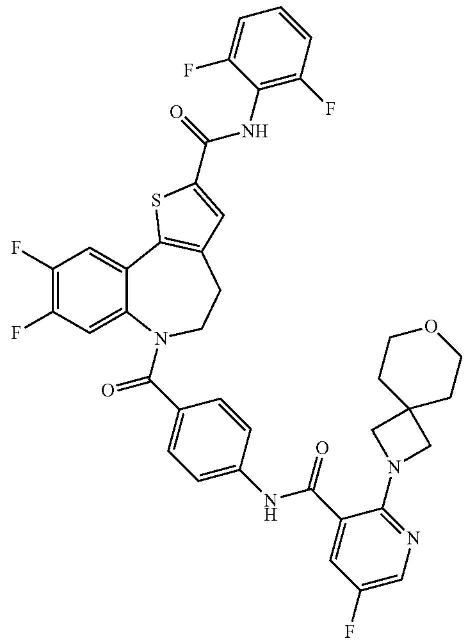 [SMILES: O=C(Nc1c(F)cccc1F)c1cc2c(s1)-c1cc(F)c(F)cc1N(C(=O)c1ccc(NC(=O)c3cc(F)cnc3N3CC4(CCOCC4)C3)cc1)CC2] |
| 74 | 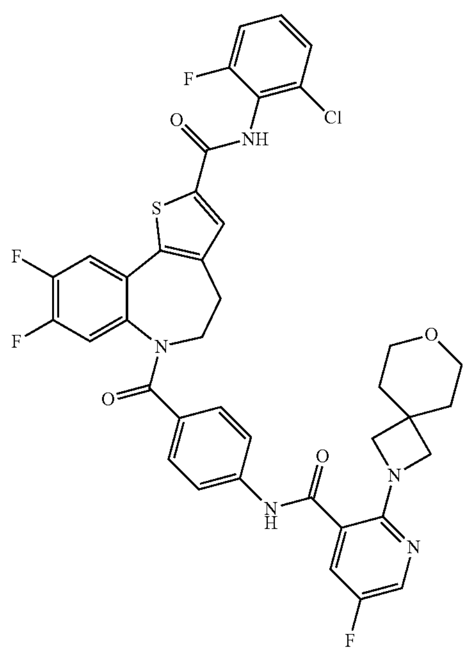 [SMILES: O=C(Nc1c(F)cccc1Cl)c1cc2c(s1)-c1cc(F)c(F)cc1N(C(=O)c1ccc(NC(=O)c3cc(F)cnc3N3CC4(CCOCC4)C3)cc1)CC2] |

| Compound | Structure |
|---|---|
| 75 | 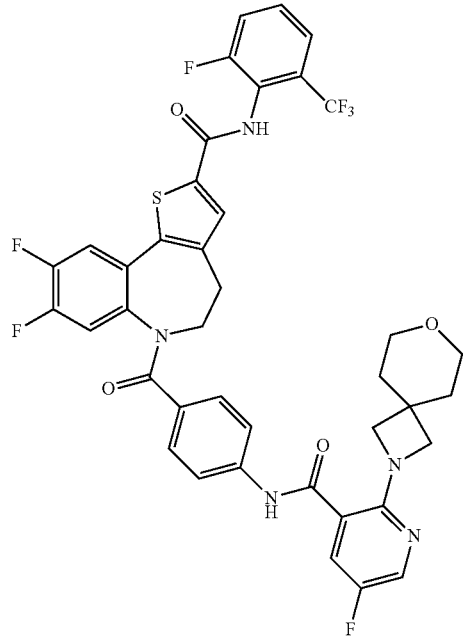 [SMILES: O=C(Nc1c(F)cccc1C(F)(F)F)c1cc2c(s1)-c1cc(F)c(F)cc1N(C(=O)c1ccc(NC(=O)c3cc(F)cnc3N3CC4(CCOCC4)C3)cc1)CC2] |
| 76 | 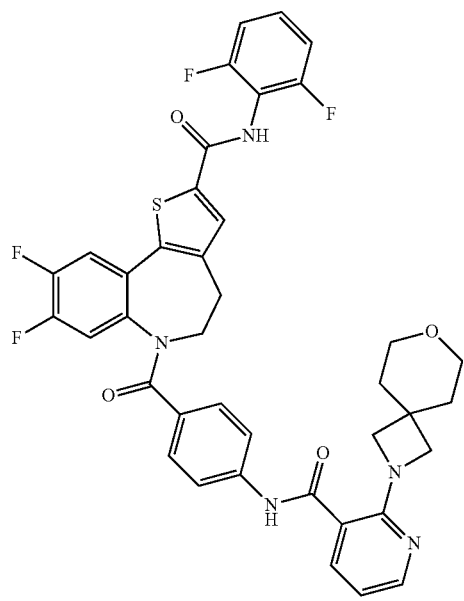 [SMILES: O=C(Nc1c(F)cccc1F)c1cc2c(s1)-c1cc(F)c(F)cc1N(C(=O)c1ccc(NC(=O)c3cccnc3N3CC4(CCOCC4)C3)cc1)CC2] |

| Compound | Structure |
|---|---|
| 77 | 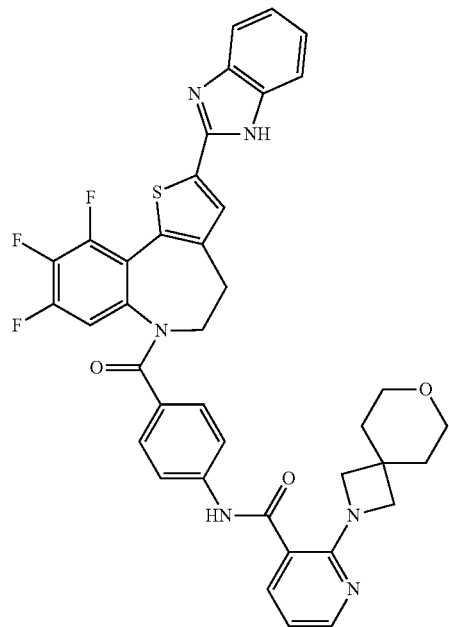 [SMILES: O=C(Nc1ccc(C(=O)N2CCc3cc(-c4nc5ccccc5[nH]4)sc3-c3c2cc(F)c(F)c3F)cc1)c1cccnc1N1CC2(CCOCC2)C1] |
| 78 | 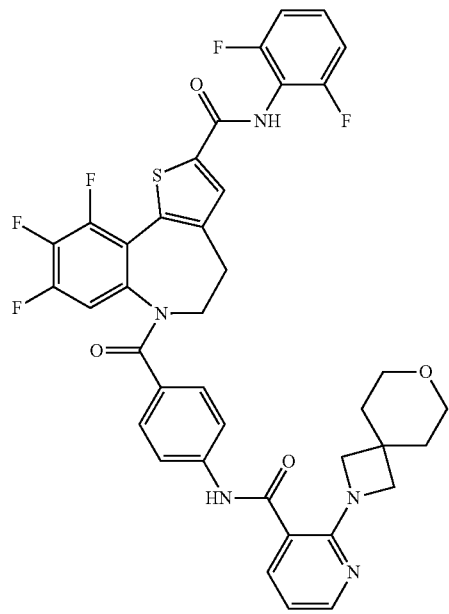 [SMILES: O=C(Nc1c(F)cccc1F)c1cc2c(s1)-c1c(cc(F)c(F)c1F)N(C(=O)c1ccc(NC(=O)c3cccnc3N3CC4(CCOCC4)C3)cc1)CC2] |

| Compound | Structure |
|---|---|
| 79 | 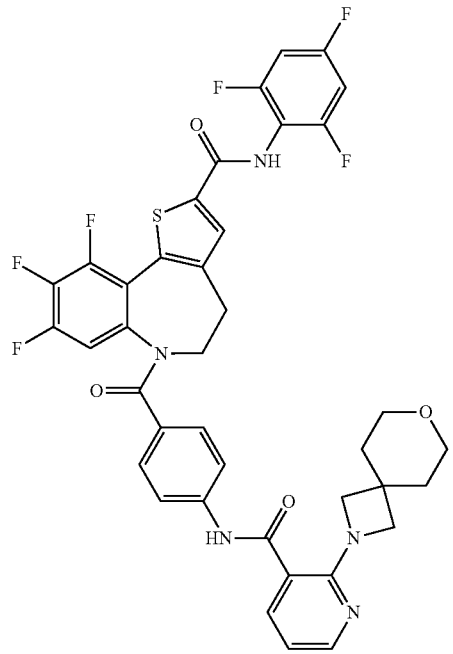 [SMILES: O=C(Nc1c(F)cc(F)cc1F)c1cc2c(s1)-c1c(cc(F)c(F)c1F)N(C(=O)c1ccc(NC(=O)c3cccnc3N3CC4(CCOCC4)C3)cc1)CC2] |
| 80 | 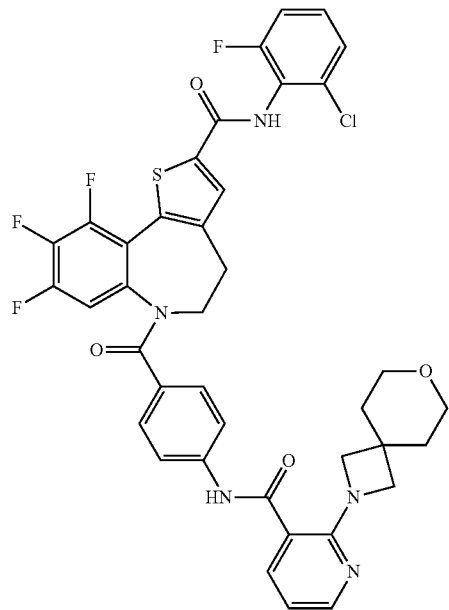 [SMILES: O=C(Nc1c(F)cccc1Cl)c1cc2c(s1)-c1c(cc(F)c(F)c1F)N(C(=O)c1ccc(NC(=O)c3cccnc3N3CC4(CCOCC4)C3)cc1)CC2] |

| Compound | Structure |
|---|---|
| 81 | 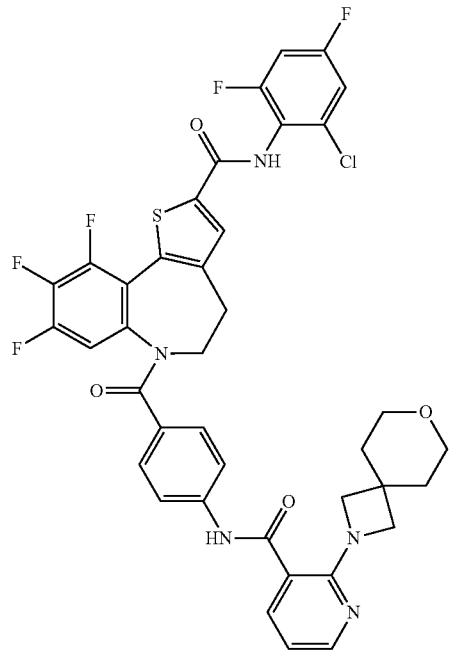 [SMILES: O=C(Nc1c(F)cc(F)cc1Cl)c1cc2c(s1)-c1c(cc(F)c(F)c1F)N(C(=O)c1ccc(NC(=O)c3cccnc3N3CC4(CCOCC4)C3)cc1)CC2] |
| 82 | 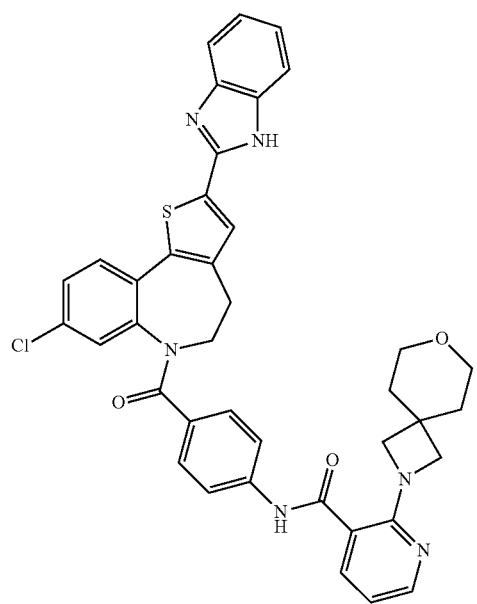 [SMILES: O=C(Nc1ccc(C(=O)N2CCc3cc(-c4nc5ccccc5[nH]4)sc3-c3ccc(Cl)cc32)cc1)c1cccnc1N1CC2(CCOCC2)C1] |

-continued
| Compound | Structure |
|---|---|
| 83 | 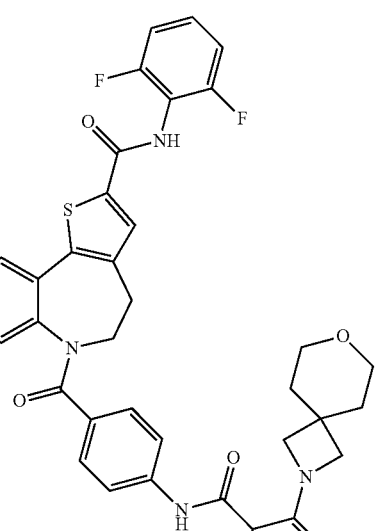 |
| 84 | 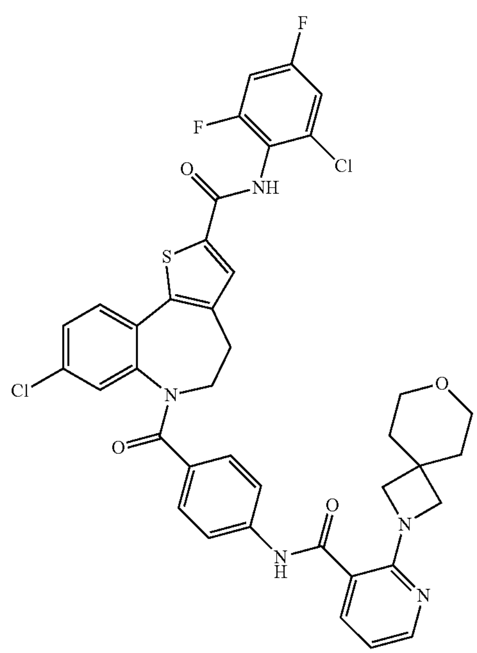 [SMILES: O=C(Nc1c(F)cc(F)cc1Cl)c1cc2c(s1)-c1ccc(Cl)cc1N(C(=O)c1ccc(NC(=O)c3cccnc3N3CC4(CCOCC4)C3)cc1)CC2] |

| Compound | Structure |
|---|---|
| 85 | 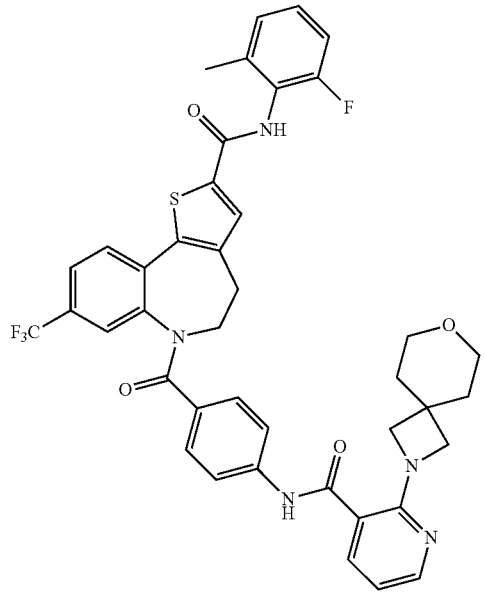 [SMILES: Cc1cccc(F)c1NC(=O)c1cc2c(s1)-c1ccc(C(F)(F)F)cc1N(C(=O)c1ccc(NC(=O)c3cccnc3N3CC4(CCOCC4)C3)cc1)CC2] |
| 86 | 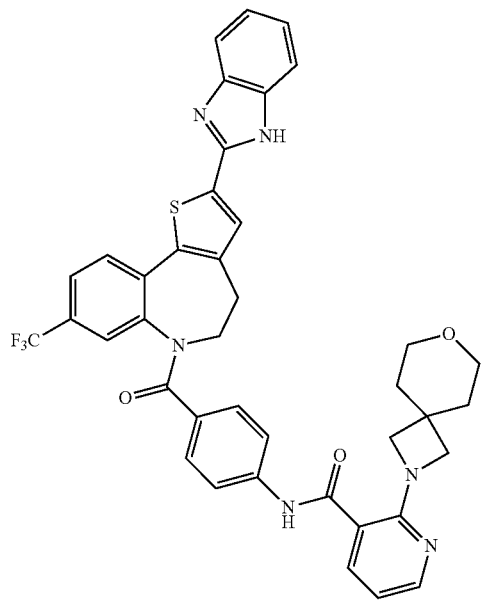 [SMILES: O=C(Nc1ccc(C(=O)N2CCc3cc(-c4nc5ccccc5[nH]4)sc3-c3ccc(C(F)(F)F)cc32)cc1)c1cccnc1N1CC2(CCOCC2)C1] |

| Compound | Structure |
|---|---|
| 87 | 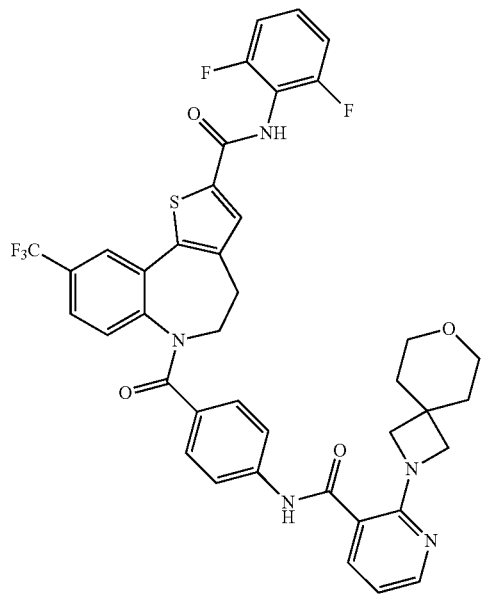 [SMILES: O=C(Nc1c(F)cccc1F)c1cc2c(s1)-c1cc(C(F)(F)F)ccc1N(C(=O)c1ccc(NC(=O)c3cccnc3N3CC4(CCOCC4)C3)cc1)CC2] |
| 88 | 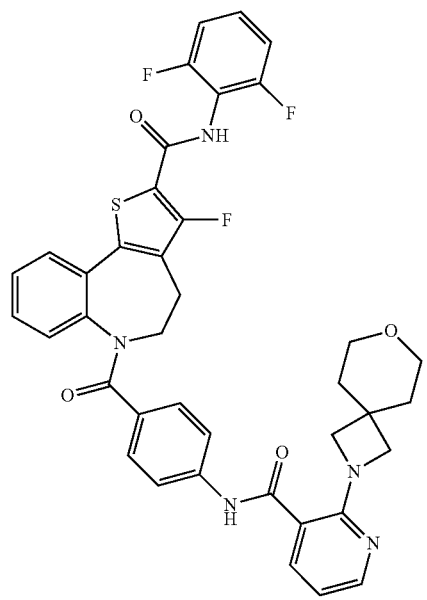 [SMILES: O=C(Nc1ccc(C(=O)N2CCc3c(sc(C(=O)Nc4c(F)cccc4F)c3F)-c3ccccc32)cc1)c1cccnc1N1CC2(CCOCC2)C1] |

| Compound | Structure |
|---|---|
| 89 | 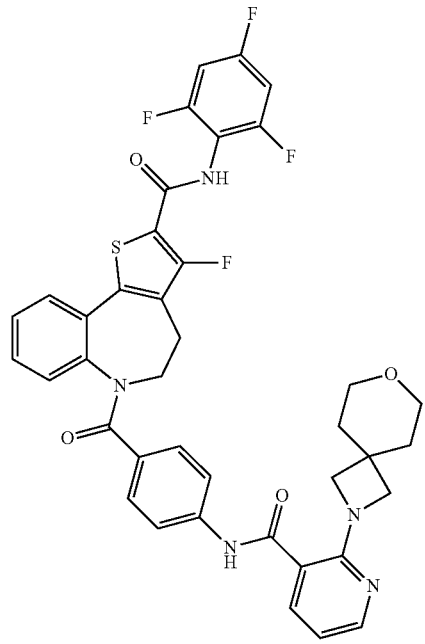 [SMILES: O=C(Nc1ccc(C(=O)N2CCc3c(sc(C(=O)Nc4c(F)cc(F)cc4F)c3F)-c3ccccc32)cc1)c1cccnc1N1CC2(CCOCC2)C1] |
| 90 | 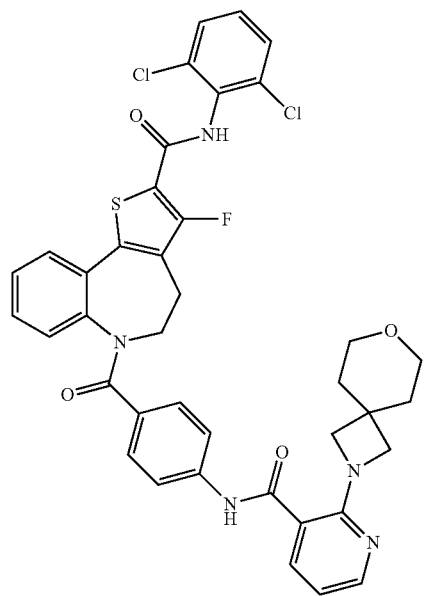 [SMILES: O=C(Nc1ccc(C(=O)N2CCc3c(sc(C(=O)Nc4c(Cl)cccc4Cl)c3F)-c3ccccc32)cc1)c1cccnc1N1CC2(CCOCC2)C1] |

-continued
| Compound | Structure |
|---|---|
| 91 | 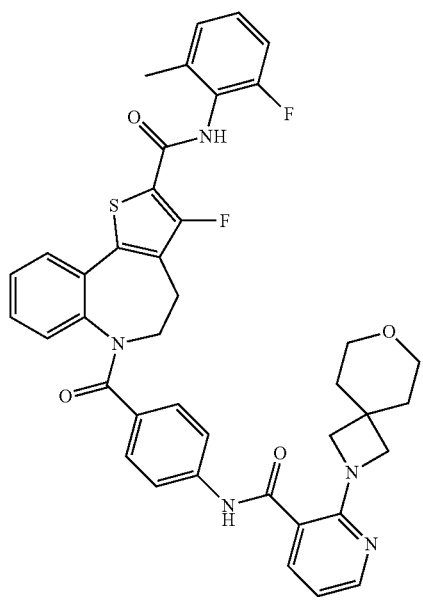 [SMILES: Cc1cccc(F)c1NC(=O)c1sc2c(c1F)CCN(C(=O)c1ccc(NC(=O)c3cccnc3N3CC4(CCOCC4)C3)cc1)c1ccccc1-2] |
| 92 | 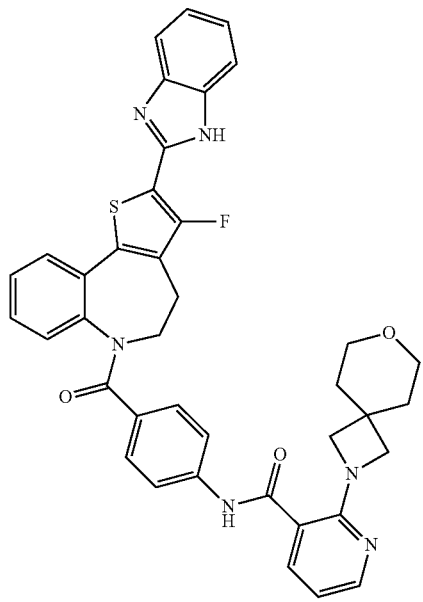 [SMILES: O=C(Nc1ccc(C(=O)N2CCc3c(sc(-c4nc5ccccc5[nH]4)c3F)-c3ccccc32)cc1)c1cccnc1N1CC2(CCOCC2)C1] |

-continued
| Compound | Structure |
|---|---|
| 93 | 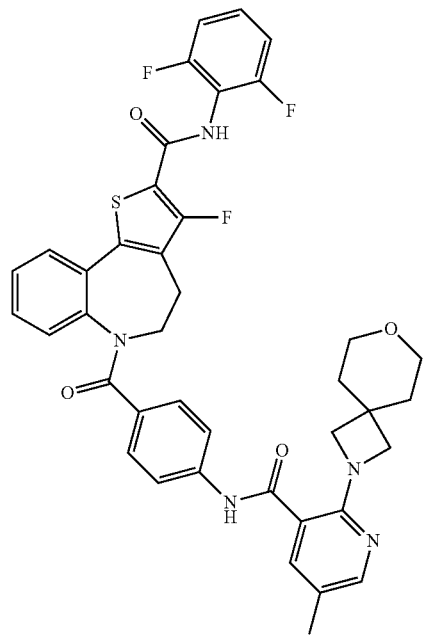 |
| 94 | 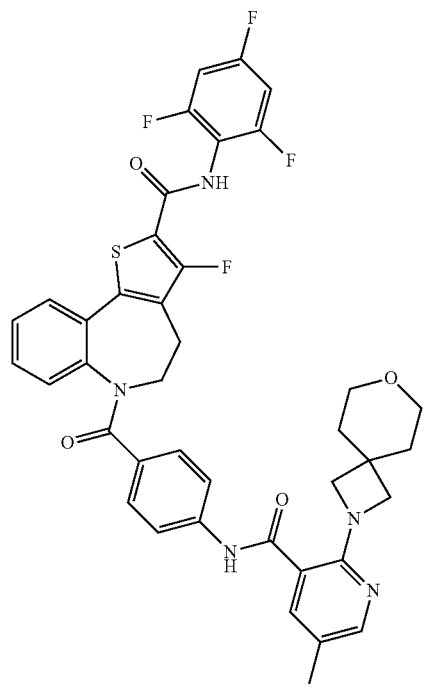 [SMILES: Cc1cnc(N2CC3(CCOCC3)C2)c(C(=O)Nc2ccc(C(=O)N3CCc4c(sc(C(=O)Nc5c(F)cc(F)cc5F)c4F)-c4ccccc43)cc2)c1] |

| Compound | Structure |
|---|---|
| 95 | 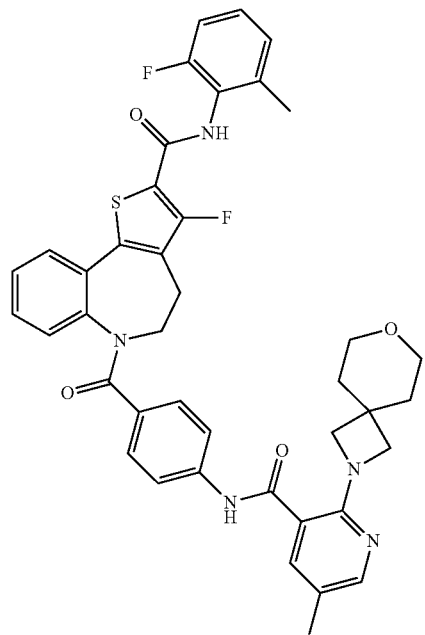 |
| 96 | 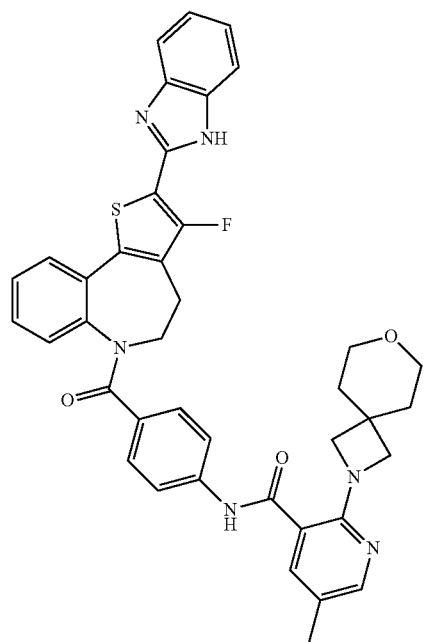 [SMILES: Cc1cnc(N2CC3(CCOCC3)C2)c(C(=O)Nc2ccc(C(=O)N3CCc4c(sc(-c5nc6ccccc6[nH]5)c4F)-c4ccccc43)cc2)c1] |

-continued
| Compound | Structure |
|---|---|
| 97 | 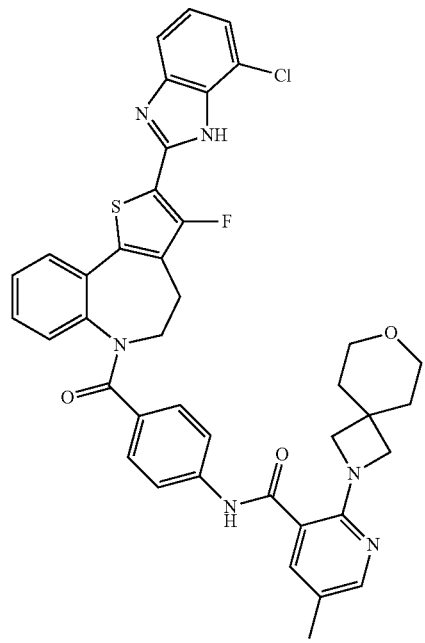 [SMILES: Cc1cnc(N2CC3(CCOCC3)C2)c(C(=O)Nc2ccc(C(=O)N3CCc4c(sc(-c5nc6cccc(Cl)c6[nH]5)c4F)-c4ccccc43)cc2)c1] |
| 98 | 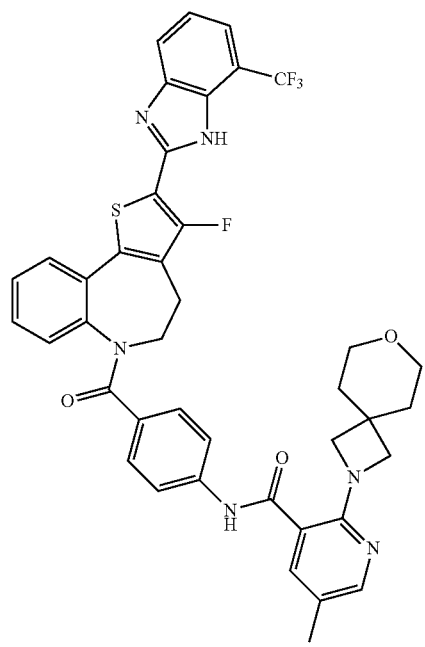 [SMILES: Cc1cnc(N2CC3(CCOCC3)C2)c(C(=O)Nc2ccc(C(=O)N3CCc4c(sc(-c5nc6cccc(C(F)(F)F)c6[nH]5)c4F)-c4ccccc43)cc2)c1] |

-continued
| Compound | Structure |
|---|---|
| 99 | 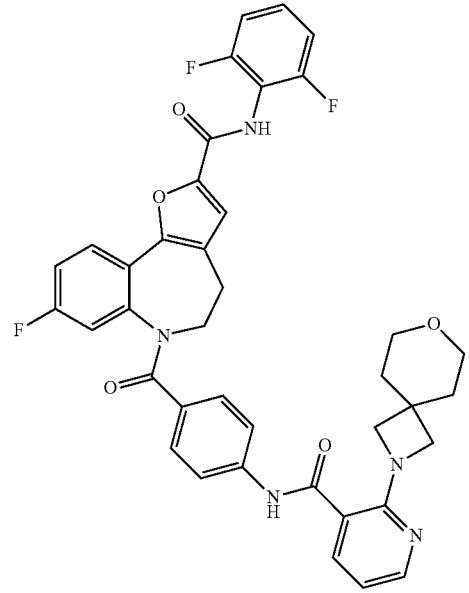 [SMILES: O=C(Nc1c(F)cccc1F)c1cc2c(o1)-c1ccc(F)cc1N(C(=O)c1ccc(NC(=O)c3cccnc3N3CC4(CCOCC4)C3)cc1)CC2] |
| 100 | 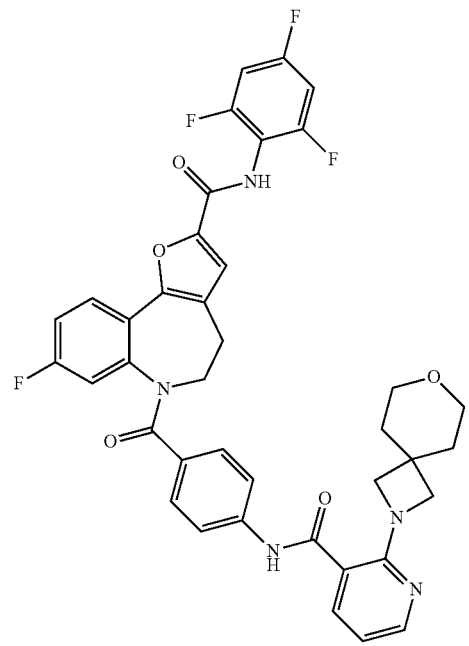 [SMILES: O=C(Nc1c(F)cc(F)cc1F)c1cc2c(o1)-c1ccc(F)cc1N(C(=O)c1ccc(NC(=O)c3cccnc3N3CC4(CCOCC4)C3)cc1)CC2] |

-continued
| Compound | Structure |
|---|---|
| 101 | 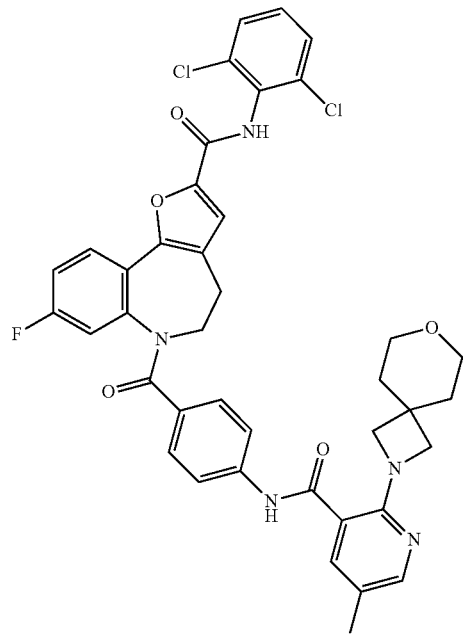 [SMILES: Cc1cnc(N2CC3(CCOCC3)C2)c(C(=O)Nc2ccc(C(=O)N3CCc4cc(C(=O)Nc5c(Cl)cccc5Cl)oc4-c4ccc(F)cc43)cc2)c1] |
| 102 | 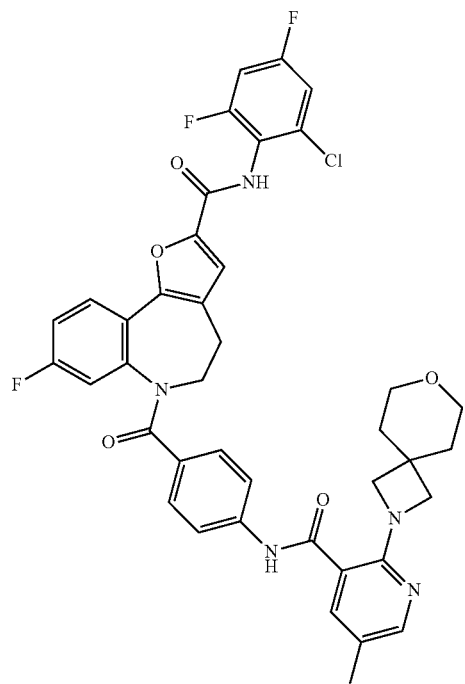 [SMILES: Cc1cnc(N2CC3(CCOCC3)C2)c(C(=O)Nc2ccc(C(=O)N3CCc4cc(C(=O)Nc5c(F)cc(F)cc5Cl)oc4-c4ccc(F)cc43)cc2)c1] |

-continued
| Compound | Structure |
|---|---|
| 103 | 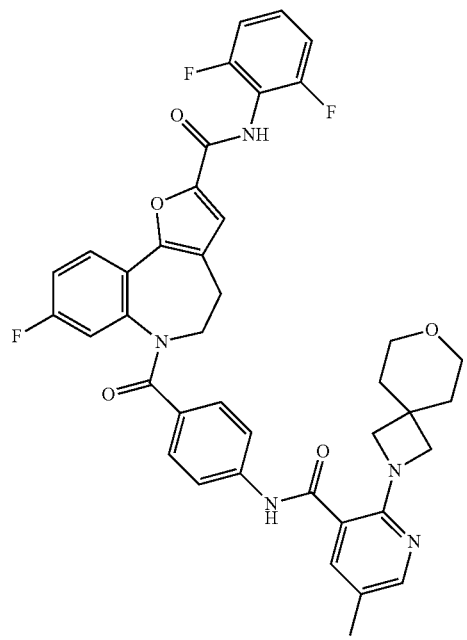 [SMILES: Cc1cnc(N2CC3(CCOCC3)C2)c(C(=O)Nc2ccc(C(=O)N3CCc4cc(C(=O)Nc5c(F)cccc5F)oc4-c4ccc(F)cc43)cc2)c1] |
| 104 | 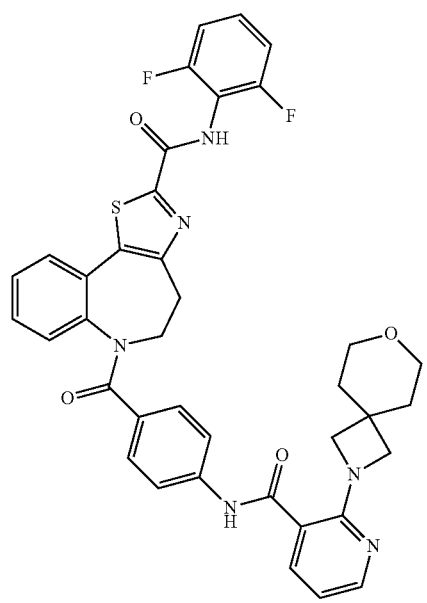 |

| Compound | Structure |
|---|---|
| 105 | 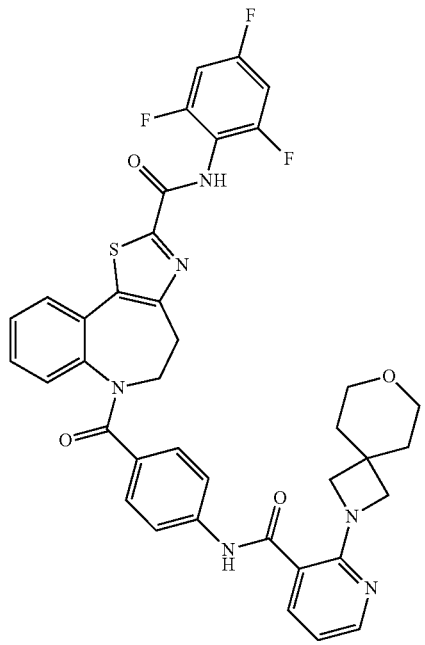 [SMILES: O=C(Nc1c(F)cc(F)cc1F)c1nc2c(s1)-c1ccccc1N(C(=O)c1ccc(NC(=O)c3cccnc3N3CC4(CCOCC4)C3)cc1)CC2] |
| 106 | 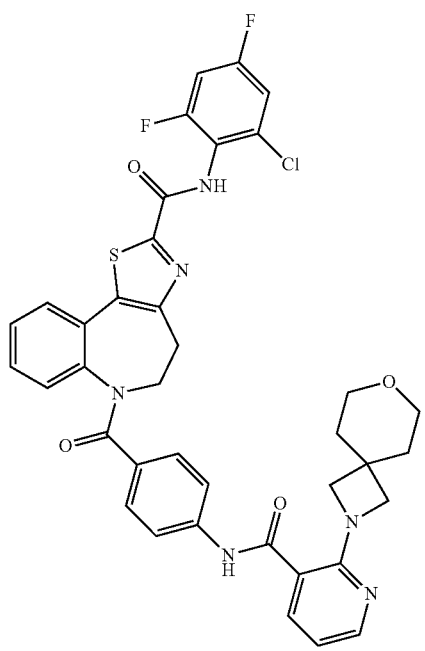 [SMILES: O=C(Nc1c(F)cc(F)cc1Cl)c1nc2c(s1)-c1ccccc1N(C(=O)c1ccc(NC(=O)c3cccnc3N3CC4(CCOCC4)C3)cc1)CC2] |

-continued
| Compound | Structure |
|---|---|
| 107 | 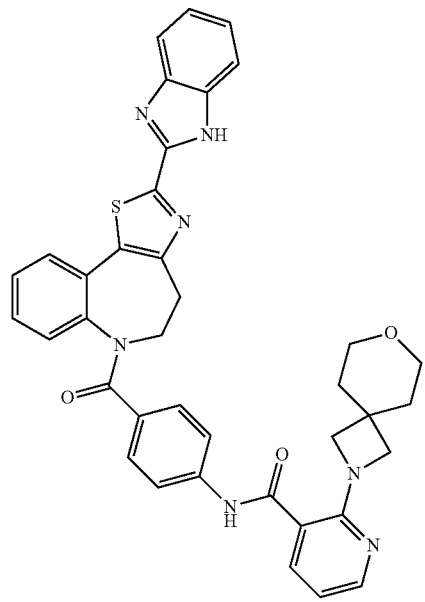 [SMILES: O=C(Nc1ccc(C(=O)N2CCc3nc(-c4nc5ccccc5[nH]4)sc3-c3ccccc32)cc1)c1cccnc1N1CC2(CCOCC2)C1] |
| 108 | 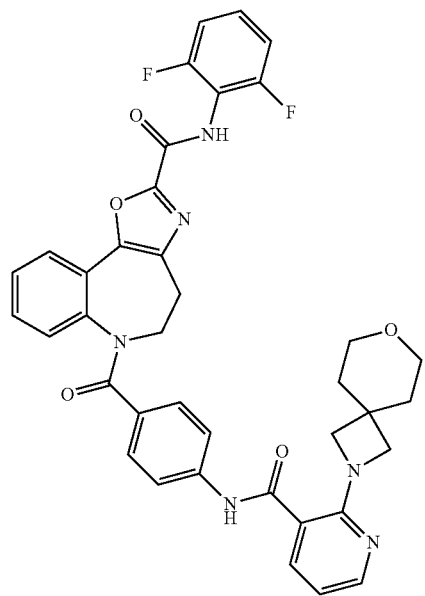 [SMILES: O=C(Nc1c(F)cccc1F)c1nc2c(o1)-c1ccccc1N(C(=O)c1ccc(NC(=O)c3cccnc3N3CC4(CCOCC4)C3)cc1)CC2] |

-continued
| Compound | Structure |
|---|---|
| 109 | 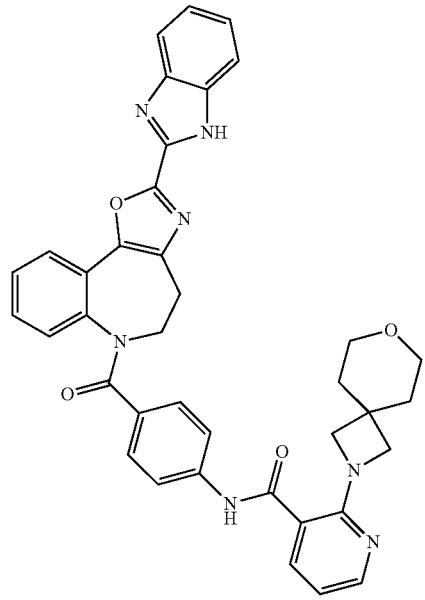 [SMILES: O=C(Nc1ccc(C(=O)N2CCc3nc(-c4nc5ccccc5[nH]4)oc3-c3ccccc32)cc1)c1cccnc1N1CC2(CCOCC2)C1] |
| 110 | 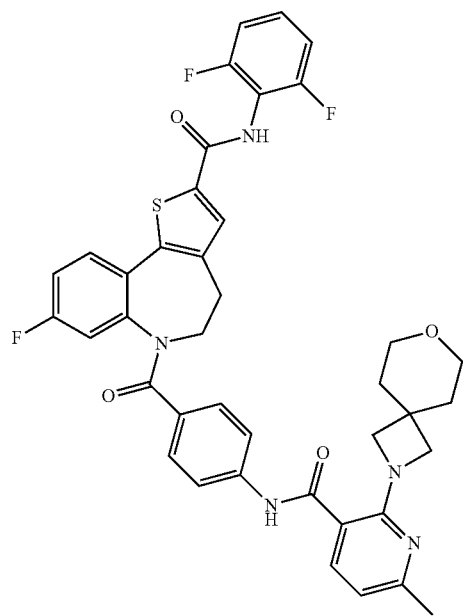 [SMILES: Cc1ccc(C(=O)Nc2ccc(C(=O)N3CCc4cc(C(=O)Nc5c(F)cccc5F)sc4-c4ccc(F)cc43)cc2)c(N2CC3(CCOCC3)C2)n1] |

| Compound | Structure |
|---|---|
| 111 | 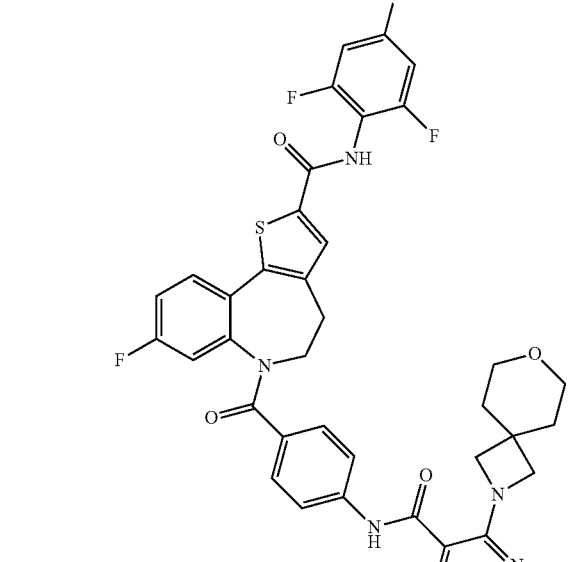 |
| 112 | 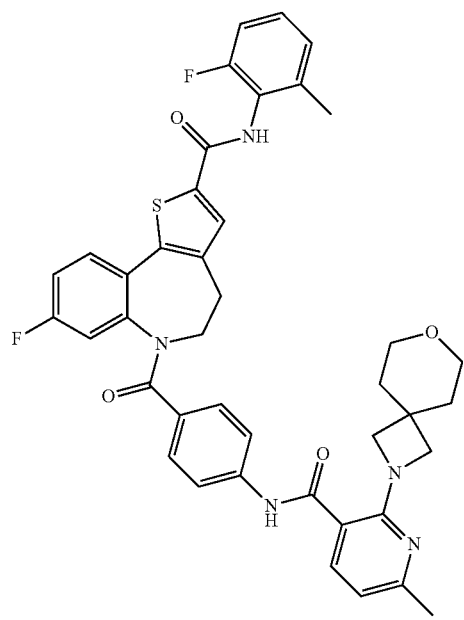 [SMILES: Cc1ccc(C(=O)Nc2ccc(C(=O)N3CCc4cc(C(=O)Nc5c(C)cccc5F)sc4-c4ccc(F)cc43)cc2)c(N2CC3(CCOCC3)C2)n1] |

-continued
| Compound | Structure |
|---|---|
| 113 | 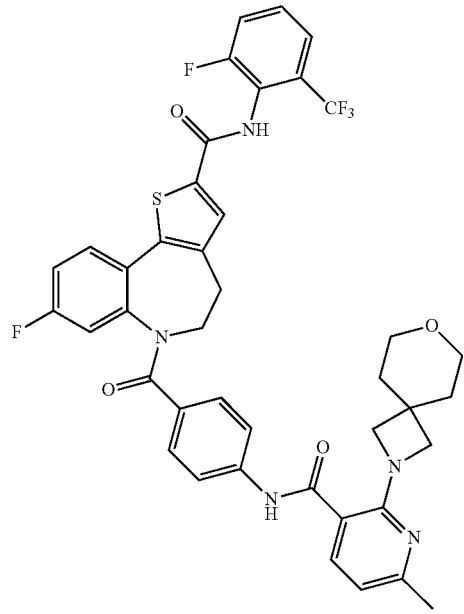 [SMILES: Cc1ccc(C(=O)Nc2ccc(C(=O)N3CCc4cc(C(=O)Nc5c(F)cccc5C(F)(F)F)sc4-c4ccc(F)cc43)cc2)c(N2CC3(CCOCC3)C2)n1] |
| 114 | 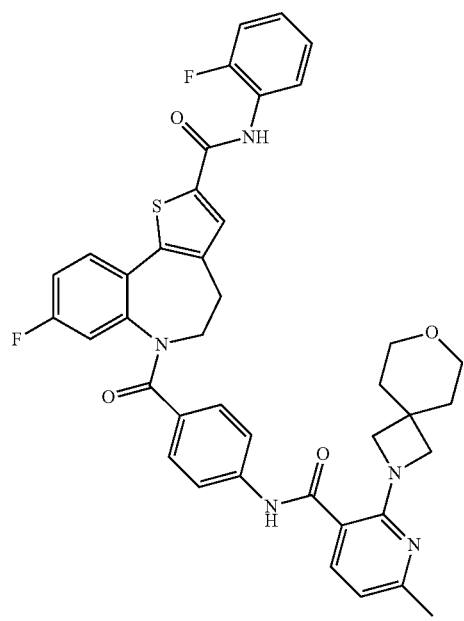 [SMILES: Cc1ccc(C(=O)Nc2ccc(C(=O)N3CCc4cc(C(=O)Nc5ccccc5F)sc4-c4ccc(F)cc43)cc2)c(N2CC3(CCOCC3)C2)n1] |

-continued
| Compound | Structure |
|---|---|
| 115 | 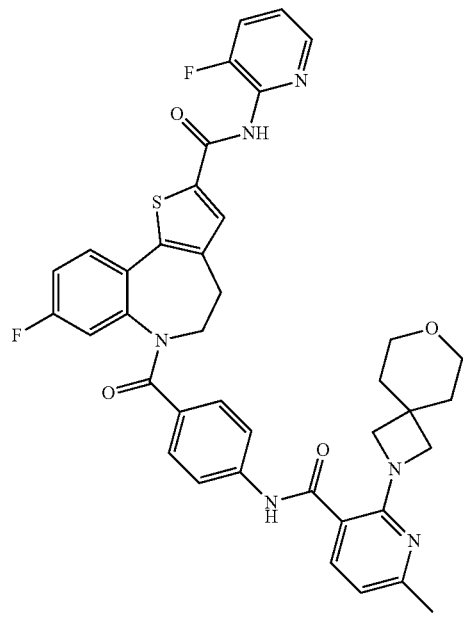 [SMILES: Cc1ccc(C(=O)Nc2ccc(C(=O)N3CCc4cc(C(=O)Nc5ncccc5F)sc4-c4ccc(F)cc43)cc2)c(N2CC3(CCOCC3)C2)n1] |
| 116 | 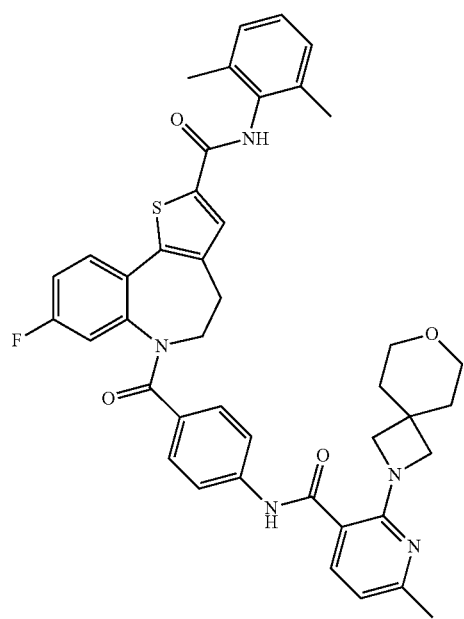 [SMILES: Cc1ccc(C(=O)Nc2ccc(C(=O)N3CCc4cc(C(=O)Nc5c(C)cccc5C)sc4-c4ccc(F)cc43)cc2)c(N2CC3(CCOCC3)C2)n1] |

US 11,091,501 B2
529                                                    530
-continued
| Compound | Structure |
|----------|-----------|
| 117 | 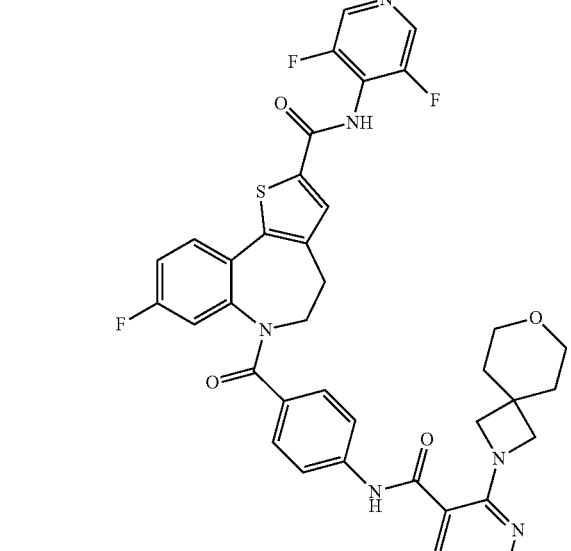 |
| 118 | 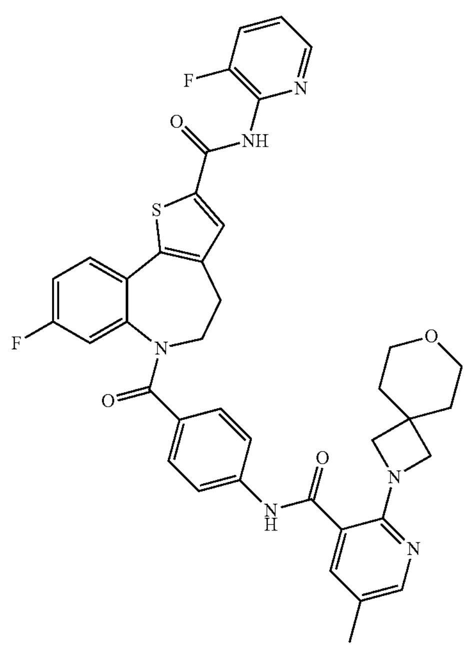 [SMILES: Cc1cnc(N2CC3(CCOCC3)C2)c(C(=O)Nc2ccc(C(=O)N3CCc4cc(C(=O)Nc5ncccc5F)sc4-c4ccc(F)cc43)cc2)c1] |

| Compound | Structure |
|---|---|
| 119 | 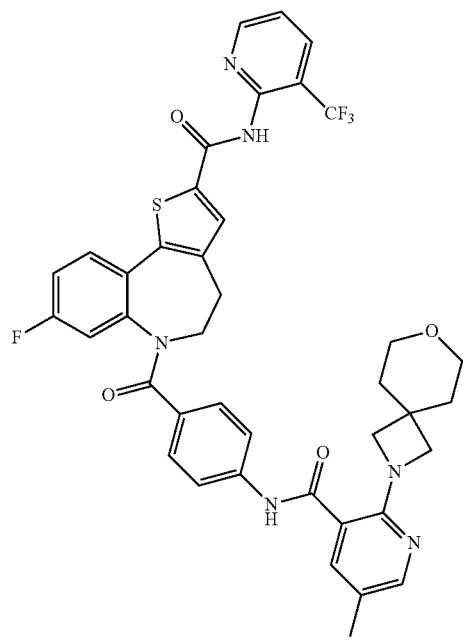 [SMILES: Cc1cnc(N2CC3(CCOCC3)C2)c(C(=O)Nc2ccc(C(=O)N3CCc4cc(C(=O)Nc5ncccc5C(F)(F)F)sc4-c4ccc(F)cc43)cc2)c1] |
| 120 | 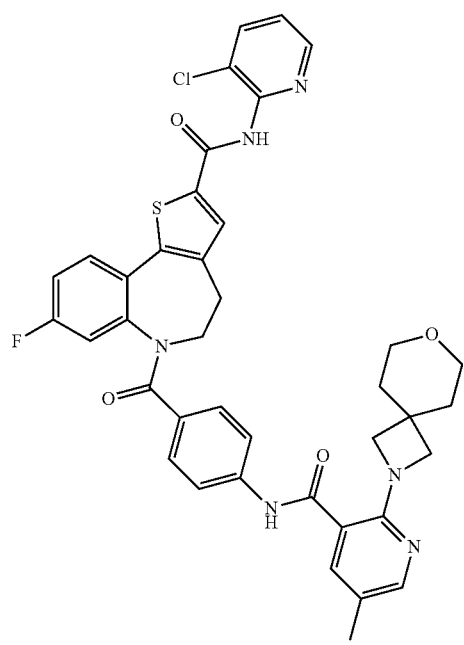 [SMILES: Cc1cnc(N2CC3(CCOCC3)C2)c(C(=O)Nc2ccc(C(=O)N3CCc4cc(C(=O)Nc5ncccc5Cl)sc4-c4ccc(F)cc43)cc2)c1] |

| Compound | Structure |
|---|---|
| 121 | 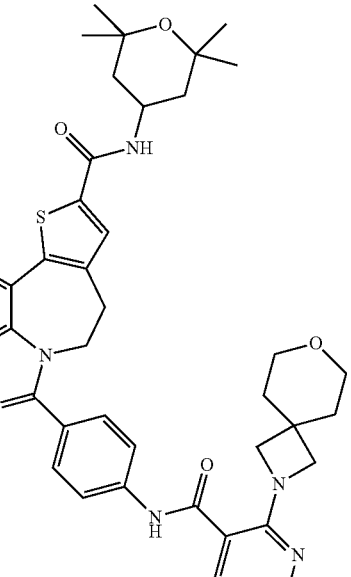 |
| 122 | 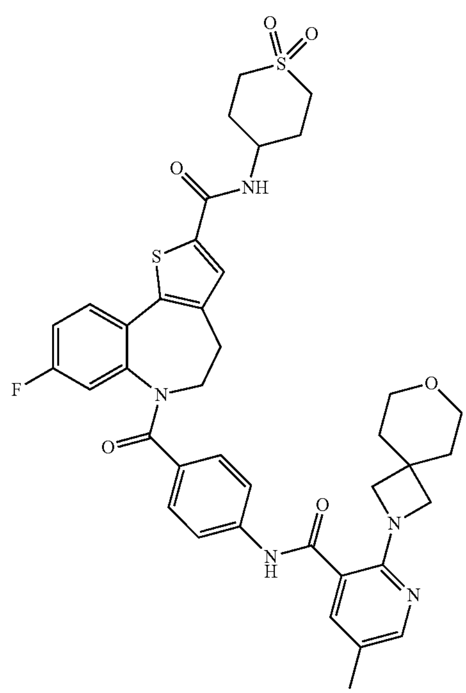 [SMILES: Cc1cnc(N2CC3(CCOCC3)C2)c(C(=O)Nc2ccc(C(=O)N3CCc4cc(C(=O)NC5CCS(=O)(=O)CC5)sc4-c4ccc(F)cc43)cc2)c1] |

-continued
| Compound | Structure |
|---|---|
| 123 | 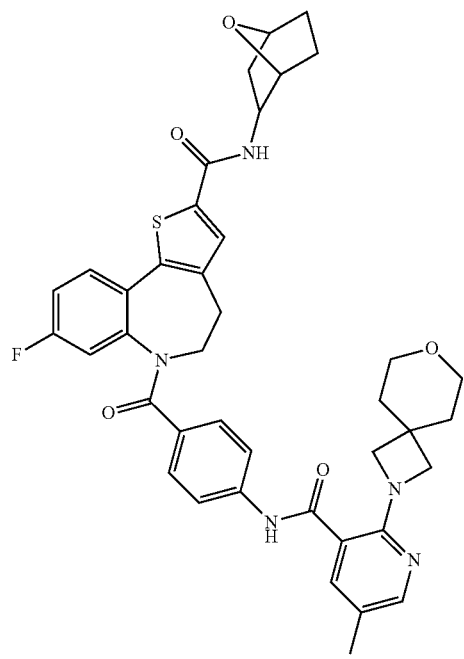 [SMILES: Cc1cnc(N2CC3(CCOCC3)C2)c(C(=O)Nc2ccc(C(=O)N3CCc4cc(C(=O)NC5CC6CCC5O6)sc4-c4ccc(F)cc43)cc2)c1] |
| 124 | 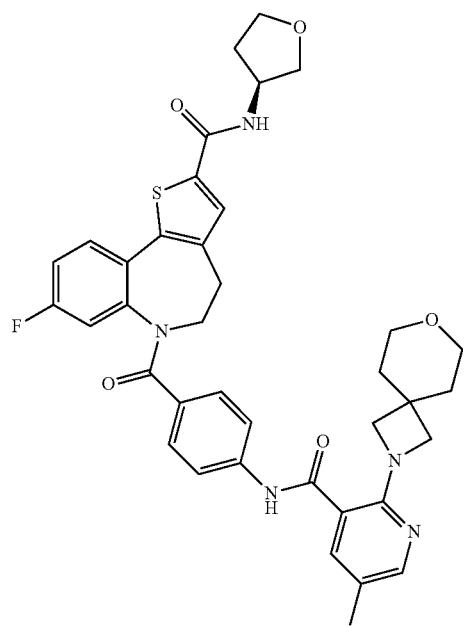 [SMILES: Cc1cnc(N2CC3(CCOCC3)C2)c(C(=O)Nc2ccc(C(=O)N3CCc4cc(C(=O)N[C@H]5CCOC5)sc4-c4ccc(F)cc43)cc2)c1] |

| Compound | Structure |
|---|---|
| 125 | 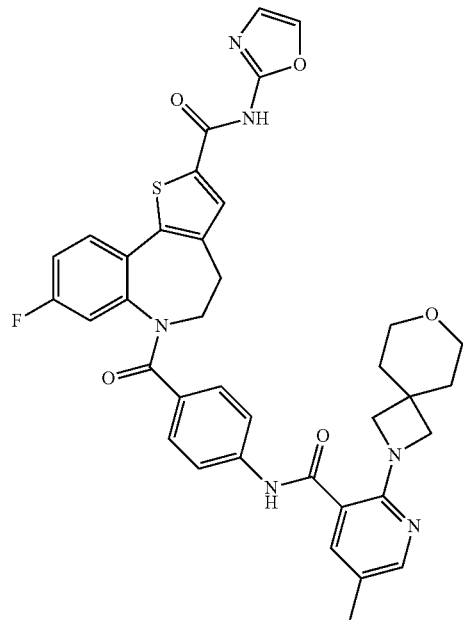 [SMILES: Cc1cnc(N2CC3(CCOCC3)C2)c(C(=O)Nc2ccc(C(=O)N3CCc4cc(C(=O)Nc5ncco5)sc4-c4ccc(F)cc43)cc2)c1] |
| 126 | 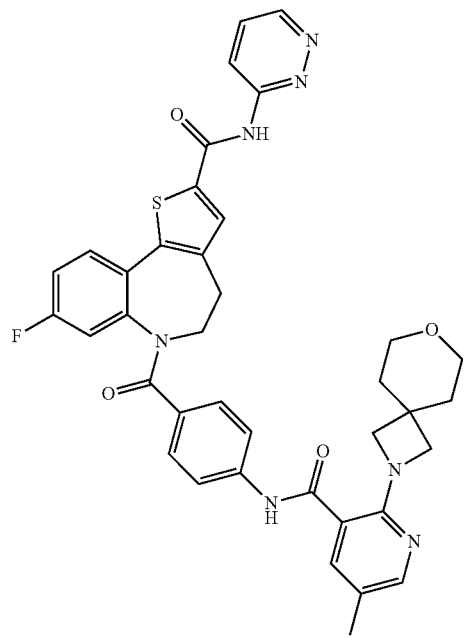 [SMILES: Cc1cnc(N2CC3(CCOCC3)C2)c(C(=O)Nc2ccc(C(=O)N3CCc4cc(C(=O)Nc5cccnn5)sc4-c4ccc(F)cc43)cc2)c1] |

-continued
| Compound | Structure |
|---|---|
| 127 | 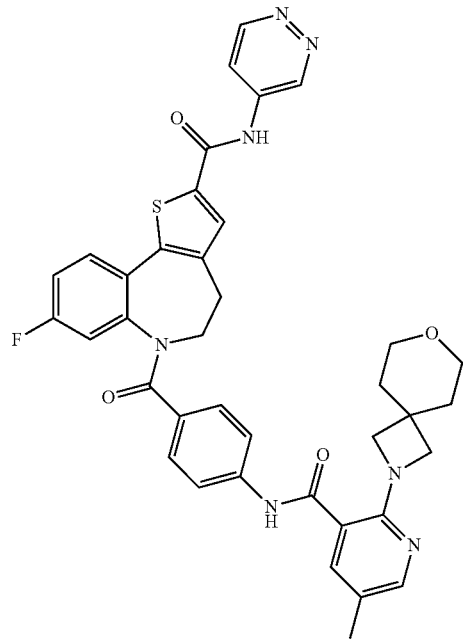 [SMILES: Cc1cnc(N2CC3(CCOCC3)C2)c(C(=O)Nc2ccc(C(=O)N3CCc4cc(C(=O)Nc5ccnnc5)sc4-c4ccc(F)cc43)cc2)c1] |
| 128 | 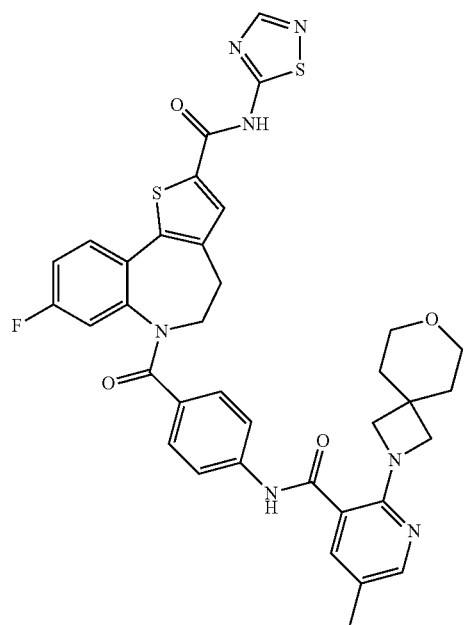 |

-continued
| Compound | Structure |
|---|---|
| 129 | 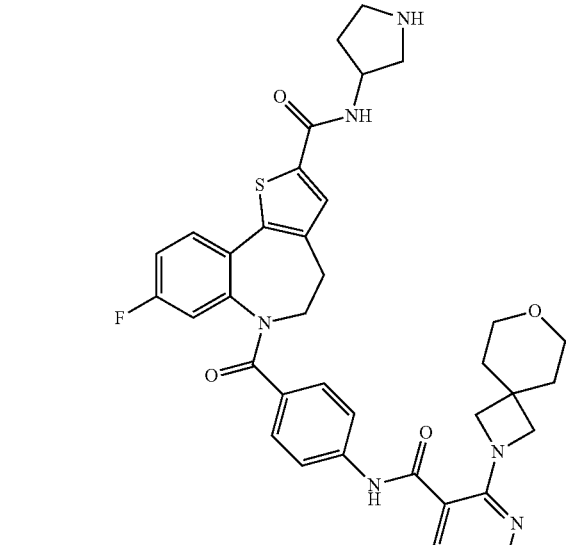 |
| 130 | 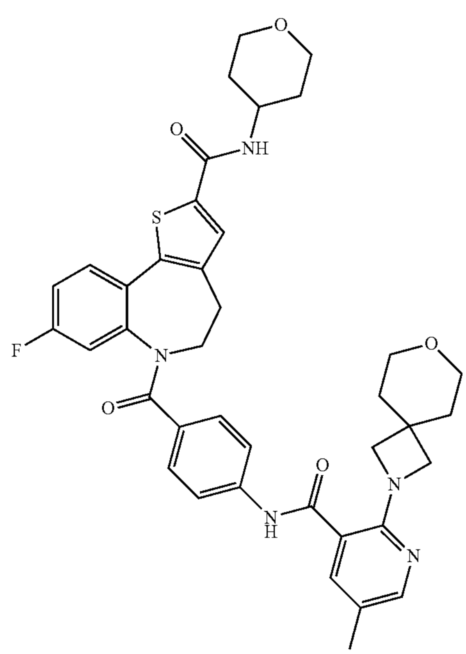 [SMILES: Cc1cnc(N2CC3(CCOCC3)C2)c(C(=O)Nc2ccc(C(=O)N3CCc4cc(C(=O)NC5CCOCC5)sc4-c4ccc(F)cc43)cc2)c1] |

-continued
| Compound | Structure |
|---|---|
| 131 | 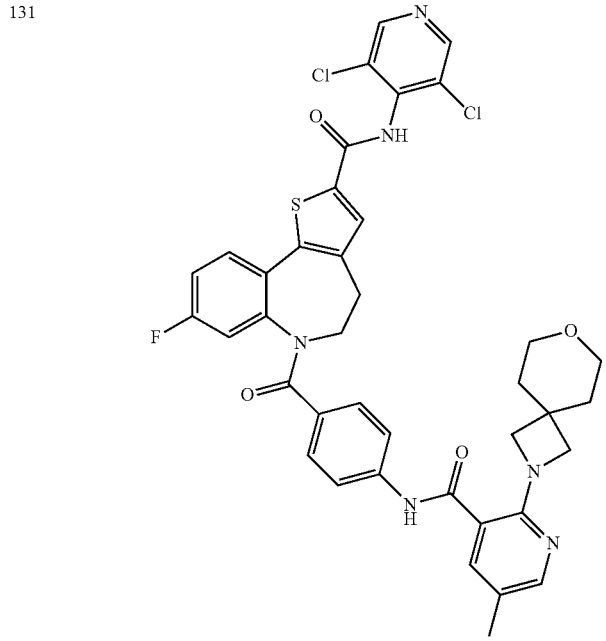 |
| 132 | 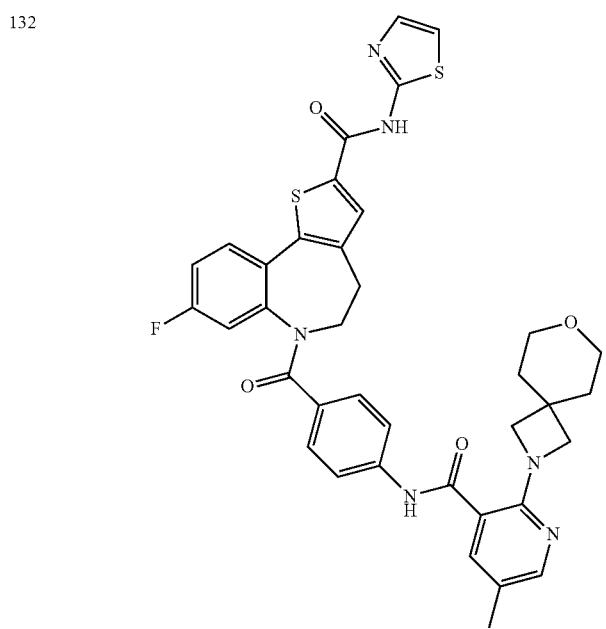 |

545
-continued
| Compound | Structure |
|---|---|
| 133 | 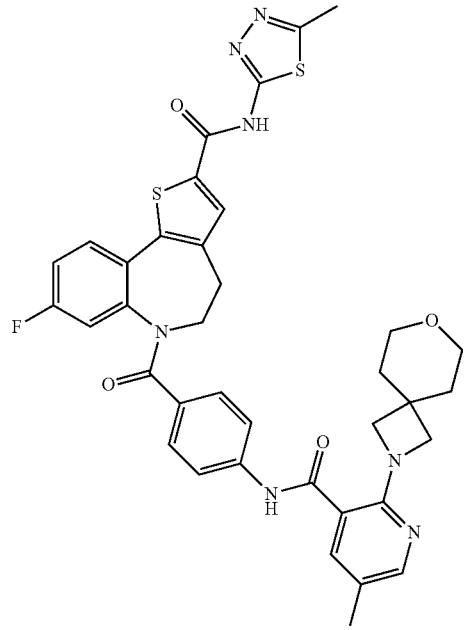 [SMILES: Cc1cnc(N2CC3(CCOCC3)C2)c(C(=O)Nc2ccc(C(=O)N3CCc4cc(C(=O)Nc5nnc(C)s5)sc4-c4ccc(F)cc43)cc2)c1] |
| 134 | 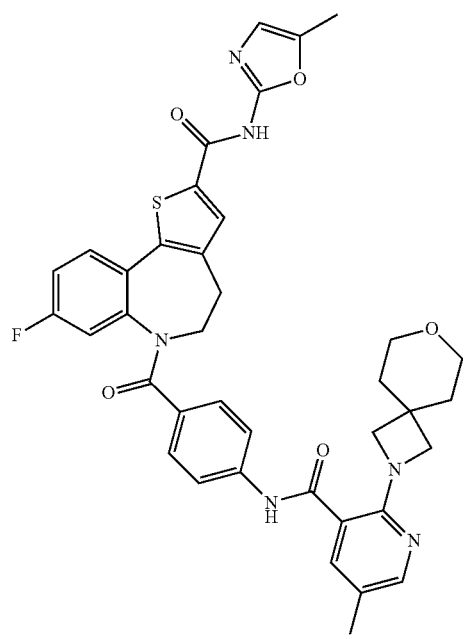 [SMILES: Cc1cnc(N2CC3(CCOCC3)C2)c(C(=O)Nc2ccc(C(=O)N3CCc4cc(C(=O)Nc5ncc(C)o5)sc4-c4ccc(F)cc43)cc2)c1] |

| Compound | Structure |
|---|---|
| 135 | 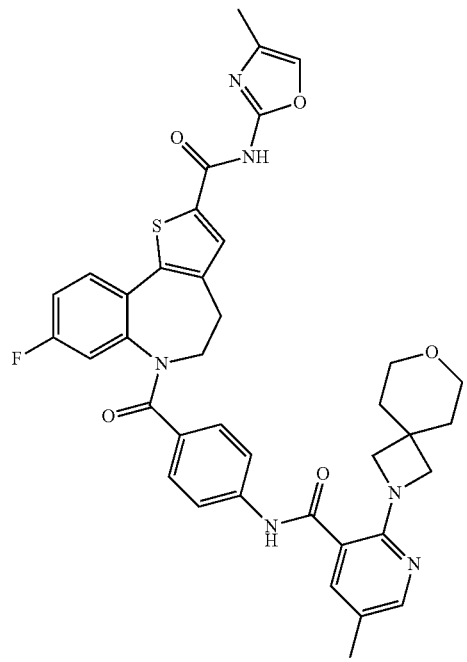 [SMILES: Cc1cnc(N2CC3(CCOCC3)C2)c(C(=O)Nc2ccc(C(=O)N3CCc4cc(C(=O)Nc5nc(C)co5)sc4-c4ccc(F)cc43)cc2)c1] |
| 136 | 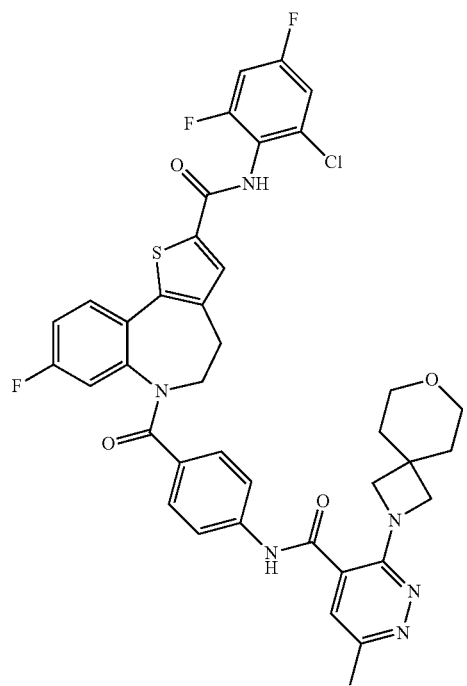 |

| Compound | Structure |
|---|---|
| 137 | 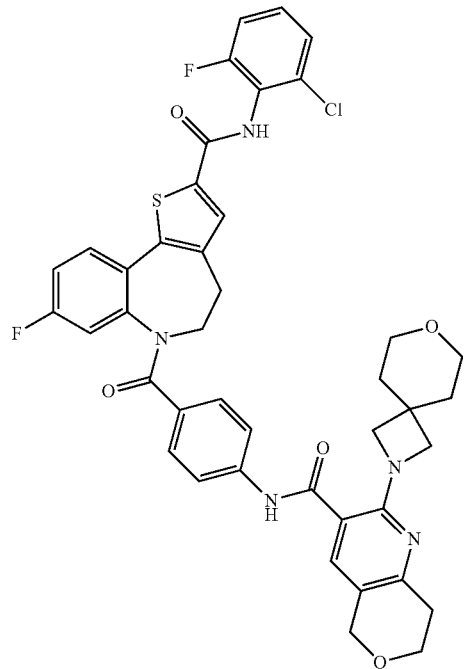 [SMILES: O=C(Nc1c(F)cccc1Cl)c1cc2c(s1)-c1ccc(F)cc1N(C(=O)c1ccc(NC(=O)c3cc4c(nc3N3CC5(CCOCC5)C3)CCOC4)cc1)CC2] |
| 138 | 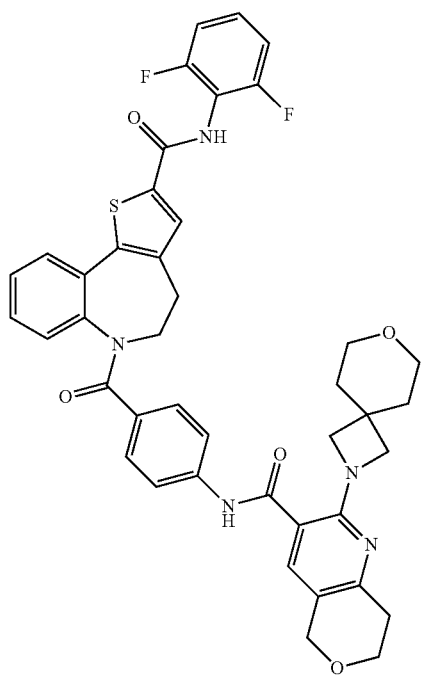 [SMILES: O=C(Nc1c(F)cccc1F)c1cc2c(s1)-c1ccccc1N(C(=O)c1ccc(NC(=O)c3cc4c(nc3N3CC5(CCOCC5)C3)CCOC4)cc1)CC2] |

-continued
| Compound | Structure |
|---|---|
| 139 | 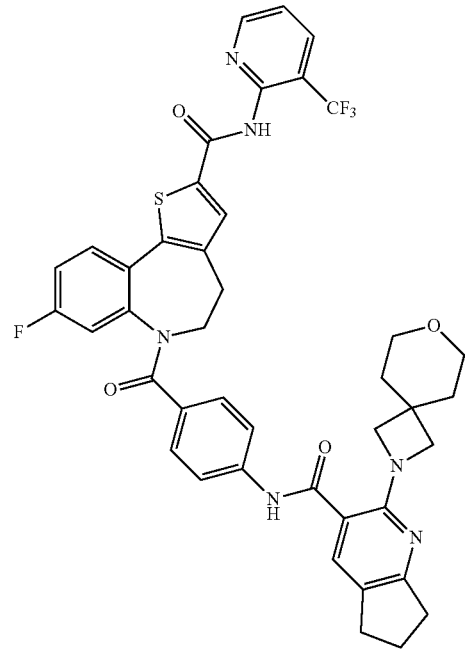 [SMILES: O=C(Nc1ncccc1C(F)(F)F)c1cc2c(s1)-c1ccc(F)cc1N(C(=O)c1ccc(NC(=O)c3cc4c(nc3N3CC5(CCOCC5)C3)CCC4)cc1)CC2] |
| 140 | 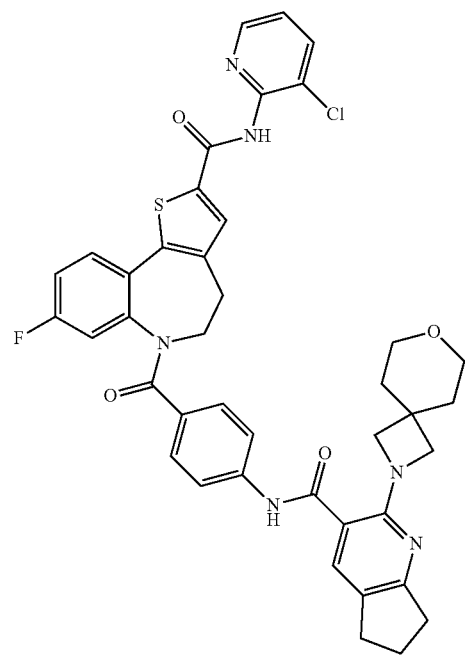 [SMILES: O=C(Nc1ncccc1Cl)c1cc2c(s1)-c1ccc(F)cc1N(C(=O)c1ccc(NC(=O)c3cc4c(nc3N3CC5(CCOCC5)C3)CCC4)cc1)CC2] |

-continued
| Compound | Structure |
|---|---|
| 141 | 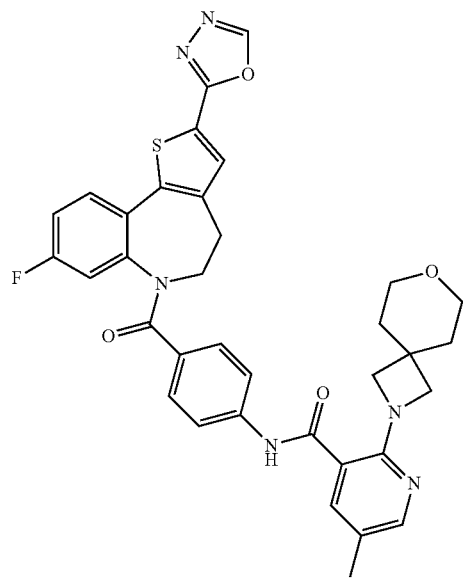 [SMILES: Cc1cnc(N2CC3(CCOCC3)C2)c(C(=O)Nc2ccc(C(=O)N3CCc4cc(-c5nnco5)sc4-c4ccc(F)cc43)cc2)c1] |
| 142 | 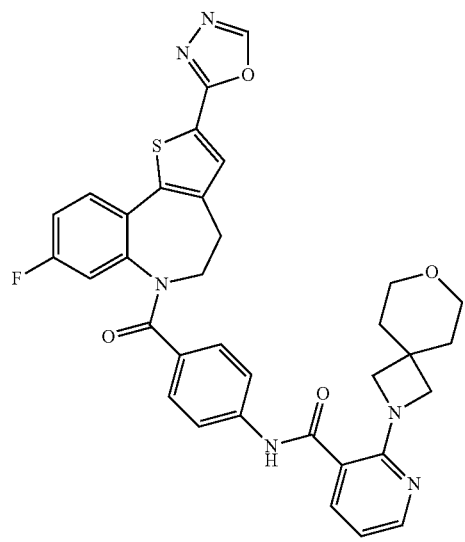 [SMILES: O=C(Nc1ccc(C(=O)N2CCc3cc(-c4nnco4)sc3-c3ccc(F)cc32)cc1)c1cccnc1N1CC2(CCOCC2)C1] |

-continued
| Compound | Structure |
|---|---|
| 143 | 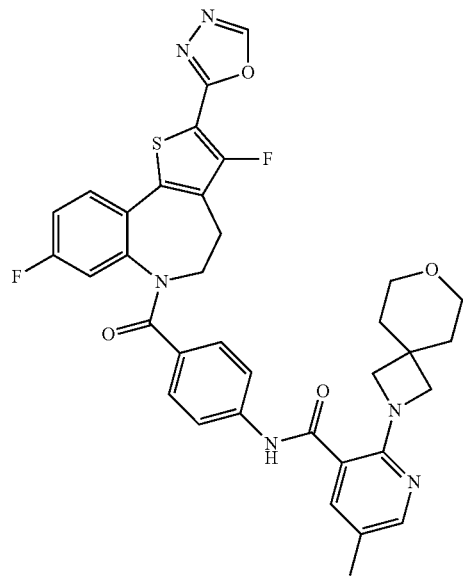 [SMILES: Cc1cnc(N2CC3(CCOCC3)C2)c(C(=O)Nc2ccc(C(=O)N3CCc4c(sc(-c5nnco5)c4F)-c4ccc(F)cc43)cc2)c1] |
| 144 | 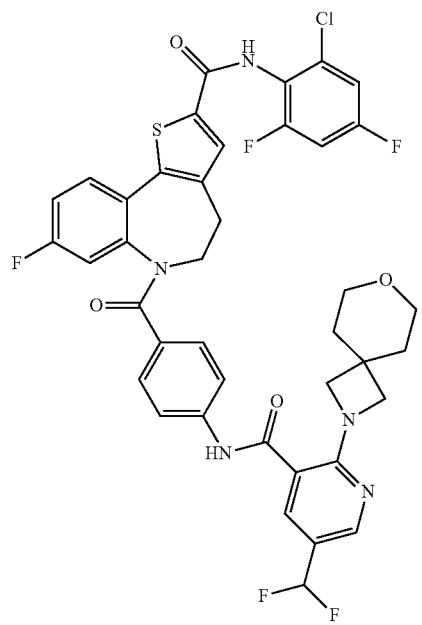 [SMILES: O=C(Nc1c(F)cc(F)cc1Cl)c1cc2c(s1)-c1ccc(F)cc1N(C(=O)c1ccc(NC(=O)c3cc(C(F)F)cnc3N3CC4(CCOCC4)C3)cc1)CC2] |

| Compound | Structure |
|---|---|
| 145 | 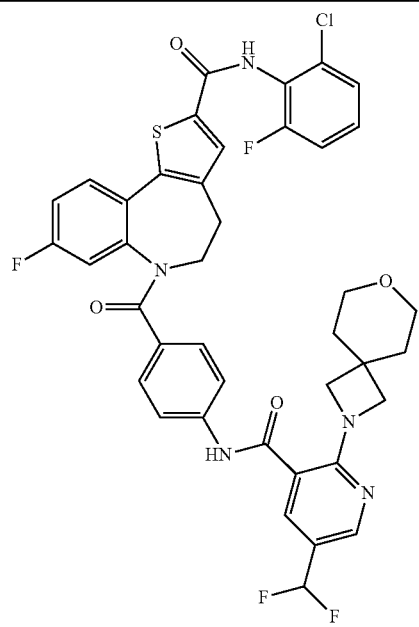 |
| 146 | 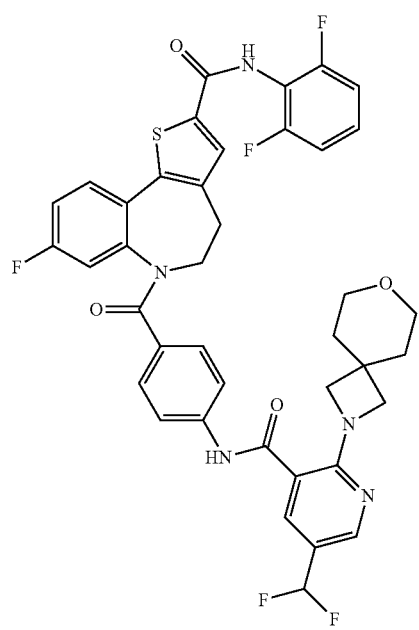 [SMILES: O=C(Nc1c(F)cccc1F)c1cc2c(s1)-c1ccc(F)cc1N(C(=O)c1ccc(NC(=O)c3cc(C(F)F)cnc3N3CC4(CCOCC4)C3)cc1)CC2] |

| Compound | Structure |
|---|---|
| 147 | 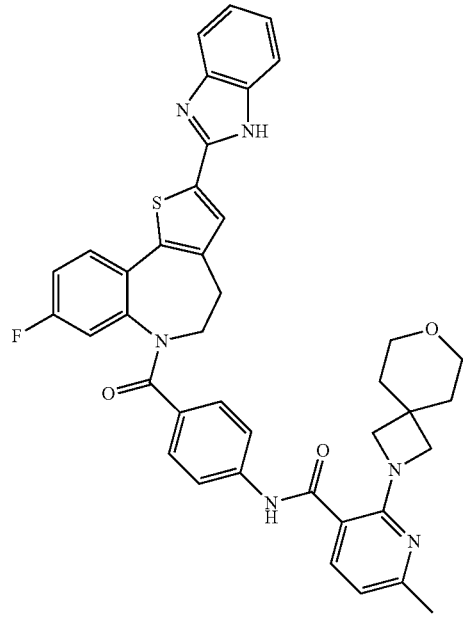 [SMILES: Cc1ccc(C(=O)Nc2ccc(C(=O)N3CCc4cc(-c5nc6ccccc6[nH]5)sc4-c4ccc(F)cc43)cc2)c(N2CC3(CCOCC3)C2)n1] |
| 148 | 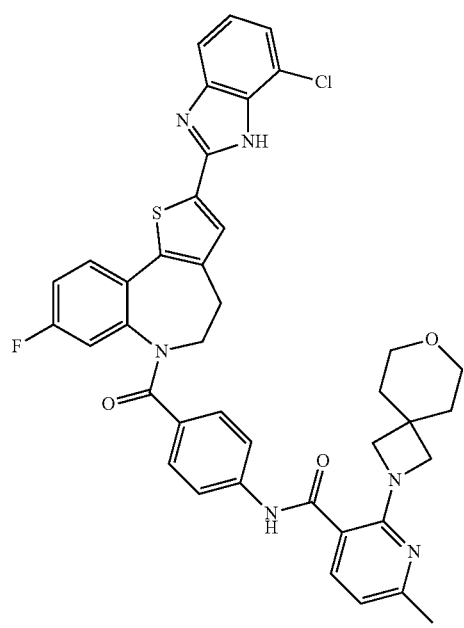 [SMILES: Cc1ccc(C(=O)Nc2ccc(C(=O)N3CCc4cc(-c5nc6cccc(Cl)c6[nH]5)sc4-c4ccc(F)cc43)cc2)c(N2CC3(CCOCC3)C2)n1] |

-continued
| Compound | Structure |
|---|---|
| 149 | 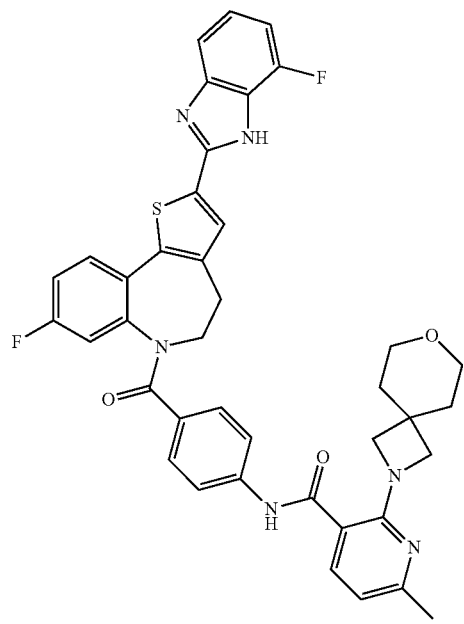 [SMILES: Cc1ccc(C(=O)Nc2ccc(C(=O)N3CCc4cc(-c5nc6cccc(F)c6[nH]5)sc4-c4ccc(F)cc43)cc2)c(N2CC3(CCOCC3)C2)n1] |
| 150 | 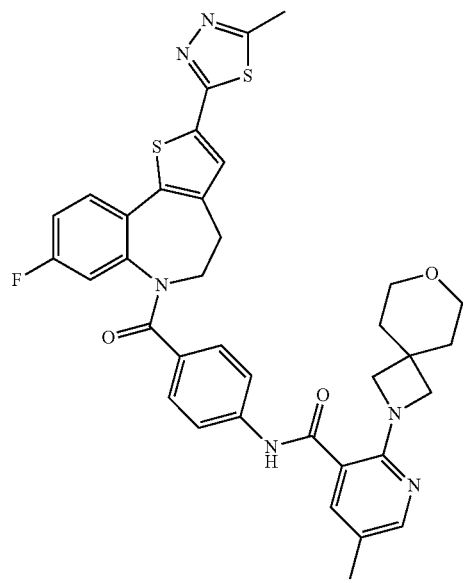 [SMILES: Cc1cnc(N2CC3(CCOCC3)C2)c(C(=O)Nc2ccc(C(=O)N3CCc4cc(-c5nnc(C)s5)sc4-c4ccc(F)cc43)cc2)c1] |

| Compound | Structure |
|---|---|
| 151 | 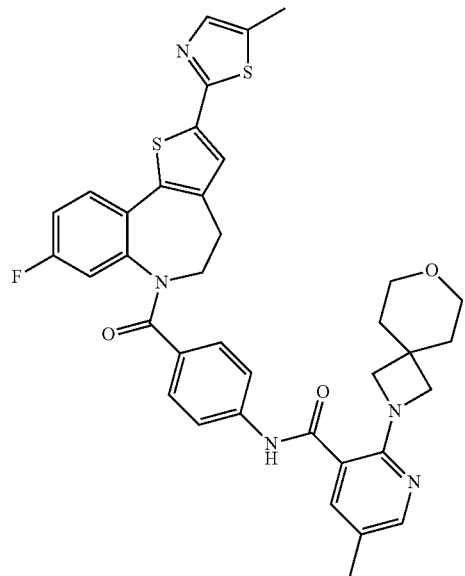 |
| 152 | 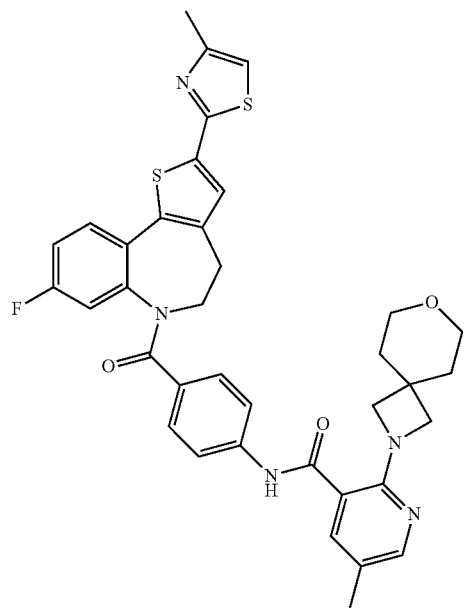 |

| Compound | Structure |
|---|---|
| 153 | 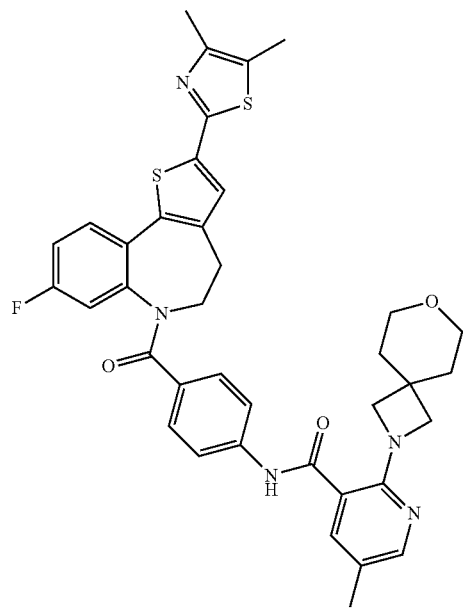 [SMILES: Cc1cnc(N2CC3(CCOCC3)C2)c(C(=O)Nc2ccc(C(=O)N3CCc4cc(-c5nc(C)c(C)s5)sc4-c4ccc(F)cc43)cc2)c1] |
| 154 | 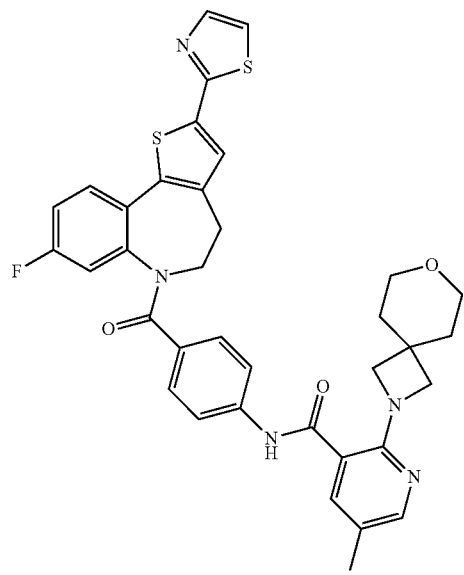 [SMILES: Cc1cnc(N2CC3(CCOCC3)C2)c(C(=O)Nc2ccc(C(=O)N3CCc4cc(-c5nccs5)sc4-c4ccc(F)cc43)cc2)c1] |

-continued

| Compound | Structure |
|---|---|
| 155 | 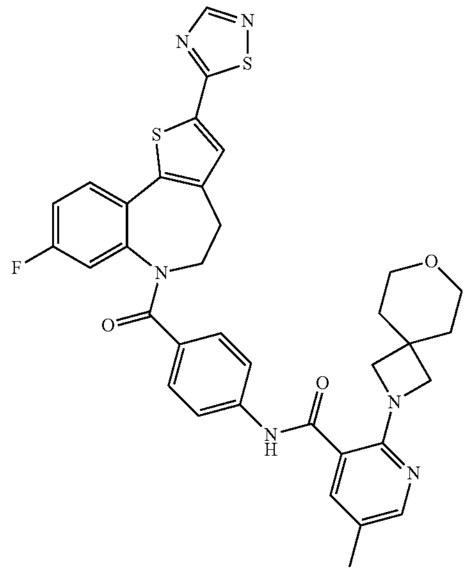 [SMILES: Cc1cnc(N2CC3(CCOCC3)C2)c(C(=O)Nc2ccc(C(=O)N3CCc4cc(-c5ncns5)sc4-c4ccc(F)cc43)cc2)c1] |
| 156 | 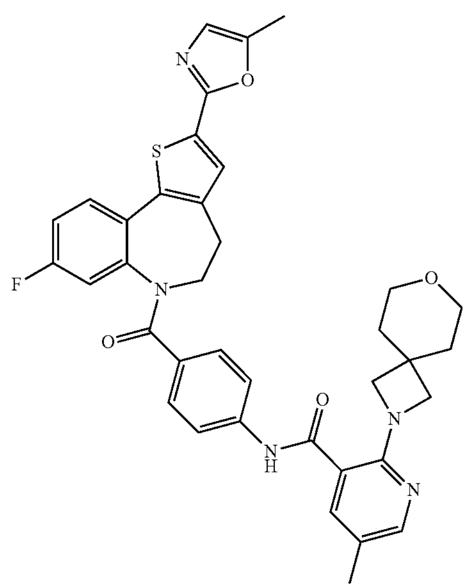 [SMILES: Cc1cnc(N2CC3(CCOCC3)C2)c(C(=O)Nc2ccc(C(=O)N3CCc4cc(-c5ncc(C)o5)sc4-c4ccc(F)cc43)cc2)c1] |

| Compound | Structure |
|---|---|
| 157 | 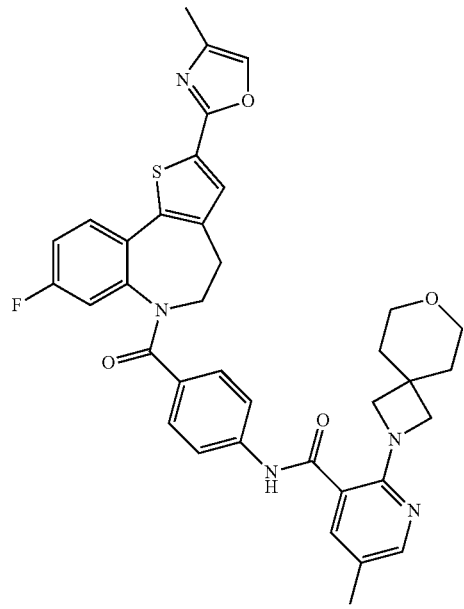 [SMILES: Cc1cnc(N2CC3(CCOCC3)C2)c(C(=O)Nc2ccc(C(=O)N3CCc4cc(-c5nc(C)co5)sc4-c4ccc(F)cc43)cc2)c1] |
| 158 | 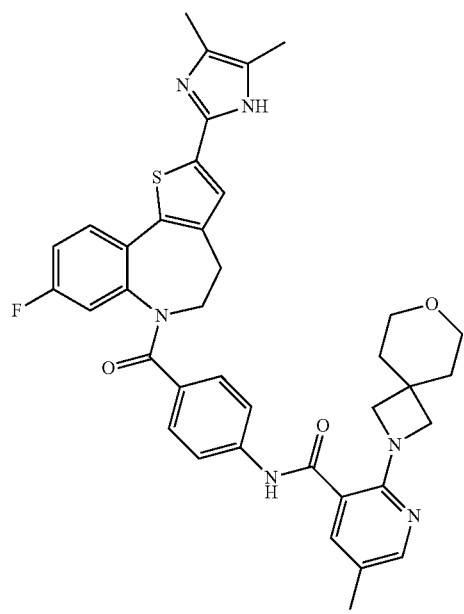 [SMILES: Cc1cnc(N2CC3(CCOCC3)C2)c(C(=O)Nc2ccc(C(=O)N3CCc4cc(-c5nc(C)c(C)[nH]5)sc4-c4ccc(F)cc43)cc2)c1] |

| Compound | Structure |
|---|---|
| 159 | 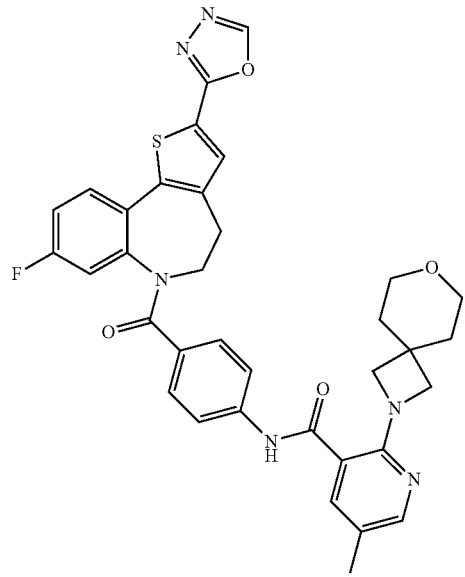 [SMILES: Cc1cnc(N2CC3(CCOCC3)C2)c(C(=O)Nc2ccc(C(=O)N3CCc4cc(-c5nnco5)sc4-c4ccc(F)cc43)cc2)c1] |
| 160 | 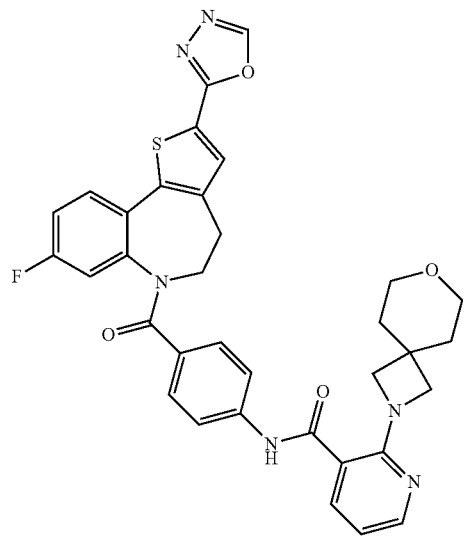 [SMILES: O=C(Nc1ccc(C(=O)N2CCc3cc(-c4nnco4)sc3-c3ccc(F)cc32)cc1)c1cccnc1N1CC2(CCOCC2)C1] |

| Compound | Structure |
|---|---|
| 161 | 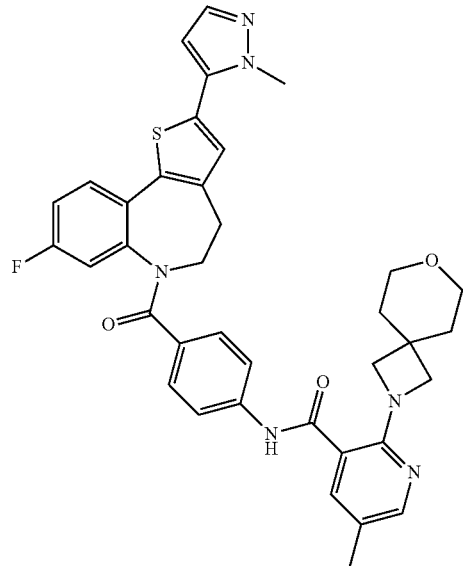 [SMILES: Cc1cnc(N2CC3(CCOCC3)C2)c(C(=O)Nc2ccc(C(=O)N3CCc4cc(-c5ccnn5C)sc4-c4ccc(F)cc43)cc2)c1] |
| 162 | 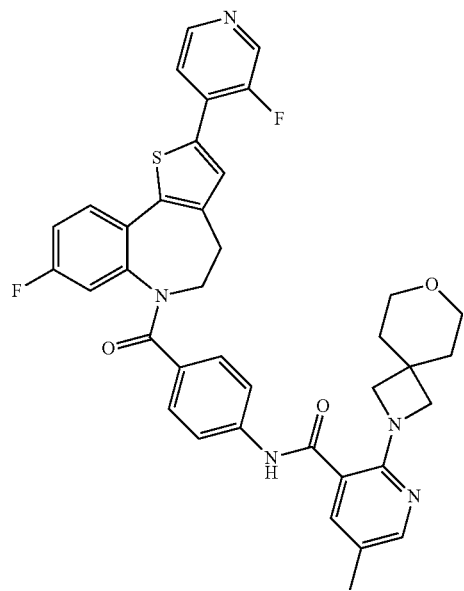 [SMILES: Cc1cnc(N2CC3(CCOCC3)C2)c(C(=O)Nc2ccc(C(=O)N3CCc4cc(-c5ccncc5F)sc4-c4ccc(F)cc43)cc2)c1] |

| Compound | Structure |
|---|---|
| 163 | 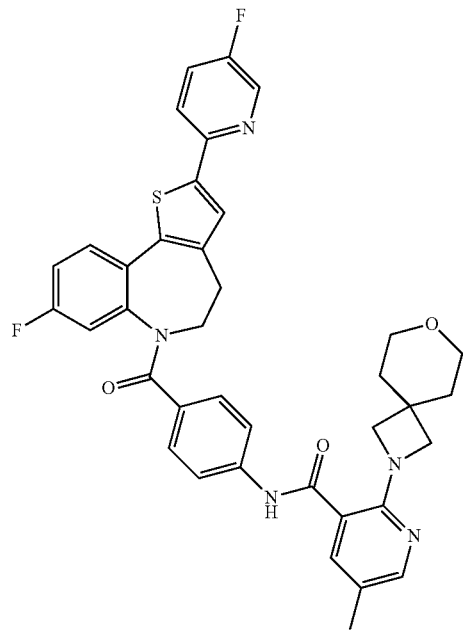 [SMILES: Cc1cnc(N2CC3(CCOCC3)C2)c(C(=O)Nc2ccc(C(=O)N3CCc4cc(-c5ccc(F)cn5)sc4-c4ccc(F)cc43)cc2)c1] |
| 164 | 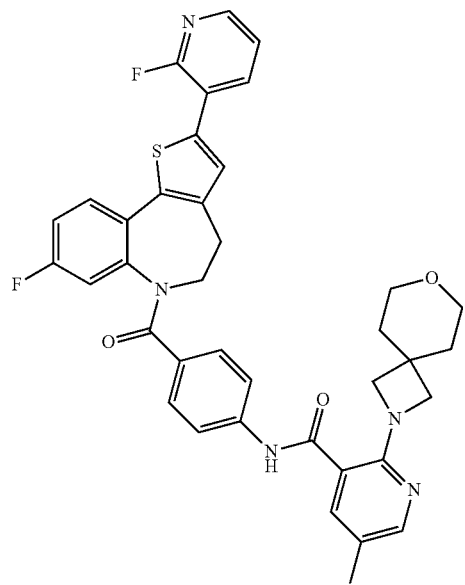 [SMILES: Cc1cnc(N2CC3(CCOCC3)C2)c(C(=O)Nc2ccc(C(=O)N3CCc4cc(-c5cccnc5F)sc4-c4ccc(F)cc43)cc2)c1] |

-continued
| Compound | Structure |
|---|---|
| 165 | 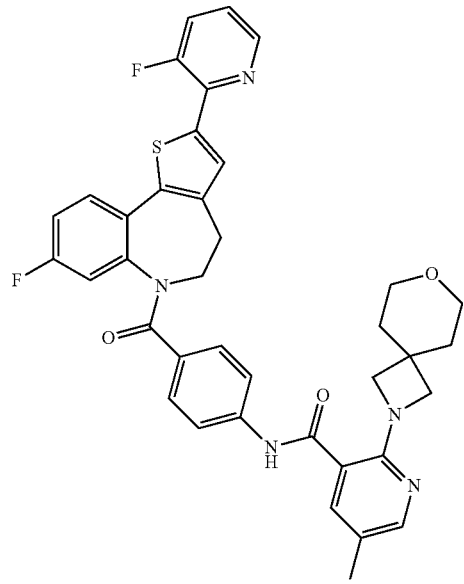 [SMILES: Cc1cnc(N2CC3(CCOCC3)C2)c(C(=O)Nc2ccc(C(=O)N3CCc4cc(-c5ncccc5F)sc4-c4ccc(F)cc43)cc2)c1] |
| 166 | 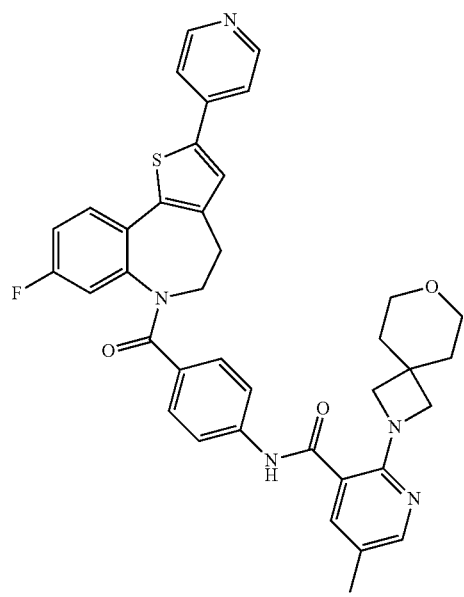 [SMILES: Cc1cnc(N2CC3(CCOCC3)C2)c(C(=O)Nc2ccc(C(=O)N3CCc4cc(-c5ccncc5)sc4-c4ccc(F)cc43)cc2)c1] |

-continued
| Compound | Structure |
|---|---|
| 167 | 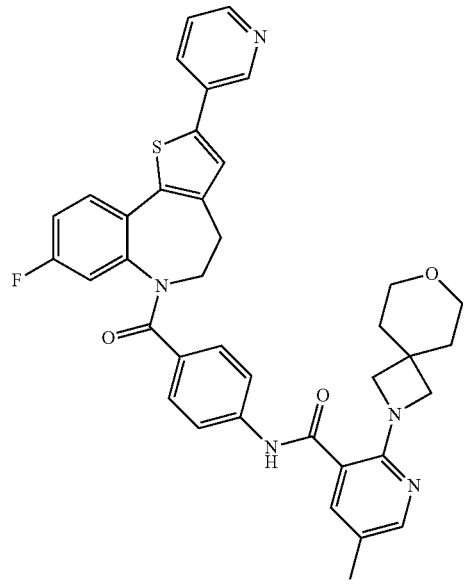 |
| 168 | 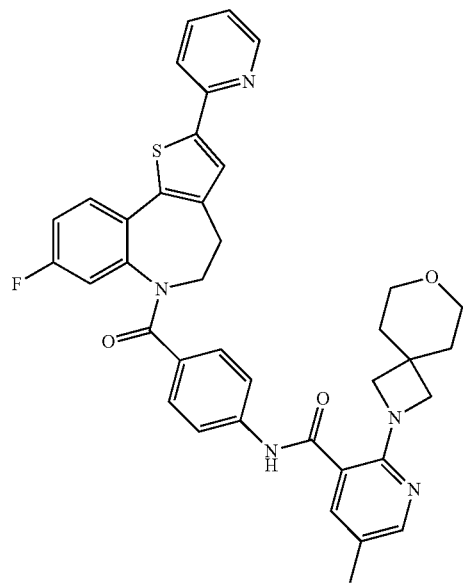 [SMILES: Cc1cnc(N2CC3(CCOCC3)C2)c(C(=O)Nc2ccc(C(=O)N3CCc4cc(-c5ccccn5)sc4-c4ccc(F)cc43)cc2)c1] |

| Compound | Structure |
|---|---|
| 169 | 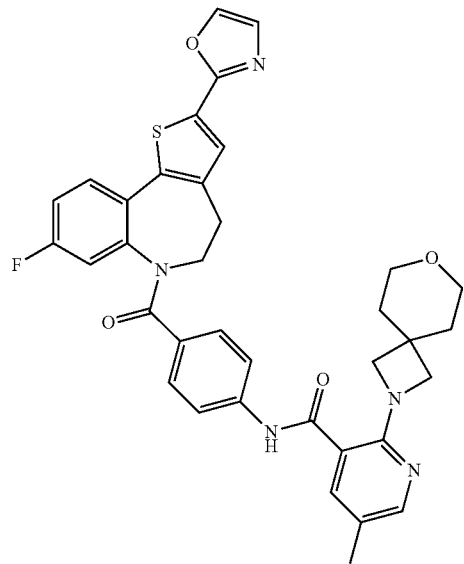 [SMILES: Cc1cnc(N2CC3(CCOCC3)C2)c(C(=O)Nc2ccc(C(=O)N3CCc4cc(-c5ncco5)sc4-c4ccc(F)cc43)cc2)c1] |
| 170 | 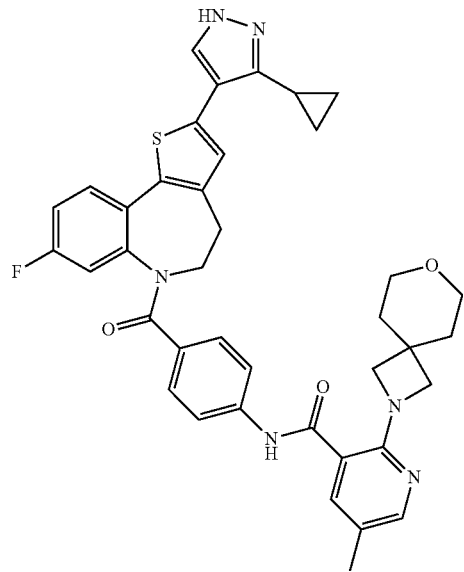 [SMILES: Cc1cnc(N2CC3(CCOCC3)C2)c(C(=O)Nc2ccc(C(=O)N3CCc4cc(-c5c[nH]nc5C5CC5)sc4-c4ccc(F)cc43)cc2)c1] |

-continued

| Compound | Structure |
|---|---|
| 171 | 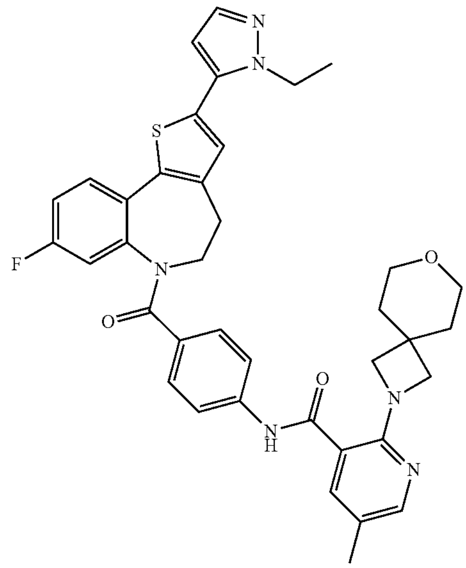 [SMILES: CCn1nccc1-c1cc2c(s1)-c1ccc(F)cc1N(C(=O)c1ccc(NC(=O)c3cc(C)cnc3N3CC4(CCOCC4)C3)cc1)CC2] |
| 172 | 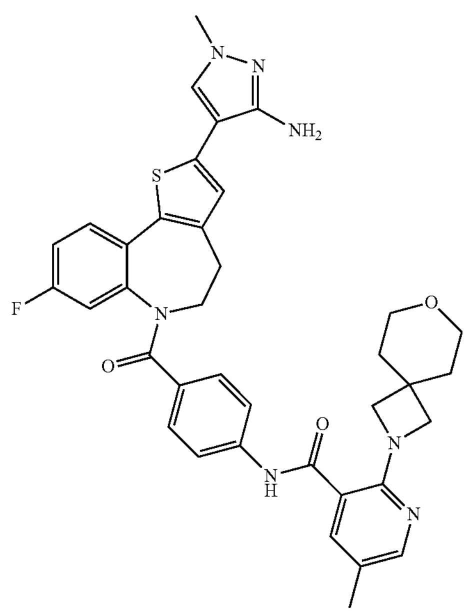 [SMILES: Cc1cnc(N2CC3(CCOCC3)C2)c(C(=O)Nc2ccc(C(=O)N3CCc4cc(-c5cn(C)nc5N)sc4-c4ccc(F)cc43)cc2)c1] |

-continued
| Compound | Structure |
|---|---|
| 173 | 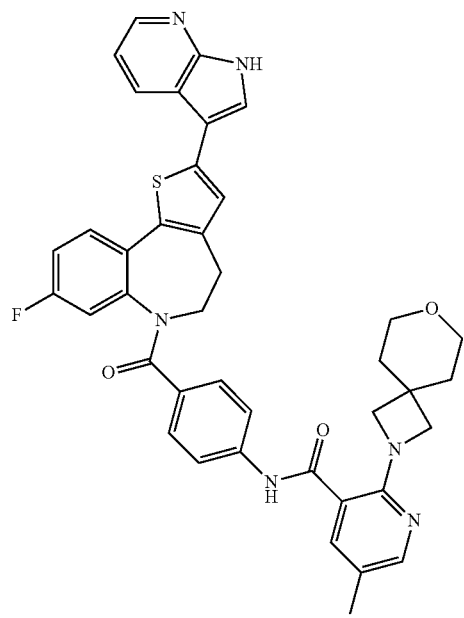 [SMILES: Cc1cnc(N2CC3(CCOCC3)C2)c(C(=O)Nc2ccc(C(=O)N3CCc4cc(-c5c[nH]c6ncccc56)sc4-c4ccc(F)cc43)cc2)c1] |
| 174 | 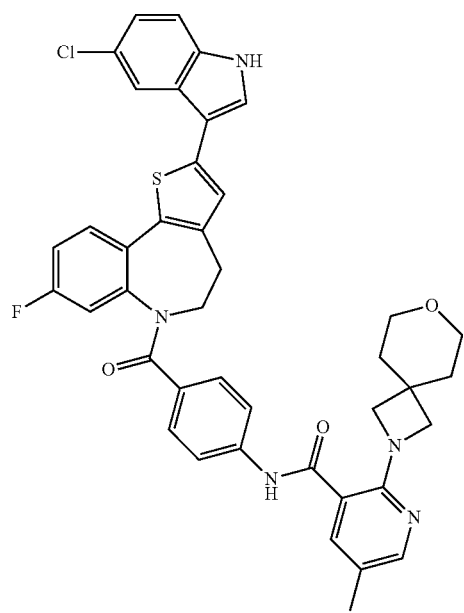 [SMILES: Cc1cnc(N2CC3(CCOCC3)C2)c(C(=O)Nc2ccc(C(=O)N3CCc4cc(-c5c[nH]c6ccc(Cl)cc56)sc4-c4ccc(F)cc43)cc2)c1] |

587
-continued
| Compound | Structure |
|---|---|
| 175 | 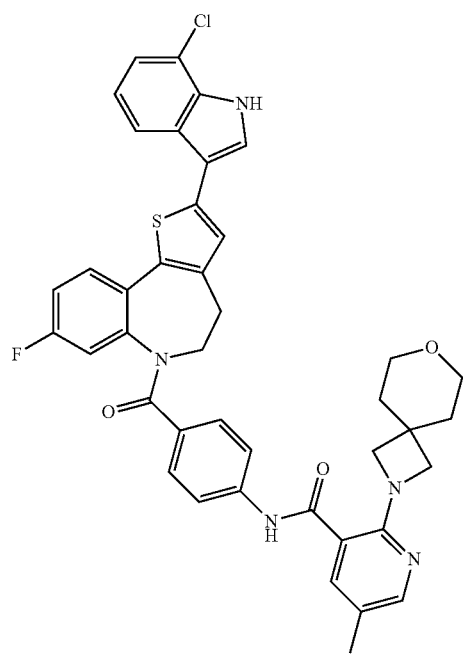 [SMILES: Cc1cnc(N2CC3(CCOCC3)C2)c(C(=O)Nc2ccc(C(=O)N3CCc4cc(-c5c[nH]c6c(Cl)cccc56)sc4-c4ccc(F)cc43)cc2)c1] |
| 176 | 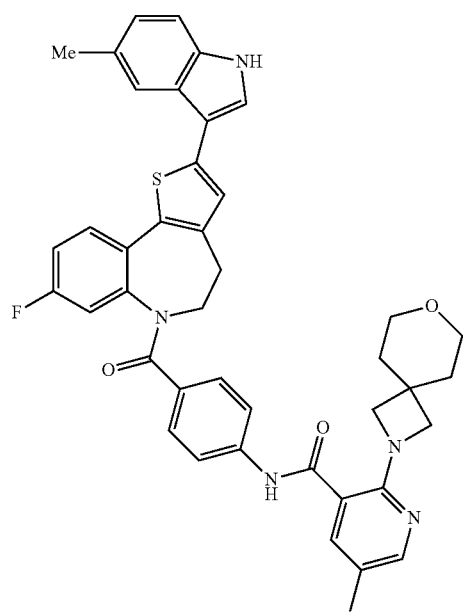 [SMILES: Cc1cnc(N2CC3(CCOCC3)C2)c(C(=O)Nc2ccc(C(=O)N3CCc4cc(-c5c[nH]c6ccc(C)cc56)sc4-c4ccc(F)cc43)cc2)c1] |

| Compound | Structure |
|---|---|
| 177 | 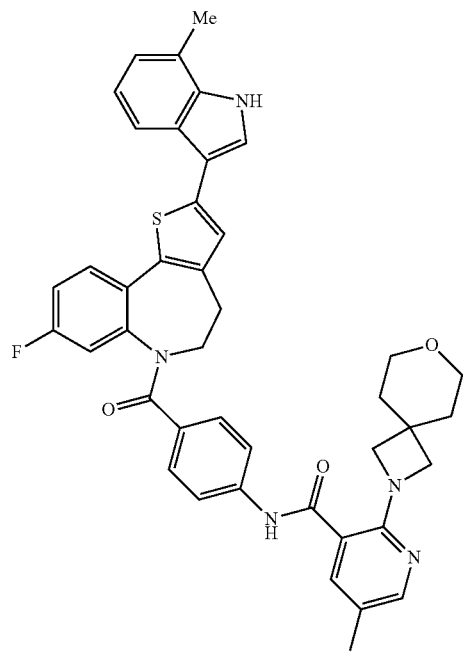 |
| 178 | 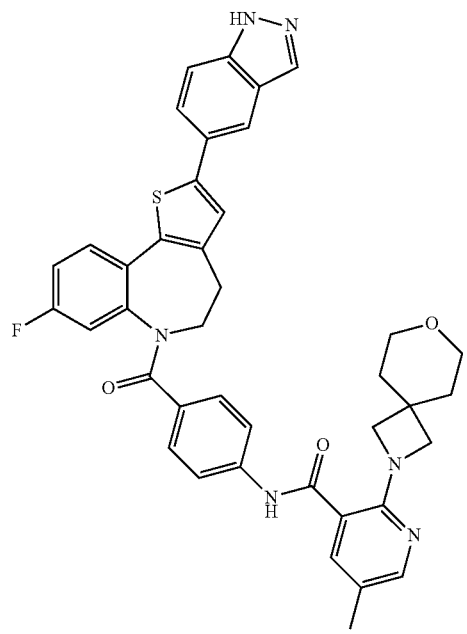 [SMILES: Cc1cnc(N2CC3(CCOCC3)C2)c(C(=O)Nc2ccc(C(=O)N3CCc4cc(-c5ccc6[nH]ncc6c5)sc4-c4ccc(F)cc43)cc2)c1] |

| Compound | Structure |
|---|---|
| 179 | 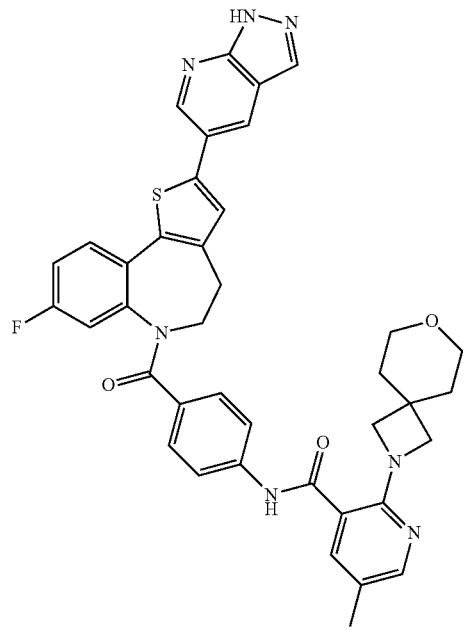 [SMILES: Cc1cnc(N2CC3(CCOCC3)C2)c(C(=O)Nc2ccc(C(=O)N3CCc4cc(-c5cnc6[nH]ncc6c5)sc4-c4ccc(F)cc43)cc2)c1] |
| 180 | 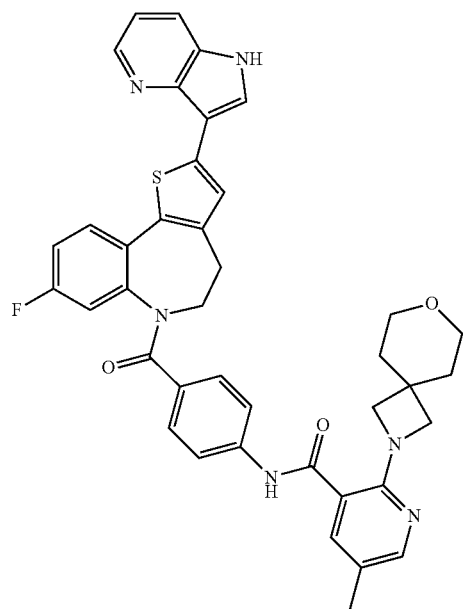 [SMILES: Cc1cnc(N2CC3(CCOCC3)C2)c(C(=O)Nc2ccc(C(=O)N3CCc4cc(-c5c[nH]c6cccnc56)sc4-c4ccc(F)cc43)cc2)c1] |

| Compound | Structure |
|---|---|
| 181 | 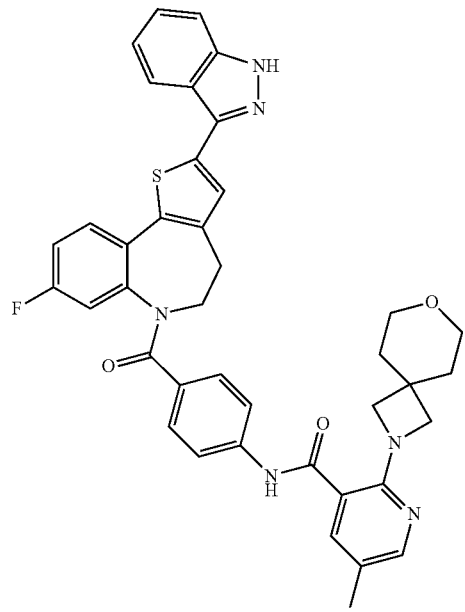 [SMILES: Cc1cnc(N2CC3(CCOCC3)C2)c(C(=O)Nc2ccc(C(=O)N3CCc4cc(-c5n[nH]c6ccccc56)sc4-c4ccc(F)cc43)cc2)c1] |
| 182 | 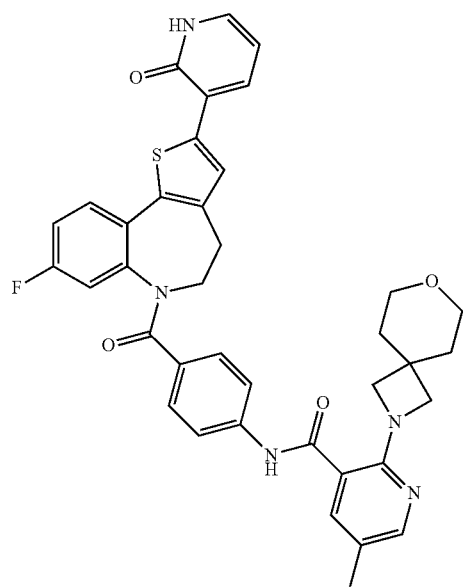 [SMILES: Cc1cnc(N2CC3(CCOCC3)C2)c(C(=O)Nc2ccc(C(=O)N3CCc4cc(-c5ccc[nH]c5=O)sc4-c4ccc(F)cc43)cc2)c1] |

-continued
| Compound | Structure |
|---|---|
| 183 | 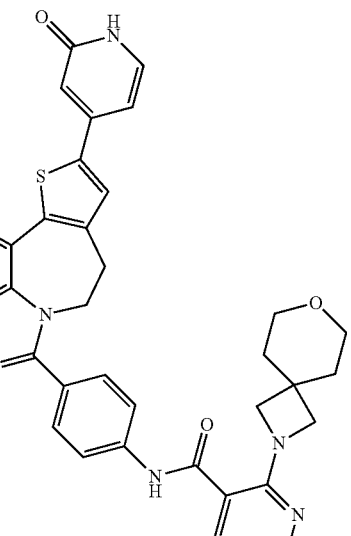 |
| 184 | 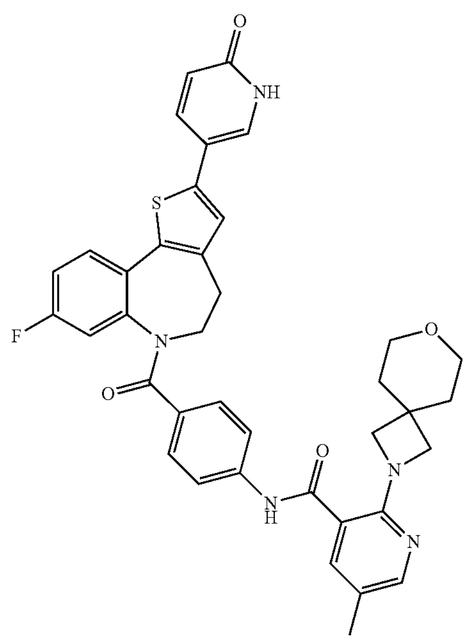 [SMILES: Cc1cnc(N2CC3(CCOCC3)C2)c(C(=O)Nc2ccc(C(=O)N3CCc4cc(-c5ccc(=O)[nH]c5)sc4-c4ccc(F)cc43)cc2)c1] |

-continued

| Compound | Structure |
|---|---|
| 185 | 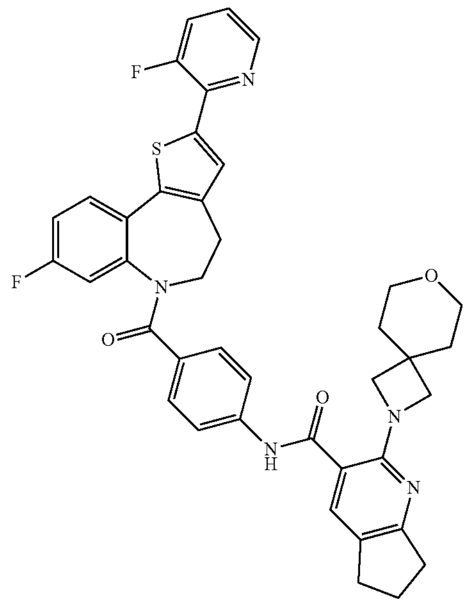 [SMILES: O=C(Nc1ccc(C(=O)N2CCc3cc(-c4ncccc4F)sc3-c3ccc(F)cc32)cc1)c1cc2c(nc1N1CC3(CCOCC3)C1)CCC2] |
| 186 | 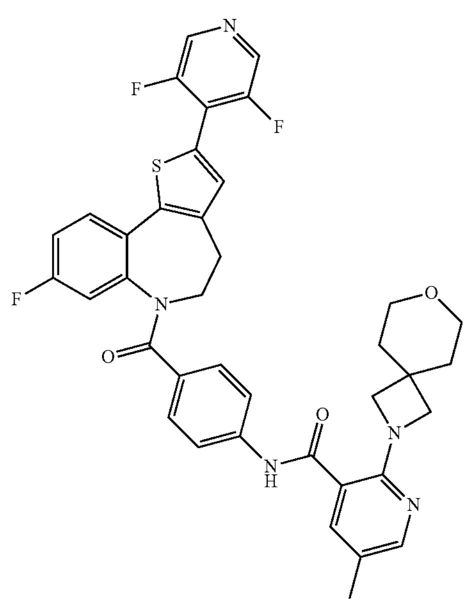 [SMILES: Cc1cnc(N2CC3(CCOCC3)C2)c(C(=O)Nc2ccc(C(=O)N3CCc4cc(-c5c(F)cncc5F)sc4-c4ccc(F)cc43)cc2)c1] |

-continued
| Compound | Structure |
|---|---|
| 187 | 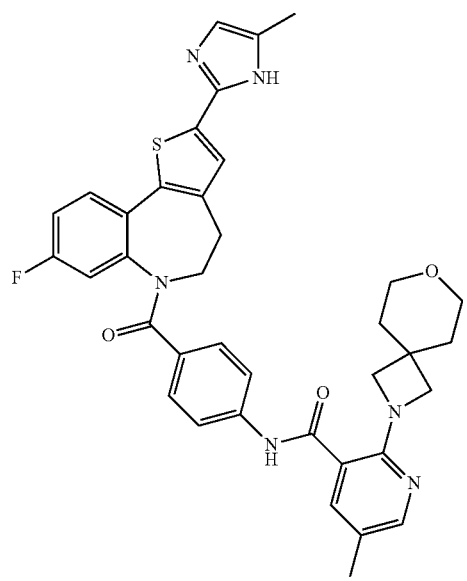 [SMILES: Cc1cnc(N2CC3(CCOCC3)C2)c(C(=O)Nc2ccc(C(=O)N3CCc4cc(-c5ncc(C)[nH]5)sc4-c4ccc(F)cc43)cc2)c1] |
| 188 | 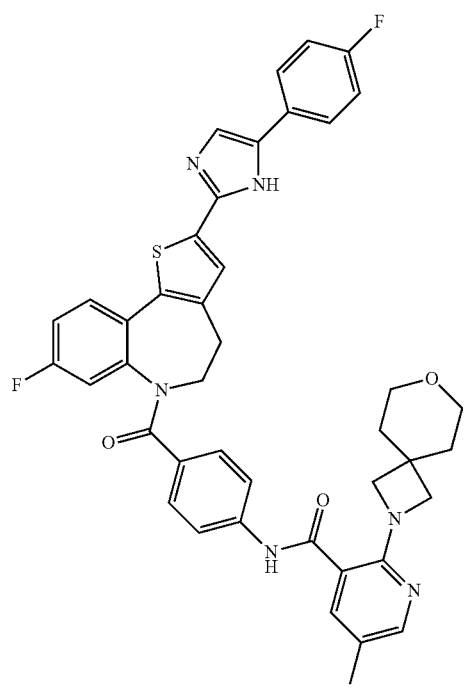 [SMILES: Cc1cnc(N2CC3(CCOCC3)C2)c(C(=O)Nc2ccc(C(=O)N3CCc4cc(-c5ncc(-c6ccc(F)cc6)[nH]5)sc4-c4ccc(F)cc43)cc2)c1] |

-continued
| Compound | Structure |
|---|---|
| 189 | 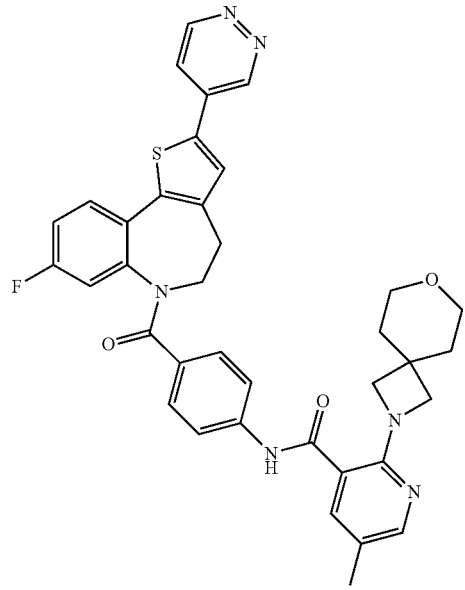 [SMILES: Cc1cnc(N2CC3(CCOCC3)C2)c(C(=O)Nc2ccc(C(=O)N3CCc4cc(-c5ccnnc5)sc4-c4ccc(F)cc43)cc2)c1] |
| 190 | 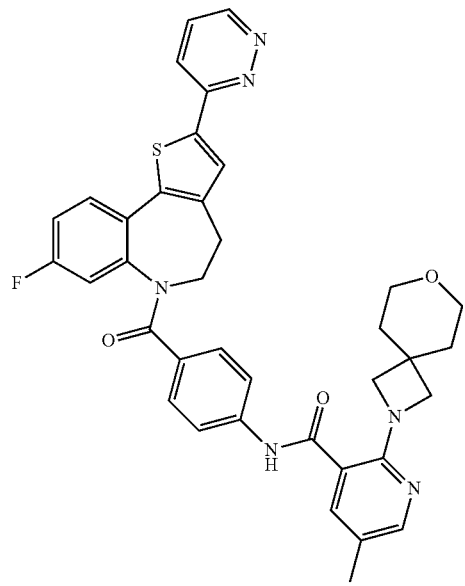 |

| Compound | Structure |
|---|---|
| 191 | 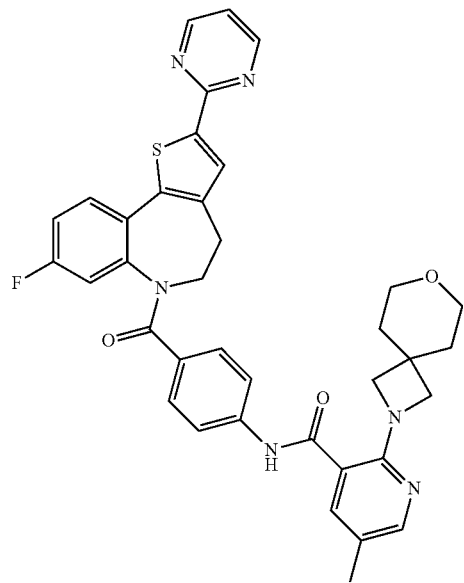 [SMILES: Cc1cnc(N2CC3(CCOCC3)C2)c(C(=O)Nc2ccc(C(=O)N3CCc4cc(-c5ncccn5)sc4-c4ccc(F)cc43)cc2)c1] |
| 192 | 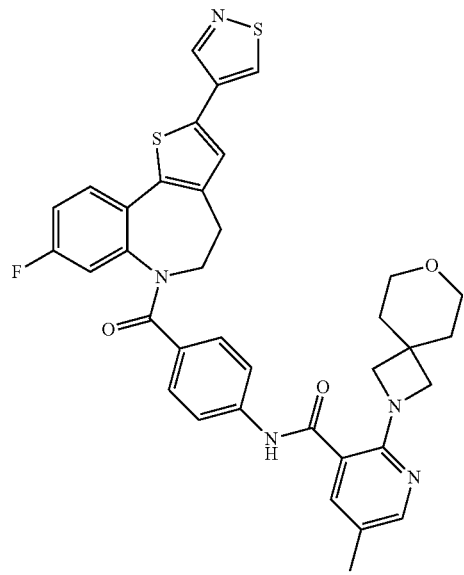 [SMILES: Cc1cnc(N2CC3(CCOCC3)C2)c(C(=O)Nc2ccc(C(=O)N3CCc4cc(-c5cnsc5)sc4-c4ccc(F)cc43)cc2)c1] |

-continued
| Compound | Structure |
|---|---|
| 193 | 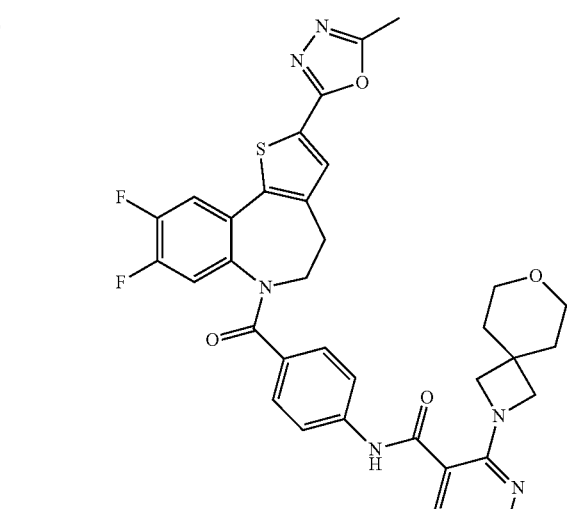 |
| 194 | 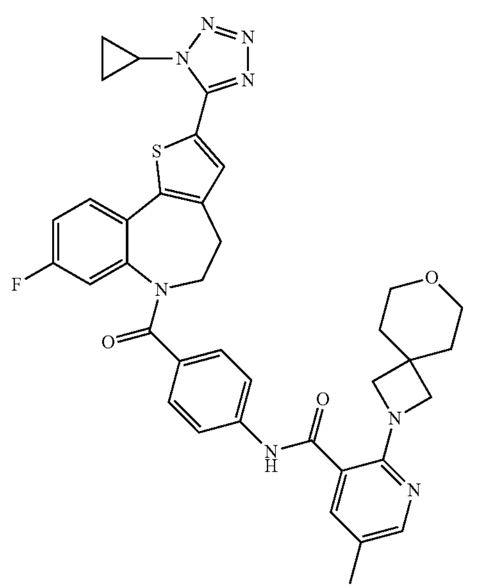 [SMILES: Cc1cnc(N2CC3(CCOCC3)C2)c(C(=O)Nc2ccc(C(=O)N3CCc4cc(-c5nnnn5C5CC5)sc4-c4ccc(F)cc43)cc2)c1] |

-continued

| Compound | Structure |
|---|---|
| 195 | 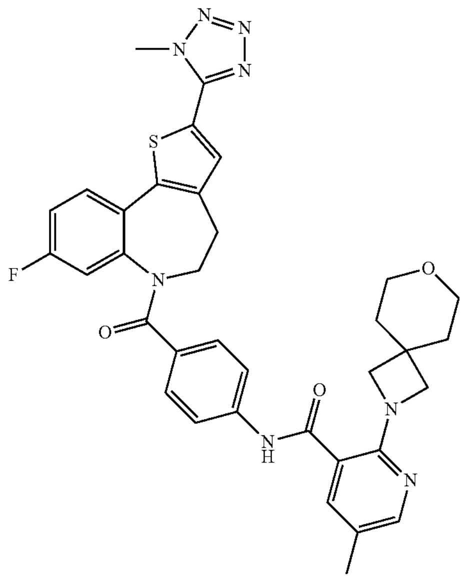 [SMILES: Cc1cnc(N2CC3(CCOCC3)C2)c(C(=O)Nc2ccc(C(=O)N3CCc4cc(-c5nnnn5C)sc4-c4ccc(F)cc43)cc2)c1] |
| 196 | 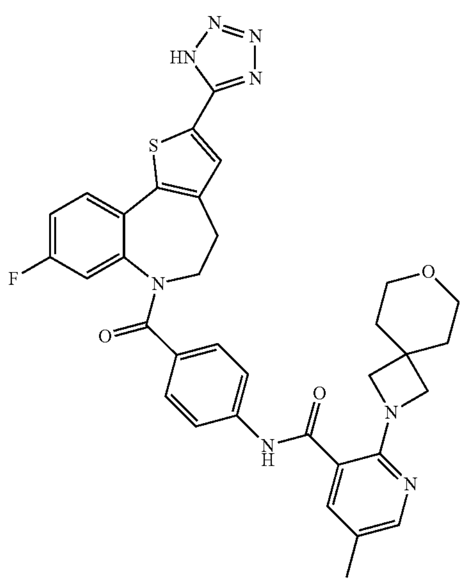 [SMILES: Cc1cnc(N2CC3(CCOCC3)C2)c(C(=O)Nc2ccc(C(=O)N3CCc4cc(-c5nnn[nH]5)sc4-c4ccc(F)cc43)cc2)c1] |

-continued
| Compound | Structure |
|---|---|
| 197 | 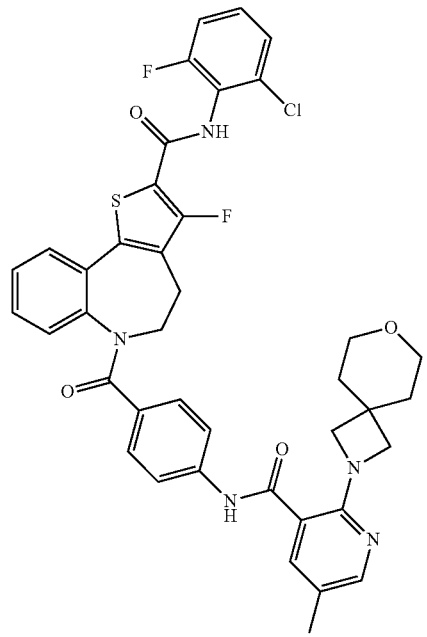 [SMILES: Cc1cnc(N2CC3(CCOCC3)C2)c(C(=O)Nc2ccc(C(=O)N3CCc4c(sc(C(=O)Nc5c(F)cccc5Cl)c4F)-c4ccccc43)cc2)c1] |
| 198 | 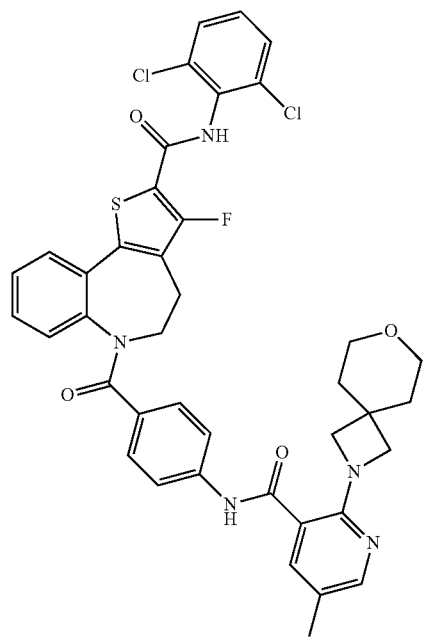 [SMILES: Cc1cnc(N2CC3(CCOCC3)C2)c(C(=O)Nc2ccc(C(=O)N3CCc4c(sc(C(=O)Nc5c(Cl)cccc5Cl)c4F)-c4ccccc43)cc2)c1] |

| Compound | Structure |
|---|---|
| 199 | 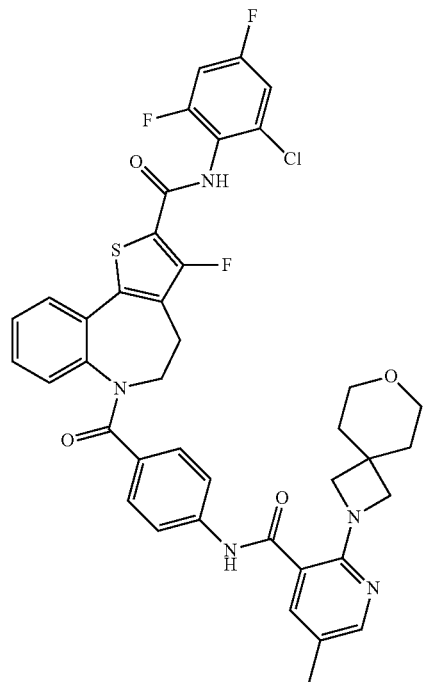 [SMILES: Cc1cnc(N2CC3(CCOCC3)C2)c(C(=O)Nc2ccc(C(=O)N3CCc4c(sc(C(=O)Nc5c(F)cc(F)cc5Cl)c4F)-c4ccccc43)cc2)c1] |
| 200 | 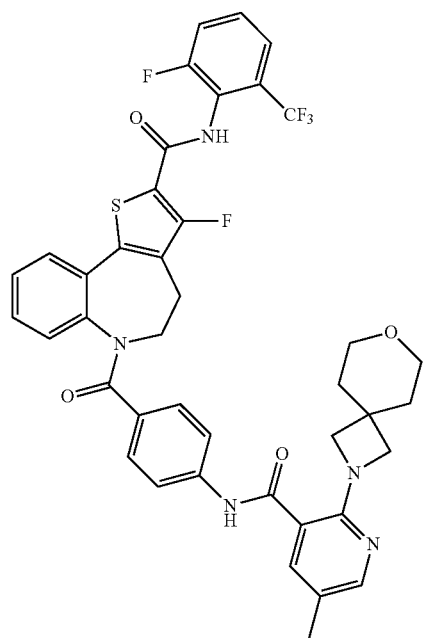 |

| Compound | Structure |
|---|---|
| 201 | 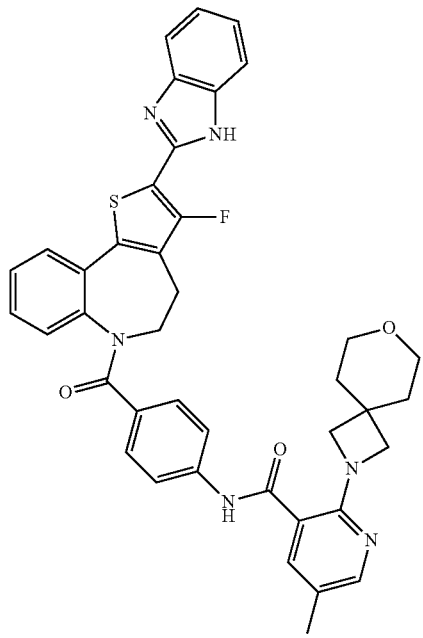 [SMILES: Cc1cnc(N2CC3(CCOCC3)C2)c(C(=O)Nc2ccc(C(=O)N3CCc4c(sc(-c5nc6ccccc6[nH]5)c4F)-c4ccccc43)cc2)c1] |
| 202 | 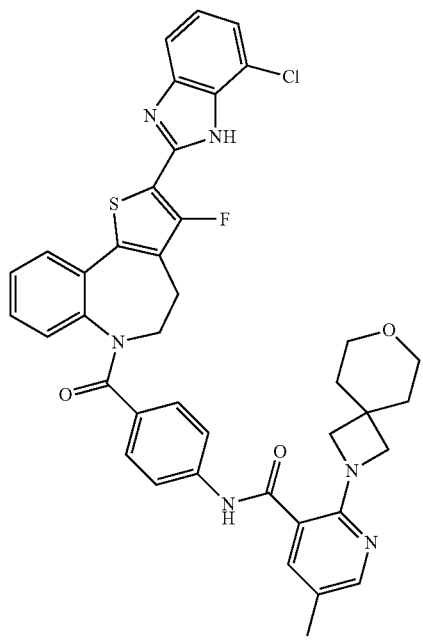 [SMILES: Cc1cnc(N2CC3(CCOCC3)C2)c(C(=O)Nc2ccc(C(=O)N3CCc4c(sc(-c5nc6cccc(Cl)c6[nH]5)c4F)-c4ccccc43)cc2)c1] |

US 11,091,501 B2
615
-continued
| Compound | Structure |
|---|---|
| 203 | 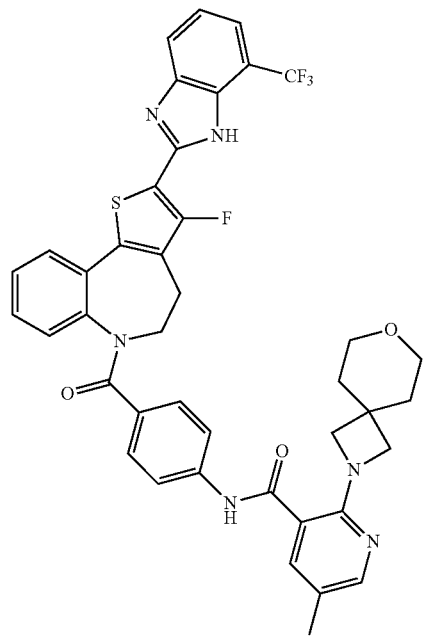 [SMILES: Cc1cnc(N2CC3(CCOCC3)C2)c(C(=O)Nc2ccc(C(=O)N3CCc4c(sc(-c5nc6cccc(C(F)(F)F)c6[nH]5)c4F)-c4ccccc43)cc2)c1] |
| 204 | 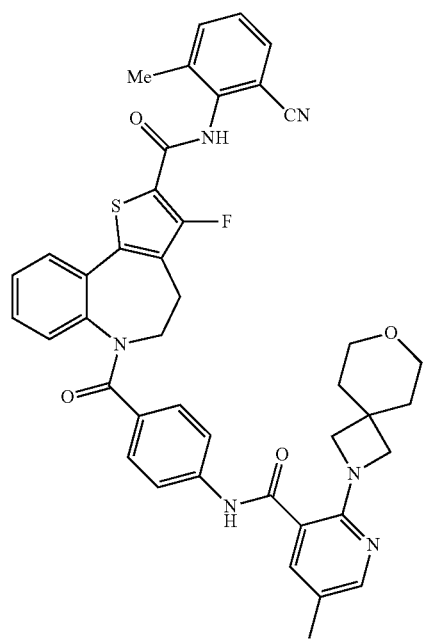 [SMILES: Cc1cnc(N2CC3(CCOCC3)C2)c(C(=O)Nc2ccc(C(=O)N3CCc4c(sc(C(=O)Nc5c(C)cccc5C#N)c4F)-c4ccccc43)cc2)c1] |
616

| Compound | Structure |
|---|---|
| 205 | 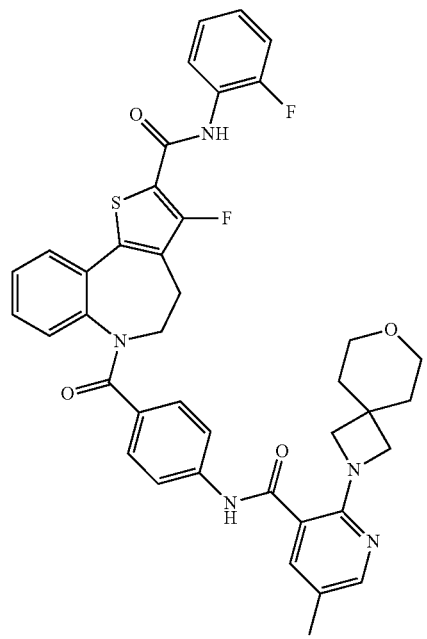 [SMILES: Cc1cnc(N2CC3(CCOCC3)C2)c(C(=O)Nc2ccc(C(=O)N3CCc4c(sc(C(=O)Nc5ccccc5F)c4F)-c4ccccc43)cc2)c1] |
| 206 | 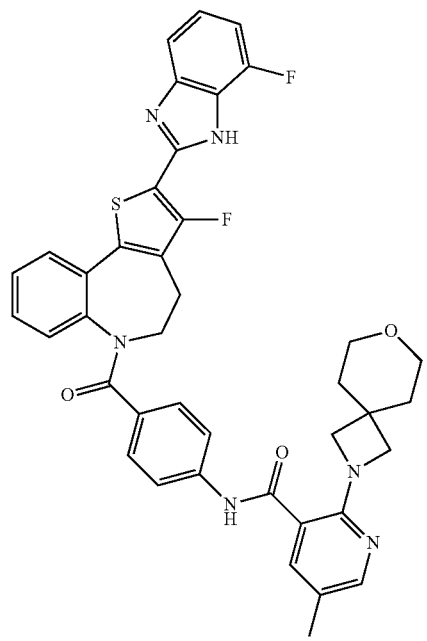 [SMILES: Cc1cnc(N2CC3(CCOCC3)C2)c(C(=O)Nc2ccc(C(=O)N3CCc4c(sc(-c5nc6cccc(F)c6[nH]5)c4F)-c4ccccc43)cc2)c1] |

-continued
| Compound | Structure |
|---|---|
| 207 | 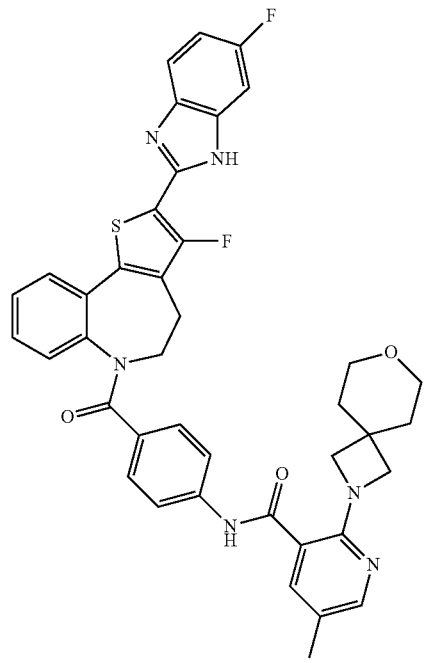 [SMILES: Cc1cnc(N2CC3(CCOCC3)C2)c(C(=O)Nc2ccc(C(=O)N3CCc4c(sc(-c5nc6ccc(F)cc6[nH]5)c4F)-c4ccccc43)cc2)c1] |
| 208 | 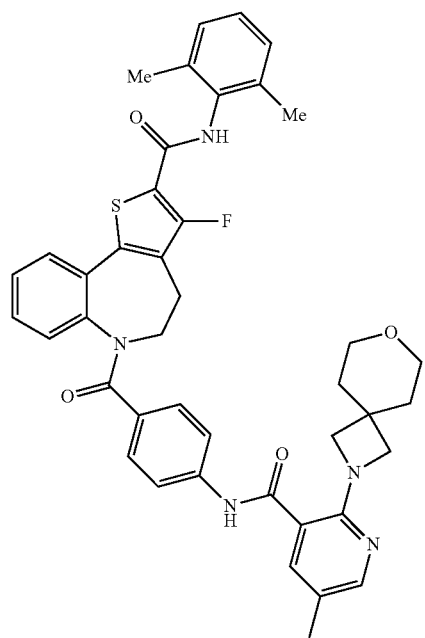 [SMILES: Cc1cnc(N2CC3(CCOCC3)C2)c(C(=O)Nc2ccc(C(=O)N3CCc4c(sc(C(=O)Nc5c(C)cccc5C)c4F)-c4ccccc43)cc2)c1] |

-continued
| Compound | Structure |
|---|---|
| 209 | 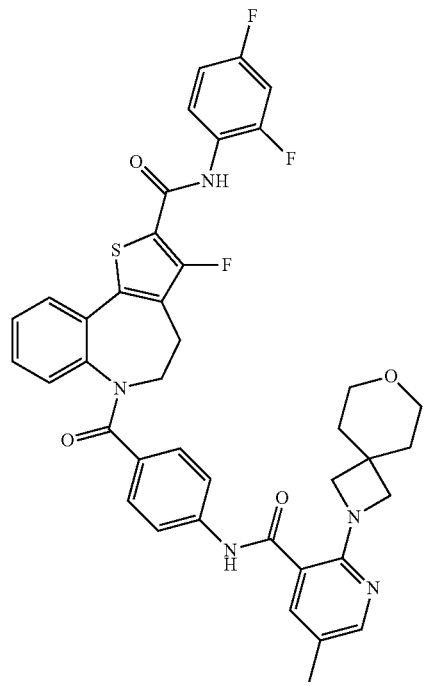 [SMILES: Cc1cnc(N2CC3(CCOCC3)C2)c(C(=O)Nc2ccc(C(=O)N3CCc4c(sc(C(=O)Nc5ccc(F)cc5F)c4F)-c4ccccc43)cc2)c1] |
| 210 | 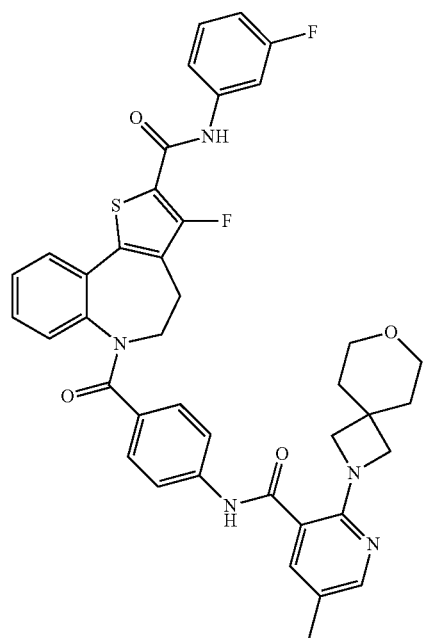 [SMILES: Cc1cnc(N2CC3(CCOCC3)C2)c(C(=O)Nc2ccc(C(=O)N3CCc4c(sc(C(=O)Nc5cccc(F)c5)c4F)-c4ccccc43)cc2)c1] |

-continued
| Compound | Structure |
|---|---|
| 211 | 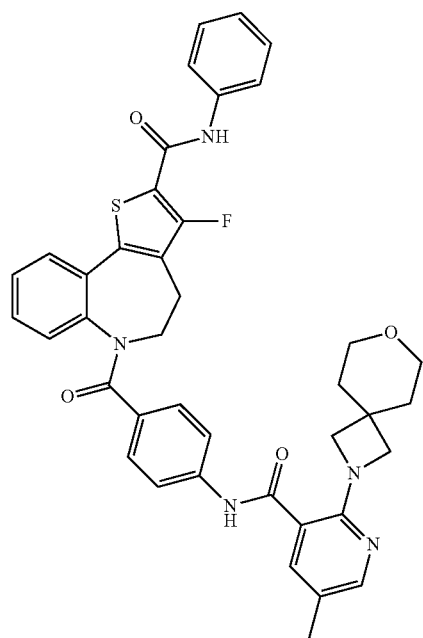 [SMILES: Cc1cnc(N2CC3(CCOCC3)C2)c(C(=O)Nc2ccc(C(=O)N3CCc4c(sc(C(=O)Nc5ccccc5)c4F)-c4ccccc43)cc2)c1] |
| 212 | 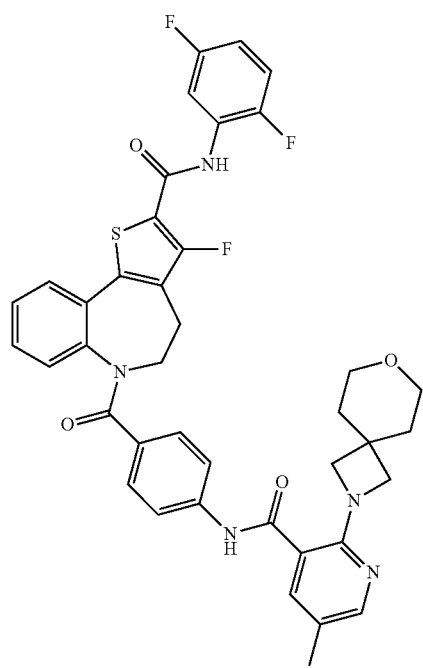 [SMILES: Cc1cnc(N2CC3(CCOCC3)C2)c(C(=O)Nc2ccc(C(=O)N3CCc4c(sc(C(=O)Nc5cc(F)ccc5F)c4F)-c4ccccc43)cc2)c1] |

-continued
| Compound | Structure |
|---|---|
| 213 | 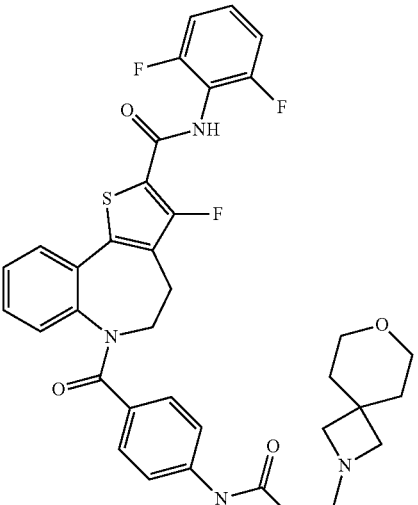 |
| 214 | 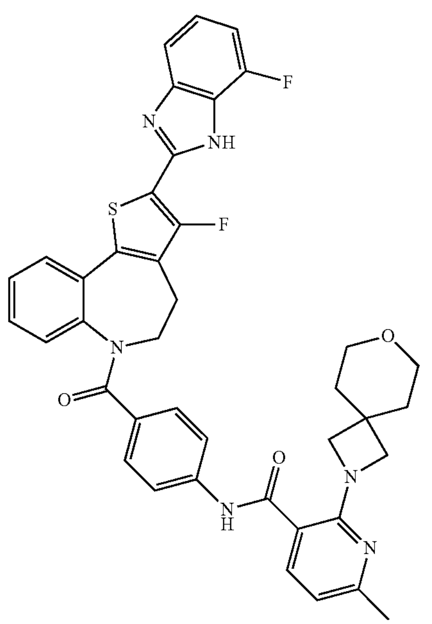 [SMILES: Cc1ccc(C(=O)Nc2ccc(C(=O)N3CCc4c(sc(-c5nc6cccc(F)c6[nH]5)c4F)-c4ccccc43)cc2)c(N2CC3(CCOCC3)C2)n1] |

| Compound | Structure |
|---|---|
| 215 | 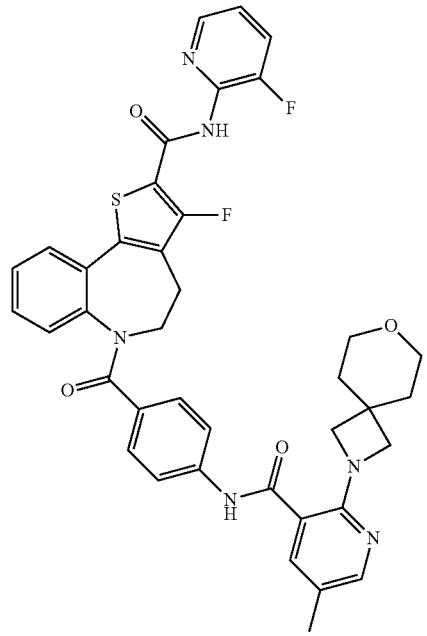 [SMILES: Cc1cnc(N2CC3(CCOCC3)C2)c(C(=O)Nc2ccc(C(=O)N3CCc4c(sc(C(=O)Nc5ncccc5F)c4F)-c4ccccc43)cc2)c1] |
| 216 | 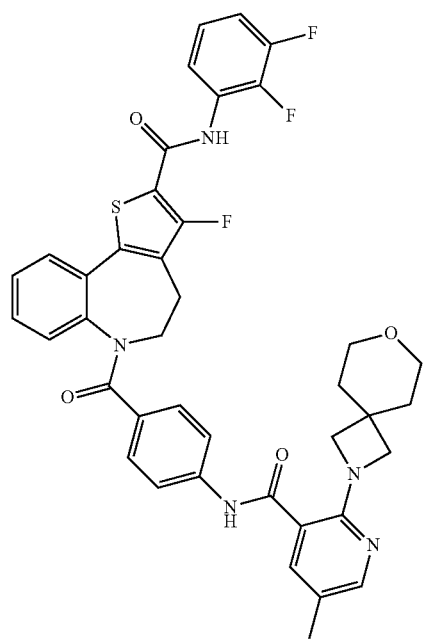 [SMILES: Cc1cnc(N2CC3(CCOCC3)C2)c(C(=O)Nc2ccc(C(=O)N3CCc4c(sc(C(=O)Nc5cccc(F)c5F)c4F)-c4ccccc43)cc2)c1] |

| Compound | Structure |
|---|---|
| 217 | 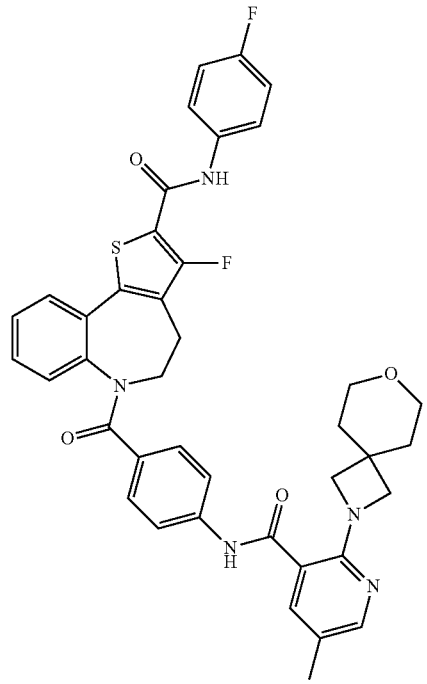 [SMILES: Cc1cnc(N2CC3(CCOCC3)C2)c(C(=O)Nc2ccc(C(=O)N3CCc4c(sc(C(=O)Nc5ccc(F)cc5)c4F)-c4ccccc43)cc2)c1] |
| 218 | 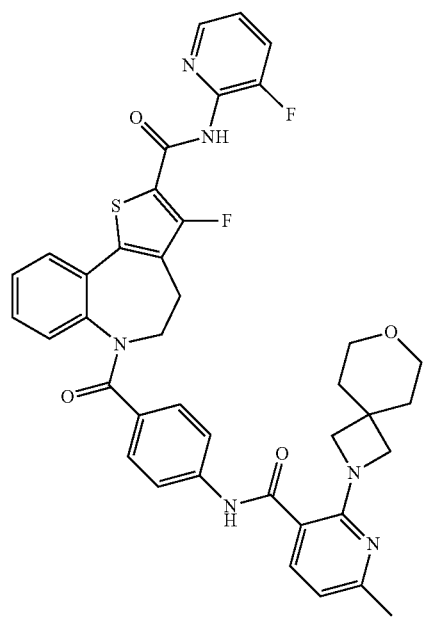 [SMILES: Cc1ccc(C(=O)Nc2ccc(C(=O)N3CCc4c(sc(C(=O)Nc5ncccc5F)c4F)-c4ccccc43)cc2)c(N2CC3(CCOCC3)C2)n1] |

| Compound | Structure |
|---|---|
| 219 | 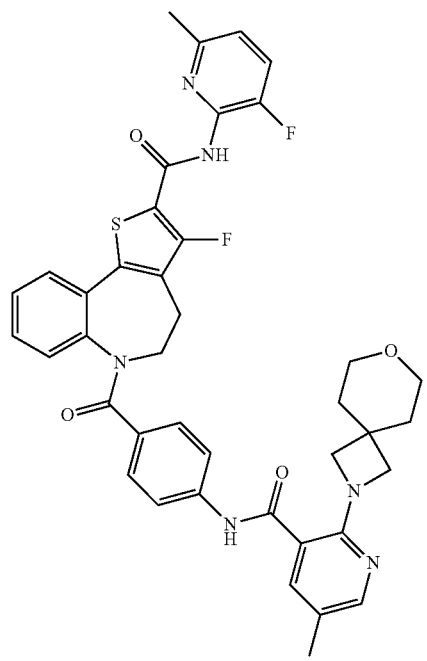 [SMILES: Cc1cnc(N2CC3(CCOCC3)C2)c(C(=O)Nc2ccc(C(=O)N3CCc4c(sc(C(=O)Nc5nc(C)ccc5F)c4F)-c4ccccc43)cc2)c1] |
| 220 | 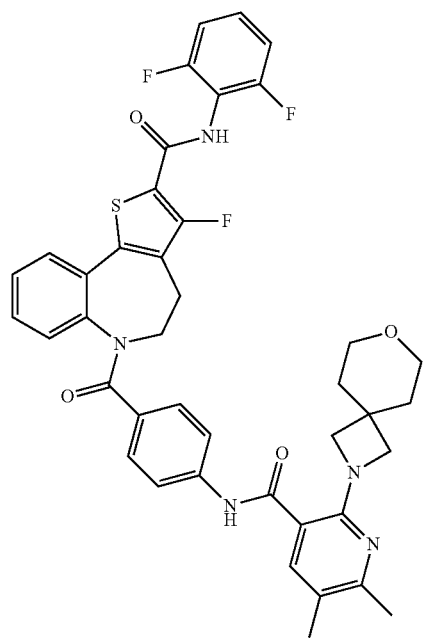 [SMILES: Cc1cc(C(=O)Nc2ccc(C(=O)N3CCc4c(sc(C(=O)Nc5c(F)cccc5F)c4F)-c4ccccc43)cc2)c(N2CC3(CCOCC3)C2)nc1C] |

| Compound | Structure |
|---|---|
| 221 | 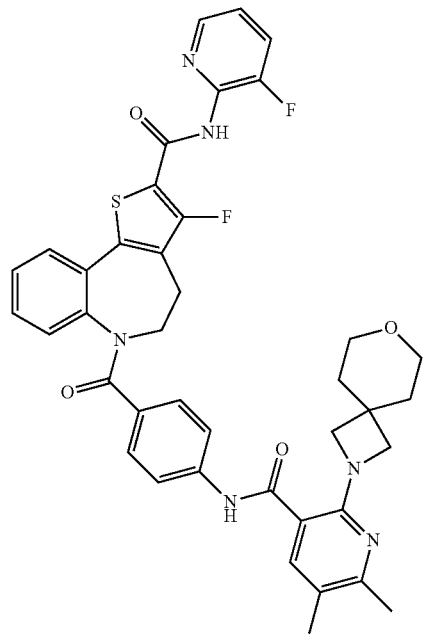 [SMILES: Cc1cc(C(=O)Nc2ccc(C(=O)N3CCc4c(sc(C(=O)Nc5ncccc5F)c4F)-c4ccccc43)cc2)c(N2CC3(CCOCC3)C2)nc1C] |
| 222 | 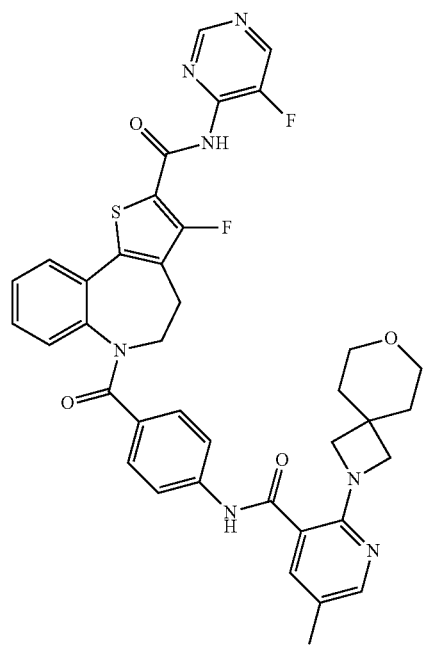 [SMILES: Cc1cnc(N2CC3(CCOCC3)C2)c(C(=O)Nc2ccc(C(=O)N3CCc4c(sc(C(=O)Nc5ncncc5F)c4F)-c4ccccc43)cc2)c1] |

| Compound | Structure |
|---|---|
| 223 | 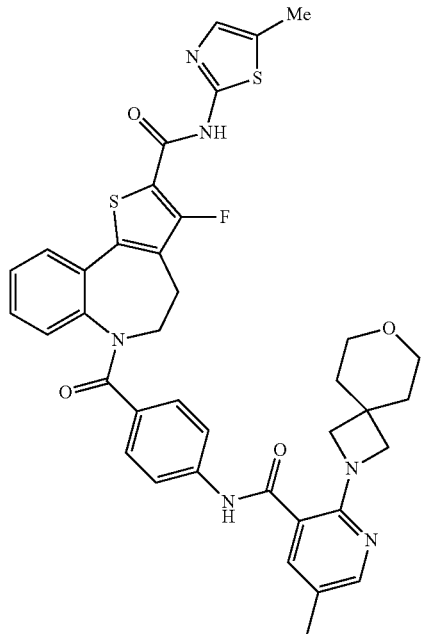 [SMILES: Cc1cnc(N2CC3(CCOCC3)C2)c(C(=O)Nc2ccc(C(=O)N3CCc4c(sc(C(=O)Nc5ncc(C)s5)c4F)-c4ccccc43)cc2)c1] |
| 224 | 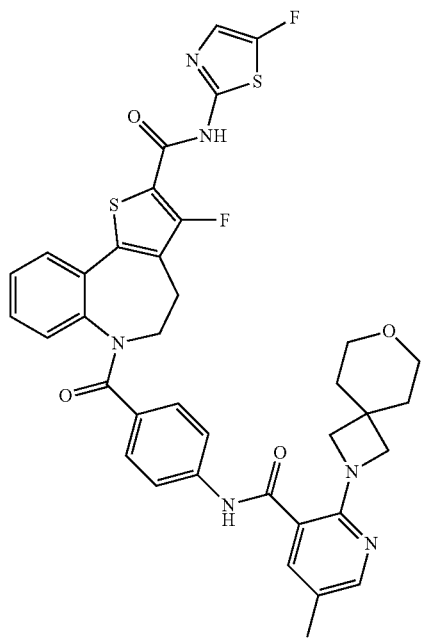 [SMILES: Cc1cnc(N2CC3(CCOCC3)C2)c(C(=O)Nc2ccc(C(=O)N3CCc4c(sc(C(=O)Nc5ncc(F)s5)c4F)-c4ccccc43)cc2)c1] |

-continued
| Compound | Structure |
|---|---|
| 225 | 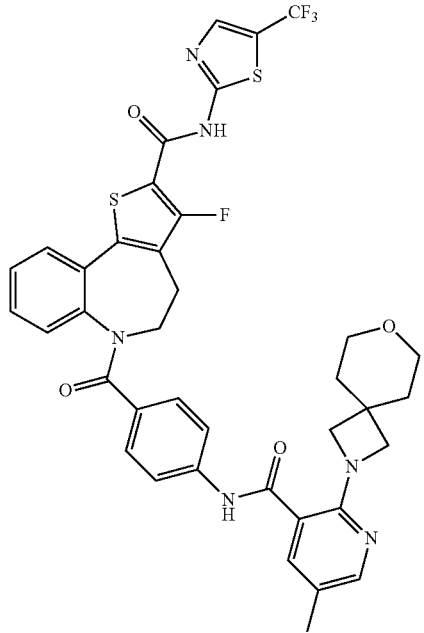 [SMILES: Cc1cnc(N2CC3(CCOCC3)C2)c(C(=O)Nc2ccc(C(=O)N3CCc4c(sc(C(=O)Nc5ncc(C(F)(F)F)s5)c4F)-c4ccccc43)cc2)c1] |
| 226 | 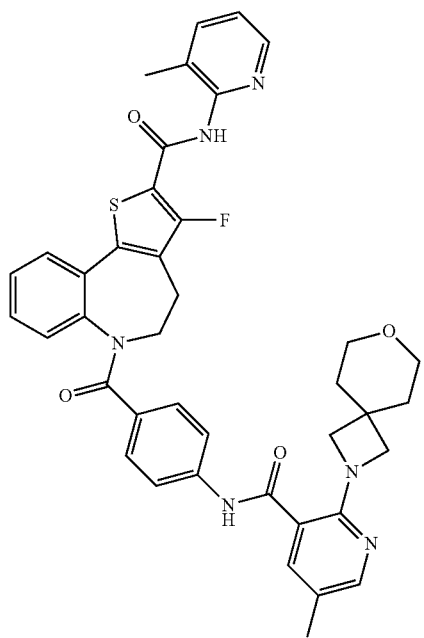 [SMILES: Cc1cnc(N2CC3(CCOCC3)C2)c(C(=O)Nc2ccc(C(=O)N3CCc4c(sc(C(=O)Nc5ncccc5C)c4F)-c4ccccc43)cc2)c1] |

-continued
| Compound | Structure |
|---|---|
| 227 | 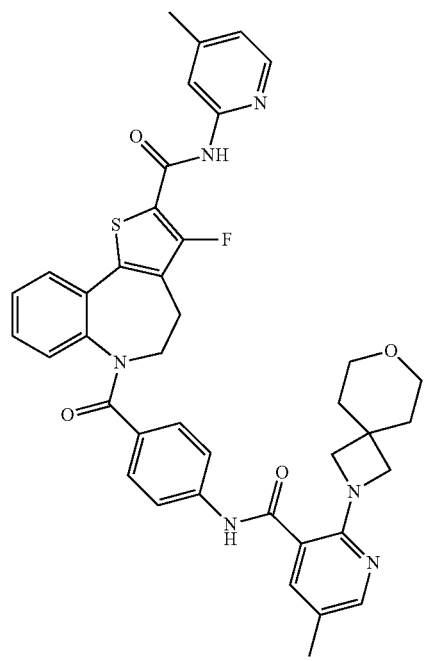 [SMILES: Cc1ccnc(NC(=O)c2sc3c(c2F)CCN(C(=O)c2ccc(NC(=O)c4cc(C)cnc4N4CC5(CCOCC5)C4)cc2)c2ccccc2-3)c1] |
| 228 | 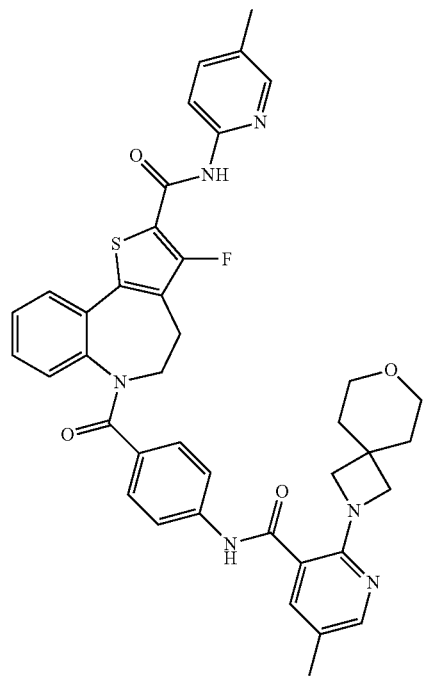 [SMILES: Cc1ccc(NC(=O)c2sc3c(c2F)CCN(C(=O)c2ccc(NC(=O)c4cc(C)cnc4N4CC5(CCOCC5)C4)cc2)c2ccccc2-3)nc1] |

| Compound | Structure |
|---|---|
| 229 | 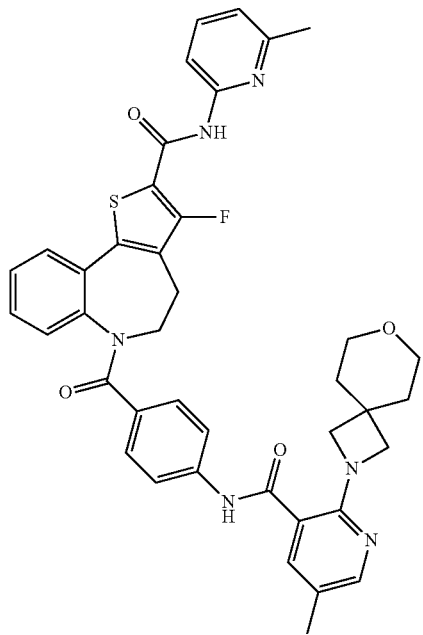 [SMILES: Cc1cnc(N2CC3(CCOCC3)C2)c(C(=O)Nc2ccc(C(=O)N3CCc4c(sc(C(=O)Nc5cccc(C)n5)c4F)-c4ccccc43)cc2)c1] |
| 230 | 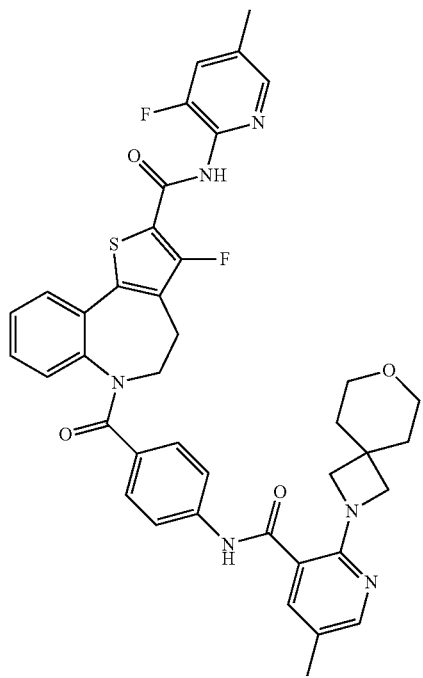 [SMILES: Cc1cnc(NC(=O)c2sc3c(c2F)CCN(C(=O)c2ccc(NC(=O)c4cc(C)cnc4N4CC5(CCOCC5)C4)cc2)c2ccccc2-3)c(F)c1] |

| Compound | Structure |
|---|---|
| 231 | 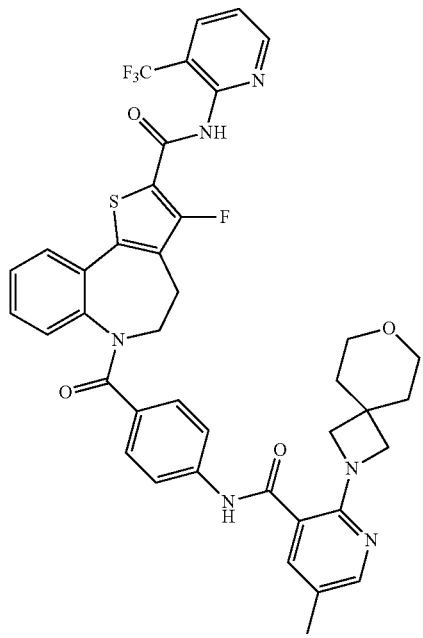 [SMILES: Cc1cnc(N2CC3(CCOCC3)C2)c(C(=O)Nc2ccc(C(=O)N3CCc4c(sc(C(=O)Nc5ncccc5C(F)(F)F)c4F)-c4ccccc43)cc2)c1] |
| 232 | 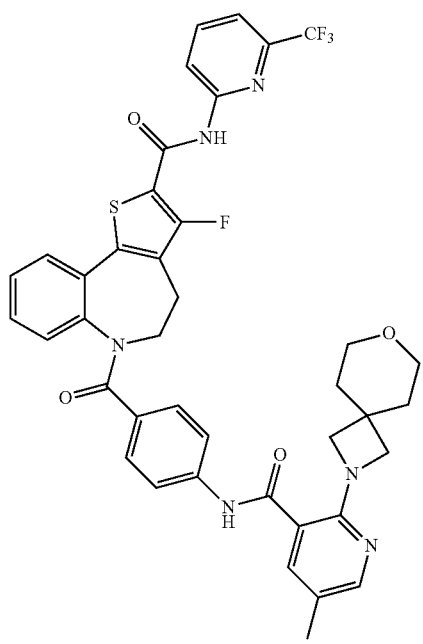 [SMILES: Cc1cnc(N2CC3(CCOCC3)C2)c(C(=O)Nc2ccc(C(=O)N3CCc4c(sc(C(=O)Nc5cccc(C(F)(F)F)n5)c4F)-c4ccccc43)cc2)c1] |

-continued
| Compound | Structure |
|---|---|
| 233 | 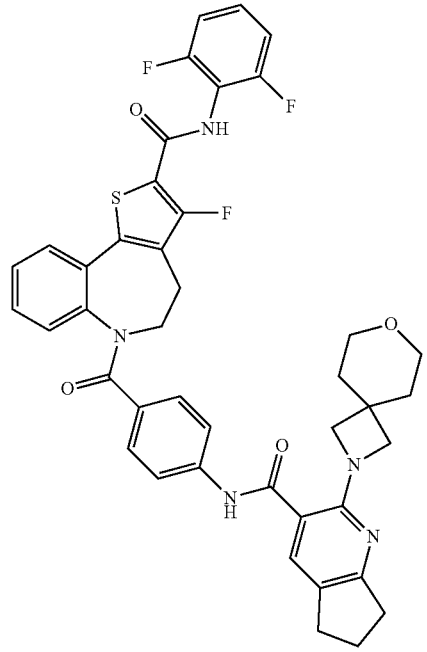 [SMILES: O=C(Nc1ccc(C(=O)N2CCc3c(sc(C(=O)Nc4c(F)cccc4F)c3F)-c3ccccc32)cc1)c1cc2c(nc1N1CC3(CCOCC3)C1)CCC2] |
| 234 | 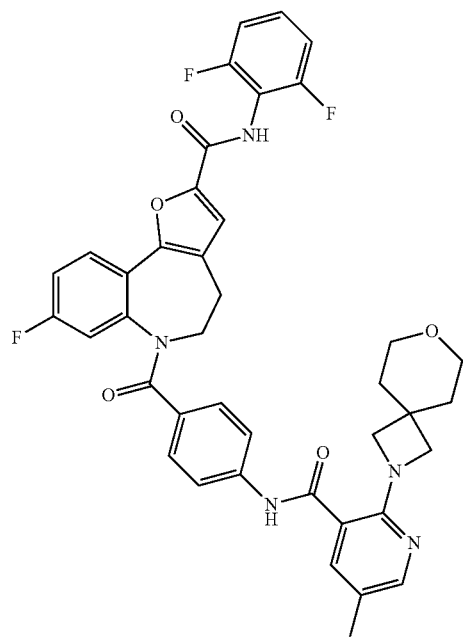 [SMILES: Cc1cnc(N2CC3(CCOCC3)C2)c(C(=O)Nc2ccc(C(=O)N3CCc4cc(C(=O)Nc5c(F)cccc5F)oc4-c4ccc(F)cc43)cc2)c1] |

| Compound | Structure |
|---|---|
| 235 | 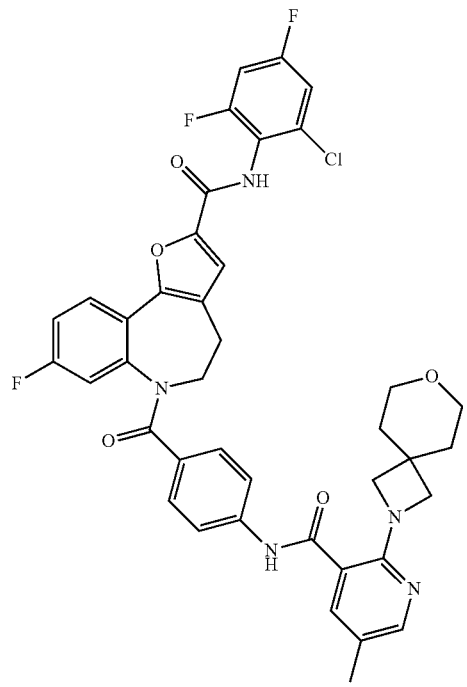 [SMILES: Cc1cnc(N2CC3(CCOCC3)C2)c(C(=O)Nc2ccc(C(=O)N3CCc4cc(C(=O)Nc5c(F)cc(F)cc5Cl)oc4-c4ccc(F)cc43)cc2)c1] |
| 236 | 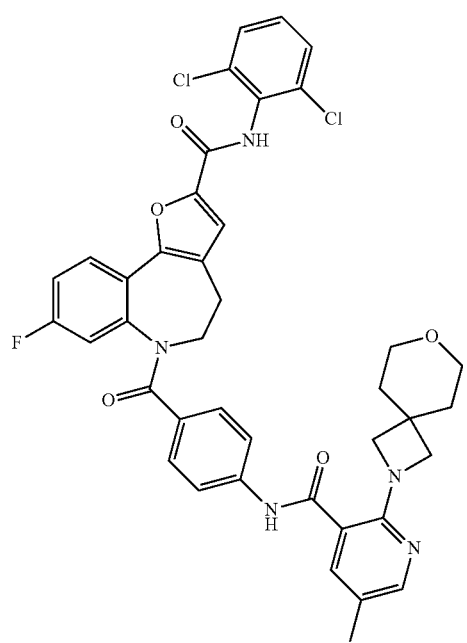 [SMILES: Cc1cnc(N2CC3(CCOCC3)C2)c(C(=O)Nc2ccc(C(=O)N3CCc4cc(C(=O)Nc5c(Cl)cccc5Cl)oc4-c4ccc(F)cc43)cc2)c1] |

| Compound | Structure |
|---|---|
| 237 | 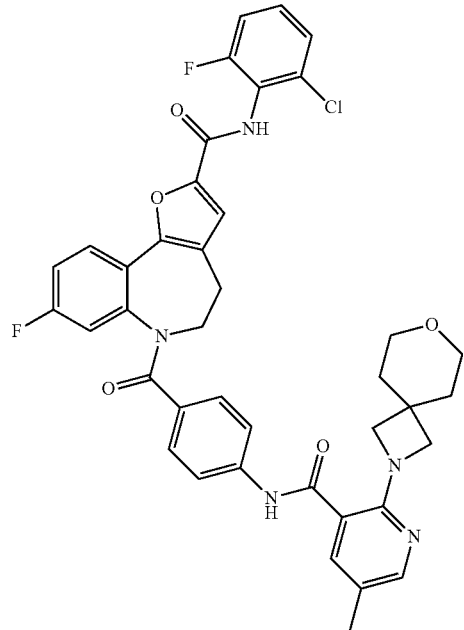 |
| 238 | 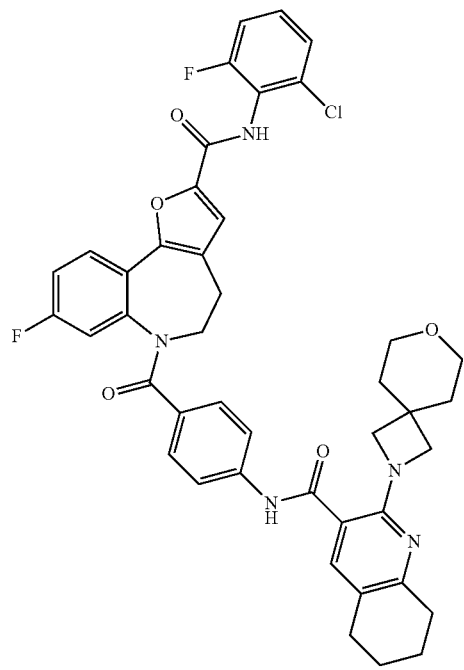 [SMILES: O=C(Nc1c(F)cccc1Cl)c1cc2c(o1)-c1ccc(F)cc1N(C(=O)c1ccc(NC(=O)c3cc4c(nc3N3CC5(CCOCC5)C3)CCCC4)cc1)CC2] |

| Compound | Structure |
|---|---|
| 239 | 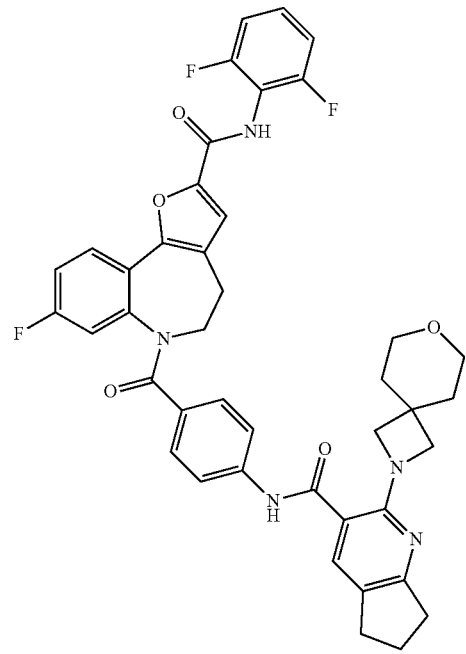 [SMILES: O=C(Nc1c(F)cccc1F)c1cc2c(o1)-c1ccc(F)cc1N(C(=O)c1ccc(NC(=O)c3cc4c(nc3N3CC5(CCOCC5)C3)CCC4)cc1)CC2] |
| 240 | 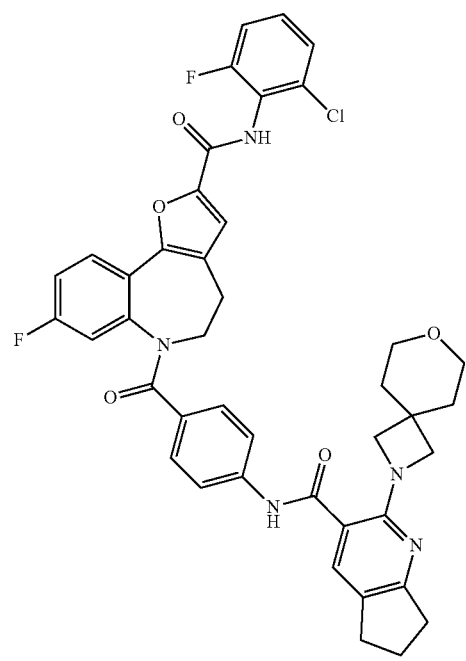 [SMILES: O=C(Nc1c(F)cccc1Cl)c1cc2c(o1)-c1ccc(F)cc1N(C(=O)c1ccc(NC(=O)c3cc4c(nc3N3CC5(CCOCC5)C3)CCC4)cc1)CC2] |

-continued
| Compound | Structure |
|---|---|
| 241 | 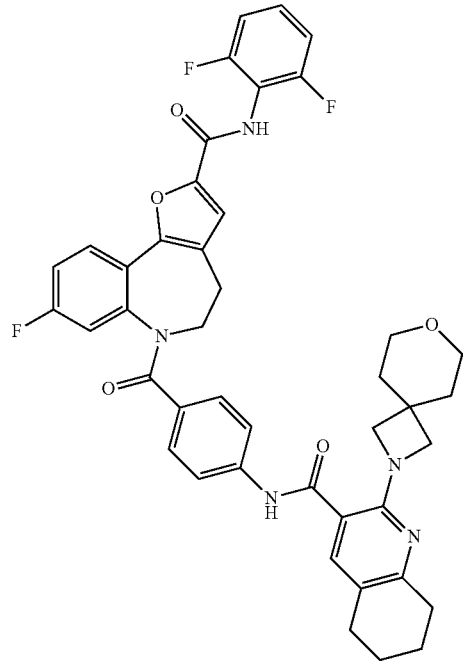 [SMILES: O=C(Nc1c(F)cccc1F)c1cc2c(o1)-c1ccc(F)cc1N(C(=O)c1ccc(NC(=O)c3cc4c(nc3N3CC5(CCOCC5)C3)CCCC4)cc1)CC2] |
| 242 | 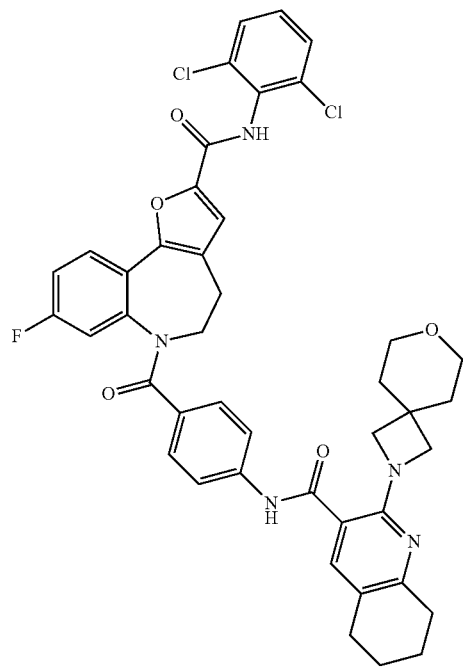 [SMILES: O=C(Nc1c(Cl)cccc1Cl)c1cc2c(o1)-c1ccc(F)cc1N(C(=O)c1ccc(NC(=O)c3cc4c(nc3N3CC5(CCOCC5)C3)CCCC4)cc1)CC2] |

| Compound | Structure |
|---|---|
| 243 | 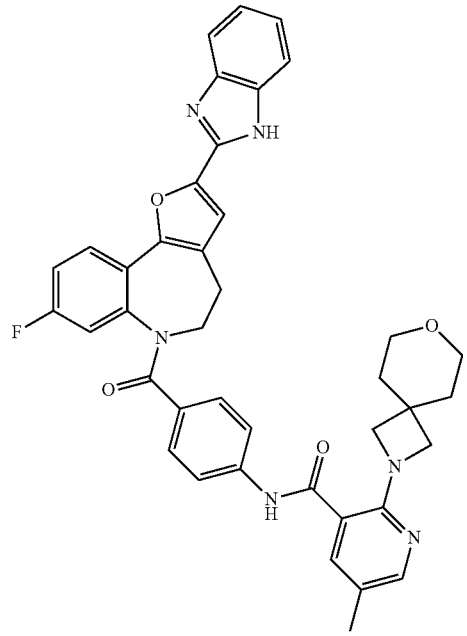 [SMILES: Cc1cnc(N2CC3(CCOCC3)C2)c(C(=O)Nc2ccc(C(=O)N3CCc4cc(-c5nc6ccccc6[nH]5)oc4-c4ccc(F)cc43)cc2)c1] |
| 244 | 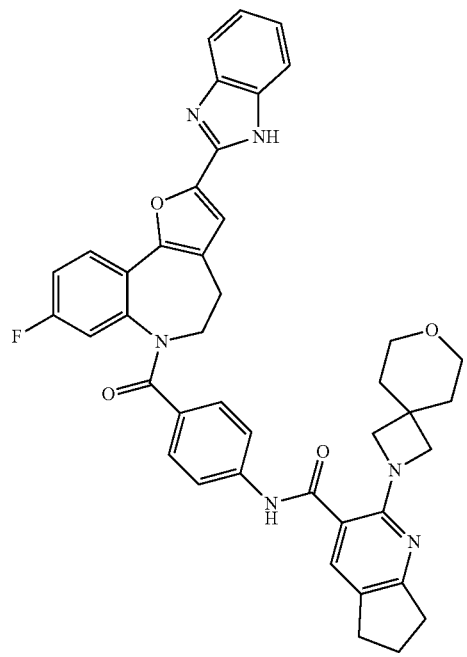 [SMILES: O=C(Nc1ccc(C(=O)N2CCc3cc(-c4nc5ccccc5[nH]4)oc3-c3ccc(F)cc32)cc1)c1cc2c(nc1N1CC3(CCOCC3)C1)CCC2] |

| Compound | Structure |
|---|---|
| 245 | 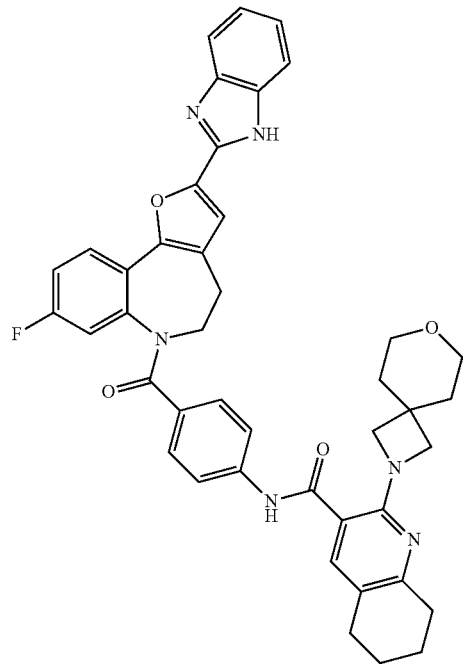 [SMILES: O=C(Nc1ccc(C(=O)N2CCc3cc(-c4nc5ccccc5[nH]4)oc3-c3ccc(F)cc32)cc1)c1cc2c(nc1N1CC3(CCOCC3)C1)CCCC2] |
| 246 | 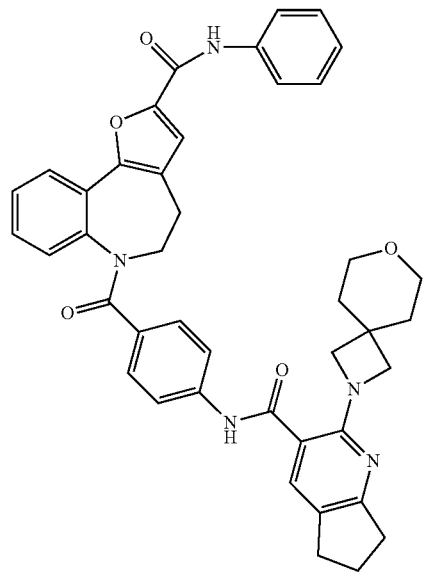 [SMILES: O=C(Nc1ccccc1)c1cc2c(o1)-c1ccccc1N(C(=O)c1ccc(NC(=O)c3cc4c(nc3N3CC5(CCOCC5)C3)CCC4)cc1)CC2] |

-continued
| Compound | Structure |
|---|---|
| 247 | 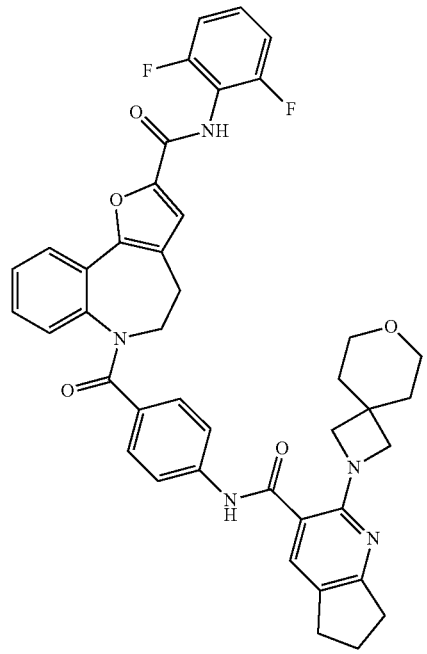 [SMILES: O=C(Nc1c(F)cccc1F)c1cc2c(o1)-c1ccccc1N(C(=O)c1ccc(NC(=O)c3cc4c(nc3N3CC5(CCOCC5)C3)CCC4)cc1)CC2] |
| 248 | 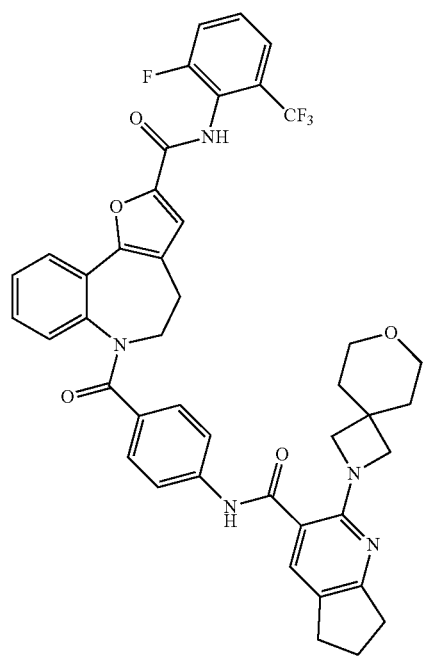 [SMILES: O=C(Nc1c(F)cccc1C(F)(F)F)c1cc2c(o1)-c1ccccc1N(C(=O)c1ccc(NC(=O)c3cc4c(nc3N3CC5(CCOCC5)C3)CCC4)cc1)CC2] |

| Compound | Structure |
|---|---|
| 249 | 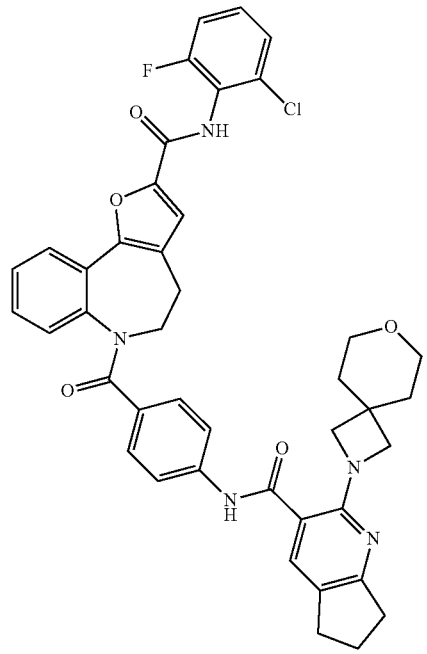 [SMILES: O=C(Nc1c(F)cccc1Cl)c1cc2c(o1)-c1ccccc1N(C(=O)c1ccc(NC(=O)c3cc4c(nc3N3CC5(CCOCC5)C3)CCC4)cc1)CC2] |
| 250 | 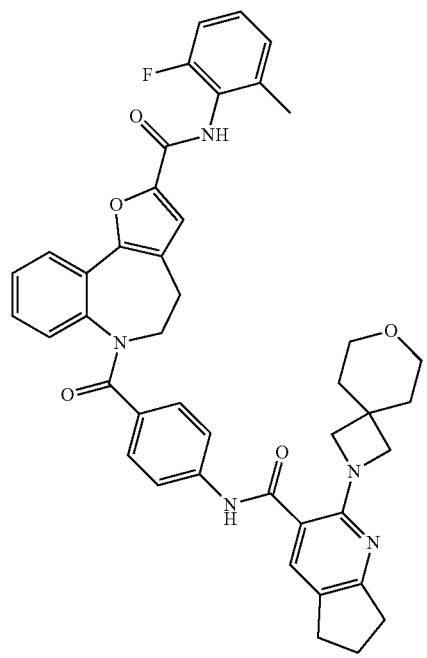 [SMILES: Cc1cccc(F)c1NC(=O)c1cc2c(o1)-c1ccccc1N(C(=O)c1ccc(NC(=O)c3cc4c(nc3N3CC5(CCOCC5)C3)CCC4)cc1)CC2] |

-continued
| Compound | Structure |
|---|---|
| 251 | 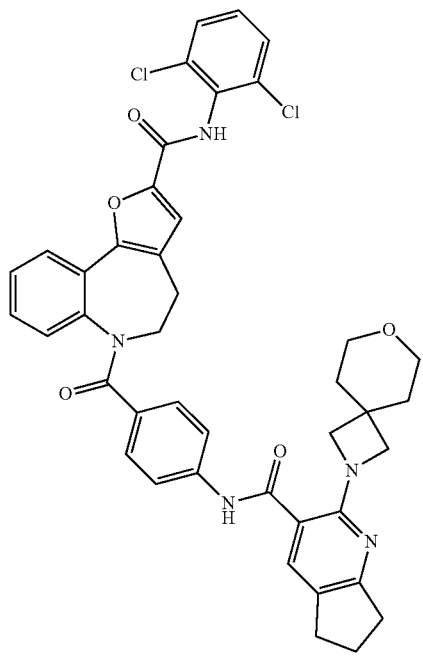 [SMILES: O=C(Nc1c(Cl)cccc1Cl)c1cc2c(o1)-c1ccccc1N(C(=O)c1ccc(NC(=O)c3cc4c(nc3N3CC5(CCOCC5)C3)CCC4)cc1)CC2] |
| 252 | 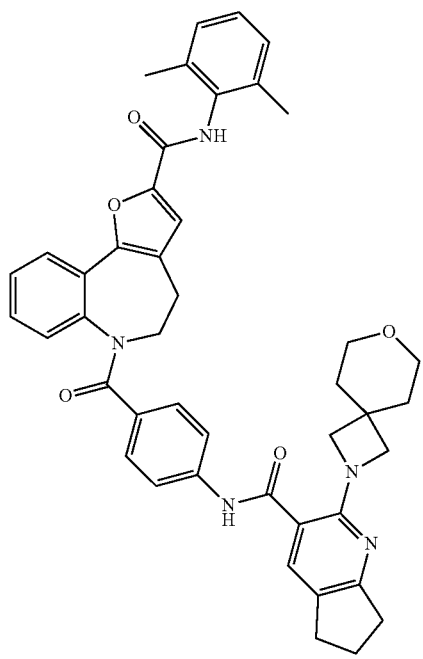 [SMILES: Cc1cccc(C)c1NC(=O)c1cc2c(o1)-c1ccccc1N(C(=O)c1ccc(NC(=O)c3cc4c(nc3N3CC5(CCOCC5)C3)CCC4)cc1)CC2] |

| Compound | Structure |
|---|---|
| 253 | 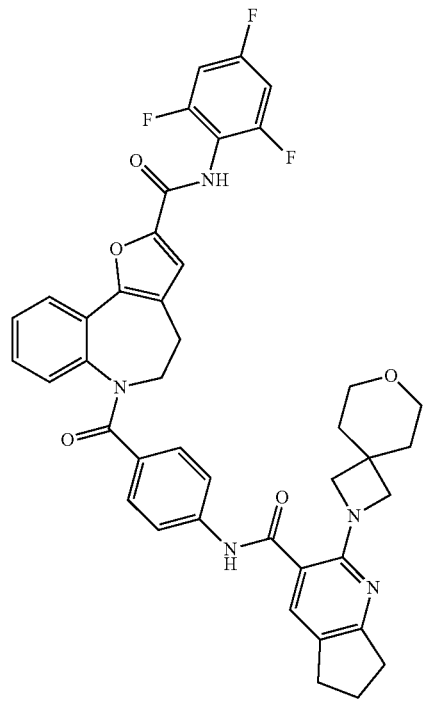 [SMILES: O=C(Nc1c(F)cc(F)cc1F)c1cc2c(o1)-c1ccccc1N(C(=O)c1ccc(NC(=O)c3cc4c(nc3N3CC5(CCOCC5)C3)CCC4)cc1)CC2] |
| 254 | 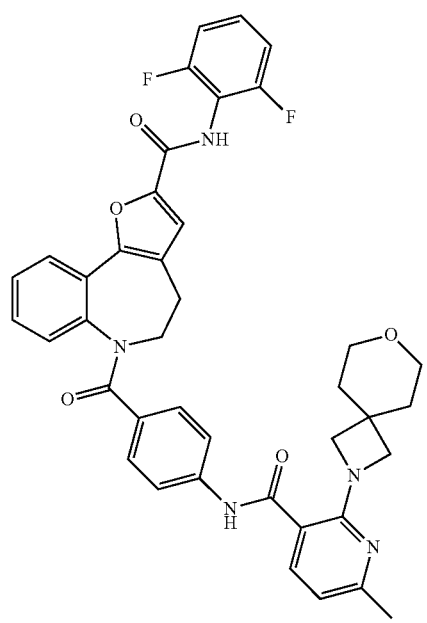 [SMILES: Cc1ccc(C(=O)Nc2ccc(C(=O)N3CCc4cc(C(=O)Nc5c(F)cccc5F)oc4-c4ccccc43)cc2)c(N2CC3(CCOCC3)C2)n1] |

| Compound | Structure |
|---|---|
| 255 | 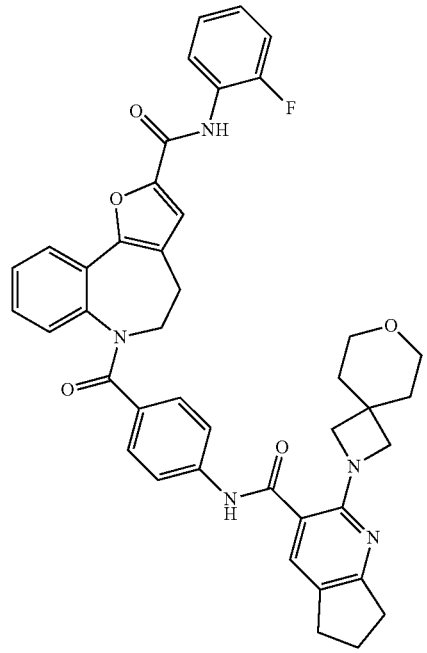 [SMILES: O=C(Nc1ccccc1F)c1cc2c(o1)-c1ccccc1N(C(=O)c1ccc(NC(=O)c3cc4c(nc3N3CC5(CCOCC5)C3)CCC4)cc1)CC2] |
| 256 | 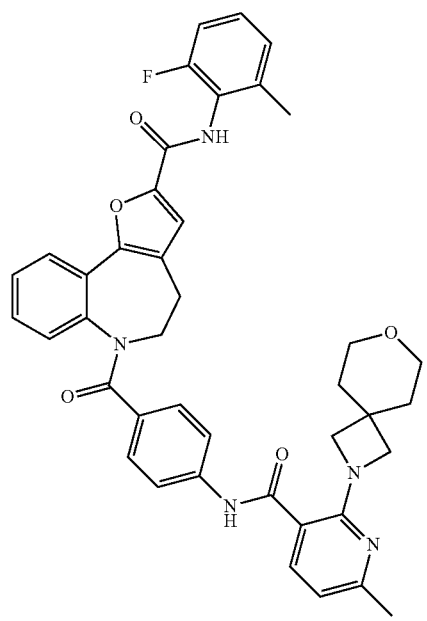 [SMILES: Cc1ccc(C(=O)Nc2ccc(C(=O)N3CCc4cc(C(=O)Nc5c(C)cccc5F)oc4-c4ccccc43)cc2)c(N2CC3(CCOCC3)C2)n1] |

| Compound | Structure |
|---|---|
| 257 | 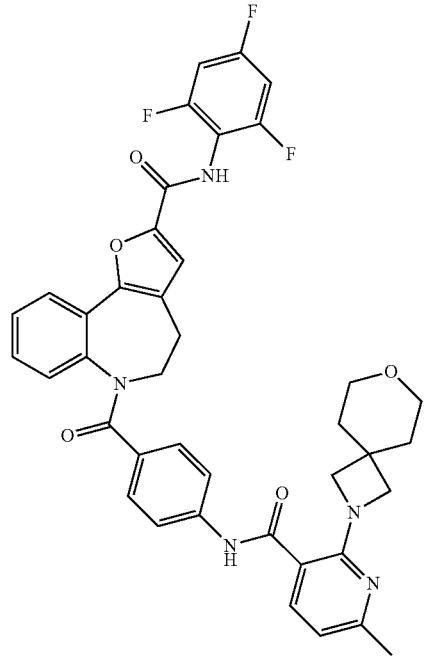 [SMILES: Cc1ccc(C(=O)Nc2ccc(C(=O)N3CCc4cc(C(=O)Nc5c(F)cc(F)cc5F)oc4-c4ccccc43)cc2)c(N2CC3(CCOCC3)C2)n1] |
| 258 | 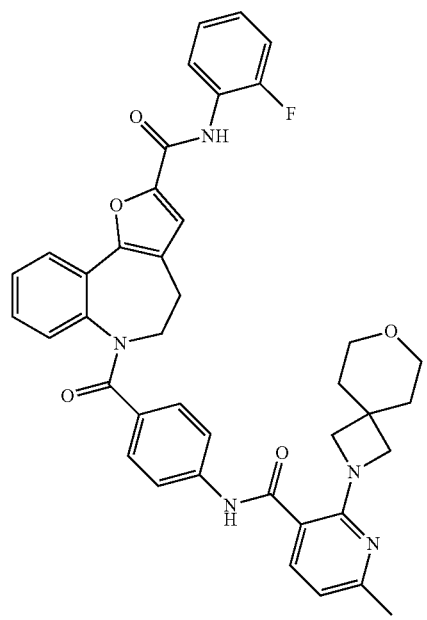 [SMILES: Cc1ccc(C(=O)Nc2ccc(C(=O)N3CCc4cc(C(=O)Nc5ccccc5F)oc4-c4ccccc43)cc2)c(N2CC3(CCOCC3)C2)n1] |

| Compound | Structure |
|---|---|
| 259 | 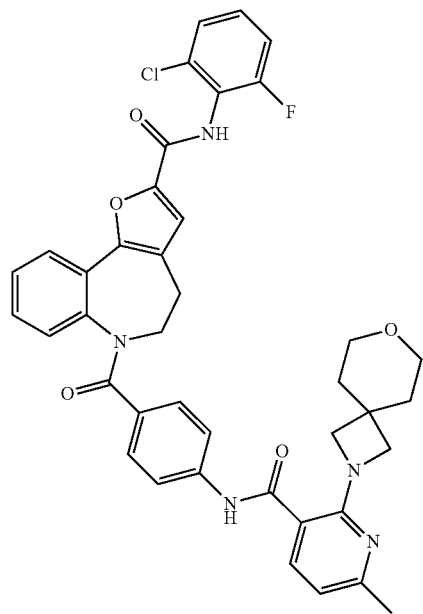 [SMILES: Cc1ccc(C(=O)Nc2ccc(C(=O)N3CCc4cc(C(=O)Nc5c(F)cccc5Cl)oc4-c4ccccc43)cc2)c(N2CC3(CCOCC3)C2)n1] |
| 260 | 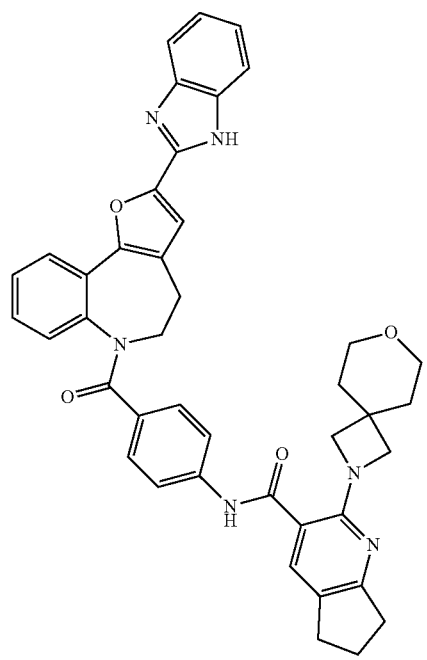 [SMILES: O=C(Nc1ccc(C(=O)N2CCc3cc(-c4nc5ccccc5[nH]4)oc3-c3ccccc32)cc1)c1cc2c(nc1N1CC3(CCOCC3)C1)CCC2] |

US 11,091,501 B2
673                                                                 674
-continued
| Compound | Structure |
|---|---|
| 261 | 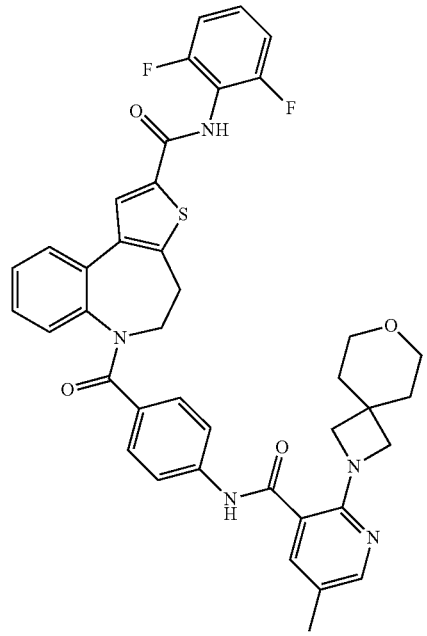 [SMILES: Cc1cnc(N2CC3(CCOCC3)C2)c(C(=O)Nc2ccc(C(=O)N3CCc4sc(C(=O)Nc5c(F)cccc5F)cc4-c4ccccc43)cc2)c1] |
| 262 | 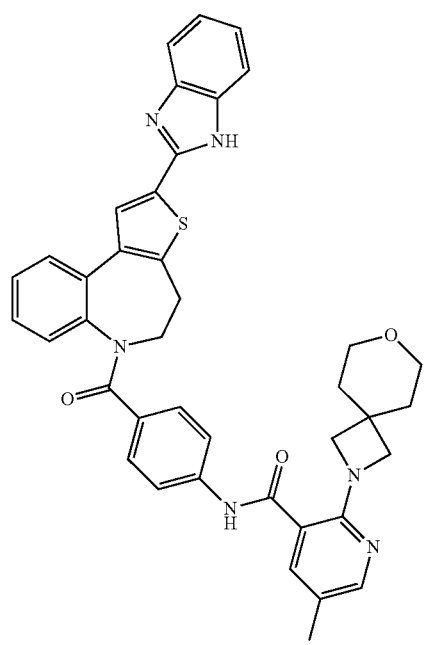 [SMILES: Cc1cnc(N2CC3(CCOCC3)C2)c(C(=O)Nc2ccc(C(=O)N3CCc4sc(-c5nc6ccccc6[nH]5)cc4-c4ccccc43)cc2)c1] |

| Compound | Structure |
|---|---|
| 263 | 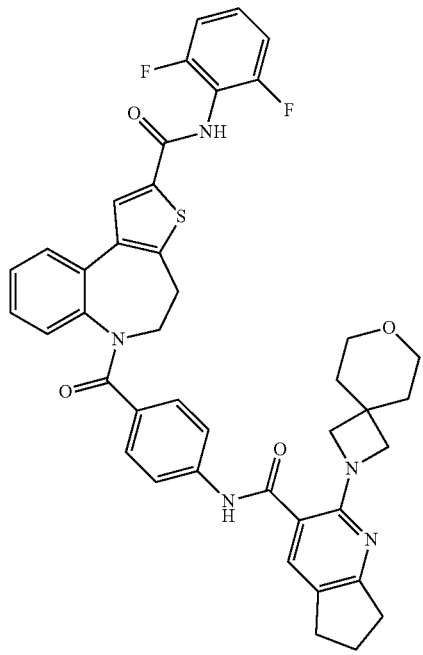 [SMILES: O=C(Nc1c(F)cccc1F)c1cc2c(s1)CCN(C(=O)c1ccc(NC(=O)c3cc4c(nc3N3CC5(CCOCC5)C3)CCC4)cc1)c1ccccc1-2] |
| 264 | 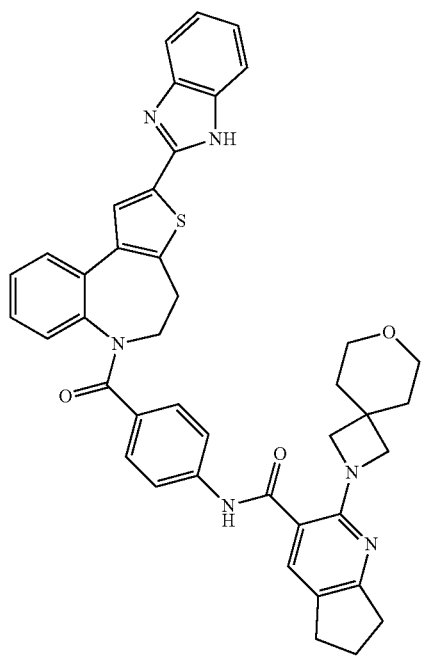 [SMILES: O=C(Nc1ccc(C(=O)N2CCc3sc(-c4nc5ccccc5[nH]4)cc3-c3ccccc32)cc1)c1cc2c(nc1N1CC3(CCOCC3)C1)CCC2] |

| Compound | Structure |
|---|---|
| 265 | 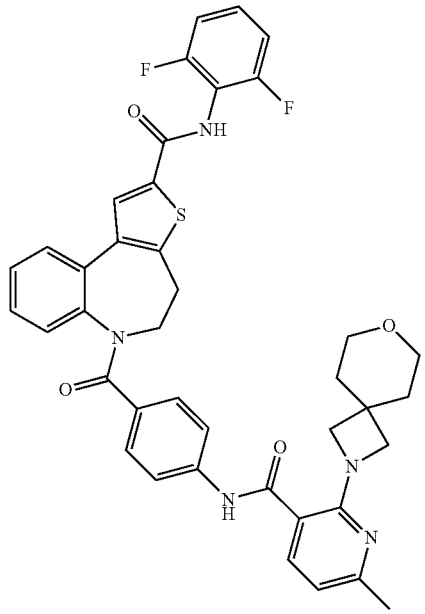 [SMILES: Cc1ccc(C(=O)Nc2ccc(C(=O)N3CCc4sc(C(=O)Nc5c(F)cccc5F)cc4-c4ccccc43)cc2)c(N2CC3(CCOCC3)C2)n1] |
| 266 | 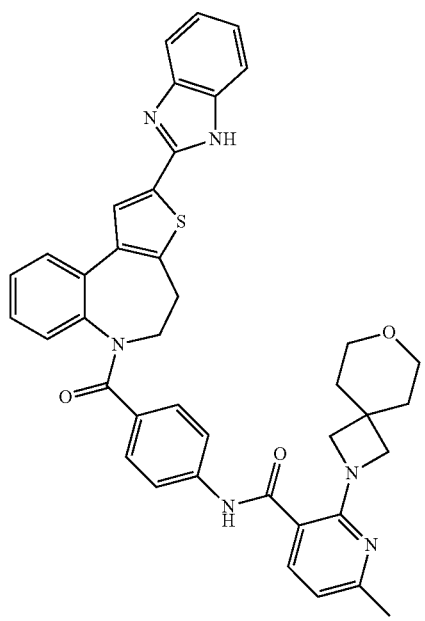 [SMILES: Cc1ccc(C(=O)Nc2ccc(C(=O)N3CCc4sc(-c5nc6ccccc6[nH]5)cc4-c4ccccc43)cc2)c(N2CC3(CCOCC3)C2)n1] |

| Compound | Structure |
|---|---|
| 267 | 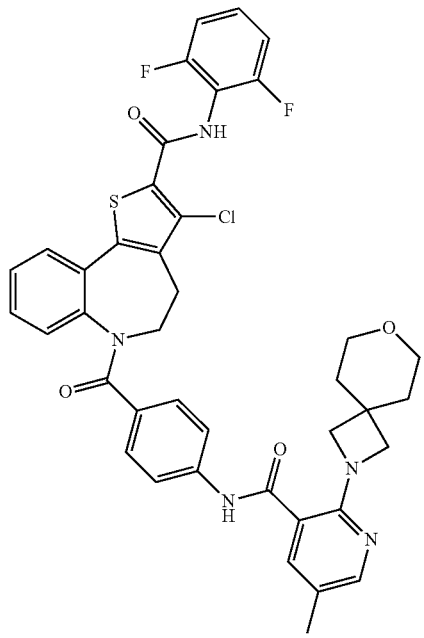 [SMILES: Cc1cnc(N2CC3(CCOCC3)C2)c(C(=O)Nc2ccc(C(=O)N3CCc4c(sc(C(=O)Nc5c(F)cccc5F)c4Cl)-c4ccccc43)cc2)c1] |
| 268 | 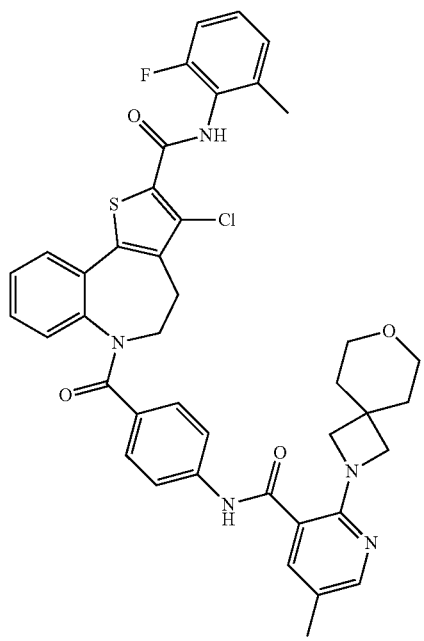 |

| Compound | Structure |
|---|---|
| 269 | 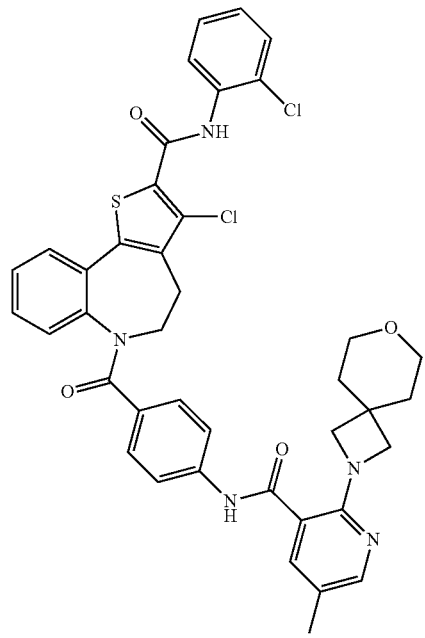 [SMILES: Cc1cnc(N2CC3(CCOCC3)C2)c(C(=O)Nc2ccc(C(=O)N3CCc4c(sc(C(=O)Nc5ccccc5Cl)c4Cl)-c4ccccc43)cc2)c1] |
| 270 | 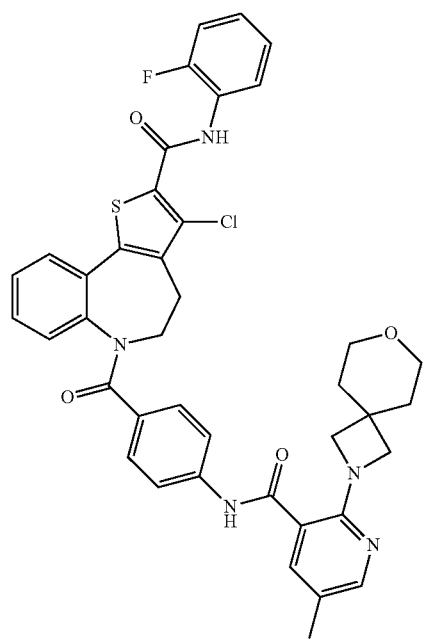 [SMILES: Cc1cnc(N2CC3(CCOCC3)C2)c(C(=O)Nc2ccc(C(=O)N3CCc4c(sc(C(=O)Nc5ccccc5F)c4Cl)-c4ccccc43)cc2)c1] |

-continued
| Compound | Structure |
|---|---|
| 271 | 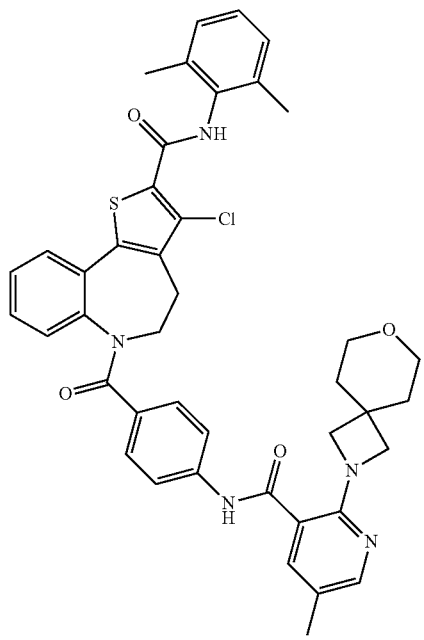 [SMILES: Cc1cnc(N2CC3(CCOCC3)C2)c(C(=O)Nc2ccc(C(=O)N3CCc4c(sc(C(=O)Nc5c(C)cccc5C)c4Cl)-c4ccccc43)cc2)c1] |
| 272 | 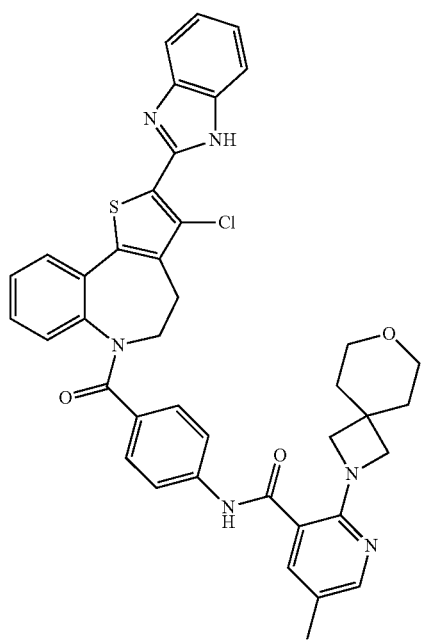 |

| Compound | Structure |
|---|---|
| 273 | 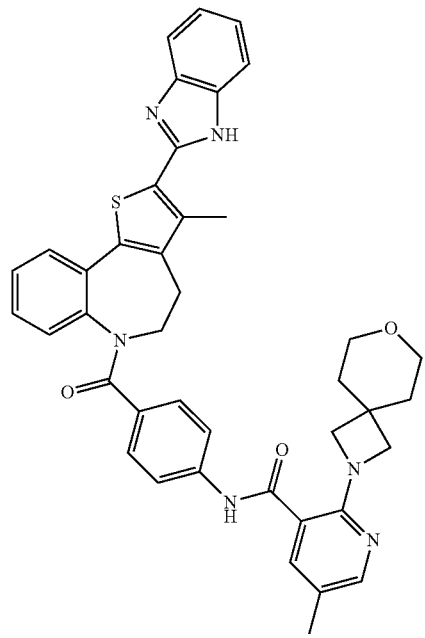 [SMILES: Cc1cnc(N2CC3(CCOCC3)C2)c(C(=O)Nc2ccc(C(=O)N3CCc4c(sc(-c5nc6ccccc6[nH]5)c4C)-c4ccccc43)cc2)c1] |
| 275 | 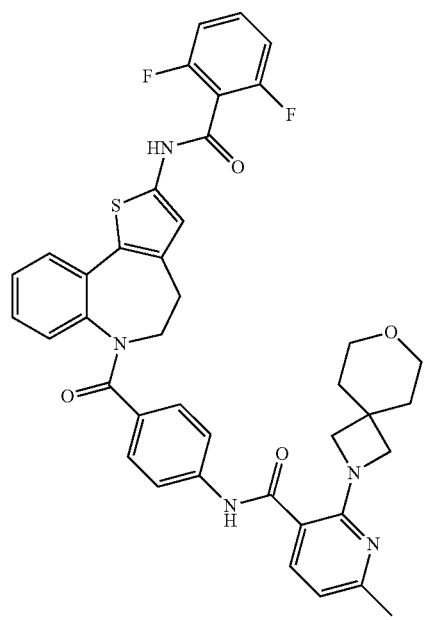 [SMILES: Cc1ccc(C(=O)Nc2ccc(C(=O)N3CCc4cc(NC(=O)c5c(F)cccc5F)sc4-c4ccccc43)cc2)c(N2CC3(CCOCC3)C2)n1] |

| Compound | Structure |
|---|---|
| 276 | 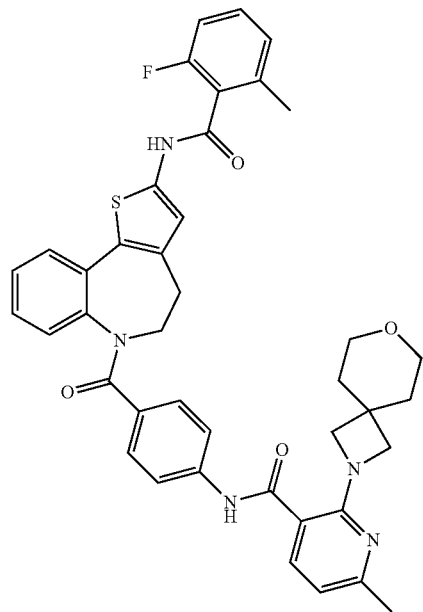 [SMILES: Cc1ccc(C(=O)Nc2ccc(C(=O)N3CCc4cc(NC(=O)c5c(C)cccc5F)sc4-c4ccccc43)cc2)c(N2CC3(CCOCC3)C2)n1] |
| 277 | 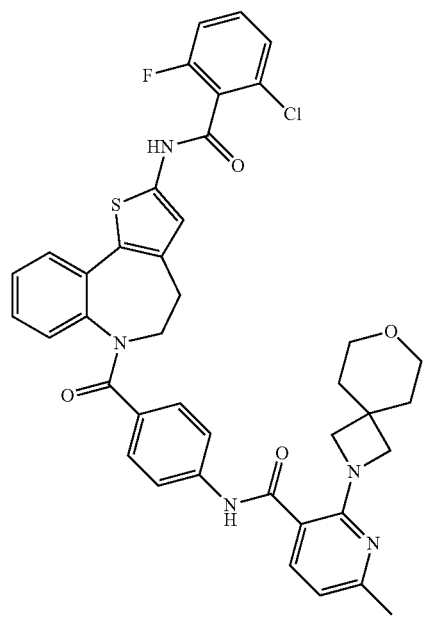 [SMILES: Cc1ccc(C(=O)Nc2ccc(C(=O)N3CCc4cc(NC(=O)c5c(F)cccc5Cl)sc4-c4ccccc43)cc2)c(N2CC3(CCOCC3)C2)n1] |

| Compound | Structure |
|---|---|
| 278 | 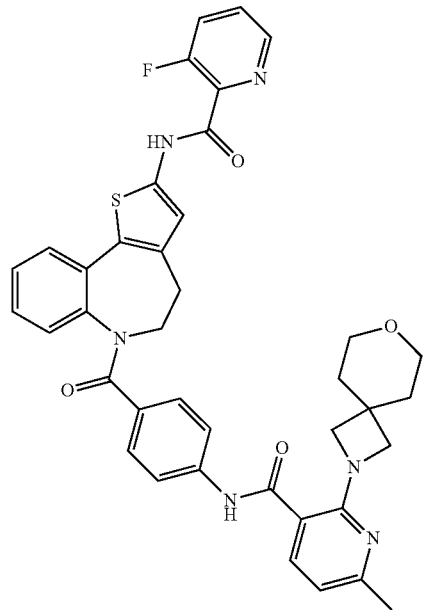 |
| 279 | 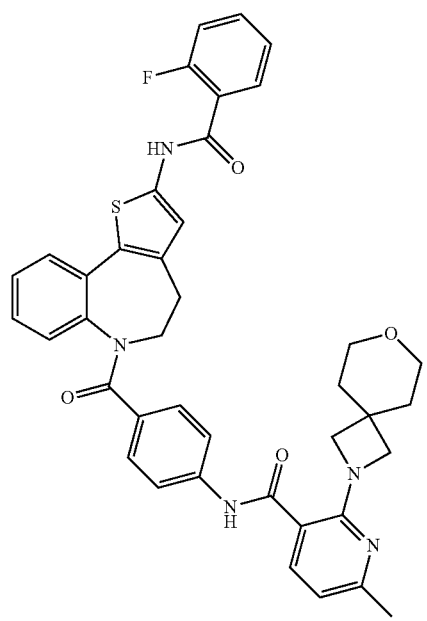 |

| Compound | Structure |
|---|---|
| 280 | 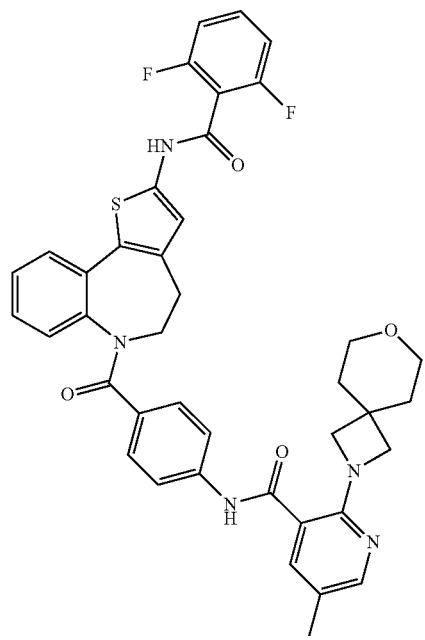 |
| 281 | 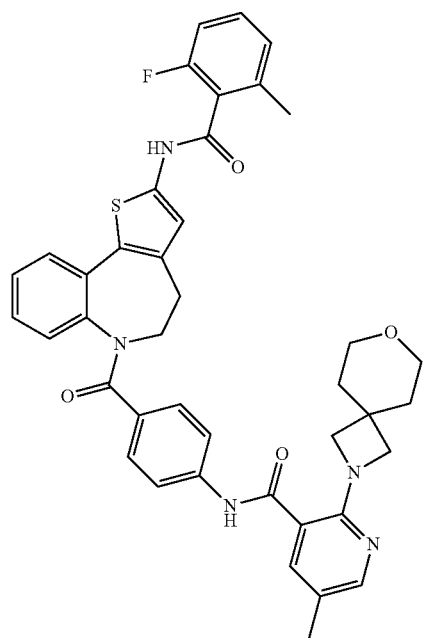 |

| Compound | Structure |
|---|---|
| 282 | 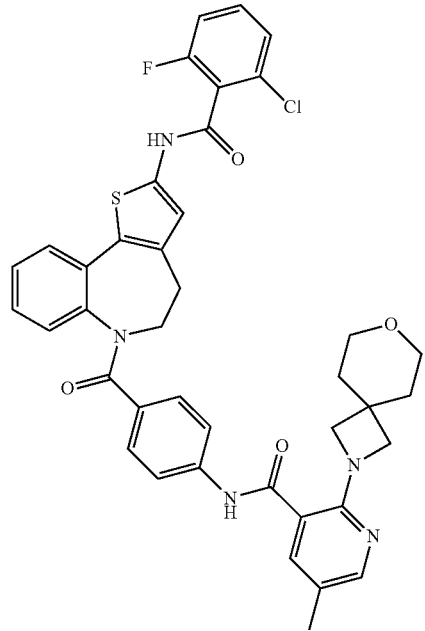 |
| 283 | 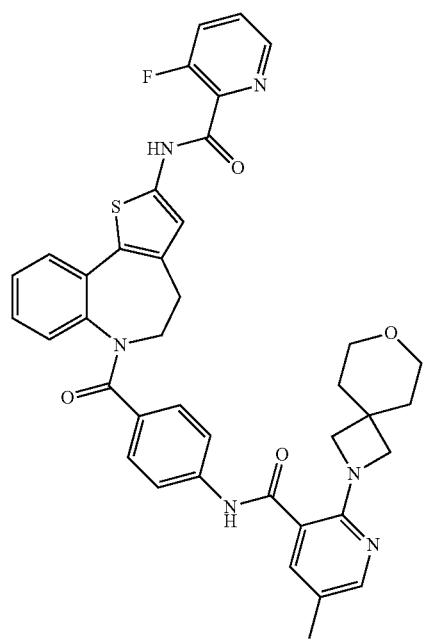 [SMILES: Cc1cnc(N2CC3(CCOCC3)C2)c(C(=O)Nc2ccc(C(=O)N3CCc4cc(NC(=O)c5ncccc5F)sc4-c4ccccc43)cc2)c1] |

| Compound | Structure |
|---|---|
| 284 | 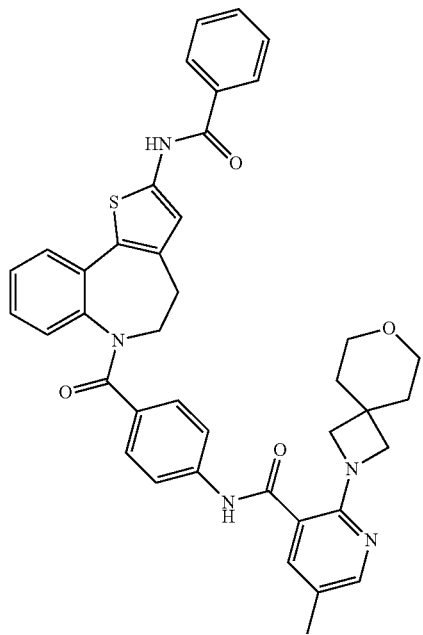 [SMILES: Cc1cnc(N2CC3(CCOCC3)C2)c(C(=O)Nc2ccc(C(=O)N3CCc4cc(NC(=O)c5ccccc5)sc4-c4ccccc43)cc2)c1] |
| 285 | 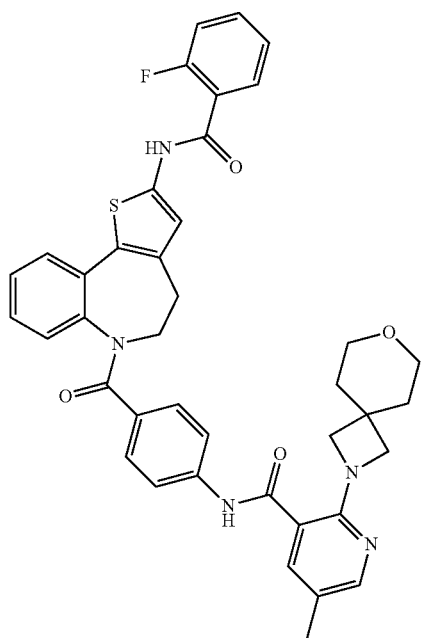 |

-continued
| Compound | Structure |
|---|---|
| 286 | 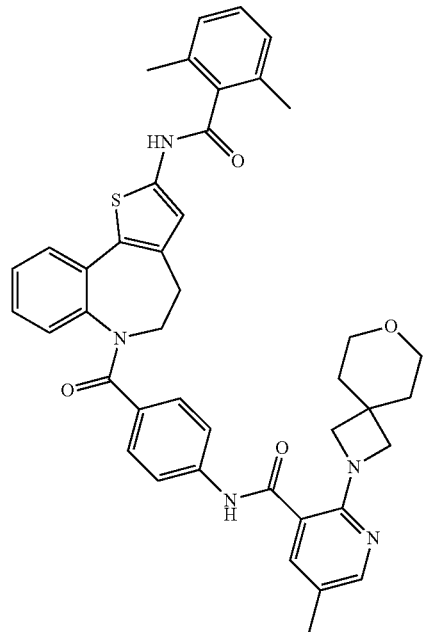 |
| 287 | 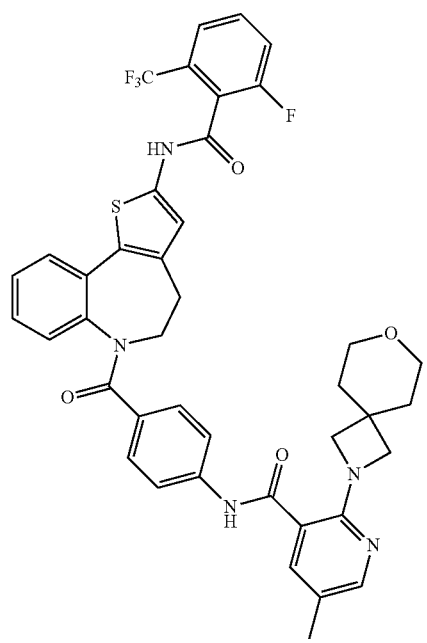 |

-continued
| Compound | Structure |
|---|---|
| 288 | 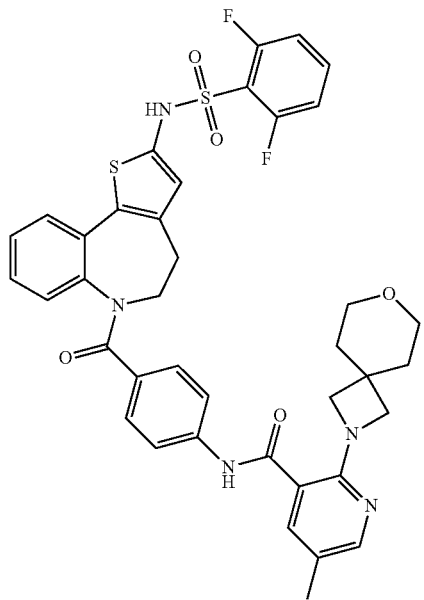 |
| 289 | 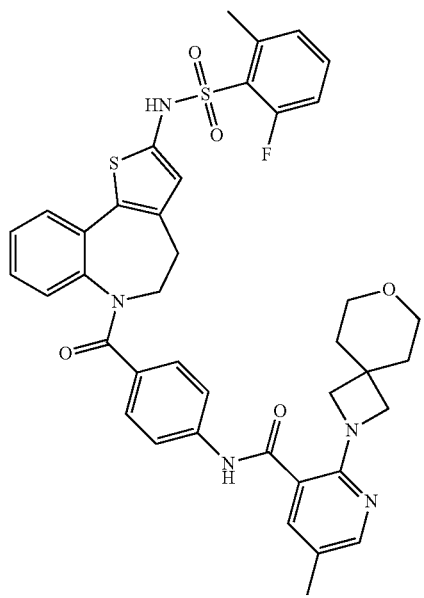 [SMILES: Cc1cnc(N2CC3(CCOCC3)C2)c(C(=O)Nc2ccc(C(=O)N3CCc4cc(NS(=O)(=O)c5c(C)cccc5F)sc4-c4ccccc43)cc2)c1] |

| Compound | Structure |
|---|---|
| 290 | 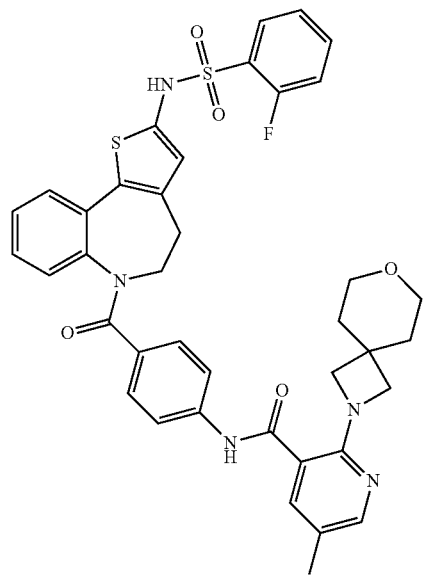 [SMILES: Cc1cnc(N2CC3(CCOCC3)C2)c(C(=O)Nc2ccc(C(=O)N3CCc4cc(NS(=O)(=O)c5ccccc5F)sc4-c4ccccc43)cc2)c1] |
| 291 | 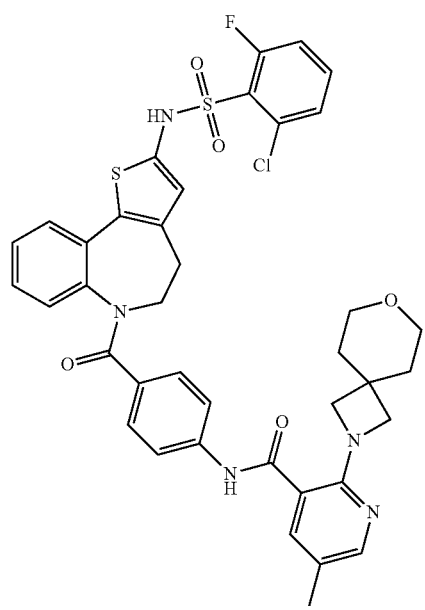 |

-continued
| Compound | Structure |
|---|---|
| 292 | 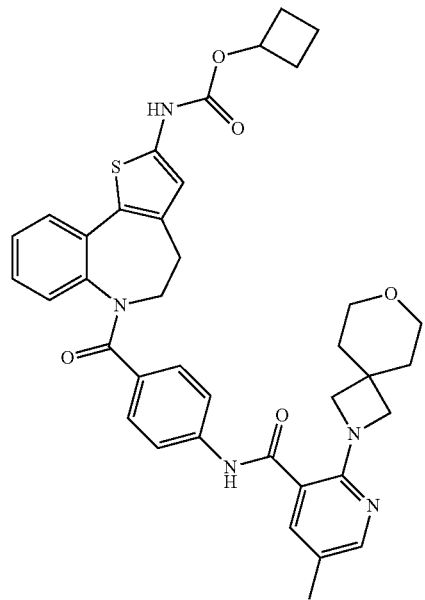 [SMILES: Cc1cnc(N2CC3(CCOCC3)C2)c(C(=O)Nc2ccc(C(=O)N3CCc4cc(NC(=O)OC5CCC5)sc4-c4ccccc43)cc2)c1] |
| 293 | 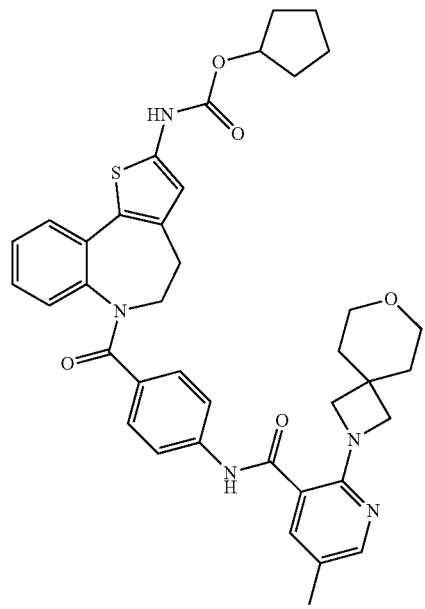 [SMILES: Cc1cnc(N2CC3(CCOCC3)C2)c(C(=O)Nc2ccc(C(=O)N3CCc4cc(NC(=O)OC5CCCC5)sc4-c4ccccc43)cc2)c1] |

-continued
| Compound | Structure |
|---|---|
| 294 | 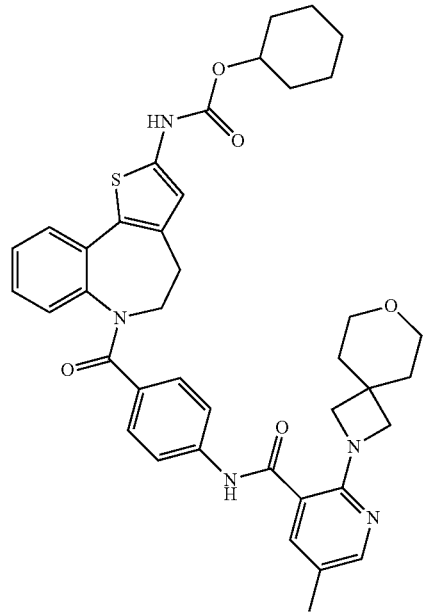 [SMILES: Cc1cnc(N2CC3(CCOCC3)C2)c(C(=O)Nc2ccc(C(=O)N3CCc4cc(NC(=O)OC5CCCCC5)sc4-c4ccccc43)cc2)c1] |
| 295 | 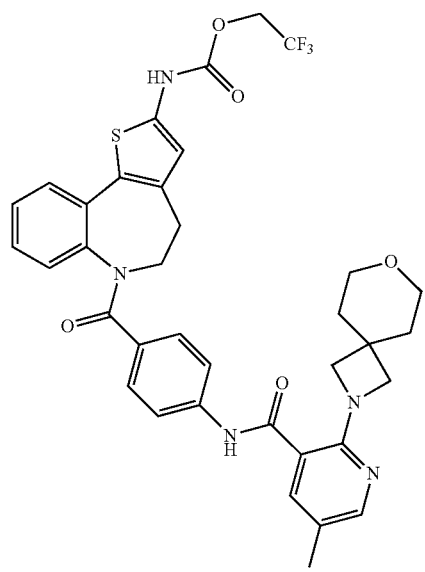 [SMILES: Cc1cnc(N2CC3(CCOCC3)C2)c(C(=O)Nc2ccc(C(=O)N3CCc4cc(NC(=O)OCC(F)(F)F)sc4-c4ccccc43)cc2)c1] |

| Compound | Structure |
|---|---|
| 296 | 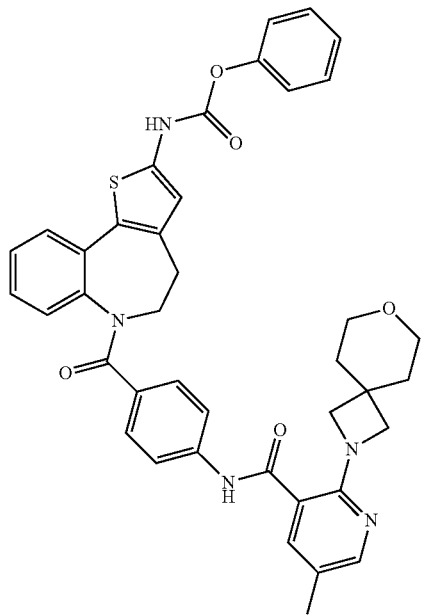 [SMILES: Cc1cnc(N2CC3(CCOCC3)C2)c(C(=O)Nc2ccc(C(=O)N3CCc4cc(NC(=O)Oc5ccccc5)sc4-c4ccccc43)cc2)c1] |
| 297 | 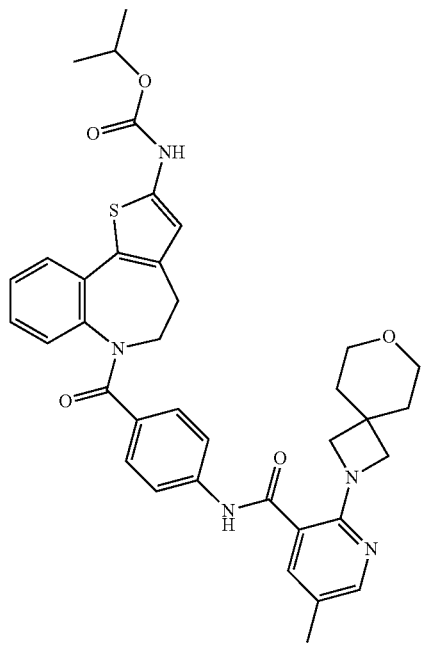 [SMILES: Cc1cnc(N2CC3(CCOCC3)C2)c(C(=O)Nc2ccc(C(=O)N3CCc4cc(NC(=O)OC(C)C)sc4-c4ccccc43)cc2)c1] |

| Compound | Structure |
|---|---|
| 298 | 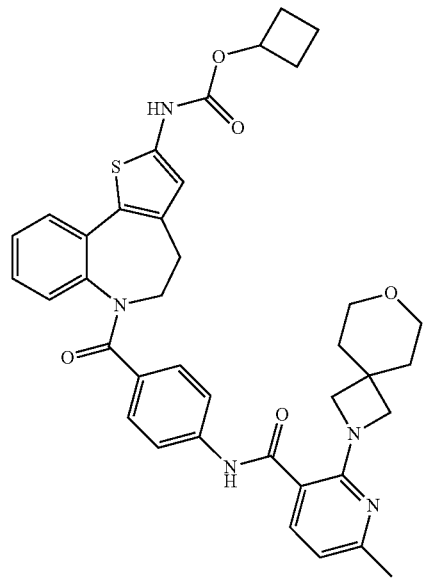 [SMILES: Cc1ccc(C(=O)Nc2ccc(C(=O)N3CCc4cc(NC(=O)OC5CCC5)sc4-c4ccccc43)cc2)c(N2CC3(CCOCC3)C2)n1] |
| 299 | 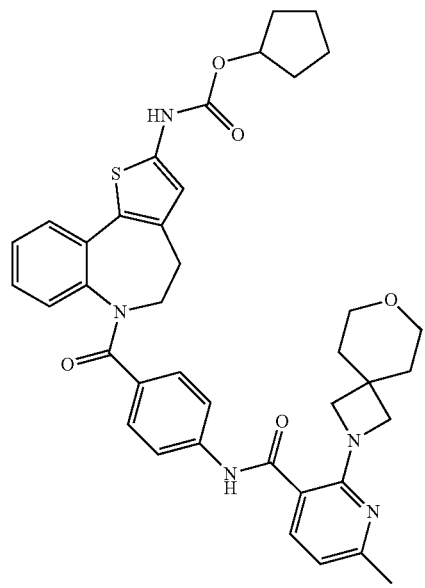 [SMILES: Cc1ccc(C(=O)Nc2ccc(C(=O)N3CCc4cc(NC(=O)OC5CCCC5)sc4-c4ccccc43)cc2)c(N2CC3(CCOCC3)C2)n1] |

-continued
| Compound | Structure |
|---|---|
| 300 | 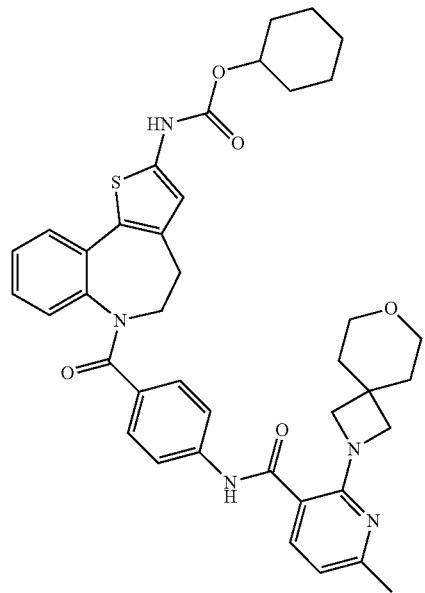 [SMILES: Cc1ccc(C(=O)Nc2ccc(C(=O)N3CCc4cc(NC(=O)OC5CCCCC5)sc4-c4ccccc43)cc2)c(N2CC3(CCOCC3)C2)n1] |
| 301 | 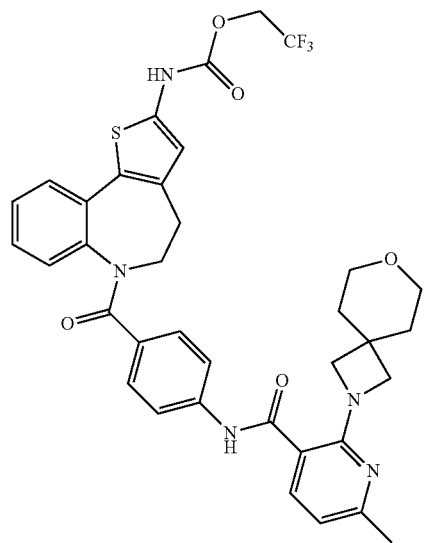 [SMILES: Cc1ccc(C(=O)Nc2ccc(C(=O)N3CCc4cc(NC(=O)OCC(F)(F)F)sc4-c4ccccc43)cc2)c(N2CC3(CCOCC3)C2)n1] |

| Compound | Structure |
|---|---|
| 302 | 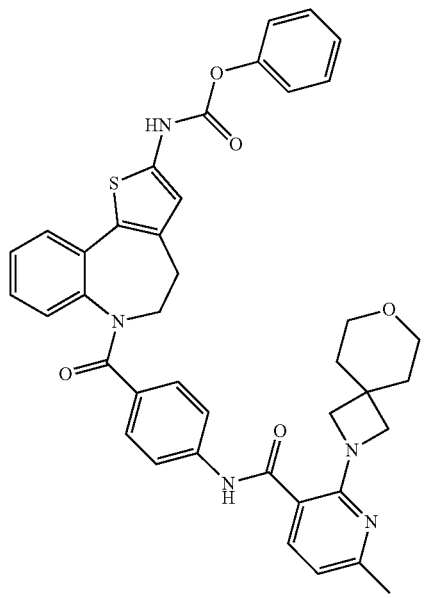 [SMILES: Cc1ccc(C(=O)Nc2ccc(C(=O)N3CCc4cc(NC(=O)Oc5ccccc5)sc4-c4ccccc43)cc2)c(N2CC3(CCOCC3)C2)n1] |
| 303 | 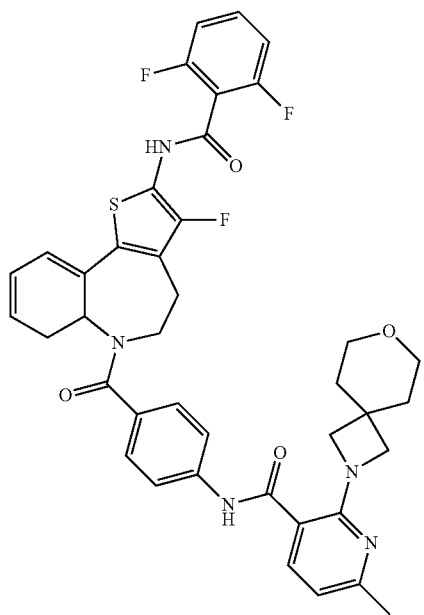 [SMILES: Cc1ccc(C(=O)Nc2ccc(C(=O)N3CCc4c(sc(NC(=O)c5c(F)cccc5F)c4F)C4=CC=CCC43)cc2)c(N2CC3(CCOCC3)C2)n1] |

-continued
| Compound | Structure |
|---|---|
| 304 | 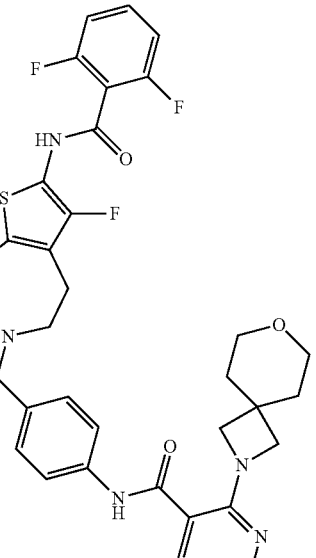 |
| 305 | 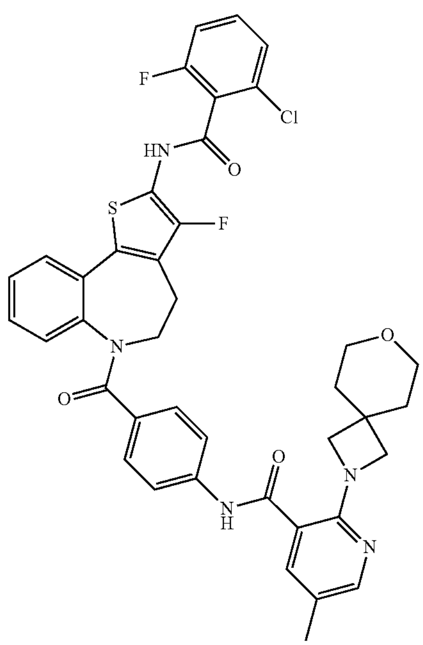 [SMILES: Cc1cnc(N2CC3(CCOCC3)C2)c(C(=O)Nc2ccc(C(=O)N3CCc4c(sc(NC(=O)c5c(F)cccc5Cl)c4F)-c4ccccc43)cc2)c1] |

-continued

| Compound | Structure |
|---|---|
| 306 | 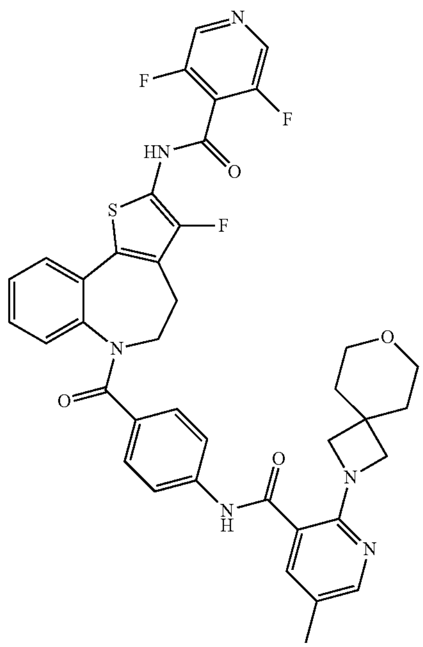 [SMILES: Cc1cnc(N2CC3(CCOCC3)C2)c(C(=O)Nc2ccc(C(=O)N3CCc4c(sc(NC(=O)c5c(F)cncc5F)c4F)-c4ccccc43)cc2)c1] |
| 307 | 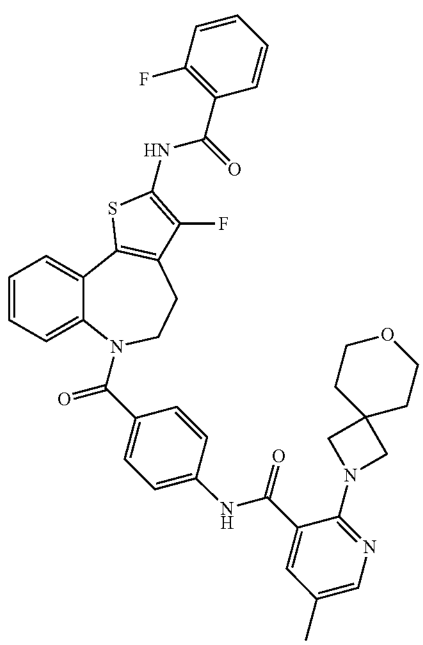 [SMILES: Cc1cnc(N2CC3(CCOCC3)C2)c(C(=O)Nc2ccc(C(=O)N3CCc4c(sc(NC(=O)c5ccccc5F)c4F)-c4ccccc43)cc2)c1] |

| Compound | Structure |
|---|---|
| 308 | 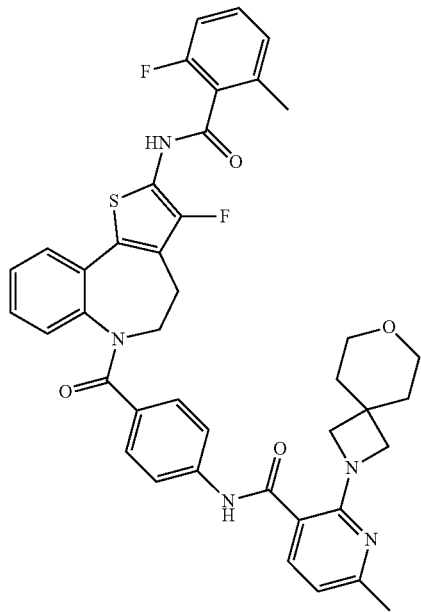 [SMILES: Cc1ccc(C(=O)Nc2ccc(C(=O)N3CCc4c(sc(NC(=O)c5c(C)cccc5F)c4F)-c4ccccc43)cc2)c(N2CC3(CCOCC3)C2)n1] |
| 309 | 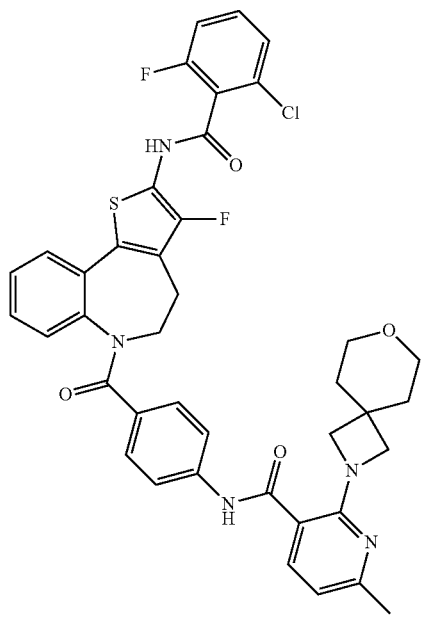 [SMILES: Cc1ccc(C(=O)Nc2ccc(C(=O)N3CCc4c(sc(NC(=O)c5c(F)cccc5Cl)c4F)-c4ccccc43)cc2)c(N2CC3(CCOCC3)C2)n1] |

| Compound | Structure |
|---|---|
| 310 | *(structure)* |
| 311 | *(structure)* |

11. A pharmaceutical composition comprising a compound according to claim 1, and a pharmaceutically acceptable carrier, diluent or excipient.

12. A method of treating or preventing an RSV infection in a subject in need thereof, comprising administering to the subject a therapeutically effective amount of a compound or a combination of compounds of claim 1.

13. The method of claim 12, further comprising the step of administering to the subject an additional anti-RSV agent.

14. The method of claim 12, further comprising administering to the subject a steroid anti-inflammatory compound.

15. A method of treating RSV and influenza in a subject in need thereof, comprising administering to the subject a therapeutically effective amount of a compound of claim 1 and a therapeutically effective amount of an anti-influenza agent.

16. The method of claim 13, wherein the compound and the additional anti-RSV agent are co-formulated.

17. The method of claim 13, wherein the compound and the additional anti-RSV agent are co-administered.

18. The method of claim 13, wherein administering the compound allows for administering of the additional anti-RSV agent at a lower dose or frequency as compared to the administering of the additional anti-RSV agent alone that is required to achieve similar results in prophylactically treating an RSV infection in a subject in need thereof.

19. The compound of claim 1, wherein n is 1, 2 or 3 and each $R_1$ is independently halogen or optionally substituted $C_1$-$C_8$-alkyl.

* * * * *

UNITED STATES PATENT AND TRADEMARK OFFICE
CERTIFICATE OF CORRECTION

PATENT NO. : 11,091,501 B2
APPLICATION NO. : 16/023422
DATED : August 17, 2021
INVENTOR(S) : In Jong Kim et al.

Page 1 of 2

It is certified that error appears in the above-identified patent and that said Letters Patent is hereby corrected as shown below:

In the Claims

At Column 395

In Claim 3, Line 10 after 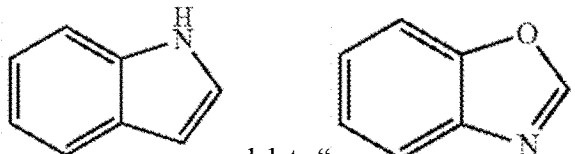, delete " 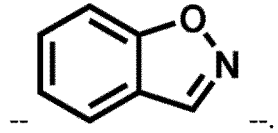 " and insert -- 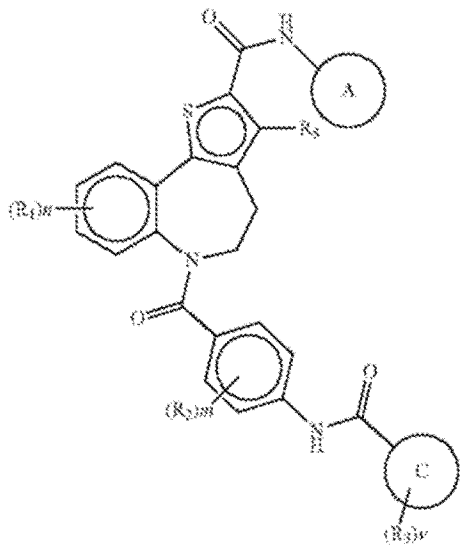 --.

At Column 399

In Claim 8, Lines 1-9 delete " " and

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,091,501 B2

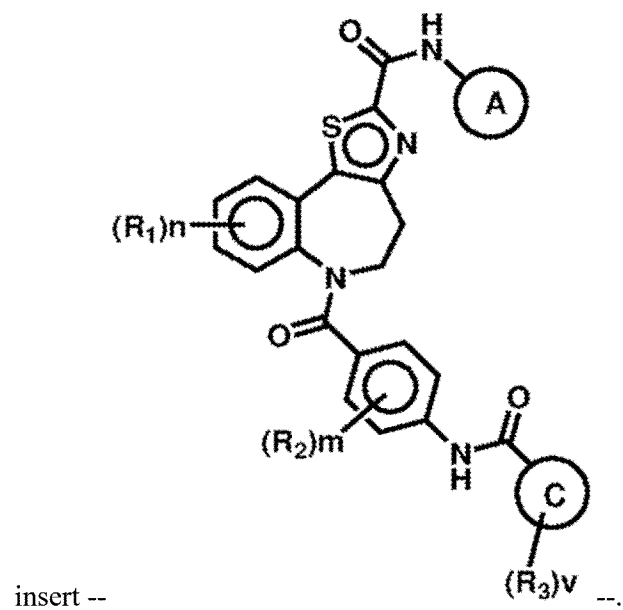

insert --                                                                 --.